United States Patent
Yousef et al.

(10) Patent No.: US 10,821,155 B2
(45) Date of Patent: Nov. 3, 2020

(54) HEPARIN-ASSOCIATED POLYPEPTIDES AND USES THEREOF

(71) Applicant: Juvena Therapeutics, Inc., Palo Alto, CA (US)

(72) Inventors: Hanadie Yousef, Palo Alto, CA (US); Thach Mai, Palo Alto, CA (US); Jeremy O'Connell, Palo Alto, CA (US)

(73) Assignee: Juvena Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 16/455,445

(22) Filed: Jun. 27, 2019

(65) Prior Publication Data

US 2020/0000882 A1    Jan. 2, 2020

Related U.S. Application Data

(60) Provisional application No. 62/690,796, filed on Jun. 27, 2018, provisional application No. 62/809,479, filed on Feb. 22, 2019.

(51) Int. Cl.

| | |
|---|---|
| *A61K 38/20* | (2006.01) |
| *A61K 9/00* | (2006.01) |
| *A61K 38/30* | (2006.01) |
| *A61K 38/17* | (2006.01) |
| *A61K 38/18* | (2006.01) |
| *A61K 38/39* | (2006.01) |
| *A61P 21/00* | (2006.01) |

(52) U.S. Cl.
CPC ........ *A61K 38/2086* (2013.01); *A61K 9/0019* (2013.01); *A61K 38/1709* (2013.01); *A61K 38/1825* (2013.01); *A61K 38/30* (2013.01); *A61K 38/39* (2013.01); *A61P 21/00* (2018.01)

(58) Field of Classification Search
None
See application file for complete search history.

(56) References Cited

U.S. PATENT DOCUMENTS

| | | | |
|---|---|---|---|
| 5,061,620 A | 10/1991 | Tsukamoto et al. | |
| 5,155,038 A * | 10/1992 | Eyal | A61K 38/39 424/77 |
| 5,843,780 A | 12/1998 | Thomson | |
| 6,200,806 B1 | 3/2001 | Thomson | |
| 7,029,913 B2 | 4/2006 | Thomson | |
| 7,837,993 B2 | 11/2010 | Conboy et al. | |
| 9,758,763 B2 | 9/2017 | Conboy et al. | |
| 10,265,372 B2 | 4/2019 | Conboy et al. | |
| 2014/0038892 A1* | 2/2014 | Yayon | C07K 14/50 514/9.1 |
| 2016/0024580 A1* | 1/2016 | Masli | C12Q 1/6883 514/20.8 |
| 2017/0315117 A1 | 11/2017 | Singh et al. | |
| 2017/0368173 A1 | 12/2017 | Kipps et al. | |
| 2019/0240156 A1* | 8/2019 | Lim | C12N 15/113 |

OTHER PUBLICATIONS

Athens Research & Technology, product information for human thrombospondin Product No. 16-20-201319 , 2 pages, no publication date.*
Barghorn et al.: Globular amyloid beta.-peptide 1-42 oligomer—a homogenous and stable neuropathological protein in Alzheimer's disease. Journal of Neurochemistry 95(3):834-847 (2005).
Bischoff: Cell cycle commitment of rat muscle satellite cells. The Journal of Cell Biology 111(1):201-207 (1990).
Bischoff: Proliferation of muscle satellite cells on intact myofibers in culture. Developmental Biology 115 (1):129-139 (1986).
Buchli et al.: Inhibition of Nogo: a key strategy to increase regeneration, plasticity and functional recovery of the lesioned central nervous system. Annals of Medicine 37(8):556-567 (2005).
Capila et al.: Heparin-protein interactions. Angew Chem Int Ed Engl.;41(3):391-412 (2002).
Carlson et al.: Loss of stem cell regenerative capacity within aged niches. Aging Cell 6: 371-382 (2007).
Chung et al.: Human Embryonic Stem Cell Lines Generated without Embryo Destruction. Cell Stem Cell 2 (2):113-117 (2008).
Conboy et al.: Aging, stem cells and tissue regeneration: lessons from muscle. Cell Cycle 4(3):407-410 (2005).
Conboy et al.: Embryonic anti-aging niche. Aging 3(5):555-563 (2011).
Conboy et al.: Heterochronic parabiosis for the study of the effects of aging on stem cells and their niches. Cell Cycle 11(12):2260-2267 (2012).
Conboy et al.: Immuno-analysis and FACS sorting of adult muscle fiber-associated stem/precursor cells. Methods Mol Biol 621:165-173 (2010).
Conboy et al.: Notch-Mediated Restoration of Regenerative Potential to Aged Muscle. Science 302:1575-1577 (2003).
Conboy et al.: Preparation of adult muscle fiber-associated stem/precursor cells. Methods Mol Biol 621:149-163 (2010).
Conboy et al.: The Regulation of Notch Signaling Controls Satellite Cell Activation and Cell Fate Determination in Postnatal Myogenesis. Dev Cell 3:397-409 (2002).
Grounds: Age-associated Changes in the Response of Skeletal Muscle Cells to Exercise and Regeneration. Ann NY Acad Sci 854:78-91 (1998).
Jensen et al.: Quantification of Alzheimer amyloid beta peptides ending at residues 40 and 42 by novel ELISA systems. Mol Med 6(4):291-302 (2000).
Kuo et al.: Water-soluble Abeta (N-40, N-42) oligomers in normal and Alzheimer disease brains. J Biol Chem 271(8):4077-4081 (1996).
Ludwig et al.: Feeder-independent culture of human embryonic stem cells. Nat Methods 3(8):637-646 (2006).
Malinowska et al.: Genistein Improves Neuropathology and Corrects Behaviour in a Mouse Model of Neurodegenerative Metabolic Disease. PLoS One; vol. 5, Issue 12; 9 pages (2010).
Morrison et al.: Prospective Identification, Isolation by Flow Cytometry, and in Vivo Self-Renewal of Multipotent Mammalian Neural Crest Stem Cells. Cell 96:737-749 (1999).

(Continued)

*Primary Examiner* — Marianne P Allen
(74) *Attorney, Agent, or Firm* — HelixIP LLP

(57) ABSTRACT

Described herein are therapeutic compositions comprising heparin-associated polypeptides useful for the treatment of soft-tissue and muscle diseases, disorders, and injuries.

14 Claims, 35 Drawing Sheets

Specification includes a Sequence Listing.

(56) References Cited

OTHER PUBLICATIONS

Morrison et al.: Regulatory Mechanisms in Stem Cell Biology. Cell 88(3):287-298 (1997).
Nguyen et al.: Surface plasmon resonance: a versatile technique for biosensor applications. Sensors (Basel). 15(5):10481-510 (2015).
Piantino et al.: An injectable, biodegradable hydrogel for trophic factor delivery enhances axonal rewiring and improves performance after spinal cord injury. Experimental Neurology 201(2):359-367 (2006).
Yousef et al.: hESC-secreted proteins can be enriched for multiple regenerative therapies by heparin-binding. Aging; vol. 5, No. 5: 357-372 (2013).
Yousef et al.: Mechanisms of action of hESC-secreted proteins that enhance human and mouse myogenesis. Aging; vol. 6, No. 8: 602-620 (2014).

\* cited by examiner

FIG. 2A
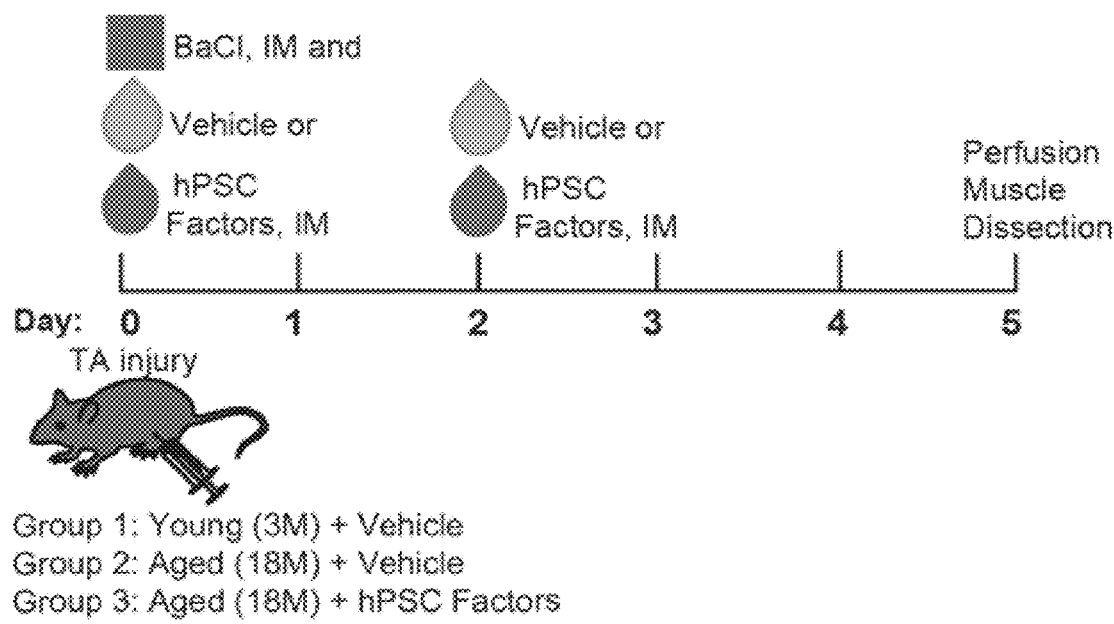
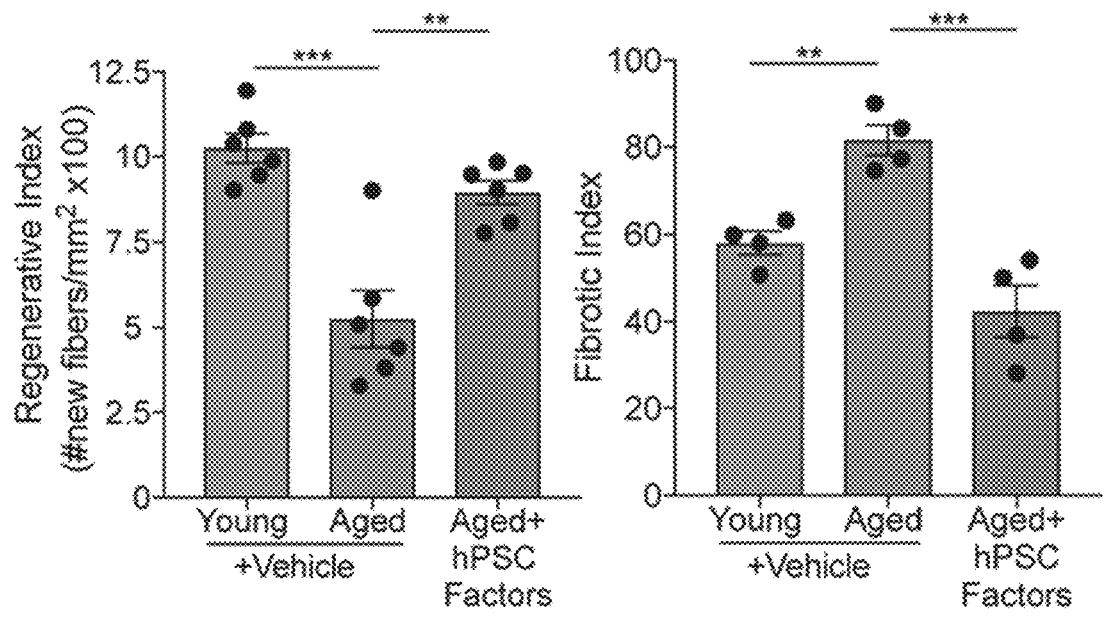
FIG. 2B

SEQUENCE LISTING

```
<160> NUMBER OF SEQ ID NOS: 70

<210> SEQ ID NO 1
<211> LENGTH: 478
<212> TYPE: PRT
<213> ORGANISM: Homo sapiens

<400> SEQUENCE: 1

Met Ala Pro Leu Arg Pro Leu Leu Ile Leu Ala Leu Leu Ala Trp Val
1               5                   10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
        35                  40                  45

Ser Cys Cys Thr Asp Tyr Thr Ala Glu Cys Lys Pro Gln Val Thr Arg
    50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Glu Ala Pro Ala Pro Glu Val Gly
        115                 120                 125

Ala Ser Lys Pro Glu Gly Ile Asp Ser Arg Pro Glu Thr Leu His Pro
    130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
    210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
    290                 295                 300
```

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
            325                 330                 335

Arg Asp Trp His Gly Val Pro Gly Gln Val Asp Ala Ala Met Ala Gly
                340                 345                 350

Arg Ile Tyr Ile Ser Gly Met Ala Pro Arg Pro Ser Leu Ala Lys Lys
            355                 360                 365

Gln Arg Phe Arg His Arg Asn Arg Lys Gly Tyr Arg Ser Gln Arg Gly
370                 375                 380

His Ser Arg Gly Arg Asn Gln Asn Ser Arg Arg Pro Ser Arg Ala Thr
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
                420                 425                 430

Ile Gln Ser Val Phe Phe Ser Gly Asp Lys Tyr Tyr Arg Val Asn
            435                 440                 445

Leu Arg Thr Arg Arg Val Asp Thr Val Asp Pro Tyr Pro Arg Ser
450                 455                 460

Ile Ala Gln Tyr Trp Leu Gly Cys Pro Ala Pro Gly His Leu
465                 470                 475

<210> SEQ ID NO 2
<211> LENGTH: 302
<212> TYPE: PRT
<213> ORGANISM: Homo sapiens

<400> SEQUENCE: 2

Met Cys Ala Glu Arg Leu Gly Gln Phe Met Thr Leu Ala Leu Val Leu
1               5                   10                  15

Ala Thr Phe Asp Pro Ala Arg Gly Thr Asp Ala Thr Asn Pro Pro Glu
            20                  25                  30

Gly Pro Gln Asp Arg Ser Ser Gln Gln Lys Gly Arg Leu Ser Leu Gln
        35                  40                  45

Asn Thr Ala Glu Ile Gln His Cys Leu Val Asn Ala Gly Asp Val Gly
50                  55                  60

Cys Gly Val Phe Glu Cys Phe Glu Asn Asn Ser Cys Glu Ile Arg Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
        115                 120                 125

Arg Glu Met Val Ser Gln Leu Gln Arg Glu Cys Tyr Leu Lys His Asp
130                 135                 140

Leu Cys Ala Ala Ala Gln Glu Asn Thr Arg Val Ile Val Glu Met Ile
145                 150                 155                 160

His Phe Lys Asp Leu Leu Leu His Glu Pro Tyr Val Asp Leu Val Asn
                165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
        195                 200                 205

```
Ser Phe Cys Thr Ser Ala Ile Gln Lys Pro Pro Thr Ala Pro Pro Glu
            210                 215                 220

Arg Gln Pro Gln Val Asp Arg Thr Lys Leu Ser Arg Ala His His Gly
225                 230                 235                 240

Glu Ala Gly His His Leu Pro Glu Pro Ser Ser Arg Glu Thr Gly Arg
                245                 250                 255

Gly Ala Lys Gly Glu Arg Gly Ser Lys Ser His Pro Asn Ala His Ala
            260                 265                 270

Arg Gly Arg Val Gly Gly Leu Gly Ala Gln Gly Pro Ser Gly Ser Ser
            275                 280                 285

Glu Trp Glu Asp Glu Gln Ser Glu Tyr Ser Asp Ile Arg Arg
290                 295                 300

<210> SEQ ID NO 3
<211> LENGTH: 2068
<212> TYPE: PRT
<213> ORGANISM: Homo sapiens

<400> SEQUENCE: 3

Met Ala Gly Arg Ser His Pro Gly Pro Leu Arg Pro Leu Pro Leu
1               5                   10                  15

Leu Val Ala Ala Cys Val Leu Pro Gly Ala Gly Gly Thr Cys Pro
                20                  25                  30

Glu Arg Ala Leu Glu Arg Arg Glu Glu Ala Asn Val Val Leu Thr
            35                  40                  45

Gly Thr Val Glu Glu Ile Leu Asn Val Asp Pro Val Gln His Thr Tyr
50                  55                  60

Ser Cys Lys Val Arg Val Trp Arg Tyr Leu Lys Gly Lys Asp Leu Val
65                  70                  75                  80

Ala Arg Glu Ser Leu Leu Asp Gly Gly Asn Lys Val Val Ile Ser Gly
                85                  90                  95

Phe Gly Asp Pro Leu Ile Cys Asp Asn Gln Val Ser Thr Gly Asp Thr
            100                 105                 110

Arg Ile Phe Phe Val Asn Pro Ala Pro Pro Tyr Leu Trp Pro Ala His
            115                 120                 125

Lys Asn Glu Leu Met Leu Asn Ser Ser Leu Met Arg Ile Thr Leu Arg
130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
                165                 170                 175

Cys Gly Phe Gly Ala Val Cys Glu Pro Asn Ala Glu Gly Pro Gly Arg
            180                 185                 190

Ala Ser Cys Val Cys Lys Lys Ser Pro Cys Pro Ser Val Val Ala Pro
            195                 200                 205

Val Cys Gly Ser Asp Ala Ser Thr Tyr Ser Asn Glu Cys Glu Leu Gln
            210                 215                 220

Arg Ala Gln Cys Ser Gln Gln Arg Arg Ile Arg Leu Leu Ser Arg Gly
225                 230                 235                 240

Pro Cys Gly Ser Arg Asp Pro Cys Ser Asn Val Thr Cys Ser Phe Gly
                245                 250                 255

Ser Thr Cys Ala Arg Ser Ala Asp Gly Leu Thr Ala Ser Cys Leu Cys
            260                 265                 270

Pro Ala Thr Cys Arg Gly Ala Pro Glu Gly Thr Val Cys Gly Ser Asp
```

```
                    275                 280                 285
Gly Ala Asp Tyr Pro Gly Glu Cys Gln Leu Leu Arg Arg Ala Cys Ala
    290                 295                 300
Arg Gln Glu Asn Val Phe Lys Lys Phe Asp Gly Pro Cys Asp Pro Cys
305                 310                 315                 320
Gln Gly Ala Leu Pro Asp Pro Ser Arg Ser Cys Arg Val Asn Pro Arg
                325                 330                 335
Thr Arg Arg Pro Glu Met Leu Leu Arg Pro Glu Ser Cys Pro Ala Arg
            340                 345                 350
Gln Ala Pro Val Cys Gly Asp Asp Gly Val Thr Tyr Glu Asn Asp Cys
        355                 360                 365
Val Met Gly Arg Ser Gly Ala Ala Arg Gly Leu Leu Leu Gln Lys Val
    370                 375                 380
Arg Ser Gly Gln Cys Gln Gly Arg Asp Gln Cys Pro Glu Pro Cys Arg
385                 390                 395                 400
Phe Asn Ala Val Cys Leu Ser Arg Arg Gly Arg Pro Arg Cys Ser Cys
                405                 410                 415
Asp Arg Val Thr Cys Asp Gly Ala Tyr Arg Pro Val Cys Ala Gln Asp
            420                 425                 430
Gly Arg Thr Tyr Asp Ser Asp Cys Trp Arg Gln Gln Ala Glu Cys Arg
        435                 440                 445
Gln Gln Arg Ala Ile Pro Ser Lys His Gln Gly Pro Cys Asp Gln Ala
    450                 455                 460
Pro Ser Pro Cys Leu Gly Val Gln Cys Ala Phe Gly Ala Thr Cys Ala
465                 470                 475                 480
Val Lys Asn Gly Gln Ala Ala Cys Glu Cys Leu Gln Ala Cys Ser Ser
                485                 490                 495
Leu Tyr Asp Pro Val Cys Gly Ser Asp Gly Val Thr Tyr Gly Ser Ala
            500                 505                 510
Cys Glu Leu Glu Ala Thr Ala Cys Thr Leu Gly Arg Glu Ile Gln Val
        515                 520                 525
Ala Arg Lys Gly Pro Cys Asp Arg Cys Gly Gln Cys Arg Phe Gly Ala
    530                 535                 540
Leu Cys Glu Ala Glu Thr Gly Arg Cys Val Cys Pro Ser Glu Cys Val
545                 550                 555                 560
Ala Leu Ala Gln Pro Val Cys Gly Ser Asp Gly His Thr Tyr Pro Ser
                565                 570                 575
Glu Cys Met Leu His Val His Ala Cys Thr His Gln Ile Ser Leu His
            580                 585                 590
Val Ala Ser Ala Gly Pro Cys Glu Thr Cys Gly Asp Ala Val Cys Ala
        595                 600                 605
Phe Gly Ala Val Cys Ser Ala Gly Gln Cys Val Cys Pro Arg Cys Glu
    610                 615                 620
His Pro Pro Pro Gly Pro Val Cys Gly Ser Asp Gly Val Thr Tyr Gly
625                 630                 635                 640
Ser Ala Cys Glu Leu Arg Glu Ala Ala Cys Leu Gln Thr Gln Ile
                645                 650                 655
Glu Glu Ala Arg Ala Gly Pro Cys Glu Gln Ala Glu Cys Gly Ser Gly
            660                 665                 670
Gly Ser Gly Ser Gly Glu Asp Gly Asp Cys Glu Gln Glu Leu Cys Arg
        675                 680                 685
Gln Arg Gly Gly Ile Trp Asp Glu Asp Ser Glu Asp Gly Pro Cys Val
    690                 695                 700
```

-continued

```
Cys Asp Phe Ser Cys Gln Ser Val Pro Gly Ser Pro Val Cys Gly Ser
705                 710                 715                 720

Asp Gly Val Thr Tyr Ser Thr Glu Cys Glu Leu Lys Lys Ala Arg Cys
            725                 730                 735

Glu Ser Gln Arg Gly Leu Tyr Val Ala Ala Gln Gly Ala Cys Arg Gly
                740                 745                 750

Pro Thr Phe Ala Pro Leu Pro Pro Val Ala Pro Leu His Cys Ala Gln
                755                 760                 765

Thr Pro Tyr Gly Cys Cys Gln Asp Asn Ile Thr Ala Ala Arg Gly Val
            770                 775                 780

Gly Leu Ala Gly Cys Pro Ser Ala Cys Gln Cys Asn Pro His Gly Ser
785                 790                 795                 800

Tyr Gly Gly Thr Cys Asp Pro Ala Thr Gly Gln Cys Ser Cys Arg Pro
                805                 810                 815

Gly Val Gly Gly Leu Arg Cys Asp Arg Cys Glu Pro Gly Phe Trp Asn
            820                 825                 830

Phe Arg Gly Ile Val Thr Asp Gly Arg Ser Gly Cys Thr Pro Cys Ser
                835                 840                 845

Cys Asp Pro Gln Gly Ala Val Arg Asp Cys Glu Gln Met Thr Gly
850                 855                 860

Leu Cys Ser Cys Lys Pro Gly Val Ala Gly Pro Lys Cys Gly Gln Cys
865                 870                 875                 880

Pro Asp Gly Arg Ala Leu Gly Pro Ala Gly Cys Glu Ala Asp Ala Ser
                885                 890                 895

Ala Pro Ala Thr Cys Ala Glu Met Arg Cys Glu Phe Gly Ala Arg Cys
                900                 905                 910

Val Glu Glu Ser Gly Ser Ala His Cys Val Cys Pro Met Leu Thr Cys
            915                 920                 925

Pro Glu Ala Asn Ala Thr Lys Val Cys Gly Ser Asp Gly Val Thr Tyr
930                 935                 940

Gly Asn Glu Cys Gln Leu Lys Thr Ile Ala Cys Arg Gln Gly Leu Gln
945                 950                 955                 960

Ile Ser Ile Gln Ser Leu Gly Pro Cys Gln Glu Ala Val Ala Pro Ser
                965                 970                 975

Thr His Pro Thr Ser Ala Ser Val Thr Val Thr Thr Pro Gly Leu Leu
            980                 985                 990

Leu Ser Gln Ala Leu Pro Ala Pro  Pro Gly Ala Leu Pro  Leu Ala Pro
            995                 1000                1005

Ser Ser  Thr Ala His Ser Gln  Thr Thr Pro Pro  Ser Ser Arg
        1010                1015                 1020

Pro Arg  Thr Thr Ala Ser Val  Pro Arg Thr Thr Val  Trp Pro Val
        1025                 1030                 1035

Leu Thr  Val Pro Pro Thr Ala  Pro Ser Pro Ala Pro  Ser Leu Val
        1040                 1045                 1050

Ala Ser  Ala Phe Gly Glu Ser  Gly Ser Thr Asp Gly  Ser Ser Asp
        1055                 1060                 1065

Glu Glu  Leu Ser Gly Asp Gln  Glu Ala Ser Gly Gly  Gly Ser Gly
        1070                 1075                 1080

Gly Leu  Glu Pro Leu Glu Gly  Ser Ser Val Ala Thr  Pro Gly Pro
        1085                 1090                 1095

Pro Val  Glu Arg Ala Ser Cys  Tyr Asn Ser Ala Leu  Gly Cys Cys
        1100                 1105                 1110
```

```
Ser Asp Gly Lys Thr Pro Ser Leu Asp Ala Glu Gly Ser Asn Cys
1115                1120                1125

Pro Ala Thr Lys Val Phe Gln Gly Val Leu Glu Leu Glu Gly Val
1130                1135                1140

Glu Gly Gln Glu Leu Phe Tyr Thr Pro Glu Met Ala Asp Pro Lys
1145                1150                1155

Ser Glu Leu Phe Gly Glu Thr Ala Arg Ser Ile Glu Ser Thr Leu
1160                1165                1170

Asp Asp Leu Phe Arg Asn Ser Asp Val Lys Lys Asp Phe Arg Ser
1175                1180                1185

Val Arg Leu Arg Asp Leu Gly Pro Gly Lys Ser Val Arg Ala Ile
1190                1195                1200

Val Asp Val His Phe Asp Pro Thr Thr Ala Phe Arg Ala Pro Asp
1205                1210                1215

Val Ala Arg Ala Leu Leu Arg Gln Ile Gln Val Ser Arg Arg Arg
1220                1225                1230

Ser Leu Gly Val Arg Arg Pro Leu Gln Glu His Val Arg Phe Met
1235                1240                1245

Asp Phe Asp Trp Phe Pro Ala Phe Ile Thr Gly Ala Thr Ser Gly
1250                1255                1260

Ala Ile Ala Ala Gly Ala Thr Ala Arg Ala Thr Thr Ala Ser Arg
1265                1270                1275

Leu Pro Ser Ser Ala Val Thr Pro Arg Ala Pro His Pro Ser His
1280                1285                1290

Thr Ser Gln Pro Val Ala Lys Thr Thr Ala Ala Pro Thr Thr Arg
1295                1300                1305

Arg Pro Pro Thr Thr Ala Pro Ser Arg Val Pro Gly Arg Arg Pro
1310                1315                1320

Pro Ala Pro Gln Gln Pro Pro Lys Pro Cys Asp Ser Gln Pro Cys
1325                1330                1335

Phe His Gly Gly Thr Cys Gln Asp Trp Ala Leu Gly Gly Gly Phe
1340                1345                1350

Thr Cys Ser Cys Pro Ala Gly Arg Gly Gly Ala Val Cys Glu Lys
1355                1360                1365

Val Leu Gly Ala Pro Val Pro Ala Phe Glu Gly Arg Ser Phe Leu
1370                1375                1380

Ala Phe Pro Thr Leu Arg Ala Tyr His Thr Leu Arg Leu Ala Leu
1385                1390                1395

Glu Phe Arg Ala Leu Glu Pro Gln Gly Leu Leu Leu Tyr Asn Gly
1400                1405                1410

Asn Ala Arg Gly Lys Asp Phe Leu Ala Leu Ala Leu Leu Asp Gly
1415                1420                1425

Arg Val Gln Leu Arg Phe Asp Thr Gly Ser Gly Pro Ala Val Leu
1430                1435                1440

Thr Ser Ala Val Pro Val Glu Pro Gly Gln Trp His Arg Leu Glu
1445                1450                1455

Leu Ser Arg His Trp Arg Arg Gly Thr Leu Ser Val Asp Gly Glu
1460                1465                1470

Thr Pro Val Leu Gly Glu Ser Pro Ser Gly Thr Asp Gly Leu Asn
1475                1480                1485

Leu Asp Thr Asp Leu Phe Val Gly Gly Val Pro Glu Asp Gln Ala
1490                1495                1500

Ala Val Ala Leu Glu Arg Thr Phe Val Gly Ala Gly Leu Arg Gly
```

|     |     |     |     |     |     |     |     |     |     |
| --- | --- | --- | --- | --- | --- | --- | --- | --- | --- |
| 1505 | | | | 1510 | | | 1515 | | |
| Cys | Ile | Arg | Leu | Leu | Asp | Val | Asn | Asn | Gln | Arg | Leu | Glu | Leu | Gly |
| 1520 | | | | | 1525 | | | 1530 | | |
| Ile | Gly | Pro | Gly | Ala | Ala | Thr | Arg | Gly | Ser | Gly | Val | Gly | Glu | Cys |
| 1535 | | | | | 1540 | | | 1545 | | |
| Gly | Asp | His | Pro | Cys | Leu | Pro | Asn | Pro | Cys | His | Gly | Gly | Ala | Pro |
| 1550 | | | | | 1555 | | | 1560 | | |
| Cys | Gln | Asn | Leu | Glu | Ala | Gly | Arg | Phe | His | Cys | Gln | Cys | Pro | Pro |
| 1565 | | | | | 1570 | | | 1575 | | |
| Gly | Arg | Val | Gly | Pro | Thr | Cys | Ala | Asp | Glu | Lys | Ser | Pro | Cys | Gln |
| 1580 | | | | | 1585 | | | 1590 | | |
| Pro | Asn | Pro | Cys | His | Gly | Ala | Ala | Pro | Cys | Arg | Val | Leu | Pro | Glu |
| 1595 | | | | | 1600 | | | 1605 | | |
| Gly | Gly | Ala | Gln | Cys | Glu | Cys | Pro | Leu | Gly | Arg | Glu | Gly | Thr | Phe |
| 1610 | | | | | 1615 | | | 1620 | | |
| Cys | Gln | Thr | Ala | Ser | Gly | Gln | Asp | Gly | Ser | Gly | Pro | Phe | Leu | Ala |
| 1625 | | | | | 1630 | | | 1635 | | |
| Asp | Phe | Asn | Gly | Phe | Ser | His | Leu | Glu | Leu | Arg | Gly | Leu | His | Thr |
| 1640 | | | | | 1645 | | | 1650 | | |
| Phe | Ala | Arg | Asp | Leu | Gly | Glu | Lys | Met | Ala | Leu | Glu | Val | Val | Phe |
| 1655 | | | | | 1660 | | | 1665 | | |
| Leu | Ala | Arg | Gly | Pro | Ser | Gly | Leu | Leu | Leu | Tyr | Asn | Gly | Gln | Lys |
| 1670 | | | | | 1675 | | | 1680 | | |
| Thr | Asp | Gly | Lys | Gly | Asp | Phe | Val | Ser | Leu | Ala | Leu | Arg | Asp | Arg |
| 1685 | | | | | 1690 | | | 1695 | | |
| Arg | Leu | Glu | Phe | Arg | Tyr | Asp | Leu | Gly | Lys | Gly | Ala | Ala | Val | Ile |
| 1700 | | | | | 1705 | | | 1710 | | |
| Arg | Ser | Arg | Glu | Pro | Val | Thr | Leu | Gly | Ala | Trp | Thr | Arg | Val | Ser |
| 1715 | | | | | 1720 | | | 1725 | | |
| Leu | Glu | Arg | Asn | Gly | Arg | Lys | Gly | Ala | Leu | Arg | Val | Gly | Asp | Gly |
| 1730 | | | | | 1735 | | | 1740 | | |
| Pro | Arg | Val | Leu | Gly | Glu | Ser | Pro | Lys | Ser | Arg | Lys | Val | Pro | His |
| 1745 | | | | | 1750 | | | 1755 | | |
| Thr | Val | Leu | Asn | Leu | Lys | Glu | Pro | Leu | Tyr | Val | Gly | Gly | Ala | Pro |
| 1760 | | | | | 1765 | | | 1770 | | |
| Asp | Phe | Ser | Lys | Leu | Ala | Arg | Ala | Ala | Ala | Val | Ser | Ser | Gly | Phe |
| 1775 | | | | | 1780 | | | 1785 | | |
| Asp | Gly | Ala | Ile | Gln | Leu | Val | Ser | Leu | Gly | Gly | Arg | Gln | Leu | Leu |
| 1790 | | | | | 1795 | | | 1800 | | |
| Thr | Pro | Glu | His | Val | Leu | Arg | Gln | Val | Asp | Val | Thr | Ser | Phe | Ala |
| 1805 | | | | | 1810 | | | 1815 | | |
| Gly | His | Pro | Cys | Thr | Arg | Ala | Ser | Gly | His | Pro | Cys | Leu | Asn | Gly |
| 1820 | | | | | 1825 | | | 1830 | | |
| Ala | Ser | Cys | Val | Pro | Arg | Glu | Ala | Ala | Tyr | Val | Cys | Leu | Cys | Pro |
| 1835 | | | | | 1840 | | | 1845 | | |
| Gly | Gly | Phe | Ser | Gly | Pro | His | Cys | Glu | Lys | Gly | Leu | Val | Glu | Lys |
| 1850 | | | | | 1855 | | | 1860 | | |
| Ser | Ala | Gly | Asp | Val | Asp | Thr | Leu | Ala | Phe | Asp | Gly | Arg | Thr | Phe |
| 1865 | | | | | 1870 | | | 1875 | | |
| Val | Glu | Tyr | Leu | Asn | Ala | Val | Thr | Glu | Ser | Glu | Leu | Ala | Asn | Glu |
| 1880 | | | | | 1885 | | | 1890 | | |
| Ile | Pro | Val | Pro | Glu | Thr | Leu | Asp | Ser | Gly | Ala | Leu | His | Ser | Glu |
| 1895 | | | | | 1900 | | | 1905 | | |

Lys Ala Leu Gln Ser Asn His Phe Glu Leu Ser Leu Arg Thr Glu
    1910                1915                1920

Ala Thr Gln Gly Leu Val Leu Trp Ser Gly Lys Ala Thr Glu Arg
    1925                1930                1935

Ala Asp Tyr Val Ala Leu Ala Ile Val Asp Gly His Leu Gln Leu
    1940                1945                1950

Ser Tyr Asn Leu Gly Ser Gln Pro Val Val Leu Arg Ser Thr Val
    1955                1960                1965

Pro Val Asn Thr Asn Arg Trp Leu Arg Val Val Ala His Arg Glu
    1970                1975                1980

Gln Arg Glu Gly Ser Leu Gln Val Gly Asn Glu Ala Pro Val Thr
    1985                1990                1995

Gly Ser Ser Pro Leu Gly Ala Thr Gln Leu Asp Thr Asp Gly Ala
    2000                2005                2010

Leu Trp Leu Gly Gly Leu Pro Glu Leu Pro Val Gly Pro Ala Leu
    2015                2020                2025

Pro Lys Ala Tyr Gly Thr Gly Phe Val Gly Cys Leu Arg Asp Val
    2030                2035                2040

Val Val Gly Arg His Pro Leu His Leu Leu Glu Asp Ala Val Thr
    2045                2050                2055

Lys Pro Glu Leu Arg Pro Cys Pro Thr Pro
    2060                2065

<210> SEQ ID NO 4
<211> LENGTH: 1172
<212> TYPE: PRT
<213> ORGANISM: Homo sapiens

<400> SEQUENCE: 4

Met Val Trp Arg Leu Val Leu Leu Ala Leu Trp Val Trp Pro Ser Thr
1               5                   10                  15

Gln Ala Gly His Gln Asp Lys Asp Thr Thr Phe Asp Leu Phe Ser Ile
            20                  25                  30

Ser Asn Ile Asn Arg Lys Thr Ile Gly Ala Lys Gln Phe Arg Gly Pro
        35                  40                  45

Asp Pro Gly Val Pro Ala Tyr Arg Phe Val Arg Phe Asp Tyr Ile Pro
    50                  55                  60

Pro Val Asn Ala Asp Asp Leu Ser Lys Ile Thr Lys Ile Met Arg Gln
65                  70                  75                  80

Lys Glu Gly Phe Phe Leu Thr Ala Gln Leu Lys Gln Asp Gly Lys Ser
                85                  90                  95

Arg Gly Thr Leu Leu Ala Leu Glu Gly Pro Gly Leu Ser Gln Arg Gln
            100                 105                 110

Phe Glu Ile Val Ser Asn Gly Pro Ala Asp Thr Leu Asp Leu Thr Tyr
        115                 120                 125

Trp Ile Asp Gly Thr Arg His Val Val Ser Leu Glu Asp Val Gly Leu
    130                 135                 140

Ala Asp Ser Gln Trp Lys Asn Val Thr Val Gln Val Ala Gly Glu Thr
145                 150                 155                 160

Tyr Ser Leu His Val Gly Cys Asp Leu Ile Asp Ser Phe Ala Leu Asp
                165                 170                 175

Glu Pro Phe Tyr Glu His Leu Gln Ala Glu Lys Ser Arg Met Tyr Val
            180                 185                 190

Ala Lys Gly Ser Ala Arg Glu Ser His Phe Arg Gly Leu Leu Gln Asn

```
            195                 200                 205
Val His Leu Val Phe Glu Asn Ser Val Glu Asp Ile Leu Ser Lys Lys
210                 215                 220

Gly Cys Gln Gln Gly Gln Gly Ala Glu Ile Asn Ala Ile Ser Glu Asn
225                 230                 235                 240

Thr Glu Thr Leu Arg Leu Gly Pro His Val Thr Thr Glu Tyr Val Gly
                    245                 250                 255

Pro Ser Ser Glu Arg Arg Pro Glu Val Cys Glu Arg Ser Cys Glu Glu
                260                 265                 270

Leu Gly Asn Met Val Gln Glu Leu Ser Gly Leu His Val Leu Val Asn
            275                 280                 285

Gln Leu Ser Glu Asn Leu Lys Arg Val Ser Asn Asp Asn Gln Phe Leu
290                 295                 300

Trp Glu Leu Ile Gly Gly Pro Pro Lys Thr Arg Asn Met Ser Ala Cys
305                 310                 315                 320

Trp Gln Asp Gly Arg Phe Phe Ala Glu Asn Glu Thr Trp Val Val Asp
                    325                 330                 335

Ser Cys Thr Thr Cys Thr Cys Lys Lys Phe Lys Thr Ile Cys His Gln
                340                 345                 350

Ile Thr Cys Pro Pro Ala Thr Cys Ala Ser Pro Ser Phe Val Glu Gly
            355                 360                 365

Glu Cys Cys Pro Ser Cys Leu His Ser Val Asp Gly Glu Gly Trp
370                 375                 380

Ser Pro Trp Ala Glu Trp Thr Gln Cys Ser Val Thr Cys Gly Ser Gly
385                 390                 395                 400

Thr Gln Gln Arg Gly Arg Ser Cys Asp Val Thr Ser Asn Thr Cys Leu
                    405                 410                 415

Gly Pro Ser Ile Gln Thr Arg Ala Cys Ser Leu Ser Lys Cys Asp Thr
                420                 425                 430

Arg Ile Arg Gln Asp Gly Gly Trp Ser His Trp Ser Pro Trp Ser Ser
                435                 440                 445

Cys Ser Val Thr Cys Gly Val Gly Asn Ile Thr Arg Ile Arg Leu Cys
450                 455                 460

Asn Ser Pro Val Pro Gln Met Gly Gly Lys Asn Cys Lys Gly Ser Gly
465                 470                 475                 480

Arg Glu Thr Lys Ala Cys Gln Gly Ala Pro Cys Pro Ile Asp Gly Arg
                485                 490                 495

Trp Ser Pro Trp Ser Pro Trp Ser Ala Cys Thr Val Thr Cys Ala Gly
                500                 505                 510

Gly Ile Arg Glu Arg Thr Arg Val Cys Asn Ser Pro Glu Pro Gln Tyr
            515                 520                 525

Gly Gly Lys Ala Cys Val Gly Asp Val Gln Glu Arg Gln Met Cys Asn
            530                 535                 540

Lys Arg Ser Cys Pro Val Asp Gly Cys Leu Ser Asn Pro Cys Phe Pro
545                 550                 555                 560

Gly Ala Gln Cys Ser Ser Phe Pro Asp Gly Ser Trp Ser Cys Gly Ser
                565                 570                 575

Cys Pro Val Gly Phe Leu Gly Asn Gly Thr His Cys Glu Asp Leu Asp
                580                 585                 590

Glu Cys Ala Leu Val Pro Asp Ile Cys Phe Ser Thr Ser Lys Val Pro
            595                 600                 605

Arg Cys Val Asn Thr Gln Pro Gly Phe His Cys Leu Pro Cys Pro Pro
610                 615                 620
```

```
Arg Tyr Arg Gly Asn Gln Pro Val Gly Val Gly Leu Glu Ala Ala Lys
625                 630                 635                 640

Thr Glu Lys Gln Val Cys Glu Pro Glu Asn Pro Cys Lys Asp Lys Thr
            645                 650                 655

His Asn Cys His Lys His Ala Glu Cys Ile Tyr Leu Gly His Phe Ser
        660                 665                 670

Asp Pro Met Tyr Lys Cys Glu Cys Gln Thr Gly Tyr Ala Gly Asp Gly
            675                 680                 685

Leu Ile Cys Gly Glu Asp Ser Asp Leu Asp Gly Trp Pro Asn Leu Asn
        690                 695                 700

Leu Val Cys Ala Thr Asn Ala Thr Tyr His Cys Ile Lys Asp Asn Cys
705                 710                 715                 720

Pro His Leu Pro Asn Ser Gly Gln Glu Asp Phe Asp Lys Asp Gly Ile
                725                 730                 735

Gly Asp Ala Cys Asp Asp Asp Asp Asn Asp Gly Val Thr Asp Glu
                740                 745                 750

Lys Asp Asn Cys Gln Leu Leu Phe Asn Pro Arg Gln Ala Asp Tyr Asp
            755                 760                 765

Lys Asp Glu Val Gly Asp Arg Cys Asp Asn Cys Pro Tyr Val His Asn
770                 775                 780

Pro Ala Gln Ile Asp Thr Asp Asn Asn Gly Glu Gly Asp Ala Cys Ser
785                 790                 795                 800

Val Asp Ile Asp Gly Asp Asp Val Phe Asn Glu Arg Asp Asn Cys Pro
                805                 810                 815

Tyr Val Tyr Asn Thr Asp Gln Arg Asp Thr Gly Asp Gly Val Gly
                820                 825                 830

Asp His Cys Asp Asn Cys Pro Leu Val His Asn Pro Asp Gln Thr Asp
        835                 840                 845

Val Asp Asn Asp Leu Val Gly Asp Gln Cys Asp Asn Asn Glu Asp Ile
850                 855                 860

Asp Asp Asp Gly His Gln Asn Asn Gln Asp Asn Cys Pro Tyr Ile Ser
865                 870                 875                 880

Asn Ala Asn Gln Ala Asp His Asp Arg Asp Gly Gln Gly Asp Ala Cys
                885                 890                 895

Asp Pro Asp Asp Asp Asn Asp Gly Val Pro Asp Asp Arg Asp Asn Cys
                900                 905                 910

Arg Leu Val Phe Asn Pro Asp Gln Glu Asp Leu Asp Gly Asp Gly Arg
            915                 920                 925

Gly Asp Ile Cys Lys Asp Asp Phe Asp Asn Asp Ile Pro Asp Ile
        930                 935                 940

Asp Asp Val Cys Pro Glu Asn Asn Ala Ile Ser Glu Thr Asp Phe Arg
945                 950                 955                 960

Asn Phe Gln Met Val Pro Leu Asp Pro Lys Gly Thr Thr Gln Ile Asp
                965                 970                 975

Pro Asn Trp Val Ile Arg His Gln Gly Lys Glu Leu Val Gln Thr Ala
            980                 985                 990

Asn Ser Asp Pro Gly Ile Ala Val  Gly Phe Asp Glu Phe  Gly Ser Val
            995                 1000                1005

Asp Phe  Ser Gly Thr Phe  Tyr  Val Asn Thr Asp Arg  Asp Asp Asp
    1010                1015                1020

Tyr Ala  Gly Phe Val Phe  Gly  Tyr Gln Ser Ser  Ser Arg Phe Tyr
    1025                1030                1035
```

```
Val Val Met Trp Lys Gln Val Thr Gln Thr Tyr Trp Glu Asp Gln
    1040                1045                1050

Pro Thr Arg Ala Tyr Gly Tyr Ser Gly Val Ser Leu Lys Val Val
    1055                1060                1065

Asn Ser Thr Thr Gly Thr Gly Glu His Leu Arg Asn Ala Leu Trp
    1070                1075                1080

His Thr Gly Asn Thr Pro Gly Gln Val Arg Thr Leu Trp His Asp
    1085                1090                1095

Pro Arg Asn Ile Gly Trp Lys Asp Tyr Thr Ala Tyr Arg Trp His
    1100                1105                1110

Leu Thr His Arg Pro Lys Thr Gly Tyr Ile Arg Val Leu Val His
    1115                1120                1125

Glu Gly Lys Gln Val Met Ala Asp Ser Gly Pro Ile Tyr Asp Gln
    1130                1135                1140

Thr Tyr Ala Gly Gly Arg Leu Gly Leu Phe Val Phe Ser Gln Glu
    1145                1150                1155

Met Val Tyr Phe Ser Asp Leu Lys Tyr Glu Cys Arg Asp Ile
    1160                1165                1170

<210> SEQ ID NO 5
<211> LENGTH: 344
<212> TYPE: PRT
<213> ORGANISM: Homo sapiens

<400> SEQUENCE: 5

Met Val Arg Ala Arg His Gln Pro Gly Gly Leu Cys Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
                35                  40                  45

Glu Leu Ser Lys Glu Glu Cys Cys Ser Thr Gly Arg Leu Ser Thr Ser
        50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
                115                 120                 125

Gly Pro Val Cys Gly Leu Asp Gly Lys Thr Tyr Arg Asn Glu Cys Ala
        130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
                180                 185                 190

Asn Arg Ile Cys Pro Glu Pro Ala Ser Ser Glu Gln Tyr Leu Cys Gly
                195                 200                 205

Asn Asp Gly Val Thr Tyr Ser Ser Ala Cys His Leu Arg Lys Ala Thr
        210                 215                 220

Cys Leu Leu Gly Arg Ser Ile Gly Leu Ala Tyr Glu Gly Lys Cys Ile
225                 230                 235                 240
```

-continued

Lys Ala Lys Ser Cys Glu Asp Ile Gln Cys Thr Gly Lys Lys Cys
            245                 250                 255

Leu Trp Asp Phe Lys Val Gly Arg Gly Arg Cys Ser Leu Cys Asp Glu
        260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp
            340

<210> SEQ ID NO 6
<211> LENGTH: 836
<212> TYPE: PRT
<213> ORGANISM: Homo sapiens

<400> SEQUENCE: 6

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe

```
                260                 265                 270
Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
        290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
        675                 680                 685
```

Leu Gln Pro Ile Ile Lys Thr Glu Gly Pro Thr Leu Thr Lys Val Lys
690                 695                 700

Ile Glu Gly Glu Pro Glu Phe Arg Leu Ile Lys Gly Glu Thr Ile
705                 710                 715                 720

Thr Glu Val Ile His Gly Glu Pro Ile Ile Lys Lys Tyr Thr Lys Ile
                    725                 730                 735

Ile Asp Gly Val Pro Val Glu Ile Thr Glu Lys Glu Thr Arg Glu Glu
                740                 745                 750

Arg Ile Ile Thr Gly Pro Glu Ile Lys Tyr Thr Arg Ile Ser Thr Gly
            755                 760                 765

Gly Gly Glu Thr Glu Thr Leu Lys Lys Leu Leu Gln Glu Glu Val
        770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                    805                 810                 815

Leu Gln Ala Asn Lys Lys Val Gln Gly Ser Arg Arg Leu Arg Glu
                820                 825                 830

Gly Arg Ser Gln
        835

<210> SEQ ID NO 7
<211> LENGTH: 216
<212> TYPE: PRT
<213> ORGANISM: Homo sapiens

<400> SEQUENCE: 7

Met Gly Ala Ala Arg Leu Leu Pro Asn Leu Thr Leu Cys Leu Gln Leu
1               5                   10                  15

Leu Ile Leu Cys Cys Gln Thr Gln Gly Glu Asn His Pro Ser Pro Asn
                20                  25                  30

Phe Asn Gln Tyr Val Arg Asp Gln Gly Ala Met Thr Asp Gln Leu Ser
            35                  40                  45

Arg Arg Gln Ile Arg Glu Tyr Gln Leu Tyr Ser Arg Thr Ser Gly Lys
50                  55                  60

His Val Gln Val Thr Gly Arg Arg Ile Ser Ala Thr Ala Glu Asp Gly
65                  70                  75                  80

Asn Lys Phe Ala Lys Leu Ile Val Glu Thr Asp Thr Phe Gly Ser Arg
                85                  90                  95

Val Arg Ile Lys Gly Ala Glu Ser Glu Lys Tyr Ile Cys Met Asn Lys
            100                 105                 110

Arg Gly Lys Leu Ile Gly Lys Pro Ser Gly Lys Ser Lys Asp Cys Val
        115                 120                 125

Phe Thr Glu Ile Val Leu Glu Asn Asn Tyr Thr Ala Phe Gln Asn Ala
130                 135                 140

Arg His Glu Gly Trp Phe Met Ala Phe Thr Arg Gln Gly Arg Pro Arg
145                 150                 155                 160

Gln Ala Ser Arg Ser Arg Gln Asn Gln Arg Glu Ala His Phe Ile Lys
                165                 170                 175

Arg Leu Tyr Gln Gly Gln Leu Pro Phe Pro Asn His Ala Glu Lys Gln
            180                 185                 190

Lys Gln Phe Glu Phe Val Gly Ser Ala Pro Thr Arg Arg Thr Lys Arg
        195                 200                 205

Thr Arg Arg Pro Gln Pro Leu Thr

<210> SEQ ID NO 8
<211> LENGTH: 961
<212> TYPE: PRT
<213> ORGANISM: Homo sapiens

<400> SEQUENCE: 8

```
Met Leu Ala Pro Arg Gly Ala Ala Val Leu Leu Leu His Leu Val Leu
1               5                   10                  15

Gln Arg Trp Leu Ala Ala Gly Ala Gln Ala Thr Pro Gln Val Phe Asp
            20                  25                  30

Leu Leu Pro Ser Ser Gln Arg Leu Asn Pro Gly Ala Leu Leu Pro
        35                  40                  45

Val Leu Thr Asp Pro Ala Leu Asn Asp Leu Tyr Val Ile Ser Thr Phe
    50                  55                  60

Lys Leu Gln Thr Lys Ser Ser Ala Thr Ile Phe Gly Leu Tyr Ser Ser
65                  70                  75                  80

Thr Asp Asn Ser Lys Tyr Phe Glu Phe Thr Val Met Gly Arg Leu Asn
                85                  90                  95

Lys Ala Ile Leu Arg Tyr Leu Lys Asn Asp Gly Lys Val His Leu Val
            100                 105                 110

Val Phe Asn Asn Leu Gln Leu Ala Asp Gly Arg Arg His Arg Ile Leu
        115                 120                 125

Leu Arg Leu Ser Asn Leu Gln Arg Gly Ala Gly Ser Leu Glu Leu Tyr
    130                 135                 140

Leu Asp Cys Ile Gln Val Asp Ser Val His Asn Leu Pro Arg Ala Phe
145                 150                 155                 160

Ala Gly Pro Ser Gln Lys Pro Glu Thr Ile Glu Leu Arg Thr Phe Gln
                165                 170                 175

Arg Lys Pro Gln Asp Phe Leu Glu Glu Leu Lys Leu Val Val Arg Gly
            180                 185                 190

Ser Leu Phe Gln Val Ala Ser Leu Gln Asp Cys Phe Leu Gln Gln Ser
        195                 200                 205

Glu Pro Leu Ala Ala Thr Gly Thr Gly Asp Phe Asn Arg Gln Phe Leu
    210                 215                 220

Gly Gln Met Thr Gln Leu Asn Gln Leu Leu Gly Glu Val Lys Asp Leu
225                 230                 235                 240

Leu Arg Gln Gln Val Lys Glu Thr Ser Phe Leu Arg Asn Thr Ile Ala
                245                 250                 255

Glu Cys Gln Ala Cys Gly Pro Leu Lys Phe Gln Ser Pro Thr Pro Ser
            260                 265                 270

Thr Val Val Pro Pro Ala Pro Ala Pro Thr Arg Pro Pro Arg
        275                 280                 285

Arg Cys Asp Ser Asn Pro Cys Phe Arg Gly Val Gln Cys Thr Asp Ser
    290                 295                 300

Arg Asp Gly Phe Gln Cys Gly Pro Cys Pro Glu Gly Tyr Thr Gly Asn
305                 310                 315                 320

Gly Ile Thr Cys Ile Asp Val Asp Glu Cys Lys Tyr His Pro Cys Tyr
                325                 330                 335

Pro Gly Val His Cys Ile Asn Leu Ser Pro Gly Phe Arg Cys Asp Ala
            340                 345                 350

Cys Pro Val Gly Phe Thr Gly Pro Met Val Gln Gly Val Gly Ile Ser
        355                 360                 365
```

```
Phe Ala Lys Ser Asn Lys Gln Val Cys Thr Asp Ile Asp Glu Cys Arg
    370             375                 380
Asn Gly Ala Cys Val Pro Asn Ser Ile Cys Val Asn Thr Leu Gly Ser
385             390                 395                 400
Tyr Arg Cys Gly Pro Cys Lys Pro Gly Tyr Thr Gly Asp Gln Ile Arg
                405                 410                 415
Gly Cys Lys Ala Glu Arg Asn Cys Arg Asn Pro Glu Leu Asn Pro Cys
            420                 425                 430
Ser Val Asn Ala Gln Cys Ile Glu Glu Arg Gln Gly Asp Val Thr Cys
        435                 440                 445
Val Cys Gly Val Gly Trp Ala Gly Asp Gly Tyr Ile Cys Gly Lys Asp
    450                 455                 460
Val Asp Ile Asp Ser Tyr Pro Asp Glu Glu Leu Pro Cys Ser Ala Arg
465             470                 475                 480
Asn Cys Lys Lys Asp Asn Cys Lys Tyr Val Pro Asn Ser Gly Gln Glu
                485                 490                 495
Asp Ala Asp Arg Asp Gly Ile Gly Asp Ala Cys Asp Glu Asp Ala Asp
            500                 505                 510
Gly Asp Gly Ile Leu Asn Glu Gln Asp Asn Cys Val Leu Ile His Asn
        515                 520                 525
Val Asp Gln Arg Asn Ser Asp Lys Asp Ile Phe Gly Asp Ala Cys Asp
    530                 535                 540
Asn Cys Leu Ser Val Leu Asn Asn Asp Gln Lys Asp Thr Asp Gly Asp
545             550                 555                 560
Gly Arg Gly Asp Ala Cys Asp Asp Met Asp Gly Asp Gly Ile Lys
                565                 570                 575
Asn Ile Leu Asp Asn Cys Pro Lys Phe Pro Asn Arg Asp Gln Arg Asp
            580                 585                 590
Lys Asp Gly Asp Gly Val Gly Asp Ala Cys Asp Ser Cys Pro Asp Val
        595                 600                 605
Ser Asn Pro Asn Gln Ser Asp Val Asp Asn Asp Leu Val Gly Asp Ser
    610                 615                 620
Cys Asp Thr Asn Gln Asp Ser Asp Gly Asp Gly His Gln Asp Ser Thr
625             630                 635                 640
Asp Asn Cys Pro Thr Val Ile Asn Ser Ala Gln Leu Asp Thr Asp Lys
                645                 650                 655
Asp Gly Ile Gly Asp Glu Cys Asp Asp Asp Asp Asn Asp Gly Ile
            660                 665                 670
Pro Asp Leu Val Pro Pro Gly Pro Asp Asn Cys Arg Leu Val Pro Asn
        675                 680                 685
Pro Ala Gln Glu Asp Ser Asn Ser Asp Gly Val Gly Asp Ile Cys Glu
    690                 695                 700
Ser Asp Phe Asp Gln Asp Gln Val Ile Asp Arg Ile Asp Val Cys Pro
705             710                 715                 720
Glu Asn Ala Glu Val Thr Leu Thr Asp Phe Arg Ala Tyr Gln Thr Val
                725                 730                 735
Val Leu Asp Pro Glu Gly Asp Ala Gln Ile Asp Pro Asn Trp Val Val
            740                 745                 750
Leu Asn Gln Gly Met Glu Ile Val Gln Thr Met Asn Ser Asp Pro Gly
        755                 760                 765
Leu Ala Val Gly Tyr Thr Ala Phe Asn Gly Val Asp Phe Glu Gly Thr
    770                 775                 780
Phe His Val Asn Thr Gln Thr Asp Asp Asp Tyr Ala Gly Phe Ile Phe
```

```
                785                 790                 795                 800
        Gly Tyr Gln Asp Ser Ser Phe Tyr Val Met Trp Lys Gln Thr
                        805                 810                 815
        Glu Gln Thr Tyr Trp Gln Ala Thr Pro Phe Arg Ala Val Ala Glu Pro
                        820                 825                 830
        Gly Ile Gln Leu Lys Ala Val Lys Ser Lys Thr Gly Pro Gly Glu His
                        835                 840                 845
        Leu Arg Asn Ser Leu Trp His Thr Gly Asp Thr Ser Asp Gln Val Arg
        850                 855                 860
        Leu Leu Trp Lys Asp Ser Arg Asn Val Gly Trp Lys Asp Lys Val Ser
        865                 870                 875                 880
        Tyr Arg Trp Phe Leu Gln His Arg Pro Gln Val Gly Tyr Ile Arg Val
                        885                 890                 895
        Arg Phe Tyr Glu Gly Ser Glu Leu Val Ala Asp Ser Gly Val Thr Ile
                        900                 905                 910
        Asp Thr Thr Met Arg Gly Gly Arg Leu Gly Val Phe Cys Phe Ser Gln
                        915                 920                 925
        Glu Asn Ile Ile Trp Ser Asn Leu Lys Tyr Arg Cys Asn Asp Thr Ile
                        930                 935                 940
        Pro Glu Asp Phe Gln Glu Phe Gln Thr Gln Asn Phe Asp Arg Phe Asp
        945                 950                 955                 960
        Asn

<210> SEQ ID NO 9
<211> LENGTH: 1170
<212> TYPE: PRT
<213> ORGANISM: Homo sapiens

<400> SEQUENCE: 9

Met Gly Leu Ala Trp Gly Leu Gly Val Leu Phe Leu Met His Val Cys
        1               5                   10                  15
        Gly Thr Asn Arg Ile Pro Glu Ser Gly Gly Asp Asn Ser Val Phe Asp
                        20                  25                  30
        Ile Phe Glu Leu Thr Gly Ala Ala Arg Lys Gly Ser Gly Arg Arg Leu
                        35                  40                  45
        Val Lys Gly Pro Asp Pro Ser Ser Pro Ala Phe Arg Ile Glu Asp Ala
        50                  55                  60
        Asn Leu Ile Pro Pro Val Pro Asp Asp Lys Phe Gln Asp Leu Val Asp
        65                  70                  75                  80
        Ala Val Arg Ala Glu Lys Gly Phe Leu Leu Leu Ala Ser Leu Arg Gln
                        85                  90                  95
        Met Lys Lys Thr Arg Gly Thr Leu Leu Ala Leu Glu Arg Lys Asp His
                        100                 105                 110
        Ser Gly Gln Val Phe Ser Val Val Ser Asn Gly Lys Ala Gly Thr Leu
                        115                 120                 125
        Asp Leu Ser Leu Thr Val Gln Gly Lys Gln His Val Val Ser Val Glu
                        130                 135                 140
        Glu Ala Leu Leu Ala Thr Gly Gln Trp Lys Ser Ile Thr Leu Phe Val
        145                 150                 155                 160
        Gln Glu Asp Arg Ala Gln Leu Tyr Ile Asp Cys Glu Lys Met Glu Asn
                        165                 170                 175
        Ala Glu Leu Asp Val Pro Ile Gln Ser Val Phe Thr Arg Asp Leu Ala
                        180                 185                 190
        Ser Ile Ala Arg Leu Arg Ile Ala Lys Gly Gly Val Asn Asp Asn Phe
```

```
            195                 200                 205
Gln Gly Val Leu Gln Asn Val Arg Phe Val Phe Gly Thr Thr Pro Glu
        210                 215                 220

Asp Ile Leu Arg Asn Lys Gly Cys Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
                260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
        290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
                340                 345                 350

Cys Pro Ile Met Pro Cys Ser Asn Ala Thr Val Pro Asp Gly Glu Cys
                355                 360                 365

Cys Pro Arg Cys Trp Pro Ser Asp Ser Ala Asp Asp Gly Trp Ser Pro
        370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
                420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
                500                 505                 510

Gln Lys Arg Ser Arg Leu Cys Asn Asn Pro Thr Pro Gln Phe Gly Gly
        515                 520                 525

Lys Asp Cys Val Gly Asp Val Thr Glu Asn Gln Ile Cys Asn Lys Gln
        530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
                580                 585                 590

Lys Glu Val Pro Asp Ala Cys Phe Asn His Asn Gly Glu His Arg Cys
                595                 600                 605

Glu Asn Thr Asp Pro Gly Tyr Asn Cys Leu Pro Cys Pro Pro Arg Phe
        610                 615                 620
```

-continued

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
            645                 650                 655

Cys Asn Lys Asn Ala Lys Cys Asn Tyr Leu Gly His Tyr Ser Asp Pro
        660                 665                 670

Met Tyr Arg Cys Glu Cys Lys Pro Gly Tyr Ala Gly Asn Gly Ile Ile
            675                 680                 685

Cys Gly Glu Asp Thr Asp Leu Asp Gly Trp Pro Asn Glu Asn Leu Val
        690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
            725                 730                 735

Ala Cys Asp Asp Asp Asp Asp Asn Asp Lys Ile Pro Asp Asp Arg Asp
        740                 745                 750

Asn Cys Pro Phe His Tyr Asn Pro Ala Gln Tyr Asp Tyr Asp Arg Asp
            755                 760                 765

Asp Val Gly Asp Arg Cys Asp Asn Cys Pro Tyr Asn His Asn Pro Asp
770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
            805                 810                 815

Tyr Asn Val Asp Gln Arg Asp Thr Asp Met Asp Gly Val Gly Asp Gln
            820                 825                 830

Cys Asp Asn Cys Pro Leu Glu His Asn Pro Asp Gln Leu Asp Ser Asp
            835                 840                 845

Ser Asp Arg Ile Gly Asp Thr Cys Asp Asn Asn Gln Asp Ile Asp Glu
850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
            885                 890                 895

Asp Asp Asp Asn Asp Gly Ile Pro Asp Asp Lys Asp Asn Cys Arg Leu
            900                 905                 910

Val Pro Asn Pro Asp Gln Lys Asp Ser Asp Gly Asp Gly Arg Gly Asp
            915                 920                 925

Ala Cys Lys Asp Asp Phe Asp His Asp Ser Val Pro Asp Ile Asp Asp
            930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
            965                 970                 975

Trp Val Val Arg His Gln Gly Lys Glu Leu Val Gln Thr Val Asn Cys
            980                 985                 990

Asp Pro Gly Leu Ala Val Gly Tyr Asp Glu Phe Asn Ala Val Asp Phe
            995                 1000                1005

Ser Gly Thr Phe Phe Ile Asn Thr Glu Arg Asp Asp Asp Tyr Ala
        1010                1015                1020

Gly Phe Val Phe Gly Tyr Gln Ser Ser Ser Arg Phe Tyr Val Val
        1025                1030                1035

```
Met Trp Lys Gln Val Thr Gln Ser Tyr Trp Asp Thr Asn Pro Thr
    1040                1045                1050

Arg Ala Gln Gly Tyr Ser Gly Leu Ser Val Lys Val Val Asn Ser
    1055                1060                1065

Thr Thr Gly Pro Gly Glu His Leu Arg Asn Ala Leu Trp His Thr
    1070                1075                1080

Gly Asn Thr Pro Gly Gln Val Arg Thr Leu Trp His Asp Pro Arg
    1085                1090                1095

His Ile Gly Trp Lys Asp Phe Thr Ala Tyr Arg Trp Arg Leu Ser
    1100                1105                1110

His Arg Pro Lys Thr Gly Phe Ile Arg Val Val Met Tyr Glu Gly
    1115                1120                1125

Lys Lys Ile Met Ala Asp Ser Gly Pro Ile Tyr Asp Lys Thr Tyr
    1130                1135                1140

Ala Gly Gly Arg Leu Gly Leu Phe Val Phe Ser Gln Glu Met Val
    1145                1150                1155

Phe Phe Ser Asp Leu Lys Tyr Glu Cys Arg Asp Pro
    1160                1165                1170

<210> SEQ ID NO 10
<211> LENGTH: 162
<212> TYPE: PRT
<213> ORGANISM: Homo sapiens

<400> SEQUENCE: 10

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 11
<211> LENGTH: 180
<212> TYPE: PRT
<213> ORGANISM: Homo sapiens

<400> SEQUENCE: 11

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
```

```
            20                  25                  30
Cys Gly Gly Glu Leu Val Asp Thr Leu Gln Phe Val Cys Gly Asp Arg
        35                  40                  45
Gly Phe Tyr Phe Ser Arg Pro Ala Ser Arg Val Ser Arg Arg Ser Arg
 50                  55                  60
Gly Ile Val Glu Glu Cys Cys Phe Arg Ser Cys Asp Leu Ala Leu Leu
 65                  70                  75                  80
Glu Thr Tyr Cys Ala Thr Pro Ala Lys Ser Glu Arg Asp Val Ser Thr
                 85                  90                  95
Pro Pro Thr Val Leu Pro Asp Asn Phe Pro Arg Tyr Pro Val Gly Lys
            100                 105                 110
Phe Phe Gln Tyr Asp Thr Trp Lys Gln Ser Thr Gln Arg Leu Arg Arg
            115                 120                 125
Gly Leu Pro Ala Leu Leu Arg Ala Arg Arg Gly His Val Leu Ala Lys
            130                 135                 140
Glu Leu Glu Ala Phe Arg Glu Ala Lys Arg His Arg Pro Leu Ile Ala
145                 150                 155                 160
Leu Pro Thr Gln Asp Pro Ala His Gly Gly Ala Pro Pro Glu Met Ala
                165                 170                 175
Ser Asn Arg Lys
            180

<210> SEQ ID NO 12
<211> LENGTH: 288
<212> TYPE: PRT
<213> ORGANISM: Homo sapiens

<400> SEQUENCE: 12

Met Val Gly Val Gly Gly Gly Asp Val Glu Asp Val Thr Pro Arg Pro
 1               5                  10                  15
Gly Gly Cys Gln Ile Ser Gly Arg Gly Ala Arg Gly Cys Asn Gly Ile
             20                  25                  30
Pro Gly Ala Ala Ala Trp Glu Ala Ala Leu Pro Arg Arg Arg Pro Arg
         35                  40                  45
Arg His Pro Ser Val Asn Pro Arg Ser Arg Ala Ala Gly Ser Pro Arg
 50                  55                  60
Thr Arg Gly Arg Arg Thr Glu Glu Arg Pro Ser Gly Ser Arg Leu Gly
 65                  70                  75                  80
Asp Arg Gly Arg Gly Arg Ala Leu Pro Gly Gly Arg Leu Gly Gly Arg
                 85                  90                  95
Gly Arg Gly Arg Ala Pro Glu Arg Val Gly Gly Arg Gly Arg Gly Arg
            100                 105                 110
Gly Thr Ala Ala Pro Arg Ala Ala Pro Ala Ala Arg Gly Ser Arg Pro
            115                 120                 125
Gly Pro Ala Gly Thr Met Ala Ala Gly Ser Ile Thr Thr Leu Pro Ala
            130                 135                 140
Leu Pro Glu Asp Gly Gly Ser Gly Ala Phe Pro Pro Gly His Phe Lys
145                 150                 155                 160
Asp Pro Lys Arg Leu Tyr Cys Lys Asn Gly Gly Phe Phe Leu Arg Ile
                165                 170                 175
His Pro Asp Gly Arg Val Asp Gly Val Arg Glu Lys Ser Asp Pro His
                180                 185                 190
Ile Lys Leu Gln Leu Gln Ala Glu Glu Arg Gly Val Val Ser Ile Lys
            195                 200                 205
```

```
Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
                260                 265                 270

Gly Pro Gly Gln Lys Ala Ile Leu Phe Leu Pro Met Ser Ala Lys Ser
                275                 280                 285
```

<210> SEQ ID NO 13
<211> LENGTH: 216
<212> TYPE: PRT
<213> ORGANISM: Homo sapiens

<400> SEQUENCE: 13

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
                35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Glu Ile Arg Pro
                115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
    195                 200                 205

Val Arg Ser Pro Ser Phe Glu Lys
            210                 215
```

<210> SEQ ID NO 14
<211> LENGTH: 147
<212> TYPE: PRT
<213> ORGANISM: Homo sapiens

<400> SEQUENCE: 14

```
Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
                20                  25                  30
```

```
Phe Leu Thr Gln His Tyr Asp Ala Lys Pro Gln Gly Arg Asp Asp Arg
         35                  40                  45

Tyr Cys Glu Ser Ile Met Arg Arg Gly Leu Thr Ser Pro Cys Lys
 50                  55                  60

Asp Ile Asn Thr Phe Ile His Gly Asn Lys Arg Ser Ile Lys Ala Ile
 65                  70                  75                  80

Cys Glu Asn Lys Asn Gly Asn Pro His Arg Glu Asn Leu Arg Ile Ser
                 85                  90                  95

Lys Ser Ser Phe Gln Val Thr Thr Cys Lys Leu His Gly Gly Ser Pro
                100                 105                 110

Trp Pro Pro Cys Gln Tyr Arg Ala Thr Ala Gly Phe Arg Asn Val Val
                115                 120                 125

Val Ala Cys Glu Asn Gly Leu Pro Val His Leu Asp Gln Ser Ile Phe
130                 135                 140

Arg Arg Pro
145

<210> SEQ ID NO 15
<211> LENGTH: 178
<212> TYPE: PRT
<213> ORGANISM: Homo sapiens

<400> SEQUENCE: 15

Met Asp Arg Ala Ala Arg Cys Ser Gly Ala Ser Ser Leu Pro Leu Leu
1               5                   10                  15

Leu Ala Leu Ala Leu Gly Leu Val Ile Leu His Cys Val Val Ala Asp
                20                  25                  30

Gly Asn Ser Thr Arg Ser Pro Glu Thr Asn Gly Leu Leu Cys Gly Asp
                35                  40                  45

Pro Glu Glu Asn Cys Ala Ala Thr Thr Thr Gln Ser Lys Arg Lys Gly
 50                  55                  60

His Phe Ser Arg Cys Pro Lys Gln Tyr Lys His Tyr Cys Ile Lys Gly
 65                  70                  75                  80

Arg Cys Arg Phe Val Val Ala Glu Gln Thr Pro Ser Cys Val Cys Asp
                 85                  90                  95

Glu Gly Tyr Ile Gly Ala Arg Cys Glu Arg Val Asp Leu Phe Tyr Leu
                100                 105                 110

Arg Gly Asp Arg Gly Gln Ile Leu Val Ile Cys Leu Ile Ala Val Met
                115                 120                 125

Val Val Phe Ile Ile Leu Val Ile Gly Val Cys Thr Cys Cys His Pro
130                 135                 140

Leu Arg Lys Arg Arg Lys Arg Lys Lys Glu Glu Glu Met Glu Thr
145                 150                 155                 160

Leu Gly Lys Asp Ile Thr Pro Ile Asn Glu Asp Ile Glu Glu Thr Asn
                165                 170                 175

Ile Ala

<210> SEQ ID NO 16
<211> LENGTH: 380
<212> TYPE: PRT
<213> ORGANISM: Homo sapiens

<400> SEQUENCE: 16

Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
```

```
            20                  25                  30
Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
     50                  55                  60

Cys Thr Val Glu Tyr Glu Leu Lys Tyr Arg Asn Ile Gly Ser Glu Thr
 65                  70                  75                  80

Trp Lys Thr Ile Ile Thr Lys Asn Leu His Tyr Lys Asp Gly Phe Asp
                 85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
            130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                 165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                 245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                 325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr
    370                 375                 380

<210> SEQ ID NO 17
<211> LENGTH: 551
<212> TYPE: PRT
<213> ORGANISM: Homo sapiens

<400> SEQUENCE: 17

Met Leu Pro Leu Leu Leu Leu Pro Leu Leu Trp Gly Gly Ser Leu Gln
 1               5                  10                  15
```

Glu Lys Pro Val Tyr Glu Leu Gln Val Gln Lys Ser Val Thr Val Gln
                    20                  25                  30

Glu Gly Leu Cys Val Leu Val Pro Cys Ser Phe Ser Tyr Pro Trp Arg
            35                  40                  45

Ser Trp Tyr Ser Ser Pro Pro Leu Tyr Val Tyr Trp Phe Arg Asp Gly
        50                  55                  60

Glu Ile Pro Tyr Tyr Ala Glu Val Val Ala Thr Asn Asn Pro Asp Arg
65                  70                  75                  80

Arg Val Lys Pro Glu Thr Gln Gly Arg Phe Arg Leu Leu Gly Asp Val
                85                  90                  95

Gln Lys Lys Asn Cys Ser Leu Ser Ile Gly Asp Ala Arg Met Glu Asp
                100                 105                 110

Thr Gly Ser Tyr Phe Phe Arg Val Glu Arg Gly Arg Asp Val Lys Tyr
            115                 120                 125

Ser Tyr Gln Gln Asn Lys Leu Asn Leu Glu Val Thr Ala Leu Ile Glu
        130                 135                 140

Lys Pro Asp Ile His Phe Leu Glu Pro Leu Glu Ser Gly Arg Pro Thr
145                 150                 155                 160

Arg Leu Ser Cys Ser Leu Pro Gly Ser Cys Glu Ala Gly Pro Pro Leu
                165                 170                 175

Thr Phe Ser Trp Thr Gly Asn Ala Leu Ser Pro Leu Asp Pro Glu Thr
            180                 185                 190

Thr Arg Ser Ser Glu Leu Thr Leu Thr Pro Arg Pro Glu Asp His Gly
        195                 200                 205

Thr Asn Leu Thr Cys Gln Met Lys Arg Gln Gly Ala Gln Val Thr Thr
210                 215                 220

Glu Arg Thr Val Gln Leu Asn Val Ser Tyr Ala Pro Gln Thr Ile Thr
225                 230                 235                 240

Ile Phe Arg Asn Gly Ile Ala Leu Glu Ile Leu Gln Asn Thr Ser Tyr
                245                 250                 255

Leu Pro Val Leu Glu Gly Gln Ala Leu Arg Leu Leu Cys Asp Ala Pro
                260                 265                 270

Ser Asn Pro Pro Ala His Leu Ser Trp Phe Gln Gly Ser Pro Ala Leu
            275                 280                 285

Asn Ala Thr Pro Ile Ser Asn Thr Gly Ile Leu Glu Leu Arg Arg Val
        290                 295                 300

Arg Ser Ala Glu Glu Gly Phe Thr Cys Arg Ala Gln His Pro Leu
305                 310                 315                 320

Gly Phe Leu Gln Ile Phe Leu Asn Leu Ser Val Tyr Ser Leu Pro Gln
                325                 330                 335

Leu Leu Gly Pro Ser Cys Ser Trp Glu Ala Glu Gly Leu His Cys Arg
                340                 345                 350

Cys Ser Phe Arg Ala Arg Pro Ala Pro Ser Leu Cys Trp Arg Leu Glu
            355                 360                 365

Glu Lys Pro Leu Glu Gly Asn Ser Ser Gln Gly Ser Phe Lys Val Asn
        370                 375                 380

Ser Ser Ser Ala Gly Pro Trp Ala Asn Ser Ser Leu Ile Leu His Gly
385                 390                 395                 400

Gly Leu Ser Ser Asp Leu Lys Val Ser Cys Lys Ala Trp Asn Ile Tyr
                405                 410                 415

Gly Ser Gln Ser Gly Ser Val Leu Leu Leu Gln Gly Arg Ser Asn Leu
                420                 425                 430

Gly Thr Gly Val Val Pro Ala Ala Leu Gly Gly Ala Gly Val Met Ala

```
                  435                 440                 445
Leu Leu Cys Ile Cys Leu Cys Leu Ile Phe Phe Leu Ile Val Lys Ala
    450                 455                 460
Arg Arg Lys Gln Ala Ala Gly Arg Pro Glu Lys Met Asp Asp Glu Asp
465                 470                 475                 480
Pro Ile Met Gly Thr Ile Thr Ser Gly Ser Arg Lys Lys Pro Trp Pro
                485                 490                 495
Asp Ser Pro Gly Asp Gln Ala Ser Pro Pro Gly Asp Ala Pro Pro Leu
                500                 505                 510
Glu Glu Gln Lys Glu Leu His Tyr Ala Ser Leu Ser Phe Ser Glu Met
                515                 520                 525
Lys Ser Arg Glu Pro Lys Asp Gln Glu Ala Pro Ser Thr Thr Glu Tyr
                530                 535                 540
Ser Glu Ile Lys Thr Ser Lys
545                 550

<210> SEQ ID NO 18
<211> LENGTH: 380
<212> TYPE: PRT
<213> ORGANISM: Homo sapiens

<400> SEQUENCE: 18

Met Glu Glu Gly Gly Asp Phe Asp Asn Tyr Tyr Gly Ala Asp Asn Gln
1               5                   10                  15
Ser Glu Cys Glu Tyr Thr Asp Trp Lys Ser Ser Gly Ala Leu Ile Pro
                20                  25                  30
Ala Ile Tyr Met Leu Val Phe Leu Gly Thr Thr Gly Asn Gly Leu
                35                  40                  45
Val Leu Trp Thr Val Phe Arg Ser Ser Arg Glu Lys Arg Arg Ser Ala
    50                  55                  60
Asp Ile Phe Ile Ala Ser Leu Ala Val Ala Asp Leu Thr Phe Val Val
65                  70                  75                  80
Thr Leu Pro Leu Trp Ala Thr Tyr Thr Tyr Arg Asp Tyr Asp Trp Pro
                85                  90                  95
Phe Gly Thr Phe Phe Cys Lys Leu Ser Ser Tyr Leu Ile Phe Val Asn
                100                 105                 110
Met Tyr Ala Ser Val Phe Cys Leu Thr Gly Leu Ser Phe Asp Arg Tyr
                115                 120                 125
Leu Ala Ile Val Arg Pro Val Ala Asn Ala Arg Leu Arg Leu Arg Val
    130                 135                 140
Ser Gly Ala Val Ala Thr Ala Val Leu Trp Val Leu Ala Ala Leu Leu
145                 150                 155                 160
Ala Met Pro Val Met Val Leu Arg Thr Thr Gly Asp Leu Glu Asn Thr
                165                 170                 175
Thr Lys Val Gln Cys Tyr Met Asp Tyr Ser Met Val Ala Thr Val Ser
                180                 185                 190
Ser Glu Trp Ala Trp Glu Val Gly Leu Gly Val Ser Ser Thr Thr Val
                195                 200                 205
Gly Phe Val Val Pro Phe Thr Ile Met Leu Thr Cys Tyr Phe Phe Ile
    210                 215                 220
Ala Gln Thr Ile Ala Gly His Phe Arg Lys Glu Arg Ile Glu Gly Leu
225                 230                 235                 240
Arg Lys Arg Arg Arg Leu Leu Ser Ile Ile Val Val Leu Val Val Thr
                245                 250                 255
```

-continued

Phe Ala Leu Cys Trp Met Pro Tyr His Leu Val Lys Thr Leu Tyr Met
                260                 265                 270

Leu Gly Ser Leu Leu His Trp Pro Cys Asp Phe Asp Leu Phe Leu Met
            275                 280                 285

Asn Ile Phe Pro Tyr Cys Thr Cys Ile Ser Tyr Val Asn Ser Cys Leu
        290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
    370                 375                 380

<210> SEQ ID NO 19
<211> LENGTH: 325
<212> TYPE: PRT
<213> ORGANISM: Homo sapiens

<400> SEQUENCE: 19

Met Leu Pro Arg Val Gly Cys Pro Ala Leu Pro Leu Pro Pro Pro Pro
1               5                   10                  15

Leu Leu Pro Leu Leu Leu Leu Leu Gly Ala Ser Gly Gly Gly Gly Gly
            20                  25                  30

Gly Ala Arg Ala Glu Val Leu Phe Arg Cys Pro Pro Cys Thr Pro Glu
        35                  40                  45

Arg Leu Ala Ala Cys Gly Pro Pro Val Ala Pro Ala Ala Val
50                  55                  60

Ala Ala Val Ala Gly Gly Ala Arg Met Pro Cys Ala Glu Leu Val Arg
65                  70                  75                  80

Glu Pro Gly Cys Gly Cys Cys Ser Val Cys Ala Arg Leu Glu Gly Glu
                85                  90                  95

Ala Cys Gly Val Tyr Thr Pro Arg Cys Gly Gln Gly Leu Arg Cys Tyr
            100                 105                 110

Pro His Pro Gly Ser Glu Leu Pro Leu Gln Ala Leu Val Met Gly Glu
        115                 120                 125

Gly Thr Cys Glu Lys Arg Arg Asp Ala Glu Tyr Gly Ala Ser Pro Glu
130                 135                 140

Gln Val Ala Asp Asn Gly Asp Asp His Ser Glu Gly Gly Leu Val Glu
145                 150                 155                 160

Asn His Val Asp Ser Thr Met Asn Met Leu Gly Gly Gly Gly Ser Ala
                165                 170                 175

Gly Arg Lys Pro Leu Lys Ser Gly Met Lys Glu Leu Ala Val Phe Arg
            180                 185                 190

Glu Lys Val Thr Glu Gln His Arg Gln Met Gly Lys Gly Gly Lys His
        195                 200                 205

His Leu Gly Leu Glu Glu Pro Lys Lys Leu Arg Pro Pro Pro Ala Arg
    210                 215                 220

Thr Pro Cys Gln Gln Glu Leu Asp Gln Val Leu Glu Arg Ile Ser Thr
225                 230                 235                 240

Met Arg Leu Pro Asp Glu Arg Gly Pro Leu Glu His Leu Tyr Ser Leu
                245                 250                 255

His Ile Pro Asn Cys Asp Lys His Gly Leu Tyr Asn Leu Lys Gln Cys
                260                 265                 270

Lys Met Ser Leu Asn Gly Gln Arg Gly Glu Cys Trp Cys Val Asn Pro
            275                 280                 285

Asn Thr Gly Lys Leu Ile Gln Gly Ala Pro Thr Ile Arg Gly Asp Pro
        290                 295                 300

Glu Cys His Leu Phe Tyr Asn Glu Gln Glu Ala Arg Gly Val His
305                 310                 315                 320

Thr Gln Arg Met Gln
                325

<210> SEQ ID NO 20
<211> LENGTH: 450
<212> TYPE: PRT
<213> ORGANISM: Homo sapiens

<400> SEQUENCE: 20

Met Gly Gly Met Lys Tyr Ile Phe Ser Leu Leu Phe Phe Leu Leu Leu
1               5                   10                  15

Glu Gly Gly Lys Thr Glu Gln Val Lys His Ser Glu Thr Tyr Cys Met
            20                  25                  30

Phe Gln Asp Lys Lys Tyr Arg Val Gly Glu Arg Trp His Pro Tyr Leu
        35                  40                  45

Glu Pro Tyr Gly Leu Val Tyr Cys Val Asn Cys Ile Cys Ser Glu Asn
    50                  55                  60

Gly Asn Val Leu Cys Ser Arg Val Arg Cys Pro Asn Val His Cys Leu
65                  70                  75                  80

Ser Pro Val His Ile Pro His Leu Cys Cys Pro Arg Cys Pro Asp Ser
                85                  90                  95

Leu Pro Pro Val Asn Asn Lys Val Thr Ser Lys Ser Cys Glu Tyr Asn
            100                 105                 110

Gly Thr Thr Tyr Gln His Gly Glu Leu Phe Val Ala Glu Gly Leu Phe
        115                 120                 125

Gln Asn Arg Gln Pro Asn Gln Cys Thr Gln Cys Ser Cys Ser Glu Gly
    130                 135                 140

Asn Val Tyr Cys Gly Leu Lys Thr Cys Pro Lys Leu Thr Cys Ala Phe
145                 150                 155                 160

Pro Val Ser Val Pro Asp Ser Cys Cys Arg Val Cys Arg Gly Asp Gly
                165                 170                 175

Glu Leu Ser Trp Glu His Ser Asp Gly Asp Ile Phe Arg Gln Pro Ala
            180                 185                 190

Asn Arg Glu Ala Arg His Ser Tyr His Arg Ser His Tyr Asp Pro Pro
        195                 200                 205

Pro Ser Arg Gln Ala Gly Gly Leu Ser Arg Phe Pro Gly Ala Arg Ser
    210                 215                 220

His Arg Gly Ala Leu Met Asp Ser Gln Gln Ala Ser Gly Thr Ile Val
225                 230                 235                 240

Gln Ile Val Ile Asn Asn Lys His Lys His Gly Gln Val Cys Val Ser
                245                 250                 255

Asn Gly Lys Thr Tyr Ser His Gly Glu Ser Trp His Pro Asn Leu Arg
            260                 265                 270

Ala Phe Gly Ile Val Glu Cys Val Leu Cys Thr Cys Asn Val Thr Lys
        275                 280                 285

Gln Glu Cys Lys Lys Ile His Cys Pro Asn Arg Tyr Pro Cys Lys Tyr

```
                290                 295                 300

Pro Gln Lys Ile Asp Gly Lys Cys Cys Lys Val Cys Pro Lys Lys
305                 310                 315                 320

Ala Lys Glu Leu Pro Gly Gln Ser Phe Asp Asn Lys Gly Tyr Phe Cys
                325                 330                 335

Gly Glu Glu Thr Met Pro Val Tyr Glu Ser Val Phe Met Glu Asp Gly
                340                 345                 350

Glu Thr Thr Arg Lys Ile Ala Leu Glu Thr Glu Arg Pro Pro Gln Val
                355                 360                 365

Glu Val His Val Trp Thr Ile Arg Lys Gly Ile Leu Gln His Phe His
                370                 375                 380

Ile Glu Lys Ile Ser Lys Arg Met Phe Glu Glu Leu Pro His Phe Lys
385                 390                 395                 400

Leu Val Thr Arg Thr Thr Leu Ser Gln Trp Lys Ile Phe Thr Glu Gly
                405                 410                 415

Glu Ala Gln Ile Ser Gln Met Cys Ser Ser Arg Val Cys Arg Thr Glu
                420                 425                 430

Leu Glu Asp Leu Val Lys Val Leu Tyr Leu Glu Arg Ser Glu Lys Gly
                435                 440                 445

His Cys
    450

<210> SEQ ID NO 21
<211> LENGTH: 576
<212> TYPE: PRT
<213> ORGANISM: Homo sapiens

<400> SEQUENCE: 21

Met Trp Ala Pro Arg Cys Arg Arg Phe Trp Ser Arg Trp Glu Gln Val
1               5                   10                  15

Ala Ala Leu Leu Leu Leu Leu Leu Leu Gly Val Pro Pro Arg Ser
                20                  25                  30

Leu Ala Leu Pro Pro Ile Arg Tyr Ser His Ala Gly Ile Cys Pro Asn
                35                  40                  45

Asp Met Asn Pro Asn Leu Trp Val Asp Ala Gln Ser Thr Cys Arg Arg
        50                  55                  60

Glu Cys Glu Thr Asp Gln Glu Cys Glu Thr Tyr Glu Lys Cys Cys Pro
65                  70                  75                  80

Asn Val Cys Gly Thr Lys Ser Cys Val Ala Ala Arg Tyr Met Asp Val
                85                  90                  95

Lys Gly Lys Lys Gly Pro Val Gly Met Pro Lys Glu Ala Thr Cys Asp
                100                 105                 110

His Phe Met Cys Leu Gln Gln Gly Ser Glu Cys Asp Ile Trp Asp Gly
                115                 120                 125

Gln Pro Val Cys Lys Cys Lys Asp Arg Cys Glu Lys Glu Pro Ser Phe
        130                 135                 140

Thr Cys Ala Ser Asp Gly Leu Thr Tyr Tyr Asn Arg Cys Tyr Met Asp
145                 150                 155                 160

Ala Glu Ala Cys Ser Lys Gly Ile Thr Leu Ala Val Val Thr Cys Arg
                165                 170                 175

Tyr His Phe Thr Trp Pro Asn Thr Ser Pro Pro Pro Glu Thr Thr
                180                 185                 190

Met His Pro Thr Thr Ala Ser Pro Glu Thr Pro Glu Leu Asp Met Ala
                195                 200                 205
```

Ala Pro Ala Leu Leu Asn Asn Pro Val His Gln Ser Val Thr Met Gly
    210                 215                 220

Glu Thr Val Ser Phe Leu Cys Asp Val Val Gly Arg Pro Arg Pro Glu
225                 230                 235                 240

Ile Thr Trp Glu Lys Gln Leu Glu Asp Arg Glu Asn Val Val Met Arg
                245                 250                 255

Pro Asn His Val Arg Gly Asn Val Val Thr Asn Ile Ala Gln Leu
            260                 265                 270

Val Ile Tyr Asn Ala Gln Leu Gln Asp Ala Gly Ile Tyr Thr Cys Thr
            275                 280                 285

Ala Arg Asn Val Ala Gly Val Leu Arg Ala Asp Phe Pro Leu Ser Val
    290                 295                 300

Val Arg Gly His Gln Ala Ala Thr Ser Glu Ser Ser Pro Asn Gly
305                 310                 315                 320

Thr Ala Phe Pro Ala Ala Glu Cys Leu Lys Pro Pro Asp Ser Glu Asp
                325                 330                 335

Cys Gly Glu Glu Gln Thr Arg Trp His Phe Asp Ala Gln Ala Asn Asn
            340                 345                 350

Cys Leu Thr Phe Thr Phe Gly His Cys His Arg Asn Leu Asn His Phe
    355                 360                 365

Glu Thr Tyr Glu Ala Cys Met Leu Ala Cys Met Ser Gly Pro Leu Ala
370                 375                 380

Ala Cys Ser Leu Pro Ala Leu Gln Gly Pro Cys Lys Ala Tyr Ala Pro
385                 390                 395                 400

Arg Trp Ala Tyr Asn Ser Gln Thr Gly Gln Cys Gln Ser Phe Val Tyr
                405                 410                 415

Gly Gly Cys Glu Gly Asn Gly Asn Asn Phe Glu Ser Arg Glu Ala Cys
            420                 425                 430

Glu Glu Ser Cys Pro Phe Pro Arg Gly Asn Gln Arg Cys Arg Ala Cys
    435                 440                 445

Lys Pro Arg Gln Lys Leu Val Thr Ser Phe Cys Arg Ser Asp Phe Val
    450                 455                 460

Ile Leu Gly Arg Val Ser Glu Leu Thr Glu Glu Pro Asp Ser Gly Arg
465                 470                 475                 480

Ala Leu Val Thr Val Asp Glu Val Leu Lys Asp Glu Lys Met Gly Leu
                485                 490                 495

Lys Phe Leu Gly Gln Glu Pro Leu Glu Val Thr Leu Leu His Val Asp
            500                 505                 510

Trp Ala Cys Pro Cys Pro Asn Val Thr Val Ser Glu Met Pro Leu Ile
    515                 520                 525

Ile Met Gly Glu Val Asp Gly Gly Met Ala Met Leu Arg Pro Asp Ser
530                 535                 540

Phe Val Gly Ala Ser Ser Ala Arg Arg Val Arg Lys Leu Arg Glu Val
545                 550                 555                 560

Met His Lys Lys Thr Cys Asp Val Leu Lys Glu Phe Leu Gly Leu His
                565                 570                 575

<210> SEQ ID NO 22
<211> LENGTH: 579
<212> TYPE: PRT
<213> ORGANISM: Homo sapiens

<400> SEQUENCE: 22

Met Lys Asp Phe Ser Asp Val Ile Leu Cys Met Glu Ala Thr Glu Ser
1               5                   10                  15

```
Ser Lys Thr Glu Phe Cys Asn Pro Ala Phe Glu Pro Glu Ser Gly Pro
         20                  25                  30

Pro Cys Pro Pro Val Phe Pro Glu Asp Ala Ser Tyr Ser Val Pro
         35                  40                  45

Ala Pro Trp His Gly Arg Arg Pro Arg Gly Leu Arg Pro Asp Cys Arg
 50                  55                  60

Phe Ser Trp Leu Cys Val Leu Leu Ser Leu Leu Leu Leu
 65                  70                  75                  80

Leu Gly Leu Leu Val Ala Ile Ile Leu Ala Gln Leu Gln Ala Ala Pro
                 85                  90                  95

Pro Ser Gly Ala Ser His Ser Pro Leu Pro Ala Gly Leu Thr Thr
             100                 105                 110

Thr Thr Thr Thr Pro Thr Ile Thr Thr Ser Gln Ala Ala Gly Thr Pro
         115                 120                 125

Lys Gly Gln Gln Glu Ser Gly Val Ser Pro Ser Pro Gln Ser Thr Cys
     130                 135                 140

Gly Gly Leu Leu Ser Gly Pro Arg Gly Phe Phe Ser Ser Pro Asn Tyr
145                 150                 155                 160

Pro Asp Pro Tyr Pro Pro Asn Thr His Cys Val Trp His Ile Gln Val
                 165                 170                 175

Ala Thr Asp His Ala Ile Gln Leu Lys Ile Glu Ala Leu Ser Ile Glu
             180                 185                 190

Ser Val Ala Ser Cys Leu Phe Asp Arg Leu Glu Leu Ser Pro Glu Pro
         195                 200                 205

Glu Gly Pro Leu Leu Arg Val Cys Gly Arg Val Pro Pro Pro Thr Leu
     210                 215                 220

Asn Thr Asn Ala Ser His Leu Leu Val Val Phe Val Ser Asp Ser Ser
225                 230                 235                 240

Val Glu Gly Phe Gly Phe His Ala Trp Tyr Gln Ala Met Ala Pro Gly
                 245                 250                 255

Arg Gly Ser Cys Ala His Asp Glu Phe Arg Cys Asp Gln Leu Ile Cys
             260                 265                 270

Leu Leu Pro Asp Ser Val Cys Asp Gly Phe Ala Asn Cys Ala Asp Gly
         275                 280                 285

Ser Asp Glu Thr Asn Cys Ser Ala Lys Phe Ser Gly Cys Gly Gly Asn
     290                 295                 300

Leu Thr Gly Leu Gln Gly Thr Phe Ser Thr Pro Ser Tyr Leu Gln Gln
305                 310                 315                 320

Tyr Pro His Gln Leu Leu Cys Thr Trp His Ile Ser Val Pro Ala Gly
                 325                 330                 335

His Ser Ile Glu Leu Gln Phe His Asn Phe Ser Leu Glu Ala Gln Asp
             340                 345                 350

Glu Cys Lys Phe Asp Tyr Val Glu Val Tyr Glu Thr Ser Ser Ser Gly
         355                 360                 365

Ala Phe Ser Leu Leu Gly Arg Phe Cys Gly Ala Glu Pro Pro His
     370                 375                 380

Leu Val Ser Ser His His Glu Leu Ala Val Leu Phe Arg Thr Asp His
385                 390                 395                 400

Gly Ile Ser Ser Gly Phe Ser Ala Thr Tyr Leu Ala Phe Asn Ala
                 405                 410                 415

Thr Glu Asn Pro Cys Gly Pro Ser Glu Leu Ser Cys Gln Ala Gly Gly
             420                 425                 430
```

```
Cys Lys Gly Val Gln Trp Met Cys Asp Met Trp Arg Asp Cys Thr Asp
        435                 440                 445
Gly Ser Asp Asn Cys Ser Gly Pro Leu Phe Pro Pro Glu Leu
450                 455                 460
Ala Cys Glu Pro Val Gln Val Glu Met Cys Leu Gly Leu Ser Tyr Asn
465                 470                 475                 480
Thr Thr Ala Phe Pro Asn Ile Trp Val Gly Met Ile Thr Gln Glu Glu
                485                 490                 495
Val Val Glu Val Leu Ser Gly Tyr Lys Ser Leu Thr Ser Leu Pro Cys
            500                 505                 510
Tyr Gln His Phe Arg Arg Leu Leu Cys Gly Leu Leu Val Pro Arg Cys
        515                 520                 525
Thr Pro Leu Gly Ser Val Leu Pro Pro Cys Arg Ser Val Cys Gln Glu
    530                 535                 540
Ala Glu His Gln Cys Gln Ser Gly Leu Ala Leu Leu Gly Thr Pro Trp
545                 550                 555                 560
Pro Phe Asn Cys Asn Arg Leu Pro Glu Ala Ala Asp Leu Glu Ala Cys
                565                 570                 575
Ala Gln Pro

<210> SEQ ID NO 23
<211> LENGTH: 578
<212> TYPE: PRT
<213> ORGANISM: Homo sapiens

<400> SEQUENCE: 23

Met Leu Pro Cys Leu Val Val Leu Leu Ala Ala Leu Leu Ser Leu Arg
1               5                   10                  15
Leu Gly Ser Asp Ala His Gly Thr Glu Leu Pro Ser Pro Pro Ser Val
            20                  25                  30
Trp Phe Glu Ala Glu Phe Phe His His Ile Leu His Trp Thr Pro Ile
        35                  40                  45
Pro Asn Gln Ser Glu Ser Thr Cys Tyr Glu Val Ala Leu Leu Arg Tyr
    50                  55                  60
Gly Ile Glu Ser Trp Asn Ser Ile Ser Asn Cys Ser Gln Thr Leu Ser
65                  70                  75                  80
Tyr Asp Leu Thr Ala Val Thr Leu Asp Leu Tyr His Ser Asn Gly Tyr
                85                  90                  95
Arg Ala Arg Val Arg Ala Val Asp Gly Ser Arg His Ser Asn Trp Thr
            100                 105                 110
Val Thr Asn Thr Arg Phe Ser Val Asp Glu Val Thr Leu Thr Val Gly
        115                 120                 125
Ser Val Asn Leu Glu Ile His Asn Gly Phe Ile Leu Gly Lys Ile Gln
    130                 135                 140
Leu Pro Arg Pro Lys Met Ala Pro Ala Asn Asp Thr Tyr Glu Ser Ile
145                 150                 155                 160
Phe Ser His Phe Arg Glu Tyr Glu Ile Ala Ile Arg Lys Val Pro Gly
                165                 170                 175
Asn Phe Thr Phe Thr His Lys Lys Val Lys His Glu Asn Phe Ser Leu
            180                 185                 190
Leu Thr Ser Gly Glu Val Gly Glu Phe Cys Val Gln Val Lys Pro Ser
        195                 200                 205
Val Ala Ser Arg Ser Asn Lys Gly Met Trp Ser Lys Glu Glu Cys Ile
    210                 215                 220
```

-continued

```
Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
            245                 250                 255

Gln Leu Tyr Val Arg Arg Lys Lys Leu Pro Ser Val Leu Leu Phe
        260                 265                 270

Lys Lys Pro Ser Pro Phe Ile Phe Ile Ser Gln Arg Pro Ser Pro Glu
            275                 280                 285

Thr Gln Asp Thr Ile His Pro Leu Asp Glu Glu Ala Phe Leu Lys Val
            290                 295                 300

Ser Pro Glu Leu Lys Asn Leu Asp Leu His Gly Ser Thr Asp Ser Gly
305                 310                 315                 320

Phe Gly Ser Thr Lys Pro Ser Leu Gln Thr Glu Glu Pro Gln Phe Leu
                325                 330                 335

Leu Pro Asp Pro His Pro Gln Ala Asp Arg Thr Leu Gly Asn Arg Glu
            340                 345                 350

Pro Pro Val Leu Gly Asp Ser Cys Ser Ser Gly Ser Ser Asn Ser Thr
            355                 360                 365

Asp Ser Gly Ile Cys Leu Gln Glu Pro Ser Leu Ser Pro Ser Thr Gly
370                 375                 380

Pro Thr Trp Glu Gln Gln Val Gly Ser Asn Ser Arg Gly Gln Asp Asp
385                 390                 395                 400

Ser Gly Ile Asp Leu Val Gln Asn Ser Glu Gly Arg Ala Gly Asp Thr
                405                 410                 415

Gln Gly Gly Ser Ala Leu Gly His His Ser Pro Pro Glu Pro Glu Val
            420                 425                 430

Pro Gly Glu Glu Asp Pro Ala Ala Val Ala Phe Gln Gly Tyr Leu Arg
            435                 440                 445

Gln Thr Arg Cys Ala Glu Lys Ala Thr Lys Thr Gly Cys Leu Glu
        450                 455                 460

Glu Glu Ser Pro Leu Thr Asp Gly Leu Gly Pro Lys Phe Gly Arg Cys
465                 470                 475                 480

Leu Val Asp Glu Ala Gly Leu His Pro Ala Leu Ala Lys Gly Tyr
                485                 490                 495

Leu Lys Gln Asp Pro Leu Glu Met Thr Leu Ala Ser Ser Gly Ala Pro
            500                 505                 510

Thr Gly Gln Trp Asn Gln Pro Thr Glu Glu Trp Ser Leu Leu Ala Leu
        515                 520                 525

Ser Ser Cys Ser Asp Leu Gly Ile Ser Asp Trp Ser Phe Ala His Asp
            530                 535                 540

Leu Ala Pro Leu Gly Cys Val Ala Ala Pro Gly Gly Leu Leu Gly Ser
545                 550                 555                 560

Phe Asn Ser Asp Leu Val Thr Leu Pro Leu Ile Ser Ser Leu Gln Ser
                565                 570                 575

Ser Glu

<210> SEQ ID NO 24
<211> LENGTH: 373
<212> TYPE: PRT
<213> ORGANISM: Homo sapiens

<400> SEQUENCE: 24

Met Arg Met Glu Asp Glu Asp Tyr Asn Thr Ser Ile Ser Tyr Gly Asp
1               5                   10                  15
```

```
Glu Tyr Pro Asp Tyr Leu Asp Ser Ile Val Val Leu Glu Asp Leu Ser
            20                  25                  30

Pro Leu Glu Ala Arg Val Thr Arg Ile Phe Leu Val Val Tyr Ser
        35                  40                  45

Ile Val Cys Phe Leu Gly Ile Leu Gly Asn Gly Leu Val Ile Ile
 50                  55                  60

Ala Thr Phe Lys Met Lys Lys Thr Val Asn Met Val Trp Phe Leu Asn
 65                  70                  75                  80

Leu Ala Val Ala Asp Phe Leu Phe Asn Val Phe Leu Pro Ile His Ile
                    85                  90                  95

Thr Tyr Ala Ala Met Asp Tyr His Trp Val Phe Gly Thr Ala Met Cys
                100                 105                 110

Lys Ile Ser Asn Phe Leu Leu Ile His Asn Met Phe Thr Ser Val Phe
            115                 120                 125

Leu Leu Thr Ile Ile Ser Ser Asp Arg Cys Ile Ser Val Leu Leu Pro
130                 135                 140

Val Trp Ser Gln Asn His Arg Ser Val Arg Leu Ala Tyr Met Ala Cys
145                 150                 155                 160

Met Val Ile Trp Val Leu Ala Phe Phe Leu Ser Ser Pro Ser Leu Val
                165                 170                 175

Phe Arg Asp Thr Ala Asn Leu His Gly Lys Ile Ser Cys Phe Asn Asn
                180                 185                 190

Phe Ser Leu Ser Thr Pro Gly Ser Ser Ser Trp Pro Thr His Ser Gln
            195                 200                 205

Met Asp Pro Val Gly Tyr Ser Arg His Met Val Val Thr Val Thr Arg
210                 215                 220

Phe Leu Cys Gly Phe Leu Val Pro Val Leu Ile Ile Thr Ala Cys Tyr
225                 230                 235                 240

Leu Thr Ile Val Cys Lys Leu Gln Arg Asn Arg Leu Ala Lys Thr Lys
                245                 250                 255

Lys Pro Phe Lys Ile Ile Val Thr Ile Ile Thr Phe Phe Leu Cys
            260                 265                 270

Trp Cys Pro Tyr His Thr Leu Asn Leu Leu Glu Leu His His Thr Ala
            275                 280                 285

Met Pro Gly Ser Val Phe Ser Leu Gly Leu Pro Leu Ala Thr Ala Leu
290                 295                 300

Ala Ile Ala Asn Ser Cys Met Asn Pro Ile Leu Tyr Val Phe Met Gly
305                 310                 315                 320

Gln Asp Phe Lys Lys Phe Lys Val Ala Leu Phe Ser Arg Leu Val Asn
                325                 330                 335

Ala Leu Ser Glu Asp Thr Gly His Ser Ser Tyr Pro Ser His Arg Ser
            340                 345                 350

Phe Thr Lys Met Ser Ser Met Asn Glu Arg Thr Ser Met Asn Glu Arg
            355                 360                 365

Glu Thr Gly Met Leu
        370

<210> SEQ ID NO 25
<211> LENGTH: 208
<212> TYPE: PRT
<213> ORGANISM: Homo sapiens

<400> SEQUENCE: 25

Met Lys Leu Leu Pro Ser Val Val Leu Lys Leu Phe Leu Ala Ala Val
 1               5                  10                  15
```

```
Leu Ser Ala Leu Val Thr Gly Glu Ser Leu Glu Arg Leu Arg Arg Gly
                20                  25                  30

Leu Ala Ala Gly Thr Ser Asn Pro Asp Pro Thr Val Ser Thr Asp
            35                  40                  45

Gln Leu Leu Pro Leu Gly Gly Gly Arg Asp Arg Lys Val Arg Asp Leu
 50                  55                  60

Gln Glu Ala Asp Leu Asp Leu Leu Arg Val Thr Leu Ser Ser Lys Pro
 65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
                100                 105                 110

Lys Asp Phe Cys Ile His Gly Glu Cys Lys Tyr Val Lys Glu Leu Arg
            115                 120                 125

Ala Pro Ser Cys Ile Cys His Pro Gly Tyr His Gly Glu Arg Cys His
 130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
                180                 185                 190

Asp Val Glu Asn Glu Glu Lys Val Lys Leu Gly Met Thr Asn Ser His
                195                 200                 205

<210> SEQ ID NO 26
<211> LENGTH: 208
<212> TYPE: PRT
<213> ORGANISM: Homo sapiens

<400> SEQUENCE: 26

Met Ala Leu Gly Gln Lys Leu Phe Ile Thr Met Ser Arg Gly Ala Gly
  1               5                  10                  15

Arg Leu Gln Gly Thr Leu Trp Ala Leu Val Phe Leu Gly Ile Leu Val
                20                  25                  30

Gly Met Val Val Pro Ser Pro Ala Gly Thr Arg Ala Asn Asn Thr Leu
            35                  40                  45

Leu Asp Ser Arg Gly Trp Gly Thr Leu Leu Ser Arg Ser Arg Ala Gly
 50                  55                  60

Leu Ala Gly Glu Ile Ala Gly Val Asn Trp Glu Ser Gly Tyr Leu Val
 65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
                100                 105                 110

Asn Pro Tyr Ser Leu Leu Glu Ile Ser Thr Val Glu Arg Gly Val Val
                115                 120                 125

Ser Leu Phe Gly Val Arg Ser Ala Leu Phe Val Ala Met Asn Ser Lys
                130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
```

```
            180                 185                 190
Ser Lys Val Ser Pro Ile Met Thr Val Thr His Phe Leu Pro Arg Ile
            195                 200                 205

<210> SEQ ID NO 27
<211> LENGTH: 1390
<212> TYPE: PRT
<213> ORGANISM: Homo sapiens

<400> SEQUENCE: 27

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
    275                 280                 285

His Ser Tyr Met Glu Met Pro Leu Glu Cys Ile Leu Thr Glu Lys Arg
290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350
```

```
Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
```

-continued

```
            770             775             780
Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
                915                 920                 925

Gln Asn Phe Thr Gly Leu Ile Ala Gly Val Val Ser Ile Ser Thr Ala
                930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
                980                 985                 990

Thr Glu Met Val Ser Asn Glu Ser Val Asp Tyr Arg Ala Thr Phe Pro
                995                1000                1005

Glu Asp Gln Phe Pro Asn Ser Ser Gln Asn Gly Ser Cys Arg Gln
       1010                1015                1020

Val Gln Tyr Pro Leu Thr Asp Met Ser Pro Ile Leu Thr Ser Gly
       1025                1030                1035

Asp Ser Asp Ile Ser Ser Pro Leu Leu Gln Asn Thr Val His Ile
       1040                1045                1050

Asp Leu Ser Ala Leu Asn Pro Glu Leu Val Gln Ala Val Gln His
       1055                1060                1065

Val Val Ile Gly Pro Ser Ser Leu Ile Val His Phe Asn Glu Val
       1070                1075                1080

Ile Gly Arg Gly His Phe Gly Cys Val Tyr His Gly Thr Leu Leu
       1085                1090                1095

Asp Asn Asp Gly Lys Lys Ile His Cys Ala Val Lys Ser Leu Asn
       1100                1105                1110

Arg Ile Thr Asp Ile Gly Glu Val Ser Gln Phe Leu Thr Glu Gly
       1115                1120                1125

Ile Ile Met Lys Asp Phe Ser His Pro Asn Val Leu Ser Leu Leu
       1130                1135                1140

Gly Ile Cys Leu Arg Ser Glu Gly Ser Pro Leu Val Val Leu Pro
       1145                1150                1155

Tyr Met Lys His Gly Asp Leu Arg Asn Phe Ile Arg Asn Glu Thr
       1160                1165                1170

His Asn Pro Thr Val Lys Asp Leu Ile Gly Phe Gly Leu Gln Val
       1175                1180                1185
```

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 28
<211> LENGTH: 1332
<212> TYPE: PRT
<213> ORGANISM: Homo sapiens

<400> SEQUENCE: 28

Met Glu Ser His Ser Arg Ala Gly Lys Ser Arg Lys Ser Ala Lys Phe
1               5                   10                  15

Arg Ser Ile Ser Arg Ser Leu Met Leu Cys Asn Ala Lys Thr Ser Asp
                20                  25                  30

Asp Gly Ser Ser Pro Asp Glu Lys Tyr Pro Asp Pro Phe Glu Ile Ser
            35                  40                  45

Leu Ala Gln Gly Lys Glu Gly Ile Phe His Ser Ser Val Gln Leu Ala
        50                  55                  60

Asp Thr Ser Glu Ala Gly Pro Ser Ser Val Pro Asp Leu Ala Leu Ala
65                  70                  75                  80

Ser Glu Ala Ala Gln Leu Gln Ala Ala Gly Asn Asp Arg Gly Lys Thr
                85                  90                  95

Cys Arg Arg Ile Phe Phe Met Lys Glu Ser Thr Ala Ser Ser Arg
                100                 105                 110

Glu Lys Pro Gly Lys Leu Glu Ala Gln Ser Ser Asn Phe Leu Phe Pro
            115                 120                 125

Lys Ala Cys His Gln Arg Ala Arg Ser Asn Ser Thr Ser Val Asn Pro
        130                 135                 140

Tyr Cys Thr Arg Glu Ile Asp Phe Pro Met Thr Lys Lys Ser Ala Ala

-continued

```
145                 150                 155                 160
Pro Thr Asp Arg Gln Pro Tyr Ser Leu Cys Ser Asn Arg Lys Ser Leu
                165                 170                 175
Ser Gln Gln Leu Asp Cys Pro Ala Gly Lys Ala Ala Gly Thr Ser Arg
                180                 185                 190
Pro Thr Arg Ser Leu Ser Thr Ala Gln Leu Val Gln Pro Ser Gly Gly
                195                 200                 205
Leu Gln Ala Ser Val Ile Ser Asn Ile Val Leu Met Lys Gly Gln Ala
210                 215                 220
Lys Gly Leu Gly Phe Ser Ile Val Gly Gly Lys Asp Ser Ile Tyr Gly
225                 230                 235                 240
Pro Ile Gly Ile Tyr Val Lys Thr Ile Phe Ala Gly Gly Ala Ala Ala
                245                 250                 255
Ala Asp Gly Arg Leu Gln Glu Gly Asp Glu Ile Leu Glu Leu Asn Gly
                260                 265                 270
Glu Ser Met Ala Gly Leu Thr His Gln Asp Ala Leu Gln Lys Phe Lys
                275                 280                 285
Gln Ala Lys Lys Gly Leu Leu Thr Leu Thr Val Arg Thr Arg Leu Thr
                290                 295                 300
Ala Pro Pro Ser Leu Cys Ser His Leu Ser Pro Pro Leu Cys Arg Ser
305                 310                 315                 320
Leu Ser Ser Ser Thr Cys Ile Thr Lys Asp Ser Ser Phe Ala Leu
                325                 330                 335
Glu Ser Pro Ser Ala Pro Ile Ser Thr Ala Lys Pro Asn Tyr Arg Ile
                340                 345                 350
Met Val Glu Val Ser Leu Gln Lys Glu Ala Gly Val Gly Leu Gly Ile
                355                 360                 365
Gly Leu Cys Ser Val Pro Tyr Phe Gln Cys Ile Ser Gly Ile Phe Val
                370                 375                 380
His Thr Leu Ser Pro Gly Ser Val Ala His Leu Asp Gly Arg Leu Arg
385                 390                 395                 400
Cys Gly Asp Glu Ile Val Glu Ile Ser Asp Ser Pro Val His Cys Leu
                405                 410                 415
Thr Leu Asn Glu Val Tyr Thr Ile Leu Ser His Cys Asp Pro Gly Pro
                420                 425                 430
Val Pro Ile Ile Val Ser Arg His Pro Asp Pro Gln Val Ser Glu Gln
                435                 440                 445
Gln Leu Lys Glu Ala Val Ala Gln Ala Val Glu Asn Thr Lys Phe Gly
                450                 455                 460
Lys Glu Arg His Gln Trp Ser Leu Glu Gly Val Lys Arg Leu Glu Ser
465                 470                 475                 480
Ser Trp His Gly Arg Pro Thr Leu Glu Lys Glu Arg Glu Lys Asn Ser
                485                 490                 495
Ala Pro Pro His Arg Arg Ala Gln Lys Val Met Ile Arg Ser Ser Ser
                500                 505                 510
Asp Ser Ser Tyr Met Ser Gly Ser Pro Gly Gly Ser Pro Gly Ser Gly
                515                 520                 525
Ser Ala Glu Lys Pro Ser Ser Asp Val Asp Ile Ser Thr His Ser Pro
                530                 535                 540
Ser Leu Pro Leu Ala Arg Glu Pro Val Val Leu Ser Ile Ala Ser Ser
545                 550                 555                 560
Arg Leu Pro Gln Glu Ser Pro Leu Pro Glu Ser Arg Asp Ser His
                565                 570                 575
```

```
Pro Pro Leu Arg Leu Lys Lys Ser Phe Glu Ile Leu Val Arg Lys Pro
            580                 585                 590

Met Ser Ser Lys Pro Lys Pro Pro Arg Lys Tyr Phe Lys Ser Asp
        595                 600                 605

Ser Asp Pro Gln Lys Ser Leu Glu Glu Arg Glu Asn Ser Ser Cys Ser
        610                 615                 620

Ser Gly His Thr Pro Pro Thr Cys Gly Gln Glu Ala Arg Glu Leu Leu
625                 630                 635                 640

Pro Leu Leu Leu Pro Gln Glu Asp Thr Ala Gly Arg Ser Pro Ser Ala
                645                 650                 655

Ser Ala Gly Cys Pro Gly Pro Gly Ile Gly Pro Gln Thr Lys Ser Ser
            660                 665                 670

Thr Glu Gly Glu Pro Gly Trp Arg Arg Ala Ser Pro Val Thr Gln Thr
        675                 680                 685

Ser Pro Ile Lys His Pro Leu Leu Lys Arg Gln Ala Arg Met Asp Tyr
        690                 695                 700

Ser Phe Asp Thr Thr Ala Glu Asp Pro Trp Val Arg Ile Ser Asp Cys
705                 710                 715                 720

Ile Lys Asn Leu Phe Ser Pro Ile Met Ser Glu Asn His Gly His Met
                725                 730                 735

Pro Leu Gln Pro Asn Ala Ser Leu Asn Glu Glu Glu Gly Thr Gln Gly
            740                 745                 750

His Pro Asp Gly Thr Pro Pro Lys Leu Asp Thr Ala Asn Gly Thr Pro
        755                 760                 765

Lys Val Tyr Lys Ser Ala Asp Ser Ser Thr Val Lys Lys Gly Pro Pro
        770                 775                 780

Val Ala Pro Lys Pro Ala Trp Phe Arg Gln Ser Leu Lys Gly Leu Arg
785                 790                 795                 800

Asn Arg Ala Ser Asp Pro Arg Gly Leu Pro Asp Pro Ala Leu Ser Thr
                805                 810                 815

Gln Pro Ala Pro Ala Ser Arg Glu His Leu Gly Ser His Ile Arg Ala
            820                 825                 830

Ser Ser Ser Ser Ser Ile Arg Gln Arg Ile Ser Ser Phe Glu Thr
        835                 840                 845

Phe Gly Ser Ser Gln Leu Pro Asp Lys Gly Ala Gln Arg Leu Ser Leu
        850                 855                 860

Gln Pro Ser Ser Gly Glu Ala Ala Lys Pro Leu Gly Lys His Glu Glu
865                 870                 875                 880

Gly Arg Phe Ser Gly Leu Leu Gly Arg Gly Ala Ala Pro Thr Leu Val
                885                 890                 895

Pro Gln Gln Pro Glu Gln Val Leu Ser Ser Gly Ser Pro Ala Ala Ser
            900                 905                 910

Glu Ala Arg Asp Pro Gly Val Ser Glu Ser Pro Pro Gly Arg Gln
        915                 920                 925

Pro Asn Gln Lys Thr Leu Pro Pro Gly Pro Asp Pro Leu Leu Arg Leu
        930                 935                 940

Leu Ser Thr Gln Ala Glu Glu Ser Gln Gly Pro Val Leu Lys Met Pro
945                 950                 955                 960

Ser Gln Arg Ala Arg Ser Phe Pro Leu Thr Arg Ser Gln Ser Cys Glu
                965                 970                 975

Thr Lys Leu Leu Asp Glu Lys Thr Ser Lys Leu Tyr Ser Ile Ser Ser
            980                 985                 990
```

-continued

```
Gln Val Ser Ser Ala Val Met Lys Ser Leu Leu Cys Leu Pro Ser Ser
            995                 1000                1005

Ile Ser Cys Ala Gln Thr Pro Cys Ile Pro Lys Glu Gly Ala Ser
    1010                1015                1020

Pro Thr Ser Ser Ser Asn Glu Asp Ser Ala Ala Asn Gly Ser Ala
    1025                1030                1035

Glu Thr Ser Ala Leu Asp Thr Gly Phe Ser Leu Asn Leu Ser Glu
    1040                1045                1050

Leu Arg Glu Tyr Thr Glu Gly Leu Thr Glu Ala Lys Glu Asp Asp
    1055                1060                1065

Asp Gly Asp His Ser Ser Leu Gln Ser Gly Gln Ser Val Ile Ser
    1070                1075                1080

Leu Leu Ser Ser Glu Glu Leu Lys Lys Leu Ile Glu Glu Val Lys
    1085                1090                1095

Val Leu Asp Glu Ala Thr Leu Lys Gln Leu Asp Gly Ile His Val
    1100                1105                1110

Thr Ile Leu His Lys Glu Glu Gly Ala Gly Leu Gly Phe Ser Leu
    1115                1120                1125

Ala Gly Gly Ala Asp Leu Glu Asn Lys Val Ile Thr Val His Arg
    1130                1135                1140

Val Phe Pro Asn Gly Leu Ala Ser Gln Glu Gly Thr Ile Gln Lys
    1145                1150                1155

Gly Asn Glu Val Leu Ser Ile Asn Gly Lys Ser Leu Lys Gly Thr
    1160                1165                1170

Thr His His Asp Ala Leu Ala Ile Leu Arg Gln Ala Arg Glu Pro
    1175                1180                1185

Arg Gln Ala Val Ile Val Thr Arg Lys Leu Thr Pro Glu Ala Met
    1190                1195                1200

Pro Asp Leu Asn Ser Ser Thr Asp Ser Ala Ala Ser Ala Ser Ala
    1205                1210                1215

Ala Ser Asp Val Ser Val Glu Ser Thr Ala Glu Ala Thr Val Cys
    1220                1225                1230

Thr Val Thr Leu Glu Lys Met Ser Ala Gly Leu Gly Phe Ser Leu
    1235                1240                1245

Glu Gly Gly Lys Gly Ser Leu His Gly Asp Lys Pro Leu Thr Ile
    1250                1255                1260

Asn Arg Ile Phe Lys Gly Ala Ala Ser Glu Gln Ser Glu Thr Val
    1265                1270                1275

Gln Pro Gly Asp Glu Ile Leu Gln Leu Gly Gly Thr Ala Met Gln
    1280                1285                1290

Gly Leu Thr Arg Phe Glu Ala Trp Asn Ile Ile Lys Ala Leu Pro
    1295                1300                1305

Asp Gly Pro Val Thr Ile Val Ile Arg Arg Lys Ser Leu Gln Ser
    1310                1315                1320

Lys Glu Thr Thr Ala Ala Gly Asp Ser
    1325                1330

<210> SEQ ID NO 29
<211> LENGTH: 459
<212> TYPE: PRT
<213> ORGANISM: Homo sapiens

<400> SEQUENCE: 29

Met Thr Ile Leu Gly Thr Thr Phe Gly Met Val Phe Ser Leu Leu Gln
1               5                   10                  15
```

```
Val Val Ser Gly Glu Ser Gly Tyr Ala Gln Asn Gly Asp Leu Glu Asp
         20                  25                  30

Ala Glu Leu Asp Asp Tyr Ser Phe Ser Cys Tyr Ser Gln Leu Glu Val
         35                  40                  45

Asn Gly Ser Gln His Ser Leu Thr Cys Ala Phe Glu Asp Pro Asp Val
 50                  55                  60

Asn Thr Thr Asn Leu Glu Phe Glu Ile Cys Gly Ala Leu Val Glu Val
 65                  70                  75                  80

Lys Cys Leu Asn Phe Arg Lys Leu Gln Glu Ile Tyr Phe Ile Glu Thr
                 85                  90                  95

Lys Lys Phe Leu Leu Ile Gly Lys Ser Asn Ile Cys Val Lys Val Gly
                100                 105                 110

Glu Lys Ser Leu Thr Cys Lys Lys Ile Asp Leu Thr Thr Ile Val Lys
             115                 120                 125

Pro Glu Ala Pro Phe Asp Leu Ser Val Ile Tyr Arg Glu Gly Ala Asn
130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
                180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Glu Trp Ser Pro Ser Tyr
210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
                260                 265                 270

Trp Pro Ser Leu Pro Asp His Lys Lys Thr Leu Glu His Leu Cys Lys
            275                 280                 285

Lys Pro Arg Lys Asn Leu Asn Val Ser Phe Asn Pro Glu Ser Phe Leu
290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
            340                 345                 350

Asp Val Val Ile Thr Pro Glu Ser Phe Gly Arg Asp Ser Ser Leu Thr
355                 360                 365

Cys Leu Ala Gly Asn Val Ser Ala Cys Asp Ala Pro Ile Leu Ser Ser
            370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
                420                 425                 430
```

```
Gln Gly Gln Pro Ile Leu Thr Ser Leu Gly Ser Asn Gln Glu Ala
            435                 440                 445
Tyr Val Thr Met Ser Ser Phe Tyr Gln Asn Gln
    450                 455

<210> SEQ ID NO 30
<211> LENGTH: 259
<212> TYPE: PRT
<213> ORGANISM: Homo sapiens

<400> SEQUENCE: 30

Met Ala Arg Ile Pro Lys Thr Leu Lys Phe Val Val Ile Val Ala
1               5                   10                  15

Val Leu Leu Pro Val Leu Ala Tyr Ser Ala Thr Thr Ala Arg Gln Glu
                20                  25                  30

Glu Val Pro Gln Gln Thr Val Ala Pro Gln Gln Arg His Ser Phe
            35                  40                  45

Lys Gly Glu Glu Cys Pro Ala Gly Ser His Arg Ser Glu His Thr Gly
    50                  55                  60

Ala Cys Asn Pro Cys Thr Glu Gly Val Asp Tyr Thr Asn Ala Ser Asn
65                  70                  75                  80

Asn Glu Pro Ser Cys Phe Pro Cys Thr Val Cys Lys Ser Asp Gln Lys
                85                  90                  95

His Lys Ser Ser Cys Thr Met Thr Arg Asp Thr Val Cys Gln Cys Lys
            100                 105                 110

Glu Gly Thr Phe Arg Asn Glu Asn Ser Pro Glu Met Cys Arg Lys Cys
            115                 120                 125

Ser Arg Cys Pro Ser Gly Glu Val Gln Val Ser Asn Cys Thr Ser Trp
    130                 135                 140

Asp Asp Ile Gln Cys Val Glu Glu Phe Gly Ala Asn Ala Thr Val Glu
145                 150                 155                 160

Thr Pro Ala Ala Glu Glu Thr Met Asn Thr Ser Pro Gly Thr Pro Ala
                165                 170                 175

Pro Ala Ala Glu Glu Thr Met Asn Thr Ser Pro Gly Thr Pro Ala Pro
            180                 185                 190

Ala Ala Glu Glu Thr Met Thr Thr Ser Pro Gly Thr Pro Ala Pro Ala
        195                 200                 205

Ala Glu Glu Thr Met Thr Thr Ser Pro Gly Thr Pro Ala Pro Ala Ala
    210                 215                 220

Glu Glu Thr Met Ile Thr Ser Pro Gly Thr Pro Ala Ser Ser His Tyr
225                 230                 235                 240

Leu Ser Cys Thr Ile Val Gly Ile Ile Val Leu Ile Val Leu Leu Ile
                245                 250                 255

Val Phe Val

<210> SEQ ID NO 31
<211> LENGTH: 513
<212> TYPE: PRT
<213> ORGANISM: Homo sapiens

<400> SEQUENCE: 31

Met Pro Gly Leu Gly Arg Arg Ala Gln Trp Leu Cys Trp Trp Trp Gly
1               5                   10                  15

Leu Leu Cys Ser Cys Cys Gly Pro Pro Leu Arg Pro Pro Leu Pro
                20                  25                  30

Ala Ala Ala Ala Ala Ala Ala Gly Gly Gln Leu Leu Gly Asp Gly Gly
```

```
                35                  40                  45
Ser Pro Gly Arg Thr Glu Gln Pro Pro Ser Pro Gln Ser Ser Ser
 50                  55                  60

Gly Phe Leu Tyr Arg Arg Leu Lys Thr Gln Glu Lys Arg Glu Met Gln
 65                  70                  75                  80

Lys Glu Ile Leu Ser Val Leu Gly Leu Pro His Arg Pro Arg Pro Leu
                 85                  90                  95

His Gly Leu Gln Gln Pro Gln Pro Ala Leu Arg Gln Gln Glu Glu
                100                 105                 110

Gln Gln Gln Gln Gln Gln Leu Pro Arg Gly Glu Pro Pro Gly Arg
                115                 120                 125

Leu Lys Ser Ala Pro Leu Phe Met Leu Asp Leu Tyr Asn Ala Leu Ser
130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
                180                 185                 190

Gly Ser Gly Gly Ala Ser Pro Leu Thr Ser Ala Gln Asp Ser Ala Phe
            195                 200                 205

Leu Asn Asp Ala Asp Met Val Met Ser Phe Val Asn Leu Val Glu Tyr
210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
                260                 265                 270

Leu Ile Ser Ile Tyr Gln Val Leu Gln Glu His Gln His Arg Asp Ser
            275                 280                 285

Asp Leu Phe Leu Leu Asp Thr Arg Val Val Trp Ala Ser Glu Glu Gly
290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
                340                 345                 350

Tyr Asp Lys Gln Pro Phe Met Val Ala Phe Phe Lys Val Ser Glu Val
            355                 360                 365

His Val Arg Thr Thr Arg Ser Ala Ser Ser Arg Arg Gln Gln Ser
370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
                420                 425                 430

Pro Lys Gly Tyr Ala Ala Asn Tyr Cys Asp Gly Glu Cys Ser Phe Pro
            435                 440                 445

Leu Asn Ala His Met Asn Ala Thr Asn His Ala Ile Val Gln Thr Leu
450                 455                 460
```

```
Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
                500                 505                 510

His

<210> SEQ ID NO 32
<211> LENGTH: 169
<212> TYPE: PRT
<213> ORGANISM: Homo sapiens

<400> SEQUENCE: 32

Met Arg Gly Thr Pro Gly Asp Ala Asp Gly Gly Gly Arg Ala Val Tyr
1               5                   10                  15

Gln Ser Met Cys Lys Pro Ile Thr Gly Thr Ile Asn Asp Leu Asn Gln
                20                  25                  30

Gln Val Trp Thr Leu Gln Gly Gln Asn Leu Val Ala Val Pro Arg Ser
            35                  40                  45

Asp Ser Val Thr Pro Val Thr Val Ala Val Ile Thr Cys Lys Tyr Pro
    50                  55                  60

Glu Ala Leu Glu Gln Gly Arg Gly Asp Pro Ile Tyr Leu Gly Ile Gln
65                  70                  75                  80

Asn Pro Glu Met Cys Leu Tyr Cys Glu Lys Val Gly Glu Gln Pro Thr
                85                  90                  95

Leu Gln Leu Lys Glu Gln Lys Ile Met Asp Leu Tyr Gly Gln Pro Glu
                100                 105                 110

Pro Val Lys Pro Phe Leu Phe Tyr Arg Ala Lys Thr Gly Arg Thr Ser
            115                 120                 125

Thr Leu Glu Ser Val Ala Phe Pro Asp Trp Phe Ile Ala Ser Ser Lys
    130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                165

<210> SEQ ID NO 33
<211> LENGTH: 177
<212> TYPE: PRT
<213> ORGANISM: Homo sapiens

<400> SEQUENCE: 33

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
                20                  25                  30

Ser Lys Met Gln Ala Phe Arg Ile Trp Asp Val Asn Gln Lys Thr Phe
            35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95
```

```
Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 34
<211> LENGTH: 462
<212> TYPE: PRT
<213> ORGANISM: Homo sapiens

<400> SEQUENCE: 34

```
Met Gly Thr Gln Ala Leu Gln Gly Phe Leu Phe Leu Leu Phe Leu Pro
1               5                   10                  15

Leu Leu Gln Pro Arg Gly Ala Ser Ala Gly Ser Leu His Ser Pro Gly
            20                  25                  30

Leu Ser Glu Cys Phe Gln Val Asn Gly Ala Asp Tyr Arg Gly His Gln
        35                  40                  45

Asn Arg Thr Gly Pro Arg Gly Ala Gly Arg Pro Cys Leu Phe Trp Asp
    50                  55                  60

Gln Thr Gln Gln His Ser Tyr Ser Ala Ser Asp Pro His Gly Arg
65                  70                  75                  80

Trp Gly Leu Gly Ala His Asn Phe Cys Arg Asn Pro Asp Gly Asp Val
                85                  90                  95

Gln Pro Trp Cys Tyr Val Ala Glu Thr Glu Glu Gly Ile Tyr Trp Arg
            100                 105                 110

Tyr Cys Asp Ile Pro Ser Cys His Met Pro Gly Tyr Leu Gly Cys Phe
        115                 120                 125

Val Asp Ser Gly Ala Pro Pro Ala Leu Ser Gly Pro Ser Gly Thr Ser
    130                 135                 140

Thr Lys Leu Thr Val Gln Val Cys Leu Arg Phe Cys Arg Met Lys Gly
145                 150                 155                 160

Tyr Gln Leu Ala Gly Val Glu Ala Gly Tyr Ala Cys Phe Cys Gly Ser
                165                 170                 175

Glu Ser Asp Leu Ala Arg Gly Arg Leu Ala Pro Ala Thr Asp Cys Asp
            180                 185                 190

Gln Ile Cys Phe Gly His Pro Gly Gln Leu Cys Gly Gly Asp Gly Arg
        195                 200                 205

Leu Gly Val Tyr Glu Val Ser Val Gly Ser Cys Gln Gly Asn Trp Thr
    210                 215                 220

Ala Pro Gln Gly Val Ile Tyr Ser Pro Asp Phe Pro Asp Glu Tyr Gly
225                 230                 235                 240

Pro Asp Arg Asn Cys Ser Trp Ala Leu Gly Pro Pro Gly Ala Ala Leu
                245                 250                 255

Glu Leu Thr Phe Arg Leu Phe Glu Leu Ala Asp Pro Arg Asp Arg Leu
            260                 265                 270

Glu Leu Arg Asp Ala Ala Ser Gly Ser Leu Leu Arg Ala Phe Asp Gly
        275                 280                 285
```

Ala Arg Pro Pro Pro Ser Gly Pro Leu Arg Leu Gly Thr Ala Ala Leu
            290                 295                 300

Leu Leu Thr Phe Arg Ser Asp Ala Arg Gly His Ala Gln Gly Phe Ala
305                 310                 315                 320

Leu Thr Tyr Arg Gly Leu Gln Asp Ala Ala Glu Asp Pro Glu Ala Pro
                325                 330                 335

Glu Gly Ser Ala Gln Thr Pro Ala Ala Pro Leu Asp Gly Ala Asn Val
                340                 345                 350

Ser Cys Ser Pro Arg Pro Gly Ala Pro Ala Ile Gly Ala Arg
            355                 360                 365

Val Phe Ser Thr Val Thr Ala Val Ser Val Leu Leu Leu Leu Leu Leu
370                 375                 380

Gly Leu Leu Arg Pro Leu Arg Arg Arg Ser Cys Leu Leu Ala Pro Gly
385                 390                 395                 400

Lys Gly Pro Pro Ala Leu Gly Ala Ser Arg Gly Pro Arg Arg Ser Trp
                405                 410                 415

Ala Val Trp Tyr Gln Gln Pro Arg Gly Val Ala Leu Pro Cys Ser Pro
                420                 425                 430

Gly Asp Pro Gln Ala Glu Gly Ser Ala Ala Gly Tyr Arg Pro Leu Ser
                435                 440                 445

Ala Ser Ser Gln Ser Ser Leu Arg Ser Leu Ile Ser Ala Leu
            450                 455                 460

<210> SEQ ID NO 35
<211> LENGTH: 386
<212> TYPE: PRT
<213> ORGANISM: Homo sapiens

<400> SEQUENCE: 35

Met Gly Leu Trp Gly Gln Ser Val Pro Thr Ala Ser Ser Ala Arg Ala
1               5                   10                  15

Gly Arg Tyr Pro Gly Ala Arg Thr Ala Ser Gly Thr Arg Pro Trp Leu
                20                  25                  30

Leu Asp Pro Lys Ile Leu Lys Phe Val Val Phe Ile Val Ala Val Leu
            35                  40                  45

Leu Pro Val Arg Val Asp Ser Ala Thr Ile Pro Arg Gln Asp Glu Val
50                  55                  60

Pro Gln Gln Thr Val Ala Pro Gln Gln Arg Arg Ser Leu Lys Glu
65                  70                  75                  80

Glu Glu Cys Pro Ala Gly Ser His Arg Ser Glu Tyr Thr Gly Ala Cys
                85                  90                  95

Asn Pro Cys Thr Glu Gly Val Asp Tyr Thr Ile Ala Ser Asn Asn Leu
            100                 105                 110

Pro Ser Cys Leu Leu Cys Thr Val Cys Lys Ser Gly Gln Thr Asn Lys
            115                 120                 125

Ser Ser Cys Thr Thr Arg Asp Thr Val Cys Gln Cys Glu Lys Gly
130                 135                 140

Ser Phe Gln Asp Lys Asn Ser Pro Glu Met Cys Arg Thr Cys Arg Thr
145                 150                 155                 160

Gly Cys Pro Arg Gly Met Val Lys Val Ser Asn Cys Thr Pro Arg Ser
                165                 170                 175

Asp Ile Lys Cys Lys Asn Glu Ser Ala Ala Ser Ser Thr Gly Lys Thr
            180                 185                 190

Pro Ala Ala Glu Glu Thr Val Thr Thr Ile Leu Gly Met Leu Ala Ser
            195                 200                 205

```
Pro Tyr His Tyr Leu Ile Ile Ile Val Val Leu Val Ile Ile Leu Ala
    210                 215                 220

Val Val Val Val Gly Phe Ser Cys Arg Lys Lys Phe Ile Ser Tyr Leu
225                 230                 235                 240

Lys Gly Ile Cys Ser Gly Gly Gly Gly Pro Glu Arg Val His Arg
                245                 250                 255

Val Leu Phe Arg Arg Arg Ser Cys Pro Ser Arg Val Pro Gly Ala Glu
            260                 265                 270

Asp Asn Ala Arg Asn Glu Thr Leu Ser Asn Arg Tyr Leu Gln Pro Thr
        275                 280                 285

Gln Val Ser Glu Gln Glu Ile Gln Gly Gln Glu Leu Ala Glu Leu Thr
    290                 295                 300

Gly Val Thr Val Glu Ser Pro Glu Glu Pro Gln Arg Leu Leu Glu Gln
305                 310                 315                 320

Ala Glu Ala Glu Gly Cys Gln Arg Arg Arg Leu Leu Val Pro Val Asn
                325                 330                 335

Asp Ala Asp Ser Ala Asp Ile Ser Thr Leu Leu Asp Ala Ser Ala Thr
            340                 345                 350

Leu Glu Glu Gly His Ala Lys Glu Thr Ile Gln Asp Gln Leu Val Gly
        355                 360                 365

Ser Glu Lys Leu Phe Glu Glu Asp Glu Ala Gly Ser Ala Thr Ser
    370                 375                 380

Cys Leu
385

<210> SEQ ID NO 36
<211> LENGTH: 350
<212> TYPE: PRT
<213> ORGANISM: Homo sapiens

<400> SEQUENCE: 36

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
            20                  25                  30

Glu Thr Glu Thr Leu Asn Lys Tyr Val Val Ile Ile Ala Tyr Ala Leu
        35                  40                  45

Val Phe Leu Leu Ser Leu Leu Gly Asn Ser Leu Val Met Leu Val Ile
    50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
```

```
                    180                 185                 190
Asn Asp Thr Ala Lys Trp Arg Met Val Leu Arg Ile Leu Pro His Thr
                195                 200                 205

Phe Gly Phe Ile Val Pro Leu Phe Val Met Leu Phe Cys Tyr Gly Phe
            210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
    290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350

<210> SEQ ID NO 37
<211> LENGTH: 120
<212> TYPE: PRT
<213> ORGANISM: Homo sapiens

<400> SEQUENCE: 37

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp Arg Phe His
        35                  40                  45

Ala Thr Ser Ala Asp Cys Cys Ile Ser Tyr Thr Pro Arg Ser Ile Pro
    50                  55                  60

Cys Ser Leu Leu Glu Ser Tyr Phe Glu Thr Asn Ser Glu Cys Ser Lys
65                  70                  75                  80

Pro Gly Val Ile Phe Leu Thr Lys Lys Gly Arg Arg Phe Cys Ala Asn
                85                  90                  95

Pro Ser Asp Lys Gln Val Gln Val Cys Val Arg Met Leu Lys Leu Asp
            100                 105                 110

Thr Arg Ile Lys Thr Arg Lys Asn
        115                 120

<210> SEQ ID NO 38
<211> LENGTH: 781
<212> TYPE: PRT
<213> ORGANISM: Homo sapiens

<400> SEQUENCE: 38

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
```

```
            35                  40                  45
Lys Gly Asn Pro Glu Glu Asp Val Asp Thr Ser Gln Val Leu Tyr
 50                  55                  60

Glu Trp Glu Gln Gly Phe Ser Gln Ser Phe Thr Gln Glu Gln Val Ala
 65                  70                  75                  80

Asp Ile Asp Gly Gln Tyr Ala Met Thr Arg Ala Gln Arg Val Arg Ala
                 85                  90                  95

Ala Met Phe Pro Glu Thr Leu Asp Glu Gly Met Gln Ile Pro Ser Thr
                100                 105                 110

Gln Phe Asp Ala Ala His Pro Thr Asn Val Gln Arg Leu Ala Glu Pro
                115                 120                 125

Ser Gln Met Leu Lys His Ala Val Asn Leu Ile Asn Tyr Gln Asp
130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
                180                 185                 190

Gln Met Val Ser Ala Ile Val Arg Thr Met Gln Asn Thr Asn Asp Val
                195                 200                 205

Glu Thr Ala Arg Cys Thr Ala Gly Thr Leu His Asn Leu Ser His His
210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
                260                 265                 270

Val Arg Leu Ala Gly Gly Leu Gln Lys Met Val Ala Leu Leu Asn Lys
                275                 280                 285

Thr Asn Val Lys Phe Leu Ala Ile Thr Thr Asp Cys Leu Gln Ile Leu
290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
                340                 345                 350

Asn Lys Pro Ala Ile Val Glu Ala Gly Gly Met Gln Ala Leu Gly Leu
                355                 360                 365

His Leu Thr Asp Pro Ser Gln Arg Leu Val Gln Asn Cys Leu Trp Thr
                370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
                420                 425                 430

Lys Asn Lys Met Met Val Cys Gln Val Gly Gly Ile Glu Ala Leu Val
                435                 440                 445

Arg Thr Val Leu Arg Ala Gly Asp Arg Glu Asp Ile Thr Glu Pro Ala
450                 455                 460
```

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
            610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
            675                 680                 685

Ala Trp Asn Glu Thr Ala Asp Leu Gly Leu Asp Ile Gly Ala Gln Gly
            690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
770                 775                 780

<210> SEQ ID NO 39
<211> LENGTH: 245
<212> TYPE: PRT
<213> ORGANISM: Homo sapiens

<400> SEQUENCE: 39

Met Ala Ala Ala Ile Ala Ser Ser Leu Ile Arg Gln Lys Arg Gln Ala
1               5                   10                  15

Arg Glu Arg Glu Lys Ser Asn Ala Cys Lys Cys Val Ser Ser Pro Ser
                20                  25                  30

Lys Gly Lys Thr Ser Cys Asp Lys Asn Lys Leu Asn Val Phe Ser Arg
            35                  40                  45

Val Lys Leu Phe Gly Ser Lys Lys Arg Arg Arg Arg Arg Pro Glu Pro

```
            50                  55                  60
Gln Leu Lys Gly Ile Val Thr Lys Leu Tyr Ser Arg Gln Gly Tyr His
 65                  70                  75                  80

Leu Gln Leu Gln Ala Asp Gly Thr Ile Asp Gly Thr Lys Asp Glu Asp
                 85                  90                  95

Ser Thr Tyr Thr Leu Phe Asn Leu Ile Pro Val Gly Leu Arg Val Val
            100                 105                 110

Ala Ile Gln Gly Val Gln Thr Lys Leu Tyr Leu Ala Met Asn Ser Glu
            115                 120                 125

Gly Tyr Leu Tyr Thr Ser Glu Leu Phe Thr Pro Glu Cys Lys Phe Lys
            130                 135                 140

Glu Ser Val Phe Glu Asn Tyr Tyr Val Thr Tyr Ser Ser Met Ile Tyr
145                 150                 155                 160

Arg Gln Gln Gln Ser Gly Arg Gly Trp Tyr Leu Gly Leu Asn Lys Glu
                165                 170                 175

Gly Glu Ile Met Lys Gly Asn His Val Lys Lys Asn Lys Pro Ala Ala
            180                 185                 190

His Phe Leu Pro Lys Pro Leu Lys Val Ala Met Tyr Lys Glu Pro Ser
            195                 200                 205

Leu His Asp Leu Thr Glu Phe Ser Arg Ser Gly Ser Gly Thr Pro Thr
210                 215                 220

Lys Ser Arg Ser Val Ser Gly Val Leu Asn Gly Gly Lys Ser Met Ser
225                 230                 235                 240

His Asn Glu Ser Thr
                245

<210> SEQ ID NO 40
<211> LENGTH: 281
<212> TYPE: PRT
<213> ORGANISM: Homo sapiens

<400> SEQUENCE: 40

Met Ala Met Met Glu Val Gln Gly Gly Pro Ser Leu Gly Gln Thr Cys
  1               5                  10                  15

Val Leu Ile Val Ile Phe Thr Val Leu Leu Gln Ser Leu Cys Val Ala
                 20                  25                  30

Val Thr Tyr Val Tyr Phe Thr Asn Glu Leu Lys Gln Met Gln Asp Lys
             35                  40                  45

Tyr Ser Lys Ser Gly Ile Ala Cys Phe Leu Lys Glu Asp Asp Ser Tyr
         50                  55                  60

Trp Asp Pro Asn Asp Glu Ser Met Asn Ser Pro Cys Trp Gln Val
 65                  70                  75                  80

Lys Trp Gln Leu Arg Gln Leu Val Arg Lys Met Ile Leu Arg Thr Ser
                 85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
            130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175
```

His Glu Lys Gly Phe Tyr Tyr Ile Tyr Ser Gln Thr Tyr Phe Arg Phe
                180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 41
<211> LENGTH: 93
<212> TYPE: PRT
<213> ORGANISM: Homo sapiens

<400> SEQUENCE: 41

Met Lys Ile Ser Val Ala Ala Ile Pro Phe Phe Leu Leu Ile Thr Ile
1               5                   10                  15

Ala Leu Gly Thr Lys Thr Glu Ser Ser Arg Gly Pro Tyr His Pro
            20                  25                  30

Ser Glu Cys Cys Phe Thr Tyr Thr Thr Tyr Lys Ile Pro Arg Gln Arg
        35                  40                  45

Ile Met Asp Tyr Tyr Glu Thr Asn Ser Gln Cys Ser Lys Pro Gly Ile
    50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90

<210> SEQ ID NO 42
<211> LENGTH: 282
<212> TYPE: PRT
<213> ORGANISM: Homo sapiens

<400> SEQUENCE: 42

Met Glu Arg Pro Ser Leu Arg Ala Leu Leu Leu Gly Ala Ala Gly Leu
1               5                   10                  15

Leu Leu Leu Leu Pro Leu Ser Ser Ser Ser Ser Asp Thr Cys
            20                  25                  30

Gly Pro Cys Glu Pro Ala Ser Cys Pro Pro Leu Pro Pro Leu Gly Cys
        35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
        115                 120                 125

Ser Gly Cys Gln Leu Arg Ala Ala Ser Gln Arg Ala Glu Ser Arg Gly
130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
            275                 280

<210> SEQ ID NO 43
<211> LENGTH: 206
<212> TYPE: PRT
<213> ORGANISM: Homo sapiens

<400> SEQUENCE: 43

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Ala Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
            85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205

<210> SEQ ID NO 44

<211> LENGTH: 233
<212> TYPE: PRT
<213> ORGANISM: Homo sapiens

<400> SEQUENCE: 44

```
Met Gly Ser Pro Arg Ser Ala Leu Ser Cys Leu Leu Leu His Leu Leu
1               5                   10                  15
Val Leu Cys Leu Gln Ala Gln Glu Gly Pro Gly Arg Gly Pro Ala Leu
            20                  25                  30
Gly Arg Glu Leu Ala Ser Leu Phe Arg Ala Gly Arg Glu Pro Gln Gly
        35                  40                  45
Val Ser Gln Gln His Val Arg Glu Gln Ser Leu Val Thr Asp Gln Leu
    50                  55                  60
Ser Arg Arg Leu Ile Arg Thr Tyr Gln Leu Tyr Ser Arg Thr Ser Gly
65                  70                  75                  80
Lys His Val Gln Val Leu Ala Asn Lys Arg Ile Asn Ala Met Ala Glu
                85                  90                  95
Asp Gly Asp Pro Phe Ala Lys Leu Ile Val Glu Thr Asp Thr Phe Gly
            100                 105                 110
Ser Arg Val Arg Val Arg Gly Ala Glu Thr Gly Leu Tyr Ile Cys Met
        115                 120                 125
Asn Lys Lys Gly Lys Leu Ile Ala Lys Ser Asn Gly Lys Gly Lys Asp
    130                 135                 140
Cys Val Phe Thr Glu Ile Val Leu Glu Asn Asn Tyr Thr Ala Leu Gln
145                 150                 155                 160
Asn Ala Lys Tyr Glu Gly Trp Tyr Met Ala Phe Thr Arg Lys Gly Arg
                165                 170                 175
Pro Arg Lys Gly Ser Lys Thr Arg Gln His Gln Arg Glu Val His Phe
            180                 185                 190
Met Lys Arg Leu Pro Arg Gly His His Thr Thr Glu Gln Ser Leu Arg
        195                 200                 205
Phe Glu Phe Leu Asn Tyr Pro Pro Phe Thr Arg Ser Leu Arg Gly Ser
    210                 215                 220
Gln Arg Thr Trp Ala Pro Glu Pro Arg
225                 230
```

<210> SEQ ID NO 45
<211> LENGTH: 651
<212> TYPE: DNA
<213> ORGANISM: Homo sapiens

<400> SEQUENCE: 45

```
atgggagccg cccgcctgct gcccaacctc actctgtgct tacagctgct gattctctgc    60
tgtcaaactc aggggagaa tcacccgtct cctaatttta accagtacgt gagggaccag   120
ggcgccatga ccgaccagct gagcaggcgg cagatccgcg agtaccaact ctacagcagg   180
accagtggca agcacgtgca ggtcaccggg cgtcgcatct ccgccaccgc cgaggacggc   240
aacaagtttg ccaagctcat agtggagacg gacacgtttg gcagccgggt tcgcatcaaa   300
ggggctgaga gtgagaagta catctgtatg aacaagaggg gcaagctcat cgggaagccc   360
agcgggaaga gcaaagactg cgtgttcacg gagatcgtgc tggagaacaa ctatacggcc   420
ttccagaacg cccggcacga gggctggttc atggccttca gcggcagggg cggcccccgc   480
caggcttccc gcagccgcca gaaccagcgc gaggccccact tcatcaagcg cctctaccaa   540
ggccagctgc ccttccccaa ccacgccgag aagcagaagc agttcgagtt tgtgggctcc   600
```

| | | |
|---|---|---|
| gccccacccc gccggaccaa gcgcacacgg cggccccagc ccctcacgta g | | 651 |

<210> SEQ ID NO 46
<211> LENGTH: 2886
<212> TYPE: DNA
<213> ORGANISM: Homo sapiens

<400> SEQUENCE: 46

| | | |
|---|---|---|
| atgctggccc cgcgcggagc cgccgtcctc ctgctgcacc tggtcctgca gcggtggcta | | 60 |
| gcggcaggcg cccaggccac cccccaggtc tttgaccttc tcccatcttc cagtcagagg | | 120 |
| ctaaacccag cgctctgct gccagtcctg acagaccccg ccctgaatga tctctatgtg | | 180 |
| atttccacct tcaagctgca gactaaaagt tcagccacca tcttcggtct ttactcttca | | 240 |
| actgacaaca gtaaatattt tgaatttact gtgatgggac gcttaaacaa agccatcctc | | 300 |
| cgttacctga agaacgatgg gaaggtgcat ttggtggttt caacaaccct gcagctggca | | 360 |
| gacggaaggc ggcacaggat cctcctgagg ctgagcaatt tgcagcgagg ggccggctcc | | 420 |
| ctagagctct acctggactg catccaggtg gattccgttc acaatctccc cagggccttt | | 480 |
| gctggcccct cccagaaacc tgagaccatt gaattgagga ctttccagag gaagccacag | | 540 |
| gacttcttgg aagagctgaa gctggtggtg agaggctcac tgttccaggt ggccagcctg | | 600 |
| caagactgct tcctgcagca gagtgagcca ctggctgcca caggcacagg gactttaac | | 660 |
| cggcagttct tgggtcaaat gacacaatta aaccaactcc tgggagaggt gaaggacctt | | 720 |
| ctgagacagc aggttaagga acatcatttt tgcgaaaca ccatagctga atgccaggct | | 780 |
| tgcggtcctc tcaagtttca gtctccgacc ccaagcacgg tggtgccccc ggctcccct | | 840 |
| gcaccgccaa cacgcccacc tcgtcggtgt gactccaacc catgtttccg aggtgtccaa | | 900 |
| tgtaccgaca gtagagatgg cttccagtgt gggccctgcc ccgagggcta cacaggaaac | | 960 |
| gggatcacct gtattgatgt tgatgagtgc aaataccatc cctgctaccc gggcgtgcac | | 1020 |
| tgcataaatt tgtctcctgg cttcagatgt gacgcctgcc cagtgggctt cacagggccc | | 1080 |
| atggtgcagg gtgttgggat cagttttgcc aagtcaaaca gcaggtctg cactgacatt | | 1140 |
| gatgagtgtc gaaatggagc gtgcgttccc aactcgatct gcgttaatac tttgggatct | | 1200 |
| taccgctgtg ggccttgtaa gccggggtat actggtgatc agataagggg atgcaaagcg | | 1260 |
| gaaagaaact gcagaaaccc agagctgaac ccttgcagtg tgaatgccca gtgcattgaa | | 1320 |
| gagaggcagg gggatgtgac atgtgtgtgt ggagtcggtt gggctggaga tggctatatc | | 1380 |
| tgtgaaagg atgtggacat cgacagttac cccgacgaag aactgccatg ctctgccagg | | 1440 |
| aactgtaaaa aggacaactg caaatatgtg ccaaattctg gccaagaaga tgcagacaga | | 1500 |
| gatggcattg gcgacgcttg tgacgaggat gctgacggag atgggatcct gaatgagcag | | 1560 |
| gataactgtg tcctgattca taatgtggac caaaggaaca gcgataaaga tatctttggg | | 1620 |
| gatgcctgtg ataactgcct gagtgtctta ataacgacc agaaagacac cgatggggat | | 1680 |
| ggaagaggag atgcctgtga tgatgacatg gatgagatg aataaaaaaa cattctggac | | 1740 |
| aactgcccaa aatttcccaa tcgtgaccaa cgggacaagg atggtgatgg tgtgggggat | | 1800 |
| gcctgtgaca gttgtcctga tgtcagcaac cctaaccagt ctgatgtgga taatgatctg | | 1860 |
| gttggggact cctgtgacac caatcaggac agtgatggag atgggcacca ggacagcaca | | 1920 |
| gacaactgcc ccaccgtcat taacagtgcc cagctggaca ccgataagga tggaattggt | | 1980 |
| gacgagtgtg atgatgatga tgacaatgat ggtatcccag acctggtgcc cctggacca | | 2040 |
| gacaactgcc ggctggtccc caacccagcc caggaggata gcaacagcga cggagtggga | | 2100 |

```
gacatctgtg agtctgactt tgaccaggac caggtcatcg atcggatcga cgtctgccca   2160
gagaacgcag aggtcaccct gaccgacttc agggcttacc agaccgtggt cctggatcct   2220
gaagggatg cccagatcga tcccaactgg gtggtcctga accagggcat ggagattgta    2280
cagaccatga acagtgatcc tggcctggca gtggggtaca cagcttttaa tggagttgac   2340
ttcgaaggga ccttccatgt gaatacccag acagatgatg actatgcagg ctttatcttt   2400
ggctaccaag atagctccag cttctacgtg gtcatgtgga agcagacgga gcagacatat   2460
tggcaagcca ccccattccg agcagttgca gaacctggca ttcagctcaa ggctgtgaag   2520
tctaagacag gtccagggga gcatctccgg aactccctgt ggcacacggg ggacaccagt   2580
gaccaggtca ggctgctgtg gaaggactcc aggaatgtgg gctggaagga caaggtgtcc   2640
taccgctggt tcctacagca caggcccag gtgggctaca tcagggtacg attttatgaa     2700
ggctctgagt tggtggctga ctctggcgtc accatagaca ccacaatgcg tggaggccga   2760
cttggcgttt tctgcttctc tcaagaaaac atcatctggt ccaacctcaa gtatcgctgc   2820
aatgacacca tccctgagga cttccaagag tttcaaaccc agaatttcga ccgcttcgat   2880
aattaa                                                              2886

<210> SEQ ID NO 47
<211> LENGTH: 3519
<212> TYPE: DNA
<213> ORGANISM: Homo sapiens

<400> SEQUENCE: 47
atggtctgga ggctggtcct gctggctctg tgggtgtggc ccagcacgca agctggtcac     60
caggacaaag acacgacctt cgacctttc agtatcagca acatcaaccg caagaccatt    120
ggcgccaagc agttccgcgg gcccgacccc ggcgtgccgg cttaccgctt cgtgcgcttt    180
gactacatcc caccggtgaa cgcagatgac ctcagcaaga tcaccaagat catgcggcag    240
aaggagggct tcttcctcac ggcccagctc aagcaggacg gcaagtccag gggcacgctg    300
ttggctctgg agggccccgg tctctcccag aggcagttcg agatcgtctc caacggcccc    360
gcggacacgc tggatctcac ctactggatt gacggcaccc ggcatgtggt ctccctggag    420
gacgtcggcc tggctgactc gcagtggaag aacgtcaccg tgcaggtggc tggcgagacc    480
tacagcttgc acgtgggctg cgacctcata gacagcttcg ctctggacga gcccttctac    540
gagcacctgc aggcggaaaa gagccggatg tacgtggcca aggctctgca gagagagt     600
cacttcaggg gtttgcttca gaacgtccac ctagtgtttg aaaactctgt ggaagatatt    660
ctaagcaaga agggttgcca gcaaggccag ggagctgaga tcaacgccat cagtgagaac    720
acagagacgc tgcgcctggg tccgcatgtc accaccgagt acgtgggccc cagctcggag    780
aggaggcccg aggtgtgcga acgtcgtgc gaggagctgg aaacatggt ccaggagctc      840
tcggggctcc acgtcctcgt gaaccagctc agcgagaacc tcaagagagt gtcgaatgat    900
aaccagtttc tctgggagct cattggtggc cctcctaaga caaggaacat gtcagcttgc    960
tggcaggatg gccggttctt tgcggaaat gaaacgtggg tggtggacag ctgcaccacg    1020
tgtacctgca agaaatttaa aaccatttgc accaaatca cctgcccgcc tgcaacctgc   1080
gccagtccat cctttgtgga aggcgaatgc tgcccttcct gcctccactc ggtggacggt    1140
gaggaggct ggtctccgtg ggcagagtgg acccagtgct ccgtgacgtg tggctctggg    1200
acccagcaga gaggccggtc ctgtgacgtc accagcaaca cctgcttggg gcctccatc    1260
```

-continued

| | | | | | |
|---|---|---|---|---|---|
| cagacacggg | cttgcagtct | gagcaagtgt | gacacccgca | tccggcagga | cggcggctgg | 1320 |
| agccactggt | caccttggtc | ttcatgctct | gtgacctgtg | gagttggcaa | tatcacacgc | 1380 |
| atccgtctct | gcaactcccc | agtgccccag | atggggggca | agaattgcaa | agggagtggc | 1440 |
| cgggagacca | aagcctgcca | gggcgcccca | tgcccaatcg | atggccgctg | agcccctgg | 1500 |
| tccccgtggt | cggcctgcac | tgtcacctgt | gccggtggga | tccgggagcg | cacccgggtc | 1560 |
| tgcaacagcc | ctgagcctca | gtacggaggg | aaggcctgcg | tggggatgt | gcaggagcgt | 1620 |
| cagatgtgca | acaagaggag | ctgccccgtg | gatggctgtt | tatccaaccc | ctgcttcccg | 1680 |
| ggagcccagt | gcagcagctt | ccccgatggg | tcctggtcat | gcggctcctg | ccctgtgggc | 1740 |
| ttcttgggca | atggcaccca | ctgtgaggac | ctggacgagt | gtgccctggt | ccccgacatc | 1800 |
| tgcttctcca | ccagcaaggt | gcctcgctgt | gtcaacactc | agcctggctt | ccactgcctg | 1860 |
| ccctgcccgc | cccgatacag | agggaaccag | cccgtcgggg | tcggcctgga | agcagccaag | 1920 |
| acggaaaagc | aagtgtgtga | gcccgaaaac | ccatgcaagg | acaagacaca | caactgccac | 1980 |
| aagcacgcgg | agtgcatcta | cctgggccac | ttcagcgacc | ccatgtacaa | gtgcgagtgc | 2040 |
| cagacaggct | acgcgggcga | cgggctcatc | tgcggggagg | actcggacct | ggacggctgg | 2100 |
| cccaacctca | atctggtctg | cgccaccaac | gccacctacc | actgcatcaa | ggataactgc | 2160 |
| ccccatctgc | caaattctgg | gcaggaagac | tttgacaagg | acgggattgg | cgatgcctgt | 2220 |
| gatgatgacg | atgacaatga | cggtgtgacc | gatgagaagg | acaactgcca | gctcctcttc | 2280 |
| aatccccgcc | aggctgacta | tgacaaggat | gaggttgggg | accgctgtga | caactgccct | 2340 |
| tacgtgcaca | cccctgccca | gatcgacaca | gacaacaatg | gagagggtga | cgcctgctcc | 2400 |
| gtggacattg | atggggacga | tgtcttcaat | gaacgagaca | attgtcccta | cgtctacaac | 2460 |
| actgaccaga | gggacacgga | tggtgacggt | gtggggatc | actgtgacaa | ctgcccctg | 2520 |
| gtgcacaacc | ctgaccagac | cgacgtggac | aatgaccttg | ttggggacca | gtgtgacaac | 2580 |
| aacgaggaca | tagatgacga | cggccaccag | aacaaccagg | acaactgccc | ctacatctcc | 2640 |
| aacgccaacc | aggctgacca | tgacagagac | ggccagggcg | acgcctgtga | ccctgatgat | 2700 |
| gacaacgatg | gcgtccccga | tgacagggac | aactgccggc | ttgtgttcaa | cccagaccag | 2760 |
| gaggacttgg | acgtgatgg | acggggtgat | atttgtaaag | atgattttga | caatgacaac | 2820 |
| atcccagata | ttgatgatgt | gtgtcctgaa | aacaatgcca | tcagtgagac | agacttcagg | 2880 |
| aacttccaga | tggtccccctt | ggatcccaaa | gggaccaccc | aaattgatcc | caactgggtc | 2940 |
| attcgccatc | aaggcaagga | gctggttcag | acagccaact | cggacccgg | catcgctgta | 3000 |
| ggttttgacg | agtttgggtc | tgtggacttc | agtggcacat | tctacgtaaa | cactgaccgg | 3060 |
| gacgacgact | atgccggctt | cgtctttggt | taccagtcaa | gcagccgctt | ctatgtggtg | 3120 |
| atgtggaagc | aggtgacgca | gacctactgg | gaggaccagc | ccacgcgggc | ctatggctac | 3180 |
| tccggcgtgt | ccctcaaggt | ggtgaactcc | accacgggga | cgggcgagca | cctgaggaac | 3240 |
| gcgctgtggc | acacggggaa | cacgccgggg | caggtgcgaa | ccttatggca | cgaccccagg | 3300 |
| aacattggct | ggaaggacta | cacggcctat | aggtggcacc | tgactcacag | gcccaagact | 3360 |
| ggctacatca | gagtcttagt | gcatgaagga | aaacaggtca | tggcagactc | aggacctatc | 3420 |
| tatgaccaaa | cctacgctgg | cgggcggctg | ggtctatttg | tcttctctca | agaaatggtc | 3480 |
| tatttctcag | acctcaagta | cgaatgcaga | gatatttaa | | | 3519 |

<210> SEQ ID NO 48
<211> LENGTH: 2886

<212> TYPE: DNA
<213> ORGANISM: Homo sapiens

<400> SEQUENCE: 48

```
atgctggccc cgcgcggagc cgccgtcctc ctgctgcacc tggtcctgca gcggtggcta      60
gcggcaggcg cccaggccac cccccaggtc tttgaccttc tcccatcttc cagtcagagg     120
ctaaacccag gcgctctgct gccagtcctg acagacccg ccctgaatga tctctatgtg      180
atttccacct tcaagctgca gactaaaagt tcagccacca tcttcggtct ttactcttca     240
actgacaaca gtaaatattt tgaatttact gtgatgggac gcttaaacaa agccatcctc     300
cgttacctga agaacgatgg gaaggtgcat ttggtggttt tcaacaacct gcagctggca     360
gacggaaggc ggcacaggat cctcctgagg ctgagcaatt gcagcgagg ggccggctcc      420
ctagagctct acctggactg catccaggtg gattccgttc acaatctccc cagggccttt     480
gctggcccct cccagaaacc tgagaccatt gaattgagga ctttccagag aagccacag      540
gacttcttgg aagagctgaa gctggtggtg agaggctcac tgttccaggt ggccagcctg     600
caagactgct tcctgcagca gagtgagcca ctggctgcca caggcacagg gactttaaac     660
cggcagttct tgggtcaaat gacacaatta aaccaactcc tgggagaggt gaaggacctt     720
ctgagacagc aggttaagga acatcatttt tgcgaaaca ccatagctga atgccaggct      780
tgcggtcctc tcaagtttca gtctccgacc ccaagcacgg tggtgccccc ggctcccct      840
gcaccgccaa cacgcccacc tcgtcggtgt gactccaacc catgtttccg aggtgtccaa     900
tgtaccgaca gtagagatgg cttccagtgt gggccctgcc ccgagggcta cacaggaaac     960
gggatcacct gtattgatgt tgatgagtgc aaataccatc cctgctaccc gggcgtgcac    1020
tgcataaatt tgtctcctgg cttcagatgt gacgcctgcc cagtgggctt cacagggccc    1080
atggtgcagg gtgttgggat cagttttgcc aagtcaaaca gcaggtctg cactgacatt    1140
gatgagtgtc gaaatggagc gtgcgttccc aactcgatct gcgttaatac tttgggatct    1200
taccgctgtg ggccttgtaa gccggggtat actggtgatc agataagggg atgcaaagcg    1260
gaaagaaact gcagaaaccc agagctgaac ccttgcagtg tgaatgccca gtgcattgaa    1320
gagaggcagg gggatgtgac atgtgtgtgt ggagtcggtt gggctggaga tggctatatc    1380
tgtggaaagg atgtggacat cgacagttac cccgacgaag aactgccatg ctctgccagg    1440
aactgtaaaa aggacaactg caaatatgtg ccaaattctg gccaagaaga tgcagacaga    1500
gatggcattg gcgacgcttg tgacgaggat gctgacggag atgggatcct gaatgagcag    1560
gataactgtg tcctgattca taatgtggac caaaggaaca gcgataaaga tatctttggg    1620
gatgcctgtg ataactgcct gagtgtctta aataacgacc agaaagacac cgatgggat    1680
ggaagaggag atgcctgtga tgatgacatg gatgagatg aataaaaaa cattctggac     1740
aactgcccaa aatttcccaa tcgtgaccaa cgggacaagg atggtgatgg tgtggggat     1800
gcctgtgaca gttgtcctga tgtcagcaac cctaaccagt ctgatgtgga taatgatctg    1860
gttggggact cctgtgacac caatcaggac agtgatggag atgggcacca ggacagcaca    1920
gacaactgcc ccaccgtcat taacagtgcc cagctggaca ccgataagga tggaattggt    1980
gacgagtgtg atgatgatga tgacaatgat ggtatcccag acctggtgcc ccctggacca    2040
gacaactgcc ggctggtccc caacccagcc caggaggata gcaacagcga cggagtggga    2100
gacatctgtg agtctgactt tgaccaggac caggtcatcg atcggatcga cgtctgccca    2160
gagaacgcag aggtcaccct gaccgacttc agggcttacc agaccgtggt cctggatcct    2220
```

| | |
|---|---|
| gaaggggatg cccagatcga tcccaactgg gtggtcctga accagggcat ggagattgta | 2280 |
| cagaccatga acagtgatcc tggcctggca gtggggtaca cagcttttaa tggagttgac | 2340 |
| ttcgaaggga ccttccatgt gaatacccag acagatgatg actatgcagg ctttatcttt | 2400 |
| ggctaccaag atagctccag cttctacgtg gtcatgtgga agcagacgga gcagacatat | 2460 |
| tggcaagcca ccccattccg agcagttgca gaacctggca ttcagctcaa ggctgtgaag | 2520 |
| tctaagacag gtccagggga gcatctccgg aactccctgt ggcacacggg ggacaccagt | 2580 |
| gaccaggtca ggctgctgtg gaaggactcc aggaatgtgg gctggaagga caaggtgtcc | 2640 |
| taccgctggt tcctacagca caggcccag gtgggctaca tcagggtacg attttatgaa | 2700 |
| ggctctgagt tggtggctga ctctggcgtc accatagaca ccacaatgcg tggaggccga | 2760 |
| cttggcgttt tctgcttctc tcaagaaaac atcatctggt ccaacctcaa gtatcgctgc | 2820 |
| aatgacacca tccctgagga cttccaagag tttcaaaccc agaatttcga ccgcttcgat | 2880 |
| aattaa | 2886 |

<210> SEQ ID NO 49
<211> LENGTH: 543
<212> TYPE: DNA
<213> ORGANISM: Homo sapiens

<400> SEQUENCE: 49

| | |
|---|---|
| atgggaatcc caatggggaa gtcgatgctg gtgcttctca ccttcttggc cttcgcctcg | 60 |
| tgctgcattg ctgcttaccg ccccagtgag accctgtgcg gcggggagct ggtggacacc | 120 |
| ctccagttcg tctgtgggga ccgcggcttc tacttcagca ggcccgcaag ccgtgtgagc | 180 |
| cgtcgcagcc gtggcatcgt tgaggagtgc tgtttccgca gctgtgacct ggccctcctg | 240 |
| gagacgtact gtgctacccc cgccaagtcc gagagggacg tgtcgacccc tccgaccgtg | 300 |
| cttccggaca acttccccag ataccccgtg ggcaagttct ccaatatga cacctggaag | 360 |
| cagtccaccc agcgcctgcg caggggcctg cctgccctcc tgcgtgcccg ccggggtcac | 420 |
| gtgctcgcca aggagctcga ggcgttcagg gaggccaaac gtcaccgtcc cctgattgct | 480 |
| ctacccaccc aagaccccgc ccacggggc gccccccag agatggccag caatcggaag | 540 |
| tga | 543 |

<210> SEQ ID NO 50
<211> LENGTH: 489
<212> TYPE: DNA
<213> ORGANISM: Homo sapiens

<400> SEQUENCE: 50

| | |
|---|---|
| atgagaattt cgaaaccaca tttgagaagt atttccatcc agtgctactt gtgtttactt | 60 |
| ctaaacagtc attttctaac tgaagctggc attcatgtct tcattttggg ctgtttcagt | 120 |
| gcagggcttc ctaaaacaga agccaactgg gtgaatgtaa taagtgattt gaaaaaaatt | 180 |
| gaagatctta ttcaatctat gcatattgat gctactttat atacggaaag tgatgttcac | 240 |
| cccagttgca aagtaacagc aatgaagtgc tttctcttgg agttacaagt tatttcactt | 300 |
| gagtccggag atgcaagtat tcatgataca gtagaaaatc tgatcatcct agcaaacaac | 360 |
| agtttgtctt ctaatgggaa tgtaacagaa tctggatgca aagaatgtga ggaactggag | 420 |
| gaaaaaaata ttaaagaatt tttgcagagt tttgtacata ttgtccaaat gttcatcaac | 480 |
| acttcttga | 489 |

-continued

```
<210> SEQ ID NO 51
<211> LENGTH: 849
<212> TYPE: DNA
<213> ORGANISM: Homo sapiens

<400> SEQUENCE: 51
atggagcggc cgtcgctgcg cgccctgctc ctcggcgccg ctgggctgct gctcctgctc      60
ctgcccctct cctcttcctc ctcttcggac acctgcggcc cctgcgagcc ggcctcctgc     120
ccgcccctgc ccccgctggg ctgcctgctg ggcgagaccc gcgacgcgtg cggctgctgc     180
cctatgtgcg cccgcggcga gggcgagccg tgcggggggtg gcggcgccgg caggggggtac     240 tgcgcgccgg gcatggagtg cgtgaagagc cgcaagaggc ggaagggtaa agccggggca     300
gcagccggcg gtccgggtgt aagcggcgtg tgcgtgtgca agagccgcta cccggtgtgc     360
ggcagcgacg gcaccaccta cccgagcggc tgccagctgc gcgccgccag ccagagggcc     420
gagagccgcg gggagaaggc catcacccag gtcagcaagg gcacctgcga gcaaggtcct     480
tccatagtga cgccccccaa ggacatctgg aatgtcactg gtgcccaggt gtacttgagc     540
tgtgaggtca tcggaatccc gacacctgtc ctcatctgga caaggtaaa aaggggtcac     600 tatggagttc aaaggacaga actcctgcct ggtgaccggg acaacctggc cattcagacc     660
cggggtggcc cagaaaagca tgaagtaact ggctgggtgc tggtatctcc tctaagtaag     720
gaagatgctg gagaatatga gtgccatgca tccaattccc aaggacaggc ttcagcatca     780
gcaaaaatta cagtggttga tgccttacat gaaataccag tgaaaaaagg tgaaggtgcc     840
gagctataa                                                              849

<210> SEQ ID NO 52
<211> LENGTH: 1437
<212> TYPE: DNA
<213> ORGANISM: Homo sapiens

<400> SEQUENCE: 52
atggcacccc tgagacccct ctcatactg gccctgctgg catgggttgc tctggctgac      60
caagagtcat gcaagggccg ctgcactgag ggcttcaacg tggacaagaa gtgccagtgt     120
gacgagctct gctcttacta ccagagctgc tgcacagact atacggctga gtgcaagccc     180
caagtgactc gcggggatgt gttcactatg ccggaggatg agtacacggt ctatgacgat     240
ggcgaggaga aaaacaatgc cactgtccat gaacaggtgg ggggcccctc cctgacctct     300
gacctccagg cccagtccaa agggaatcct gagcagacac tgttctgaa acctgaggaa     360 gaggcccctg cgcctgaggt gggcgcctct aagcctgagg ggatagactc aaggcctgag     420
acccttcatc cagggagacc tcagcccccca gcagaggagg agctgtgcag tgggaagccc     480
ttcgacgcct tcaccgacct caagaacggt tccctctttg ccttccgagg gcagtactgc     540
tatgaactgg acgaaaaggc agtgaggcct gggtacccca agctcatccg agatgtctgg     600
ggcatcgagg gccccatcga tgccgccttc acccgcatca actgtcaggg gaagacctac     660
ctcttcaagg gtagtcagta ctggcgcttt gaggatggtg tcctggaccc tgattacccc     720
cgaaatatct ctgacggctt cgatggcatc ccggacaacg tggatgcagc cttggccctc     780
cctgcccata gctacagtgg ccgggagcgg gtctacttct tcaaggggaa acagtactgg     840
gagtaccagt tccagcacca gcccagtcag gaggagtgtg aaggcagctc cctgtcggct     900
gtgtttgaac acttgccat gatgcagcgg gacagctggg aggacatctt cgagcttctc     960 ttctgggca gaacctctgc tggtaccaga cagccccagt tcattagccg ggactggcac    1020
```

```
ggtgtgccag ggcaagtgga cgcagccatg gctggccgca tctacatctc aggcatggca    1080
ccccgcccct ccttggccaa gaaacaaagg tttaggcatc gcaaccgcaa aggctaccgt    1140
tcacaacgag gccacagccg tggccgcaac cagaactccc gccggccatc ccgcgccacg    1200
tggctgtcct tgttctccag tgaggagagc aacttgggag ccaacaacta tgatgactac    1260
aggatggact ggcttgtgcc tgccacctgt gaacccatcc agagtgtctt cttcttctct    1320
ggagacaagt actaccgagt caatcttcgc acacggcgag tggacactgt ggaccctccc    1380
tacccacgct ccatcgctca gtactggctg ggctgcccag ctcctggcca tctgtag       1437
```

<210> SEQ ID NO 53
<211> LENGTH: 2511
<212> TYPE: DNA
<213> ORGANISM: Homo sapiens

<400> SEQUENCE: 53

```
atgattccct ttttacccat gttttctcta ctattgctgc ttattgttaa ccctataaac      60
gccaacaatc attatgacaa gatcttggct catagtcgta tcaggggtcg ggaccaaggc     120
ccaaatgtct gtgcccttca acagattttg ggcaccaaaa agaaatactt cagcacttgt     180
aagaactggt ataaaaagtc catctgtgga cagaaaacga ctgtgttata tgaatgttgc     240
cctggttata tgagaatgga aggaatgaaa ggctgcccag cagttttgcc cattgaccat     300
gtttatggca ctctgggcat cgtgggagcc accacaacgc agcgctattc tgacgcctca     360
aaactgaggg aggagatcga gggaagggga tccttcactt actttgcacc gagtaatgag     420
gcttgggaca acttggattc tgatatccgt agaggtttgg agagcaacgt gaatgttgaa     480
ttactgaatg ctttacatag tcacatgatt aataagagaa tgttgaccaa ggacttaaaa     540
aatggcatga ttattccttc aatgtataac aatttggggc ttttcattaa ccattatcct     600
aatggggttg tcactgttaa ttgtgctcga atcatccatg gaaccagat gcaacaaat      660 ggtgttgtcc atgtcattga ccgtgtgctt acacaaattg gtacctcaat tcaagacttc     720
attgaagcag aagatgacct ttcatctttt agagcagctg ccatcacatc ggacatattg     780
gaggcccttg aagagacgg tcacttcaca ctctttgctc ccaccaatga ggcttttgag      840
aaacttccac gaggtgtcct agaaaggatc atgggagaca aagtggcttc cgaagctctt     900
atgaagtacc acatcttaaa tactctccag tgttctgagt ctattatggg aggagcagtc     960
tttgagacgc tggaaggaaa tacaattgag ataggatgtg acggtgacag tataacagta    1020
aatgaatcaa aaatggtgaa caaaaaggat attgtgacaa ataatggtgt gatccatttg    1080
attgatcagg tcctaattcc tgattctgcc aaacaagtta ttgagctggc tggaaaacag    1140
caaaccacct tcacggatct gtggcccaa ttaggcttgg catctgctct gaggccagat     1200
ggagaataca ctttgctggc acctgtgaat aatgcatttt ctgatgatac tctcagcatg    1260
gatcagcgcc tccttaaatt aattctgcag aatcacatat tgaaagtaaa agttggcctt    1320
aatgagcttt acaacgggca atactggaa accatcggag gcaaacagct cagagtcttc    1380
gtatatcgta cagctgtctg cattgaaaat tcatgcatgg agaaagggag taagcaaggg    1440
agaaacggtg cgattcacat attccgcgag atcatcaagc cagcagagaa atccctccat    1500
gaaaagttaa acaagataa gcgctttagc accttcctca gcctacttga agctgcagac    1560
ttgaaagagc tcctgacaca acctggagac tggacattat ttgtgccaac caatgatgct    1620
tttaagggaa tgactagtga agaaaaagaa attctgatac gggacaaaaa tgctcttcaa    1680
aacatcattc tttatcacct gacaccagga gttttcattg gaaaaggatt tgaacctggt    1740
```

```
gttactaaca ttttaaagac cacacaagga agcaaaatct ttctgaaaga agtaaatgat   1800
acacttctgg tgaatgaatt gaaatcaaaa gaatctgaca tcatgacaac aaatggtgta   1860
attcatgttg tagataaact cctctatcca gcagacacac ctgttggaaa tgatcaactg   1920
ctggaaatac ttaataaatt aatcaaatac atccaaatta agtttgttcg tggtagcacc   1980
ttcaaagaaa tccccgtgac tgtctataca actaaaatta taaccaaagt tgtggaacca   2040
aaaattaaag tgattgaagg cagtcttcag cctattatca aaactgaagg acccacacta   2100
acaaaagtca aaattgaagg tgaacctgaa ttcagactga ttaagaagg tgaaacaata    2160 actgaagtga tccatggaga gccaattatt aaaaaataca ccaaaatcat tgatggagtg   2220
cctgtggaaa taactgaaaa agagacacga gaagaacgaa tcattacagg tcctgaaata   2280
aaatacacta ggatttctac tggaggtgga gaaacagaag aaactctgaa gaaattgtta   2340
caagaagagg tcaccaaggt caccaaattc attgaaggtg gtgatggtca tttatttgaa   2400
gatgaagaaa ttaaaagact gcttcaggga gacacacccg tgaggaagtt gcaagccaac   2460
aaaaaagttc aaggatctag aagacgatta agggaaggtc gttctcagtg a            2511

<210> SEQ ID NO 54
<211> LENGTH: 1128
<212> TYPE: DNA
<213> ORGANISM: Homo sapiens

<400> SEQUENCE: 54
atgaaggtct ggctgctgct tggtcttctg ctggtgcacg aagcgctgga ggatgttact     60
ggccaacacc ttcccaagaa caagcgtcca aaagaaccag gagagaatag aatcaaacct   120
accaacaaga aggtgaagcc caaaattcct aaaatgaagg acagggactc agccaattca   180
gcaccaaaga cgcagtctat catgatgcaa gtgctggata aaggtcgctt ccagaaaccc   240
gccgctaccc tgagtctgct ggcggggcaa actgtagagc ttcgatgtaa agggagtaga   300
attgggtgga gctaccctgc gtatctggac accttaaagg attctcgcct cagcgtcaag   360
cagaatgagc gctacggcca gttgactctg gtcaactcca cctcggcaga cacaggtgaa   420
ttcagctgct gggtgcagct ctgcagcggc tacatctgca ggaaggacga ggccaaaacg   480
ggctccacct acatcttttt tacagagaaa ggagaactct ttgtaccttc tcccagctac   540
ttcgatgttg tctacttgaa cccggacaga caggctgtgg ttccttgtcg ggtgaccgtg   600
ctgtcggcca aagtcacgct ccacaggaa ttcccagcca aggagatccc agccaatgga   660
acggacattt ttatgacat gaagcggggc tttgtgtatc tgcaacctca ttccgagcac   720
cagggtgtgg tttactgcag ggcggaggcc ggggcagat ctcagatctc cgtcaagtac   780
cagctgctct acgtggcggt tcccagtggc cctcccctcaa caaccatctt ggcttcttca   840
aacaaagtga aagtggggac gacatcagt gtgctctgca ctgtcctggg ggagcccgat   900
gtggaggtgg agttcacctg gatcttccca ggcagaagg atgaaaggcc tgtgacgatc   960
caagacactt ggaggttgat ccacagagga ctgggacaca ccacgagaat ctcccagagt   1020
gtcattacag tggaagactt tgagacgatt gatgcaggat attacatttg cactgctcag   1080
aatcttcaag acagaccac agtagctacc actgttgagt tttcctga                1128

<210> SEQ ID NO 55
<211> LENGTH: 375
<212> TYPE: PRT
<213> ORGANISM: Homo sapiens
```

<400> SEQUENCE: 55

```
Met Lys Val Trp Leu Leu Gly Leu Leu Val His Glu Ala Leu
  1               5                  10                  15

Glu Asp Val Thr Gly Gln His Leu Pro Lys Asn Lys Arg Pro Lys Glu
             20                  25                  30

Pro Gly Glu Asn Arg Ile Lys Pro Thr Asn Lys Lys Val Lys Pro Lys
         35                  40                  45

Ile Pro Lys Met Lys Asp Arg Asp Ser Ala Asn Ser Ala Pro Lys Thr
 50                  55                  60

Gln Ser Ile Met Met Gln Val Leu Asp Lys Gly Arg Phe Gln Lys Pro
 65                  70                  75                  80

Ala Ala Thr Leu Ser Leu Leu Ala Gly Gln Thr Val Glu Leu Arg Cys
                 85                  90                  95

Lys Gly Ser Arg Ile Gly Trp Ser Tyr Pro Ala Tyr Leu Asp Thr Phe
                100                 105                 110

Lys Asp Ser Arg Leu Ser Val Lys Gln Asn Glu Arg Tyr Gly Gln Leu
            115                 120                 125

Thr Leu Val Asn Ser Thr Ser Ala Asp Thr Gly Glu Phe Ser Cys Trp
    130                 135                 140

Val Gln Leu Cys Ser Gly Tyr Ile Cys Arg Lys Asp Glu Ala Lys Thr
145                 150                 155                 160

Gly Ser Thr Tyr Ile Phe Phe Thr Glu Lys Gly Glu Leu Phe Val Pro
                165                 170                 175

Ser Pro Ser Tyr Phe Asp Val Val Tyr Leu Asn Pro Asp Arg Gln Ala
            180                 185                 190

Val Val Pro Cys Arg Val Thr Val Leu Ser Ala Lys Val Thr Leu His
        195                 200                 205

Arg Glu Phe Pro Ala Lys Glu Ile Pro Ala Asn Gly Thr Asp Ile Val
210                 215                 220

Tyr Asp Met Lys Arg Gly Phe Val Tyr Leu Gln Pro His Ser Glu His
225                 230                 235                 240

Gln Gly Val Val Tyr Cys Arg Ala Glu Ala Gly Gly Arg Ser Gln Ile
                245                 250                 255

Ser Val Lys Tyr Gln Leu Leu Tyr Val Ala Val Pro Ser Gly Pro Pro
            260                 265                 270

Ser Thr Thr Ile Leu Ala Ser Ser Asn Lys Val Lys Ser Gly Asp Asp
        275                 280                 285

Ile Ser Val Leu Cys Thr Val Leu Gly Glu Pro Asp Val Glu Val Glu
290                 295                 300

Phe Thr Trp Ile Phe Pro Gly Gln Lys Asp Glu Arg Pro Val Thr Ile
305                 310                 315                 320

Gln Asp Thr Trp Arg Leu Ile His Arg Gly Leu Gly His Thr Thr Arg
                325                 330                 335

Ile Ser Gln Ser Val Ile Thr Val Glu Asp Phe Glu Thr Ile Asp Ala
            340                 345                 350

Gly Tyr Tyr Ile Cys Thr Ala Gln Asn Leu Gln Gly Gln Thr Thr Val
        355                 360                 365

Ala Thr Thr Val Glu Phe Ser
    370                 375
```

<210> SEQ ID NO 56
<211> LENGTH: 679
<212> TYPE: PRT
<213> ORGANISM: Homo sapiens

<400> SEQUENCE: 56

```
Met Val Pro Gly Val Pro Gly Ala Val Leu Thr Leu Cys Leu Trp Leu
1               5                   10                  15
Ala Ala Ser Ser Gly Cys Leu Ala Ala Gly Pro Gly Ala Ala Ala Ala
            20                  25                  30
Arg Arg Leu Asp Glu Ser Leu Ser Ala Gly Ser Val Gln Arg Ala Arg
        35                  40                  45
Cys Ala Ser Arg Cys Leu Ser Leu Gln Ile Thr Arg Ile Ser Ala Phe
    50                  55                  60
Phe Gln His Phe Gln Asn Asn Gly Ser Leu Val Trp Cys Gln Asn His
65                  70                  75                  80
Lys Gln Cys Ser Lys Leu Glu Pro Cys Lys Glu Ser Gly Asp Leu Arg
                85                  90                  95
Lys His Gln Cys Gln Ser Phe Cys Glu Pro Leu Phe Pro Lys Lys Ser
            100                 105                 110
Tyr Glu Cys Leu Thr Ser Cys Glu Phe Leu Lys Tyr Ile Leu Leu Val
        115                 120                 125
Lys Gln Gly Asp Cys Pro Ala Pro Glu Lys Ala Ser Gly Phe Ala Ala
    130                 135                 140
Ala Cys Val Glu Ser Cys Glu Val Asp Asn Glu Cys Ser Gly Val Lys
145                 150                 155                 160
Lys Cys Cys Ser Asn Gly Cys Gly His Thr Cys Gln Val Pro Lys Thr
                165                 170                 175
Leu Tyr Lys Gly Val Pro Leu Lys Pro Arg Lys Glu Leu Arg Phe Thr
            180                 185                 190
Glu Leu Gln Ser Gly Gln Leu Glu Val Lys Trp Ser Ser Lys Phe Asn
        195                 200                 205
Ile Ser Ile Glu Pro Val Ile Tyr Val Val Gln Arg Arg Trp Asn Tyr
    210                 215                 220
Gly Ile His Pro Ser Glu Asp Ala Thr His Trp Gln Thr Val Ala
225                 230                 235                 240
Gln Thr Thr Asp Glu Arg Val Gln Leu Thr Asp Ile Arg Pro Ser Arg
                245                 250                 255
Trp Tyr Gln Phe Arg Val Ala Ala Val Asn Val His Gly Thr Arg Gly
            260                 265                 270
Phe Thr Ala Pro Ser Lys His Phe Arg Ser Ser Lys Asp Pro Ser Ala
        275                 280                 285
Pro Pro Ala Pro Ala Asn Leu Arg Leu Ala Asn Ser Thr Val Asn Ser
    290                 295                 300
Asp Gly Ser Val Thr Val Thr Ile Val Trp Asp Leu Pro Glu Glu Pro
305                 310                 315                 320
Asp Ile Pro Val His His Tyr Lys Val Phe Trp Ser Trp Met Val Ser
                325                 330                 335
Ser Lys Ser Leu Val Pro Thr Lys Lys Arg Arg Lys Thr Thr Asp
            340                 345                 350
Gly Phe Gln Asn Ser Val Ile Leu Glu Lys Leu Gln Pro Asp Cys Asp
        355                 360                 365
Tyr Val Val Glu Leu Gln Ala Ile Thr Tyr Trp Gly Gln Thr Arg Leu
    370                 375                 380
Lys Ser Ala Lys Val Ser Leu His Phe Thr Ser Thr His Ala Thr Asn
385                 390                 395                 400
Asn Lys Glu Gln Leu Val Lys Thr Arg Lys Gly Gly Ile Gln Thr Gln
```

```
                    405                 410                 415
Leu Pro Phe Gln Arg Arg Pro Thr Arg Pro Leu Glu Val Gly Ala
            420                 425                 430

Pro Phe Tyr Gln Asp Gly Gln Leu Gln Val Lys Val Tyr Trp Lys Lys
            435                 440                 445

Thr Glu Asp Pro Thr Val Asn Arg Tyr His Val Arg Trp Phe Pro Glu
        450                 455                 460

Ala Cys Ala His Asn Arg Thr Thr Gly Ser Glu Ala Ser Ser Gly Met
465                 470                 475                 480

Thr His Glu Asn Tyr Ile Ile Leu Gln Asp Leu Ser Phe Ser Cys Lys
                485                 490                 495

Tyr Lys Val Thr Val Gln Pro Ile Arg Pro Lys Ser His Ser Lys Ala
            500                 505                 510

Glu Ala Val Phe Phe Thr Thr Pro Pro Cys Ser Ala Leu Lys Gly Lys
            515                 520                 525

Ser His Lys Pro Val Gly Cys Leu Gly Glu Ala Gly His Val Leu Ser
        530                 535                 540

Lys Val Leu Ala Lys Pro Glu Asn Leu Ser Ala Ser Phe Ile Val Gln
545                 550                 555                 560

Asp Val Asn Ile Thr Gly His Phe Ser Trp Lys Met Ala Lys Ala Asn
                565                 570                 575

Leu Tyr Gln Pro Met Thr Gly Phe Gln Val Thr Trp Ala Glu Val Thr
            580                 585                 590

Thr Glu Ser Arg Gln Asn Ser Leu Pro Asn Ser Ile Ile Ser Gln Ser
            595                 600                 605

Gln Ile Leu Pro Ser Asp His Tyr Val Leu Thr Val Pro Asn Leu Arg
        610                 615                 620

Pro Ser Thr Leu Tyr Arg Leu Glu Val Gln Val Leu Thr Pro Gly Gly
625                 630                 635                 640

Glu Gly Pro Ala Thr Ile Lys Thr Phe Arg Thr Pro Glu Leu Pro Pro
                645                 650                 655

Ser Ser Ala His Arg Ser His Leu Lys His Arg His Pro His His Tyr
            660                 665                 670

Lys Pro Ser Pro Glu Arg Tyr
            675
```

<210> SEQ ID NO 57
<211> LENGTH: 2043
<212> TYPE: DNA
<213> ORGANISM: Homo sapiens

<400> SEQUENCE: 57

```
atggtgcccg gggtgcccgg cgcggtcctg accctctgcc tctggctggc ggcctccagc      60
ggctgcctgg cggccggccc cggcgcggct gctgcgcggc ggctggacga gtcgctgtct     120
gccgggagcg tccagcgcgc tcgctgcgcc tccaggtgcc tgagcctgca gatcactcgc     180
atctccgcct tcttccagca cttccagaac aatggttccc tggtttggtg ccagaatcac     240
aagcaatgtt ctaagtgcct ggagccctgc aaggaatcag gggacctgag gaaacaccag     300
tgccaaagct tttgtgagcc tctcttcccc aagaagagct acgaatgctt gaccagctgt     360
gagttcctca atacatcctg gttggtgaag caggggact gtccggctcc tgagaaagcc     420
agtggatttg cggccgcctg tgttgaaagc tgcgaagttg acaatgagtg ctctggggtg     480
aagaaatgtt gttcgaatgg ggtgtggaca cacctgtcaag tacccaagac tctgtacaaa     540
```

```
ggtgtccccc tgaagcccag aaaagagtta cgatttacag aactgcagtc tggacagctg    600
gaggttaagt ggtcctcgaa attcaatatt tctattgagc ctgtgatcta tgtggtacaa    660
agaagatgga attatggaat ccatcctagc gaagatgacg ccactcactg gcagacagtg    720
gcccagacca cagacgagcg agttcaactg actgacataa gacccagccg atggtaccag    780
tttcgagtgg ctgctgtgaa tgtgcatgga actcgaggct tcactgcccc cagcaaacac    840
ttccgttctt ccaaagatcc atctgcccca ccagcaccgg ctaacctccg gctgccaaac    900
tccaccgtca acagtgatgg gagtgtgacc gtcactatag tttgggatct ccccgaggag    960
ccggacatcc ctgtgcatca ttacaaggtc ttttggagct ggatggtcag cagtaagtct   1020
cttgtcccaa caagaagaa gcggagaaag actacggatg ggtttcaaaa ttctgtgatc   1080
ctggagaaac tccagccaga ctgtgactat gttgtggaat tgcaagccat aacgtactgg   1140
ggacagacac ggctgaagag tgcaaaggtg tcccttcact tcacatcgac acatgcaacc   1200
aacaacaaag aacagcttgt gaaaactaga aaggtggaa ttcaaacaca actccctttt   1260
caaagacgac gacccactcg cccgctggaa gtcggagctc ccttctatca ggatggccaa   1320
ctgcaagtta aagtctactg gaagaagaca gaagatccca ctgtcaaccg atatcatgtg   1380
cggtggtttc ctgaagcgtg tgcccacaac agaacaaccg gatcagaggc atcatctggc   1440
atgacccacg aaaattacat aattcttcaa gatctgtcat tttcctgcaa gtataaggtg   1500
actgtccaac caatacggcc aaaaagtcac tccaaggcag aagctgtttt cttcactact   1560
ccaccatgct ctgctcttaa ggggaagagc cacaagcctg ttggctgcct gggcgaagca   1620
ggtcatgttc tttctaaggt gctagctaag cctgagaacc tttctgcttc attcatcgtc   1680
caggatgtga acatcaccgg tcactttct tggaagatgg ccaaggccaa tctctatcag   1740
cccatgactg ggtttcaagt gacttgggct gaggtcacta cggaaagcag acagaacagc   1800
ctacccaaca gcattatttc acagtcccag atcctgcctt ccgatcatta tgtcctaaca   1860
gtgcccaatc tgagaccatc tactctttac cgactggaag tgcaagtgct gaccccagga   1920
ggggaggggc cggccaccat caagacgttc cggacgccgg agctcccacc ctcttcagca   1980
cacagatctc atcttaagca tcgtcatcca catcattaca agccttctcc agaaagatac   2040
taa                                                                  2043
```

<210> SEQ ID NO 58
<211> LENGTH: 1085
<212> TYPE: PRT
<213> ORGANISM: Homo sapiens

<400> SEQUENCE: 58

```
Met Gly Leu Ala Trp Gly Leu Gly Val Leu Phe Leu Met His Val Cys
1               5                   10                  15

Gly Thr Leu Leu Ala Leu Glu Arg Lys Asp His Ser Gly Gln Val Phe
                20                  25                  30

Ser Val Val Ser Asn Gly Lys Ala Gly Thr Leu Asp Leu Ser Leu Thr
            35                  40                  45

Val Gln Gly Lys Gln His Val Val Ser Val Glu Glu Ala Leu Leu Ala
        50                  55                  60

Thr Gly Gln Trp Lys Ser Ile Thr Leu Phe Val Gln Glu Asp Arg Ala
    65                  70                  75                  80

Gln Leu Tyr Ile Asp Cys Glu Lys Met Glu Asn Ala Glu Leu Asp Val
                85                  90                  95

Pro Ile Gln Ser Val Phe Thr Arg Asp Leu Ala Ser Ile Ala Arg Leu
```

-continued

```
              100                 105                 110
Arg Ile Ala Lys Gly Gly Val Asn Asp Asn Phe Gln Gly Val Leu Gln
            115                 120                 125

Asn Val Arg Phe Val Phe Gly Thr Thr Pro Glu Asp Ile Leu Arg Asn
            130                 135                 140

Lys Gly Cys Ser Ser Ser Thr Ser Val Leu Leu Thr Leu Asp Asn Asn
145                 150                 155                 160

Val Val Asn Gly Ser Ser Pro Ala Ile Arg Thr Asn Tyr Ile Gly His
                165                 170                 175

Lys Thr Lys Asp Leu Gln Ala Ile Cys Gly Ile Ser Cys Asp Glu Leu
            180                 185                 190

Ser Ser Met Val Leu Glu Leu Arg Gly Leu Arg Thr Ile Val Thr Thr
            195                 200                 205

Leu Gln Asp Ser Ile Arg Lys Val Thr Glu Glu Asn Lys Glu Leu Ala
            210                 215                 220

Asn Glu Leu Arg Arg Pro Pro Leu Cys Tyr His Asn Gly Val Gln Tyr
225                 230                 235                 240

Arg Asn Asn Glu Glu Trp Thr Val Asp Ser Cys Thr Glu Cys His Cys
                245                 250                 255

Gln Asn Ser Val Thr Ile Cys Lys Lys Val Ser Cys Pro Ile Met Pro
                260                 265                 270

Cys Ser Asn Ala Thr Val Pro Asp Gly Glu Cys Cys Pro Arg Cys Trp
            275                 280                 285

Pro Ser Asp Ser Ala Asp Asp Gly Trp Ser Pro Trp Ser Glu Trp Thr
            290                 295                 300

Ser Cys Ser Thr Ser Cys Gly Asn Gly Ile Gln Gln Arg Gly Arg Ser
305                 310                 315                 320

Cys Asp Ser Leu Asn Asn Arg Cys Glu Gly Ser Ser Val Gln Thr Arg
                325                 330                 335

Thr Cys His Ile Gln Glu Cys Asp Lys Arg Phe Lys Gln Asp Gly Gly
                340                 345                 350

Trp Ser His Trp Ser Pro Trp Ser Ser Cys Ser Val Thr Cys Gly Asp
            355                 360                 365

Gly Val Ile Thr Arg Ile Arg Leu Cys Asn Ser Pro Ser Pro Gln Met
            370                 375                 380

Asn Gly Lys Pro Cys Glu Gly Glu Ala Arg Glu Thr Lys Ala Cys Lys
385                 390                 395                 400

Lys Asp Ala Cys Pro Ile Asn Gly Gly Trp Gly Pro Trp Ser Pro Trp
                405                 410                 415

Asp Ile Cys Ser Val Thr Cys Gly Gly Gly Val Gln Lys Arg Ser Arg
                420                 425                 430

Leu Cys Asn Asn Pro Thr Pro Gln Phe Gly Gly Lys Asp Cys Val Gly
            435                 440                 445

Asp Val Thr Glu Asn Gln Ile Cys Asn Lys Gln Asp Cys Pro Ile Asp
            450                 455                 460

Gly Cys Leu Ser Asn Pro Cys Phe Ala Gly Val Lys Cys Thr Ser Tyr
465                 470                 475                 480

Pro Asp Gly Ser Trp Lys Cys Gly Ala Cys Pro Pro Gly Tyr Ser Gly
                485                 490                 495

Asn Gly Ile Gln Cys Thr Asp Val Asp Glu Cys Lys Glu Val Pro Asp
                500                 505                 510

Ala Cys Phe Asn His Asn Gly Glu His Arg Cys Glu Asn Thr Asp Pro
            515                 520                 525
```

Gly Tyr Asn Cys Leu Pro Cys Pro Arg Phe Thr Gly Ser Gln Pro
    530                 535                 540

Phe Gly Gln Gly Val Glu His Ala Thr Ala Asn Lys Gln Val Cys Lys
545                 550                 555                 560

Pro Arg Asn Pro Cys Thr Asp Gly Thr His Asp Cys Asn Lys Asn Ala
                565                 570                 575

Lys Cys Asn Tyr Leu Gly His Tyr Ser Asp Pro Met Tyr Arg Cys Glu
            580                 585                 590

Cys Lys Pro Gly Tyr Ala Gly Asn Gly Ile Ile Cys Gly Glu Asp Thr
        595                 600                 605

Asp Leu Asp Gly Trp Pro Asn Glu Asn Leu Val Cys Val Ala Asn Ala
    610                 615                 620

Thr Tyr His Cys Lys Lys Asp Asn Cys Pro Asn Leu Pro Asn Ser Gly
625                 630                 635                 640

Gln Glu Asp Tyr Asp Lys Asp Gly Ile Gly Asp Ala Cys Asp Asp Asp
                645                 650                 655

Asp Asp Asn Asp Lys Ile Pro Asp Asp Arg Asp Asn Cys Pro Phe His
            660                 665                 670

Tyr Asn Pro Ala Gln Tyr Asp Tyr Asp Arg Asp Asp Val Gly Asp Arg
        675                 680                 685

Cys Asp Asn Cys Pro Tyr Asn His Asn Pro Asp Gln Ala Asp Thr Asp
    690                 695                 700

Asn Asn Gly Glu Gly Asp Ala Cys Ala Ala Asp Ile Asp Gly Asp Gly
705                 710                 715                 720

Ile Leu Asn Glu Arg Asp Asn Cys Gln Tyr Val Tyr Asn Val Asp Gln
                725                 730                 735

Arg Asp Thr Asp Met Asp Gly Val Gly Asp Gln Cys Asp Asn Cys Pro
            740                 745                 750

Leu Glu His Asn Pro Asp Gln Leu Asp Ser Asp Ser Asp Arg Ile Gly
        755                 760                 765

Asp Thr Cys Asp Asn Asn Gln Asp Ile Asp Glu Asp Gly His Gln Asn
    770                 775                 780

Asn Leu Asp Asn Cys Pro Tyr Val Pro Asn Ala Asn Gln Ala Asp His
785                 790                 795                 800

Asp Lys Asp Gly Lys Gly Asp Ala Cys Asp His Asp Asp Asp Asn Asp
                805                 810                 815

Gly Ile Pro Asp Asp Lys Asp Asn Cys Arg Leu Val Pro Asn Pro Asp
            820                 825                 830

Gln Lys Asp Ser Asp Gly Asp Gly Arg Gly Asp Ala Cys Lys Asp Asp
        835                 840                 845

Phe Asp His Asp Ser Val Pro Asp Ile Asp Asp Ile Cys Pro Glu Asn
    850                 855                 860

Val Asp Ile Ser Glu Thr Asp Phe Arg Arg Phe Gln Met Ile Pro Leu
865                 870                 875                 880

Asp Pro Lys Gly Thr Ser Gln Asn Asp Pro Asn Trp Val Val Arg His
                885                 890                 895

Gln Gly Lys Glu Leu Val Gln Thr Val Asn Cys Asp Pro Gly Leu Ala
            900                 905                 910

Val Gly Tyr Asp Glu Phe Asn Ala Val Asp Phe Ser Gly Thr Phe Phe
        915                 920                 925

Ile Asn Thr Glu Arg Asp Asp Asp Tyr Ala Gly Phe Val Phe Gly Tyr
    930                 935                 940

```
Gln Ser Ser Ser Arg Phe Tyr Val Val Met Trp Lys Gln Val Thr Gln
945                 950                 955                 960

Ser Tyr Trp Asp Thr Asn Pro Thr Arg Ala Gln Gly Tyr Ser Gly Leu
                965                 970                 975

Ser Val Lys Val Val Asn Ser Thr Thr Gly Pro Gly Glu His Leu Arg
            980                 985                 990

Asn Ala Leu Trp His Thr Gly Asn Thr Pro Gly Gln Val Arg Thr Leu
        995                 1000                1005

Trp His Asp Pro Arg His Ile Gly Trp Lys Asp Phe Thr Ala Tyr
    1010                1015                1020

Arg Trp Arg Leu Ser His Arg Pro Lys Thr Gly Phe Ile Arg Val
    1025                1030                1035

Val Met Tyr Glu Gly Lys Lys Ile Met Ala Asp Ser Gly Pro Ile
    1040                1045                1050

Tyr Asp Lys Thr Tyr Ala Gly Gly Arg Gly Leu Phe Val Phe
    1055                1060                1065

Ser Gln Glu Met Val Phe Phe Ser Asp Leu Lys Tyr Glu Cys Arg
    1070                1075                1080

Asp Pro
    1085

<210> SEQ ID NO 59
<211> LENGTH: 205
<212> TYPE: PRT
<213> ORGANISM: Homo sapiens

<400> SEQUENCE: 59

Met Gly Ala Ala Arg Leu Leu Pro Asn Leu Thr Leu Cys Leu Gln Leu
1               5                   10                  15

Leu Ile Leu Cys Cys Gln Thr Gln Tyr Val Arg Asp Gln Gly Ala Met
            20                  25                  30

Thr Asp Gln Leu Ser Arg Arg Gln Ile Arg Glu Tyr Gln Leu Tyr Ser
        35                  40                  45

Arg Thr Ser Gly Lys His Val Gln Val Thr Gly Arg Arg Ile Ser Ala
    50                  55                  60

Thr Ala Glu Asp Gly Asn Lys Phe Ala Lys Leu Ile Val Glu Thr Asp
65                  70                  75                  80

Thr Phe Gly Ser Arg Val Arg Ile Lys Gly Ala Glu Ser Glu Lys Tyr
                85                  90                  95

Ile Cys Met Asn Lys Arg Gly Lys Leu Ile Gly Lys Pro Ser Gly Lys
            100                 105                 110

Ser Lys Asp Cys Val Phe Thr Glu Ile Val Leu Glu Asn Asn Tyr Thr
        115                 120                 125

Ala Phe Gln Asn Ala Arg His Glu Gly Trp Phe Met Ala Phe Thr Arg
    130                 135                 140

Gln Gly Arg Pro Arg Gln Ala Ser Arg Ser Arg Gln Asn Gln Arg Glu
145                 150                 155                 160

Ala His Phe Ile Lys Arg Leu Tyr Gln Gly Gln Leu Pro Phe Pro Asn
                165                 170                 175

His Ala Glu Lys Gln Lys Gln Phe Glu Phe Val Gly Ser Ala Pro Thr
            180                 185                 190

Arg Arg Thr Lys Arg Thr Arg Arg Pro Gln Pro Leu Thr
        195                 200                 205

<210> SEQ ID NO 60
```

-continued

```
<211> LENGTH: 779
<212> TYPE: PRT
<213> ORGANISM: Homo sapiens

<400> SEQUENCE: 60

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
```

```
            385                 390                 395                 400

Gly Glu Tyr Thr Leu Leu Ala Pro Val Asn Asn Ala Phe Ser Asp Asp
                    405                 410                 415

Thr Leu Ser Met Asp Gln Arg Leu Leu Lys Leu Ile Leu Gln Asn His
                420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
        450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                    485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
        530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                    565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
        610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                    645                 650                 655

Arg Gly Ser Thr Phe Lys Glu Ile Pro Val Thr Val Tyr Lys Pro Ile
                660                 665                 670

Ile Lys Lys Tyr Thr Lys Ile Ile Asp Gly Val Pro Val Glu Ile Thr
            675                 680                 685

Glu Lys Glu Thr Arg Glu Glu Arg Ile Ile Thr Gly Pro Glu Ile Lys
        690                 695                 700

Tyr Thr Arg Ile Ser Thr Gly Gly Glu Thr Glu Glu Thr Leu Lys
705                 710                 715                 720

Lys Leu Leu Gln Glu Glu Val Thr Lys Val Thr Lys Phe Ile Glu Gly
                    725                 730                 735

Gly Asp Gly His Leu Phe Glu Asp Glu Ile Lys Arg Leu Leu Gln
                740                 745                 750

Gly Asp Thr Pro Val Arg Lys Leu Gln Ala Asn Lys Lys Val Gln Gly
            755                 760                 765

Ser Arg Arg Arg Leu Arg Glu Gly Arg Ser Gln
        770                 775

<210> SEQ ID NO 61
<211> LENGTH: 781
<212> TYPE: PRT
<213> ORGANISM: Homo sapiens
```

<400> SEQUENCE: 61

```
Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65              70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
```

```
            405                 410                 415
Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
            450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
                515                 520                 525

Gly Asp Trp Thr Leu Phe Val Pro Thr Asn Asp Ala Phe Lys Gly Met
                530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                    565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
                595                 600                 605

Ser Lys Glu Ser Asp Ile Met Thr Thr Asn Gly Val Ile His Val Val
            610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                    645                 650                 655

Arg Gly Ser Thr Phe Lys Glu Ile Pro Val Thr Val Tyr Arg Pro Thr
                660                 665                 670

Leu Thr Lys Val Lys Ile Glu Gly Glu Pro Glu Phe Arg Leu Ile Lys
                675                 680                 685

Glu Gly Glu Thr Ile Thr Glu Val Ile His Gly Glu Pro Ile Ile Lys
                690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
                    725                 730                 735

Arg Ile Ser Thr Gly Gly Gly Glu Thr Glu Thr Leu Lys Lys Leu
                740                 745                 750

Leu Gln Glu Asp Thr Pro Val Arg Lys Leu Gln Ala Asn Lys Lys Val
                755                 760                 765

Gln Gly Ser Arg Arg Arg Leu Arg Glu Gly Arg Ser Gln
            770                 775                 780

<210> SEQ ID NO 62
<211> LENGTH: 751
<212> TYPE: PRT
<213> ORGANISM: Homo sapiens

<400> SEQUENCE: 62
```

```
Met Ile Pro Phe Leu Pro Met Phe Ser Leu Leu Leu Leu Ile Val
1               5               10              15

Asn Pro Ile Asn Ala Asn Asn His Tyr Asp Lys Ile Leu Ala His Ser
            20              25              30

Arg Ile Arg Gly Arg Asp Gln Gly Pro Asn Val Cys Ala Leu Gln Gln
        35              40              45

Ile Leu Gly Thr Lys Lys Lys Tyr Phe Ser Thr Cys Lys Asn Trp Tyr
    50              55              60

Lys Lys Ser Ile Cys Gly Gln Lys Thr Thr Val Leu Tyr Glu Cys Cys
65              70              75              80

Pro Gly Tyr Met Arg Met Glu Gly Met Lys Gly Cys Pro Ala Val Leu
                85              90              95

Pro Ile Asp His Val Tyr Gly Thr Leu Gly Ile Val Gly Ala Thr Thr
            100             105             110

Thr Gln Arg Tyr Ser Asp Ala Ser Lys Leu Arg Glu Glu Ile Glu Gly
        115             120             125

Lys Gly Ser Phe Thr Tyr Phe Ala Pro Ser Asn Glu Ala Trp Asp Asn
    130             135             140

Leu Asp Ser Asp Ile Arg Arg Gly Leu Glu Ser Asn Val Asn Val Glu
145             150             155             160

Leu Leu Asn Ala Leu His Ser His Met Ile Asn Lys Arg Met Leu Thr
                165             170             175

Lys Asp Leu Lys Asn Gly Met Ile Ile Pro Ser Met Tyr Asn Asn Leu
            180             185             190

Gly Leu Phe Ile Asn His Tyr Pro Asn Gly Val Val Thr Val Asn Cys
        195             200             205

Ala Arg Ile Ile His Gly Asn Gln Ile Ala Thr Asn Gly Val Val His
    210             215             220

Val Ile Asp Arg Val Leu Thr Gln Ile Gly Thr Ser Ile Gln Asp Phe
225             230             235             240

Ile Glu Ala Glu Asp Asp Leu Ser Ser Phe Arg Ala Ala Ala Ile Thr
                245             250             255

Ser Asp Ile Leu Glu Ala Leu Gly Arg Asp Gly His Phe Thr Leu Phe
            260             265             270

Ala Pro Thr Asn Glu Ala Phe Glu Lys Leu Pro Arg Gly Val Leu Glu
        275             280             285

Arg Ile Met Gly Asp Lys Val Ala Ser Glu Ala Leu Met Lys Tyr His
    290             295             300

Ile Leu Asn Thr Leu Gln Cys Ser Glu Ser Ile Met Gly Gly Ala Val
305             310             315             320

Phe Glu Thr Leu Glu Gly Asn Thr Ile Glu Ile Gly Cys Asp Gly Asp
                325             330             335

Ser Ile Thr Val Asn Gly Ile Lys Met Val Asn Lys Lys Asp Ile Val
            340             345             350

Thr Asn Asn Gly Val Ile His Leu Ile Asp Gln Val Leu Ile Pro Asp
        355             360             365

Ser Ala Lys Gln Val Ile Glu Leu Ala Gly Lys Gln Gln Thr Thr Phe
    370             375             380

Thr Asp Leu Val Ala Gln Leu Gly Leu Ala Ser Ala Leu Arg Pro Asp
385             390             395             400

Gly Glu Tyr Thr Leu Leu Ala Pro Val Asn Asn Ala Phe Ser Asp Asp
                405             410             415

Thr Leu Ser Met Asp Gln Arg Leu Leu Lys Leu Ile Leu Gln Asn His
```

```
                420             425             430
Ile Leu Lys Val Lys Val Gly Leu Asn Glu Leu Tyr Asn Gly Gln Ile
            435             440             445

Leu Glu Thr Ile Gly Gly Lys Gln Leu Arg Val Phe Val Tyr Arg Thr
    450             455             460

Ala Val Cys Ile Glu Asn Ser Cys Met Glu Lys Gly Ser Lys Gln Gly
465             470             475             480

Arg Asn Gly Ala Ile His Ile Phe Arg Glu Ile Ile Lys Pro Ala Glu
            485             490             495

Lys Ser Leu His Glu Lys Leu Lys Gln Asp Lys Arg Phe Ser Thr Phe
        500             505             510

Leu Ser Leu Leu Glu Ala Ala Asp Leu Lys Glu Leu Leu Thr Gln Pro
    515             520             525

Gly Asp Trp Thr Leu Phe Val Pro Thr Asn Asp Ala Phe Lys Gly Met
    530             535             540

Thr Ser Glu Glu Lys Glu Ile Leu Ile Arg Asp Lys Asn Ala Leu Gln
545             550             555             560

Asn Ile Ile Leu Tyr His Leu Thr Pro Gly Val Phe Ile Gly Lys Gly
            565             570             575

Phe Glu Pro Gly Val Thr Asn Ile Leu Lys Thr Thr Gln Gly Ser Lys
            580             585             590

Ile Phe Leu Lys Glu Val Asn Asp Thr Leu Leu Val Asn Glu Leu Lys
        595             600             605

Ser Lys Glu Ser Asp Ile Met Thr Thr Asn Gly Val Ile His Val Val
    610             615             620

Asp Lys Leu Leu Tyr Pro Ala Asp Thr Pro Val Gly Asn Asp Gln Leu
625             630             635             640

Leu Glu Ile Leu Asn Lys Leu Ile Lys Tyr Ile Gln Ile Lys Phe Val
            645             650             655

Arg Gly Ser Thr Phe Lys Glu Ile Pro Val Thr Val Tyr Lys Pro Ile
            660             665             670

Ile Lys Lys Tyr Thr Lys Ile Ile Asp Gly Val Pro Val Glu Ile Thr
        675             680             685

Glu Lys Glu Thr Arg Glu Glu Arg Ile Ile Thr Gly Pro Glu Ile Lys
    690             695             700

Tyr Thr Arg Ile Ser Thr Gly Gly Glu Thr Glu Glu Thr Leu Lys
705             710             715             720

Lys Leu Leu Gln Glu Asp Thr Pro Val Arg Lys Leu Gln Ala Asn Lys
            725             730             735

Lys Val Gln Gly Ser Arg Arg Arg Leu Arg Glu Gly Arg Ser Gln
            740             745             750

<210> SEQ ID NO 63
<211> LENGTH: 809
<212> TYPE: PRT
<213> ORGANISM: Homo sapiens

<400> SEQUENCE: 63

Met Ile Pro Phe Leu Pro Met Phe Ser Leu Leu Leu Leu Ile Val
1               5               10              15

Asn Pro Ile Asn Ala Asn Asn His Tyr Asp Lys Ile Leu Ala His Ser
            20              25              30

Arg Ile Arg Gly Arg Asp Gln Gly Pro Asn Val Cys Ala Leu Gln Gln
        35              40              45
```

```
Ile Leu Gly Thr Lys Lys Lys Tyr Phe Ser Thr Cys Lys Asn Trp Tyr
 50                  55                  60

Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
        210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
        290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
        370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
```

```
            465                 470                 475                 480
        Arg Asn Gly Ala Ile His Ile Phe Arg Glu Ile Ile Lys Pro Ala Glu
                        485                 490                 495
        Lys Ser Leu His Glu Lys Leu Lys Gln Asp Lys Arg Phe Ser Thr Phe
                        500                 505                 510
        Leu Ser Leu Leu Glu Ala Ala Asp Leu Lys Glu Leu Leu Thr Gln Pro
                        515                 520                 525
        Gly Asp Trp Thr Leu Phe Val Pro Thr Asn Asp Ala Phe Lys Gly Met
                        530                 535                 540
        Thr Ser Glu Glu Lys Glu Ile Leu Ile Arg Asp Lys Asn Ala Leu Gln
        545                 550                 555                 560
        Asn Ile Ile Leu Tyr His Leu Thr Pro Gly Val Phe Ile Gly Lys Gly
                        565                 570                 575
        Phe Glu Pro Gly Val Thr Asn Ile Leu Lys Thr Thr Gln Gly Ser Lys
                        580                 585                 590
        Ile Phe Leu Lys Glu Val Asn Asp Thr Leu Leu Val Asn Glu Leu Lys
                        595                 600                 605
        Ser Lys Glu Ser Asp Ile Met Thr Thr Asn Gly Val Ile His Val Val
                        610                 615                 620
        Asp Lys Leu Leu Tyr Pro Ala Asp Thr Pro Val Gly Asn Asp Gln Leu
        625                 630                 635                 640
        Leu Glu Ile Leu Asn Lys Leu Ile Lys Tyr Ile Gln Ile Lys Phe Val
                        645                 650                 655
        Arg Gly Ser Thr Phe Lys Glu Ile Pro Val Thr Val Tyr Arg Pro Thr
                        660                 665                 670
        Leu Thr Lys Val Lys Ile Glu Gly Glu Pro Glu Phe Arg Leu Ile Lys
                        675                 680                 685
        Glu Gly Glu Thr Ile Thr Glu Val Ile His Gly Glu Pro Ile Ile Lys
                        690                 695                 700
        Lys Tyr Thr Lys Ile Ile Asp Gly Val Pro Val Glu Ile Thr Glu Lys
        705                 710                 715                 720
        Glu Thr Arg Glu Glu Arg Ile Ile Thr Gly Pro Glu Ile Lys Tyr Thr
                        725                 730                 735
        Arg Ile Ser Thr Gly Gly Gly Glu Thr Glu Thr Leu Lys Lys Leu
                        740                 745                 750
        Leu Gln Glu Glu Val Thr Lys Val Thr Lys Phe Ile Glu Gly Gly Asp
                        755                 760                 765
        Gly His Leu Phe Glu Asp Glu Ile Lys Arg Leu Leu Gln Gly Asp
                        770                 775                 780
        Thr Pro Val Arg Lys Leu Gln Ala Asn Lys Lys Val Gln Gly Ser Arg
        785                 790                 795                 800
        Arg Arg Leu Arg Glu Gly Arg Ser Gln
                        805

<210> SEQ ID NO 64
<211> LENGTH: 749
<212> TYPE: PRT
<213> ORGANISM: Homo sapiens

<400> SEQUENCE: 64

Met Ile Pro Phe Leu Pro Met Phe Ser Leu Leu Leu Leu Leu Ile Val
1               5                   10                  15
Asn Pro Ile Asn Ala Asn Asn His Tyr Asp Lys Ile Leu Ala His Ser
                20                  25                  30
```

-continued

Arg Ile Arg Gly Arg Asp Gln Gly Pro Asn Val Cys Ala Leu Gln Gln
         35                  40                  45

Ile Leu Gly Thr Lys Lys Tyr Phe Ser Thr Cys Lys Asn Trp Tyr
 50                  55                  60

Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr

```
                450             455             460
Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
            530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
            610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Ser Pro Glu
                660                 665                 670

Ile Lys Tyr Thr Arg Ile Ser Thr Gly Gly Glu Thr Glu Glu Thr
            675                 680                 685

Leu Lys Lys Leu Leu Gln Glu Glu Val Thr Lys Val Thr Lys Phe Ile
            690                 695                 700

Glu Gly Gly Asp Gly His Leu Phe Glu Asp Glu Ile Lys Arg Leu
705                 710                 715                 720

Leu Gln Gly Asp Thr Pro Val Arg Lys Leu Gln Ala Asn Lys Lys Val
                725                 730                 735

Gln Gly Ser Arg Arg Arg Leu Arg Glu Gly Arg Ser Gln
                740                 745

<210> SEQ ID NO 65
<211> LENGTH: 721
<212> TYPE: PRT
<213> ORGANISM: Homo sapiens

<400> SEQUENCE: 65

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
        50                  55                  60

Lys Lys Ser Ile Cys Gly Gln Lys Thr Thr Val Leu Tyr Glu Cys Cys
65                  70                  75                  80
```

```
Pro Gly Tyr Met Arg Met Glu Gly Met Lys Gly Cys Pro Ala Val Leu
                85                  90                  95
Pro Ile Asp His Val Tyr Gly Thr Leu Gly Ile Val Gly Ala Thr Thr
            100                 105                 110
Thr Gln Arg Tyr Ser Asp Ala Ser Lys Leu Arg Glu Glu Ile Glu Gly
        115                 120                 125
Lys Gly Ser Phe Thr Tyr Phe Ala Pro Ser Asn Glu Ala Trp Asp Asn
    130                 135                 140
Leu Asp Ser Asp Ile Arg Arg Gly Leu Glu Ser Asn Val Asn Val Glu
145                 150                 155                 160
Leu Leu Asn Ala Leu His Ser His Met Ile Asn Lys Arg Met Leu Thr
                165                 170                 175
Lys Asp Leu Lys Asn Gly Met Ile Ile Pro Ser Met Tyr Asn Asn Leu
            180                 185                 190
Gly Leu Phe Ile Asn His Tyr Pro Asn Gly Val Val Thr Val Asn Cys
        195                 200                 205
Ala Arg Ile Ile His Gly Asn Gln Ile Ala Thr Asn Gly Val Val His
    210                 215                 220
Val Ile Asp Arg Val Leu Thr Gln Ile Gly Thr Ser Ile Gln Asp Phe
225                 230                 235                 240
Ile Glu Ala Glu Asp Asp Leu Ser Ser Phe Arg Ala Ala Ala Ile Thr
                245                 250                 255
Ser Asp Ile Leu Glu Ala Leu Gly Arg Asp Gly His Phe Thr Leu Phe
            260                 265                 270
Ala Pro Thr Asn Glu Ala Phe Glu Lys Leu Pro Arg Gly Val Leu Glu
        275                 280                 285
Arg Ile Met Gly Asp Lys Val Ala Ser Glu Ala Leu Met Lys Tyr His
    290                 295                 300
Ile Leu Asn Thr Leu Gln Cys Ser Glu Ser Ile Met Gly Gly Ala Val
305                 310                 315                 320
Phe Glu Thr Leu Glu Gly Asn Thr Ile Glu Ile Gly Cys Asp Gly Asp
                325                 330                 335
Ser Ile Thr Val Asn Gly Ile Lys Met Val Asn Lys Asp Ile Val
            340                 345                 350
Thr Asn Asn Gly Val Ile His Leu Ile Asp Gln Val Leu Ile Pro Asp
        355                 360                 365
Ser Ala Lys Gln Val Ile Glu Leu Ala Gly Lys Gln Gln Thr Thr Phe
    370                 375                 380
Thr Asp Leu Val Ala Gln Leu Gly Leu Ala Ser Ala Leu Arg Pro Asp
385                 390                 395                 400
Gly Glu Tyr Thr Leu Leu Ala Pro Val Asn Asn Ala Phe Ser Asp Asp
                405                 410                 415
Thr Leu Ser Met Asp Gln Arg Leu Leu Lys Leu Ile Leu Gln Asn His
            420                 425                 430
Ile Leu Lys Val Lys Val Gly Leu Asn Glu Leu Tyr Asn Gly Gln Ile
        435                 440                 445
Leu Glu Thr Ile Gly Gly Lys Gln Leu Arg Val Phe Val Tyr Arg Thr
    450                 455                 460
Ala Val Cys Ile Glu Asn Ser Cys Met Glu Lys Gly Ser Lys Gln Gly
465                 470                 475                 480
Arg Asn Gly Ala Ile His Ile Phe Arg Glu Ile Ile Lys Pro Ala Glu
                485                 490                 495
Lys Ser Leu His Glu Lys Leu Lys Gln Asp Lys Arg Phe Ser Thr Phe
```

```
                500             505             510
Leu Ser Leu Leu Glu Ala Ala Asp Leu Lys Glu Leu Leu Thr Gln Pro
            515                 520                 525
Gly Asp Trp Thr Leu Phe Val Pro Thr Asn Asp Ala Phe Lys Gly Met
        530                 535                 540
Thr Ser Glu Glu Lys Glu Ile Leu Ile Arg Asp Lys Asn Ala Leu Gln
545                 550                 555                 560
Asn Ile Ile Leu Tyr His Leu Thr Pro Gly Val Phe Ile Gly Lys Gly
                565                 570                 575
Phe Glu Pro Gly Val Thr Asn Ile Leu Lys Thr Thr Gln Gly Ser Lys
            580                 585                 590
Ile Phe Leu Lys Glu Val Asn Asp Thr Leu Leu Val Asn Glu Leu Lys
        595                 600                 605
Ser Lys Glu Ser Asp Ile Met Thr Thr Asn Gly Val Ile His Val Val
    610                 615                 620
Asp Lys Leu Leu Tyr Pro Ala Asp Thr Pro Val Gly Asn Asp Gln Leu
625                 630                 635                 640
Leu Glu Ile Leu Asn Lys Leu Ile Lys Tyr Ile Gln Ile Lys Phe Val
                645                 650                 655
Arg Gly Ser Thr Phe Lys Glu Ile Pro Val Thr Val Tyr Ser Pro Glu
            660                 665                 670
Ile Lys Tyr Thr Arg Ile Ser Thr Gly Gly Glu Thr Glu Glu Thr
        675                 680                 685
Leu Lys Lys Leu Leu Gln Glu Asp Thr Pro Val Arg Lys Leu Gln Ala
    690                 695                 700
Asn Lys Lys Val Gln Gly Ser Arg Arg Arg Leu Arg Glu Gly Arg Ser
705                 710                 715                 720
Gln
```

<210> SEQ ID NO 66
<211> LENGTH: 183
<212> TYPE: PRT
<213> ORGANISM: Homo sapiens

<400> SEQUENCE: 66

```
Met Gly Ile Pro Met Gly Lys Ser Met Leu Val Leu Leu Thr Phe Leu
1               5                   10                  15
Ala Phe Ala Ser Cys Cys Ile Ala Ala Tyr Arg Pro Ser Glu Thr Leu
            20                  25                  30
Cys Gly Gly Glu Leu Val Asp Thr Leu Gln Phe Val Cys Gly Asp Arg
        35                  40                  45
Gly Phe Tyr Phe Arg Leu Pro Gly Arg Pro Ala Ser Arg Val Ser Arg
    50                  55                  60
Arg Ser Arg Gly Ile Val Glu Glu Cys Cys Phe Arg Ser Cys Asp Leu
65                  70                  75                  80
Ala Leu Leu Glu Thr Tyr Cys Ala Thr Pro Ala Lys Ser Glu Arg Asp
                85                  90                  95
Val Ser Thr Pro Pro Thr Val Leu Pro Asp Asn Phe Pro Arg Tyr Pro
            100                 105                 110
Val Gly Lys Phe Phe Gln Tyr Asp Thr Trp Lys Gln Ser Thr Gln Arg
        115                 120                 125
Leu Arg Arg Gly Leu Pro Ala Leu Leu Arg Ala Arg Arg Gly His Val
    130                 135                 140
Leu Ala Lys Glu Leu Glu Ala Phe Arg Glu Ala Lys Arg His Arg Pro
```

```
145                 150                 155                 160
Leu Ile Ala Leu Pro Thr Gln Asp Pro Ala His Gly Gly Ala Pro Pro
                165                 170                 175
Glu Met Ala Ser Asn Arg Lys
            180

<210> SEQ ID NO 67
<211> LENGTH: 236
<212> TYPE: PRT
<213> ORGANISM: Homo sapiens

<400> SEQUENCE: 67

Met Val Ser Pro Asp Pro Gln Ile Ile Val Ala Pro Glu Thr Glu
1               5                   10                  15

Leu Ala Ser Met Gln Val Gln Arg Thr Glu Asp Gly Val Thr Ile Ile
                20                  25                  30

Gln Ile Phe Trp Val Gly Arg Lys Gly Glu Leu Leu Arg Arg Thr Pro
            35                  40                  45

Val Ser Ser Ala Met Gln Thr Pro Met Gly Ile Pro Met Gly Lys Ser
50                  55                  60

Met Leu Val Leu Leu Thr Phe Leu Ala Phe Ala Ser Cys Cys Ile Ala
65                  70                  75                  80

Ala Tyr Arg Pro Ser Glu Thr Leu Cys Gly Gly Glu Leu Val Asp Thr
                85                  90                  95

Leu Gln Phe Val Cys Gly Asp Arg Gly Phe Tyr Phe Ser Arg Pro Ala
            100                 105                 110

Ser Arg Val Ser Arg Arg Ser Arg Gly Ile Val Glu Cys Cys Phe
        115                 120                 125

Arg Ser Cys Asp Leu Ala Leu Leu Glu Thr Tyr Cys Ala Thr Pro Ala
130                 135                 140

Lys Ser Glu Arg Asp Val Ser Thr Pro Pro Thr Val Leu Pro Asp Asn
145                 150                 155                 160

Phe Pro Arg Tyr Pro Val Gly Lys Phe Phe Gln Tyr Asp Thr Trp Lys
                165                 170                 175

Gln Ser Thr Gln Arg Leu Arg Arg Gly Leu Pro Ala Leu Leu Arg Ala
            180                 185                 190

Arg Arg Gly His Val Leu Ala Lys Glu Leu Glu Ala Phe Arg Glu Ala
        195                 200                 205

Lys Arg His Arg Pro Leu Ile Ala Leu Pro Thr Gln Asp Pro Ala His
210                 215                 220

Gly Gly Ala Pro Pro Glu Met Ala Ser Asn Arg Lys
225                 230                 235

<210> SEQ ID NO 68
<211> LENGTH: 135
<212> TYPE: PRT
<213> ORGANISM: Homo sapiens

<400> SEQUENCE: 68

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
                20                  25                  30

Ile Glu Asp Leu Ile Gln Ser Met His Ile Asp Ala Thr Leu Tyr Thr
            35                  40                  45

Glu Ser Asp Val His Pro Ser Cys Lys Val Thr Ala Met Lys Cys Phe
```

```
                50                  55                  60
Leu Leu Glu Leu Gln Val Ile Ser Leu Glu Ser Gly Asp Ala Ser Ile
 65                  70                  75                  80

His Asp Thr Val Glu Asn Leu Ile Ile Leu Ala Asn Asn Ser Leu Ser
                 85                  90                  95

Ser Asn Gly Asn Val Thr Glu Ser Gly Cys Lys Glu Cys Glu Glu Leu
                100                 105                 110

Glu Glu Lys Asn Ile Lys Glu Phe Leu Gln Ser Phe Val His Ile Val
            115                 120                 125

Gln Met Phe Ile Asn Thr Ser
    130                 135

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 69

His His His His His His
 1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 70

His His His His His His His His His His
 1               5                  10
```

HEPARIN-ASSOCIATED POLYPEPTIDES AND USES THEREOF

PRIORITY

This application claims priority to U.S. Provisional Application No. 62/690,796 filed Jun. 27, 2018, and U.S. Provisional Application No. 62/809,479 filed Feb. 22, 2019, both of which are incorporated by reference in their entirety herein.

SEQUENCE LISTING

The instant application contains a Sequence Listing which has been submitted electronically in ASCII format and is hereby incorporated by reference in its entirety. Said ASCII copy, created on Jun. 26, 2019, is named 54275-702 201 SL.txt and is 277,008 bytes in size.

BACKGROUND

As the average life span increases, increasing emphasis is placed upon "healthy aging." Individuals would like to live more active lifestyles as they age, and as a result, many aging disorders can have a significant impact on the quality of life of aging individuals. Treatments directed to regenerative ends have utility for treating aging diseases. Additionally, many treatments for aging disorders can be applicable to younger individuals who have suffered illness, injury, or who possess genetic or developmental defects leading to premature tissue loss, wasting, or weakening.

SUMMARY

As individuals age, tissue progenitor cells lose their regenerative potential. Described herein, in certain aspects, are heparin-associated polypeptides that can restore some or all of this regenerative potential, and are thus useful in the treatment of aging disorders that result in tissue loss or underperformance, and rehabilitation from injury. Described herein are therapeutic compositions comprising heparin-associated polypeptides and methods of treating disorders associated with aging, injury, or illness. In certain embodiments, the therapeutic compositions comprise one or more heparin-associated polypeptides that possess mitogenic (i.e., regenerative) and/or fusion promoting activity to a somatic cell, such as a tissue progenitor cell. In certain embodiments, the therapeutic compositions have activity towards muscle and soft tissue progenitor cells. In certain embodiments these compositions possess utility in treating sarcopenia, cachexia, muscular dystrophy, acute and chronic muscle wasting diseases, and muscle, ligament, or tendon injury, or any combination of these diseases or conditions.

In one aspect, described herein is a composition comprising: (a) a first therapeutic polypeptide comprising a first polypeptide of Table 2, and (b) a second therapeutic polypeptide comprising a second polypeptide of Table 2. In certain embodiments, the first polypeptide of Table 2 is a first polypeptide of Table 1 and/or the second polypeptide of Table 2 is a second polypeptide of Table 1. In certain embodiments, the first polypeptide of Table 2 comprises THBS1, THBS2, THBS4, FGF17, VTN, POSTN, IGF2, or IL-15, or any combination thereof. In certain embodiments, the second polypeptide of Table 2 comprises THBS1, THBS2, THBS4, FGF17, VTN, POSTN, IGF2, or IL-15, or any combination thereof.

In certain embodiments, the first polypeptide of Table 2 comprises THBS1 and/or a sequence comprising at least about 90% homology to amino acids 19-1170 of SEQ ID NO: 9; and the second polypeptide of Table 2 comprises THBS2 and/or a sequence comprising at least about 90% homology to amino acids 19-1172 of SEQ ID NO: 4.

In certain embodiments, the first polypeptide of Table 2 comprises THBS1 and/or a sequence comprising at least about 90% homology to amino acids 19-1170 of SEQ ID NO: 9; and the second polypeptide of Table 2 comprises THBS4 and/or a sequence comprising at least about 90% homology to amino acids 27-961 of SEQ ID NO: 8.

In certain embodiments, the first polypeptide of Table 2 comprises THBS1 and/or a sequence comprising at least about 90% homology to amino acids 19-1170 of SEQ ID NO: 9; and the second polypeptide of Table 2 comprises FGF17 and/or a sequence comprising at least about 90% homology to amino acids 23-2165 of SEQ ID NO: 7.

In certain embodiments, the first polypeptide of Table 2 comprises THBS1 and/or a sequence comprising at least about 90% homology to amino acids 19-1170 of SEQ ID NO: 9; and the second polypeptide of Table 2 comprises VTN and/or a sequence comprising at least about 90% homology to amino acids 20-478 of SEQ ID NO: 1.

In certain embodiments, the first polypeptide of Table 2 comprises THBS1 and/or a sequence comprising at least about 90% homology to amino acids 19-1170 of SEQ ID NO: 9; and the second polypeptide of Table 2 comprises POSTN and/or a sequence comprising at least about 90% homology to amino acids 22-836 of SEQ ID NO: 6.

In certain embodiments, the first polypeptide of Table 2 comprises THBS1 and/or a sequence comprising at least about 90% homology to amino acids 19-1170 of SEQ ID NO: 9; and the second polypeptide of Table 2 comprises IGF2 and/or a sequence comprising at least about 90% homology to amino acids 25-91 of SEQ ID NO: 11.

In certain embodiments, the first polypeptide of Table 2 comprises THBS1 and/or a sequence comprising at least about 90% homology to amino acids 19-1170 of SEQ ID NO: 9; and the second polypeptide of Table 2 comprises IL-15 and/or a sequence comprising at least about 90% homology to amino acids 49-162 of SEQ ID NO: 10.

In certain embodiments, the first polypeptide of Table 2 comprises THBS2 and/or a sequence comprising at least about 90% homology to amino acids 19-1172 of SEQ ID NO: 4; and the second polypeptide of Table 2 comprises THBS4 and/or a sequence comprising at least about 90% homology to amino acids 27-961 of SEQ ID NO: 8. In certain embodiments, the composition further comprises IL-15 and/or a polypeptide comprising at least about 90% homology to amino acids 49-162 of SEQ ID NO: 10. In certain embodiments, the composition further comprises IGF2 and/or a polypeptide comprising at least about 90% homology to amino acids 25-91 of SEQ ID NO: 11.

In certain embodiments, the first polypeptide of Table 2 comprises THBS2 and/or a sequence comprising at least about 90% homology to amino acids 19-1172 of SEQ ID NO: 4; and the second polypeptide of Table 2 comprises FGF17 and/or a sequence comprising at least about 90% homology to amino acids 23-2165 of SEQ ID NO: 7.

In certain embodiments, the first polypeptide of Table 2 comprises THBS2 and/or a sequence comprising at least about 90% homology to amino acids 19-1172 of SEQ ID NO: 4; and the second polypeptide of Table 2 comprises VTN and/or a sequence comprising at least about 90% homology to amino acids 20-478 of SEQ ID NO: 1.

In certain embodiments, the first polypeptide of Table 2 comprises THBS2 and/or a sequence comprising at least about 90% homology to amino acids 19-1172 of SEQ ID NO: 4; and the second polypeptide of Table 2 comprises POSTN and/or a sequence comprising at least about 90% homology to amino acids 22-836 of SEQ ID NO: 6.

In certain embodiments, the first polypeptide of Table 2 comprises THBS2 and/or a sequence comprising at least about 90% homology to amino acids 19-1172 of SEQ ID NO: 4; and the second polypeptide of Table 2 comprises IGF2 and/or a sequence comprising at least about 90% homology to amino acids 25-91 of SEQ ID NO: 11.

In certain embodiments, the first polypeptide of Table 2 comprises THBS2 and/or a sequence comprising at least about 90% homology to amino acids 19-1172 of SEQ ID NO: 4; and the second polypeptide of Table 2 comprises IL-15 and/or a sequence comprising at least about 90% homology to amino acids 49-162 of SEQ ID NO: 10.

In certain embodiments, the first polypeptide of Table 2 comprises THBS4 and/or a sequence comprising at least about 90% homology to amino acids 27-961 of SEQ ID NO: 8; and the second polypeptide of Table 2 comprises FGF17 and/or a sequence comprising at least about 90% homology to amino acids 23-2165 of SEQ ID NO: 7.

In certain embodiments, the first polypeptide of Table 2 comprises THBS4 and/or a sequence comprising at least about 90% homology to amino acids 27-961 of SEQ ID NO: 8; and the second polypeptide of Table 2 comprises VTN and/or a sequence comprising at least about 90% homology to amino acids 20-478 of SEQ ID NO: 1.

In certain embodiments, the first polypeptide of Table 2 comprises THBS4 and/or a sequence comprising at least about 90% homology to amino acids 27-961 of SEQ ID NO: 8; and the second polypeptide of Table 2 comprises POSTN and/or a sequence comprising at least about 90% homology to amino acids 22-836 of SEQ ID NO: 6.

In certain embodiments, the first polypeptide of Table 2 comprises THBS4 and/or a sequence comprising at least about 90% homology to amino acids 27-961 of SEQ ID NO: 8; and the second polypeptide of Table 2 comprises IGF2 and/or a sequence comprising at least about 90% homology to amino acids 25-91 of SEQ ID NO: 11.

In certain embodiments, the first polypeptide of Table 2 comprises THBS4 and/or a sequence comprising at least about 90% homology to amino acids 27-961 of SEQ ID NO: 8; and the second polypeptide of Table 2 comprises IL-15 and/or a sequence comprising at least about 90% homology to amino acids 49-162 of SEQ ID NO: 10.

In certain embodiments, the first polypeptide of Table 2 comprises FGF17 and/or a sequence comprising at least about 90% homology to amino acids 23-2165 of SEQ ID NO: 7; and the second polypeptide of Table 2 comprises VTN and/or a sequence comprising at least about 90% homology to amino acids 20-478 of SEQ ID NO: 1.

In certain embodiments, the first polypeptide of Table 2 comprises FGF17 and/or a sequence comprising at least about 90% homology to amino acids 23-2165 of SEQ ID NO: 7; and the second polypeptide of Table 2 comprises POSTN and/or a sequence comprising at least about 90% homology to amino acids 22-836 of SEQ ID NO: 6.

In certain embodiments, the first polypeptide of Table 2 comprises FGF17 and/or a sequence comprising at least about 90% homology to amino acids 23-2165 of SEQ ID NO: 7; and the second polypeptide of Table 2 comprises IGF2 and/or a sequence comprising at least about 90% homology to amino acids 25-91 of SEQ ID NO: 11.

In certain embodiments, the first polypeptide of Table 2 comprises FGF17 and/or a sequence comprising at least about 90% homology to amino acids 23-2165 of SEQ ID NO: 7; and the second polypeptide of Table 2 comprises IL-15 and/or a sequence comprising at least about 90% homology to amino acids 49-162 of SEQ ID NO: 10.

In certain embodiments, the first polypeptide of Table 2 comprises VTN and/or a sequence comprising at least about 90% homology to amino acids 20-478 of SEQ ID NO: 1; and the second polypeptide of Table 2 comprises POSTN and/or a sequence comprising at least about 90% homology to amino acids 22-836 of SEQ ID NO: 6.

In certain embodiments, the first polypeptide of Table 2 comprises VTN and/or a sequence comprising at least about 90% homology to amino acids 20-478 of SEQ ID NO: 1; and the second polypeptide of Table 2 comprises IGF2 and/or a sequence comprising at least about 90% homology to amino acids 25-91 of SEQ ID NO: 11.

In certain embodiments, the first polypeptide of Table 2 comprises VTN and/or a sequence comprising at least about 90% homology to amino acids 20-478 of SEQ ID NO: 1; and the second polypeptide of Table 2 comprises IL-15 and/or a sequence comprising at least about 90% homology to amino acids 49-162 of SEQ ID NO: 10.

In certain embodiments, the first polypeptide of Table 2 comprises POSTN and/or a sequence comprising at least about 90% homology to amino acids 22-836 of SEQ ID NO: 6; and the second polypeptide of Table 2 comprises IGF2 and/or a sequence comprising at least about 90% homology to amino acids 25-91 of SEQ ID NO: 11.

In certain embodiments, the first polypeptide of Table 2 comprises POSTN and/or a sequence comprising at least about 90% homology to amino acids 22-836 of SEQ ID NO: 6; and the second polypeptide of Table 2 comprises IL-15 and/or a sequence comprising at least about 90% homology to amino acids 49-162 of SEQ ID NO: 10.

In certain embodiments, the first polypeptide of Table 2 comprises IGF2 and/or a sequence comprising at least about 90% homology to amino acids 25-91 of SEQ ID NO: 11; and the second polypeptide of Table 2 comprises IL-15 and/or a sequence comprising at least about 90% homology to amino acids 49-162 of SEQ ID NO: 10.

In certain embodiments, the first therapeutic polypeptide has been recombinantly produced, the second polypeptide has been recombinantly produced, or both the first and second therapeutic polypeptides have been recombinantly produced. In certain embodiments, the first therapeutic polypeptide has been produced in a mammalian, yeast, insect or bacteria cell, the second polypeptide has been produced in a mammalian, yeast, insect or bacteria cell, or both the first and second therapeutic polypeptides have been produced in a mammalian, yeast, insect or bacteria cell. In certain embodiments, the first therapeutic polypeptide and/or the second therapeutic polypeptide have been produced in a mammalian cell and the mammalian cell is a human cell. In some cases the human cell is a human embryonic kidney-derived epithelial cell (e.g., HEK293 cell). In certain embodiments, the first therapeutic polypeptide has been produced in a mammalian cell and the mammalian cell is a Chinese Hamster Ovary (CHO) cell or mouse myeloma cell. In certain embodiments, the second therapeutic polypeptide has been produced in a mammalian cell and the mammalian cell is a Chinese Hamster Ovary (CHO) cell or mouse myeloma cell. In certain embodiments, the first therapeutic polypeptide and/or the second therapeutic polypeptide has been purified from a human biological sample. In some cases, the human biological sample is human plasma. In certain embodiments, the composition further comprises a pharmaceutically acceptable excipient. In certain embodiments, the composition is formulated for administration by injection. In certain embodiments, the injection is intramuscular. In certain embodiments, the injection is subcutaneous. In certain embodiments, the injection is intravenous.

In another aspect, described herein is a composition comprising a polypeptide of Table 2 and a pharmaceutically acceptable excipient. In certain embodiments, the polypeptide comprises VTN and/or a sequence comprising at least about 90% homology to amino acids 20-478 of SEQ ID NO: 1. In certain embodiments, the polypeptide comprises POSTN and/or a sequence comprising at least about 90% homology to amino acids 22-836 of SEQ ID NO: 6. In certain embodiments, the polypeptide comprises FGF17 and/or a sequence comprising at least about 90% homology to amino acids 23-2165 of SEQ ID NO: 7. In certain embodiments, the polypeptide comprises THBS2 and/or a sequence comprising at least about 90% homology to amino acids 19-1172 of SEQ ID NO: 4. In certain embodiments, the polypeptide comprises THBS4 and/or a sequence comprising at least about 90% homology to amino acids 27-961 of SEQ ID NO: 8. In certain embodiments, the polypeptide comprises THBS1 and/or a sequence comprising at least about 90% homology to amino acids 19-1170 of SEQ ID NO: 9. In certain embodiments, the polypeptide comprises IL-15 and/or a sequence comprising at least about 90% homology to amino acids 49-162 of SEQ ID NO: 10. In certain embodiments, the polypeptide comprises IGF2 and/or a sequence comprising at least about 90% homology to amino acids 25-91 of SEQ ID NO: 11. In certain embodiments, the polypeptide has been produced in a mammalian cell and the mammalian cell is a human cell. In some cases the human cell is a human embryonic kidney-derived epithelial cell (e.g., HEK293 cells). In certain embodiments, the polypeptide has been expressed from a Chinese Hamster Ovary (CHO) cell, or mouse myeloma (NS0) cell, insect, or a bacterial cell. In some cases the bacterial cell is an $E.\ coli$ cell. In certain embodiments, the polypeptide has been purified from a human biological sample. In some cases, the human biological sample is human plasma. In certain embodiments, the polypeptide is synthetically produced. In certain embodiments, the polypeptide possesses mitogenic and/or fusion promoting activity. Further described is a nucleic acid encoding the polypeptide described herein. Further described is a cell line comprising the nucleic acid.

Further described herein is a method of treating a disease or condition in a subject in need thereof, the method comprising administering to the subject a composition described herein. In certain embodiments, the disease or condition comprises an aging disorder, muscle wasting disorder, muscle injury, or injury to connective tissue, or a combination thereof. In certain embodiments, the subject has the aging disorder and the aging disorder comprises sarcopenia. In certain embodiments, the subject has the muscle wasting disorder and the muscle wasting disorder comprises muscular dystrophy. In certain embodiments, the subject has the muscle wasting disorder and the muscle wasting is a result of obesity, disease progression, metabolic disorder, or therapeutic treatment, or a combination thereof. In certain embodiments, the metabolic disorder is diabetes. In some cases the diabetes is Type 2 Diabetes. In certain embodiments, the subject has the muscle wasting disorder and the muscle wasting is cachexia, e.g., muscular cachexia.

In another aspect, described herein is a composition comprising: (a) a first therapeutic polypeptide comprising THBS1, THBS2, THBS4, FGF17, VTN, POSTN, IGF2, or IL-15, and (b) a second therapeutic polypeptide comprising THBS1, THBS2, THBS4, FGF17, VTN, POSTN, IGF2, or IL-15. In certain embodiments, the first therapeutic polypeptide has been recombinantly produced, the second polypeptide has been recombinantly produced, or both the first and second therapeutic polypeptides have been recombinantly produced. In certain embodiments, the first therapeutic polypeptide has been produced in a mammalian, yeast, insect or bacteria cell, the second polypeptide has been produced in a mammalian, yeast, insect or bacteria cell, or both the first and second therapeutic polypeptides have been produced in a mammalian, yeast, insect or bacteria cell. In certain embodiments, the polypeptide has been produced in a mammalian cell and the mammalian cell is a human cell. In some cases the human cell is a human embryonic kidney-derived epithelial cell (e.g., HEK293 cells). In certain embodiments, the first therapeutic polypeptide has been produced in a mammalian cell and the mammalian cell is a Chinese Hamster Ovary (CHO) cell or mouse myeloma cell. In certain embodiments, the second therapeutic polypeptide has been produced in a mammalian cell and the mammalian cell is a Chinese Hamster Ovary (CHO) cell or mouse myeloma cell. In certain embodiments, the polypeptide has been purified from a human biological sample. In some cases, the human biological sample is human plasma.

In certain embodiments, the first therapeutic polypeptide comprises IL-15 and/or a sequence comprising at least about 90% homology to amino acids 49-162 of SEQ ID NO: 10; and the second therapeutic polypeptide comprises THBS2 and/or a sequence comprising at least about 90% homology to amino acids 19-1172 of SEQ ID NO: 4. In certain embodiments, the first therapeutic polypeptide comprises IL-15 and/or a sequence comprising at least about 90% homology to amino acids 49-162 of SEQ ID NO: 10; and the second therapeutic polypeptide comprises THBS4 and/or a sequence comprising at least about 90% homology to amino acids 27-961 of SEQ ID NO: 8. In certain embodiments, the first therapeutic polypeptide comprises IGF2 and/or a sequence comprising at least about 90% homology to amino acids 25-91 of SEQ ID NO: 11; and the second therapeutic polypeptide comprises THBS2 and/or a sequence comprising at least about 90% homology to amino acids 19-1172 of SEQ ID NO: 4. In certain embodiments, the first therapeutic polypeptide comprises IGF2 and/or a sequence comprising at least about 90% homology to amino acids 25-91 of SEQ ID NO: 11; and the second therapeutic polypeptide comprises THBS4 and/or a sequence comprising at least about 90% homology to amino acids 27-961 of SEQ ID NO: 8. In certain embodiments, the first therapeutic polypeptide comprises THBS4 and/or a sequence comprising at least about 90% homology to amino acids 27-961 of SEQ ID NO: 8; and the second therapeutic polypeptide comprises THBS2 and/or a sequence comprising at least about 90% homology to amino acids 19-1172 of SEQ ID NO: 4. In certain embodiments, the composition further comprises IL-15 and/or a sequence comprising at least about 90% homology to amino acids 49-162 of SEQ ID NO: 10. In certain embodiments, the composition further comprises IGF2 and/or a sequence comprising at least about 90% homology to amino acids 25-91 of SEQ ID NO: 11. In certain embodiments, the composition further comprises a pharmaceutically acceptable excipient. In certain embodiments, the composition is formulated for administration by injection. In certain embodiments, the injection is intramuscular. In certain embodiments, the injection is subcutaneous. In certain embodiments, the injection is intravenous.

In certain embodiments, described herein is a composition comprising THBS2 and THBS4. The composition may comprise VTN. The composition may comprise ANOS1. The composition may comprise IL-15. The composition may comprise IGF2. In certain embodiments, the composition comprises THBS2, THBS4, and VTN. In certain embodiments, the composition comprises THBS2, THBS4, and ANOS1. In certain embodiments, the composition comprises THBS2, THBS4, and IL-15. In certain embodiments, the composition comprises THBS2, THBS4, and IGF2. In certain embodiments, the composition further comprises a pharmaceutically acceptable excipient. In certain embodiments, the composition is formulated for administration by injection. In certain embodiments, the injection is intramuscular. In certain embodiments, the injection is subcutaneous. In certain embodiments, the injection is intravenous.

In certain embodiment, described herein is a composition comprising THBS1 and FGF17. In certain embodiment, described herein is a composition comprising THBS2 and VTN. In certain embodiment, described herein is a composition comprising THBS1 and VTN. In certain embodiment, described herein is a composition comprising THBS1 and THBS2. In certain embodiment, described herein is a composition comprising THBS2 and FGF17. In certain embodiment, described herein is a composition comprising THBS1 and THBS4. In certain embodiment, described herein is a composition comprising VTN and FGF17. In certain embodiment, described herein is a composition comprising THBS4 and VTN. In certain embodiment, described herein is a composition comprising THBS4 and FGF17. In certain embodiments, the composition further comprises a pharmaceutically acceptable excipient. In certain embodiments, the composition is formulated for administration by injection. In certain embodiments, the injection is intramuscular. In certain embodiments, the injection is subcutaneous. In certain embodiments, the injection is intravenous.

Further described is a method of treating a disease or condition in a subject in need thereof, the method comprising administering to the subject a composition described herein. In certain embodiments, the disease or condition comprises an aging disorder, muscle wasting disorder, muscle injury, or injury to connective tissue, or a combination thereof. In certain embodiments, the subject has the aging disorder and the aging disorder comprises sarcopenia. In certain embodiments, the subject has the muscle wasting disorder and the muscle wasting disorder comprises muscular dystrophy. In certain embodiments, the subject has the muscle wasting disorder and the muscle wasting is a result of obesity, metabolic disorder, disease progression, or therapeutic treatment, or a combination thereof. In certain embodiments, the metabolic disorder is diabetes. In some cases the diabetes is Type 2 Diabetes. In certain embodiments, the subject has the muscle wasting disorder and the muscle wasting is cachexia, e.g., muscular cachexia.

In a certain aspect, described herein, is a composition comprising a mitogenic and/or fusion promoting polypeptide, wherein the polypeptide is a heparin-associated polypeptide secreted from a stem cell or a transformed cell line, wherein the heparin-associated polypeptide possesses mitogenic and/or fusion promoting activity. In certain embodiments, the composition comprises a plurality of mitogenic and/or fusion promoting polypeptides. In certain embodiments, the plurality comprises two, three, four, five, six, seven, eight, nine, ten or more polypeptides. In certain embodiments, the mitogenic and/or fusion promoting polypeptide or plurality of mitogenic and/or fusion promoting polypeptides are isolated and purified. In certain embodiments, the mitogenic and/or fusion promoting polypeptide or plurality of mitogenic and/or fusion promoting polypeptides are recombinantly produced. In certain embodiments, the mitogenic and/or fusion promoting polypeptide or plurality of mitogenic and/or fusion promoting polypeptides are secreted from a stem cell. In certain embodiments, the stem cell is a pluripotent stem cell. In certain embodiments, the stem cell is an induced pluripotent stem cell. In certain embodiments, the mitogenic activity comprises the ability to increase proliferation in a somatic cell and/or increase the ability of another heparin-associated polypeptide to increase proliferation in a somatic cell. In certain embodiments, the fusion promoting activity comprises the ability to increase fusion of a plurality of somatic cells and/or increase the ability of another heparin-associated polypeptide to increase fusion in a plurality of somatic cells. In certain embodiments, the somatic cell is a muscle, muscle progenitor cell, tenocyte, or tenocyte precursor. In certain embodiments, the somatic cell is a mammalian cell. In certain embodiments, the somatic cell is a human cell. In certain embodiments, any one of the mitogenic and/or fusion promoting polypeptides or plurality of mitogenic and/or fusion promoting polypeptides are produced in a heterologous cellular production system. In certain embodiments, any one of the mitogenic and/or fusion promoting polypeptides or plurality of mitogenic and/or fusion promoting polypeptides are synthetically produced. In certain embodiments, the polypeptides are purified from human plasma. In certain embodiments, the polypeptides are purified from a mammalian cell, insect cell, or bacterial cell. The mammalian cell may be a human cell. In certain embodiments, the mitogenic and/or fusion promoting polypeptide or plurality of mitogenic and/or fusion promoting polypeptides comprises one or more modifications to improve activity, stability, or increase polypeptide yield from a heterologous cellular production system, or any combination thereof. In certain embodiments, the modification is an alteration of one or more amino acids in the polypeptide sequence of mitogenic and/or fusion promoting polypeptide compared to the wildtype polypeptide sequence of the mitogenic and/or fusion promoting polypeptide. In certain embodiments, the mitogenic and/or fusion promoting polypeptide(s) are encoded by a nucleic acid. In certain embodiments, the cell line comprises the nucleic acid encoding the mitogenic and/or fusion promoting polypeptide(s). In certain embodiments, the cell line is a eukaryotic cell line. In certain embodiments, the composition comprises the mitogenic and/or fusion promoting polypeptide or plurality of mitogenic and/or fusion promoting polypeptides and a pharmaceutically acceptable excipient, carrier, or diluent. In certain embodiments, the composition is formulated in injectable form. In certain embodiments, the composition is for use in a method of treating an aging disorder, a muscle wasting disorder, a muscle injury, or an injury to a connective tissue, or any combination thereof. In certain embodiments, the aging disorder is sarcopenia. In certain embodiments, the muscle wasting disorder is muscular dystrophy. In certain embodiments, the muscle wasting disorder is cachexia, e.g., muscular cachexia. In certain embodiments, described herein, is a method of treating an individual with aging disorder, a muscle wasting disorder, a muscle injury, or an injury to a connective tissue, or any combination thereof, the method comprising administering to the individual the composition of mitogenic and/or fusion promoting polypeptides. In certain embodiments, the aging disorder is sarcopenia. In certain embodiments, the muscle wasting disorder is muscular dystrophy. In certain embodiments, the muscle wasting disorder is cachexia, e.g., muscular cachexia. In certain embodiments, described herein, is a method of producing a composition suitable for the treatment of an aging disorder comprising admixing a pharmaceutically acceptable excipient, carrier, or diluent with the mitogenic and/or fusion promoting polypeptide or plurality of mitogenic and/or fusion promoting polypeptides described herein. In certain embodiments, described herein, is a method of producing a mitogenic and/or fusion promoting polypeptide comprising culturing a cell line comprising a nucleic acid expressing a mitogenic and/or fusion promoting polypeptide under conditions sufficient to produce the mitogenic and/or fusion promoting polypeptide.

In another aspect, described herein, is a composition comprising a mitogenic and/or fusion promoting polypeptide, wherein the mitogenic and/or fusion promoting polypeptide is identified by: (a) identifying at least one polypeptide in a mixture of a plurality of polypeptides secreted from a stem cell or a transformed cell line that can be purified with heparin coated matrix; and (b) determining the mitogenic and/or fusion promoting activity of the at least one polypeptide for a somatic cell, wherein the at least one polypeptide is identified as a mitogenic and/or fusion promoting polypeptide if the at least one polypeptide exhibits mitogenic and/or fusion promoting activity. In certain embodiments, the composition comprises a plurality of mitogenic and/or fusion promoting polypeptides. In certain embodiments, the plurality comprises three, four, five, six, seven, eight, nine, ten or more polypeptides. In certain embodiments, the mitogenic and/or fusion promoting polypeptide or plurality of mitogenic and/or fusion promoting polypeptides are isolated and purified. In certain embodiments, the mitogenic and/or fusion promoting polypeptide or plurality of mitogenic and/or fusion promoting polypeptides are recombinantly produced. In certain embodiments, the mitogenic and/or fusion promoting polypeptide or plurality of mitogenic and/or fusion promoting polypeptides are secreted from a stem cell. In certain embodiments, the stem cell is a pluripotent stem cell. In certain embodiments, the stem cell is an induced pluripotent stem cell. In certain embodiments, the mitogenic and/or fusion promoting activity comprises the ability to increase proliferation in a somatic cell or increase the ability of another heparin-associated polypeptide to increase proliferation in a somatic cell. In certain embodiments, the fusion promoting activity comprises the ability to increase fusion of a plurality of somatic cells or increase the ability of another heparin-associated polypeptide to increase fusion in a plurality of somatic cells. In certain embodiments, the somatic cell is a muscle, muscle progenitor cell, tenocyte, or tenocyte precursor. In certain embodiments, the somatic cell is a mammalian cell. In certain embodiments, the somatic cell is a human cell. In certain embodiments, any one of the mitogenic and/or fusion promoting polypeptides or plurality of mitogenic and/or fusion promoting polypeptides are produced in a heterologous cellular production system. In certain embodiments, any one of the mitogenic and/or fusion promoting polypeptides or plurality of mitogenic and/or fusion promoting polypeptides are synthetically produced. In certain embodiments, the polypeptides are purified from human plasma. In certain embodiments, the polypeptides are purified from a mammalian cell, insect cell, or bacterial cell. The mammalian cell may be a human cell. In certain embodiments, the mitogenic and/or fusion promoting polypeptide or plurality of mitogenic and/or fusion promoting polypeptides comprises one or more modifications to improve activity, stability, or increase polypeptide yield from a heterologous cellular production system. In certain embodiments, the modification is an alteration of one or more amino acids in the polypeptide sequence of the mitogenic and/or fusion promoting polypeptide compared to the wildtype polypeptide sequence of the mitogenic and/or fusion promoting polypeptide. In certain embodiments, the mitogenic and/or fusion promoting polypeptide(s) are encoded by a nucleic acid. In certain embodiments, the cell line comprises the nucleic acid encoding the mitogenic and/or fusion promoting polypeptide(s). In certain embodiments, the cell line is a eukaryotic cell line. In certain embodiments, the composition comprises the mitogenic and/or fusion promoting polypeptide or plurality of mitogenic and/or fusion promoting polypeptides and a pharmaceutically acceptable excipient, carrier, or diluent. In certain embodiments, the composition is formulated in injectable form. In certain embodiments, the composition is for use in a method of treating an aging disorder, a muscle wasting disorder, a muscle injury, or an injury to a connective tissue, or any combination thereof. In certain embodiments, the aging disorder is sarcopenia. In certain embodiments, the muscle wasting disorder is muscular dystrophy. In certain embodiments, the muscle wasting disorder is cachexia, e.g., muscular cachexia. In certain embodiments, described herein, is a method of treating an individual with aging disorder, a muscle wasting disorder, a muscle injury, or an injury to a connective tissue, or any combination thereof, the method comprising administering to the individual the composition of mitogenic and/or fusion promoting polypeptides. In certain embodiments, the aging disorder is sarcopenia. In certain embodiments, the muscle wasting disorder is muscular dystrophy. In certain embodiments, the muscle wasting disorder is cachexia, e.g., muscular cachexia. In certain embodiments, described herein, is a method of producing a composition suitable for the treatment of an aging disorder comprising admixing a pharmaceutically acceptable excipient, carrier, or diluent with the mitogenic and/or fusion promoting polypeptide or plurality of mitogenic and/or fusion promoting polypeptides described herein. In certain embodiments, described herein, is a method of producing a mitogenic and/or fusion promoting polypeptide comprising culturing a cell line comprising a nucleic acid expressing a mitogenic and/or fusion promoting polypeptide under conditions sufficient to produce the mitogenic and/or fusion promoting polypeptide.

In another aspect, described herein, is a composition comprising a mitogenic and/or fusion promoting polypeptide, wherein the mitogenic and/or fusion promoting polypeptide comprises ADAMTS12, INS-IGF2, AOC1, SOD3, CLU, ITIH1, APLP1, THBS1, COCH, ITIH2, APLP2, THBS3, COL11A1, LAMA1, APOB, TNXB, COL12A1, LAMA2, APOE, VEGFA, COL14A1, LAMA5, APOH, VTN, COL18A1, LAMB1, APP, ZNF207, COL1A1, LAMB2, CCDC80, COL1A2, LTF, CFH, COL2A1, MATN2, CLEC3B, COL3A1, MDK, COL25A1, COL5A1, MST1, COL5A3, COL5A2, NID1, CYR61, COL6A1, NPNT, F2, COL6A2, OLFML3, FGF2, COL6A3, PCOLCE, FGFBP3, CTGF, POSTN, FSTL1, DCD, PTN, HDGF, DRAXIN, RARRES2, KNG1, ECM1, RELN, NDNF, FBLN1, SFRP1, NRP1, FBN1, SLIT3, PAFAH1B1, FBN2, SPON1, PCOLCE2, FN1, STC1, PTPRF, FST, STC2, PTPRS, HGFAC, SVEP1, RPL22, IGFBP2, THBS2, RPL29, a protein listed in Table 2, or a protein listed in Table 1, or any combination thereof. In certain embodiments, the mitogenic and/or fusion promoting polypeptide comprises VTN, STC2, AGRN, POSTN, FGF17, THBS2, FST, THBS4, IGF2, IL-15, or THBS1, or a combination thereof. In certain embodiments, the mitogenic and/or fusion promoting polypeptide comprises one or more of VTN, POSTN, FGF17, THBS2, IGF2, IL-15, THBS1, and THBS4. In certain embodiments, the mitogenic and/or fusion promoting polypeptide comprises VTN. In certain embodiments, the mitogenic and/or fusion promoting polypeptide comprises STC2. In certain embodiments, the mitogenic and/or fusion promoting polypeptide comprises AGRN. In certain embodiments, the mitogenic and/or fusion promoting polypeptide comprises THBS2. In certain embodiments, the mitogenic and/or fusion promoting polypeptide comprises FST. In certain embodiments, the mitogenic and/or fusion promoting polypeptide comprises POSTN. In certain embodiments, the mitogenic and/or fusion promoting polypeptide comprises FGF17. In certain embodiments, the mitogenic and/or fusion promoting polypeptide comprises THBS4. In certain embodiments, the mitogenic and/or fusion promoting polypeptide comprises IGF2. In certain embodiments, the mitogenic and/or fusion promoting polypeptide comprises IL-15. In certain embodiments, the mitogenic and/or fusion promoting polypeptide comprises THBS1. In certain embodiments, the composition comprises a plurality of mitogenic and/or fusion promoting polypeptides. In certain embodiments, the plurality comprises three, four, five, six, seven, eight, nine, ten or more polypeptides. The plurality of polypeptides may comprise one, two, three, four, five, six, seven, eight, nine, ten or more polypeptides of Table 2. The plurality of polypeptides may comprise one, two, three, four, five, six, seven, eight, nine, ten or more polypeptides of Table 1. In certain embodiments, the plurality of mitogenic and/or fusion promoting polypeptides comprises IGF2, THBS2, and THBS4. In certain embodiments, the plurality of mitogenic and/or fusion promoting polypeptides comprises IL-15, THBS2, and THBS4. In certain embodiments, the plurality of mitogenic and/or fusion promoting polypeptides comprises THBS2 and THBS4. In certain embodiments, the plurality of mitogenic and/or fusion promoting polypeptides comprises THBS2, THBS4, and VTN. In certain embodiments, the plurality of mitogenic and/or fusion promoting polypeptides comprises THBS2, THBS4, and ANOS1. In certain embodiments, the plurality of mitogenic and/or fusion promoting polypeptides comprises THBS2, THBS4, and IL-15. In certain embodiments, the plurality of mitogenic and/or fusion promoting polypeptides comprises THBS2, THBS4, and IGF2. In certain embodiments, the plurality of mitogenic and/or fusion promoting polypeptides comprises THBS1 and FGF17. In certain embodiments, the plurality of mitogenic and/or fusion promoting polypeptides comprises THBS2 and VTN. In certain embodiments, the plurality of mitogenic and/or fusion promoting polypeptides comprises THBS1 and VTN. In certain embodiments, the plurality of mitogenic and/or fusion promoting polypeptides comprises THBS1 and THBS2. In certain embodiments, the plurality of mitogenic and/or fusion promoting polypeptides comprises THBS2 and FGF17. In certain embodiments, the plurality of mitogenic and/or fusion promoting polypeptides comprises THBS1 and THBS4. In certain embodiments, the plurality of mitogenic and/or fusion promoting polypeptides comprises VTN and FGF17. In certain embodiments, the plurality of mitogenic and/or fusion promoting polypeptides comprises THBS4 and VTN. In certain embodiments, the plurality of mitogenic and/or fusion promoting polypeptides comprises THBS4 and FGF17. In certain embodiments, the mitogenic and/or fusion promoting polypeptide or plurality of mitogenic and/or fusion promoting polypeptides are isolated and purified. In certain embodiments, the mitogenic and/or fusion promoting polypeptide or plurality of mitogenic and/or fusion promoting polypeptides are recombinantly produced. In certain embodiments, the mitogenic and/or fusion promoting polypeptide or plurality of mitogenic and/or fusion promoting polypeptides are secreted from a stem cell. In certain embodiments, the stem cell is a pluripotent stem cell. In certain embodiments, the stem cell is an induced pluripotent stem cell. In certain embodiments, the mitogenic activity comprises the ability to increase proliferation in a somatic cell or increase the ability of another heparin-associated polypeptide to increase proliferation in a somatic cell. In certain embodiments, the fusion promoting activity comprises the ability to increase fusion of a plurality of somatic cells and/or increase the ability of another heparin-associated polypeptide to increase fusion in a plurality of somatic cells. In certain embodiments, the somatic cell is a muscle, muscle progenitor cell, tenocyte, or tenocyte precursor. In certain embodiments, the somatic cell is a mammalian cell. In certain embodiments, the somatic cell is a human cell. In certain embodiments, any one of the mitogenic and/or fusion promoting polypeptides or plurality of mitogenic and/or fusion promoting polypeptides are produced in a heterologous cellular production system. In certain embodiments, any one of the mitogenic and/or fusion promoting polypeptides or plurality of mitogenic and/or fusion promoting polypeptides are synthetically produced. In certain embodiments, the polypeptides are purified from human plasma. In certain embodiments, the polypeptides are purified from a mammalian cell, insect cell, or bacterial cell. The mammalian cell may be a human cell. In certain embodiments, the mitogenic and/or fusion promoting polypeptide or plurality of mitogenic and/or fusion promoting polypeptides comprises one or more modifications to improve activity, stability, or increase polypeptide yield from a heterologous cellular production system. In certain embodiments, the modification is an alteration of one or more amino acids in the polypeptide sequence of the mitogenic and/or fusion promoting polypeptide compared to the wildtype polypeptide sequence of the mitogenic and/or fusion promoting polypeptide. In certain embodiments, the mitogenic and/or fusion promoting polypeptide(s) are encoded by a nucleic acid. In certain embodiments, the cell line comprises the nucleic acid encoding the mitogenic and/or fusion promoting polypeptide(s). In certain embodiments, the cell line is a eukaryotic cell line. In certain embodiments, the composition comprises the mitogenic and/or fusion promoting polypeptide or plurality of mitogenic and/or fusion promoting polypeptides and a pharmaceutically acceptable excipient, carrier, or diluent. In certain embodiments, the composition is formulated in injectable form. In certain embodiments, the composition is for use in a method of treating an aging disorder, a muscle wasting disorder, a muscle injury, or an injury to a connective tissue, or a combination thereof. In certain embodiments, the aging disorder is sarcopenia. In certain embodiments, the muscle wasting disorder is muscular dystrophy. In certain embodiments, the muscle wasting disorder is cachexia, e.g., muscular cachexia. In certain embodiments, described herein, is a method of treating an individual with aging disorder, a muscle wasting disorder, a muscle injury, or an injury to a connective tissue, or a combination thereof, the method comprising administering to the individual the composition of mitogenic and/or fusion promoting polypeptides. In certain embodiments, the aging disorder is sarcopenia. In certain embodiments, the muscle wasting disorder is muscular dystrophy. In certain embodiments, the muscle wasting disorder is cachexia, e.g., muscular cachexia. In certain embodiments, described herein, is a method of producing a composition suitable for the treatment of an aging disorder comprising admixing a pharmaceutically acceptable excipient, carrier, or diluent with the mitogenic and/or fusion promoting polypeptide or plurality of mitogenic and/or fusion promoting polypeptides described herein. In certain embodiments, described herein, is a method of producing a mitogenic and/or fusion promoting polypeptide comprising culturing a cell line comprising a nucleic acid expressing a mitogenic and/or fusion promoting polypeptide under conditions sufficient to produce the mitogenic and/or fusion promoting polypeptide.

In another aspect, described herein, is a composition comprising a mitogenic and/or fusion promoting polypeptide, wherein the mitogenic and/or fusion promoting polypeptide comprises VTN, STC2, AGRN, POSTN, FGF17, THBS2, FST, THBS4, IGF2, IL-15, or THBS1, or a combination thereof. In certain embodiments, the mitogenic and/or fusion promoting polypeptide comprises one or more of VTN, POSTN, FGF17, THBS2, THBS4, IGF2, IL-15, and THBS1. In certain embodiments, the mitogenic and/or fusion promoting polypeptide comprises VTN. In certain embodiments, the mitogenic and/or fusion promoting polypeptide comprises STC2. In certain embodiments, the mitogenic and/or fusion promoting polypeptide comprises AGRN. In certain embodiments, the mitogenic and/or fusion promoting polypeptide comprises THBS2. In certain embodiments, the mitogenic and/or fusion promoting polypeptide comprises FST. In certain embodiments, the mitogenic and/or fusion promoting polypeptide comprises POSTN. In certain embodiments, the mitogenic and/or fusion promoting polypeptide comprises FGF17. In certain embodiments, the mitogenic and/or fusion promoting polypeptide comprises THBS4. In certain embodiments, the mitogenic and/or fusion promoting polypeptide comprises IGF2. In certain embodiments, the mitogenic and/or fusion promoting polypeptide comprises IL-15. In certain embodiments, the mitogenic and/or fusion promoting polypeptide comprises THBS1. In certain embodiments, the composition comprises a mixture of a plurality of different mitogenic and/or fusion promoting polypeptides. In certain embodiments, the plurality of different mitogenic and/or fusion promoting polypeptides comprise three, four, or five different mitogenic and/or fusion promoting polypeptides. The plurality of polypeptides may comprise one, two, three, four, five, six, seven, eight, nine, ten or more polypeptides of Table 2. The plurality of polypeptides may comprise one, two, three, four, five, six, seven, eight, nine, ten or more polypeptides of Table 1. In certain embodiments, the plurality of mitogenic and/or fusion promoting polypeptides comprises IGF2, THBS2, and THBS4. In certain embodiments, the plurality of mitogenic and/or fusion promoting polypeptides comprises IL-15, THBS2, and THBS4. In certain embodiments, the plurality of mitogenic and/or fusion promoting polypeptides comprises THBS2 and THBS4. In certain embodiments, the plurality of mitogenic and/or fusion promoting polypeptides comprises THBS2, THBS4, and VTN. In certain embodiments, the plurality of mitogenic and/or fusion promoting polypeptides comprises THBS2, THBS4, and ANOS1. In certain embodiments, the plurality of mitogenic and/or fusion promoting polypeptides comprises THBS2, THBS4, and IL-15. In certain embodiments, the plurality of mitogenic and/or fusion promoting polypeptides comprises THBS2, THBS4, and IGF2. In certain embodiments, the plurality of mitogenic and/or fusion promoting polypeptides comprises THBS1 and FGF17. In certain embodiments, the plurality of mitogenic and/or fusion promoting polypeptides comprises THBS2 and VTN.

In certain embodiments, the plurality of mitogenic and/or fusion promoting polypeptides comprises THBS1 and VTN. In certain embodiments, the plurality of mitogenic and/or fusion promoting polypeptides comprises THBS1 and THBS2. In certain embodiments, the plurality of mitogenic and/or fusion promoting polypeptides comprises THBS2 and FGF17. In certain embodiments, the plurality of mitogenic and/or fusion promoting polypeptides comprises THBS1 and THBS4. In certain embodiments, the plurality of mitogenic and/or fusion promoting polypeptides comprises VTN and FGF17. In certain embodiments, the plurality of mitogenic and/or fusion promoting polypeptides comprises THBS4 and VTN. In certain embodiments, the plurality of mitogenic and/or fusion promoting polypeptides comprises THBS4 and FGF17. In certain embodiments, the mitogenic and/or fusion promoting polypeptide or plurality of mitogenic and/or fusion promoting polypeptides are isolated and purified. In certain embodiments, the mitogenic and/or fusion promoting polypeptide or plurality of mitogenic and/or fusion promoting polypeptides are recombinantly or synthetically produced. In certain embodiments, the polypeptides are purified from human plasma. In certain embodiments, the polypeptides are purified from a mammalian cell, insect cell, or bacterial cell. The mammalian cell may be a human cell. In certain embodiments, the mitogenic and/or fusion promoting polypeptide or plurality of mitogenic and/or fusion promoting polypeptides are secreted from a stem cell. In certain embodiments, the stem cell is a pluripotent stem cell. In certain embodiments, the stem cell is an induced pluripotent stem cell. In certain embodiments, the mitogenic activity comprises increasing proliferation in a muscle cell precursor. In certain embodiments, the fusion promoting activity comprises the ability to increase fusion of a plurality of somatic cells and/or increase the ability of another heparin-associated polypeptide to increase fusion in a plurality of somatic cells. In certain embodiments, the muscle cell precursor is a myoblast. In certain embodiments, the somatic cell is a mammalian cell. In certain embodiments, the somatic cell is a human cell. In certain embodiments, the mitogenic and/or fusion promoting polypeptide or plurality of mitogenic and/or fusion promoting polypeptides comprise one or more modifications to improve activity, stability, or increase polypeptide yield from a heterologous cellular production system. In certain embodiments, the modification is an alteration of one or more amino acids in the polypeptide sequence of the mitogenic and/or fusion promoting polypeptide compared to the wildtype polypeptide sequence of the mitogenic and/or fusion promoting polypeptide. In certain embodiments, the modification is a fusion of a mitogenic and/or fusion promoting polypeptide to a non-mitogenic or fusion promoting polypeptide. In certain embodiments, the non-mitogenic or fusion promoting polypeptide comprises an immunoglobulin Fc region or serum albumin. In certain embodiments, the non-mitogenic or fusion promoting polypeptide is a human polypeptide. In certain embodiments, the mitogenic and/or fusion promoting polypeptide or plurality of mitogenic and/or fusion promoting polypeptides are concatemerized. In certain embodiments, the concatemerized polypeptides are separated by a polypeptide linker. In certain embodiments, the concatemerized polypeptides are the same polypeptide. In certain embodiments, the concatemerized polypeptides are different polypeptides. In certain embodiments, the concatemerized polypeptides are covalently concatemerized through a non-peptide linkage. In certain embodiments, the concatemerized polypeptides are non-covalently concatemerized. In certain embodiments, a nucleic acid encodes the mitogenic and/or fusion promoting polypeptide. In certain embodiments, a cell line comprises the nucleic acid. In certain embodiments, the cell line is a eukaryotic cell line. In certain embodiments, the mitogenic and/or fusion promoting polypeptide or plurality of mitogenic and/or fusion promoting polypeptides comprises a pharmaceutically acceptable excipient, carrier, or diluent. In certain embodiments, the pharmaceutically acceptable excipient, carrier, or diluent increases the function of the mitogenic and/or fusion promoting polypeptide or plurality of mitogenic and/or fusion promoting polypeptides. In certain embodiments, the function comprises increasing proliferation in a muscle cell precursor, increasing stability of the mitogenic and/or fusion promoting polypeptide or plurality of mitogenic and/or fusion promoting polypeptides, or increasing bioavailability of the mitogenic and/or fusion promoting polypeptide or plurality of mitogenic and/or fusion promoting polypeptides. In certain embodiments, the composition is for subcutaneous, intravenous, intramuscular, or topical administration. In certain embodiments, the composition is for use in a method of treating an aging disorder, a muscle wasting disorder, a muscle injury, or an injury to a connective tissue, or a combination thereof. In certain embodiments, the aging disorder is sarcopenia. In certain embodiments, the muscle wasting disorder is muscular dystrophy. In certain embodiments, the muscle wasting disorder is cachexia, e.g., muscular cachexia. In certain embodiments, described herein, is a method of treating an individual with an aging disorder, a muscle wasting disorder, a muscle injury, or an injury to a connective tissue, or a combination thereof, the method comprising administering to the individual the composition. In certain embodiments, described herein, is a method of increasing proliferation of a muscle cell or connective tissue cell precursor in an individual comprising administering to the individual the composition. In certain embodiments, the individual is afflicted with or suspected of being afflicted with an aging disorder, a muscle wasting disorder, a muscle injury, or an injury to a connective tissue, or a combination thereof. In certain embodiments, the aging disorder is sarcopenia. In certain embodiments, the muscle wasting disorder is muscular dystrophy. In certain embodiments, the muscle wasting disorder is cachexia, e.g., muscular cachexia.

Also described is a method of producing a composition suitable for the treatment of an aging disorder, a muscle wasting disorder, a muscle injury, or an injury to a connective tissue, or a combination thereof, the method comprising admixing a pharmaceutically acceptable excipient, carrier, or diluent with the mitogenic and/or fusion promoting polypeptide or plurality of mitogenic and/or fusion promoting polypeptides. Also described is a method of producing a mitogenic and/or fusion promoting polypeptide comprising culturing a cell line comprising a nucleic acid encoding mitogenic and/or fusion promoting polypeptide or plurality of mitogenic and/or fusion promoting polypeptides under conditions sufficient to produce the mitogenic and/or fusion promoting polypeptide.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 2A shows time-points for dosing and analysis of the effects of the entire pool of heparin-associated polypeptides in an acute injury model in aged mice. Squares denote injury inducing intramuscular injection (IM) with Barium Chloride; circles denote administration of treatment or vehicle.

FIG. 2B shows the results of the experiment outlined in FIG. 2A. Administration of hPSC derived factors resulted in improved new fiber formation (regenerative index, left) and reduced scaring (fibrotic index, right) in aged mice to levels similar to those in young mice, both of which were markedly better than vehicle-treated old mice. Stars indicate degree of significance from one-way ANOVA tests.

FIG. 3A depicts the methodology for targeted heparin purification of secreted proteins from media supernatant, isobaric labeling, reverse phase fractionation, and SPS-MS3 mass spectrometry instrument method. FIG. 3B depicts a silver stain gel of heparin purified proteins (left two lanes) compared to buffer only (right most lane), demonstrating enrichment of many protein species by their molecular weight. FIG. 3C depicts a 2D heat map of the intensity (color) of peptides separated by m/z (y-axis) compared to elution from reverse phase nHPLC separation (x-axis). FIG. 3D depicts a K-means clustered heat map of all proteins found in a representative experiment demonstrating the differential abundance of many proteins specifically in the secretome of undifferentiated hPSCs.

FIG. 4A shows representative micrographs taken from cells treated with fusion media (neg. control), defined growth media (pos. control), Optimem, supernatant from differentiated hESC, supernatant from undifferentiated hESC, heparin binding proteins eluted from supernatant of undifferentiated hESC under two different conditions, and supernatant of undifferentiated hESC that has been depleted of heparin binding proteins. FIG. 4B shows data expressed as % of nuclei stained with BrdU or % cells stained for embryonic myosin heavy chain (eMyHC).

FIG. 6A shows the effect of IGFBP5 at 1 ug/mL, FIG. 6B show the effect of THBS4 at 1 ug/mL, FIG. 6C shows the effect of VTN at 10 ug/mL, FIG. 6D shows the effect of FGF17 at 250 ng/mL, and FIG. 6E shows the effect of IGFBP7 at 500 ng/mL—all demonstrated notable effects in injury activated primary human myoblasts, young (18 years old) and aged (both 68 years old), grown in vitro.

FIG. 7D shows the synergistic effects of THBS1 with VTN. FIG. 7E shows the synergistic effects of THB with THBS2. FIG. 7F shows the synergistic effects of THBS1 with THBS4. FIG. 7G shows the synergistic effects of lower concentrations of THBS2 with varying concentrations of THBS4. FIG. 7H shows the synergistic effects higher concentrations of THBS2 with varying concentrations of THBS4. FIG. 7I shows the synergistic effects of THBS2 with VTN. FIG. 7J shows the synergistic effects of THBS2 with FGF17. FIG. 7K shows the synergistic effects of THBS4 with VTN. FIG. 7L shows the synergistic effects of THBS4 with FGF17. FIG. 7M shows the synergistic effects of VTN with FGF17.

DETAILED DESCRIPTION

Figure 1:
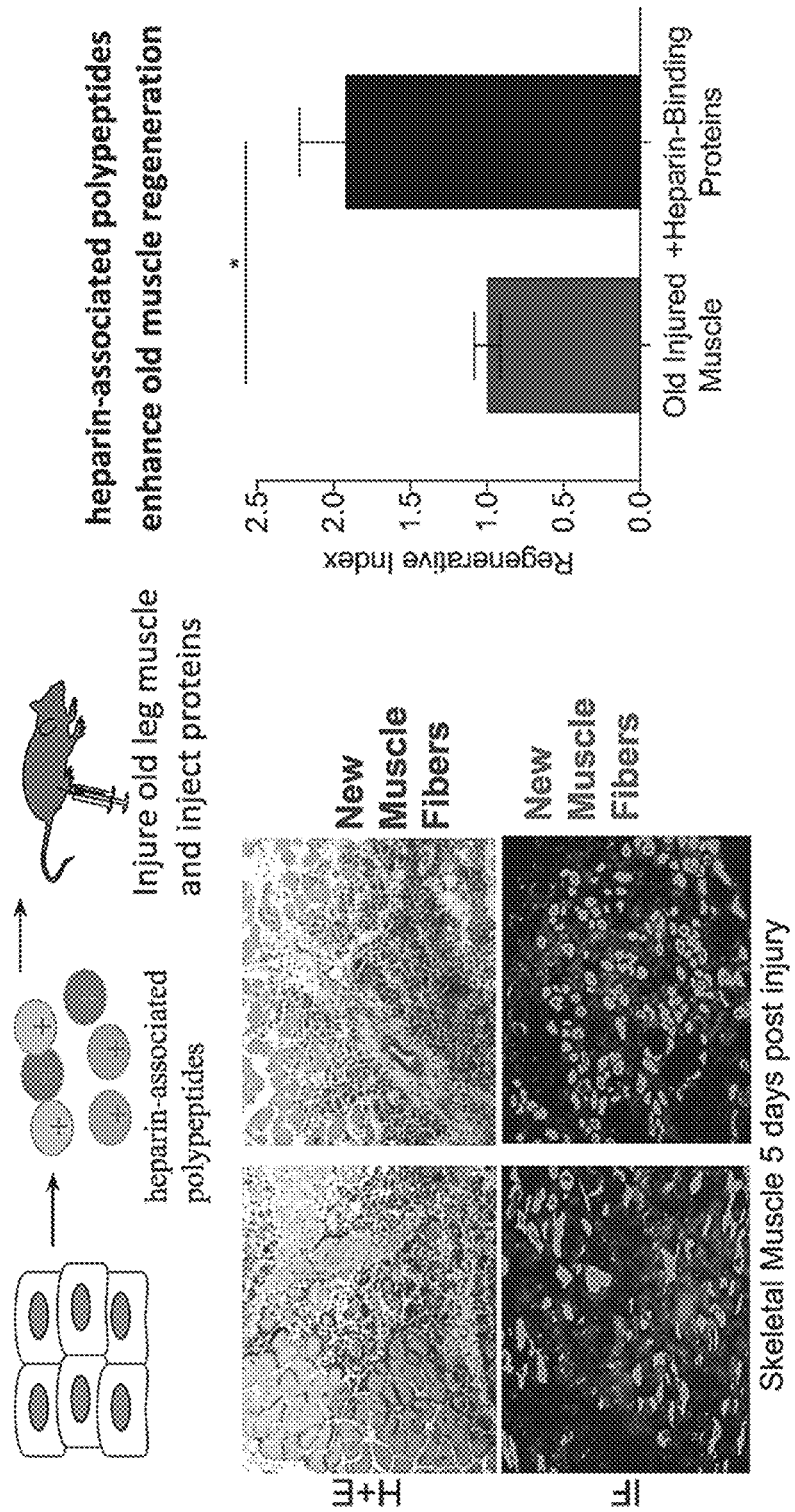
FIG. 1 shows histology and immunofluorescence staining of injured and regenerated muscle tissue from aged mice treated with heparin-associated polypeptides or vehicle control.

In one aspect, described herein is a composition comprising a mitogenic and/or fusion promoting polypeptide, wherein the mitogenic and/or fusion promoting polypeptide is identified by: (a) identifying at least one polypeptide in a mixture of a plurality of polypeptides secreted from a stem cell or a transformed cell line that can be enriched through association of the mixture with heparin-conjugated beads; and (b) determining the mitogenic and/or fusion promoting activity of the at least one polypeptide for a somatic cell, wherein at least one polypeptide is identified as a mitogenic and/or fusion promoting polypeptide if at least one polypeptide exhibits mitogenic and/or fusion promoting activity.

In another aspect, described herein is a composition comprising a mitogenic and/or fusion promoting polypeptide, wherein the polypeptide is a heparin-associated polypeptide secreted from a stem cell or a transformed cell line, wherein the heparin-associated polypeptide possesses mitogenic and/or fusion promoting activity. In certain embodiments, the composition is for use in a method of treating an aging disorder, a muscle wasting disorder, a muscle injury, or an injury to a connective tissue, or a combination thereof. In certain embodiments, the composition is for use in a method of increasing proliferation of a muscle cell or connective tissue cell precursor in an individual. In certain embodiments, the individual is afflicted with or suspected of being afflicted with an aging disorder, a muscle wasting disorder, a muscle injury, or an injury to a connective tissue, or a combination thereof. In certain embodiments, the aging disorder is sarcopenia. In certain embodiments, the muscle wasting disorder is muscular dystrophy. In certain embodiments, the muscle wasting disorder is cachexia, e.g., muscular cachexia. In another aspect, described herein, is a composition comprising a mitogenic and/or fusion promoting polypeptide, wherein the mitogenic and/or fusion promoting polypeptide comprises ADAMTS12, INS-IGF2, AOC1, SOD3, CLU, ITIH1, APLP1, THBS1, COCH, ITIH2, APLP2, THBS3, COL11A1, LAMA1, APOB, TNXB, COL12A1, LAMA2, APOE, VEGFA, COL14A1, LAMA5, APOH, VTN, COL18A1, LAMB1, APP, ZNF207, COL1A1, LAMB2, CCDC80, COL1A2, LTF, CFH, COL2A1, MATN2, CLEC3B, COL3A1, MDK, COL25A1, COL5A1, MST1, COL5A3, COL5A2, NID1, CYR61, COL6A1, NPNT, F2, COL6A2, OLFML3, FGF2, COL6A3, PCOLCE, FGFBP3, CTGF, POSTN, FSTL1, DCD, PTN, HDGF, DRAXIN, RARRES2, KNG1, ECM1, RELN, NDNF, FBLN1, SFRP1, NRP1, FBN1, SLIT3, PAFAH1B1, FBN2, SPON1, PCOLCE2, FN1, STC1, PTPRF, FST, STC2, PTPRS, HGFAC, SVEP1, RPL22, IGFBP2, THBS2, RPL29, a protein listed in Table 2, or a protein listed in Table 1, or any combination thereof. In certain embodiments, the mitogenic and/or fusion promoting polypeptide comprises one or more of VTN, POSTN, FGF17, THBS2, THBS4, IGF2, IL-15, and THBS1. In certain embodiments, the mitogenic and/or fusion promoting polypeptide comprises VTN. In certain embodiments, the mitogenic and/or fusion promoting polypeptide comprises THBS2. In certain embodiments, the mitogenic and/or fusion promoting polypeptide comprises POSTN. In certain embodiments, the mitogenic and/or fusion promoting polypeptide comprises FGF17. In certain embodiments, the mitogenic and/or fusion promoting polypeptide comprises THBS4. In certain embodiments, the mitogenic and/or fusion promoting polypeptide comprises IGF2. In certain embodiments, the mitogenic and/or fusion promoting polypeptide comprises IL-15. In certain embodiments, the mitogenic and/or fusion promoting polypeptide comprises THBS1. In certain embodiments, the composition comprises a mixture of a plurality of different mitogenic and/or fusion promoting polypeptides. In certain embodiments, the plurality of different mitogenic and/or fusion promoting polypeptides comprise three, four, or five different mitogenic and/or fusion promoting polypeptides. The plurality of polypeptides may comprise one, two, three, four, five, six, seven, eight, nine, ten or more polypeptides of Table 2. The plurality of polypeptides may comprise one, two, three, four, five, six, seven, eight, nine, ten or more polypeptides of Table 1. In certain embodiments, the plurality of mitogenic and/or fusion promoting polypeptides comprises IGF2, THBS2, and THBS4. In certain embodiments, the plurality of mitogenic and/or fusion promoting polypeptides comprises IL-15, THBS2, and THBS4. In certain embodiments, the plurality of mitogenic and/or fusion promoting polypeptides comprises THBS2 and THBS4. In certain embodiments, the plurality of mitogenic and/or fusion promoting polypeptides comprises THBS2, THBS4, and VTN. In certain embodiments, the plurality of mitogenic and/or fusion promoting polypeptides comprises THBS2, THBS4, and ANOS1. In certain embodiments, the plurality of mitogenic and/or fusion promoting polypeptides comprises THBS2, THBS4, and IL-15. In certain embodiments, the plurality of mitogenic and/or fusion promoting polypeptides comprises THBS2, THBS4, and IGF2. In certain embodiments, the plurality of mitogenic and/or fusion promoting polypeptides comprises THBS1 and FGF17. In certain embodiments, the plurality of mitogenic and/or fusion promoting polypeptides comprises THBS2 and VTN. In certain embodiments, the plurality of mitogenic and/or fusion promoting polypeptides comprises THBS1 and VTN. In certain embodiments, the plurality of mitogenic and/or fusion promoting polypeptides comprises THBS1 and THBS2. In certain embodiments, the plurality of mitogenic and/or fusion promoting polypeptides comprises THBS2 and FGF17. In certain embodiments, the plurality of mitogenic and/or fusion promoting polypeptides comprises THBS1 and THBS4. In certain embodiments, the plurality of mitogenic and/or fusion promoting polypeptides comprises VTN and FGF17. In certain embodiments, the plurality of mitogenic and/or fusion promoting polypeptides comprises THBS4 and VTN. In certain embodiments, the plurality of mitogenic and/or fusion promoting polypeptides comprises THBS4 and FGF17. In certain embodiments, the composition is for use in a method of treating an aging disorder, a muscle wasting disorder, a muscle injury, or an injury to a connective tissue, or any combination thereof. In certain embodiments, the composition is for use in a method of increasing proliferation of a muscle cell and/or connective tissue cell precursor in an individual. In certain embodiments, the individual is afflicted with or suspected of being afflicted with an aging disorder, a muscle wasting disorder, a muscle injury, or an injury to a connective tissue, or a combination thereof. In certain embodiments, the aging disorder is sarcopenia. In certain embodiments, the muscle wasting disorder is muscular dystrophy. In certain embodiments, the muscle wasting disorder is cachexia, e.g., muscular cachexia.

In another aspect, described herein, is a composition comprising a mitogenic and/or fusion promoting polypeptide, wherein the mitogenic and/or fusion promoting polypeptide comprises VTN, STC2, AGRN, POSTN, FGF17, THBS2, FST, or THBS4, or a combination thereof. In certain embodiments, the mitogenic of fusion promoting polypeptide comprises at least one of VTN, POSTN, FGF17, THBS2, and THBS4. In certain embodiments, the mitogenic and/or fusion promoting polypeptide comprises one or more of VTN, POSTN, FGF17, THBS2, THBS4, IGF2, IL-15, and THBS1. In certain embodiments, the mitogenic and/or fusion promoting polypeptide comprises VTN. In certain embodiments, the mitogenic and/or fusion promoting polypeptide comprises THBS2. In certain embodiments, the mitogenic and/or fusion promoting polypeptide comprises POSTN. In certain embodiments, the mitogenic and/or fusion promoting polypeptide comprises FGF17. In certain embodiments, the mitogenic and/or fusion promoting polypeptide comprises THBS4. In certain embodiments, the mitogenic and/or fusion promoting polypeptide comprises IGF2. In certain embodiments, the mitogenic and/or fusion promoting polypeptide comprises IL-15. In certain embodiments, the mitogenic and/or fusion promoting polypeptide comprises THBS1. In certain embodiments, the composition comprises a mixture of a plurality of different mitogenic and/or fusion promoting polypeptides. In certain embodiments, the plurality of different mitogenic and/or fusion promoting polypeptides comprise three, four, or five different mitogenic and/or fusion promoting polypeptides. The plurality of polypeptides may comprise one, two, three, four, five, six, seven, eight, nine, ten or more polypeptides of Table 2. The plurality of polypeptides may comprise one, two, three, four, five, six, seven, eight, nine, ten or more polypeptides of Table 1. In certain embodiments, the plurality of mitogenic and/or fusion promoting polypeptides comprises IGF2, THBS2, and THBS4. In certain embodiments, the plurality of mitogenic and/or fusion promoting polypeptides comprises IL-15, THBS2, and THBS4. In certain embodiments, the plurality of mitogenic and/or fusion promoting polypeptides comprises THBS2 and THBS4. In certain embodiments, the plurality of mitogenic and/or fusion promoting polypeptides comprises THBS2, THBS4, and VTN. In certain embodiments, the plurality of mitogenic and/or fusion promoting polypeptides comprises THBS2, THBS4, and ANOS1. In certain embodiments, the plurality of mitogenic and/or fusion promoting polypeptides comprises THBS2, THBS4, and IL-15. In certain embodiments, the plurality of mitogenic and/or fusion promoting polypeptides comprises THBS2, THBS4, and IGF2. In certain embodiments, the plurality of mitogenic and/or fusion promoting polypeptides comprises THBS1 and FGF17. In certain embodiments, the plurality of mitogenic and/or fusion promoting polypeptides comprises THBS2 and VTN. In certain embodiments, the plurality of mitogenic and/or fusion promoting polypeptides comprises THBS1 and VTN. In certain embodiments, the plurality of mitogenic and/or fusion promoting polypeptides comprises THBS1 and THBS2. In certain embodiments, the plurality of mitogenic and/or fusion promoting polypeptides comprises THBS2 and FGF17. In certain embodiments, the plurality of mitogenic and/or fusion promoting polypeptides comprises THBS1 and THBS4. In certain embodiments, the plurality of mitogenic and/or fusion promoting polypeptides comprises VTN and FGF17. In certain embodiments, the plurality of mitogenic and/or fusion promoting polypeptides comprises THBS4 and VTN. In certain embodiments, the plurality of mitogenic and/or fusion promoting polypeptides comprises THBS4 and FGF17. In certain embodiments, the composition is for use in a method of treating an aging disorder, a muscle wasting disorder, a muscle injury, or an injury to a connective tissue, or a combination thereof. In certain embodiments, the composition is for use in a method of increasing proliferation of a muscle cell and/or connective tissue cell precursor in an individual. In certain embodiments, the individual is afflicted with or suspected of being afflicted with an aging disorder, a muscle wasting disorder, a muscle injury, or an injury to a connective tissue, or a combination thereof. In certain embodiments, the aging disorder is sarcopenia. In certain embodiments, the muscle wasting disorder is muscular dystrophy. In certain embodiments, the muscle wasting disorder is cachexia, e.g., muscular cachexia.

In the following description, certain specific details are set forth in order to provide a thorough understanding of various embodiments. However, one skilled in the art will understand that the embodiments provided may be practiced without these details. Unless the context requires otherwise, throughout the specification and claims that follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein a composition that is "consisting essentially" of the recited components is a composition that only has the recited elements as active ingredients, but can comprise other non-active components that do not appreciably modify the function or activity of the recited components. Any list disclosed herein that is recited as "comprising" can be recited as "consisting essentially," to exclude non-recited polypeptide or protein components.

As used herein "heparin-associated polypeptide" means any polypeptide that directly binds to heparin with a $K_D$ of less than 1 micromolar, or any polypeptide that associates with one or more polypeptides that bind directly to heparin with a $K_D$ of less than 1 micromolar. This $K_D$ can be measured using a method such as surface plasmon resonance. See e.g., Nguyen et al., "Surface plasmon resonance: a versatile technique for biosensor applications." *Sensors (Basel)*. 2015 May 5; 15(5):10481-510. Alternatively, a heparin-associated polypeptide is one that is enriched by a factor of at least 5-fold, 10-fold, 100-fold, or 1,000 from a complex mixture of polypeptides (e.g., a cell supernatant) by the use of heparin bound to a bead or other matrix support, or co-purifies with such a polypeptide.

As used herein "heparin-binding polypeptide" means any polypeptide that directly binds to heparin with a $K_D$ of less than 1 micromolar. Heparin-binding polypeptides can interact with heparin at steady-state under normal growth conditions, but in other instances heparin-binding polypeptides may interact with heparin transiently under normal growth conditions or only under certain conditions as a result of a signaling or environmental stimulus. Heparin binding-polypeptides may interact with heparin as a result of post-translational modifications such as phosphorylation, dephosphorylation, acetylation, deacetylation, lipidation, delipidation, glycosylation, or deglycosylation, or combinations thereof.

As used herein "pluripotent stem cell" or "pluripotent cell" (PSC) means a cell that has the ability to differentiate into several different cell types that are derivatives of all of the three germinal layers (endoderm, mesoderm, and ectoderm). Pluripotent stem cells are capable of forming teratomas. Examples of pluripotent stem cells are embryonic stem cells (ESCs), embryonic germ stem cells (EGCs), embryonic Carcinoma Cells (ECCs), and induced pluripotent stem cells (iPSCs). PSC may be from any organism of interest, including, primate, human; canine; feline; murine; equine; porcine; avian; camel; bovine; ovine, and so on.

As used herein "somatic cell" means any cell of an organism that, in the absence of experimental manipulation, does not ordinarily give rise to all types of cells in an organism. In other words, somatic cells are cells that have differentiated sufficiently that they will not naturally generate cells of all three germ layers of the body, i.e., ectoderm, mesoderm and endoderm. For example, somatic cells would include muscle cells and muscle progenitor cells, the latter of which may be able to self-renew and naturally give rise to all or some cell types of the skeletal, cardiac, or smooth muscle but cannot give rise to cells of the ectoderm or endoderm lineages.

As used herein the term "about" refers to an amount that is near the stated amount by 10% or less.

As used herein the terms "individual" "subject," and "patient" are interchangeable. The individual can be mammal such as a horse, cow, pig, chicken, goat, rabbit, mouse, rat, dog, or cat. In certain embodiments, the individual is a human person.

The terms "polypeptide" and "protein" are used interchangeably to refer to a polymer of amino acid residues. Polypeptides, including the provided polypeptide chains and other peptides, e.g., linkers and binding peptides, may include amino acid residues including natural and/or non-natural amino acid residues. The terms also include post-translational modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts that produce the proteins, errors due to PCR amplification, or errors in protein translation.

In some embodiments, a recombinant protein is a protein expressed in a system other than a human, e.g., the protein is expressed from bacteria, yeast, or mammalian cells in culture. In some cases, the protein is expressed from Chinese Hamster Ovary cells (CHO cells). In some cases, the protein is expressed from mouse myeloma cells, e.g., (NS0) cells. In some cases, the protein is expressed from *E. coli.*

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Exogenous" with respect to a nucleic acid or polynucleotide indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid also can be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. The exogenous elements may be added to a construct, for example using genetic recombination. Genetic recombination is the breaking and rejoining of DNA strands to form new molecules of DNA encoding a novel set of genetic information. Often exogenous nucleic acids will include a translatable sequence lacking introns that has been cloned from a cDNA.

As described herein a "mitogenic polypeptide" is one that induces one or more stages of mitosis, including interphase, prophase, metaphase, anaphase, and telophase. In certain embodiments, a mitogenic polypeptide is one that induces mitosis in any one or more of a soft-tissue cell, a soft-tissue precursor cell, a muscle cell, a muscle precursor cell, or a tenocyte.

As described herein a "fusion promoting" polypeptide is one that promotes fusion of muscle cells or muscle cell precursors. Fusion of muscle precursors like C2C12 cells is an experimental marker of differentiation and can be monitored by increases in eMyHC or increased number of nuclei per eMyHC positive cell a by a statistically measurable change of at least 25% magnititude (p<0.05) relative to vehicle treated cells grown in otherwise identical conditions.

In some embodiments, reference to a fusion, fusion polypeptide, or fusion protein refers to a synthetically and/or recombinantly produced molecule in which two or more amino acid sequences are connected, e.g., by a peptide bond and/or linker. In some cases, the two or more amino acid sequences are linked via a linker comprising one or more amino acids. In other cases, the two or more amino acid sequences are not linked via a linker, e.g., the two sequences are directly connected by a peptide bond. In some cases, at least one of the two or more amino acid sequences comprises a polypeptide described herein. For example, the polypeptide described herein is a polypeptide comprising VTN, POSTN, FGF17, THBS2, THBS4, THBS1, IL-15, or IGF2, or a combination thereof.

In some embodiments, reference to a conjugate, polypeptide conjugate, or protein conjugate refers to a synthetically and/or recombinantly produced molecule comprising a chemical entity covalently bound to one or more amino acids of an amino acid sequence. In some cases, the conjugation is selective such that the chemical entity is connected to a specific amino acid of the amino acid sequence. In some embodiments, the amino acid sequence comprises a polypeptide described herein. For example, the polypeptide described herein is a polypeptide comprising VTN, POSTN, FGF17, THBS2, THBS4, THBS1, IL-15, or IGF2, or a combination thereof.

In some embodiments, a polypeptide described herein is a proteoform of a protein listed in Table 2. In some embodiments, as used herein a proteoform describes a molecular form of a protein product arising from a gene encoding a protein, such as a protein listed in Table 2. In some cases, a proteoform includes proteins that arise from the same gene as a result of genetic variation, alternatively spliced RNA transcripts, post-translational modifications, or polypeptide cleavage event.

Heparin-Associated Polypeptides

In one aspect, polypeptides described herein that are useful for treating an aging disease or injury comprise one or more polypeptides secreted from an induced pluripotent stem cell, an embryonic stem cell, a tissue progenitor cell, or a transformed cell line that bind to heparin. In certain embodiments, a plurality of 1, 2, 3, 4, 5, 6, 7, 8, 9, 10 or more heparin-associated polypeptides are included in a composition comprising a pharmaceutically acceptable excipient, carrier, or diluent. In some cases the composition comprises one, two, three, four, five, six, seven, eight, nine, ten or more polypeptides of Table 2. In some cases the composition comprises one, two, three, four, five, six, seven, eight, nine, ten or more polypeptides of Table 1.

In certain aspects, there are three biochemical features that are common across all potential therapeutic heparin-associated polypeptides: 1) they are secreted by human pluripotent stem cells; 2) they can be purified by heparin agarose beads from a complex mixture, and 3) their molecular weight equals or exceeds 3.5 kDa.

In certain aspects, there are certain structure-function relationships that potentially link disparate therapeutic polypeptides into a genus of heparin-associated therapeutic polypeptides. Included among these are the ability to be secreted, which may require: 1) an N-terminal signal sequence (aprox. 15-30 amino acids in length); and/or 2) the presence of one or more post translational modifications added in the Endoplasmic Reticulum or the Golgi apparatus to promote stability, such as glycosylation or the presence of disulfide bonds. It is estimated that 2,000 to 3,000 polypeptides encoded by the human genome can be secreted by one or more cell types. In addition to being secretory polypeptides the therapeutic polypeptides may comprise a heparin-binding domain, or, alternatively associate with heparin-binding domain comprising polypeptides. Heparin is a linear polymer of saccharides in 1-4 alpha linkages that form a spiraling chain, commonly associated with its role in binding plasma proteins to reduce clotting (See Capila and Lindhart, "Heparin-protein interactions" *Angew Chem Int Ed Engl.* 2002 Feb. 1; 41(3):391-412). Currently, predicting heparin-binding from protein sequence alone is a challenge for the field due to the structural heterogeneity of heparin polymers and the large and variable number of shallow binding pockets thought to be important for stabilizing the interaction. Several hundred heparin-associated polypeptides have been empirically tested for heparin binding, using a few heparin chain configurations. Based on these studies many binding motifs have been proposed, but none have been proven necessary and sufficient. One common motif appears to be a sequence of repeating basic residues that orient onto a common surface of the secondary structure for interacting with the matching pattern of sulfate groups on heparin chains. Therefore many heparin-binding therapeutic polypeptides may contain patterns of basic residues (arginine or lysine) clustered in some part of the protein, though agnostic to the exact sequence.

In certain embodiments, the heparin-associated therapeutic polypeptide is a secreted polypeptide. In certain embodiments, the heparin-associated therapeutic polypeptide is a secreted polypeptide that comprises 1, 2, 3, 4, 5, 6, 7, 8, 9, 10 or more disulfide bonds. In certain embodiments, the heparin-associated therapeutic polypeptide is a secreted polypeptide that comprises 1, 2, 3, 4, 5, 6, 7, 8, 9, 10 or N-liked or O-linked glycans. In certain embodiments, the heparin-associated therapeutic polypeptide is greater than about 3.5 kilodaltons. In other embodiments, the heparin-associated is greater than about 5, 7.5, 10, 15, or 20 kilodaltons. In certain embodiments, the heparin-associated therapeutic polypeptide is one that comprises a region exhibiting enrichment for basic amino acids arginine or lysine. The region can be about 5, 10, 15, 20, 25, 30, 35, 40, 45, 50, 55, 60, 65, 70, 75, 80, 85, 90, 95, or 100 amino acids in length, and comprise an amount of basic residues that is greater than would be 10%, 20%, 30%, 40%, 50%, 60%, 70%, 80%, 100%, 150%, or 200% greater than expected given random chance. In certain embodiments, the heparin-associated therapeutic polypeptide does not comprise a basic DNA binding motif, such as those found in bZIP transcription factors. In a certain embodiment, the heparin-associated polypeptide is heparin binding polypeptide.

The heparin-associated polypeptides, described herein, can comprise one or more amino acid modifications that promote stability and/or facilitate production. In certain embodiments, the polypeptide can comprise one or more covalent modifications that promote stability (e.g., PEGylation). Other modifications of the heparin-associated polypeptide(s) are contemplated herein. For example, the heparin-associated polypeptide(s) may be linked to one of a variety of non-proteinaceous polymers, e.g., polyethylene glycol, polypropylene glycol, polyoxyalkylenes, or copolymers of polyethylene glycol, polysialic acid, glycolic acid, or polypropylene glycol. In certain embodiments, the heparin-associated polypeptide may be fused or conjugated to another protein to increase stability and or bioavailability. In certain embodiments, the heparin-associated polypeptide may be a fusion with an Fc region of an immunoglobulin or with serum albumin.

The heparin-associated polypeptides described herein can be encapsulated in nanospheres or nanoparticles to increase stability. In certain embodiments, the nanospheres or nanoparticles are biodegradable or bioabsorbable. Certain types of nanospheres can be deployed such as polylactic acid (PLA), polyglycolic acid (PGA), or Poly(D,L-lactic-coglycolic-acid) (PLGA) microspheres or nanospheres. In certain embodiments, the heparin-associated polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In certain embodiments, the heparin-associated-polypeptide may be concatemerized to increase stability and or bioavailability. In certain embodiments, the heparin-associated polypeptide(s) comprises concatemers of the same or of different heparin-associated binding polypeptides. Concatemers can be separated by polypeptide linkers, for example a Gly-Ser linker of any suitable length. In certain embodiments, the Gly-Ser linker comprises a $G_4S_1$ linker. In certain embodiments, the concatemers comprise 1, 2, 3, 4, 5 or more of the same heparin-associated polypeptide as a single polypeptide separated by a Gly-Ser linker. In certain embodiments, the concatemers comprise 1, 2, 3, 4, 5 or more different heparin-associated polypeptides as a single polypeptide separated by a Gly-Ser linker. In certain embodiments, the concatemers comprise 1, 2, 3, 4, 5 or more of the same heparin-associated polypeptide covalently linked through a non-peptide linkage, such as for example a disulfide bridge. In certain embodiments, the concatemers comprise 1, 2, 3, 4, 5 or more different heparin-associated polypeptides covalently linked through a non-peptide linkage, such as for example a disulfide bridge. In certain embodiments, the concatemers comprise 1, 2, 3, 4, 5 or more of the same heparin-associated polypeptide non-covalently linked, such as for example, by a streptavidin-biotin interaction or protein-protein interaction. In certain embodiments, the concatemers comprise 1, 2, 3, 4, 5 or more different heparin-associated polypeptides non-covalently linked such as for example, by a streptavidin-biotin interaction or protein-protein interaction.

Additional modifications to heparin-associated polypeptide comprise deletions of 1, 2, 3, 4, 5, 6, 7, 8, 9, 10, 15, 20, 25, 30, 35, 40, 45, 50, 55, 60, 65, 70, 75, 80, 85, 90, 95, 100 amino acids from the N-terminal or C-terminal ends of the heparin-associated polypeptide. In certain embodiments, the heparin-associated polypeptide comprises the deletion of known inhibitory domains or deletion of domains not associated with the heparin-associated-polypeptides functions in inducing proliferation of muscle, connective, or soft-tissue cell precursors.

The heparin-associated polypeptides herein can comprise cleavage products of a pro-protein. Cleavage of a pro-protein can result in activation or higher activity of said pro-protein. In certain embodiments, heparin-associated polypeptides are produced that correspond to a cleaved or active form of the pro-protein. In certain embodiments, the heparin-associated polypeptides comprise only the active domain of a heparin associated pro-protein (e.g., the minimal portion sufficient to create a biological effect).

In certain embodiments, the heparin-associated polypeptide comprises one or more of the polypeptides listed in Table 1 and/or Table 2. In certain embodiments, the polypeptide is at least about 85%, 90%, 95%, 97%, 98%, 99%, or 100% identical to a polypeptide listed in Table 1 and/or Table 2, or an isoform thereof. In certain embodiments, the polypeptide is at least about 85%, 90%, 95%, 97%, 98%, 99%, or 100% identical to a sequence selected from SEQ ID NOS: 1-44, 55, 56, and 58-70.

TABLE 1

Exemplary Therapeutic Polypeptides

| Polypeptide | SEQ ID | Modified Amino Acid Sequences Tested |
|---|---|---|
| Vitronectin (VTN) | 1 | Asp20 to Leu478, purified from Human plasma-derived |
| Periostin (POSTN) | 6 | Asn22 to Gln836, with a C-terminal 6-His tag (SEQ ID NO: 69), purified from Mouse myeloma cell line, NS0 |
| Thrombospondin 2 (THBS2) | 4 | Gly19 to Ile1172, with a C-terminal 10-His tag (SEQ ID NO: 70), purified from Mouse myeloma cell line, NS0 |
| Thrombospondin 4 (THBS4) | 8 | Ala22 to Asn961, with a C-terminal 10-His tag (SEQ ID NO: 70), purified from Chinese Hamster Ovary cell line |
| Fibroblast growth factor 2 (FGF 2) | 12 | Pro143 to Ser288, purified E. coli |
| Fibroblast growth factor 19 (FGF 19) | 13 | Leu25 to Lys216 purified from E. coli |
| Angiogenin (ANG) | 14 | Gln25 to Pro147, purified from E. coli |
| Probetacellulin (BTC) | 15 | Asp32 to Tyr111, purified from E. coli |
| Interleukin-13 receptor alpha 2 | 16 | Arg21 to Ala228, purified from mouse myeloma cell line, NS0 |
| Siglec-5/CD170 | 17 | Glu17 to Thr434, purified from mouse myeloma cell line, NS0 |
| Interleukin-15 | 10 | Asn49 to Ser162, purified from E. coli |
| Apelin receptor (APJ) | 18 | |
| Insulin-like growth factor-binding protein 2 (IGFBP-2) | 19 | Glu40 to Gln328, purified from mouse myeloma cell line, NS0 |
| Chordin-Like 1 (CHRDL1) | 20 | Glu22-Cys450, purified from mouse myeloma cell line, NS0 |

TABLE 1-continued

Exemplary Therapeutic Polypeptides

| Polypeptide | SEQ ID | Modified Amino Acid Sequences Tested |
|---|---|---|
| WAP, Kazal, immunoglobulin, Kunitz and NTR domain-containing protein 2 | 21 | Leu35 to His 576, purified from mouse myeloma cell line, NS0 |
| Membrane frizzled-related protein (MFRP) | 22 | Ser101 to Pro579, purified from mouse myeloma cell line, NS0 |
| Interleukin-10 receptor alpha | 23 | His22 to Asn235, purified from human cell line HEK293 |
| Chemokine like receptor 1, Chemerin Receptor 23 (Chem R23) | 24 | |
| HB-EGF | 25 | Asp63 to Leu148, purified from insect cells |
| fibroblast growth factor 6 | 26 | Gly67 to Ile208, purified from *E. coli* |
| Hepatocyte Growth Factor | 27 | Gln32 to Ser728, purified from insect cells |
| Interleukin-16 | 28 | Pro2 to Ser130, purified from *E. coli* |
| Interleukin-7 receptor alpha | 29 | Glu21 to Lys261, purified from mouse myeloma cell line, NS0 |
| Tumor necrosis factor receptor superfamily member 10C | 30 | Ala26 to Ala221, purified from mouse myeloma cell line, NS0 |
| Bone morphogenetic protein 6 | 31 | Gln382 to His51,3 purified from *E. coli* |
| Interleukin-36 gamma | 32 | Ser18 to Asp169, purified from *E. coli* |
| interleukin-1 receptor antagonist (IL-1RA) | 33 | Val2 to Asp155, purified from *E. coli* |
| Kremen protein 2 | 34 | Gln19 to Ala364, purified from mouse myeloma cell line, NS0 |
| Tumor necrosis factor receptor superfamily member 10D | 35 | |
| C-X-C chemokine receptor type 1 | 36 | |
| C—C motif chemokine 23 | 37 | |
| Catenin, Beta | 38 | |
| Fibroblast growth factor 13, 1B | 39 | |
| Tumor necrosis factor ligand superfamily member 10 | 40 | Glu108 to Leu261, purified from *E. coli* |
| C—C motif chemokine 14 | 41 | Ser35 to Glu111, purified from *E. coli* |
| Thrombospondin 1 (THBS1) | 9 | Asn19-Pro1170, with Thr523Ala substitution plus 10His tag, purified from mouse myeloma cell line, NS0 |
| Insulin-like growth factor binding protein 7 | 42 | Asp30 to Leu282 with a K95R mutation with an N-terminal 10-His tag (SEQ ID NO: 70), purified from Mouse myeloma cell line, NS0 |
| Fibroblast growth factor 4 | 43 | Ser54 to Leu206, purified from *E. coli* |
| Fibroblast growth factor 17 (FGF17) | 7 | Thr23 to Thr216, purified from *E. coli* |
| Fibroblast growth factor 8 | 44 | Gln23 to Arg204, purified from *E. coli* |
| Insulin-like growth factor 2 (IGF2) | 11 | Ala25 to Glu91, purified from *E. coli* |
| THBS1 isoform 2 | 58 | |
| FGF17 isoform 2 | 59 | |
| POSTN isoform 2 | 60 | |
| POSTN isoform 3 | 61 | |
| POSTN isoform 4 | 62 | |
| POSTN isoform 5 | 63 | |
| POSTN isoform 6 | 64 | |
| POSTN isoform 7 | 65 | |
| IGF2 isoform 2 | 66 | |
| IGF2 isoform 3 | 67 | |
| IL15 isoform 2 | 68 | |
| STC2 | 2 | |
| AGRN | 3 | |
| FST | 5 | |
| PDGFRL | 55 | Gln22 to Ser375, purified from HEK293 cells |
| ANOS1 | 56 | Ala25 to Tyr680, purified from CHO cells |

TABLE 2

Factors enriched in the supernatants of undifferentiated human pluripotent stem cells.

| Gene Name | Uniprot ID | Entrez Gene ID | Ensembl ID | Peptide No. |
|---|---|---|---|---|
| A1BG | P04217 | 1 | ENSG00000121410 | 1 |
| A2M | P01023 | 2 | ENSG00000175899 | 2 |
| ABCF1 | Q8NE71 | 23 | ENSG00000204574 | 3 |
| ACADVL | P49748 | 37 | ENSG00000072778 | 4 |
| ACLY | P53396 | 47 | ENSG00000131473 | 5 |
| ACP1 | P24666 | 52 | ENSG00000143727 | 6 |
| ACP5 | P13686 | 54 | ENSG00000102575 | 7 |
| ACTG1 | P63261 | 71 | ENSG00000184009 | 8 |
| ACTN1 | P12814 | 87 | ENSG00000072110 | 9 |
| ACTR3 | P61158 | 10096 | ENSG00000115091 | 10 |
| ADAMTS1 | Q9UHI8 | 9510 | ENSG00000154734 | 11 |
| ADAMTS12 | P58397 | 81792 | ENSG00000151388 | 12 |
| ADAMTS19 | Q8TE59 | 171019 | ENSG00000145808 | 13 |
| ADAMTS7 | Q9UKP4 | 11173 | ENSG00000136378 | 14 |
| ADAMTS8 | Q9UP79 | 11095 | ENSG00000134917 | 15 |
| ADRM1 | Q16186 | 11047 | ENSG00000130706 | 16 |
| AEBP1 | Q8IUX7 | 165 | ENSG00000106624 | 17 |
| AFM | P43652 | 173 | ENSG00000079557 | 18 |
| AFP | P02771 | 174 | ENSG00000081051 | 19 |
| AGPS | O00116 | 8540 | ENSG00000018510 | 20 |
| AGRN | O00468 | 375790 | ENSG00000188157 | 21 |
| AGT | P01019 | 183 | ENSG00000135744 | 22 |
| AHCYL2 | Q96HN2 | 23382 | ENSG00000158467 | 23 |
| AHSG | P02765 | 197 | ENSG00000145192 | 24 |
| AIMP1 | Q12904 | 9255 | ENSG00000164022 | 25 |
| ALB | P02768 | 213 | ENSG00000163631 | 26 |
| ALCAM | Q13740 | 214 | ENSG00000170017 | 27 |
| ALDH9A1 | P49189 | 223 | ENSG00000143149 | 28 |
| ALDOA | P04075 | 226 | ENSG00000149925 | 29 |
| ALPL | P05186 | 249 | ENSG00000162551 | 30 |
| AMBP | P02760 | 259 | ENSG00000106927 | 31 |
| ANG | P03950 | 283 | ENSG00000214274 | 32 |
| ANGPTL4 | Q9BY76 | 51129 | ENSG00000167772 | 33 |
| ANOS1 | P23352 | 3730 | ENSG00000011201 | 34 |
| ANXA1 | P04083 | 301 | ENSG00000135046 | 35 |
| ANXA2 | P07355 | 302 | ENSG00000182718 | 36 |
| ANXA2P2 | A6NMY6 | | | 37 |
| AOC1 | P19801 | 26 | ENSG00000002726 | 38 |
| AP2A1 | O95782 | 160 | ENSG00000196961 | 39 |
| AP2A2 | O94973 | 161 | ENSG00000183020 | 40 |
| AP3D1 | O14617 | 8943 | ENSG00000065000 | 41 |
| APLP2 | Q06481 | 334 | ENSG00000084234 | 42 |
| APOA1 | P02647 | 335 | ENSG00000118137 | 43 |
| APOA2 | P02652 | 336 | ENSG00000158874 | 44 |
| APOB | P04114 | 338 | ENSG00000084674 | 45 |
| APOC3 | P02656 | 345 | ENSG00000110245 | 46 |
| APOD | P05090 | 347 | ENSG00000189058 | 47 |
| APOE | P02649 | 348 | ENSG00000130203 | 48 |
| APOH | P02749 | 350 | ENSG00000091583 | 49 |
| APOM | O95445 | 55937 | ENSG00000204444 | 50 |
| ARCN1 | P48444 | 372 | ENSG00000095139 | 51 |
| ARHGEF1 | Q92888 | 9138 | ENSG00000076928 | 52 |
| ARHGEF28 | Q8N1W1 | 64283 | ENSG00000214944 | 53 |
| ARPC1B | O15143 | 10095 | ENSG00000130429 | 54 |
| ARRB1 | P49407 | 408 | ENSG00000137486 | 55 |
| ARSK | Q6UWY0 | 153642 | ENSG00000164291 | 56 |
| ART4 | Q93070 | 420 | ENSG00000111339 | 57 |
| ASNA1 | O43681 | 439 | ENSG00000198356 | 58 |
| ASNS | P08243 | 440 | ENSG00000070669 | 59 |
| ATP6AP2 | O75787 | 10159 | ENSG00000182220 | 60 |
| ATRN | O75882 | 8455 | ENSG00000088812 | 61 |
| AZGP1 | P25311 | 563 | ENSG00000160862 | 62 |
| B3GALT6 | Q96L58 | 126792 | ENSG00000176022 | 63 |
| B3GNT7 | Q8NFL0 | 93010 | ENSG00000156966 | 64 |
| B4GALT1 | P15291 | 2683 | ENSG00000086062 | 65 |
| B4GALT4 | O60513 | 8702 | ENSG00000121578 | 66 |
| B4GAT1 | O43505 | 11041 | ENSG00000174684 | 67 |
| BCAM | P50895 | 4059 | ENSG00000187244 | 68 |
| BGN | P21810 | 633 | ENSG00000182492 | 69 |
| BLVRB | P30043 | 645 | ENSG00000090013 | 70 |
| BMP1 | P13497 | 649 | ENSG00000168487 | 71 |
| BMP7 | P18075 | 655 | ENSG00000101144 | 72 |
| BOC | Q9BWV1 | 91653 | ENSG00000144857 | 73 |
| BRD3 | Q15059 | 8019 | ENSG00000169925 | 74 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| BSG | P35613 | 682 | ENSG00000172270 | 75 |
| BTBD17 | A6NE02 | 388419 | ENSG00000204347 | 76 |
| BTD | P43251 | 686 | ENSG00000169814 | 77 |
| BZW2 | Q9Y6E2 | 28969 | ENSG00000136261 | 78 |
| C11orf24 | Q96F05 | 53838 | ENSG00000171067 | 79 |
| C1QA | P02745 | 712 | ENSG00000173372 | 80 |
| C1QBP | Q07021 | 708 | ENSG00000108561 | 81 |
| C1QC | P02747 | 714 | ENSG00000159189 | 82 |
| C1QTNF3 | Q9BXJ4 | 114899 | ENSG00000082196 | 83 |
| C1QTNF3-AMACR | E9PGA6 | | ENSG00000273294 | 84 |
| C1QTNF4 | Q9BXJ3 | 114900 | ENSG00000172247 | 85 |
| C1RL | Q9NZP8 | 51279 | ENSG00000139178 | 86 |
| C1S | P09871 | 716 | ENSG00000182326 | 87 |
| C20orf27 | Q9GZN8 | 54976 | ENSG00000101220 | 88 |
| C3 | P01024 | 718 | ENSG00000125730 | 89 |
| C4A | P0C0L4 | 720 | ENSG00000206340 | 90 |
| C4B | A0A140TA29 | | ENSG00000236625 | 91 |
| C4BPA | P04003 | 722 | ENSG00000123838 | 92 |
| C5 | P01031 | 727 | ENSG00000106804 | 93 |
| C7 | P10643 | 730 | ENSG00000112936 | 94 |
| C8B | P07358 | 732 | ENSG00000021852 | 95 |
| C9 | P02748 | 735 | ENSG00000113600 | 96 |
| CA11 | O75493 | 770 | ENSG00000063180 | 97 |
| CALM2 | P0DP24 | 801 | ENSG00000143933 | 98 |
| CALR | P27797 | 811 | ENSG00000179218 | 99 |
| CALU | O43852 | 813 | ENSG00000128595 | 100 |
| CAND1 | Q86VP6 | 55832 | ENSG00000111530 | 101 |
| CANT1 | Q8WVQ1 | 124583 | ENSG00000171302 | 102 |
| CANX | P27824 | 821 | ENSG00000127022 | 103 |
| CAPG | P40121 | 822 | ENSG00000042493 | 104 |
| CAPN1 | P07384 | 823 | ENSG00000014216 | 105 |
| CAPZA2 | P47755 | 830 | ENSG00000198898 | 106 |
| CARM1 | Q86X55 | 10498 | ENSG00000142453 | 107 |
| CARS | P49589 | 833 | ENSG00000110619 | 108 |
| CBL | P22681 | 867 | ENSG00000110395 | 109 |
| CBX3 | Q13185 | 11335 | ENSG00000122565 | 110 |
| CCAR2 | Q8N163 | 57805 | ENSG00000158941 | 111 |
| CCBE1 | Q6UXH8 | 147372 | ENSG00000183287 | 112 |
| CCDC80 | Q76M96 | 151887 | ENSG00000091986 | 113 |
| CCK | P06307 | 885 | ENSG00000187094 | 114 |
| CCT2 | P78371 | 10576 | ENSG00000166226 | 115 |
| CCT4 | P50991 | 10575 | ENSG00000115484 | 116 |
| CCT7 | Q99832 | 10574 | ENSG00000135624 | 117 |
| CD5 | P06127 | 921 | ENSG00000110448 | 118 |
| CDC40 | O60508 | 51362 | ENSG00000168438 | 119 |
| CDH1 | P12830 | 999 | ENSG00000039068 | 120 |
| CDH9 | Q9ULB4 | 1007 | ENSG00000113100 | 121 |
| CDON | Q4KMG0 | 50937 | ENSG00000064309 | 122 |
| CDSN | Q15517 | 1041 | ENSG00000137197 | 123 |
| CENPV | Q7Z7K6 | 201161 | ENSG00000166582 | 124 |
| CFB | P00751 | 629 | ENSG00000241253 | 125 |
| CFC1 | P0CG37 | 55997 | ENSG00000136698 | 126 |
| CFD | P00746 | 1675 | ENSG00000197766 | 127 |
| CFH | P08603 | 3075 | ENSG00000000971 | 128 |
| CFI | P05156 | 3426 | ENSG00000205403 | 129 |
| CHAD | O15335 | 1101 | ENSG00000136457 | 130 |
| CHD4 | Q14839 | 1108 | ENSG00000111642 | 131 |
| CHD8 | Q9HCK8 | 57680 | ENSG00000100888 | 132 |
| CHGA | P10645 | 1113 | ENSG00000100604 | 133 |
| CHID1 | Q9BWS9 | 66005 | ENSG00000177830 | 134 |
| CHRDL1 | Q9BU40 | 91851 | ENSG00000101938 | 135 |
| CHST11 | Q9NPF2 | 50515 | ENSG00000171310 | 136 |
| CHST6 | Q9GZX3 | 4166 | ENSG00000183196 | 137 |
| CHSY1 | Q86X52 | 22856 | ENSG00000131873 | 138 |
| CHSY3 | Q70JA7 | 337876 | ENSG00000198108 | 139 |
| CILP2 | Q8IUL8 | 148113 | ENSG00000160161 | 140 |
| CKAP5 | Q14008 | 9793 | ENSG00000175216 | 141 |
| CKMT1A | C9J8F6 | | ENSG00000223572 | 142 |
| CKMT2 | P17540 | 1160 | ENSG00000131730 | 143 |
| CLDN6 | P56747 | 9074 | ENSG00000184697 | 144 |
| CLEC3B | P05452 | 7123 | ENSG00000163815 | 145 |
| CLPX | O76031 | 10845 | ENSG00000166855 | 146 |
| CLSTN3 | Q9BQT9 | 9746 | ENSG00000139182 | 147 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| CLTC | Q00610 | 1213 | ENSG00000141367 | 148 |
| CLU | P10909 | 1191 | ENSG00000120885 | 149 |
| CNOT1 | A5YKK6 | 23019 | ENSG00000125107 | 150 |
| COCH | O43405 | 1690 | ENSG00000100473 | 151 |
| COL11A1 | P12107 | 1301 | ENSG00000060718 | 152 |
| COL11A2 | P13942 | 1302 | ENSG00000227801 | 153 |
| COL12A1 | Q99715 | 1303 | ENSG00000111799 | 154 |
| COL14A1 | Q05707 | 7373 | ENSG00000187955 | 155 |
| COL16A1 | Q07092 | 1307 | ENSG00000084636 | 156 |
| COL18A1 | P39060 | 80781 | ENSG00000182871 | 157 |
| COL1A1 | P02452 | 1277 | ENSG00000108821 | 158 |
| COL1A2 | P08123 | 1278 | ENSG00000164692 | 159 |
| COL22A1 | Q8NFW1 | 169044 | ENSG00000169436 | 160 |
| COL25A1 | Q9BXS0 | 84570 | ENSG00000188517 | 161 |
| COL26A1 | Q96A83 | 136227 | ENSG00000160963 | 162 |
| COL2A1 | P02458 | 1280 | ENSG00000139219 | 163 |
| COL3A1 | P02461 | 1281 | ENSG00000168542 | 164 |
| COL4A1 | P02462 | 1282 | ENSG00000187498 | 165 |
| COL4A2 | P08572 | 1284 | ENSG00000134871 | 166 |
| COL4A3 | Q01955 | 1285 | ENSG00000169031 | 167 |
| COL4A6 | Q14031 | 1288 | ENSG00000197565 | 168 |
| COL5A1 | P20908 | 1289 | ENSG00000130635 | 169 |
| COL5A2 | P05997 | 1290 | ENSG00000204262 | 170 |
| COL5A3 | P25940 | 50509 | ENSG00000080573 | 171 |
| COL6A1 | P12109 | 1291 | ENSG00000142156 | 172 |
| COL6A2 | P12110 | 1292 | ENSG00000142173 | 173 |
| COL6A3 | P12111 | 1293 | ENSG00000163359 | 174 |
| COL9A2 | Q14055 | 1298 | ENSG00000049089 | 175 |
| COLEC10 | Q9Y6Z7 | 10584 | ENSG00000184374 | 176 |
| COMP | P49747 | 1311 | ENSG00000105664 | 177 |
| COPA | P53621 | 1314 | ENSG00000122218 | 178 |
| COTL1 | Q14019 | 23406 | ENSG00000103187 | 179 |
| CP | P00450 | 1356 | ENSG00000047457 | 180 |
| CPA4 | Q9UI42 | 51200 | ENSG00000128510 | 181 |
| CPE | P16870 | 1363 | ENSG00000109472 | 182 |
| CPN1 | P15169 | 1369 | ENSG00000120054 | 183 |
| CPNE1 | Q99829 | 8904 | ENSG00000214078 | 184 |
| CPVL | Q9H3G5 | 54504 | ENSG00000106066 | 185 |
| CPXM1 | Q96SM3 | 56265 | ENSG00000088882 | 186 |
| CPXM2 | Q8N436 | 119587 | ENSG00000121898 | 187 |
| CPZ | Q66K79 | 8532 | ENSG00000109625 | 188 |
| CRIM1 | Q9NZV1 | 51232 | ENSG00000150938 | 189 |
| CRISPLD1 | Q9H336 | 83690 | ENSG00000121005 | 190 |
| CRLF1 | O75462 | 9244 | ENSG00000006016 | 191 |
| CRYL1 | Q9Y2S2 | 51084 | ENSG00000165475 | 192 |
| CS | O75390 | 1431 | ENSG00000062485 | 193 |
| CSDE1 | O75534 | 7812 | ENSG00000009307 | 194 |
| CSF2RA | P15509 | 1438 | ENSG00000198223 | 195 |
| CST1 | P01037 | 1469 | ENSG00000170373 | 196 |
| CS13 | P01034 | 1471 | ENSG00000101439 | 197 |
| CS14 | P01036 | 1472 | ENSG00000101441 | 198 |
| CTGF | Q5M8T4 | 1490 | | 199 |
| CTNNA1 | P35221 | 1495 | ENSG00000044115 | 200 |
| CTSD | P07339 | 1509 | ENSG00000117984 | 201 |
| CTSV | O60911 | 1515 | ENSG00000136943 | 202 |
| CUL2 | Q13617 | 8453 | ENSG00000108094 | 203 |
| CUL3 | Q13618 | 8452 | ENSG00000036257 | 204 |
| CUL4B | Q13620 | 8450 | ENSG00000158290 | 205 |
| CUTA | O60888 | 51596 | ENSG00000112514 | 206 |
| CXADR | P78310 | 1525 | ENSG00000154639 | 207 |
| CXCL12 | P48061 | 6387 | ENSG00000107562 | 208 |
| CYR61 | Q6FI18 | 3491 | | 209 |
| DAG1 | Q14118 | 1605 | ENSG00000173402 | 210 |
| DARS | P14868 | 1615 | ENSG00000115866 | 211 |
| DBNL | Q9UJU6 | 28988 | ENSG00000136279 | 212 |
| DCD | P81605 | 117159 | ENSG00000161634 | 213 |
| DDOST | P39656 | 1650 | ENSG00000244038 | 214 |
| DDR1 | Q08345 | 780 | ENSG00000137332 | 215 |
| DDX17 | Q92841 | 10521 | ENSG00000100201 | 216 |
| DDX39B | Q13838 | 7919 | ENSG00000215425 | 217 |
| DENND5A | Q61Q26 | 23258 | ENSG00000184014 | 218 |
| DHFR | P00374 | 1719 | ENSG00000228716 | 219 |
| DHX29 | Q7Z478 | 54505 | ENSG00000067248 | 220 |
| DKK1 | O94907 | 22943 | ENSG00000107984 | 221 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| DKK3 | Q9UBP4 | 27122 | ENSG00000050165 | 222 |
| DKK4 | Q9UBT3 | 27121 | ENSG00000104371 | 223 |
| DLG3 | Q92796 | 1741 | ENSG00000082458 | 224 |
| DMBT1 | Q9UGM3 | 1755 | ENSG00000187908 | 225 |
| DNAAF5 | Q86Y56 | 54919 | ENSG00000164818 | 226 |
| DNAJB11 | Q9UB54 | 51726 | ENSG00000090520 | 227 |
| DNAJC3 | Q13217 | 5611 | ENSG00000102580 | 228 |
| DNMT1 | P26358 | 1786 | ENSG00000130816 | 229 |
| DRAXIN | Q8NBI3 | 374946 | ENSG00000162490 | 230 |
| DRG1 | Q9Y295 | 4733 | ENSG00000185721 | 231 |
| DSG2 | Q14126 | 1829 | ENSG00000046604 | 232 |
| ECM1 | Q16610 | 1893 | ENSG00000143369 | 233 |
| EDA | Q92838 | 1896 | ENSG00000158813 | 234 |
| EDIL3 | O43854 | 10085 | ENSG00000164176 | 235 |
| EEF1G | P26641 | 1937 | ENSG00000254772 | 236 |
| EFEMP1 | Q12805 | 2202 | ENSG00000115380 | 237 |
| EFTUD2 | Q15029 | 9343 | ENSG00000108883 | 238 |
| EGFLAM | Q63HQ2 | 133584 | ENSG00000164318 | 239 |
| EIF1AY | O14602 | 9086 | ENSG00000198692 | 240 |
| EIF2B4 | Q9U110 | 8890 | ENSG00000115211 | 241 |
| EIF2S1 | P05198 | 1965 | ENSG00000134001 | 242 |
| EIF2S2 | P20042 | 8894 | ENSG00000125977 | 243 |
| EIF3A | Q14152 | 8661 | ENSG00000107581 | 244 |
| EIF3C | Q99613 | 8663 | ENSG00000184110 | 245 |
| EIF3F | O00303 | 8665 | ENSG00000175390 | 246 |
| EIF3H | O15372 | 8667 | ENSG00000147677 | 247 |
| EIF3M | Q7L2H7 | 10480 | ENSG00000149100 | 248 |
| EIF5 | P55010 | 1983 | ENSG00000100664 | 249 |
| EIF5B | O60841 | 9669 | ENSG00000158417 | 250 |
| ELAC2 | Q9BQ52 | 60528 | ENSG00000006744 | 251 |
| ELP3 | Q9H9T3 | 55140 | ENSG00000134014 | 252 |
| EMILIN2 | Q9BXX0 | 84034 | ENSG00000132205 | 253 |
| EPHA4 | P54764 | 2043 | ENSG00000116106 | 254 |
| EPHB2 | P29323 | 2048 | ENSG00000133216 | 255 |
| EPHB4 | P54760 | 2050 | ENSG00000196411 | 256 |
| EPRS | P07814 | 2058 | ENSG00000136628 | 257 |
| ERBB3 | P21860 | 2065 | ENSG00000065361 | 258 |
| ERLIN1 | O75477 | 10613 | ENSG00000107566 | 259 |
| ERVMER34-1 | Q9H9K5 | 100288413 | ENSG00000226887 | 260 |
| EXTL2 | Q9UBQ6 | 2135 | ENSG00000162694 | 261 |
| EZR | P15311 | 7430 | ENSG00000092820 | 262 |
| F10 | P00742 | 2159 | ENSG00000126218 | 263 |
| F13A1 | P00488 | 2162 | ENSG00000124491 | 264 |
| F2 | P00734 | 2147 | ENSG00000180210 | 265 |
| F5 | P12259 | 2153 | ENSG00000198734 | 266 |
| FAM129B | Q96TA1 | 64855 | ENSG00000136830 | 267 |
| FAP | Q12884 | 2191 | ENSG00000078098 | 268 |
| FAT1 | Q14517 | 2195 | ENSG00000083857 | 269 |
| FBLN1 | P23142 | 2192 | ENSG00000077942 | 270 |
| FBLN2 | P98095 | 2199 | ENSG00000163520 | 271 |
| FBN1 | P35555 | 2200 | | 272 |
| FBN2 | P35556 | 2201 | ENSG00000138829 | 273 |
| FERMT2 | Q96AC1 | 10979 | ENSG00000073712 | 274 |
| FGB | P02675 | 2244 | ENSG00000171564 | 275 |
| FGF17 | O60258 | 8822 | ENSG00000158815 | 276 |
| FGF2 | P09038 | 2247 | ENSG00000138685 | 277 |
| FGF8 | P55075 | 2253 | ENSG00000107831 | 278 |
| FGF4 | P08620 | 2249 | ENSG00000075388 | 279 |
| FGF6 | P10767 | 2251 | ENSG00000111241 | 280 |
| FGFBP3 | Q8TAT2 | 143282 | ENSG00000174721 | 281 |
| FGFR1 | P11362 | 2260 | ENSG00000077782 | 282 |
| FGFR2 | P21802 | 2263 | ENSG00000066468 | 283 |
| FGFR4 | P22455 | 2264 | ENSG00000160867 | 284 |
| FGFRL1 | Q8N441 | 53834 | ENSG00000127418 | 285 |
| FH | P07954 | 2271 | ENSG00000091483 | 286 |
| FLT | P17948 | 2321 | ENSG00000102755 | 287 |
| FN1 | P02751 | 2335 | ENSG00000115414 | 288 |
| FRAS1 | Q86XX4 | 80144 | ENSG00000138759 | 289 |
| FRZB | Q92765 | 2487 | ENSG00000162998 | 290 |
| FST | P19883 | 10468 | ENSG00000134363 | 291 |
| FSTL1 | Q12841 | 11167 | ENSG00000163430 | 292 |
| FUCA2 | Q9BTY2 | 2519 | ENSG00000001036 | 293 |
| FXR1 | P51114 | 8087 | ENSG00000114416 | 294 |
| GALNT1 | Q10472 | 2589 | ENSG00000141429 | 295 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| GALNT16 | Q8N428 | 57452 | ENSG00000100626 | 296 |
| GALNT2 | Q10471 | 2590 | ENSG00000143641 | 297 |
| GALNT7 | Q86SF2 | 51809 | ENSG00000109586 | 298 |
| GANAB | Q14697 | 23193 | ENSG00000089597 | 299 |
| GARS | P41250 | 2617 | ENSG00000106105 | 300 |
| GBA | P04062 | 2629 | ENSG00000177628 | 301 |
| GC | P02774 | 2638 | ENSG00000145321 | 302 |
| GCNT1 | Q02742 | 2650 | ENSG00000187210 | 303 |
| GDF11 | O95390 | 10220 | ENSG00000135414 | 304 |
| GDF15 | Q99988 | 9518 | ENSG00000130513 | 305 |
| GDF6 | Q6KF10 | 392255 | ENSG00000156466 | 306 |
| GEMIN5 | Q8TEQ6 | 25929 | ENSG00000082516 | 307 |
| GFAP | P14136 | 2670 | ENSG00000131095 | 308 |
| GGH | Q92820 | 8836 | ENSG00000137563 | 309 |
| GLB1 | P16278 | 2720 | ENSG00000170266 | 310 |
| GLG1 | Q92896 | 2734 | ENSG00000090863 | 311 |
| GM2A | P17900 | 2760 | ENSG00000196743 | 312 |
| GNAS | O95467 | 2778 | ENSG00000087460 | 313 |
| GOLM1 | Q8NBJ4 | 51280 | ENSG00000135052 | 314 |
| GOT2 | P00505 | 2806 | ENSG00000125166 | 315 |
| GPC1 | P35052 | 2817 | ENSG00000063660 | 316 |
| GPC3 | P51654 | 2719 | ENSG00000147257 | 317 |
| GPC4 | O75487 | 2239 | ENSG00000076716 | 318 |
| GPI | P06744 | 2821 | ENSG00000105220 | 319 |
| GPRC5B | Q9NZH0 | 51704 | ENSG00000167191 | 320 |
| GPX4 | P36969 | 2879 | ENSG00000167468 | 321 |
| GREM1 | O60565 | 26585 | ENSG00000166923 | 322 |
| GRN | P28799 | 2896 | ENSG00000030582 | 323 |
| GRSF1 | Q12849 | 2926 | ENSG00000132463 | 324 |
| GSN | P06396 | 2934 | ENSG00000148180 | 325 |
| GSPT1 | P15170 | 2935 | ENSG00000103342 | 326 |
| GTF3C3 | Q9Y5Q9 | 9330 | ENSG00000119041 | 327 |
| HABP2 | Q14520 | 3026 | ENSG00000148702 | 328 |
| HADHB | P55084 | 3032 | ENSG00000138029 | 329 |
| HAPLN1 | P10915 | 1404 | ENSG00000145681 | 330 |
| HAPLN3 | Q96S86 | 145864 | | 331 |
| HAPLN4 | Q86UW8 | 404037 | | 332 |
| HARS | P12081 | 3035 | ENSG00000170445 | 333 |
| HBB | P68871 | 3043 | ENSG00000244734 | 334 |
| HBS1L | Q9Y450 | 10767 | ENSG00000112339 | 335 |
| HDGF | P51858 | 3068 | ENSG00000143321 | 336 |
| HDGFL2 | Q7Z4V5 | 84717 | ENSG00000167674 | 337 |
| HDLBP | Q00341 | 3069 | ENSG00000115677 | 338 |
| HGF | P14210 | 3082 | ENSG00000019991 | 339 |
| HGFAC | Q04756 | 3083 | ENSG00000109758 | 340 |
| HIST1H1C | P16403 | 3006 | ENSG00000187837 | 341 |
| HIST1H1E | P10412 | 3008 | ENSG00000168298 | 342 |
| HLA-C | P04222 | | ENSG00000225691 | 343 |
| HMCN1 | Q96RW7 | 83872 | ENSG00000143341 | 344 |
| HMCN2 | Q8NDA2 | | ENSG00000148357 | 345 |
| HMGB1 | P09429 | 3146 | ENSG00000189403 | 346 |
| HMGB2 | P26583 | 3148 | ENSG00000164104 | 347 |
| HMGB3 | O15347 | 3149 | ENSG00000029993 | 348 |
| HMGN1 | P05114 | 3150 | ENSG00000205581 | 349 |
| HMGN5 | P82970 | 79366 | ENSG00000198157 | 350 |
| HNRNPA2B1 | P22626 | 3181 | ENSG00000122566 | 351 |
| HNRNPDL | O14979 | 9987 | ENSG00000152795 | 352 |
| HP | P00738 | 3240 | ENSG00000257017 | 353 |
| HP1BP3 | Q5SSJ5 | 50809 | ENSG00000127483 | 354 |
| HPR | P00739 | 3250 | ENSG00000261701 | 355 |
| HPX | P02790 | 3263 | ENSG00000110169 | 356 |
| HS3ST3A1 | Q9Y663 | 9955 | ENSG00000153976 | 357 |
| HS6ST1 | O60243 | 9394 | ENSG00000136720 | 358 |
| HS6ST2 | Q96MM7 | 90161 | ENSG00000171004 | 359 |
| HSD17B10 | Q99714 | 3028 | ENSG00000072506 | 360 |
| HSD17B4 | P51659 | 3295 | ENSG00000133835 | 361 |
| HSP90AA1 | P07900 | 3320 | ENSG00000080824 | 362 |
| HSP90AB1 | P08238 | 3326 | ENSG00000096384 | 363 |
| HSP90B1 | P14625 | 7184 | ENSG00000166598 | 364 |
| HSPA5 | P11021 | 3309 | ENSG00000044574 | 365 |
| HSPG2 | P98160 | 3339 | ENSG00000142798 | 366 |
| HTRA1 | Q92743 | 5654 | ENSG00000166033 | 367 |
| HYOU1 | Q9Y4L1 | 10525 | ENSG00000149428 | 368 |
| IARS | P41252 | 3376 | ENSG00000196305 | 369 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| ICAM2 | P13598 | 3384 | ENSG00000108622 | 370 |
| IDE | P14735 | 3416 | ENSG00000119912 | 371 |
| IDH1 | O75874 | 3417 | ENSG00000138413 | 372 |
| IDH2 | P48735 | 3418 | ENSG00000182054 | 373 |
| IGF1 | P05019 | 3479 | ENSG00000017427 | 374 |
| IGF2 | P01344 | 3481 | ENSG00000167244 | 375 |
| IGFBP2 | P18065 | 3485 | ENSG00000115457 | 376 |
| IGFBP3 | P17936 | 3486 | ENSG00000146674 | 377 |
| IGFBP4 | P22692 | 3487 | ENSG00000141753 | 378 |
| IGFBP5 | P24593 | 3488 | ENSG00000115461 | 379 |
| IGFBP6 | P24592 | 3489 | ENSG00000167779 | 380 |
| IGFBP7 | Q16270 | 3490 | ENSG00000163453 | 381 |
| IGFBPL1 | Q8WX77 | 347252 | ENSG00000137142 | 382 |
| IGHA1 | P01876 | | ENSG00000211895 | 383 |
| IGHA2 | P01877 | | ENSG00000211890 | 384 |
| IGHG1 | P01857 | | ENSG00000211896 | 385 |
| IGHG2 | P01859 | | ENSG00000211893 | 386 |
| IGHG4 | P01861 | | ENSG00000211892 | 387 |
| IGHM | P01871 | | ENSG00000211899 | 388 |
| IGKC | P01834 | | | 389 |
| IGKV2-28 | A0A075B6P5 | | ENSG00000244116 | 390 |
| IGKV2D-40 | P01614 | | ENSG00000251039 | 391 |
| IGKV3D-20 | A0A0C4DH25 | | ENSG00000211625 | 392 |
| IGLC2 | P0DOY2 | | ENSG00000211677 | 393 |
| IGLC3 | P0DOY3 | | ENSG00000211679 | 394 |
| IGLV2-11 | P01706 | | ENSG00000211668 | 395 |
| IGSF1 | Q8N6C5 | 3547 | ENSG00000147255 | 396 |
| IGSF10 | Q6WRI0 | 285313 | ENSG00000152580 | 397 |
| ILF2 | Q12905 | 3608 | ENSG00000143621 | 398 |
| INHBA | P08476 | 3624 | ENSG00000122641 | 399 |
| INS | P01308 | 3630 | ENSG00000254647 | 400 |
| INS-IGF2 | F8WCM5 | 723961 | ENSG00000129965 | 401 |
| IPO11 | Q9U126 | 51194 | ENSG00000086200 | 402 |
| IPO5 | O00410 | 3843 | ENSG00000065150 | 403 |
| IPO8 | O15397 | 10526 | ENSG00000133704 | 404 |
| IQGAP1 | P46940 | 8826 | ENSG00000140575 | 405 |
| ISOC1 | Q96CN7 | 51015 | ENSG00000066583 | 406 |
| ITGAL | P20701 | 3683 | ENSG00000005844 | 407 |
| ITIH1 | P19827 | 3697 | ENSG00000055957 | 408 |
| ITIH2 | P19823 | 3698 | ENSG00000151655 | 409 |
| ITIH3 | Q06033 | 3699 | ENSG00000162267 | 410 |
| ITIH4 | Q14624 | 3700 | ENSG00000055955 | 411 |
| ITIH5 | Q86UX2 | 80760 | ENSG00000123243 | 412 |
| ITLN2 | Q8WWU7 | 142683 | ENSG00000158764 | 413 |
| JCHAIN | P01591 | 3512 | ENSG00000132465 | 414 |
| KARS | Q15046 | 3735 | ENSG00000065427 | 415 |
| KDM1A | O60341 | 23028 | ENSG00000004487 | 416 |
| KMT2A | Q03164 | 4297 | ENSG00000118058 | 417 |
| KNG1 | P01042 | 3827 | ENSG00000113889 | 418 |
| KRT10 | P13645 | 3858 | ENSG00000186395 | 419 |
| KRT14 | P02533 | 3861 | ENSG00000186847 | 420 |
| KRT17 | Q04695 | 3872 | ENSG00000128422 | 421 |
| KRT18 | P05783 | 3875 | ENSG00000111057 | 422 |
| KRT8 | P05787 | 3856 | ENSG00000170421 | 423 |
| LACRT | Q9GZZ8 | 90070 | ENSG00000135413 | 424 |
| LAG3 | P18627 | 3902 | ENSG00000089692 | 425 |
| LAMA1 | P25391 | 284217 | ENSG00000101680 | 426 |
| LAMA2 | P24043 | 3908 | ENSG00000196569 | 427 |
| LAMA5 | O15230 | 3911 | ENSG00000130702 | 428 |
| LAMB1 | P07942 | 3912 | ENSG00000091136 | 429 |
| LAMB2 | P55268 | 3913 | ENSG00000172037 | 430 |
| LAMC1 | P11047 | 3915 | ENSG00000135862 | 431 |
| LARS | Q9P2J5 | 51520 | ENSG00000133706 | 432 |
| LCAT | P04180 | 3931 | ENSG00000213398 | 433 |
| LCN1 | P31025 | 3933 | ENSG00000160349 | 434 |
| LDHA | P00338 | 3939 | ENSG00000134333 | 435 |
| LECT2 | O14960 | 3950 | ENSG00000145826 | 436 |
| LEFTY1 | O75610 | 10637 | ENSG00000243709 | 437 |
| LEFTY2 | O00292 | 7044 | ENSG00000143768 | 438 |
| LEFTYA | | | | 439 |
| LFNG | Q8NES3 | 3955 | ENSG00000106003 | 440 |
| LGALS3BP | Q08380 | 3959 | ENSG00000108679 | 441 |
| LGALS7 | M0R281 | | ENSG00000205076 | 442 |
| LIG3 | P49916 | 3980 | ENSG00000005156 | 443 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| LINGO1 | Q96FE5 | 84894 | ENSG00000169783 | 444 |
| LIPG | Q9Y5X9 | 9388 | ENSG00000101670 | 445 |
| LMAN2 | Q12907 | 10960 | ENSG00000169223 | 446 |
| LMNA | P02545 | 4000 | ENSG00000160789 | 447 |
| LOXL1 | Q08397 | 4016 | ENSG00000129038 | 448 |
| LOXL2 | Q9Y4K0 | 4017 | ENSG00000134013 | 449 |
| LOXL3 | P58215 | 84695 | ENSG00000115318 | 450 |
| LPL | P06858 | 4023 | ENSG00000175445 | 451 |
| LRG1 | P02750 | 116844 | ENSG00000171236 | 452 |
| LRP1 | Q07954 | 4035 | ENSG00000123384 | 453 |
| LRPAP1 | P30533 | 4043 | ENSG00000163956 | 454 |
| LRRC59 | Q96AG4 | 55379 | ENSG00000108829 | 455 |
| LRRTM4 | Q86VH4 | 80059 | ENSG00000176204 | 456 |
| LSR | Q86X29 | 51599 | ENSG00000105699 | 457 |
| LTBP1 | Q14766 | 4052 | ENSG00000049323 | 458 |
| LTBP4 | Q8N2S1 | 8425 | ENSG00000090006 | 459 |
| LTF | P02788 | 4057 | ENSG00000012223 | 460 |
| LUM | P51884 | 4060 | ENSG00000139329 | 461 |
| LYAR | Q9NX58 | 55646 | ENSG00000145220 | 462 |
| LYZ | P61626 | 4069 | ENSG00000090382 | 463 |
| MANF | P55145 | 7873 | ENSG00000145050 | 464 |
| MAP2K2 | P36507 | 5605 | ENSG00000126934 | 465 |
| MAP4 | P27816 | 4134 | ENSG00000047849 | 466 |
| MAPK1 | P28482 | 5594 | ENSG00000100030 | 467 |
| MASP1 | P48740 | 5648 | ENSG00000127241 | 468 |
| MATN2 | O00339 | 4147 | ENSG00000132561 | 469 |
| MATN3 | O15232 | 4148 | ENSG00000132031 | 470 |
| MATR3 | P43243 | 9782 | ENSG00000015479 | 471 |
| MAZ | P56270 | 4150 | ENSG00000103495 | 472 |
| MBNL1 | Q9NR56 | 4154 | ENSG00000152601 | 473 |
| MCM5 | P33992 | 4174 | ENSG00000100297 | 474 |
| MDH2 | P40926 | 4191 | ENSG00000146701 | 475 |
| MDK | P21741 | 4192 | ENSG00000110492 | 476 |
| MEGF10 | Q96KG7 | 84466 | ENSG00000145794 | 477 |
| MEGF6 | O75095 | 1953 | ENSG00000162591 | 478 |
| METAP2 | P50579 | 10988 | ENSG00000111142 | 479 |
| METTL14 | Q9HCE5 | 57721 | ENSG00000145388 | 480 |
| MFAP2 | P55001 | 4237 | ENSG00000117122 | 481 |
| MFGE8 | Q08431 | 4240 | ENSG00000140545 | 482 |
| MGAT1 | P26572 | 4245 | ENSG00000131446 | 483 |
| MIF | P14174 | 4282 | ENSG00000240972 | 484 |
| MINPP1 | Q9UNW1 | 9562 | ENSG00000107789 | 485 |
| MMP2 | P08253 | 4313 | ENSG00000087245 | 486 |
| MMP9 | P14780 | 4318 | ENSG00000100985 | 487 |
| MSMB | P08118 | 4477 | ENSG00000263639 | 488 |
| MSN | P26038 | 4478 | ENSG00000147065 | 489 |
| MST1 | P26927 | 4485 | ENSG00000173531 | 490 |
| MST1L | Q2TV78 | 11223 | | 491 |
| MTDH | Q86UE4 | 92140 | ENSG00000147649 | 492 |
| MTHFD1 | P11586 | 4522 | ENSG00000100714 | 493 |
| MTHFD2 | P13995 | 10797 | ENSG00000065911 | 494 |
| MXRA5 | Q9NR99 | 25878 | ENSG00000101825 | 495 |
| MYBBP1A | Q9BQG0 | 10514 | ENSG00000132382 | 496 |
| MYL3 | P08590 | 4634 | ENSG00000160808 | 497 |
| MYL4 | P12829 | 4635 | ENSG00000198336 | 498 |
| NAA15 | Q9BXJ9 | 80155 | ENSG00000164134 | 499 |
| NAMPT | P43490 | 10135 | ENSG00000105835 | 500 |
| NASP | P49321 | 4678 | ENSG00000132780 | 501 |
| NCAM1 | P13591 | 4684 | ENSG00000149294 | 502 |
| NCAN | O14594 | 1463 | ENSG00000130287 | 503 |
| NDNF | Q8TB73 | 79625 | ENSG00000173376 | 504 |
| NDST1 | P52848 | 3340 | ENSG00000070614 | 505 |
| NECTIN1 | Q15223 | 5818 | ENSG00000110400 | 506 |
| NECTIN3 | Q9NQS3 | 25945 | ENSG00000177707 | 507 |
| NELL2 | Q99435 | 4753 | ENSG00000184613 | 508 |
| NID1 | P14543 | 4811 | ENSG00000116962 | 509 |
| NID2 | Q14112 | 22795 | ENSG00000087303 | 510 |
| NIPBL | Q6KC79 | 25836 | ENSG00000164190 | 511 |
| NLGN3 | Q9NZ94 | 54413 | ENSG00000196338 | 512 |
| NLGN4Y | Q8NFZ3 | 22829 | ENSG00000165246 | 513 |
| NME1-NME2 | J3KPD9 | | ENSG00000011052 | 514 |
| NMT1 | P30419 | 4836 | ENSG00000136448 | 515 |
| NOLC1 | Q14978 | 9221 | ENSG00000166197 | 516 |
| NOV | A0A024R9J4 | 4856 | | 517 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| NPC2 | P61916 | 10577 | ENSG00000119655 | 518 |
| NPM3 | O75607 | 10360 | ENSG00000107833 | 519 |
| NPTX1 | Q15818 | 4884 |  | 520 |
| NPTX2 | P47972 | 4885 | ENSG00000106236 | 521 |
| NPTXR | O95502 | 23467 | ENSG00000221890 | 522 |
| NRG1 | Q02297 | 3084 | ENSG00000157168 | 523 |
| NRG2 | O14511 | 9542 | ENSG00000158458 | 524 |
| NRP1 | O14786 | 8829 | ENSG00000099250 | 525 |
| NRP2 | O60462 | 8828 | ENSG00000118257 | 526 |
| NSUN5 | Q96P11 | 55695 | ENSG00000130305 | 527 |
| NTS | P30990 | 4922 | ENSG00000133636 | 528 |
| NUBP2 | Q9Y5Y2 | 10101 | ENSG00000095906 | 529 |
| NUCB1 | Q02818 | 4924 | ENSG00000104805 | 530 |
| NUMA1 | Q14980 | 4926 | ENSG00000137497 | 531 |
| NUP155 | O75694 | 9631 | ENSG00000113569 | 532 |
| OAF | Q86UD1 | 220323 | ENSG00000184232 | 533 |
| OLA1 | Q9NTK5 | 29789 | ENSG00000138430 | 534 |
| OLFM2 | O95897 | 93145 |  | 535 |
| OLFML2A | Q68BL7 | 169611 | ENSG00000185585 | 536 |
| OLFML3 | Q9NRN5 | 56944 | ENSG00000116774 | 537 |
| ORM1 | P02763 | 5004 | ENSG00000229314 | 538 |
| ORM2 | P19652 | 5005 | ENSG00000228278 | 539 |
| P4HB | P07237 | 5034 | ENSG00000185624 | 540 |
| PACSIN2 | Q9UNF0 | 11252 | ENSG00000100266 | 541 |
| PAFAH1B1 | P43034 | 5048 | ENSG00000007168 | 542 |
| PAIP1 | Q9H074 | 10605 | ENSG00000172239 | 543 |
| PAM | P19021 | 5066 | ENSG00000145730 | 544 |
| PAMR1 | Q6UXH9 | 25891 | ENSG00000149090 | 545 |
| PAPLN | O95428 | 89932 | ENSG00000100767 | 546 |
| PAPPA | Q13219 | 5069 | ENSG00000182752 | 547 |
| PARP1 | P09874 | 142 | ENSG00000143799 | 548 |
| PC | P11498 | 5091 | ENSG00000173599 | 549 |
| PCDH1 | Q08174 | 5097 | ENSG00000156453 | 550 |
| PCLO | Q9Y6V0 | 27445 | ENSG00000186472 | 551 |
| PCOLCE | Q15113 | 5118 | ENSG00000106333 | 552 |
| PCOLCE2 | Q9UKZ9 | 26577 | ENSG00000163710 | 553 |
| PCSK5 | Q92824 | 5125 | ENSG00000099139 | 554 |
| PCSK9 | Q8NBP7 | 255738 | ENSG00000169174 | 555 |
| PDCD6IP | Q8WUM4 | 10015 | ENSG00000170248 | 556 |
| PDGFD | Q9GZP0 | 80310 | ENSG00000170962 | 557 |
| PDGFRL | Q15198 | 5157 | ENSG00000104213 | 558 |
| PDIA3 | P30101 | 2923 | ENSG00000167004 | 559 |
| PDIA4 | P13667 | 9601 | ENSG00000155660 | 560 |
| PDIA5 | Q14554 | 10954 | ENSG00000065485 | 561 |
| PDIA6 | Q15084 | 10130 | ENSG00000143870 | 562 |
| PFAS | O15067 | 5198 | ENSG00000178921 | 563 |
| PFKP | Q01813 | 5214 | ENSG00000067057 | 564 |
| PFN1 | P07737 | 5216 | ENSG00000108518 | 565 |
| PGD | P52209 | 5226 | ENSG00000142657 | 566 |
| PGLYRP2 | Q96PD5 | 114770 | ENSG00000161031 | 567 |
| PHGDH | O43175 | 26227 | ENSG00000092621 | 568 |
| PI16 | Q6UXB8 | 221476 | ENSG00000164530 | 569 |
| PIGR | P01833 | 5284 | ENSG00000162896 | 570 |
| PIP | P12273 | 5304 | ENSG00000159763 | 571 |
| PKDCC | Q504Y2 | 91461 | ENSG00000162878 | 572 |
| PKM | P14618 | 5315 | ENSG00000067225 | 573 |
| PLAT | P00750 | 5327 | ENSG00000104368 | 574 |
| PLAU | P00749 | 5328 | ENSG00000122861 | 575 |
| PLCB3 | Q01970 | 5331 | ENSG00000149782 | 576 |
| PLEC | Q15149 | 5339 | ENSG00000178209 | 577 |
| PLG | P00747 | 5340 | ENSG00000122194 | 578 |
| PLIN4 | Q96Q06 | 729359 | ENSG00000167676 | 579 |
| PLOD1 | Q02809 | 5351 | ENSG00000083444 | 580 |
| PLOD2 | O00469 | 5352 | ENSG00000152952 | 581 |
| PLOD3 | O60568 | 8985 | ENSG00000106397 | 582 |
| PLTP | P55058 | 5360 | ENSG00000100979 | 583 |
| POLL | Q9UGP5 | 27343 | ENSG00000166169 | 584 |
| POMC | P01189 | 5443 | ENSG00000115138 | 585 |
| POSTN | Q15063 | 10631 | ENSG00000133110 | 586 |
| PPIA | P62937 | 5478 | ENSG00000196262 | 587 |
| PPIB | P23284 | 5479 | ENSG00000166794 | 588 |
| PPP1CA | P62136 | 5499 | ENSG00000172531 | 589 |
| PPP1CC | P36873 | 5501 | ENSG00000186298 | 590 |
| PPP2R1A | P30153 | 5518 | ENSG00000105568 | 591 |

TABLE 2-continued

Factors enriched in the supernatants of
undifferentiated human pluripotent stem cells.

| Gene Name | Uniprot ID | Entrez Gene ID | Ensembl ID | Peptide No. |
|---|---|---|---|---|
| PPT1 | P50897 | 5538 | ENSG00000131238 | 592 |
| PRB3 | Q04118 | | ENSG00000197870 | 593 |
| PRB4 | P10163 | | | 594 |
| PRCP | P42785 | 5547 | ENSG00000137509 | 595 |
| PRDX2 | P32119 | 7001 | ENSG00000167815 | 596 |
| PRDX4 | Q13162 | 10549 | ENSG00000123131 | 597 |
| PRDX5 | P30044 | 25824 | ENSG00000126432 | 598 |
| PRG4 | Q92954 | 10216 | ENSG00000116690 | 599 |
| PRKDC | P78527 | 5591 | ENSG00000253729 | 600 |
| PRMT1 | Q99873 | 3276 | ENSG00000126457 | 601 |
| PRMT5 | O14744 | 10419 | ENSG00000100462 | 602 |
| PROM1 | O43490 | 8842 | ENSG00000007062 | 603 |
| PRPF19 | Q9UMS4 | 27339 | ENSG00000110107 | 604 |
| PRPF40A | O75400 | 55660 | ENSG00000196504 | 605 |
| PRPF4B | Q13523 | 8899 | ENSG00000112739 | 606 |
| PRPF6 | O94906 | 24148 | ENSG00000101161 | 607 |
| PRPF8 | Q6P2Q9 | 10594 | ENSG00000174231 | 608 |
| PRPSAP2 | O60256 | 5636 | ENSG00000141127 | 609 |
| PRR4 | Q16378 | 11272 | ENSG00000111215 | 610 |
| PRSS2 | P07478 | 5645 | ENSG00000275896 | 611 |
| PRSS23 | O95084 | 11098 | ENSG00000150687 | 612 |
| PRSS3 | P35030 | 5646 | ENSG00000010438 | 613 |
| PRTG | Q2VWP7 | 283659 | ENSG00000166450 | 614 |
| PSIP1 | O75475 | 11168 | ENSG00000164985 | 615 |
| PSMB6 | P28072 | 5694 | ENSG00000142507 | 616 |
| PSMD1 | Q99460 | 5707 | ENSG00000173692 | 617 |
| PSMD2 | Q13200 | 5708 | ENSG00000175166 | 618 |
| PSMD5 | Q16401 | 5711 | ENSG00000095261 | 619 |
| PSMD6 | Q15008 | 9861 | ENSG00000163636 | 620 |
| PSMD8 | P48556 | 5714 | ENSG00000099341 | 621 |
| PSME3 | P61289 | 10197 | ENSG00000131467 | 622 |
| PTK2 | Q05397 | 5747 | ENSG00000169398 | 623 |
| PTK7 | Q13308 | 5754 | ENSG00000112655 | 624 |
| PTN | P21246 | 5764 | ENSG00000105894 | 625 |
| PTPRC | P08575 | 5788 | ENSG00000081237 | 626 |
| PTPRD | P23468 | 5789 | ENSG00000153707 | 627 |
| PTPRF | P10586 | 5792 | ENSG00000142949 | 628 |
| PTPRS | Q13332 | 5802 | ENSG00000105426 | 629 |
| PTPRZ1 | P23471 | 5803 | ENSG00000106278 | 630 |
| PUF60 | Q9UHX1 | 22827 | ENSG00000179950 | 631 |
| PXDN | Q92626 | 7837 | ENSG00000130508 | 632 |
| PZP | P20742 | | ENSG00000126838 | 633 |
| QPRT | Q15274 | 23475 | ENSG00000103485 | 634 |
| QSOX1 | O00391 | 5768 | ENSG00000116260 | 635 |
| RAB7A | P51149 | 7879 | ENSG00000075785 | 636 |
| RACK1 | P63244 | 10399 | ENSG00000204628 | 637 |
| RARRES2 | Q99969 | 5919 | ENSG00000106538 | 638 |
| RBMX | P38159 | 27316 | ENSG00000147274 | 639 |
| RBP4 | P02753 | 5950 | ENSG00000138207 | 640 |
| RCC1 | P18754 | 1104 | ENSG00000180198 | 641 |
| RCOR1 | Q9UKL0 | 23186 | ENSG00000089902 | 642 |
| RECQL | P46063 | 5965 | ENSG00000004700 | 643 |
| RELN | P78509 | 5649 | ENSG00000189056 | 644 |
| RNASE1 | P07998 | 6035 | ENSG00000129538 | 645 |
| RNASE4 | P34096 | 6038 | ENSG00000258818 | 646 |
| ROBO1 | Q9Y6N7 | 6091 | ENSG00000169855 | 647 |
| RPL14 | P50914 | 9045 | ENSG00000188846 | 648 |
| RPL18 | Q07020 | 6141 | ENSG00000063177 | 649 |
| RPL19 | P84098 | 6143 | ENSG00000108298 | 650 |
| RPL23A | P62750 | 6147 | ENSG00000198242 | 651 |
| RPL26 | P61254 | 6154 | ENSG00000161970 | 652 |
| RPL29 | P47914 | 6159 | ENSG00000162244 | 653 |
| RPL3 | P39023 | 6122 | ENSG00000100316 | 654 |
| RPL35 | P42766 | 11224 | ENSG00000136942 | 655 |
| RPL4 | P36578 | 6124 | ENSG00000174444 | 656 |
| RPL9 | A0A2R8Y5Y7 | | ENSG00000163682 | 657 |
| RPLP0 | P05388 | 6175 | ENSG00000089157 | 658 |
| RPLP1 | P05386 | 6176 | ENSG00000137818 | 659 |
| RPLP2 | P05387 | 6181 | ENSG00000177600 | 660 |
| RPN2 | P04844 | 6185 | ENSG00000118705 | 661 |
| RPS13 | P62277 | 6207 | ENSG00000110700 | 662 |
| RPS20 | P60866 | 6224 | ENSG00000008988 | 663 |
| RPS23 | P62266 | 6228 | ENSG00000186468 | 664 |
| RPS27A | P62979 | 6233 | ENSG00000143947 | 665 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| RPS27L | Q71UM5 | 51065 | ENSG00000185088 | 666 |
| RPS3 | P23396 | 6188 | ENSG00000149273 | 667 |
| RRBP1 | Q9P2E9 | 6238 | ENSG00000125844 | 668 |
| RSF1 | Q96T23 | 51773 | ENSG00000048649 | 669 |
| RSL1D1 | O76021 | 26156 | ENSG00000171490 | 670 |
| RTF1 | Q92541 | 23168 | ENSG00000137815 | 671 |
| RTN4 | Q9NQC3 | 57142 | ENSG00000115310 | 672 |
| RTN4RL2 | Q86UN3 | 349667 | ENSG00000186907 | 673 |
| RUVBL2 | Q9Y230 | 10856 | ENSG00000183207 | 674 |
| S100A12 | P80511 | 6283 | ENSG00000163221 | 675 |
| S100A13 | Q99584 | 6284 | ENSG00000189171 | 676 |
| S100A7 | P31151 | 6278 | ENSG00000143556 | 677 |
| S100A8 | P05109 | 6279 | ENSG00000143546 | 678 |
| S100A9 | P06702 | 6280 | ENSG00000163220 | 679 |
| SAP30 | O75446 | 8819 | ENSG00000164105 | 680 |
| SARS | P49591 | 6301 | ENSG00000031698 | 681 |
| SBSN | Q6UWP8 | 374897 | ENSG00000189001 | 682 |
| SCG3 | Q8WXD2 | 29106 | ENSG00000104112 | 683 |
| SCGB2A2 | Q13296 | 4250 | ENSG00000110484 | 684 |
| SCUBE1 | Q8IWY4 | 80274 | ENSG00000159307 | 685 |
| SCUBE3 | Q8IX30 | 222663 | ENSG00000146197 | 686 |
| SDC1 | P18827 | 6382 | ENSG00000115884 | 687 |
| SDC4 | P31431 | 6385 | ENSG00000124145 | 688 |
| SDCBP | O00560 | 6386 | ENSG00000137575 | 689 |
| SDF4 | Q9BRK5 | 51150 | ENSG00000078808 | 690 |
| SEC13 | P55735 | 6396 | ENSG00000157020 | 691 |
| SELENOP | P49908 | 6414 | ENSG00000250722 | 692 |
| SEMA3A | Q14563 | 10371 | ENSG00000075213 | 693 |
| SEMA3F | Q13275 | 6405 | ENSG00000001617 | 694 |
| SEMA4B | Q9NPR2 | 10509 | ENSG00000185033 | 695 |
| SEMA4D | Q92854 | 10507 | ENSG00000187764 | 696 |
| SEMA5A | Q13591 | 9037 | ENSG00000112902 | 697 |
| SEMA6A | Q9H2E6 | 57556 | ENSG00000092421 | 698 |
| SEMA6D | Q8NFY4 | 80031 | ENSG00000137872 | 699 |
| SEMG1 | P04279 | 6406 | ENSG00000124233 | 700 |
| SEPT9 | Q9UHD8 | 10801 | ENSG00000184640 | 701 |
| SERBP1 | Q8NC51 | 26135 | ENSG00000142864 | 702 |
| SERPINA1 | P01009 | 5265 | ENSG00000197249 | 703 |
| SERPINA3 | P01011 | 12 | ENSG00000196136 | 704 |
| SERPINA5 | P05154 | 5104 | ENSG00000188488 | 705 |
| SERPINA7 | P05543 | 6906 | ENSG00000123561 | 706 |
| SERPINB12 | Q96P63 | 89777 | ENSG00000166634 | 707 |
| SERPINB3 | P29508 | 6317 | ENSG00000057149 | 708 |
| SERPINB9 | P50453 | 5272 | ENSG00000170542 | 709 |
| SERPINC1 | P01008 | 462 | ENSG00000117601 | 710 |
| SERPIND1 | P05546 | 3053 | ENSG00000099937 | 711 |
| SERPINE1 | P05121 | 5054 | ENSG00000106366 | 712 |
| SERPINE2 | P07093 | 5270 | ENSG00000135919 | 713 |
| SERPINF1 | P36955 | 5176 | ENSG00000132386 | 714 |
| SERPINF2 | P08697 | 5345 | ENSG00000167711 | 715 |
| SERPING1 | P05155 | 710 | ENSG00000149131 | 716 |
| SERPINH1 | P50454 | 871 | ENSG00000149257 | 717 |
| SERPINI1 | Q99574 | 5274 | ENSG00000163536 | 718 |
| SF3B1 | O75533 | 23451 | ENSG00000115524 | 719 |
| SF3B2 | Q13435 | 10992 | ENSG00000087365 | 720 |
| SF3B3 | Q15393 | 23450 | ENSG00000189091 | 721 |
| SFPQ | P23246 | 6421 | ENSG00000116560 | 722 |
| SFRP1 | Q8N474 | 6422 | ENSG00000104332 | 723 |
| SFRP2 | Q96HF1 | 6423 | ENSG00000145423 | 724 |
| SH2B1 | Q9NRF2 | 25970 | ENSG00000178188 | 725 |
| SHBG | P04278 | 6462 | ENSG00000129214 | 726 |
| SHMT1 | P34896 | 6470 | ENSG00000176974 | 727 |
| SKIV2L2 | L8E9T8 | | | 728 |
| SLC1A5 | Q15758 | 6510 | ENSG00000105281 | 729 |
| SLC2A14 | Q8TDB8 | 144195 | ENSG00000173262 | 730 |
| SLC39A10 | Q9ULF5 | 57181 | ENSG00000196950 | 731 |
| SLIT2 | O94813 | 9353 | | 732 |
| SLIT3 | O75094 | 6586 | ENSG00000184347 | 733 |
| SLPI | P03973 | 6590 | ENSG00000124107 | 734 |
| SLTM | Q9NWH9 | 79811 | ENSG00000137776 | 735 |
| SLURP1 | P55000 | 57152 | ENSG00000126233 | 736 |
| SMARCC1 | Q92922 | 6599 | ENSG00000173473 | 737 |
| SMARCD1 | Q96GM5 | 6602 | ENSG00000066117 | 738 |
| SMARCD2 | Q92925 | 6603 | ENSG00000108604 | 739 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| SMC1A | Q14683 | 8243 | ENSG00000072501 | 740 |
| SMC3 | Q9UQE7 | 9126 | ENSG00000108055 | 741 |
| SMOC1 | Q9H4F8 | 64093 | ENSG00000198732 | 742 |
| SMOC2 | Q9H3U7 | 64094 | ENSG00000112562 | 743 |
| SMPDL3B | Q92485 | 27293 | ENSG00000130768 | 744 |
| SMR3B | P02814 | 10879 | ENSG00000171201 | 745 |
| SNRPB | P14678 | 6628 | ENSG00000125835 | 746 |
| SNRPD1 | P62314 | 6632 | ENSG00000167088 | 747 |
| SNRPD3 | P62318 | 6634 | ENSG00000100028 | 748 |
| SOD3 | P08294 | 6649 | ENSG00000109610 | 749 |
| SPARC | P09486 | 6678 | ENSG00000113140 | 750 |
| SPINT1 | O43278 | 6692 | ENSG00000166145 | 751 |
| SPINT2 | O43291 | 10653 | ENSG00000167642 | 752 |
| SPOCK1 | Q08629 | 6695 | ENSG00000152377 | 753 |
| SPON1 | Q9HCB6 | 10418 | ENSG00000262655 | 754 |
| SPP1 | P10451 | 6696 | ENSG00000118785 | 755 |
| SRP14 | P37108 | 6727 | ENSG00000140319 | 756 |
| SRPX | P78539 | 8406 | ENSG00000101955 | 757 |
| SRPX2 | O60687 | 27286 | ENSG00000102359 | 758 |
| SRSF1 | Q07955 | 6426 | ENSG00000136450 | 759 |
| SSB | P05455 | 6741 | ENSG00000138385 | 760 |
| SSC5D | A1L4H1 | 284297 | ENSG00000179954 | 761 |
| ST6GAL1 | P15907 | 6480 | ENSG00000073849 | 762 |
| ST6GAL2 | Q96JF0 | 84620 | ENSG00000144057 | 763 |
| STAG1 | Q8WVM7 | 10274 | ENSG00000118007 | 764 |
| STC1 | P52823 | 6781 | ENSG00000159167 | 765 |
| STC2 | O76061 | 8614 | ENSG00000113739 | 766 |
| SUB1 | P53999 | 10923 | ENSG00000113387 | 767 |
| SULF2 | Q8IWU5 | 55959 | ENSG00000196562 | 768 |
| SUMF2 | Q8NBJ7 | 25870 | ENSG00000129103 | 769 |
| SUPT16H | Q9Y5B9 | 11198 | ENSG00000092201 | 770 |
| SUPT6H | Q7KZ85 | 6830 | ENSG00000109111 | 771 |
| SVEP1 | Q4LDE5 | 79987 | ENSG00000165124 | 772 |
| SYNCRIP | O60506 | 10492 | ENSG00000135316 | 773 |
| TAGLN2 | P37802 | 8407 | ENSG00000158710 | 774 |
| TBL1XR1 | Q9BZK7 | 79718 | ENSG00000177565 | 775 |
| TCN2 | P20062 | 6948 | ENSG00000185339 | 776 |
| TCOF1 | Q13428 | 6949 | ENSG00000070814 | 777 |
| IF | P02787 | 7018 | ENSG00000091513 | 778 |
| TFAM | Q00059 | 7019 | ENSG00000108064 | 779 |
| TFPI | P10646 | 7035 | ENSG00000003436 | 780 |
| TFRC | P02786 | 7037 | ENSG00000072274 | 781 |
| TGFB2 | P61812 | 7042 | ENSG00000092969 | 782 |
| TGFBI | Q15582 | 7045 | ENSG00000120708 | 783 |
| THBS1 | P07996 | 7057 | ENSG00000137801 | 784 |
| THBS2 | P35442 | 7058 | ENSG00000186340 | 785 |
| THBS3 | P49746 | 7059 | ENSG00000169231 | 786 |
| THBS4 | P35443 | 7060 | ENSG00000113296 | 787 |
| THOC3 | Q96J01 | 84321 | ENSG00000051596 | 788 |
| THSD7A | Q9UPZ6 | 221981 | ENSG00000005108 | 789 |
| TIMP1 | P01033 | 7076 | ENSG00000102265 | 790 |
| TIMP2 | P16035 | 7077 | ENSG00000035862 | 791 |
| TIMP3 | P35625 | 7078 | ENSG00000100234 | 792 |
| TINAGL1 | Q9GZM7 | 64129 | ENSG00000142910 | 793 |
| TJP1 | Q07157 | 7082 | ENSG00000104067 | 794 |
| TNC | P24821 | 3371 | ENSG00000041982 | 795 |
| TNN | Q9UQP3 | 63923 | | 796 |
| TNXB | P22105 | 7148 | ENSG00000168477 | 797 |
| TOP1 | P11387 | 7150 | ENSG00000198900 | 798 |
| TPM4 | P67936 | 7171 | ENSG00000167460 | 799 |
| TPP2 | P29144 | 7174 | ENSG00000134900 | 800 |
| TRIM28 | Q13263 | 10155 | ENSG00000130726 | 801 |
| TRIP10 | Q15642 | 9322 | ENSG00000125733 | 802 |
| TRMT1 | Q9NXH9 | 55621 | ENSG00000104907 | 803 |
| TSKU | Q8WUA8 | 25987 | ENSG00000182704 | 804 |
| TTR | P02766 | 7276 | ENSG00000118271 | 805 |
| TUBB4A | P04350 | 10382 | ENSG00000104833 | 806 |
| TUFM | P49411 | 7284 | ENSG00000178952 | 807 |
| TWSG1 | Q9GZX9 | 57045 | ENSG00000128791 | 808 |
| TXN | P10599 | 7295 | ENSG00000136810 | 809 |
| TXNDC16 | Q9P2K2 | 57544 | ENSG00000087301 | 810 |
| TXNDC5 | Q8NBS9 | 81567 | ENSG00000239264 | 811 |
| U2AF2 | P26368 | 11338 | ENSG00000063244 | 812 |
| UBE2O | Q9C0C9 | 63893 | ENSG00000175931 | 813 |

TABLE 2-continued

Factors enriched in the supernatants of undifferentiated human pluripotent stem cells.

| Gene Name | Uniprot ID | Entrez Gene ID | Ensembl ID | Peptide No. |
|---|---|---|---|---|
| UBR4 | Q5T4S7 | 23352 | ENSG00000127481 | 814 |
| UCHL1 | P09936 | 7345 | ENSG00000154277 | 815 |
| UCHL3 | P15374 | 7347 | ENSG00000118939 | 816 |
| UFL1 | O94874 | 23376 | ENSG00000014123 | 817 |
| UGP2 | Q16851 | 7360 | ENSG00000169764 | 818 |
| USP11 | P51784 | 8237 | ENSG00000102226 | 819 |
| USP14 | P54578 | 9097 | ENSG00000101557 | 820 |
| USP43 | Q70EL4 | 124739 | ENSG00000154914 | 821 |
| UTP4 | Q969X6 | 84916 | ENSG00000141076 | 822 |
| VARS | P26640 | 7407 | ENSG00000096171 | 823 |
| VASN | Q6EMK4 | 114990 | ENSG00000168140 | 824 |
| VCAN | P13611 | 1462 | ENSG00000038427 | 825 |
| VCP | P55072 | 7415 | ENSG00000165280 | 826 |
| VEGFA | P15692 | 7422 | ENSG00000112715 | 827 |
| VIT | Q6UXI7 | 5212 | ENSG00000205221 | 828 |
| VNN1 | O95497 | 8876 | ENSG00000112299 | 829 |
| VPS35 | Q96QK1 | 55737 | ENSG00000069329 | 830 |
| VTN | P04004 | 7448 | ENSG00000109072 | 831 |
| VWF | P04275 | 7450 | ENSG00000110799 | 832 |
| WDR3 | Q9UNX4 | 10885 | ENSG00000065183 | 833 |
| WDR36 | Q8NI36 | 134430 | ENSG00000134987 | 834 |
| WDR4 | P57081 | 10785 | ENSG00000160193 | 835 |
| WDR43 | Q15061 | 23160 | ENSG00000163811 | 836 |
| WFIKKN1 | Q96NZ8 | 117166 | ENSG00000127578 | 837 |
| WFIKKN2 | Q8TEU8 | 124857 | ENSG00000173714 | 838 |
| XRCC5 | P13010 | 7520 | ENSG00000079246 | 839 |
| XYLT1 | Q86Y38 | 64131 | ENSG00000103489 | 840 |
| XYLT2 | Q9H1B5 | 64132 | ENSG00000015532 | 841 |
| YBX1 | P67809 | 4904 | ENSG00000065978 | 842 |
| YBX3 | P16989 | 8531 | ENSG00000060138 | 843 |
| ZG16B | Q96DA0 | 124220 | ENSG00000162078 | 844 |
| ZNF207 | O43670 | 7756 | ENSG00000010244 | 845 |
| ZNF326 | Q5BKZ1 | 284695 | ENSG00000162664 | 846 |
| ZNF706 | Q9Y5V0 | 51123 | ENSG00000120963 | 847 |
| APLP1 | P51693 | 333 | ENSG00000105290 | 848 |
| APP | P05067 | 351 | ENSG00000142192 | 849 |
| NPNT | Q6UXI9 | 255743 | ENSG00000168743 | 850 |
| RPL22 | Q6UXI9 | 6146 | ENSG00000116251 | 851 |
| FGF19 | O95750 | 9965 | ENSG00000162344 | 852 |
| BTC | P35070 | 685 | ENSG00000174808 | 853 |
| IL13RA2 | Q14627 | 3598 | ENSG00000123496 | 854 |
| CD170 | O15389 |  | ENSG00000105501 | 855 |
| IL15 | P40933 | 3600 | ENSG00000164136 | 856 |
| WAP | Q8TEU8 |  | ENSG00000173714 | 857 |
| MFRP | Q9BY79 | 83552 | ENSG00000235718 | 858 |
| IL10Ra | Q13651 | 3587 | ENSG00000110324 | 859 |
| ChemR23 | Q99788 | 1240 | ENSG00000174600 | 860 |
| HBEGF | Q99075 | 1839 | ENSG00000113070 | 861 |
| IL16 | Q14005 | 3603 | ENSG00000172349 | 862 |
| IL7Ra | P16871 | 3575 | ENSG00000168685 | 863 |
| TNFSF10C | O14798 | 8794 | ENSG00000173535 | 864 |
| BMP6 | P22004 | 654 | ENSG00000153162 | 865 |
| IL36g | P14778 | 56300 | ENSG00000136688 | 866 |
| IL1RA | P18510 | 3557 | ENSG00000136689 | 867 |
| KREMEN2 | Q8NCW0 | 79412 |  | 868 |
| TNFSF10D | Q9UBN6 | 8793 | ENSG00000173530 | 869 |
| CXCCR1 | P49238 | 1524 | ENSG00000168329 | 870 |
| CCL23 | P55773 | 6368 | ENSG00000276114 | 871 |
| Catenin | P35222 | 1499 | ENSG00000168036 | 872 |
| TNFSF10 | P50591 | 8743 | ENSG00000121858 | 873 |
| CCL14 | Q16627 | 6358 | ENSG00000276409 | 874 |
| IL2 | P60568 | 3558 | ENSG00000109471 | 875 |
| FGF1 | P05230 | 2246 | ENSG00000113578 | 876 |

In certain embodiments, the heparin-associated polypeptide comprises one or more of the polypeptides listed in Table 2, Table 1, or a proteoform thereof. In certain embodiments, the heparin-associated polypeptide is at least about 85%, 90%, 95%, 97%, 98%, 99%, or 100% identical to a polypeptide listed in Table 2, Table 1, or a proteoform thereof. In certain embodiments, the heparin-associated polypeptide comprises a polypeptide at least about 85%, 90%, 95%, 97%, 98%, 99%, or 100% identical to ADAMTS12, INS-IGF2, AOC1, SOD3, CLU, ITIH1, APLP1, THBS1, COCH, ITIH2, APLP2, THBS3, COL11A1, LAMA1, APOB, TNXB, COL12A1, LAMA2, APOE, VEGFA, COL14A1, LAMA5, APOH, VTN, COL18A1, LAMB1, APP, ZNF207, COL1A1, LAMB2, CCDC80, COL1A2, LTF, CFH, COL2A1, MATN2, CLEC3B, COL3A1, MDK, COL25A1, COL5A1, MST1, COL5A3, COL5A2, NID1, CYR61, COL6A1, NPNT, F2, COL6A2, OLFML3, FGF2, COL6A3, PCOLCE, FGFBP3, CTGF, POSTN, FSTL1, DCD, PTN, HDGF, DRAXIN, RARRES2, KNG1, ECM1, RELN, NDNF, FBLN1, SFRP1, NRP1, FBN1, SLIT3, PAFAH1B1, FBN2, SPON1, PCOLCE2, FN1, STC1, PTPRF, FST, STC2, PTPRS, HGFAC, SVEP1, RPL22, IGFBP2, THBS2, or RPL29, or any combination thereof. In certain embodiments, the heparin-associated polypeptide comprises a polypeptide at least about 85%, 90%, 95%, 97%, 98%, 99%, or 100% identical to VTN, POSTN, FGF17, THBS2, THBS4, THBS1, IL-15, or IGF2, or any combination thereof. In certain embodiments, the heparin-associated polypeptide comprises THBS1. In certain embodiments, the heparin-associated polypeptide comprises THBS2. In certain embodiments, the heparin-associated polypeptide comprises THBS4. In certain embodiments, the heparin-associated polypeptide comprises FGF17. In certain embodiments, the heparin-associated polypeptide comprises VTN. In certain embodiments, the heparin-associated polypeptide comprises POSTN. In certain embodiments, the heparin-associated polypeptide comprises IGF2. In certain embodiments, the heparin-associated polypeptide comprises IL-15. In certain embodiments, described herein, is a composition comprising any 1, 2, 3, 4, 5, 6, 7, 8, 9, 10 or more polypeptides at least about 85%, 90%, 95%, 97%, 98%, 99%, or 100% identical to a polypeptide Table 2, Table 1, ADAMTS12, INS-IGF2, AOC1, SOD3, CLU, ITIH1, APLP1, THBS1, COCH, ITIH2, APLP2, THBS3, COL11A1, LAMA1, APOB, TNXB, COL12A1, LAMA2, APOE, VEGFA, COL14A1, LAMA5, APOH, VTN, COL18A1, LAMB1, APP, ZNF207, COL1A1, LAMB2, CCDC80, COL1A2, LTF, CFH, COL2A1, MATN2, CLEC3B, COL3A1, MDK, COL25A1, COL5A1, MST1, COL5A3, COL5A2, NID1, CYR61, COL6A1, NPNT, F2, COL6A2, OLFML3, FGF2, COL6A3, PCOLCE, FGFBP3, CTGF, POSTN, FSTL1, DCD, PTN, HDGF, DRAXIN, RARRES2, KNG1, ECM1, RELN, NDNF, FBLN1, SFRP1, NRP1, FBN1, SLIT3, PAFAH1B1, FBN2, SPON1, PCOLCE2, FN1, STC1, PTPRF, FST, STC2, PTPRS, HGFAC, SVEP1, RPL22, IGFBP2, THBS2, RPL29, a proteoform thereof, or a combination thereof; and a pharmaceutically acceptable excipient, carrier, or diluent. In certain embodiments, the composition comprises a plurality of peptides from Table 2; and optionally a pharmaceutically acceptable excipient, carrier, or diluent. In some cases the plurality comprises 1, 2, 3, 4, 5, 6, 7, 8, 9, 10 or more polypeptides of Table 2. In some cases, one or more of the plurality of polypeptides is at least about 85%, 90%, 95%, 97%, 98%, 99%, or 100% identical to a polypeptide of Table 2. In certain embodiments, the composition comprises a plurality of peptides from Table 1; and optionally a pharmaceutically acceptable excipient, carrier, or diluent. In some cases the plurality comprises 1, 2, 3, 4, 5, 6, 7, 8, 9, 10 or more polypeptides of Table 1. In some cases, one or more of the plurality of polypeptides is at least about 85%, 90%, 95%, 97%, 98%, 99%, or 100% identical to a polypeptide of Table 1. In certain embodiments, the composition comprises THBS1. In certain embodiments, the composition comprises THBS2. In certain embodiments, the composition comprises THBS4. In certain embodiments, the composition comprises FGF17. In certain embodiments, the composition comprises VTN. In certain embodiments, the composition comprises POSTN. In certain embodiments, the composition comprises IGF2. In certain embodiments, the composition comprises IL-15. In certain embodiments, the composition comprises IGF2, THBS2, and THBS4. In certain embodiments, the composition comprises IL-15, THBS2, and THBS4. In certain embodiments, the composition comprises THBS2 and THBS4. In certain embodiments, the composition comprises THBS2, THBS4, and VTN. In certain embodiments, the composition comprises THBS2, THBS4, and ANOS1. In certain embodiments, the composition comprises THBS2, THBS4, and IL-15. In certain embodiments, the composition comprises THBS2, THBS4, and IGF2. In certain embodiments, the composition comprises THBS1 and FGF17. In certain embodiments, the composition comprises THBS2 and VTN. In certain embodiments, the composition comprises THBS1 and VTN. In certain embodiments, the composition comprises THBS1 and THBS2. In certain embodiments, the composition comprises THBS2 and FGF17. In certain embodiments, the composition comprises THBS1 and THBS4. In certain embodiments, the composition comprises VTN and FGF17. In certain embodiments, the composition comprises THBS4 and VTN. In certain embodiments, the composition comprises THBS4 and FGF17. In certain embodiments, described herein, is a composition comprising any 1, 2, 3, 4, 5, 6, 7, 8, 9, 10 or more polypeptides at least about 85%, 90%, 95%, 97%, 98%, 99%, or 100% identical to CTGF, THBS1, THBS2, THBS3, HGFAC, IGFBP3, IGFBP5, IGFBP7, IGFBP4, SFRP1, STC1, STC2, IGFBP2; and a pharmaceutically acceptable excipient, carrier, or diluent. In certain embodiments, described herein, is a composition comprising 1, 2, 3, 4, 5, 6, 7, 8, 9, 10 or more polypeptides, wherein one or more the polypeptides are at least about 85%, 90%, 95%, 97%, 98%, 99%, or 100% identical to VTN, POSTN, FGF17, THBS2, THBS1, IGF2, IL-15, or THBS4; and a pharmaceutically acceptable excipient, carrier, or diluent.

In certain embodiments, described herein is a composition comprising a polypeptide comprising at least about 85%, 90%, 95%, 97%, 98%, 99%, or 100% homology or identity to SEQ ID NO: 1 or amino acids 20-478 of SEQ ID NO: 1, and a pharmaceutically acceptable excipient, carrier, or diluent. In some cases, the polypeptide does not comprise a signal sequence of SEQ ID NO: 1. In certain embodiments, described herein is a composition comprising a polypeptide comprising at least about 85%, 90%, 95%, 97%, 98%, 99%, or 100% homology or identity to SEQ ID NO: 2, and a pharmaceutically acceptable excipient, carrier, or diluent. In some cases, the polypeptide does not comprise a signal sequence of SEQ ID NO: 2. In certain embodiments, described herein is a composition comprising a polypeptide comprising at least about 85%, 90%, 95%, 97%, 98%, 99%, or 100% homology or identity to SEQ ID NO: 3, and a pharmaceutically acceptable excipient, carrier, or diluent. In some cases, the polypeptide does not comprise a signal sequence of SEQ ID NO: 3. In certain embodiments, described herein is a composition comprising a polypeptide comprising at least about 85%, 90%, 95%, 97%, 98%, 99%, or 100% homology or identity to SEQ ID NO: 4 or amino acids 19-1172 of SEQ ID NO: 4, and a pharmaceutically acceptable excipient, carrier, or diluent. In some cases, the polypeptide does not comprise a signal sequence of SEQ ID NO: 4. In certain embodiments, described herein is a composition comprising a polypeptide comprising at least about 85%, 90%, 95%, 97%, 98%, 99%, or 100% homology or identity to SEQ ID NO: 5, and a pharmaceutically acceptable excipient, carrier, or diluent. In some cases, the polypeptide does not comprise a signal sequence of SEQ ID NO: 5. In certain embodiments, described herein is a composition comprising a polypeptide comprising at least about 85%, 90%, 95%, 97%, 98%, 99%, or 100% homology or identity to SEQ ID NO: 6 or amino acids 22-836 of SEQ ID NO: 6, and a pharmaceutically acceptable excipient, carrier, or diluent. In some cases, the polypeptide does not comprise a signal sequence of SEQ ID NO: 6. In certain embodiments, described herein is a composition comprising a polypeptide comprising at least about 85%, 90%, 95%, 97%, 98%, 99%, or 100% homology or identity to SEQ ID NO: 7 or amino acids 23-216 of SEQ ID NO: 7, and a pharmaceutically acceptable excipient, carrier, or diluent. In some cases, the polypeptide does not comprise a signal sequence of SEQ ID NO: 7. In certain embodiments, described herein is a composition comprising a polypeptide comprising at least about 85%, 90%, 95%, 97%, 98%, 99%, or 100% homology or identity to SEQ ID NO: 8 or amino acids 27-961 of SEQ ID NO: 8, and a pharmaceutically acceptable excipient, carrier, or diluent. In some cases, the polypeptide does not comprise a signal sequence of SEQ ID NO: 8. In certain embodiments, described herein is a composition comprising a polypeptide comprising at least about 85%, 90%, 95%, 97%, 98%, 99%, or 100% homology or identity to SEQ ID NO: 9 or amino acids 19-1170 of SEQ ID NO: 9, and a pharmaceutically acceptable excipient, carrier, or diluent. In some cases, the polypeptide does not comprise a signal sequence of SEQ ID NO: 9. In certain embodiments, described herein is a composition comprising a polypeptide comprising at least about 85%, 90%, 95%, 97%, 98%, 99%, or 100% homology or identity to SEQ ID NO: 10 or amino acids 49-162 of SEQ ID NO: 10, and a pharmaceutically acceptable excipient, carrier, or diluent. In some cases, the polypeptide does not comprise a signal sequence of SEQ ID NO: 10. In certain embodiments, described herein is a composition comprising a polypeptide comprising at least about 85%, 90%, 95%, 97%, 98%, 99%, or 100% homology or identity to SEQ ID NO: 11 or amino acids 25-91 of SEQ ID NO: 11, and a pharmaceutically acceptable excipient, carrier, or diluent. In some cases, the polypeptide does not comprise a signal sequence of SEQ ID NO: 11.

In certain embodiments, described herein is a composition comprising a polypeptide comprising at least about 85%, 90%, 95%, 97%, 98%, 99%, or 100% homology or identity to SEQ ID NO: 12, and a pharmaceutically acceptable excipient, carrier, or diluent. In some cases, the polypeptide does not comprise a signal sequence of SEQ ID NO: 12. In certain embodiments, described herein is a composition comprising a polypeptide comprising at least about 85%, 90%, 95%, 97%, 98%, 99%, or 100% homology or identity to SEQ ID NO: 13, and a pharmaceutically acceptable excipient, carrier, or diluent. In some cases, the polypeptide does not comprise a signal sequence of SEQ ID NO: 13. In certain embodiments, described herein is a composition comprising a polypeptide comprising at least about 85%, 90%, 95%, 97%, 98%, 99%, or 100% homology or identity to SEQ ID NO: 14, and a pharmaceutically acceptable excipient, carrier, or diluent. In some cases, the polypeptide does not comprise a signal sequence of SEQ ID NO: 14. In certain embodiments, described herein is a composition comprising a polypeptide comprising at least about 85%, 90%, 95%, 97%, 98%, 99%, or 100% homology or identity to SEQ ID NO: 15 and a pharmaceutically acceptable excipient, carrier, or diluent. In some cases, the polypeptide does not comprise a signal sequence of SEQ ID NO: 15. In certain embodiments, described herein is a composition comprising a polypeptide comprising at least about 85%, 90%, 95%, 97%, 98%, 99%, or 100% homology or identity to SEQ ID NO: 16, and a pharmaceutically acceptable excipient, carrier, or diluent. In some cases, the polypeptide does not comprise a signal sequence of SEQ ID NO: 16. In certain embodiments, described herein is a composition comprising a polypeptide comprising at least about 85%, 90%, 95%, 97%, 98%, 99%, or 100% homology or identity to SEQ ID NO: 17, and a pharmaceutically acceptable excipient, carrier, or diluent. In some cases, the polypeptide does not comprise a signal sequence of SEQ ID NO: 17. In certain embodiments, described herein is a composition comprising a polypeptide comprising at least about 85%, 90%, 95%, 97%, 98%, 99%, or 100% homology or identity to SEQ ID NO: 18, and a pharmaceutically acceptable excipient, carrier, or diluent. In some cases, the polypeptide does not comprise a signal sequence of SEQ ID NO: 18. In certain embodiments, described herein is a composition comprising a polypeptide comprising at least about 85%, 90%, 95%, 97%, 98%, 99%, or 100% homology or identity to SEQ ID NO: 19, and a pharmaceutically acceptable excipient, carrier, or diluent. In some cases, the polypeptide does not comprise a signal sequence of SEQ ID NO: 19.

In certain embodiments, described herein is a composition comprising a polypeptide comprising at least about 85%, 90%, 95%, 97%, 98%, 99%, or 100% homology or identity to SEQ ID NO: 20, and a pharmaceutically acceptable excipient, carrier, or diluent. In some cases, the polypeptide does not comprise a signal sequence of SEQ ID NO: 20. In certain embodiments, described herein is a composition comprising a polypeptide comprising at least about 85%, 90%, 95%, 97%, 98%, 99%, or 100% homology or identity to SEQ ID NO: 21, and a pharmaceutically acceptable excipient, carrier, or diluent. In some cases, the polypeptide does not comprise a signal sequence of SEQ ID NO: 21. In certain embodiments, described herein is a composition comprising a polypeptide comprising at least about 85%, 90%, 95%, 97%, 98%, 99%, or 100% homology or identity to SEQ ID NO: 22, and a pharmaceutically acceptable excipient, carrier, or diluent. In some cases, the polypeptide does not comprise a signal sequence of SEQ ID NO: 22. In certain embodiments, described herein is a composition comprising a polypeptide comprising at least about 85%, 90%, 95%, 97%, 98%, 99%, or 100% homology or identity to SEQ ID NO: 23, and a pharmaceutically acceptable excipient, carrier, or diluent. In some cases, the polypeptide does not comprise a signal sequence of SEQ ID NO: 23. In certain embodiments, described herein is a composition comprising a polypeptide comprising at least about 85%, 90%, 95%, 97%, 98%, 99%, or 100% homology or identity to SEQ ID NO: 24, and a pharmaceutically acceptable excipient, carrier, or diluent. In some cases, the polypeptide does not comprise a signal sequence of SEQ ID NO: 24. In certain embodiments, described herein is a composition comprising a polypeptide comprising at least about 85%, 90%, 95%, 97%, 98%, 99%, or 100% homology or identity to SEQ ID NO: 25, and a pharmaceutically acceptable excipient, carrier, or diluent. In some cases, the polypeptide does not comprise a signal sequence of SEQ ID NO: 25. In certain embodiments, described herein is a composition comprising a polypeptide comprising at least about 85%, 90%, 95%, 97%, 98%, 99%, or 100% homology or identity to SEQ ID NO: 26, and a pharmaceutically acceptable excipient, carrier, or diluent. In some cases, the polypeptide does not comprise a signal sequence of SEQ ID NO: 26. In certain embodiments, described herein is a composition comprising a polypeptide comprising at least about 85%, 90%, 95%, 97%, 98%, 99%, or 100% homology or identity to SEQ ID NO: 27, and a pharmaceutically acceptable excipient, carrier, or diluent. In some cases, the polypeptide does not comprise a signal sequence of SEQ ID NO: 27. In certain embodiments, described herein is a composition comprising a polypeptide comprising at least about 85%, 90%, 95%, 97%, 98%, 99%, or 100% homology or identity to SEQ ID NO: 28, and a pharmaceutically acceptable excipient, carrier, or diluent. In some cases, the polypeptide does not comprise a signal sequence of SEQ ID NO: 28. In certain embodiments, described herein is a composition comprising a polypeptide comprising at least about 85%, 90%, 95%, 97%, 98%, 99%, or 100% homology or identity to SEQ ID NO: 29, and a pharmaceutically acceptable excipient, carrier, or diluent. In some cases, the polypeptide does not comprise a signal sequence of SEQ ID NO: 29.

In certain embodiments, described herein is a composition comprising a polypeptide comprising at least about 85%, 90%, 95%, 97%, 98%, 99%, or 100% homology or identity to SEQ ID NO: 30, and a pharmaceutically acceptable excipient, carrier, or diluent. In some cases, the polypeptide does not comprise a signal sequence of SEQ ID NO: 30. In certain embodiments, described herein is a composition comprising a polypeptide comprising at least about 85%, 90%, 95%, 97%, 98%, 99%, or 100% homology or identity to SEQ ID NO: 31, and a pharmaceutically acceptable excipient, carrier, or diluent. In some cases, the polypeptide does not comprise a signal sequence of SEQ ID NO: 31. In certain embodiments, described herein is a composition comprising a polypeptide comprising at least about 85%, 90%, 95%, 97%, 98%, 99%, or 100% homology or identity to SEQ ID NO: 32, and a pharmaceutically acceptable excipient, carrier, or diluent. In some cases, the polypeptide does not comprise a signal sequence of SEQ ID NO: 32. In certain embodiments, described herein is a composition comprising a polypeptide comprising at least about 85%, 90%, 95%, 97%, 98%, 99%, or 100% homology or identity to SEQ ID NO: 33, and a pharmaceutically acceptable excipient, carrier, or diluent. In some cases, the polypeptide does not comprise a signal sequence of SEQ ID NO: 33. In certain embodiments, described herein is a composition comprising a polypeptide comprising at least about 85%, 90%, 95%, 97%, 98%, 99%, or 100% homology or identity to SEQ ID NO: 34, and a pharmaceutically acceptable excipient, carrier, or diluent. In some cases, the polypeptide does not comprise a signal sequence of SEQ ID NO: 34. In certain embodiments, described herein is a composition comprising a polypeptide comprising at least about 85%, 90%, 95%, 97%, 98%, 99%, or 100% homology or identity to SEQ ID NO: 35, and a pharmaceutically acceptable excipient, carrier, or diluent. In some cases, the polypeptide does not comprise a signal sequence of SEQ ID NO: 35. In certain embodiments, described herein is a composition comprising a polypeptide comprising at least about 85%, 90%, 95%, 97%, 98%, 99%, or 100% homology or identity to SEQ ID NO: 36, and a pharmaceutically acceptable excipient, carrier, or diluent. In some cases, the polypeptide does not comprise a signal sequence of SEQ ID NO: 36. In certain embodiments, described herein is a composition comprising a polypeptide comprising at least about 85%, 90%, 95%, 97%, 98%, 99%, or 100% homology or identity to SEQ ID NO: 37, and a pharmaceutically acceptable excipient, carrier, or diluent. In some cases, the polypeptide does not comprise a signal sequence of SEQ ID NO: 37. In certain embodiments, described herein is a composition comprising a polypeptide comprising at least about 85%, 90%, 95%, 97%, 98%, 99%, or 100% homology or identity to SEQ ID NO: 38, and a pharmaceutically acceptable excipient, carrier, or diluent. In some cases, the polypeptide does not comprise a signal sequence of SEQ ID NO: 38. In certain embodiments, described herein is a composition comprising a polypeptide comprising at least about 85%, 90%, 95%, 97%, 98%, 99%, or 100% homology or identity to SEQ ID NO: 39, and a pharmaceutically acceptable excipient, carrier, or diluent. In some cases, the polypeptide does not comprise a signal sequence of SEQ ID NO: 39.

In certain embodiments, described herein is a composition comprising a polypeptide comprising at least about 85%, 90%, 95%, 97%, 98%, 99%, or 100% homology or identity to SEQ ID NO: 40, and a pharmaceutically acceptable excipient, carrier, or diluent. In some cases, the polypeptide does not comprise a signal sequence of SEQ ID NO: 40. In certain embodiments, described herein is a composition comprising a polypeptide comprising at least about 85%, 90%, 95%, 97%, 98%, 99%, or 100% homology or identity to SEQ ID NO: 41, and a pharmaceutically acceptable excipient, carrier, or diluent. In some cases, the polypeptide does not comprise a signal sequence of SEQ ID NO: 41. In certain embodiments, described herein is a composition comprising a polypeptide comprising at least about 85%, 90%, 95%, 97%, 98%, 99%, or 100% homology or identity to SEQ ID NO: 42, and a pharmaceutically acceptable excipient, carrier, or diluent. In some cases, the polypeptide does not comprise a signal sequence of SEQ ID NO: 42. In certain embodiments, described herein is a composition comprising a polypeptide comprising at least about 85%, 90%, 95%, 97%, 98%, 99%, or 100% homology or identity to SEQ ID NO: 43, and a pharmaceutically acceptable excipient, carrier, or diluent. In some cases, the polypeptide does not comprise a signal sequence of SEQ ID NO: 43. In certain embodiments, described herein is a composition comprising a polypeptide comprising at least about 85%, 90%, 95%, 97%, 98%, 99%, or 100% homology or identity to SEQ ID NO: 44, and a pharmaceutically acceptable excipient, carrier, or diluent. In some cases, the polypeptide does not comprise a signal sequence of SEQ ID NO: 44. In certain embodiments, described herein is a composition comprising a polypeptide comprising at least about 85%, 90%, 95%, 97%, 98%, 99%, or 100% homology or identity to SEQ ID NO: 58, and a pharmaceutically acceptable excipient, carrier, or diluent. In some cases, the polypeptide does not comprise a signal sequence of SEQ ID NO: 58. In certain embodiments, described herein is a composition comprising a polypeptide comprising at least about 85%, 90%, 95%, 97%, 98%, 99%, or 100% homology or identity to SEQ ID NO: 59, and a pharmaceutically acceptable excipient, carrier, or diluent. In some cases, the polypeptide does not comprise a signal sequence of SEQ ID NO: 59. In certain embodiments, described herein is a composition comprising a polypeptide comprising at least about 85%, 90%, 95%, 97%, 98%, 99%, or 100% homology or identity to SEQ ID NO: 60, and a pharmaceutically acceptable excipient, carrier, or diluent. In some cases, the polypeptide does not comprise a signal sequence of SEQ ID NO: 60. In certain embodiments, described herein is a composition comprising a polypeptide comprising at least about 85%, 90%, 95%, 97%, 98%, 99%, or 100% homology or identity to SEQ ID NO: 61, and a pharmaceutically acceptable excipient, carrier, or diluent. In some cases, the polypeptide does not comprise a signal sequence of SEQ ID NO: 61. In certain embodiments, described herein is a composition comprising a polypeptide comprising at least about 85%, 90%, 95%, 97%, 98%, 99%, or 100% homology or identity to SEQ ID NO: 62, and a pharmaceutically acceptable excipient, carrier, or diluent. In some cases, the polypeptide does not comprise a signal sequence of SEQ ID NO: 62. In certain embodiments, described herein is a composition comprising a polypeptide comprising at least about 85%, 90%, 95%, 97%, 98%, 99%, or 100% homology or identity to SEQ ID NO: 63, and a pharmaceutically acceptable excipient, carrier, or diluent. In some cases, the polypeptide does not comprise a signal sequence of SEQ ID NO: 63. In certain embodiments, described herein is a composition comprising a polypeptide comprising at least about 85%, 90%, 95%, 97%, 98%, 99%, or 100% homology or identity to SEQ ID NO: 64, and a pharmaceutically acceptable excipient, carrier, or diluent. In some cases, the polypeptide does not comprise a signal sequence of SEQ ID NO: 64. In certain embodiments, described herein is a composition comprising a polypeptide comprising at least about 85%, 90%, 95%, 97%, 98%, 99%, or 100% homology or identity to SEQ ID NO: 65, and a pharmaceutically acceptable excipient, carrier, or diluent. In some cases, the polypeptide does not comprise a signal sequence of SEQ ID NO: 65. In certain embodiments, described herein is a composition comprising a polypeptide comprising at least about 85%, 90%, 95%, 97%, 98%, 99%, or 100% homology or identity to SEQ ID NO: 66, and a pharmaceutically acceptable excipient, carrier, or diluent. In some cases, the polypeptide does not comprise a signal sequence of SEQ ID NO: 66. In certain embodiments, described herein is a composition comprising a polypeptide comprising at least about 85%, 90%, 95%, 97%, 98%, 99%, or 100% homology or identity to SEQ ID NO: 67, and a pharmaceutically acceptable excipient, carrier, or diluent. In some cases, the polypeptide does not comprise a signal sequence of SEQ ID NO: 67. In certain embodiments, described herein is a composition comprising a polypeptide comprising at least about 85%, 90%, 95%, 97%, 98%, 99%, or 100% homology or identity to SEQ ID NO: 68, and a pharmaceutically acceptable excipient, carrier, or diluent. In some cases, the polypeptide does not comprise a signal sequence of SEQ ID NO: 68. In certain embodiments, described herein is a composition comprising a polypeptide comprising at least about 85%, 90%, 95%, 97%, 98%, 99%, or 100% homology or identity to SEQ ID NO: 69, and a pharmaceutically acceptable excipient, carrier, or diluent. In some cases, the polypeptide does not comprise a signal sequence of SEQ ID NO: 69. In certain embodiments, described herein is a composition comprising a polypeptide comprising at least about 85%, 90%, 95%, 97%, 98%, 99%, or 100% homology or identity to SEQ ID NO: 70, and a pharmaceutically acceptable excipient, carrier, or diluent. In some cases, the polypeptide does not comprise a signal sequence of SEQ ID NO: 70.

In certain embodiments, described herein is a composition comprising a plurality of polypeptides at least about 85%, 90%, 95%, 97%, 98%, 99%, or 100% identical to ADAMTS12, INS-IGF2, AOC1, SOD3, CLU, ITIH1, APLP1, THBS1, COCH, ITIH2, APLP2, THBS3, COL11A1, LAMA1, APOB, TNXB, COL12A1, LAMA2, APOE, VEGFA, COL14A1, LAMA5, APOH, VTN, COL18A1, LAMB1, APP, ZNF207, COL1A1, LAMB2, CCDC80, COL1A2, LTF, CFH, COL2A1, MATN2, CLEC3B, COL3A1, MDK, COL25A1, COL5A1, MST1, COL5A3, COL5A2, NID1, CYR61, COL6A1, NPNT, F2, COL6A2, OLFML3, FGF2, COL6A3, PCOLCE, FGFBP3, CTGF, POSTN, FSTL1, DCD, PTN, HDGF, DRAXIN, RARRES2, KNG1, ECM1, RELN, NDNF, FBLN1, SFRP1, NRP1, FBN1, SLIT3, PAFAH1B1, FBN2, SPON1, PCOLCE2, FN1, STC1, PTPRF, FST, STC2, PTPRS, HGFAC, SVEP1, RPL22, IGFBP2, THBS2, RPL29, and combinations thereof; and a pharmaceutically acceptable excipient, carrier, or diluent. In certain embodiments, described herein is a composition comprising a plurality of polypeptides at least about 85%, 90%, 95%, 97%, 98%, 99%, or 100% identical to CTGF, THBS1, THBS2, THBS3, HGFAC, IGFBP3, IGFBP5, IGFBP7, IGFBP4, SFRP1, STC1, STC2, IGFBP2; and a pharmaceutically acceptable excipient, carrier, or diluent.

In certain embodiments, described herein, is a composition consisting essentially of a plurality of polypeptides at least about 85%, 90%, 95%, 97%, 98%, 99%, or 100% identical to ADAMTS12, INS-IGF2, AOC1, SOD3, CLU, ITIH1, APLP1, THBS1, COCH, ITIH2, APLP2, THBS3, COL11A1, LAMA1, APOB, TNXB, COL12A1, LAMA2, APOE, VEGFA, COL14A1, LAMA5, APOH, VTN, COL18A1, LAMB1, APP, ZNF207, COL1A1, LAMB2, CCDC80, COL1A2, LTF, CFH, COL2A1, MATN2, CLEC3B, COL3A1, MDK, COL25A1, COL5A1, MST1, COL5A3, COL5A2, NID1, CYR61, COL6A1, NPNT, F2, COL6A2, OLFML3, FGF2, COL6A3, PCOLCE, FGFBP3, CTGF, POSTN, FSTL1, DCD, PTN, HDGF, DRAXIN, RARRES2, KNG1, ECM1, RELN, NDNF, FBLN1, SFRP1, NRP1, FBN1, SLIT3, PAFAH1B1, FBN2, SPON1, PCOLCE2, FN1, STC1, PTPRF, FST, STC2, PTPRS, HGFAC, SVEP1, RPL22, IGFBP2, THBS2, RPL29, and combinations thereof; and a pharmaceutically acceptable excipient, carrier, or diluent. In certain embodiments, described herein, is a composition consisting essentially of a plurality of polypeptides at least about 85%, 90%, 95%, 97%, 98%, 99%, or 100% identical to CTGF, THBS1, THBS2, THBS3, HGFAC, IGFBP3, IGFBP5, IGFBP7, IGFBP4, SFRP1, STC1, STC2, IGFBP2; and a pharmaceutically acceptable excipient, carrier, or diluent.

In certain embodiments, described herein, is a composition consisting essentially of any 1, 2, 3, 4, 5, 6, 7, 8, 9, 10 or more polypeptides at least about 85%, 90%, 95%, 97%, 98%, 99%, or 100% identical to ADAMTS12, INS-IGF2, AOC1, SOD3, CLU, ITIH1, APLP1, THBS1, COCH, ITIH2, APLP2, THBS3, COL11A1, LAMA1, APOB, TNXB, COL12A1, LAMA2, APOE, VEGFA, COL14A1, LAMA5, APOH, VTN, COL18A1, LAMB1, APP, ZNF207, COL1A1, LAMB2, CCDC80, COL1A2, LTF, CFH, COL2A1, MATN2, CLEC3B, COL3A1, MDK, COL25A1, COL5A1, MST1, COL5A3, COL5A2, NID1, CYR61, COL6A1, NPNT, F2, COL6A2, OLFML3, FGF2, COL6A3, PCOLCE, FGFBP3, CTGF, POSTN, FSTL1, DCD, PTN, HDGF, DRAXIN, RARRES2, KNG1, ECM1, RELN, NDNF, FBLN1, SFRP1, NRP1, FBN1, SLIT3, PAFAH1B1, FBN2, SPON1, PCOLCE2, FN1, STC1, PTPRF, FST, STC2, PTPRS, HGFAC, SVEP1, RPL22, IGFBP2, THBS2, and RPL29; and a pharmaceutically acceptable excipient, carrier, or diluent. In certain embodiments, described herein, is a composition consisting essentially of any 1, 2, 3, 4, 5, 6, 7, 8, 9, 10 or more polypeptides at least about 85%, 90%, 95%, 97%, 98%, 99%, or 100% identical to CTGF, THBS1, THBS2, THBS3, HGFAC, IGFBP3, IGFBP5, IGFBP7, IGFBP4, SFRP1, STC1, STC2, IGFBP2; and a pharmaceutically acceptable excipient, carrier, or diluent.

In certain embodiments, described herein, is a composition consisting of any 1, 2, 3, 4, 5, 6, 7, 8, 9, 10 or more polypeptides at least about 85%, 90%, 95%, 97%, 98%, 99%, or 100% identical to ADAMTS12, INS-IGF2, AOC1, SOD3, CLU, ITIH1, APLP1, THBS1, COCH, ITIH2, APLP2, THBS3, COL11A1, LAMA1, APOB, TNXB, COL12A1, LAMA2, APOE, VEGFA, COL14A1, LAMA5, APOH, VTN, COL18A1, LAMB1, APP, ZNF207, COL1A1, LAMB2, CCDC80, COL1A2, LTF, CFH, COL2A1, MATN2, CLEC3B, COL3A1, MDK, COL25A1, COL5A1, MST1, COL5A3, COL5A2, NID1, CYR61, COL6A1, NPNT, F2, COL6A2, OLFML3, FGF2, COL6A3, PCOLCE, FGFBP3, CTGF, POSTN, FSTL1, DCD, PTN, HDGF, DRAXIN, RARRES2, KNG1, ECM1, RELN, NDNF, FBLN1, SFRP1, NRP1, FBN1, SLIT3, PAFAH1B1, FBN2, SPON1, PCOLCE2, FN1, STC1, PTPRF, FST, STC2, PTPRS, HGFAC, SVEP1, RPL22, IGFBP2, THBS2, and RPL29; and a pharmaceutically acceptable excipient, carrier, or diluent. In certain embodiments, described herein, is a composition consisting of any 1, 2, 3, 4, 5, 6, 7, 8, 9, 10 or more polypeptides at least about 85%, 90%, 95%, 97%, 98%, 99%, or 100% identical to CTGF, THBS1, THBS2, THBS3, HGFAC, IGFBP3, IGFBP5, IGFBP7, IGFBP4, SFRP1, STC1, STC2, IGFBP2; and a pharmaceutically acceptable excipient, carrier, or diluent.

In certain embodiments, compositions comprising heparin-associated polypeptides do not comprise fibroblast growth factors (FGF). In certain embodiments, compositions comprising heparin-associated polypeptides do not comprise fibroblast growth factor 2 (FGF2). In certain embodiments, compositions comprising heparin-associated polypeptides do not comprise FGF19, Angiogenin, BTC, IL-13 R alpha 2, Siglec-5/CD170, IL-15, APJ, IGFBP-2, Chordin-Like 1, GASP-1/WFIKKNRP, MFRP, IL-10 R alpha, Chem R23, HB-EGF, FGF-6, HGF, IL-16, IL-7 R alpha, TRAIL R3/TNFRSF10C, BMP-6, IL-1 F9/IL-1 H1, IL-1 beta, Kremen-2, TRAIL R4/TNFRSF10D, CXCR1/IL-8 RA, Ck beta 8-1/CCL23, Beta-catenin, FGF-13 1B, TRAIL/TNFSF10, CCL14/HCC-1/HCC-3, or FGF-4, or a combination thereof.

In certain aspects, heparin-associated binding polypeptides and compositions of heparin-associated binding polypeptides herein comprise polypeptides that increase the proliferation of muscle cell precursors, and/or increase their differentiation into muscle cells. In certain embodiments, the heparin-associated polypeptides increase proliferation of a muscle cell precursor by at least about 20%, 30%, 40%, 50%, or 100% compared to a muscle cell precursor not treated with the heparin-associated binding polypeptide. In certain embodiments, the heparin-associated polypeptides increase proliferation of a myoblast by at least about 20%, 30%, 40%, 50%, 100%, 200%, or 500% compared to a myoblast not treated with the heparin-associated binding polypeptide. In certain embodiments, the myoblast is a human myoblast cell line. In certain embodiments, the myoblast is a mouse myoblast cell line (e.g., C2C12). Proliferation can be measured by BrdU or EdU incorporation, which can be quantified using suitable methods such as, by way of non-limiting embodiment, microscopy, flow cytometry, or ELISA.

In certain embodiments, the heparin-associated polypeptides increase differentiation and/or fusion of a muscle cell precursor by at least about 50%, 75%, 100%, 200%, or 500% compared to a muscle cell precursor not treated with the heparin-associated binding polypeptide. In certain embodiments, the heparin-associated polypeptides increase differentiation of a myoblast by at least about 50%, 75%, or 100% compared to a myoblast not treated with the heparin-associated binding polypeptide. In certain embodiments, the myoblast is a human myoblast cell line. In certain embodiments, the myoblast is a mouse myoblast cell line (e.g., C2C12). Differentiation can be measured and/or quantified by eMyHC staining, which detects fusion of a myoblast or muscle cell precursor. This staining can be quantified, for example, by microscopy or flow cytometry.

Heparin-associated polypeptides that increase muscle or connective tissue cell precursor proliferation and/or differentiation are useful in methods of treating muscle or connective tissue disorders. These disorders can arise from the normal aging process, injury related to trauma or physical exertion, genetic predispositions, or incident to other disease states.

Heparin-associated binding polypeptides that are useful for increasing muscle cell precursor differentiation or proliferation are described herein, and in certain embodiments comprise Vitronectin (VTN), Stanniocalcin-2 (STC2), Periostin (POSTN), Agrin (AGRN), Fibroblast growth factor (FGF17, also known as Fibroblast growth factor 13 or FGF13), Thrombospondin 2 (THBS2), follistatin (FST), Thrombospondin 4 (THBS4), Thrombospondin 1 (THBS1), Insulin-like growth factor 2 (IGF2), or Interleukin 15 (IL-15), or any combination thereof. In certain embodiments, any one, two, three, four, or five of VTN, STC2, AGRN, THBS2, or FST are present in a composition useful for increasing muscle cell precursor proliferation or muscle cell differentiation. In certain embodiments, any one, two, three, four, five, six, seven, or eight of VTN, POSTN, FGF17, THBS2, THBS1, IL-15, IGF2, and THBS4 are present in a composition useful for increasing muscle cell precursor proliferation or muscle cell differentiation.

In certain embodiments, a heparin-associated binding polypeptide composition comprises Vitronectin (VTN). VTN may be further included in the composition with any one, two, three, four, five, six, seven, eight, nine, or all polypeptides selected from STC2, AGRN, POSTN, FGF17, THBS2, FST, THBS1, IL-15, IGF2, and THBS4. In certain embodiments, the composition comprises VTN and STC2. In certain embodiments, the composition comprises VTN and AGRN. In certain embodiments, the composition comprises VTN and THBS2. In certain embodiments, the composition comprises VTN and FST. In certain embodiments, the composition comprises VTN and POSTN. In certain embodiments, the composition comprises VTN and FGF17. In certain embodiments, the composition comprises VTN and THBS4. In certain embodiments, the composition comprises VTN and THBS1. In certain embodiments, the composition comprises VTN and IGF2. In certain embodiments, the composition comprises VTN and IL-15. Human VTN is disclosed in SEQ ID NO: 1. In certain embodiments, the VTN of the heparin-associated binding polypeptide composition comprises an amino acid sequence that is at least about 80%, 85%, 90%, 95%, 97%, 98%, 99%, or 100% identical to SEQ ID NO: 1 or amino acids 20-478 of SEQ ID NO: 1. In certain embodiments, the VTN polypeptide lacks a secretory leader sequence, e.g., amino acids 1-19 of SEQ ID NO: 1. In certain embodiments, the VTN polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, or 100 amino acids from the N-terminal or C-terminal end of the polypeptide, including increments therein. In certain embodiments, the VTN polypeptide comprises one or more additional modifications to increase stability. In certain embodiments, the VTN polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the VTN polypeptide is fused with an Fc region of an immunoglobulin or with serum albumin. In certain embodiments, the VTN polypeptide is present in a concatemer with one, two, three, four or more distinct polypeptides selected from STC2, AGRN, THBS2, THBS1, THBS4, FGF17, POSTN, IGF2, IL-15 and FST. In certain embodiments, the VTN polypeptide is present in a concatemer with one, two, three, four or more distinct polypeptides selected from POSTN, FGF17, THBS2, THBS1, IGF2, IL-15, and THBS4. In certain embodiments, the VTN polypeptide is present in a concatemer with one, two, three, four, or more distinct VTN polypeptides. In certain embodiments, the VTN polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA). In some cases, the VTN polypeptide is prepared recombinantly in an expression system (e.g., bacteria, yeast, mammalian, insect). In some cases, the VTN polypeptide is prepared by chemical synthesis.

In certain embodiments, a heparin-associated binding polypeptide composition comprises Periostin (POSTN). POSTN may be further included in the composition with any one, two, three, five, six, or all polypeptides selected from VTN, FGF17, THBS2, THBS1, IGF2, IL-15, and THBS4. In certain embodiments, the composition comprises POSTN and VTN. In certain embodiments, the composition comprises POSTN and FGF17. In certain embodiments, the composition comprises POSTN and THBS2. In certain embodiments, the composition comprises POSTN and THBS4. In certain embodiments, the composition comprises POSTN and THBS1. In certain embodiments, the composition comprises POSTN and IGF2. In certain embodiments, the composition comprises POSTN and IL-15. Human POSTN is disclosed in SEQ ID NO: 6. In certain embodiments, the POSTN of the heparin-associated binding polypeptide composition comprises an amino acid sequence that is at least about 80%, 85%, 90%, 95%, 97%, 98%, 99%, or 100% identical to SEQ ID NO: 6 or amino acids 22-836 of SEQ ID NO: 6. In certain embodiments, the POSTN polypeptide lacks a secretory leader sequence, e.g., amino acids 1-21 of SEQ ID NO: 6. In certain embodiments, the POSTN polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, or 100 amino acids from the N-terminal or C-terminal end of the polypeptide, including increments therein. In certain embodiments, the POSTN polypeptide comprises one or more additional modifications to increase stability. In certain embodiments, the POSTN polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the POSTN polypeptide is fused with an Fc region of an immunoglobulin or with serum albumin. In certain embodiments, the POSTN polypeptide is present in a concatemer with one, two, three, four or more distinct polypeptides selected from VTN, FGF17, THBS2, THBS1, IGF2, IL-15 and THBS4. In certain embodiments, the POSTN polypeptide is present in a concatemer with one, two, three, four, or more distinct POSTN polypeptides. In certain embodiments, the POSTN polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA). In some cases, the POSTN polypeptide is prepared recombinantly in an expression system (e.g., bacteria, yeast, mammalian, insect). In some cases, the POSTN polypeptide is prepared by chemical synthesis.

In certain embodiments, a heparin-associated binding polypeptide composition comprises Fibroblast growth factor (FGF17). FGF17 may be further included in the composition with any one, two, three, four, five, six or all polypeptides selected from VTN, POSTN, THBS2, THBS1, IL-15, IGF2, and THBS4. In certain embodiments, the composition comprises FGF17 and VTN. In certain embodiments, the composition comprises FGF17 and POSTN. In certain embodiments, the composition comprises FGF17 and THBS2. In certain embodiments, the composition comprises FGF17 and THBS4. In certain embodiments, the composition comprises FGF17 and THBS1. In certain embodiments, the composition comprises FGF17 and IGF2. In certain embodiments, the composition comprises FGF17 and IL-15. Human FGF17 is disclosed in SEQ ID NO: 7. In certain embodiments, the FGF17 of the heparin-associated binding polypeptide composition comprises an amino acid sequence that is at least about 80%, 85%, 90%, 95%, 97%, 98%, 99%, or 100% identical to SEQ ID NO: 7, or amino acids 23-216 of SEQ ID NO: 7. In certain embodiments, the FGF17 polypeptide lacks a secretory leader sequence, e.g., amino acids 1-22 of SEQ ID NO: 7. In certain embodiments, the FGF17 polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, or 300 amino acids from the N-terminal or C-terminal end of the polypeptide, including increments therein. In certain embodiments, the FGF17 polypeptide comprises one or more additional modifications to increase stability. In certain embodiments, the FGF17 polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the FGF17 polypeptide is fused with an Fc region of an immunoglobulin or with serum albumin. In certain embodiments, the FGF17 polypeptide is present in a concatemer with one, two, three, four or more distinct polypeptides selected from VTN, POSTN, THBS2, THBS1, IGF2, IL-15, and THBS4. In certain embodiments, the FGF17 polypeptide is present in a concatemer with one, two, three, four, or more distinct FGF17 polypeptides. In certain embodiments, the FGF17 polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA). In some cases, the FGF17 polypeptide is prepared recombinantly in an expression system (e.g., bacteria, yeast, mammalian, insect). In some cases, the FGF17 polypeptide is prepared by chemical synthesis.

In certain embodiments, a heparin-associated binding polypeptide composition comprises Stanniocalcin-2 (STC2). STC-2 may be further included in the composition with any one, two, three, four or more polypeptides selected from VTN, AGRN, THBS2, THBS1, THBS4, POSTN, FGF17, IGF2, IL-15, and FST. In certain embodiments, the composition comprises STC2 and VTN. In certain embodiments, the composition comprises STC2 and AGRN. In certain embodiments, the composition comprises STC2 and THBS2. In certain embodiments, the composition comprises STC2 and FST. Human STC2 is disclosed in SEQ ID NO: 2. In certain embodiments, the STC2 of the heparin-associated binding polypeptide composition comprises an amino acid sequence that is at least about 80%, 85%, 90%, 95%, 97%, 98%, 99%, or 100% identical to SEQ ID NO: 2. In certain embodiments, the STC2 polypeptide lacks a secretory leader sequence. In certain embodiments, the STC2 polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, or 100 amino acids from the N-terminal or C-terminal end of the polypeptide, including increments therein. In certain embodiments, the STC2 polypeptide comprises one or more additional modifications to increase stability. In certain embodiments, the STC2 polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the STC2 polypeptide is fused with an Fc region of an immunoglobulin or with serum albumin. In certain embodiments, the STC2 polypeptide is present in a concatemer with one, two, three, four or more distinct polypeptides selected from VTN, AGRN, THBS2, THBS1, THBS4, FGF17, POSTN, IGF2, IL 15, and FST. In certain embodiments, the STC2 polypeptide is present in a concatemer with one, two, three, four, or more distinct STC2 polypeptides. In certain embodiments, the STC2 polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In certain embodiments, a heparin-associated binding polypeptide composition comprises Agrin (AGRN). AGRN may be further included in the composition with any one, two, three, four or more polypeptides selected from VTN, STC2, THBS2, THBS1, THBS4, FGF17, POSTN, IGF2, IL-15, and FST. In certain embodiments, the composition comprises AGRN and VTN. In certain embodiments, the composition comprises AGRN and STC2. In certain embodiments, the composition comprises AGRN and THBS2. In certain embodiments, the composition comprises AGRN and FST. Human AGRN is disclosed in SEQ ID NO: 3. In certain embodiments, the AGRN of the heparin-associated binding polypeptide composition comprises an amino acid sequence that is at least about 80%, 85%, 90%, 95%, 97%, 98%, 99%, or 100% identical to SEQ ID NO: 3.

In certain embodiments, the AGRN polypeptide lacks a secretory leader sequence. In certain embodiments, the AGRN polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, or 300 amino acids from the N-terminal or C-terminal end of the polypeptide, including increments therein. In certain embodiments, the AGRN polypeptide comprises one or more additional modifications to increase stability. In certain embodiments, the AGRN polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the AGRN polypeptide is fused with an Fc region of an immunoglobulin or with serum albumin. In certain embodiments, the AGRN polypeptide is present in a concatemer with one, two, three, or four other distinct polypeptides selected from VTN, STC2, THBS2, THBS1, THBS4, FGF17, POSTN, IGF2, IL-15, and FST. In certain embodiments, the AGRN polypeptide is present in a concatemer with one, two, three, four, or more distinct AGRN polypeptides. In certain embodiments, the AGRN polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In certain embodiments, a heparin-associated binding polypeptide composition comprises Thrombospondin 2 (THBS2). THBS2 may be further included in the composition with any one, two, three, four, five, six or all polypeptides selected from VTN, STC2, AGRN, THBS1, IL-15, IGF2, and FST. In certain embodiments, the composition comprises THBS2 and VTN. In certain embodiments, the composition comprises THBS2 and STC2. In certain embodiments, the composition comprises THBS2 and AGRN. In certain embodiments, the composition comprises THBS2 and FST. In certain embodiments, the composition comprises AGRN and FST. In certain embodiments, the composition comprises THBS2 and THBS1. In certain embodiments, the composition comprises THBS2 and IGF2. In certain embodiments, the composition comprises THBS2 and IL-15. THBS2 may be further included in the composition with any one, two, three, four, five, six, or all polypeptides selected from VTN, POSTN, FGF17, THBS1, IL-15, IGF2, and THBS4. In certain embodiments, the composition comprises THBS2 and VTN. In certain embodiments, the composition comprises THBS2 and POSTN. In certain embodiments, the composition comprises THBS2 and FGF17. In certain embodiments, the composition comprises THBS2 and THBS4. In certain embodiments, the composition comprises FGF17 and THBS4. Human THBS2 is disclosed in SEQ ID NO: 4. In certain embodiments, the THBS2 of the heparin-associated binding polypeptide composition comprises an amino acid sequence that is at least about 80%, 85%, 90%, 95%, 97%, 98%, 99%, or 100% identical to SEQ ID NO: 4 or amino acids 19-1,172 of SEQ ID NO: 4. In certain embodiments, the THBS2 polypeptide lacks a secretory leader sequence, e.g., amino acids 1-18 of SEQ ID NO: 4. In certain embodiments, the THBS2 polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, or 300 amino acids from the N-terminal or C-terminal end of the polypeptide, including increments therein. In certain embodiments, the THBS2 polypeptide comprises one or more additional modifications to increase stability. In certain embodiments, the THBS2 polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the THBS2 polypeptide is fused with an Fc region of an immunoglobulin or with serum albumin. In certain embodiments, the THBS2 polypeptide is present in a concatemer with one, two, three, four or more distinct polypeptides selected from VTN, STC2, AGRN, THBS1, THBS4, FGF17, POSTN, IGF2, IL-15, and FST. In certain embodiments, the THBS2 polypeptide is present in a concatemer with one, two, three, four or more distinct polypeptides selected from VTN, POSTN, THBS1, IGF2, IL-15, FGF17, and THBS4. In certain embodiments, the THBS2 polypeptide is present in a concatemer with one, two, three, four, or more distinct THBS2 polypeptides. In certain embodiments, the THBS2 polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA). In some cases, the THBS2 polypeptide is prepared recombinantly in an expression system (e.g., bacteria, yeast, mammalian, insect). In some cases, the THBS2 polypeptide is prepared by chemical synthesis.

In certain embodiments, a heparin-associated binding polypeptide composition comprises Thrombospondin 4 (THBS4). THBS4 may be further included in the composition with any one, two, three, four, five, six or all polypeptides selected from VTN, POSTN, FGF17, THBS1, IL-15, IGF2, and THBS2. In certain embodiments, the composition comprises THBS4 and VTN. In certain embodiments, the composition comprises THBS4 and POSTN. In certain embodiments, the composition comprises THBS4 and FGF17. In certain embodiments, the composition comprises THBS4 and THBS2. In certain embodiments, the composition comprises THBS4 and THBS1. In certain embodiments, the composition comprises THBS4 and IL-15. In certain embodiments, the composition comprises THBS4 and IGF2. Human THBS4 is disclosed in SEQ ID NO: 8. In certain embodiments, the THBS4 of the heparin-associated binding polypeptide composition comprises an amino acid sequence that is at least about 80%, 85%, 90%, 95%, 97%, 98%, 99%, or 100% identical to SEQ ID NO: 8 or amino acids 27-961 of SEQ ID NO: 8. In certain embodiments, the THBS4 polypeptide lacks a secretory leader sequence, e.g., amino acids 1-26 of SEQ ID NO: 8. In certain embodiments, the THBS4 polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, or 100 amino acids from the N-terminal or C-terminal end of the polypeptide, including increments therein. In certain embodiments, the THBS4 polypeptide comprises one or more additional modifications to increase stability. In certain embodiments, the THBS4 polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the THBS4 polypeptide is fused with an Fc region of an immunoglobulin or with serum albumin. In certain embodiments, the THBS4 polypeptide is present in a concatemer with one, two, three, four or more distinct polypeptides selected from VTN, POSTN, FGF17, THBS1, IGF2, IL-15, and THBS2. In certain embodiments, the THBS4 polypeptide is present in a concatemer with one, two, three, four, or more distinct THBS4 polypeptides. In certain embodiments, the THBS4 polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA). In some cases, the THBS4 polypeptide is prepared recombinantly in an expression system (e.g., bacteria, yeast, mammalian, insect). In some cases, the THBS2 polypeptide is prepared by chemical synthesis.

In certain embodiments, a heparin-associated binding polypeptide composition comprises follistatin (FST). FST may be further included in the composition with any one, two, three, four or more polypeptides selected from VTN, STC2, AGRN, THBS1, THBS4, FGF17, POSTN, IGF2, IL-15, and THBS2. In certain embodiments, the composition comprises FST and VTN. In certain embodiments, the composition comprises FST and STC2. In certain embodiments, the composition comprises FST and AGRN. In certain embodiments, the composition comprises FST and THBS2. Human FST is disclosed in SEQ ID NO: 5. In certain embodiments, the FST of the heparin-associated binding polypeptide composition comprises an amino acid sequence that is at least about 80%, 85%, 90%, 95%, 97%, 98%, 99%, or 100% identical to SEQ ID NO: 5. In certain embodiments, the FST polypeptide lacks a secretory leader sequence. In certain embodiments, the FST polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, or 100 amino acids from the N-terminal or C-terminal end of the polypeptide, including increments therein. In certain embodiments, the FST polypeptide comprises one or more additional modifications to increase stability. In certain embodiments, the FST polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the FST polypeptide is fused with an Fc region of an immunoglobulin or with serum albumin. In certain embodiments, the FST polypeptide is present in a concatemer with one, two, three, four or more distinct polypeptides selected from VTN, STC2, AGRN, THBS1, THBS4, FGF17, POSTN, IGF2, IL-15, and THBS2. In certain embodiments, the FST polypeptide is present in a concatemer with one, two, three, four, or more distinct FST polypeptides. In certain embodiments, the FST polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In certain embodiments, a heparin-associated binding polypeptide composition comprises Thrombospondin 1 (THBS1). THSB1 may be further included in the composition with any one, two, three, four, five, six, seven, eight or all polypeptides selected from VTN, STC2, AGRN, THBS4, FGF17, POSTN, IGF2, IL-15, and THBS2. In certain embodiments, the composition comprises THSB1 and VTN. In certain embodiments, the composition comprises THSB1 and STC2. In certain embodiments, the composition comprises THSB1 and AGRN. In certain embodiments, the composition comprises THSB1 and THBS2. In certain embodiments, the composition comprises THSB1 and THBS4. In certain embodiments, the composition comprises THSB1 and FGF17. In certain embodiments, the composition comprises THSB1 and POSTN. In certain embodiments, the composition comprises THSB1 and IGF2. In certain embodiments, the composition comprises THSB1 and IL-15. Human THSB1 is disclosed in SEQ ID NO: 9. In certain embodiments, the THSB1 of the heparin-associated binding polypeptide composition comprises an amino acid sequence that is at least about 80%, 85%, 90%, 95%, 97%, 98%, 99%, or 100% identical to SEQ ID NO: 9 or amino acids 19-1170 of SEQ ID NO: 9. In certain embodiments, the THSB1 polypeptide lacks a secretory leader sequence. In certain embodiments, the THSB1 polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, or 100 amino acids from the N-terminal or C-terminal end of the polypeptide, including increments therein. In certain embodiments, the THSB1 polypeptide comprises one or more additional modifications to increase stability. In certain embodiments, the THSB1 polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the THSB1 polypeptide is fused with an Fc region of an immunoglobulin or with serum albumin. In certain embodiments, the THSB1 polypeptide is present in a concatemer with one, two, three, four or more distinct polypeptides selected from VTN, STC2, AGRN, THBS4, FGF17, POSTN, IGF2, IL-15 and THBS2. In certain embodiments, the THSB1 polypeptide is present in a concatemer with one, two, three, four, or more distinct THSB1 polypeptides. In certain embodiments, the THSB1 polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA). In some cases, the THBS1 polypeptide is prepared recombinantly in an expression system (e.g., bacteria, yeast, mammalian, insect). In some cases, the THBS1 polypeptide is prepared by chemical synthesis.

In certain embodiments, a heparin-associated binding polypeptide composition comprises Interleukin-15 (IL-15). IL-15 may be further included in the composition with any one, two, three, four or more polypeptides selected from VTN, STC2, AGRN, THBS1, THBS4, IGF2, POSTN, FGF17, and THBS2. In certain embodiments, the composition comprises IL-15 and VTN. In certain embodiments, the composition comprises IL-15 and STC2. In certain embodiments, the composition comprises IL-15 and AGRN. In certain embodiments, the composition comprises IL-15 and THBS2. In certain embodiments, the composition comprises IL-15 and THBS1. In certain embodiments, the composition comprises IL-15 and THBS4. In certain embodiments, the composition comprises IL-15 and IGF2. In certain embodiments, the composition comprises IL-15 and POSTN. In certain embodiments, the composition comprises IL-15 and FGF17. In certain embodiments, the composition comprises IL-15 and THBS1. Human IL-15 is disclosed in SEQ ID NO: 10. In certain embodiments, the IL-15 of the heparin-associated binding polypeptide composition comprises an amino acid sequence that is at least about 80%, 85%, 90%, 95%, 97%, 98%, 99%, or 100% identical to SEQ ID NO: 10 or amino acids 49-162 of SEQ ID NO: 10. In certain embodiments, the IL-15 polypeptide lacks a secretory leader sequence. In certain embodiments, the IL-15 polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, or 100 amino acids from the N-terminal or C-terminal end of the polypeptide, including increments therein. In certain embodiments, the IL-15 polypeptide comprises one or more additional modifications to increase stability. In certain embodiments, the IL-15 polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the IL-15 polypeptide is fused with an Fc region of an immunoglobulin or with serum albumin. In certain embodiments, the IL-15 polypeptide is present in a concatemer with one, two, three, four or more distinct polypeptides selected from VTN, STC2, AGRN, THBS1, THBS4, FGF17, POSTN, IGF2, and THBS2. In certain embodiments, the IL-15 polypeptide is present in a concatemer with one, two, three, four, or more distinct IL-15 polypeptides. In certain embodiments, the IL-15 polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA). In some cases, the IL-15 polypeptide is prepared recombinantly in an expression system (e.g., bacteria, yeast, mammalian, insect). In some cases, the THBS1 polypeptide is prepared by chemical synthesis.

In certain embodiments, a heparin-associated binding polypeptide composition comprises Insulin-like growth factor 2 (IGF2). IGF2 may be further included in the composition with any one, two, three, four or more polypeptides selected from VTN, STC2, AGRN, THBS1, THBS4, POSTN, FGF17, IL-15 and THBS2. In certain embodiments, the composition comprises IGF2 and VTN. In certain embodiments, the composition comprises IGF2 and STC2. In certain embodiments, the composition comprises IGF2 and AGRN. In certain embodiments, the composition comprises IGF2 and THBS2. In certain embodiments, the composition comprises IGF2 and THBS1. In certain embodiments, the composition comprises IGF2 and THBS4. In certain embodiments, the composition comprises IGF2 and IL-15. In certain embodiments, the composition comprises IGF2 and POSTN. In certain embodiments, the composition comprises IGF2 and FGF17. Human IGF2 is disclosed in SEQ ID NO: 11. In certain embodiments, the IGF2 of the heparin-associated binding polypeptide composition comprises an amino acid sequence that is at least about 80%, 85%, 90%, 95%, 97%, 98%, 99%, or 100% identical to SEQ ID NO: 10 or amino acids 25-91 of SEQ ID NO: 11. In certain embodiments, the IGF2 polypeptide lacks a secretory leader sequence. In certain embodiments, the IGF2 polypeptide is modified by a deletion of 1, 2, 3, 4, 5, 6, 7, 8, 9, 10, 15, 20, 25, 30, 35, 40, 45, 50, 55, 60, 65, 70, 75, 80, 85, 90, 95, or 100 amino acids from the N-terminal or C-terminal end of the polypeptide, including increments therein. In certain embodiments, the IGF2 polypeptide comprises one or more additional modifications to increase stability. In certain embodiments, the IGF2 polypeptide is covalently conjugated to polyethylene glycol, polypropylene glycol, polyoxyalkylenes, or copolymers of polyethylene glycol, polysialic acid, glycolic acid, or polypropylene glycol. In certain embodiments, the heparin-associated polypeptide is fused or conjugated to another protein to increase stability and or bioavailability. In certain embodiments, the IGF2 polypeptide is fused with an Fc region of an immunoglobulin or with serum albumin. In certain embodiments, the IGF2 polypeptide is present in a concatemer with one, two, three, four or more distinct polypeptides selected from VTN, STC2, AGRN, THBS1, THBS4, FGF17, POSTN, IL-15, and THBS2. In certain embodiments, the IGF2 polypeptide is present in a concatemer with one, two, three, four, or more distinct IGF2 polypeptides. In certain embodiments, the IGF2 polypeptide is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA). In some cases, the IGF2 polypeptide is prepared recombinantly in an expression system (e.g., bacteria, yeast, mammalian, insect). In some cases, the THBS1 polypeptide is prepared by chemical synthesis.

In certain embodiments, the heparin-associated binding polypeptide composition comprises any two polypeptides selected from VTN, POSTN, FGF17, THBS2, THBS1, IGF2, IL-15, and THBS4. In certain embodiments, the composition comprises THBS1. In certain embodiments, the composition comprises THBS2. In certain embodiments, the composition comprises THBS4. In certain embodiments, the composition comprises FGF17. In certain embodiments, the composition comprises VTN. In certain embodiments, the composition comprises POSTN. In certain embodiments, the composition comprises IGF2. In certain embodiments, the composition comprises IL-15. In certain embodiments, the composition comprises VTN and POSTN. In certain embodiments, the composition comprises VTN and FGF17. In certain embodiments, the composition comprises VTN and THBS2. In certain embodiments, the composition comprises VTN and THBS1. In certain embodiments, the composition comprises VTN and IGF2. In certain embodiments, the composition comprises VTN and IL-15. In certain embodiments, the composition comprises VTN and THBS4. In certain embodiments, the composition comprises POSTN and FGF17. In certain embodiments, the composition comprises POSTN and THBS2. In certain embodiments, the composition comprises POSTN and THBS1. In certain embodiments, the composition comprises POSTN and IGF2. In certain embodiments, the composition comprises POSTN and IL-15. In certain embodiments, the composition comprises POSTN and THBS4. In certain embodiments, the composition comprises FGF17 and THBS2. In certain embodiments, the composition comprises FGF17 and THBS1. In certain embodiments, the composition comprises FGF17 and IGF2. In certain embodiments, the composition comprises FGF17 and IL-15. In certain embodiments, the composition comprises FGF17 and THBS4. In certain embodiments, the composition comprises THBS2 and THBS1. In certain embodiments, the composition comprises THBS2 and IGF2. In certain embodiments, the composition comprises THBS2 and IL-15. In certain embodiments, the composition comprises THBS2 and THBS4. In certain embodiments, the composition comprises THBS1 and IGF2. In certain embodiments, the composition comprises THBS1 and IL-15. In certain embodiments, the composition comprises THBS1 and THBS4. In certain embodiments, the composition comprises IGF2 and IL-15. In certain embodiments, the composition comprises IGF2 and THBS4. In certain embodiments, the composition comprises IL-15 and THBS4.

In certain embodiments, the heparin-associated binding polypeptide composition comprising any two polypeptides selected from VTN, POSTN, FGF17, THBS2, THBS1, IGF2, IL-15, and THBS4, comprises one or more additional modifications to increase stability. In certain embodiments, one or more of the heparin-associated polypeptides is covalently conjugated to polyethylene glycol, polypropylene glycol, polyoxyalkylenes, or copolymers of polyethylene glycol, polysialic acid, glycolic acid, or polypropylene glycol. In certain embodiments, one or more of the heparin-associated polypeptides is fused or conjugated to another protein to increase stability and or bioavailability. In certain embodiments, one or more of the heparin-associated polypeptides is fused with an Fc region of an immunoglobulin or with serum albumin. In certain embodiments, one or more of the heparin-associated polypeptides is present in a concatemer with one, two, three, or four other distinct polypeptides selected from THBS2, VTN, POSTN, FGF17, THBS1, IGF2, IL-15, and THBS4. In certain embodiments, one or more of the heparin-associated polypeptides is present in a concatemer with one, two, three, four, or more distinct polypeptides. In certain embodiments, one or more of the heparin-associated polypeptides is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In certain embodiments, the heparin-associated binding polypeptide composition comprises any three polypeptides selected from VTN, POSTN, FGF17, THBS2, THBS1, IGF2, IL-15, and THBS4. In certain embodiments, the composition comprises THBS1. In certain embodiments, the composition comprises THBS2. In certain embodiments, the composition comprises THBS4. In certain embodiments, the composition comprises FGF17. In certain embodiments, the composition comprises VTN. In certain embodiments, the composition comprises POSTN. In certain embodiments, the composition comprises IGF2. In certain embodiments, the composition comprises IL-15. In certain embodiments, the composition comprises IGF2, THBS2, and THBS4. In certain embodiments, the composition comprises IL-15, THBS2, and THBS4. In certain embodiments, the composition comprises THBS2 and THBS4. In certain embodiments, the composition comprises THBS2, THBS4, and VTN. In certain embodiments, the composition comprises THBS2, THBS4, and ANOS1. In certain embodiments, the composition comprises THBS2, THBS4, and IL-15. In certain embodiments, the composition comprises THBS2, THBS4, and IGF2. In certain embodiments, the composition comprises THBS1 and FGF17. In certain embodiments, the composition comprises THBS2 and VTN. In certain embodiments, the composition comprises THBS1 and VTN. In certain embodiments, the composition comprises THBS1 and THBS2. In certain embodiments, the composition comprises THBS2 and FGF17. In certain embodiments, the composition comprises THBS1 and THBS4. In certain embodiments, the composition comprises VTN and FGF17. In certain embodiments, the composition comprises THBS4 and VTN. In certain embodiments, the composition comprises THBS4 and FGF17.

In certain embodiments, the composition comprises VTN, POSTN, and FGF17. In certain embodiments, the composition comprises VTN, POSTN, and THBS2. In certain embodiments, the composition comprises VTN, POSTN, and FGF17. In certain embodiments, the composition comprises VTN, POSTN, THBS2. In certain embodiments, the composition comprises VTN, POSTN, and THBS1. In certain embodiments, the composition comprises VTN, POSTN, IGF2. In certain embodiments, the composition comprises VTN, POSTN, and IL-15. In certain embodiments, the composition comprises VTN, POSTN, and THBS4.

In certain embodiments, the composition comprises VTN, FGF17, and THBS2. In certain embodiments, the composition comprises VTN, FGF17, and POSTN. In certain embodiments, the composition comprises VTN, FGF17, and THBS2. In certain embodiments, the composition comprises VTN, FGF17, and THBS1. In certain embodiments, the composition comprises VTN, FGF17, and IGF2. In certain embodiments, the composition comprises VTN, FGF17, and IL-15. In certain embodiments, the composition comprises VTN, FGF17, and THBS4.

In certain embodiments, the composition comprises VTN, THBS2, and POSTN. In certain embodiments, the composition comprises VTN, THBS2, and FGF17. In certain embodiments, the composition comprises VTN, THBS2, and THBS1. In certain embodiments, the composition comprises VTN, THBS2, and IGF2. In certain embodiments, the composition comprises VTN, THBS2, and IL-15. In certain embodiments, the composition comprises VTN, THBS2, and THBS4.

In certain embodiments, the composition comprises VTN, THBS1, and POSTN. In certain embodiments, the composition comprises VTN, THBS1, and FGF17. In certain embodiments, the composition comprises VTN, THBS1, and THBS2. In certain embodiments, the composition comprises VTN, THBS1, and IGF2. In certain embodiments, the composition comprises VTN, THBS1, and IL-15. In certain embodiments, the composition comprises VTN, THBS1, and THBS4.

In certain embodiments, the composition comprises VTN, IGF2, and POSTN. In certain embodiments, the composition comprises VTN, IGF2, and FGF17. In certain embodiments, the composition comprises VTN, IGF2, and THBS2. In certain embodiments, the composition comprises VTN, IGF2, and THBS1. In certain embodiments, the composition comprises VTN, IGF2, and IL-15. In certain embodiments, the composition comprises VTN, IGF2, and THBS4.

In certain embodiments, the composition comprises VTN, IL-15, and POSTN. In certain embodiments, the composition comprises VTN, IL-15, and FGF17. In certain embodiments, the composition comprises VTN, IL-15, and THBS2. In certain embodiments, the composition comprises VTN, IL-15, and THBS1. In certain embodiments, the composition comprises VTN, IL-15, and IGF2. In certain embodiments, the composition comprises VTN, IL-15, and THBS4.

In certain embodiments, the composition comprises VTN, TBHS4, and POSTN. In certain embodiments, the composition comprises VTN, TBHS4, and FGF17. In certain embodiments, the composition comprises VTN, TBHS4, and THBS2. In certain embodiments, the composition comprises VTN, TBHS4, and THBS1. In certain embodiments, the composition comprises VTN, TBHS4, and IGF2. In certain embodiments, the composition comprises VTN, TBHS4, and IL-15.

In certain embodiments, the composition comprises POSTN, FGF17, and VTN. In certain embodiments, the composition comprises POSTN, FGF17, and TBHS2. In certain embodiments, the composition comprises POSTN, FGF17, and THBS1. In certain embodiments, the composition comprises POSTN, FGF17, and IGF2. In certain embodiments, the composition comprises POSTN, FGF17, and IL-15. In certain embodiments, the composition comprises POSTN, FGF17, and THBS4.

In certain embodiments, the composition comprises POSTN, THBS2, and VTN. In certain embodiments, the composition comprises POSTN, THBS2, and FGF17. In certain embodiments, the composition comprises POSTN, THBS2, and THBS1. In certain embodiments, the composition comprises POSTN, THBS2, and IGF2. In certain embodiments, the composition comprises POSTN, THBS2, and IL-15. In certain embodiments, the composition comprises POSTN, THBS2, and THBS4.

In certain embodiments, the composition comprises POSTN, THBS1, and VTN. In certain embodiments, the composition comprises POSTN, THBS1, and FGF17. In certain embodiments, the composition comprises POSTN, THBS1, and THBS2. In certain embodiments, the composition comprises POSTN, THBS1, and IGF2. In certain embodiments, the composition comprises POSTN, THBS1, and IL-15. In certain embodiments, the composition comprises POSTN, THBS1, and THBS4.

In certain embodiments, the composition comprises POSTN, IGF2, and VTN. In certain embodiments, the composition comprises POSTN, IGF2, and FGF17. In certain embodiments, the composition comprises POSTN, IGF2, and THBS2. In certain embodiments, the composition comprises POSTN, IGF2, and THBS1. In certain embodiments, the composition comprises POSTN, IGF2, and IL-15. In certain embodiments, the composition comprises POSTN, IGF2, and THBS4.

In certain embodiments, the composition comprises POSTN, IL-15, and VTN. In certain embodiments, the composition comprises POSTN, IL-15, and FGF17. In certain embodiments, the composition comprises POSTN, IL-15, and THBS2. In certain embodiments, the composition comprises POSTN, IL-15, and THBS1. In certain embodiments, the composition comprises POSTN, IL-15, and IGF2. In certain embodiments, the composition comprises POSTN, IL-15, and THBS4.

In certain embodiments, the composition comprises POSTN, THBS4, and VTN. In certain embodiments, the composition comprises POSTN, THBS4, and FGF17. In certain embodiments, the composition comprises POSTN, THBS4, and THBS2. In certain embodiments, the composition comprises POSTN, THBS4, and THBS1. In certain embodiments, the composition comprises POSTN, THBS4, and IGF2. In certain embodiments, the composition comprises POSTN, THBS4, and IL-15.

In certain embodiments, the composition comprises FGF17, THBS2, and VTN. In certain embodiments, the composition comprises FGF17, THBS2, and POSTN. In certain embodiments, the composition comprises FGF17, THBS2, and THBS1. In certain embodiments, the composition comprises FGF17, THBS2, and IGF2. In certain embodiments, the composition comprises FGF17, THBS2, and IL-15. In certain embodiments, the composition comprises FGF17, THBS2, and THBS4.

In certain embodiments, the composition comprises FGF17, THBS1, and VTN. In certain embodiments, the composition comprises FGF17, THBS1, and POSTN. In certain embodiments, the composition comprises FGF17, THBS1, and THBS2. In certain embodiments, the composition comprises FGF17, THBS1, and IGF2. In certain embodiments, the composition comprises FGF17, THBS1, and IL-15. In certain embodiments, the composition comprises FGF17, THBS1, and THBS4.

In certain embodiments, the composition comprises FGF17, IGF2, and VTN. In certain embodiments, the composition comprises FGF17, IGF2, and POSTN. In certain embodiments, the composition comprises FGF17, IGF2, and THBS2. In certain embodiments, the composition comprises FGF17, IGF2, and THBS1. In certain embodiments, the composition comprises FGF17, IGF2, and IL-15. In certain embodiments, the composition comprises FGF17, IGF2, and THBS4.

In certain embodiments, the composition comprises FGF17, IL-15, and VTN. In certain embodiments, the composition comprises FGF17, IL-15, and POSTN. In certain embodiments, the composition comprises FGF17, IL-15, and THBS2. In certain embodiments, the composition comprises FGF17, IL-15, and THBS1. In certain embodiments, the composition comprises FGF17, IL-15, and IGF2. In certain embodiments, the composition comprises FGF17, IL-15, and THBS4.

In certain embodiments, the composition comprises FGF17, THBS4, and VTN. In certain embodiments, the composition comprises FGF17, THBS4, and POSTN. In certain embodiments, the composition comprises FGF17, THBS4, and THBS2. In certain embodiments, the composition comprises FGF17, THBS4, and THBS1. In certain embodiments, the composition comprises FGF17, THBS4, and IGF2. In certain embodiments, the composition comprises FGF17, THBS4, and IL-15.

In certain embodiments, the composition comprises THBS2, THBS1, and VTN. In certain embodiments, the composition comprises THBS2, THBS1, and POSTN. In certain embodiments, the composition comprises THBS2, THBS1, and FGF17. In certain embodiments, the composition comprises THBS2, THBS1, and IGF2. In certain embodiments, the composition comprises THBS2, THBS1, and IL-15. In certain embodiments, the composition comprises THBS2, THBS1, and THBS4.

In certain embodiments, the composition comprises THBS2, IGF2, and VTN. In certain embodiments, the composition comprises THBS2, IGF2, and POSTN. In certain embodiments, the composition comprises THBS2, IGF2, and FGF17. In certain embodiments, the composition comprises THBS2, IGF2, and THBS1. In certain embodiments, the composition comprises THBS2, IGF2, and IL-15. In certain embodiments, the composition comprises THBS2, IGF2, and THBS4.

In certain embodiments, the composition comprises THBS2, IL-15, and VTN. In certain embodiments, the composition comprises THBS2, IL-15, and POSTN. In certain embodiments, the composition comprises THBS2, IL-15, and FGF17. In certain embodiments, the composition comprises THBS2, IL-15, and THBS1. In certain embodiments, the composition comprises THBS2, IL-15, and IGF2. In certain embodiments, the composition comprises THBS2, IL-15, and THBS4.

In certain embodiments, the composition comprises THBS2, THBS4, and VTN. In certain embodiments, the composition comprises THBS2, THBS4, and POSTN. In certain embodiments, the composition comprises THBS2, THBS4, and FGF17. In certain embodiments, the composition comprises THBS2, THBS4, and THBS1. In certain embodiments, the composition comprises THBS2, THBS4, and IGF2. In certain embodiments, the composition comprises THBS2, THBS4, and IL-15.

In certain embodiments, the composition comprises THBS1, IGF2, and VTN. In certain embodiments, the composition comprises THBS1, IGF2, and POSTN. In certain embodiments, the composition comprises THBS1, IGF2, and FGF17. In certain embodiments, the composition comprises THBS1, IGF2, and THBS2. In certain embodiments, the composition comprises THBS1, IGF2, and IL-15. In certain embodiments, the composition comprises THBS1, IGF2, and THBS4.

In certain embodiments, the composition comprises THBS1, IL-15, and VTN. In certain embodiments, the composition comprises THBS1, IL-15, and POSTN. In certain embodiments, the composition comprises THBS1, IL-15, and FGF17. In certain embodiments, the composition comprises THBS1, IL-15, and THBS2. In certain embodiments, the composition comprises THBS1, IL-15, and IGF2. In certain embodiments, the composition comprises THBS1, IL-15, and THBS4.

In certain embodiments, the composition comprises THBS1, and THBS4, and VTN. In certain embodiments, the composition comprises THBS1, and THBS4, and POSTN. In certain embodiments, the composition comprises THBS1, and THBS4, and FGF17. In certain embodiments, the composition comprises THBS1, and THBS4, and THBS2. In certain embodiments, the composition comprises THBS1, and THBS4, and IGF2. In certain embodiments, the composition comprises THBS1, and THBS4, and IL-15.

In certain embodiments, the composition comprises IGF2, IL-15, and VTN. In certain embodiments, the composition comprises IGF2, IL-15, and POSTN. In certain embodiments, the composition comprises IGF2, IL-15, and FGF17. In certain embodiments, the composition comprises IGF2, IL-15, and THBS2. In certain embodiments, the composition comprises IGF2, IL-15, and THBS1. In certain embodiments, the composition comprises IGF2, IL-15, and THBS4.

In certain embodiments, the composition comprises IGF2, THBS4, and VTN. In certain embodiments, the composition comprises IGF2, THBS4, and POSTN. In certain embodiments, the composition comprises IGF2, THBS4, and FGF17. In certain embodiments, the composition comprises IGF2, THBS4, and THBS2. In certain embodiments, the composition comprises IGF2, THBS4, and THBS1. In certain embodiments, the composition comprises IGF2, THBS4, and IL-15.

In certain embodiments, the composition comprises IL-15, and THBS4, and VTN. In certain embodiments, the composition comprises IL-15, and THBS4, and POSTN. In certain embodiments, the composition comprises IL-15, and THBS4, and FGF17. In certain embodiments, the composition comprises IL-15, and THBS4, and THBS2. In certain embodiments, the composition comprises IL-15, and THBS4, and THBS1. In certain embodiments, the composition comprises IL-15, and THBS4, and IGF2.

In certain embodiments, the composition comprises VTN, POSTN, and FGF17. In certain embodiments, the composition comprises VTN, POSTN, and THBS2. In certain embodiments, the composition comprises VTN, POSTN, and THBS4. In certain embodiments, the composition comprises VTN, FGF17, and POSTN. In certain embodiments, the composition comprises VTN, FGF17, and THBS2. In certain embodiments, the composition comprises VTN, FGF17, and THBS4. In certain embodiments, the composition comprises VTN, THBS2, and POSTN. In certain embodiments, the composition comprises VTN, THBS2, and FGF17. In certain embodiments, the composition comprises VTN, THBS2, and THBS4. In certain embodiments, the composition comprises VTN, THBS4, and POSTN. In certain embodiments, the composition comprises VTN, THBS4, and FGF17. In certain embodiments, the composition comprises VTN, THBS4, and THBS2. In certain embodiments, the composition comprises POSTN, VTN, and THBS4. In certain embodiments, the composition comprises POSTN, VTN, and FGF17. In certain embodiments, the composition comprises POSTN, VTN, and THBS2. In certain embodiments, the composition comprises POSTN, FGF17, and THBS4. In certain embodiments, the composition comprises POSTN, FGF17, and VTN. In certain embodiments, the composition comprises POSTN, FGF17, and THBS2. In certain embodiments, the composition comprises POSTN, THBS2, and THBS4. In certain embodiments, the composition comprises POSTN, THBS2, and VTN. In certain embodiments, the composition comprises POSTN, THBS2, and FGF17. In certain embodiments, the composition comprises POSTN, THBS4, and THBS2. In certain embodiments, the composition comprises POSTN, THBS4, and VTN. In certain embodiments, the composition comprises POSTN, THBS4, and FGF17. In certain embodiments, the composition comprises FGF17, VTN, and THBS2. In certain embodiments, the composition comprises FGF17, VTN, and THBS4. In certain embodiments, the composition comprises FGF17, VTN, and POSTN. In certain embodiments, the composition comprises FGF17, POSTN, and THBS2. In certain embodiments, the composition comprises FGF17, POSTN, and THBS4. In certain embodiments, the composition comprises FGF17, POSTN, and VTN. In certain embodiments, the composition comprises FGF17, THBS2, and POSTN. In certain embodiments, the composition comprises FGF17, THBS2, and THBS4. In certain embodiments, the composition comprises FGF17, THBS2, and VTN. In certain embodiments, the composition comprises FGF17, THBS4, and POSTN. In certain embodiments, the composition comprises FGF17, THBS4, and THBS2. In certain embodiments, the composition comprises FGF17, THBS4, and VTN. In certain embodiments, the composition comprises THBS2, VTN, and POSTN. In certain embodiments, the composition comprises THBS2, VTN, and FGF17. In certain embodiments, the composition comprises THBS2, VTN, and THBS4. In certain embodiments, the composition comprises THBS2, POSTN, and VTN. In certain embodiments, the composition comprises THBS2, POSTN, and FGF17. In certain embodiments, the composition comprises THBS2, POSTN, and THBS4. In certain embodiments, the composition comprises THBS2, FGF17, and VTN. In certain embodiments, the composition comprises THBS2, FGF17, and POSTN. In certain embodiments, the composition comprises THBS2, FGF17, and THBS4. In certain embodiments, the composition comprises THBS2, THBS4, and VTN. In certain embodiments, the composition comprises THBS2, THBS4, and POSTN. In certain embodiments, the composition comprises THBS2, THBS4, and FGF17. In certain embodiments, the composition comprises THBS4, VTN, and THBS2. In certain embodiments, the composition comprises THBS4, VTN, and POSTN. In certain embodiments, the composition comprises THBS4, VTN, and FGF17. In certain embodiments, the composition comprises THBS4, POSTN, and THBS2. In certain embodiments, the composition comprises THBS4, POSTN, and VTN. In certain embodiments, the composition comprises THBS4, POSTN, and FGF17. In certain embodiments, the composition comprises THBS4, FGF17, and THBS2. In certain embodiments, the composition comprises THBS4, FGF17, and VTN. In certain embodiments, the composition comprises THBS4, FGF17, and POSTN. In certain embodiments, the composition comprises THBS4, THBS2, and FGF17. In certain embodiments, the composition comprises THBS4, THBS2, and VTN. In certain embodiments, the composition comprises THBS4, THBS2, and POSTN.

In certain embodiments, the heparin-associated binding polypeptide composition comprising any three polypeptides selected from VTN, POSTN, FGF17, THBS2, THBS1, IGF2, IL-15, and THBS4, comprises one or more additional modifications to increase stability. In certain embodiments, one or more of the heparin-associated polypeptides is covalently conjugated to polyethylene glycol, polypropylene glycol, polyoxyalkylenes, or copolymers of polyethylene glycol, polysialic acid, glycolic acid, or polypropylene glycol. In certain embodiments, one or more of the heparin-associated polypeptides is fused or conjugated to another protein to increase stability and or bioavailability. In certain embodiments, one or more of the heparin-associated polypeptides is fused with an Fc region of an immunoglobulin or with serum albumin. In certain embodiments, one or more of the heparin-associated polypeptides is present in a concatemer with one, two, three, or four other distinct polypeptides selected from THBS2, VTN, POSTN, FGF17, THBS1, IGF2, IL-15, and THBS4. In certain embodiments, one or more of the heparin-associated polypeptides is present in a concatemer with one, two, three, four, or more distinct polypeptides. In certain embodiments, one or more of the heparin-associated polypeptides is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In certain embodiments, the heparin-associated binding polypeptide composition comprises any four polypeptides selected from VTN, POSTN, FGF17, THBS1, IGF2, IL-15, THBS2, and THBS4. In certain embodiments, the composition comprises VTN, POSTN, FGF17, and THBS2. In certain embodiments, the composition comprises VTN, POSTN, FGF17, and THBS4. In certain embodiments, the composition comprises VTN, POSTN, THBS2, and FGF17. In certain embodiments, the composition comprises VTN, POSTN, THBS2, and THBS4. In certain embodiments, the composition comprises VTN, POSTN, THBS4, and FGF17. In certain embodiments, the composition comprises VTN, POSTN, THBS4, and THBS2. In certain embodiments, the composition comprises VTN, FGF17, POSTN, and THBS4. In certain embodiments, the composition comprises VTN, FGF17, POSTN, and THBS2. In certain embodiments, the composition comprises VTN, FGF17, THBS2, and THBS4. In certain embodiments, the composition comprises VTN, FGF17, THBS2, and POSTN. In certain embodiments, the composition comprises VTN, FGF17, THBS4, and THBS2. In certain embodiments, the composition comprises VTN, FGF17, THBS4, and POSTN. In certain embodiments, the composition comprises VTN, THBS2, POSTN, and FGF17. In certain embodiments, the composition comprises VTN, THBS2, POSTN, and THBS4. In certain embodiments, the composition comprises VTN, THBS2, FGF17, and POSTN. In certain embodiments, the composition comprises VTN, THBS2, FGF17, and THBS4. In certain embodiments, the composition comprises VTN, THBS2, THBS4, and POSTN. In certain embodiments, the composition comprises VTN, THBS2, THBS4, and FGF17. In certain embodiments, the composition comprises VTN, THBS4, POSTN, and THBS2. In certain embodiments, the composition comprises VTN, THBS4, POSTN, and FGF17. In certain embodiments, the composition comprises VTN, THBS4, FGF17, and THBS2. In certain embodiments, the composition comprises VTN, THBS4, FGF17, and POSTN. In certain embodiments, the composition comprises VTN, THBS4, THBS2, and FGF17. In certain embodiments, the composition comprises VTN, THBS4, THBS2, and POSTN. In certain embodiments, the composition comprises POSTN, VTN, THBS4, and FGF17. In certain embodiments, the composition comprises POSTN, VTN, THBS4, and THBS2. In certain embodiments, the composition comprises POSTN, VTN, FGF17, and THBS4. In certain embodiments, the composition comprises POSTN, VTN, FGF17, and THBS2. In certain embodiments, the composition comprises POSTN, VTN, THBS2, and THBS4. In certain embodiments, the composition comprises POSTN, VTN, THBS2, and FGF17. In certain embodiments, the composition comprises POSTN, FGF17, THBS2, and THBS4. In certain embodiments, the composition comprises POSTN, FGF17, THBS4, and VTN. In certain embodiments, the composition comprises POSTN, FGF17, VTN, and THBS2. In certain embodiments, the composition comprises POSTN, FGF17, VTN, and THBS4. In certain embodiments, the composition comprises POSTN, FGF17, THBS2, and VTN. In certain embodiments, the composition comprises POSTN, FGF17, THBS2, and THBS4. In certain embodiments, the composition comprises POSTN, THBS2, THBS4, and VTN. In certain embodiments, the composition comprises POSTN, THBS2, THBS4, and FGF17. In certain embodiments, the composition comprises POSTN, THBS2, VTN, and THBS4. In certain embodiments, the composition comprises POSTN, THBS2, VTN, and FGF17. In certain embodiments, the composition comprises POSTN, THBS2, FGF17, and THBS4. In certain embodiments, the composition comprises POSTN, THBS2, FGF17, and VTN. In certain embodiments, the composition comprises POSTN, THBS4, THBS2, and FGF17. In certain embodiments, the composition comprises POSTN, THBS4, THBS2, and VTN. In certain embodiments, the composition comprises POSTN, THBS4, VTN, and FGF17. In certain embodiments, the composition comprises POSTN, THBS4, VTN, and THBS2. In certain embodiments, the composition comprises POSTN, THBS4, FGF17, and VTN. In certain embodiments, the composition comprises POSTN, THBS4, FGF17, and THBS2. In certain embodiments, the composition comprises FGF17, VTN, THBS2, and THBS4. In certain embodiments, the composition comprises FGF17, VTN, THBS2, and POSTN. In certain embodiments, the composition comprises FGF17, VTN, THBS4, and THBS2. In certain embodiments, the composition comprises FGF17, VTN, THBS4, and POSTN. In certain embodiments, the composition comprises FGF17, VTN, POSTN, and THBS2. In certain embodiments, the composition comprises FGF17, VTN, POSTN, and THBS4. In certain embodiments, the composition comprises FGF17, POSTN, THBS2, and VTN. In certain embodiments, the composition comprises FGF17, POSTN, THBS2, and THBS4. In certain embodiments, the composition comprises FGF17, POSTN, THBS4, and VTN. In certain embodiments, the composition comprises FGF17, POSTN, THBS4, and THBS2. In certain embodiments, the composition comprises FGF17, POSTN, VTN, and THBS4. In certain embodiments, the composition comprises FGF17, POSTN, VTN, and THBS2. In certain embodiments, the composition comprises FGF17, THBS2, POSTN, and THBS4. In certain embodiments, the composition comprises FGF17, THBS2, POSTN, and VTN. In certain embodiments, the composition comprises FGF17, THBS2, THBS4, and POSTN. In certain embodiments, the composition comprises FGF17, THBS2, THBS4, and VTN. In certain embodiments, the composition comprises FGF17, THBS2, VTN, and POSTN. In certain embodiments, the composition comprises FGF17, THBS2, VTN, and THBS4. In certain embodiments, the composition comprises FGF17, THBS4, POSTN, and VTN. In certain embodiments, the composition comprises FGF17, THBS4, POSTN, and THBS2. In certain embodiments, the composition comprises FGF17, THBS4, THBS2, and VTN. In certain embodiments, the composition comprises FGF17, THBS4, THBS2, and POSTN. In certain embodiments, the composition comprises FGF17, THBS4, VTN, and THBS2. In certain embodiments, the composition comprises FGF17, THBS4, VTN, and POSTN. In certain embodiments, the composition comprises THBS2, VTN, POSTN, and FGF17. In certain embodiments, the composition comprises THBS2, VTN, POSTN, and THBS4. In certain embodiments, the composition comprises THBS2, VTN, FGF17, and POSTN. In certain embodiments, the composition comprises THBS2, VTN, FGF17, and THBS4. In certain embodiments, the composition comprises THBS2, VTN, THBS4, and POSTN. In certain embodiments, the composition comprises THBS2, VTN, THBS4, and FGF17. In certain embodiments, the composition comprises THBS2, POSTN, VTN, and THBS4. In certain embodiments, the composition comprises THBS2, POSTN, VTN, and FGF17. In certain embodiments, the composition comprises THBS2, POSTN, FGF17, and THBS4. In certain embodiments, the composition comprises THBS2, POSTN, FGF17, and VTN. In certain embodiments, the composition comprises THBS2, POSTN, THBS4, and FGF17. In certain embodiments, the composition comprises THBS2, POSTN, THBS4, and VTN. In certain embodiments, the composition comprises THBS2, FGF17, VTN, and POSTN. In certain embodiments, the composition comprises THBS2, FGF17, VTN, and THBS4. In certain embodiments, the composition comprises THBS2, FGF17, POSTN, and VTN. In certain embodiments, the composition comprises THBS2, FGF17, POSTN, and THBS4. In certain embodiments, the composition comprises THBS2, FGF17, THBS4, and VTN. In certain embodiments, the composition comprises THBS2, FGF17, THBS4, and POSTN. In certain embodiments, the composition comprises THBS2, THBS4, VTN, and FGF17. In certain embodiments, the composition comprises THBS2, THBS4, VTN, and POSTN. In certain embodiments, the composition comprises THBS2, THBS4, POSTN, and FGF17. In certain embodiments, the composition comprises THBS2, THBS4, POSTN, and VTN. In certain embodiments, the composition comprises THBS2, THBS4, FGF17, and POSTN. In certain embodiments, the composition comprises THBS2, THBS4, FGF17, and VTN. In certain embodiments, the composition comprises THBS4, VTN, THBS2, and POSTN. In certain embodiments, the composition comprises THBS4, VTN, THBS2, and FGF17. In certain embodiments, the composition comprises THBS4, VTN, POSTN, and THBS2. In certain embodiments, the composition comprises THBS4, VTN, POSTN, and FGF17. In certain embodiments, the composition comprises THBS4, VTN, FGF17, and THBS2. In certain embodiments, the composition comprises THBS4, VTN, FGF17, and POSTN. In certain embodiments, the composition comprises THBS4, POSTN, THBS2, and FGF17. In certain embodiments, the composition comprises THBS4, POSTN, THBS2, and VTN. In certain embodiments, the composition comprises THBS4, POSTN, VTN, and FGF17. In certain embodiments, the composition comprises THBS4, POSTN, VTN, and THBS2. In certain embodiments, the composition comprises THBS4, POSTN, FGF17, and VTN. In certain embodiments, the composition comprises THBS4, POSTN, FGF17, and THBS2. In certain embodiments, the composition comprises THBS4, FGF17, THBS2, and VTN. In certain embodiments, the composition comprises THBS4, FGF17, THBS2, and POSTN. In certain embodiments, the composition comprises THBS4, FGF17, VTN, and THBS2. In certain embodiments, the composition comprises THBS4, FGF17, VTN, and POSTN. In certain embodiments, the composition comprises THBS4, FGF17, POSTN, and THBS2. In certain embodiments, the composition comprises THBS4, FGF17, POSTN, and VTN. In certain embodiments, the composition comprises THBS4, THBS2, FGF17, and POSTN. In certain embodiments, the composition comprises THBS4, THBS2, FGF17, and VTN. In certain embodiments, the composition comprises THBS4, THBS2, VTN, and POSTN. In certain embodiments, the composition comprises THBS4, THBS2, VTN, and FGF17. In certain embodiments, the composition comprises THBS4, THBS2, POSTN, and VTN. In certain embodiments, the composition comprises THBS4, THBS2, POSTN, and FGF17.

In certain embodiments, the composition comprises VTN, POSTN, FGF17, and a polypeptide comprising VTN, POSTN, FGF17, THBS2, THBS1, IGF2, IL-15, or THBS4. In certain embodiments, the composition comprises VTN, POSTN, THBS2, and a polypeptide comprising VTN, POSTN, FGF17, THBS2, THBS1, IGF2, IL-15, or THBS4. In certain embodiments, the composition comprises VTN, POSTN, FGF17, and a polypeptide comprising VTN, POSTN, FGF17, THBS2, THBS1, IGF2, IL-15, or THBS4. In certain embodiments, the composition comprises VTN, POSTN, THBS2, and a polypeptide comprising VTN, POSTN, FGF17, THBS2, THBS1, IGF2, IL-15, or THBS4. In certain embodiments, the composition comprises VTN, POSTN, THBS1, and a polypeptide comprising VTN, POSTN, FGF17, THBS2, THBS1, IGF2, IL-15, or THBS4. In certain embodiments, the composition comprises VTN, POSTN, IGF2, and a polypeptide comprising VTN, POSTN, FGF17, THBS2, THBS1, IGF2, IL-15, or THBS4. In certain embodiments, the composition comprises VTN, POSTN, IL-15, and a polypeptide comprising VTN, POSTN, FGF17, THBS2, THBS1, IGF2, IL-15, or THBS4. In certain embodiments, the composition comprises VTN, POSTN, THBS4, and a polypeptide comprising VTN, POSTN, FGF17, THBS2, THBS1, IGF2, IL-15, or THBS4.

In certain embodiments, the composition comprises VTN, FGF17, THBS2, and a polypeptide comprising VTN, POSTN, FGF17, THBS2, THBS1, IGF2, IL-15, or THBS4. In certain embodiments, the composition comprises VTN, FGF17, POSTN, and a polypeptide comprising VTN, POSTN, FGF17, THBS2, THBS1, IGF2, IL-15, or THBS4. In certain embodiments, the composition comprises VTN, FGF17, THBS2, and a polypeptide comprising VTN, POSTN, FGF17, THBS2, THBS1, IGF2, IL-15, or THBS4. In certain embodiments, the composition comprises VTN, FGF17, THBS1, and a polypeptide comprising VTN, POSTN, FGF17, THBS2, THBS1, IGF2, IL-15, or THBS4. In certain embodiments, the composition comprises VTN, FGF17, IGF2, and a polypeptide comprising VTN, POSTN, FGF17, THBS2, THBS1, IGF2, IL-15, or THBS4. In certain embodiments, the composition comprises VTN, FGF17, IL-15, and a polypeptide comprising VTN, POSTN, FGF17, THBS2, THBS1, IGF2, IL-15, or THBS4. In certain embodiments, the composition comprises VTN, FGF17, THBS4, and a polypeptide comprising VTN, POSTN, FGF17, THBS2, THBS1, IGF2, IL-15, or THBS4.

In certain embodiments, the composition comprises VTN, THBS2, POSTN, and a polypeptide comprising VTN, POSTN, FGF17, THBS2, THBS1, IGF2, IL-15, or THBS4. In certain embodiments, the composition comprises VTN, THBS2, FGF17, and a polypeptide comprising VTN, POSTN, FGF17, THBS2, THBS1, IGF2, IL-15, or THBS4. In certain embodiments, the composition comprises VTN, THBS2, THBS1, and a polypeptide comprising VTN, POSTN, FGF17, THBS2, THBS1, IGF2, IL-15, or THBS4. In certain embodiments, the composition comprises VTN, THBS2, IGF2, and a polypeptide comprising VTN, POSTN, FGF17, THBS2, THBS1, IGF2, IL-15, or THBS4. In certain embodiments, the composition comprises VTN, THBS2, IL-15, and a polypeptide comprising VTN, POSTN, FGF17, THBS2, THBS1, IGF2, IL-15, or THBS4. In certain embodiments, the composition comprises VTN, THBS2, THBS4, and a polypeptide comprising VTN, POSTN, FGF17, THBS2, THBS1, IGF2, IL-15, or THBS4.

In certain embodiments, the composition comprises VTN, THBS1, POSTN, and a polypeptide comprising VTN, POSTN, FGF17, THBS2, THBS1, IGF2, IL-15, or THBS4. In certain embodiments, the composition comprises VTN, THBS1, FGF17, and a polypeptide comprising VTN, POSTN, FGF17, THBS2, THBS1, IGF2, IL-15, or THBS4. In certain embodiments, the composition comprises VTN, THBS1, THBS2, and a polypeptide comprising VTN, POSTN, FGF17, THBS2, THBS1, IGF2, IL-15, or THBS4. In certain embodiments, the composition comprises VTN, THBS1, IGF2, and a polypeptide comprising VTN, POSTN, FGF17, THBS2, THBS1, IGF2, IL-15, or THBS4. In certain embodiments, the composition comprises VTN, THBS1, IL-15, and a polypeptide comprising VTN, POSTN, FGF17, THBS2, THBS1, IGF2, IL-15, or THBS4. In certain embodiments, the composition comprises VTN, THBS1, THBS4, and a polypeptide comprising VTN, POSTN, FGF17, THBS2, THBS1, IGF2, IL-15, or THBS4.

In certain embodiments, the composition comprises VTN, IGF2, POSTN, and a polypeptide comprising VTN, POSTN, FGF17, THBS2, THBS1, IGF2, IL-15, or THBS4. In certain embodiments, the composition comprises VTN, IGF2, FGF17, and a polypeptide comprising VTN, POSTN, FGF17, THBS2, THBS1, IGF2, IL-15, or THBS4. In certain embodiments, the composition comprises VTN, IGF2, THBS2, and a polypeptide comprising VTN, POSTN, FGF17, THBS2, THBS1, IGF2, IL-15, or THBS4. In certain embodiments, the composition comprises VTN, IGF2, THBS1, and a polypeptide comprising VTN, POSTN, FGF17, THBS2, THBS1, IGF2, IL-15, or THBS4. In certain embodiments, the composition comprises VTN, IGF2, IL-15, and a polypeptide comprising VTN, POSTN, FGF17, THBS2, THBS1, IGF2, IL-15, or THBS4. In certain embodiments, the composition comprises VTN, IGF2, THBS4, and a polypeptide comprising VTN, POSTN, FGF17, THBS2, THBS1, IGF2, IL-15, or THBS4.

In certain embodiments, the composition comprises VTN, IL-15, POSTN, and a polypeptide comprising VTN, POSTN, FGF17, THBS2, THBS1, IGF2, IL-15, or THBS4. In certain embodiments, the composition comprises VTN, IL-15, FGF17, and a polypeptide comprising VTN, POSTN, FGF17, THBS2, THBS1, IGF2, IL-15, or THBS4. In certain embodiments, the composition comprises VTN, IL-15, THBS2, and a polypeptide comprising VTN, POSTN, FGF17, THBS2, THBS1, IGF2, IL-15, or THBS4. In certain embodiments, the composition comprises VTN, IL-15, THBS1, and a polypeptide comprising VTN, POSTN, FGF17, THBS2, THBS1, IGF2, IL-15, or THBS4. In certain embodiments, the composition comprises VTN, IL-15, IGF2, and a polypeptide comprising VTN, POSTN, FGF17, THBS2, THBS1, IGF2, IL-15, or THBS4. In certain embodiments, the composition comprises VTN, IL-15, THBS4, and a polypeptide comprising VTN, POSTN, FGF17, THBS2, THBS1, IGF2, IL-15, or THBS4.

In certain embodiments, the composition comprises VTN, TBHS4, POSTN, and a polypeptide comprising VTN, POSTN, FGF17, THBS2, THBS1, IGF2, IL-15, or THBS4. In certain embodiments, the composition comprises VTN, TBHS4, FGF17, and a polypeptide comprising VTN, POSTN, FGF17, THBS2, THBS1, IGF2, IL-15, or THBS4. In certain embodiments, the composition comprises VTN, TBHS4, THBS2, and a polypeptide comprising VTN, POSTN, FGF17, THBS2, THBS1, IGF2, IL-15, or THBS4. In certain embodiments, the composition comprises VTN, TBHS4, THBS1, and a polypeptide comprising VTN, POSTN, FGF17, THBS2, THBS1, IGF2, IL-15, or THBS4. In certain embodiments, the composition comprises VTN, TBHS4, IGF2, and a polypeptide comprising VTN, POSTN, FGF17, THBS2, THBS1, IGF2, IL-15, or THBS4. In certain embodiments, the composition comprises VTN, TBHS4, IL-15, and a polypeptide comprising VTN, POSTN, FGF17, THBS2, THBS1, IGF2, IL-15, or THBS4.

In certain embodiments, the composition comprises POSTN, FGF17, VTN, and a polypeptide comprising VTN, POSTN, FGF17, THBS2, THBS1, IGF2, IL-15, or THBS4. In certain embodiments, the composition comprises POSTN, FGF17, TBHS2, and a polypeptide comprising VTN, POSTN, FGF17, THBS2, THBS1, IGF2, IL-15, or THBS4. In certain embodiments, the composition comprises POSTN, FGF17, THBS1, and a polypeptide comprising VTN, POSTN, FGF17, THBS2, THBS1, IGF2, IL-15, or THBS4. In certain embodiments, the composition comprises POSTN, FGF17, IGF2, and a polypeptide comprising VTN, POSTN, FGF17, THBS2, THBS1, IGF2, IL-15, or THBS4. In certain embodiments, the composition comprises POSTN, FGF17, IL-15, and a polypeptide comprising VTN, POSTN, FGF17, THBS2, THBS1, IGF2, IL-15, or THBS4. In certain embodiments, the composition comprises POSTN, FGF17, THBS4, and a polypeptide comprising VTN, POSTN, FGF17, THBS2, THBS1, IGF2, IL-15, or THBS4.

In certain embodiments, the composition comprises POSTN, THBS2, VTN, and a polypeptide comprising VTN, POSTN, FGF17, THBS2, THBS1, IGF2, IL-15, or THBS4. In certain embodiments, the composition comprises POSTN, THBS2, FGF17, and a polypeptide comprising VTN, POSTN, FGF17, THBS2, THBS1, IGF2, IL-15, or THBS4. In certain embodiments, the composition comprises POSTN, THBS2, THBS1, and a polypeptide comprising VTN, POSTN, FGF17, THBS2, THBS1, IGF2, IL-15, or THBS4. In certain embodiments, the composition comprises POSTN, THBS2, IGF2, and a polypeptide comprising VTN, POSTN, FGF17, THBS2, THBS1, IGF2, IL-15, or THBS4. In certain embodiments, the composition comprises POSTN, THBS2, IL-15, and a polypeptide comprising VTN, POSTN, FGF17, THBS2, THBS1, IGF2, IL-15, or THBS4. In certain embodiments, the composition comprises POSTN, THBS2, THBS4, and a polypeptide comprising VTN, POSTN, FGF17, THBS2, THBS1, IGF2, IL-15, or THBS4.

In certain embodiments, the composition comprises POSTN, THBS1, VTN, and a polypeptide comprising VTN, POSTN, FGF17, THBS2, THBS1, IGF2, IL-15, or THBS4. In certain embodiments, the composition comprises POSTN, THBS1, FGF17, and a polypeptide comprising VTN, POSTN, FGF17, THBS2, THBS1, IGF2, IL-15, or THBS4. In certain embodiments, the composition comprises POSTN, THBS1, THBS2, and a polypeptide comprising VTN, POSTN, FGF17, THBS2, THBS1, IGF2, IL-15, or THBS4. In certain embodiments, the composition comprises POSTN, THBS1, IGF2, and a polypeptide comprising VTN, POSTN, FGF17, THBS2, THBS1, IGF2, IL-15, or THBS4. In certain embodiments, the composition comprises POSTN, THBS1, IL-15, and a polypeptide comprising VTN, POSTN, FGF17, THBS2, THBS1, IGF2, IL-15, or THBS4. In certain embodiments, the composition comprises POSTN, THBS1, THBS4, and a polypeptide comprising VTN, POSTN, FGF17, THBS2, THBS1, IGF2, IL-15, or THBS4.

In certain embodiments, the composition comprises POSTN, IGF2, VTN, and a polypeptide comprising VTN, POSTN, FGF17, THBS2, THBS1, IGF2, IL-15, or THBS4. In certain embodiments, the composition comprises POSTN, IGF2, FGF17, and a polypeptide comprising VTN, POSTN, FGF17, THBS2, THBS1, IGF2, IL-15, or THBS4. In certain embodiments, the composition comprises POSTN, IGF2, THBS2, and a polypeptide comprising VTN, POSTN, FGF17, THBS2, THBS1, IGF2, IL-15, or THBS4. In certain embodiments, the composition comprises POSTN, IGF2, THBS1, and a polypeptide comprising VTN, POSTN, FGF17, THBS2, THBS1, IGF2, IL-15, or THBS4. In certain embodiments, the composition comprises POSTN, IGF2, IL-15, and a polypeptide comprising VTN, POSTN, FGF17, THBS2, THBS1, IGF2, IL-15, or THBS4. In certain embodiments, the composition comprises POSTN, IGF2, THBS4, and a polypeptide comprising VTN, POSTN, FGF17, THBS2, THBS1, IGF2, IL-15, or THBS4.

In certain embodiments, the composition comprises POSTN, IL-15, VTN, and a polypeptide comprising VTN, POSTN, FGF17, THBS2, THBS1, IGF2, IL-15, or THBS4. In certain embodiments, the composition comprises POSTN, IL-15, FGF17, and a polypeptide comprising VTN, POSTN, FGF17, THBS2, THBS1, IGF2, IL-15, or THBS4. In certain embodiments, the composition comprises POSTN, IL-15, THBS2, and a polypeptide comprising VTN, POSTN, FGF17, THBS2, THBS1, IGF2, IL-15, or THBS4. In certain embodiments, the composition comprises POSTN, IL-15, THBS1, and a polypeptide comprising VTN, POSTN, FGF17, THBS2, THBS1, IGF2, IL-15, or THBS4. In certain embodiments, the composition comprises POSTN, IL-15, IGF2, and a polypeptide comprising VTN, POSTN, FGF17, THBS2, THBS1, IGF2, IL-15, or THBS4. In certain embodiments, the composition comprises POSTN, IL-15, THBS4, and a polypeptide comprising VTN, POSTN, FGF17, THBS2, THBS1, IGF2, IL-15, or THBS4.

In certain embodiments, the composition comprises POSTN, THBS4, VTN, and a polypeptide comprising VTN, POSTN, FGF17, THBS2, THBS1, IGF2, IL-15, or THBS4. In certain embodiments, the composition comprises POSTN, THBS4, FGF17, and a polypeptide comprising VTN, POSTN, FGF17, THBS2, THBS1, IGF2, IL-15, or THBS4. In certain embodiments, the composition comprises POSTN, THBS4, THBS2, and a polypeptide comprising VTN, POSTN, FGF17, THBS2, THBS1, IGF2, IL-15, or THBS4. In certain embodiments, the composition comprises POSTN, THBS4, THBS1, and a polypeptide comprising VTN, POSTN, FGF17, THBS2, THBS1, IGF2, IL-15, or THBS4. In certain embodiments, the composition comprises POSTN, THBS4, IGF2, and a polypeptide comprising VTN, POSTN, FGF17, THBS2, THBS1, IGF2, IL-15, or THBS4. In certain embodiments, the composition comprises POSTN, THBS4, IL-15, and a polypeptide comprising VTN, POSTN, FGF17, THBS2, THBS1, IGF2, IL-15, or THBS4.

In certain embodiments, the composition comprises FGF17, THBS2, VTN, and a polypeptide comprising VTN, POSTN, FGF17, THBS2, THBS1, IGF2, IL-15, or THBS4. In certain embodiments, the composition comprises FGF17, THBS2, POSTN, and a polypeptide comprising VTN, POSTN, FGF17, THBS2, THBS1, IGF2, IL-15, or THBS4. In certain embodiments, the composition comprises FGF17, THBS2, THBS1, and a polypeptide comprising VTN, POSTN, FGF17, THBS2, THBS1, IGF2, IL-15, or THBS4. In certain embodiments, the composition comprises FGF17, THBS2, IGF2, and a polypeptide comprising VTN, POSTN, FGF17, THBS2, THBS1, IGF2, IL-15, or THBS4. In certain embodiments, the composition comprises FGF17, THBS2, IL-15, and a polypeptide comprising VTN, POSTN, FGF17, THBS2, THBS1, IGF2, IL-15, or THBS4. In certain embodiments, the composition comprises FGF17, THBS2, THBS4, and a polypeptide comprising VTN, POSTN, FGF17, THBS2, THBS1, IGF2, IL-15, or THBS4.

In certain embodiments, the composition comprises FGF17, THBS1, VTN, and a polypeptide comprising VTN, POSTN, FGF17, THBS2, THBS1, IGF2, IL-15, or THBS4. In certain embodiments, the composition comprises FGF17, THBS1, POSTN, and a polypeptide comprising VTN, POSTN, FGF17, THBS2, THBS1, IGF2, IL-15, or THBS4. In certain embodiments, the composition comprises FGF17, THBS1, THBS2, and a polypeptide comprising VTN, POSTN, FGF17, THBS2, THBS1, IGF2, IL-15, or THBS4. In certain embodiments, the composition comprises FGF17, THBS1, IGF2, and a polypeptide comprising VTN, POSTN, FGF17, THBS2, THBS1, IGF2, IL-15, or THBS4. In certain embodiments, the composition comprises FGF17, THBS1, IL-15, and a polypeptide comprising VTN, POSTN, FGF17, THBS2, THBS1, IGF2, IL-15, or THBS4. In certain embodiments, the composition comprises FGF17, THBS1, THBS4, and a polypeptide comprising VTN, POSTN, FGF17, THBS2, THBS1, IGF2, IL-15, or THBS4.

In certain embodiments, the composition comprises FGF17, IGF2, VTN, and a polypeptide comprising VTN, POSTN, FGF17, THBS2, THBS1, IGF2, IL-15, or THBS4. In certain embodiments, the composition comprises FGF17, IGF2, POSTN, and a polypeptide comprising VTN, POSTN, FGF17, THBS2, THBS1, IGF2, IL-15, or THBS4. In certain embodiments, the composition comprises FGF17, IGF2, THBS2, and a polypeptide comprising VTN, POSTN, FGF17, THBS2, THBS1, IGF2, IL-15, or THBS4. In certain embodiments, the composition comprises FGF17, IGF2, THBS1, and a polypeptide comprising VTN, POSTN, FGF17, THBS2, THBS1, IGF2, IL-15, or THBS4. In certain embodiments, the composition comprises FGF17, IGF2, IL-15, and a polypeptide comprising VTN, POSTN, FGF17, THBS2, THBS1, IGF2, IL-15, or THBS4. In certain embodiments, the composition comprises FGF17, IGF2, THBS4, and a polypeptide comprising VTN, POSTN, FGF17, THBS2, THBS1, IGF2, IL-15, or THBS4.

In certain embodiments, the composition comprises FGF17, IL-15, VTN, and a polypeptide comprising VTN, POSTN, FGF17, THBS2, THBS1, IGF2, IL-15, or THBS4. In certain embodiments, the composition comprises FGF17, IL-15, POSTN, and a polypeptide comprising VTN, POSTN, FGF17, THBS2, THBS1, IGF2, IL-15, or THBS4. In certain embodiments, the composition comprises FGF17, IL-15, THBS2, and a polypeptide comprising VTN, POSTN, FGF17, THBS2, THBS1, IGF2, IL-15, or THBS4. In certain embodiments, the composition comprises FGF17, IL-15, THBS1, and a polypeptide comprising VTN, POSTN, FGF17, THBS2, THBS1, IGF2, IL-15, or THBS4. In certain embodiments, the composition comprises FGF17, IL-15, IGF2, and a polypeptide comprising VTN, POSTN, FGF17, THBS2, THBS1, IGF2, IL-15, or THBS4. In certain embodiments, the composition comprises FGF17, IL-15, THBS4, and a polypeptide comprising VTN, POSTN, FGF17, THBS2, THBS1, IGF2, IL-15, or THBS4.

In certain embodiments, the composition comprises FGF17, THBS4, VTN, and a polypeptide comprising VTN, POSTN, FGF17, THBS2, THBS1, IGF2, IL-15, or THBS4. In certain embodiments, the composition comprises FGF17, THBS4, POSTN, and a polypeptide comprising VTN, POSTN, FGF17, THBS2, THBS1, IGF2, IL-15, or THBS4. In certain embodiments, the composition comprises FGF17, THBS4, THBS2, and a polypeptide comprising VTN, POSTN, FGF17, THBS2, THBS1, IGF2, IL-15, or THBS4. In certain embodiments, the composition comprises FGF17, THBS4, THBS1, and a polypeptide comprising VTN, POSTN, FGF17, THBS2, THBS1, IGF2, IL-15, or THBS4. In certain embodiments, the composition comprises FGF17, THBS4, IGF2, and a polypeptide comprising VTN, POSTN, FGF17, THBS2, THBS1, IGF2, IL-15, or THBS4. In certain embodiments, the composition comprises FGF17, THBS4, IL-15, and a polypeptide comprising VTN, POSTN, FGF17, THBS2, THBS1, IGF2, IL-15, or THBS4.

In certain embodiments, the composition comprises THBS2, THBS1, VTN, and a polypeptide comprising VTN, POSTN, FGF17, THBS2, THBS1, IGF2, IL-15, or THBS4. In certain embodiments, the composition comprises THBS2, THBS1, POSTN, and a polypeptide comprising VTN, POSTN, FGF17, THBS2, THBS1, IGF2, IL-15, or THBS4. In certain embodiments, the composition comprises THBS2, THBS1, FGF17, and a polypeptide comprising VTN, POSTN, FGF17, THBS2, THBS1, IGF2, IL-15, or THBS4. In certain embodiments, the composition comprises THBS2, THBS1, IGF2, and a polypeptide comprising VTN, POSTN, FGF17, THBS2, THBS1, IGF2, IL-15, or THBS4. In certain embodiments, the composition comprises THBS2, THBS1, IL-15, and a polypeptide comprising VTN, POSTN, FGF17, THBS2, THBS1, IGF2, IL-15, or THBS4. In certain embodiments, the composition comprises THBS2, THBS1, THBS4, and a polypeptide comprising VTN, POSTN, FGF17, THBS2, THBS1, IGF2, IL-15, or THBS4.

In certain embodiments, the composition comprises THBS2, IGF2, VTN, and a polypeptide comprising VTN, POSTN, FGF17, THBS2, THBS1, IGF2, IL-15, or THBS4. In certain embodiments, the composition comprises THBS2, IGF2, POSTN, and a polypeptide comprising VTN, POSTN, FGF17, THBS2, THBS1, IGF2, IL-15, or THBS4. In certain embodiments, the composition comprises THBS2, IGF2, FGF17, and a polypeptide comprising VTN, POSTN, FGF17, THBS2, THBS1, IGF2, IL-15, or THBS4. In certain embodiments, the composition comprises THBS2, IGF2, THBS1, and a polypeptide comprising VTN, POSTN, FGF17, THBS2, THBS1, IGF2, IL-15, or THBS4. In certain embodiments, the composition comprises THBS2, IGF2, IL-15, and a polypeptide comprising VTN, POSTN, FGF17, THBS2, THBS1, IGF2, IL-15, or THBS4. In certain embodiments, the composition comprises THBS2, IGF2, THBS4, and a polypeptide comprising VTN, POSTN, FGF17, THBS2, THBS1, IGF2, IL-15, or THBS4.

In certain embodiments, the composition comprises THBS2, IL-15, VTN, and a polypeptide comprising VTN, POSTN, FGF17, THBS2, THBS1, IGF2, IL-15, or THBS4. In certain embodiments, the composition comprises THBS2, IL-15, POSTN, and a polypeptide comprising VTN, POSTN, FGF17, THBS2, THBS1, IGF2, IL-15, or THBS4. In certain embodiments, the composition comprises THBS2, IL-15, FGF17, and a polypeptide comprising VTN, POSTN, FGF17, THBS2, THBS1, IGF2, IL-15, or THBS4. In certain embodiments, the composition comprises THBS2, IL-15, THBS1, and a polypeptide comprising VTN, POSTN, FGF17, THBS2, THBS1, IGF2, IL-15, or THBS4. In certain embodiments, the composition comprises THBS2, IL-15, IGF2, and a polypeptide comprising VTN, POSTN, FGF17, THBS2, THBS1, IGF2, IL-15, or THBS4. In certain embodiments, the composition comprises THBS2, IL-15, THBS4, and a polypeptide comprising VTN, POSTN, FGF17, THBS2, THBS1, IGF2, IL-15, or THBS4.

In certain embodiments, the composition comprises THBS2, THBS4, VTN, and a polypeptide comprising VTN, POSTN, FGF17, THBS2, THBS1, IGF2, IL-15, or THBS4. In certain embodiments, the composition comprises THBS2, THBS4, POSTN, and a polypeptide comprising VTN, POSTN, FGF17, THBS2, THBS1, IGF2, IL-15, or THBS4. In certain embodiments, the composition comprises THBS2, THBS4, FGF17, and a polypeptide comprising VTN, POSTN, FGF17, THBS2, THBS1, IGF2, IL-15, or THBS4. In certain embodiments, the composition comprises THBS2, THBS4, THBS1, and a polypeptide comprising VTN, POSTN, FGF17, THBS2, THBS1, IGF2, IL-15, or THBS4. In certain embodiments, the composition comprises THBS2, THBS4, IGF2, and a polypeptide comprising VTN, POSTN, FGF17, THBS2, THBS1, IGF2, IL-15, or THBS4. In certain embodiments, the composition comprises THBS2, THBS4, IL-15, and a polypeptide comprising VTN, POSTN, FGF17, THBS2, THBS1, IGF2, IL-15, or THBS4.

In certain embodiments, the composition comprises THBS1, IGF2, VTN, and a polypeptide comprising VTN, POSTN, FGF17, THBS2, THBS1, IGF2, IL-15, or THBS4. In certain embodiments, the composition comprises THBS1, IGF2, POSTN, and a polypeptide comprising VTN, POSTN, FGF17, THBS2, THBS1, IGF2, IL-15, or THBS4. In certain embodiments, the composition comprises THBS1, IGF2, FGF17, and a polypeptide comprising VTN, POSTN, FGF17, THBS2, THBS1, IGF2, IL-15, or THBS4. In certain embodiments, the composition comprises THBS1, IGF2, THBS2, and a polypeptide comprising VTN, POSTN, FGF17, THBS2, THBS1, IGF2, IL-15, or THBS4. In certain embodiments, the composition comprises THBS1, IGF2, IL-15, and a polypeptide comprising VTN, POSTN, FGF17, THBS2, THBS1, IGF2, IL-15, or THBS4. In certain embodiments, the composition comprises THBS1, IGF2, THBS4, and a polypeptide comprising VTN, POSTN, FGF17, THBS2, THBS1, IGF2, IL-15, or THBS4.

In certain embodiments, the composition comprises THBS1, IL-15, VTN, and a polypeptide comprising VTN, POSTN, FGF17, THBS2, THBS1, IGF2, IL-15, or THBS4. In certain embodiments, the composition comprises THBS1, IL-15, POSTN, and a polypeptide comprising VTN, POSTN, FGF17, THBS2, THBS1, IGF2, IL-15, or THBS4. In certain embodiments, the composition comprises THBS1, IL-15, FGF17, and a polypeptide comprising VTN, POSTN, FGF17, THBS2, THBS1, IGF2, IL-15, or THBS4. In certain embodiments, the composition comprises THBS1, IL-15, THBS2, and a polypeptide comprising VTN, POSTN, FGF17, THBS2, THBS1, IGF2, IL-15, or THBS4. In certain embodiments, the composition comprises THBS1, IL-15, IGF2, and a polypeptide comprising VTN, POSTN, FGF17, THBS2, THBS1, IGF2, IL-15, or THBS4. In certain embodiments, the composition comprises THBS1, IL-15, THBS4, and a polypeptide comprising VTN, POSTN, FGF17, THBS2, THBS1, IGF2, IL-15, or THBS4.

In certain embodiments, the composition comprises THBS1, and THBS4, VTN, and a polypeptide comprising VTN, POSTN, FGF17, THBS2, THBS1, IGF2, IL-15, or THBS4. In certain embodiments, the composition comprises THBS1, THBS4, POSTN, and a polypeptide comprising VTN, POSTN, FGF17, THBS2, THBS1, IGF2, IL-15, or THBS4. In certain embodiments, the composition comprises THBS1, THBS4, FGF17, and a polypeptide comprising VTN, POSTN, FGF17, THBS2, THBS1, IGF2, IL-15, or THBS4. In certain embodiments, the composition comprises THBS1, THBS4, THBS2, and a polypeptide comprising VTN, POSTN, FGF17, THBS2, THBS1, IGF2, IL-15, or THBS4. In certain embodiments, the composition comprises THBS1, THBS4, IGF2, and a polypeptide comprising VTN, POSTN, FGF17, THBS2, THBS1, IGF2, IL-15, or THBS4. In certain embodiments, the composition comprises THBS1, THBS4, IL-15, and a polypeptide comprising VTN, POSTN, FGF17, THBS2, THBS1, IGF2, IL-15, or THBS4.

In certain embodiments, the composition comprises IGF2, IL-15, VTN, and a polypeptide comprising VTN, POSTN, FGF17, THBS2, THBS1, IGF2, IL-15, or THBS4. In certain embodiments, the composition comprises IGF2, IL-15, POSTN, and a polypeptide comprising VTN, POSTN, FGF17, THBS2, THBS1, IGF2, IL-15, or THBS4. In certain embodiments, the composition comprises IGF2, IL-15, FGF17, and a polypeptide comprising VTN, POSTN, FGF17, THBS2, THBS1, IGF2, IL-15, or THBS4. In certain embodiments, the composition comprises IGF2, IL-15, THBS2, and a polypeptide comprising VTN, POSTN, FGF17, THBS2, THBS1, IGF2, IL-15, or THBS4. In certain embodiments, the composition comprises IGF2, IL-15, THBS1, and a polypeptide comprising VTN, POSTN, FGF17, THBS2, THBS1, IGF2, IL-15, or THBS4. In certain embodiments, the composition comprises IGF2, IL-15, THBS4, and a polypeptide comprising VTN, POSTN, FGF17, THBS2, THBS1, IGF2, IL-15, or THBS4.

In certain embodiments, the composition comprises IGF2, THBS4, VTN, and a polypeptide comprising VTN, POSTN, FGF17, THBS2, THBS1, IGF2, IL-15, or THBS4. In certain embodiments, the composition comprises IGF2, THBS4, POSTN, and a polypeptide comprising VTN, POSTN, FGF17, THBS2, THBS1, IGF2, IL-15, or THBS4. In certain embodiments, the composition comprises IGF2, THBS4, FGF17, and a polypeptide comprising VTN, POSTN, FGF17, THBS2, THBS1, IGF2, IL-15, or THBS4. In certain embodiments, the composition comprises IGF2, THBS4, THBS2, and a polypeptide comprising VTN, POSTN, FGF17, THBS2, THBS1, IGF2, IL-15, or THBS4. In certain embodiments, the composition comprises IGF2, THBS4, THBS1, and a polypeptide comprising VTN, POSTN, FGF17, THBS2, THBS1, IGF2, IL-15, or THBS4. In certain embodiments, the composition comprises IGF2, THBS4, IL-15, and a polypeptide comprising VTN, POSTN, FGF17, THBS2, THBS1, IGF2, IL-15, or THBS4.

In certain embodiments, the composition comprises IL-15, THBS4, VTN, and a polypeptide comprising VTN, POSTN, FGF17, THBS2, THBS1, IGF2, IL-15, or THBS4. In certain embodiments, the composition comprises IL-15, THBS4, POSTN, and a polypeptide comprising VTN, POSTN, FGF17, THBS2, THBS1, IGF2, IL-15, or THBS4. In certain embodiments, the composition comprises IL-15, THBS4, FGF17, and a polypeptide comprising VTN, POSTN, FGF17, THBS2, THBS1, IGF2, IL-15, or THBS4. In certain embodiments, the composition comprises IL-15, THBS4, THBS2, and a polypeptide comprising VTN, POSTN, FGF17, THBS2, THBS1, IGF2, IL-15, or THBS4. In certain embodiments, the composition comprises IL-15, THBS4, THBS1, and a polypeptide comprising VTN, POSTN, FGF17, THBS2, THBS1, IGF2, IL-15, or THBS4. In certain embodiments, the composition comprises IL-15, THBS4, IGF2, and a polypeptide comprising VTN, POSTN, FGF17, THBS2, THBS1, IGF2, IL-15, or THBS4.

In certain embodiments, the heparin-associated binding polypeptide composition comprising any four polypeptides selected from VTN, POSTN, FGF17, THBS2, THBS1, IGF2, IL-15, and THBS4, comprises one or more additional modifications to increase stability. In certain embodiments, one or more of the heparin-associated polypeptides is covalently conjugated to polyethylene glycol, polypropylene glycol, polyoxyalkylenes, or copolymers of polyethylene glycol, polysialic acid, glycolic acid, or polypropylene glycol. In certain embodiments, one or more of the heparin-associated polypeptides is fused or conjugated to another protein to increase stability and or bioavailability. In certain embodiments, one or more of the heparin-associated polypeptides is fused with an Fc region of an immunoglobulin or with serum albumin. In certain embodiments, one or more of the heparin-associated polypeptides is present in a concatemer with one, two, three, four or more distinct polypeptides selected from THBS2, VTN, POSTN, FGF17, THBS1, IL-15, IGF2, and THBS4. In certain embodiments, one or more of the heparin-associated polypeptides is present in a concatemer with one, two, three, four, or more distinct polypeptides. In certain embodiments, one or more of the heparin-associated polypeptides is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In certain embodiments, the heparin-associated binding polypeptide composition comprises any three polypeptides selected from VTN, STC2, AGRN, THBS2, and FST. In certain embodiments, the composition comprises VTN, STC2, and AGRN. In certain embodiments, the composition comprises VTN, STC2, and THBS2. In certain embodiments, the composition comprises VTN, STC2, and FST. In certain embodiments, the composition comprises VTN, AGRN, and STC2. In certain embodiments, the composition comprises VTN, AGRN, and THBS2. In certain embodiments, the composition comprises VTN, AGRN, and FST. In certain embodiments, the composition comprises VTN, THBS2, and STC2. In certain embodiments, the composition comprises VTN, THBS2, and AGRN. In certain embodiments, the composition comprises VTN, THBS2, and FST. In certain embodiments, the composition comprises VTN, FST, and STC2. In certain embodiments, the composition comprises VTN, FST, and AGRN. In certain embodiments, the composition comprises VTN, FST, and THBS2. In certain embodiments, the composition comprises STC2, VTN, and FST. In certain embodiments, the composition comprises STC2, VTN, and AGRN. In certain embodiments, the composition comprises STC2, VTN, and THBS2. In certain embodiments, the composition comprises STC2, AGRN, and FST. In certain embodiments, the composition comprises STC2, AGRN, and VTN. In certain embodiments, the composition comprises STC2, AGRN, and THBS2. In certain embodiments, the composition comprises STC2, THBS2, and FST. In certain embodiments, the composition comprises STC2, THBS2, and VTN. In certain embodiments, the composition comprises STC2, THBS2, and AGRN. In certain embodiments, the composition comprises STC2, FST, and THBS2. In certain embodiments, the composition comprises STC2, FST, and VTN. In certain embodiments, the composition comprises STC2, FST, and AGRN. In certain embodiments, the composition comprises AGRN, VTN, and THBS2. In certain embodiments, the composition comprises AGRN, VTN, and FST. In certain embodiments, the composition comprises AGRN, VTN, and STC2. In certain embodiments, the composition comprises AGRN, STC2, and THBS2. In certain embodiments, the composition comprises AGRN, STC2, and FST. In certain embodiments, the composition comprises AGRN, STC2, and VTN. In certain embodiments, the composition comprises AGRN, THBS2, and STC2. In certain embodiments, the composition comprises AGRN, THBS2, and FST. In certain embodiments, the composition comprises AGRN, THBS2, and VTN. In certain embodiments, the composition comprises AGRN, FST, and STC2. In certain embodiments, the composition comprises AGRN, FST, and THBS2. In certain embodiments, the composition comprises AGRN, FST, and VTN. In certain embodiments, the composition comprises THBS2, VTN, and STC2. In certain embodiments, the composition comprises THBS2, VTN, and AGRN. In certain embodiments, the composition comprises THBS2, VTN, and FST. In certain embodiments, the composition comprises THBS2, STC2, and VTN. In certain embodiments, the composition comprises THBS2, STC2, and AGRN. In certain embodiments, the composition comprises THBS2, STC2, and FST. In certain embodiments, the composition comprises THBS2, AGRN, and VTN. In certain embodiments, the composition comprises THBS2, AGRN, and STC2. In certain embodiments, the composition comprises THBS2, AGRN, and FST. In certain embodiments, the composition comprises THBS2, FST, and VTN. In certain embodiments, the composition comprises THBS2, FST, and STC2. In certain embodiments, the composition comprises THBS2, FST, and AGRN. In certain embodiments, the composition comprises FST, VTN, and THBS2. In certain embodiments, the composition comprises FST, VTN, and STC2. In certain embodiments, the composition comprises FST, VTN, and AGRN. In certain embodiments, the composition comprises FST, STC2, and THBS2. In certain embodiments, the composition comprises FST, STC2, and VTN. In certain embodiments, the composition comprises FST, STC2, and AGRN. In certain embodiments, the composition comprises FST, AGRN, and THBS2. In certain embodiments, the composition comprises FST, AGRN, and VTN. In certain embodiments, the composition comprises FST, AGRN, and STC2. In certain embodiments, the composition comprises FST, THBS2, and AGRN. In certain embodiments, the composition comprises FST, THBS2, and VTN. In certain embodiments, the composition comprises FST, THBS2, and STC2. In certain embodiments, one or more of the heparin-associated polypeptides comprise one or more additional modifications to increase stability. In certain embodiments, one or more of the heparin-associated polypeptides is covalently conjugated to polyethylene glycol, polypropylene glycol, polyoxyalkylenes, or copolymers of polyethylene glycol, polysialic acid, glycolic acid, or polypropylene glycol. In certain embodiments, one or more of the heparin-associated polypeptide is fused or conjugated to another protein to increase stability and or bioavailability. In certain embodiments, one or more of the heparin-associated polypeptides is fused with an Fc region of an immunoglobulin or with serum albumin. In certain embodiments, one or more of the heparin-associated polypeptides is present in a concatemer with one, two, three, four or more distinct polypeptides selected from THBS2, VTN, STC2, AGRN, or FST. In certain embodiments, one or more of the heparin-associated polypeptides is present in a concatemer with one, two, three, four, or more distinct polypeptides. In certain embodiments, one or more of the heparin-associated polypeptides is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In certain embodiments, the heparin-associated binding polypeptide composition comprises any four polypeptides selected from VTN, STC2, AGRN, THBS2, and FST. In certain embodiments, the composition comprises VTN, STC2, AGRN, and THBS2. In certain embodiments, the composition comprises VTN, STC2, AGRN, and FST. In certain embodiments, the composition comprises VTN, STC2, THBS2, and AGRN. In certain embodiments, the composition comprises VTN, STC2, THBS2, and FST. In certain embodiments, the composition comprises VTN, STC2, FST, and AGRN. In certain embodiments, the composition comprises VTN, STC2, FST, and THBS2. In certain embodiments, the composition comprises VTN, AGRN, STC2, and FST. In certain embodiments, the composition comprises VTN, AGRN, STC2, and THBS2. In certain embodiments, the composition comprises VTN, AGRN, THBS2, and FST. In certain embodiments, the composition comprises VTN, AGRN, THBS2, and STC2. In certain embodiments, the composition comprises VTN, AGRN, FST, and THBS2. In certain embodiments, the composition comprises VTN, AGRN, FST, and STC2. In certain embodiments, the composition comprises VTN, THBS2, STC2, and AGRN. In certain embodiments, the composition comprises VTN, THBS2, STC2, and FST. In certain embodiments, the composition comprises VTN, THBS2, AGRN, and STC2. In certain embodiments, the composition comprises VTN, THBS2, AGRN, and FST. In certain embodiments, the composition comprises VTN, THBS2, FST, and STC2. In certain embodiments, the composition comprises VTN, THBS2, FST, and AGRN. In certain embodiments, the composition comprises VTN, FST, STC2, and THBS2. In certain embodiments, the composition comprises VTN, FST, STC2, and AGRN. In certain embodiments, the composition comprises VTN, FST, AGRN, and THBS2. In certain embodiments, the composition comprises VTN, FST, AGRN, and STC2. In certain embodiments, the composition comprises VTN, FST, THBS2, and AGRN. In certain embodiments, the composition comprises VTN, FST, THBS2, and STC2. In certain embodiments, the composition comprises STC2, VTN, FST, and AGRN. In certain embodiments, the composition comprises STC2, VTN, FST, and THBS2. In certain embodiments, the composition comprises STC2, VTN, AGRN, and FST. In certain embodiments, the composition comprises STC2, VTN, AGRN, and THBS2. In certain embodiments, the composition comprises STC2, VTN, THBS2, and FST. In certain embodiments, the composition comprises STC2, VTN, THBS2, and AGRN. In certain embodiments, the composition comprises STC2, AGRN, FST, and THBS2. In certain embodiments, the composition comprises STC2, AGRN, FST, and VTN. In certain embodiments, the composition comprises STC2, AGRN, VTN, and THBS2. In certain embodiments, the composition comprises STC2, AGRN, VTN, and FST. In certain embodiments, the composition comprises STC2, AGRN, THBS2, and VTN. In certain embodiments, the composition comprises STC2, AGRN, THBS2, and FST. In certain embodiments, the composition comprises STC2, THBS2, FST, and VTN. In certain embodiments, the composition comprises STC2, THBS2, FST, and AGRN. In certain embodiments, the composition comprises STC2, THBS2, VTN, and FST. In certain embodiments, the composition comprises STC2, THBS2, VTN, and AGRN. In certain embodiments, the composition comprises STC2, THBS2, AGRN, and FST. In certain embodiments, the composition comprises STC2, THBS2, AGRN, and VTN. In certain embodiments, the composition comprises STC2, FST, THBS2, and AGRN. In certain embodiments, the composition comprises STC2, FST, THBS2, and VTN. In certain embodiments, the composition comprises STC2, FST, VTN, and AGRN. In certain embodiments, the composition comprises STC2, FST, VTN, and THBS2. In certain embodiments, the composition comprises STC2, FST, AGRN, and VTN. In certain embodiments, the composition comprises STC2, FST, AGRN, and THBS2. In certain embodiments, the composition comprises AGRN, VTN, THBS2, and FST. In certain embodiments, the composition comprises AGRN, VTN, THBS2, and STC2. In certain embodiments, the composition comprises AGRN, VTN, FST, and THBS2. In certain embodiments, the composition comprises AGRN, VTN, FST, and STC2. In certain embodiments, the composition comprises AGRN, VTN, STC2, and THBS2. In certain embodiments, the composition comprises AGRN, VTN, STC2, and FST. In certain embodiments, the composition comprises AGRN, STC2, THBS2, and VTN. In certain embodiments, the composition comprises AGRN, STC2, THBS2, and FST. In certain embodiments, the composition comprises AGRN, STC2, FST, and VTN. In certain embodiments, the composition comprises AGRN, STC2, FST, and THBS2. In certain embodiments, the composition comprises AGRN, STC2, VTN, and FST. In certain embodiments, the composition comprises AGRN, STC2, VTN, and THBS2. In certain embodiments, the composition comprises AGRN, THBS2, STC2, and FST. In certain embodiments, the composition comprises AGRN, THBS2, STC2, and VTN. In certain embodiments, the composition comprises AGRN, THBS2, FST, and STC2. In certain embodiments, the composition comprises AGRN, THBS2, FST, and VTN. In certain embodiments, the composition comprises AGRN, THBS2, VTN, and STC2. In certain embodiments, the composition comprises AGRN, THBS2, VTN, and FST. In certain embodiments, the composition comprises AGRN, FST, STC2, and VTN. In certain embodiments, the composition comprises AGRN, FST, STC2, and THBS2. In certain embodiments, the composition comprises AGRN, FST, THBS2, and VTN. In certain embodiments, the composition comprises AGRN, FST, THBS2, and STC2. In certain embodiments, the composition comprises AGRN, FST, VTN, and THBS2. In certain embodiments, the composition comprises AGRN, FST, VTN, and STC2. In certain embodiments, the composition comprises THBS2, VTN, STC2, and AGRN. In certain embodiments, the composition comprises THBS2, VTN, STC2, and FST. In certain embodiments, the composition comprises THBS2, VTN, AGRN, and STC2. In certain embodiments, the composition comprises THBS2, VTN, AGRN, and FST. In certain embodiments, the composition comprises THBS2, VTN, FST, and STC2. In certain embodiments, the composition comprises THBS2, VTN, FST, and AGRN. In certain embodiments, the composition comprises THBS2, STC2, VTN, and FST. In certain embodiments, the composition comprises THBS2, STC2, VTN, and AGRN. In certain embodiments, the composition comprises THBS2, STC2, AGRN, and FST. In certain embodiments, the composition comprises THBS2, STC2, AGRN, and VTN. In certain embodiments, the composition comprises THBS2, STC2, FST, and AGRN. In certain embodiments, the composition comprises THBS2, STC2, FST, and VTN. In certain embodiments, the composition comprises THBS2, AGRN, VTN, and STC2. In certain embodiments, the composition comprises THBS2, AGRN, VTN, and FST. In certain embodiments, the composition comprises THBS2, AGRN, STC2, and VTN. In certain embodiments, the composition comprises THBS2, AGRN, STC2, and FST. In certain embodiments, the composition comprises THBS2, AGRN, FST, and VTN. In certain embodiments, the composition comprises THBS2, AGRN, FST, and STC2. In certain embodiments, the composition comprises THBS2, FST, VTN, and AGRN. In certain embodiments, the composition comprises THBS2, FST, VTN, and STC2. In certain embodiments, the composition comprises THBS2, FST, STC2, and AGRN. In certain embodiments, the composition comprises THBS2, FST, STC2, and VTN. In certain embodiments, the composition comprises THBS2, FST, AGRN, and STC2. In certain embodiments, the composition comprises THBS2, FST, AGRN, and VTN. In certain embodiments, the composition comprises FST, VTN, THBS2, and STC2. In certain embodiments, the composition comprises FST, VTN, THBS2, and AGRN. In certain embodiments, the composition comprises FST, VTN, STC2, and THBS2. In certain embodiments, the composition comprises FST, VTN, STC2, and AGRN. In certain embodiments, the composition comprises FST, VTN, AGRN, and THBS2. In certain embodiments, the composition comprises FST, VTN, AGRN, and STC2. In certain embodiments, the composition comprises FST, STC2, THBS2, and AGRN. In certain embodiments, the composition comprises FST, STC2, THBS2, and VTN. In certain embodiments, the composition comprises FST, STC2, VTN, and AGRN. In certain embodiments, the composition comprises FST, STC2, VTN, and THBS2. In certain embodiments, the composition comprises FST, STC2, AGRN, and VTN. In certain embodiments, the composition comprises FST, STC2, AGRN, and THBS2. In certain embodiments, the composition comprises FST, AGRN, THBS2, and VTN. In certain embodiments, the composition comprises FST, AGRN, THBS2, and STC2. In certain embodiments, the composition comprises FST, AGRN, VTN, and THBS2. In certain embodiments, the composition comprises FST, AGRN, VTN, and STC2. In certain embodiments, the composition comprises FST, AGRN, STC2, and THBS2. In certain embodiments, the composition comprises FST, AGRN, STC2, and VTN. In certain embodiments, the composition comprises FST, THBS2, AGRN, and STC2. In certain embodiments, the composition comprises FST, THBS2, AGRN, and VTN. In certain embodiments, the composition comprises FST, THBS2, VTN, and STC2. In certain embodiments, the composition comprises FST, THBS2, VTN, and AGRN. In certain embodiments, the composition comprises FST, THBS2, STC2, and VTN. In certain embodiments, the composition comprises FST, THBS2, STC2, and AGRN. In certain embodiments, one or more of the heparin-associated polypeptides comprise one or more additional modifications to increase stability. In certain embodiments, one or more of the heparin-associated polypeptides is covalently conjugated to polyethylene glycol, polypropylene glycol, polyoxyalkylenes, or copolymers of polyethylene glycol, polysialic acid, glycolic acid, or polypropylene glycol. In certain embodiments, one or more of the heparin-associated polypeptides is fused or conjugated to another protein to increase stability and or bioavailability. In certain embodiments, one or more of the heparin-associated polypeptides is fused with an Fc region of an immunoglobulin or with serum albumin. In certain embodiments, one or more of the heparin-associated polypeptides is present in a concatemer with one, two, three, or four other distinct polypeptides selected from THBS2, VTN, STC2, AGRN, or FST. In certain embodiments, one or more of the heparin-associated polypeptides is present in a concatemer with one, two, three, four, or more distinct polypeptides. In certain embodiments, one or more of the heparin-associated polypeptides is included in a composition comprising a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid)

(PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In some embodiments, a composition herein comprises polypeptide 1 and one or more polypeptides from Table 2. In some embodiments, a composition herein comprises polypeptide 2 and one or more polypeptides from Table 2. In some embodiments, a composition herein comprises polypeptide 3 and one or more polypeptides from Table 2. In some embodiments, a composition herein comprises polypeptide 4 and one or more polypeptides from Table 2. In some embodiments, a composition herein comprises polypeptide 5 and one or more polypeptides from Table 2. In some embodiments, a composition herein comprises polypeptide 6 and one or more polypeptides from Table 2. In some embodiments, a composition herein comprises polypeptide 7 and one or more polypeptides from Table 2. In some embodiments, a composition herein comprises polypeptide 8 and one or more polypeptides from Table 2. In some embodiments, a composition herein comprises polypeptide 9 and one or more polypeptides from Table 2. In some embodiments, a composition herein comprises polypeptide 10 and one or more polypeptides from Table 2. In some embodiments, a composition herein comprises polypeptide 11 and one or more polypeptides from Table 2. In some embodiments, a composition herein comprises polypeptide 12 and one or more polypeptides from Table 2. In some embodiments, a composition herein comprises polypeptide 13 and one or more polypeptides from Table 2. In some embodiments, a composition herein comprises polypeptide 14 and one or more polypeptides from Table 2. In some embodiments, a composition herein comprises polypeptide 15 and one or more polypeptides from Table 2. In some embodiments, a composition herein comprises polypeptide 16 and one or more polypeptides from Table 2. In some embodiments, a composition herein comprises polypeptide 17 and one or more polypeptides from Table 2. In some embodiments, a composition herein comprises polypeptide 18 and one or more polypeptides from Table 2. In some embodiments, a composition herein comprises polypeptide 19 and one or more polypeptides from Table 2. In some embodiments, a composition herein comprises polypeptide 21 and one or more polypeptides from Table 2. In some embodiments, a composition herein comprises polypeptide 22 and one or more polypeptides from Table 2. In some embodiments, a composition herein comprises polypeptide 23 and one or more polypeptides from Table 2. In some embodiments, a composition herein comprises polypeptide 24 and one or more polypeptides from Table 2. In some embodiments, a composition herein comprises polypeptide 25 and one or more polypeptides from Table 2. In some embodiments, a composition herein comprises polypeptide 26 and one or more polypeptides from Table 2. In some embodiments, a composition herein comprises polypeptide 27 and one or more polypeptides from Table 2. In some embodiments, a composition herein comprises polypeptide 28 and one or more polypeptides from Table 2. In some embodiments, a composition herein comprises polypeptide 29 and one or more polypeptides from Table 2. In some embodiments, a composition herein comprises polypeptide 30 and one or more polypeptides from Table 2. In some embodiments, a composition herein comprises polypeptide 31 and one or more polypeptides from Table 2. In some embodiments, a composition herein comprises polypeptide 32 and one or more polypeptides from Table 2. In some embodiments, a composition herein comprises polypeptide 33 and one or more polypeptides from Table 2. In some embodiments, a composition herein comprises polypeptide 34 and one or more polypeptides from Table 2. In some embodiments, a composition herein comprises polypeptide 35 and one or more polypeptides from Table 2. In some embodiments, a composition herein comprises polypeptide 36 and one or more polypeptides from Table 2. In some embodiments, a composition herein comprises polypeptide 37 and one or more polypeptides from Table 2. In some embodiments, a composition herein comprises polypeptide 38 and one or more polypeptides from Table 2. In some embodiments, a composition herein comprises polypeptide 39 and one or more polypeptides from Table 2. In some embodiments, a composition herein comprises polypeptide 40 and one or more polypeptides from Table 2. In some embodiments, a composition herein comprises polypeptide 41 and one or more polypeptides from Table 2. In some embodiments, a composition herein comprises polypeptide 42 and one or more polypeptides from Table 2. In some embodiments, a composition herein comprises polypeptide 43 and one or more polypeptides from Table 2. In some embodiments, a composition herein comprises polypeptide 44 and one or more polypeptides from Table 2. In some embodiments, a composition herein comprises polypeptide 45 and one or more polypeptides from Table 2. In some embodiments, a composition herein comprises polypeptide 46 and one or more polypeptides from Table 2. In some embodiments, a composition herein comprises polypeptide 47 and one or more polypeptides from Table 2. In some embodiments, a composition herein comprises polypeptide 48 and one or more polypeptides from Table 2. In some embodiments, a composition herein comprises polypeptide 49 and one or more polypeptides from Table 2. In some embodiments, a composition herein comprises polypeptide 50 and one or more polypeptides from Table 2. In some embodiments, a composition herein comprises polypeptide 51 and one or more polypeptides from Table 2. In some embodiments, a composition herein comprises polypeptide 52 and one or more polypeptides from Table 2. In some embodiments, a composition herein comprises polypeptide 53 and one or more polypeptides from Table 2. In some embodiments, a composition herein comprises polypeptide 54 and one or more polypeptides from Table 2. In some embodiments, a composition herein comprises polypeptide 55 and one or more polypeptides from Table 2. In some embodiments, a composition herein comprises polypeptide 56 and one or more polypeptides from Table 2. In some embodiments, a composition herein comprises polypeptide 57 and one or more polypeptides from Table 2. In some embodiments, a composition herein comprises polypeptide 58 and one or more polypeptides from Table 2. In some embodiments, a composition herein comprises polypeptide 59 and one or more polypeptides from Table 2. In some embodiments, a composition herein comprises polypeptide 60 and one or more polypeptides from Table 2. In some embodiments, a composition herein comprises polypeptide 61 and one or more polypeptides from Table 2. In some embodiments, a composition herein comprises polypeptide 62 and one or more polypeptides from Table 2. In some embodiments, a composition herein comprises polypeptide 63 and one or more polypeptides from Table 2. In some embodiments, a composition herein comprises polypeptide 64 and one or more polypeptides from Table 2. In some embodiments, a composition herein comprises polypeptide 65 and one or more polypeptides from Table 2. In some embodiments, a composition herein comprises polypeptide 66 and one or more polypeptides from Table 2. In some embodiments, a composition herein comprises polypeptide 67 and one or more polypeptides from Table 2. In some embodiments, a composition herein comprises polypeptide 68 and one or more polypeptides from Table 2. In some embodiments, a composition herein comprises polypeptide 69 and one or more polypeptides from Table 2. In some embodiments, a composition herein comprises polypeptide 70 and one or more polypeptides from Table 2. In some embodiments, a composition herein comprises polypeptide 71 and one or more polypeptides from Table 2. In some embodiments, a composition herein comprises polypeptide 72 and one or more polypeptides from Table 2. In some embodiments, a composition herein comprises polypeptide 73 and one or more polypeptides from Table 2. In some embodiments, a composition herein comprises polypeptide 74 and one or more polypeptides from Table 2. In some embodiments, a composition herein comprises polypeptide 75 and one or more polypeptides from Table 2. In some embodiments, a composition herein comprises polypeptide 76 and one or more polypeptides from Table 2. In some embodiments, a composition herein comprises polypeptide 77 and one or more polypeptides from Table 2. In some embodiments, a composition herein comprises polypeptide 78 and one or more polypeptides from Table 2. In some embodiments, a composition herein comprises polypeptide 79 and one or more polypeptides from Table 2. In some embodiments, a composition herein comprises polypeptide 80 and one or more polypeptides from Table 2. In some embodiments, a composition herein comprises polypeptide 81 and one or more polypeptides from Table 2. In some embodiments, a composition herein comprises polypeptide 82 and one or more polypeptides from Table 2. In some embodiments, a composition herein comprises polypeptide 83 and one or more polypeptides from Table 2. In some embodiments, a composition herein comprises polypeptide 84 and one or more polypeptides from Table 2. In some embodiments, a composition herein comprises polypeptide 85 and one or more polypeptides from Table 2. In some embodiments, a composition herein comprises polypeptide 86 and one or more polypeptides from Table 2. In some embodiments, a composition herein comprises polypeptide 87 and one or more polypeptides from Table 2. In some embodiments, a composition herein comprises polypeptide 88 and one or more polypeptides from Table 2. In some embodiments, a composition herein comprises polypeptide 89 and one or more polypeptides from Table 2. In some embodiments, a composition herein comprises polypeptide 90 and one or more polypeptides from Table 2. In some embodiments, a composition herein comprises polypeptide 91 and one or more polypeptides from Table 2. In some embodiments, a composition herein comprises polypeptide 92 and one or more polypeptides from Table 2. In some embodiments, a composition herein comprises polypeptide 93 and one or more polypeptides from Table 2. In some embodiments, a composition herein comprises polypeptide 94 and one or more polypeptides from Table 2. In some embodiments, a composition herein comprises polypeptide 95 and one or more polypeptides from Table 2. In some embodiments, a composition herein comprises polypeptide 96 and one or more polypeptides from Table 2. In some embodiments, a composition herein comprises polypeptide 97 and one or more polypeptides from Table 2. In some embodiments, a composition herein comprises polypeptide 98 and one or more polypeptides from Table 2. In some embodiments, a composition herein comprises polypeptide 99 and one or more polypeptides from Table 2. In some embodiments, a composition herein comprises polypeptide 100 and one or more polypeptides from Table 2.

In some embodiments, a composition herein comprises polypeptide 101 and one or more polypeptides from Table 2. In some embodiments, a composition herein comprises polypeptide 102 and one or more polypeptides from Table 2. In some embodiments, a composition herein comprises polypeptide 103 and one or more polypeptides from Table 2. In some embodiments, a composition herein comprises polypeptide 104 and one or more polypeptides from Table 2. In some embodiments, a composition herein comprises polypeptide 105 and one or more polypeptides from Table 2. In some embodiments, a composition herein comprises polypeptide 106 and one or more polypeptides from Table 2. In some embodiments, a composition herein comprises polypeptide 107 and one or more polypeptides from Table 2. In some embodiments, a composition herein comprises polypeptide 108 and one or more polypeptides from Table 2. In some embodiments, a composition herein comprises polypeptide 109 and one or more polypeptides from Table 2. In some embodiments, a composition herein comprises polypeptide 110 and one or more polypeptides from Table 2. In some embodiments, a composition herein comprises polypeptide 111 and one or more polypeptides from Table 2. In some embodiments, a composition herein comprises polypeptide 112 and one or more polypeptides from Table 2. In some embodiments, a composition herein comprises polypeptide 113 and one or more polypeptides from Table 2. In some embodiments, a composition herein comprises polypeptide 114 and one or more polypeptides from Table 2. In some embodiments, a composition herein comprises polypeptide 115 and one or more polypeptides from Table 2. In some embodiments, a composition herein comprises polypeptide 116 and one or more polypeptides from Table 2. In some embodiments, a composition herein comprises polypeptide 117 and one or more polypeptides from Table 2. In some embodiments, a composition herein comprises polypeptide 118 and one or more polypeptides from Table 2. In some embodiments, a composition herein comprises polypeptide 119 and one or more polypeptides from Table 2. In some embodiments, a composition herein comprises polypeptide 121 and one or more polypeptides from Table 2. In some embodiments, a composition herein comprises polypeptide 122 and one or more polypeptides from Table 2. In some embodiments, a composition herein comprises polypeptide 123 and one or more polypeptides from Table 2. In some embodiments, a composition herein comprises polypeptide 124 and one or more polypeptides from Table 2. In some embodiments, a composition herein comprises polypeptide 125 and one or more polypeptides from Table 2. In some embodiments, a composition herein comprises polypeptide 126 and one or more polypeptides from Table 2. In some embodiments, a composition herein comprises polypeptide 127 and one or more polypeptides from Table 2. In some embodiments, a composition herein comprises polypeptide 128 and one or more polypeptides from Table 2. In some embodiments, a composition herein comprises polypeptide 129 and one or more polypeptides from Table 2. In some embodiments, a composition herein comprises polypeptide 130 and one or more polypeptides from Table 2. In some embodiments, a composition herein comprises polypeptide 131 and one or more polypeptides from Table 2. In some embodiments, a composition herein comprises polypeptide 132 and one or more polypeptides from Table 2. In some embodiments, a composition herein comprises polypeptide 133 and one or more polypeptides from Table 2.

In some embodiments, a composition herein comprises polypeptide 134 and one or more polypeptides from Table 2.
In some embodiments, a composition herein comprises polypeptide 135 and one or more polypeptides from Table 2.
In some embodiments, a composition herein comprises polypeptide 136 and one or more polypeptides from Table 2.
In some embodiments, a composition herein comprises polypeptide 137 and one or more polypeptides from Table 2.
In some embodiments, a composition herein comprises polypeptide 138 and one or more polypeptides from Table 2.
In some embodiments, a composition herein comprises polypeptide 139 and one or more polypeptides from Table 2.
In some embodiments, a composition herein comprises polypeptide 140 and one or more polypeptides from Table 2.
In some embodiments, a composition herein comprises polypeptide 141 and one or more polypeptides from Table 2.
In some embodiments, a composition herein comprises polypeptide 142 and one or more polypeptides from Table 2.
In some embodiments, a composition herein comprises polypeptide 143 and one or more polypeptides from Table 2.
In some embodiments, a composition herein comprises polypeptide 144 and one or more polypeptides from Table 2.
In some embodiments, a composition herein comprises polypeptide 145 and one or more polypeptides from Table 2.
In some embodiments, a composition herein comprises polypeptide 146 and one or more polypeptides from Table 2.
In some embodiments, a composition herein comprises polypeptide 147 and one or more polypeptides from Table 2.
In some embodiments, a composition herein comprises polypeptide 148 and one or more polypeptides from Table 2.
In some embodiments, a composition herein comprises polypeptide 149 and one or more polypeptides from Table 2.
In some embodiments, a composition herein comprises polypeptide 150 and one or more polypeptides from Table 2.
In some embodiments, a composition herein comprises polypeptide 151 and one or more polypeptides from Table 2.
In some embodiments, a composition herein comprises polypeptide 152 and one or more polypeptides from Table 2.
In some embodiments, a composition herein comprises polypeptide 153 and one or more polypeptides from Table 2.
In some embodiments, a composition herein comprises polypeptide 154 and one or more polypeptides from Table 2.
In some embodiments, a composition herein comprises polypeptide 155 and one or more polypeptides from Table 2.
In some embodiments, a composition herein comprises polypeptide 156 and one or more polypeptides from Table 2.
In some embodiments, a composition herein comprises polypeptide 157 and one or more polypeptides from Table 2.
In some embodiments, a composition herein comprises polypeptide 158 and one or more polypeptides from Table 2.
In some embodiments, a composition herein comprises polypeptide 159 and one or more polypeptides from Table 2.
In some embodiments, a composition herein comprises polypeptide 160 and one or more polypeptides from Table 2.
In some embodiments, a composition herein comprises polypeptide 161 and one or more polypeptides from Table 2.
In some embodiments, a composition herein comprises polypeptide 162 and one or more polypeptides from Table 2.
In some embodiments, a composition herein comprises polypeptide 163 and one or more polypeptides from Table 2.
In some embodiments, a composition herein comprises polypeptide 164 and one or more polypeptides from Table 2.
In some embodiments, a composition herein comprises polypeptide 165 and one or more polypeptides from Table 2.
In some embodiments, a composition herein comprises polypeptide 166 and one or more polypeptides from Table 2.
In some embodiments, a composition herein comprises polypeptide 167 and one or more polypeptides from Table 2.
In some embodiments, a composition herein comprises polypeptide 168 and one or more polypeptides from Table 2.
In some embodiments, a composition herein comprises polypeptide 169 and one or more polypeptides from Table 2.
In some embodiments, a composition herein comprises polypeptide 170 and one or more polypeptides from Table 2.
In some embodiments, a composition herein comprises polypeptide 171 and one or more polypeptides from Table 2.
In some embodiments, a composition herein comprises polypeptide 172 and one or more polypeptides from Table 2.
In some embodiments, a composition herein comprises polypeptide 173 and one or more polypeptides from Table 2.
In some embodiments, a composition herein comprises polypeptide 174 and one or more polypeptides from Table 2.
In some embodiments, a composition herein comprises polypeptide 175 and one or more polypeptides from Table 2.
In some embodiments, a composition herein comprises polypeptide 176 and one or more polypeptides from Table 2.
In some embodiments, a composition herein comprises polypeptide 177 and one or more polypeptides from Table 2.
In some embodiments, a composition herein comprises polypeptide 178 and one or more polypeptides from Table 2.
In some embodiments, a composition herein comprises polypeptide 179 and one or more polypeptides from Table 2.
In some embodiments, a composition herein comprises polypeptide 180 and one or more polypeptides from Table 2.
In some embodiments, a composition herein comprises polypeptide 181 and one or more polypeptides from Table 2.
In some embodiments, a composition herein comprises polypeptide 182 and one or more polypeptides from Table 2.
In some embodiments, a composition herein comprises polypeptide 183 and one or more polypeptides from Table 2.
In some embodiments, a composition herein comprises polypeptide 184 and one or more polypeptides from Table 2.
In some embodiments, a composition herein comprises polypeptide 185 and one or more polypeptides from Table 2.
In some embodiments, a composition herein comprises polypeptide 186 and one or more polypeptides from Table 2.
In some embodiments, a composition herein comprises polypeptide 187 and one or more polypeptides from Table 2.
In some embodiments, a composition herein comprises polypeptide 188 and one or more polypeptides from Table 2.
In some embodiments, a composition herein comprises polypeptide 189 and one or more polypeptides from Table 2.
In some embodiments, a composition herein comprises polypeptide 190 and one or more polypeptides from Table 2.
In some embodiments, a composition herein comprises polypeptide 191 and one or more polypeptides from Table 2.
In some embodiments, a composition herein comprises polypeptide 192 and one or more polypeptides from Table 2.
In some embodiments, a composition herein comprises polypeptide 193 and one or more polypeptides from Table 2.
In some embodiments, a composition herein comprises polypeptide 194 and one or more polypeptides from Table 2.
In some embodiments, a composition herein comprises polypeptide 195 and one or more polypeptides from Table 2.
In some embodiments, a composition herein comprises polypeptide 196 and one or more polypeptides from Table 2.
In some embodiments, a composition herein comprises polypeptide 197 and one or more polypeptides from Table 2.
In some embodiments, a composition herein comprises polypeptide 198 and one or more polypeptides from Table 2.
In some embodiments, a composition herein comprises polypeptide 199 and one or more polypeptides from Table 2.
In some embodiments, a composition herein comprises polypeptide 200 and one or more polypeptides from Table 2.

In some embodiments, a composition herein comprises polypeptide 201 and one or more polypeptides from Table 2.
In some embodiments, a composition herein comprises polypeptide 202 and one or more polypeptides from Table 2.
In some embodiments, a composition herein comprises polypeptide 203 and one or more polypeptides from Table 2.
In some embodiments, a composition herein comprises polypeptide 204 and one or more polypeptides from Table 2.
In some embodiments, a composition herein comprises polypeptide 205 and one or more polypeptides from Table 2.
In some embodiments, a composition herein comprises polypeptide 206 and one or more polypeptides from Table 2.
In some embodiments, a composition herein comprises polypeptide 207 and one or more polypeptides from Table 2.
In some embodiments, a composition herein comprises polypeptide 208 and one or more polypeptides from Table 2.
In some embodiments, a composition herein comprises polypeptide 209 and one or more polypeptides from Table 2.
In some embodiments, a composition herein comprises polypeptide 210 and one or more polypeptides from Table 2.
In some embodiments, a composition herein comprises polypeptide 211 and one or more polypeptides from Table 2.
In some embodiments, a composition herein comprises polypeptide 212 and one or more polypeptides from Table 2.
In some embodiments, a composition herein comprises polypeptide 213 and one or more polypeptides from Table 2.
In some embodiments, a composition herein comprises polypeptide 214 and one or more polypeptides from Table 2.
In some embodiments, a composition herein comprises polypeptide 215 and one or more polypeptides from Table 2.
In some embodiments, a composition herein comprises polypeptide 216 and one or more polypeptides from Table 2.
In some embodiments, a composition herein comprises polypeptide 217 and one or more polypeptides from Table 2.
In some embodiments, a composition herein comprises polypeptide 218 and one or more polypeptides from Table 2.
In some embodiments, a composition herein comprises polypeptide 219 and one or more polypeptides from Table 2.
In some embodiments, a composition herein comprises polypeptide 221 and one or more polypeptides from Table 2.
In some embodiments, a composition herein comprises polypeptide 222 and one or more polypeptides from Table 2.
In some embodiments, a composition herein comprises polypeptide 223 and one or more polypeptides from Table 2.
In some embodiments, a composition herein comprises polypeptide 224 and one or more polypeptides from Table 2.
In some embodiments, a composition herein comprises polypeptide 225 and one or more polypeptides from Table 2.
In some embodiments, a composition herein comprises polypeptide 226 and one or more polypeptides from Table 2.
In some embodiments, a composition herein comprises polypeptide 227 and one or more polypeptides from Table 2.
In some embodiments, a composition herein comprises polypeptide 228 and one or more polypeptides from Table 2.
In some embodiments, a composition herein comprises polypeptide 229 and one or more polypeptides from Table 2.
In some embodiments, a composition herein comprises polypeptide 230 and one or more polypeptides from Table 2.
In some embodiments, a composition herein comprises polypeptide 231 and one or more polypeptides from Table 2.
In some embodiments, a composition herein comprises polypeptide 232 and one or more polypeptides from Table 2.
In some embodiments, a composition herein comprises polypeptide 233 and one or more polypeptides from Table 2.
In some embodiments, a composition herein comprises polypeptide 234 and one or more polypeptides from Table 2.
In some embodiments, a composition herein comprises polypeptide 235 and one or more polypeptides from Table 2.
In some embodiments, a composition herein comprises polypeptide 236 and one or more polypeptides from Table 2.
In some embodiments, a composition herein comprises polypeptide 237 and one or more polypeptides from Table 2.
In some embodiments, a composition herein comprises polypeptide 238 and one or more polypeptides from Table 2.
In some embodiments, a composition herein comprises polypeptide 239 and one or more polypeptides from Table 2.
In some embodiments, a composition herein comprises polypeptide 240 and one or more polypeptides from Table 2.
In some embodiments, a composition herein comprises polypeptide 241 and one or more polypeptides from Table 2.
In some embodiments, a composition herein comprises polypeptide 242 and one or more polypeptides from Table 2.
In some embodiments, a composition herein comprises polypeptide 243 and one or more polypeptides from Table 2.
In some embodiments, a composition herein comprises polypeptide 244 and one or more polypeptides from Table 2.
In some embodiments, a composition herein comprises polypeptide 245 and one or more polypeptides from Table 2.
In some embodiments, a composition herein comprises polypeptide 246 and one or more polypeptides from Table 2.
In some embodiments, a composition herein comprises polypeptide 247 and one or more polypeptides from Table 2.
In some embodiments, a composition herein comprises polypeptide 248 and one or more polypeptides from Table 2.
In some embodiments, a composition herein comprises polypeptide 249 and one or more polypeptides from Table 2.
In some embodiments, a composition herein comprises polypeptide 250 and one or more polypeptides from Table 2.
In some embodiments, a composition herein comprises polypeptide 251 and one or more polypeptides from Table 2.
In some embodiments, a composition herein comprises polypeptide 252 and one or more polypeptides from Table 2.
In some embodiments, a composition herein comprises polypeptide 253 and one or more polypeptides from Table 2.
In some embodiments, a composition herein comprises polypeptide 254 and one or more polypeptides from Table 2.
In some embodiments, a composition herein comprises polypeptide 255 and one or more polypeptides from Table 2.
In some embodiments, a composition herein comprises polypeptide 256 and one or more polypeptides from Table 2.
In some embodiments, a composition herein comprises polypeptide 257 and one or more polypeptides from Table 2.
In some embodiments, a composition herein comprises polypeptide 258 and one or more polypeptides from Table 2.
In some embodiments, a composition herein comprises polypeptide 259 and one or more polypeptides from Table 2.
In some embodiments, a composition herein comprises polypeptide 260 and one or more polypeptides from Table 2.
In some embodiments, a composition herein comprises polypeptide 261 and one or more polypeptides from Table 2.
In some embodiments, a composition herein comprises polypeptide 262 and one or more polypeptides from Table 2.
In some embodiments, a composition herein comprises polypeptide 263 and one or more polypeptides from Table 2.
In some embodiments, a composition herein comprises polypeptide 264 and one or more polypeptides from Table 2.
In some embodiments, a composition herein comprises polypeptide 265 and one or more polypeptides from Table 2.
In some embodiments, a composition herein comprises polypeptide 266 and one or more polypeptides from Table 2.
In some embodiments, a composition herein comprises polypeptide 267 and one or more polypeptides from Table 2.
In some embodiments, a composition herein comprises polypeptide 268 and one or more polypeptides from Table 2.

In some embodiments, a composition herein comprises polypeptide 269 and one or more polypeptides from Table 2. In some embodiments, a composition herein comprises polypeptide 270 and one or more polypeptides from Table 2. In some embodiments, a composition herein comprises polypeptide 271 and one or more polypeptides from Table 2. In some embodiments, a composition herein comprises polypeptide 272 and one or more polypeptides from Table 2. In some embodiments, a composition herein comprises polypeptide 273 and one or more polypeptides from Table 2. In some embodiments, a composition herein comprises polypeptide 274 and one or more polypeptides from Table 2. In some embodiments, a composition herein comprises polypeptide 275 and one or more polypeptides from Table 2. In some embodiments, a composition herein comprises polypeptide 276 and one or more polypeptides from Table 2. In some embodiments, a composition herein comprises polypeptide 277 and one or more polypeptides from Table 2. In some embodiments, a composition herein comprises polypeptide 278 and one or more polypeptides from Table 2. In some embodiments, a composition herein comprises polypeptide 279 and one or more polypeptides from Table 2. In some embodiments, a composition herein comprises polypeptide 280 and one or more polypeptides from Table 2. In some embodiments, a composition herein comprises polypeptide 281 and one or more polypeptides from Table 2. In some embodiments, a composition herein comprises polypeptide 282 and one or more polypeptides from Table 2. In some embodiments, a composition herein comprises polypeptide 283 and one or more polypeptides from Table 2. In some embodiments, a composition herein comprises polypeptide 284 and one or more polypeptides from Table 2. In some embodiments, a composition herein comprises polypeptide 285 and one or more polypeptides from Table 2. In some embodiments, a composition herein comprises polypeptide 286 and one or more polypeptides from Table 2. In some embodiments, a composition herein comprises polypeptide 287 and one or more polypeptides from Table 2. In some embodiments, a composition herein comprises polypeptide 288 and one or more polypeptides from Table 2. In some embodiments, a composition herein comprises polypeptide 289 and one or more polypeptides from Table 2. In some embodiments, a composition herein comprises polypeptide 290 and one or more polypeptides from Table 2. In some embodiments, a composition herein comprises polypeptide 291 and one or more polypeptides from Table 2. In some embodiments, a composition herein comprises polypeptide 292 and one or more polypeptides from Table 2. In some embodiments, a composition herein comprises polypeptide 293 and one or more polypeptides from Table 2. In some embodiments, a composition herein comprises polypeptide 294 and one or more polypeptides from Table 2. In some embodiments, a composition herein comprises polypeptide 295 and one or more polypeptides from Table 2. In some embodiments, a composition herein comprises polypeptide 296 and one or more polypeptides from Table 2. In some embodiments, a composition herein comprises polypeptide 297 and one or more polypeptides from Table 2. In some embodiments, a composition herein comprises polypeptide 298 and one or more polypeptides from Table 2. In some embodiments, a composition herein comprises polypeptide 299 and one or more polypeptides from Table 2. In some embodiments, a composition herein comprises polypeptide 300 and one or more polypeptides from Table 2. In some embodiments, a composition herein comprises polypeptide 401 and one or more polypeptides from Table 2. In some embodiments, a composition herein comprises polypeptide 402 and one or more polypeptides from Table 2. In some embodiments, a composition herein comprises polypeptide 403 and one or more polypeptides from Table 2. In some embodiments, a composition herein comprises polypeptide 404 and one or more polypeptides from Table 2. In some embodiments, a composition herein comprises polypeptide 405 and one or more polypeptides from Table 2. In some embodiments, a composition herein comprises polypeptide 406 and one or more polypeptides from Table 2. In some embodiments, a composition herein comprises polypeptide 407 and one or more polypeptides from Table 2. In some embodiments, a composition herein comprises polypeptide 408 and one or more polypeptides from Table 2. In some embodiments, a composition herein comprises polypeptide 409 and one or more polypeptides from Table 2. In some embodiments, a composition herein comprises polypeptide 410 and one or more polypeptides from Table 2. In some embodiments, a composition herein comprises polypeptide 411 and one or more polypeptides from Table 2. In some embodiments, a composition herein comprises polypeptide 412 and one or more polypeptides from Table 2. In some embodiments, a composition herein comprises polypeptide 413 and one or more polypeptides from Table 2. In some embodiments, a composition herein comprises polypeptide 414 and one or more polypeptides from Table 2. In some embodiments, a composition herein comprises polypeptide 415 and one or more polypeptides from Table 2. In some embodiments, a composition herein comprises polypeptide 416 and one or more polypeptides from Table 2. In some embodiments, a composition herein comprises polypeptide 417 and one or more polypeptides from Table 2. In some embodiments, a composition herein comprises polypeptide 418 and one or more polypeptides from Table 2. In some embodiments, a composition herein comprises polypeptide 419 and one or more polypeptides from Table 2. In some embodiments, a composition herein comprises polypeptide 421 and one or more polypeptides from Table 2. In some embodiments, a composition herein comprises polypeptide 422 and one or more polypeptides from Table 2. In some embodiments, a composition herein comprises polypeptide 423 and one or more polypeptides from Table 2. In some embodiments, a composition herein comprises polypeptide 424 and one or more polypeptides from Table 2. In some embodiments, a composition herein comprises polypeptide 425 and one or more polypeptides from Table 2. In some embodiments, a composition herein comprises polypeptide 426 and one or more polypeptides from Table 2. In some embodiments, a composition herein comprises polypeptide 427 and one or more polypeptides from Table 2. In some embodiments, a composition herein comprises polypeptide 428 and one or more polypeptides from Table 2. In some embodiments, a composition herein comprises polypeptide 429 and one or more polypeptides from Table 2. In some embodiments, a composition herein comprises polypeptide 430 and one or more polypeptides from Table 2. In some embodiments, a composition herein comprises polypeptide 431 and one or more polypeptides from Table 2. In some embodiments, a composition herein comprises polypeptide 432 and one or more polypeptides from Table 2. In some embodiments, a composition herein comprises polypeptide 433 and one or more polypeptides from Table 2. In some embodiments, a composition herein comprises polypeptide 434 and one or more polypeptides from Table 2. In some embodiments, a composition herein comprises polypeptide 435 and one or more polypeptides from Table 2. In some embodiments, a composition herein comprises polypeptide 436 and one or more polypeptides from Table 2.

In some embodiments, a composition herein comprises polypeptide 437 and one or more polypeptides from Table 2.
In some embodiments, a composition herein comprises polypeptide 438 and one or more polypeptides from Table 2.
In some embodiments, a composition herein comprises polypeptide 439 and one or more polypeptides from Table 2.
In some embodiments, a composition herein comprises polypeptide 440 and one or more polypeptides from Table 2.
In some embodiments, a composition herein comprises polypeptide 441 and one or more polypeptides from Table 2.
In some embodiments, a composition herein comprises polypeptide 442 and one or more polypeptides from Table 2.
In some embodiments, a composition herein comprises polypeptide 443 and one or more polypeptides from Table 2.
In some embodiments, a composition herein comprises polypeptide 444 and one or more polypeptides from Table 2.
In some embodiments, a composition herein comprises polypeptide 445 and one or more polypeptides from Table 2.
In some embodiments, a composition herein comprises polypeptide 446 and one or more polypeptides from Table 2.
In some embodiments, a composition herein comprises polypeptide 447 and one or more polypeptides from Table 2.
In some embodiments, a composition herein comprises polypeptide 448 and one or more polypeptides from Table 2.
In some embodiments, a composition herein comprises polypeptide 449 and one or more polypeptides from Table 2.
In some embodiments, a composition herein comprises polypeptide 450 and one or more polypeptides from Table 2.
In some embodiments, a composition herein comprises polypeptide 451 and one or more polypeptides from Table 2.
In some embodiments, a composition herein comprises polypeptide 452 and one or more polypeptides from Table 2.
In some embodiments, a composition herein comprises polypeptide 453 and one or more polypeptides from Table 2.
In some embodiments, a composition herein comprises polypeptide 454 and one or more polypeptides from Table 2.
In some embodiments, a composition herein comprises polypeptide 455 and one or more polypeptides from Table 2.
In some embodiments, a composition herein comprises polypeptide 456 and one or more polypeptides from Table 2.
In some embodiments, a composition herein comprises polypeptide 457 and one or more polypeptides from Table 2.
In some embodiments, a composition herein comprises polypeptide 458 and one or more polypeptides from Table 2.
In some embodiments, a composition herein comprises polypeptide 459 and one or more polypeptides from Table 2.
In some embodiments, a composition herein comprises polypeptide 460 and one or more polypeptides from Table 2.
In some embodiments, a composition herein comprises polypeptide 461 and one or more polypeptides from Table 2.
In some embodiments, a composition herein comprises polypeptide 462 and one or more polypeptides from Table 2.
In some embodiments, a composition herein comprises polypeptide 463 and one or more polypeptides from Table 2.
In some embodiments, a composition herein comprises polypeptide 464 and one or more polypeptides from Table 2.
In some embodiments, a composition herein comprises polypeptide 465 and one or more polypeptides from Table 2.
In some embodiments, a composition herein comprises polypeptide 466 and one or more polypeptides from Table 2.
In some embodiments, a composition herein comprises polypeptide 467 and one or more polypeptides from Table 2.
In some embodiments, a composition herein comprises polypeptide 468 and one or more polypeptides from Table 2.
In some embodiments, a composition herein comprises polypeptide 469 and one or more polypeptides from Table 2.
In some embodiments, a composition herein comprises polypeptide 470 and one or more polypeptides from Table 2.
In some embodiments, a composition herein comprises polypeptide 471 and one or more polypeptides from Table 2.
In some embodiments, a composition herein comprises polypeptide 472 and one or more polypeptides from Table 2.
In some embodiments, a composition herein comprises polypeptide 473 and one or more polypeptides from Table 2.
In some embodiments, a composition herein comprises polypeptide 474 and one or more polypeptides from Table 2.
In some embodiments, a composition herein comprises polypeptide 475 and one or more polypeptides from Table 2.
In some embodiments, a composition herein comprises polypeptide 476 and one or more polypeptides from Table 2.
In some embodiments, a composition herein comprises polypeptide 477 and one or more polypeptides from Table 2.
In some embodiments, a composition herein comprises polypeptide 478 and one or more polypeptides from Table 2.
In some embodiments, a composition herein comprises polypeptide 479 and one or more polypeptides from Table 2.
In some embodiments, a composition herein comprises polypeptide 480 and one or more polypeptides from Table 2.
In some embodiments, a composition herein comprises polypeptide 481 and one or more polypeptides from Table 2.
In some embodiments, a composition herein comprises polypeptide 482 and one or more polypeptides from Table 2.
In some embodiments, a composition herein comprises polypeptide 483 and one or more polypeptides from Table 2.
In some embodiments, a composition herein comprises polypeptide 484 and one or more polypeptides from Table 2.
In some embodiments, a composition herein comprises polypeptide 485 and one or more polypeptides from Table 2.
In some embodiments, a composition herein comprises polypeptide 486 and one or more polypeptides from Table 2.
In some embodiments, a composition herein comprises polypeptide 487 and one or more polypeptides from Table 2.
In some embodiments, a composition herein comprises polypeptide 488 and one or more polypeptides from Table 2.
In some embodiments, a composition herein comprises polypeptide 489 and one or more polypeptides from Table 2.
In some embodiments, a composition herein comprises polypeptide 490 and one or more polypeptides from Table 2.
In some embodiments, a composition herein comprises polypeptide 491 and one or more polypeptides from Table 2.
In some embodiments, a composition herein comprises polypeptide 492 and one or more polypeptides from Table 2.
In some embodiments, a composition herein comprises polypeptide 493 and one or more polypeptides from Table 2.
In some embodiments, a composition herein comprises polypeptide 494 and one or more polypeptides from Table 2.
In some embodiments, a composition herein comprises polypeptide 495 and one or more polypeptides from Table 2.
In some embodiments, a composition herein comprises polypeptide 496 and one or more polypeptides from Table 2.
In some embodiments, a composition herein comprises polypeptide 497 and one or more polypeptides from Table 2.
In some embodiments, a composition herein comprises polypeptide 498 and one or more polypeptides from Table 2.
In some embodiments, a composition herein comprises polypeptide 499 and one or more polypeptides from Table 2.
In some embodiments, a composition herein comprises polypeptide 500 and one or more polypeptides from Table 2.
In some embodiments, a composition herein comprises polypeptide 501 and one or more polypeptides from Table 2.
In some embodiments, a composition herein comprises polypeptide 502 and one or more polypeptides from Table 2.
In some embodiments, a composition herein comprises polypeptide 503 and one or more polypeptides from Table 2.

In some embodiments, a composition herein comprises polypeptide 504 and one or more polypeptides from Table 2. In some embodiments, a composition herein comprises polypeptide 505 and one or more polypeptides from Table 2. In some embodiments, a composition herein comprises polypeptide 506 and one or more polypeptides from Table 2. In some embodiments, a composition herein comprises polypeptide 507 and one or more polypeptides from Table 2. In some embodiments, a composition herein comprises polypeptide 508 and one or more polypeptides from Table 2. In some embodiments, a composition herein comprises polypeptide 509 and one or more polypeptides from Table 2. In some embodiments, a composition herein comprises polypeptide 510 and one or more polypeptides from Table 2. In some embodiments, a composition herein comprises polypeptide 511 and one or more polypeptides from Table 2. In some embodiments, a composition herein comprises polypeptide 512 and one or more polypeptides from Table 2. In some embodiments, a composition herein comprises polypeptide 513 and one or more polypeptides from Table 2. In some embodiments, a composition herein comprises polypeptide 514 and one or more polypeptides from Table 2. In some embodiments, a composition herein comprises polypeptide 515 and one or more polypeptides from Table 2. In some embodiments, a composition herein comprises polypeptide 516 and one or more polypeptides from Table 2. In some embodiments, a composition herein comprises polypeptide 517 and one or more polypeptides from Table 2. In some embodiments, a composition herein comprises polypeptide 518 and one or more polypeptides from Table 2. In some embodiments, a composition herein comprises polypeptide 519 and one or more polypeptides from Table 2. In some embodiments, a composition herein comprises polypeptide 521 and one or more polypeptides from Table 2. In some embodiments, a composition herein comprises polypeptide 522 and one or more polypeptides from Table 2. In some embodiments, a composition herein comprises polypeptide 523 and one or more polypeptides from Table 2. In some embodiments, a composition herein comprises polypeptide 524 and one or more polypeptides from Table 2. In some embodiments, a composition herein comprises polypeptide 525 and one or more polypeptides from Table 2. In some embodiments, a composition herein comprises polypeptide 526 and one or more polypeptides from Table 2. In some embodiments, a composition herein comprises polypeptide 527 and one or more polypeptides from Table 2. In some embodiments, a composition herein comprises polypeptide 528 and one or more polypeptides from Table 2. In some embodiments, a composition herein comprises polypeptide 529 and one or more polypeptides from Table 2. In some embodiments, a composition herein comprises polypeptide 530 and one or more polypeptides from Table 2. In some embodiments, a composition herein comprises polypeptide 531 and one or more polypeptides from Table 2. In some embodiments, a composition herein comprises polypeptide 532 and one or more polypeptides from Table 2. In some embodiments, a composition herein comprises polypeptide 533 and one or more polypeptides from Table 2. In some embodiments, a composition herein comprises polypeptide 534 and one or more polypeptides from Table 2. In some embodiments, a composition herein comprises polypeptide 535 and one or more polypeptides from Table 2. In some embodiments, a composition herein comprises polypeptide 536 and one or more polypeptides from Table 2. In some embodiments, a composition herein comprises polypeptide 537 and one or more polypeptides from Table 2. In some embodiments, a composition herein comprises polypeptide 538 and one or more polypeptides from Table 2. In some embodiments, a composition herein comprises polypeptide 539 and one or more polypeptides from Table 2. In some embodiments, a composition herein comprises polypeptide 540 and one or more polypeptides from Table 2. In some embodiments, a composition herein comprises polypeptide 541 and one or more polypeptides from Table 2. In some embodiments, a composition herein comprises polypeptide 542 and one or more polypeptides from Table 2. In some embodiments, a composition herein comprises polypeptide 543 and one or more polypeptides from Table 2. In some embodiments, a composition herein comprises polypeptide 544 and one or more polypeptides from Table 2. In some embodiments, a composition herein comprises polypeptide 545 and one or more polypeptides from Table 2. In some embodiments, a composition herein comprises polypeptide 546 and one or more polypeptides from Table 2. In some embodiments, a composition herein comprises polypeptide 547 and one or more polypeptides from Table 2. In some embodiments, a composition herein comprises polypeptide 548 and one or more polypeptides from Table 2. In some embodiments, a composition herein comprises polypeptide 549 and one or more polypeptides from Table 2. In some embodiments, a composition herein comprises polypeptide 550 and one or more polypeptides from Table 2. In some embodiments, a composition herein comprises polypeptide 551 and one or more polypeptides from Table 2. In some embodiments, a composition herein comprises polypeptide 552 and one or more polypeptides from Table 2. In some embodiments, a composition herein comprises polypeptide 553 and one or more polypeptides from Table 2. In some embodiments, a composition herein comprises polypeptide 554 and one or more polypeptides from Table 2. In some embodiments, a composition herein comprises polypeptide 555 and one or more polypeptides from Table 2. In some embodiments, a composition herein comprises polypeptide 556 and one or more polypeptides from Table 2. In some embodiments, a composition herein comprises polypeptide 557 and one or more polypeptides from Table 2. In some embodiments, a composition herein comprises polypeptide 558 and one or more polypeptides from Table 2. In some embodiments, a composition herein comprises polypeptide 559 and one or more polypeptides from Table 2. In some embodiments, a composition herein comprises polypeptide 560 and one or more polypeptides from Table 2. In some embodiments, a composition herein comprises polypeptide 561 and one or more polypeptides from Table 2. In some embodiments, a composition herein comprises polypeptide 562 and one or more polypeptides from Table 2. In some embodiments, a composition herein comprises polypeptide 563 and one or more polypeptides from Table 2. In some embodiments, a composition herein comprises polypeptide 564 and one or more polypeptides from Table 2. In some embodiments, a composition herein comprises polypeptide 565 and one or more polypeptides from Table 2. In some embodiments, a composition herein comprises polypeptide 566 and one or more polypeptides from Table 2. In some embodiments, a composition herein comprises polypeptide 567 and one or more polypeptides from Table 2. In some embodiments, a composition herein comprises polypeptide 568 and one or more polypeptides from Table 2. In some embodiments, a composition herein comprises polypeptide 569 and one or more polypeptides from Table 2. In some embodiments, a composition herein comprises polypeptide 570 and one or more polypeptides from Table 2. In some embodiments, a composition herein comprises polypeptide 571 and one or more polypeptides from Table 2.

In some embodiments, a composition herein comprises polypeptide 572 and one or more polypeptides from Table 2. In some embodiments, a composition herein comprises polypeptide 573 and one or more polypeptides from Table 2. In some embodiments, a composition herein comprises polypeptide 574 and one or more polypeptides from Table 2. In some embodiments, a composition herein comprises polypeptide 575 and one or more polypeptides from Table 2. In some embodiments, a composition herein comprises polypeptide 576 and one or more polypeptides from Table 2. In some embodiments, a composition herein comprises polypeptide 577 and one or more polypeptides from Table 2. In some embodiments, a composition herein comprises polypeptide 578 and one or more polypeptides from Table 2. In some embodiments, a composition herein comprises polypeptide 579 and one or more polypeptides from Table 2. In some embodiments, a composition herein comprises polypeptide 580 and one or more polypeptides from Table 2. In some embodiments, a composition herein comprises polypeptide 581 and one or more polypeptides from Table 2. In some embodiments, a composition herein comprises polypeptide 582 and one or more polypeptides from Table 2. In some embodiments, a composition herein comprises polypeptide 583 and one or more polypeptides from Table 2. In some embodiments, a composition herein comprises polypeptide 584 and one or more polypeptides from Table 2. In some embodiments, a composition herein comprises polypeptide 585 and one or more polypeptides from Table 2. In some embodiments, a composition herein comprises polypeptide 586 and one or more polypeptides from Table 2. In some embodiments, a composition herein comprises polypeptide 587 and one or more polypeptides from Table 2. In some embodiments, a composition herein comprises polypeptide 588 and one or more polypeptides from Table 2. In some embodiments, a composition herein comprises polypeptide 589 and one or more polypeptides from Table 2. In some embodiments, a composition herein comprises polypeptide 590 and one or more polypeptides from Table 2. In some embodiments, a composition herein comprises polypeptide 591 and one or more polypeptides from Table 2. In some embodiments, a composition herein comprises polypeptide 592 and one or more polypeptides from Table 2. In some embodiments, a composition herein comprises polypeptide 593 and one or more polypeptides from Table 2. In some embodiments, a composition herein comprises polypeptide 594 and one or more polypeptides from Table 2. In some embodiments, a composition herein comprises polypeptide 595 and one or more polypeptides from Table 2. In some embodiments, a composition herein comprises polypeptide 596 and one or more polypeptides from Table 2. In some embodiments, a composition herein comprises polypeptide 597 and one or more polypeptides from Table 2. In some embodiments, a composition herein comprises polypeptide 598 and one or more polypeptides from Table 2. In some embodiments, a composition herein comprises polypeptide 599 and one or more polypeptides from Table 2. In some embodiments, a composition herein comprises polypeptide 600 and one or more polypeptides from Table 2.

In some embodiments, a composition herein comprises polypeptide 701 and one or more polypeptides from Table 2. In some embodiments, a composition herein comprises polypeptide 702 and one or more polypeptides from Table 2. In some embodiments, a composition herein comprises polypeptide 703 and one or more polypeptides from Table 2. In some embodiments, a composition herein comprises polypeptide 704 and one or more polypeptides from Table 2. In some embodiments, a composition herein comprises polypeptide 705 and one or more polypeptides from Table 2. In some embodiments, a composition herein comprises polypeptide 706 and one or more polypeptides from Table 2. In some embodiments, a composition herein comprises polypeptide 707 and one or more polypeptides from Table 2. In some embodiments, a composition herein comprises polypeptide 708 and one or more polypeptides from Table 2. In some embodiments, a composition herein comprises polypeptide 709 and one or more polypeptides from Table 2. In some embodiments, a composition herein comprises polypeptide 710 and one or more polypeptides from Table 2. In some embodiments, a composition herein comprises polypeptide 711 and one or more polypeptides from Table 2. In some embodiments, a composition herein comprises polypeptide 712 and one or more polypeptides from Table 2. In some embodiments, a composition herein comprises polypeptide 713 and one or more polypeptides from Table 2. In some embodiments, a composition herein comprises polypeptide 714 and one or more polypeptides from Table 2. In some embodiments, a composition herein comprises polypeptide 715 and one or more polypeptides from Table 2. In some embodiments, a composition herein comprises polypeptide 716 and one or more polypeptides from Table 2. In some embodiments, a composition herein comprises polypeptide 717 and one or more polypeptides from Table 2. In some embodiments, a composition herein comprises polypeptide 718 and one or more polypeptides from Table 2. In some embodiments, a composition herein comprises polypeptide 719 and one or more polypeptides from Table 2. In some embodiments, a composition herein comprises polypeptide 721 and one or more polypeptides from Table 2. In some embodiments, a composition herein comprises polypeptide 722 and one or more polypeptides from Table 2. In some embodiments, a composition herein comprises polypeptide 723 and one or more polypeptides from Table 2. In some embodiments, a composition herein comprises polypeptide 724 and one or more polypeptides from Table 2. In some embodiments, a composition herein comprises polypeptide 725 and one or more polypeptides from Table 2. In some embodiments, a composition herein comprises polypeptide 726 and one or more polypeptides from Table 2. In some embodiments, a composition herein comprises polypeptide 727 and one or more polypeptides from Table 2. In some embodiments, a composition herein comprises polypeptide 728 and one or more polypeptides from Table 2. In some embodiments, a composition herein comprises polypeptide 729 and one or more polypeptides from Table 2. In some embodiments, a composition herein comprises polypeptide 730 and one or more polypeptides from Table 2. In some embodiments, a composition herein comprises polypeptide 731 and one or more polypeptides from Table 2. In some embodiments, a composition herein comprises polypeptide 732 and one or more polypeptides from Table 2. In some embodiments, a composition herein comprises polypeptide 733 and one or more polypeptides from Table 2. In some embodiments, a composition herein comprises polypeptide 734 and one or more polypeptides from Table 2. In some embodiments, a composition herein comprises polypeptide 735 and one or more polypeptides from Table 2. In some embodiments, a composition herein comprises polypeptide 736 and one or more polypeptides from Table 2. In some embodiments, a composition herein comprises polypeptide 737 and one or more polypeptides from Table 2. In some embodiments, a composition herein comprises polypeptide 738 and one or more polypeptides from Table 2. In some embodiments, a composition herein comprises polypeptide 739 and one or more polypeptides from Table 2.

In some embodiments, a composition herein comprises polypeptide 740 and one or more polypeptides from Table 2. In some embodiments, a composition herein comprises polypeptide 741 and one or more polypeptides from Table 2. In some embodiments, a composition herein comprises polypeptide 742 and one or more polypeptides from Table 2. In some embodiments, a composition herein comprises polypeptide 743 and one or more polypeptides from Table 2. In some embodiments, a composition herein comprises polypeptide 744 and one or more polypeptides from Table 2. In some embodiments, a composition herein comprises polypeptide 745 and one or more polypeptides from Table 2. In some embodiments, a composition herein comprises polypeptide 746 and one or more polypeptides from Table 2. In some embodiments, a composition herein comprises polypeptide 747 and one or more polypeptides from Table 2. In some embodiments, a composition herein comprises polypeptide 748 and one or more polypeptides from Table 2. In some embodiments, a composition herein comprises polypeptide 749 and one or more polypeptides from Table 2. In some embodiments, a composition herein comprises polypeptide 750 and one or more polypeptides from Table 2. In some embodiments, a composition herein comprises polypeptide 751 and one or more polypeptides from Table 2. In some embodiments, a composition herein comprises polypeptide 752 and one or more polypeptides from Table 2. In some embodiments, a composition herein comprises polypeptide 753 and one or more polypeptides from Table 2. In some embodiments, a composition herein comprises polypeptide 754 and one or more polypeptides from Table 2. In some embodiments, a composition herein comprises polypeptide 755 and one or more polypeptides from Table 2. In some embodiments, a composition herein comprises polypeptide 756 and one or more polypeptides from Table 2. In some embodiments, a composition herein comprises polypeptide 757 and one or more polypeptides from Table 2. In some embodiments, a composition herein comprises polypeptide 758 and one or more polypeptides from Table 2. In some embodiments, a composition herein comprises polypeptide 759 and one or more polypeptides from Table 2. In some embodiments, a composition herein comprises polypeptide 760 and one or more polypeptides from Table 2. In some embodiments, a composition herein comprises polypeptide 761 and one or more polypeptides from Table 2. In some embodiments, a composition herein comprises polypeptide 762 and one or more polypeptides from Table 2. In some embodiments, a composition herein comprises polypeptide 763 and one or more polypeptides from Table 2. In some embodiments, a composition herein comprises polypeptide 764 and one or more polypeptides from Table 2. In some embodiments, a composition herein comprises polypeptide 765 and one or more polypeptides from Table 2. In some embodiments, a composition herein comprises polypeptide 766 and one or more polypeptides from Table 2. In some embodiments, a composition herein comprises polypeptide 767 and one or more polypeptides from Table 2. In some embodiments, a composition herein comprises polypeptide 768 and one or more polypeptides from Table 2. In some embodiments, a composition herein comprises polypeptide 769 and one or more polypeptides from Table 2. In some embodiments, a composition herein comprises polypeptide 770 and one or more polypeptides from Table 2. In some embodiments, a composition herein comprises polypeptide 771 and one or more polypeptides from Table 2. In some embodiments, a composition herein comprises polypeptide 772 and one or more polypeptides from Table 2. In some embodiments, a composition herein comprises polypeptide 773 and one or more polypeptides from Table 2. In some embodiments, a composition herein comprises polypeptide 774 and one or more polypeptides from Table 2. In some embodiments, a composition herein comprises polypeptide 775 and one or more polypeptides from Table 2. In some embodiments, a composition herein comprises polypeptide 776 and one or more polypeptides from Table 2. In some embodiments, a composition herein comprises polypeptide 777 and one or more polypeptides from Table 2. In some embodiments, a composition herein comprises polypeptide 778 and one or more polypeptides from Table 2. In some embodiments, a composition herein comprises polypeptide 779 and one or more polypeptides from Table 2. In some embodiments, a composition herein comprises polypeptide 780 and one or more polypeptides from Table 2. In some embodiments, a composition herein comprises polypeptide 781 and one or more polypeptides from Table 2. In some embodiments, a composition herein comprises polypeptide 782 and one or more polypeptides from Table 2. In some embodiments, a composition herein comprises polypeptide 783 and one or more polypeptides from Table 2. In some embodiments, a composition herein comprises polypeptide 784 and one or more polypeptides from Table 2. In some embodiments, a composition herein comprises polypeptide 785 and one or more polypeptides from Table 2. In some embodiments, a composition herein comprises polypeptide 786 and one or more polypeptides from Table 2. In some embodiments, a composition herein comprises polypeptide 787 and one or more polypeptides from Table 2. In some embodiments, a composition herein comprises polypeptide 788 and one or more polypeptides from Table 2. In some embodiments, a composition herein comprises polypeptide 789 and one or more polypeptides from Table 2. In some embodiments, a composition herein comprises polypeptide 790 and one or more polypeptides from Table 2. In some embodiments, a composition herein comprises polypeptide 791 and one or more polypeptides from Table 2. In some embodiments, a composition herein comprises polypeptide 792 and one or more polypeptides from Table 2. In some embodiments, a composition herein comprises polypeptide 793 and one or more polypeptides from Table 2. In some embodiments, a composition herein comprises polypeptide 794 and one or more polypeptides from Table 2. In some embodiments, a composition herein comprises polypeptide 795 and one or more polypeptides from Table 2. In some embodiments, a composition herein comprises polypeptide 796 and one or more polypeptides from Table 2. In some embodiments, a composition herein comprises polypeptide 797 and one or more polypeptides from Table 2. In some embodiments, a composition herein comprises polypeptide 798 and one or more polypeptides from Table 2. In some embodiments, a composition herein comprises polypeptide 799 and one or more polypeptides from Table 2. In some embodiments, a composition herein comprises polypeptide 800 and one or more polypeptides from Table 2. In some embodiments, a composition herein comprises polypeptide 801 and one or more polypeptides from Table 2. In some embodiments, a composition herein comprises polypeptide 802 and one or more polypeptides from Table 2. In some embodiments, a composition herein comprises polypeptide 803 and one or more polypeptides from Table 2. In some embodiments, a composition herein comprises polypeptide 804 and one or more polypeptides from Table 2. In some embodiments, a composition herein comprises polypeptide 805 and one or more polypeptides from Table 2. In some embodiments, a composition herein comprises polypeptide 806 and one or more polypeptides from Table 2.

In some embodiments, a composition herein comprises polypeptide 807 and one or more polypeptides from Table 2.
In some embodiments, a composition herein comprises polypeptide 808 and one or more polypeptides from Table 2.
In some embodiments, a composition herein comprises polypeptide 809 and one or more polypeptides from Table 2.
In some embodiments, a composition herein comprises polypeptide 810 and one or more polypeptides from Table 2.
In some embodiments, a composition herein comprises polypeptide 811 and one or more polypeptides from Table 2.
In some embodiments, a composition herein comprises polypeptide 812 and one or more polypeptides from Table 2.
In some embodiments, a composition herein comprises polypeptide 813 and one or more polypeptides from Table 2.
In some embodiments, a composition herein comprises polypeptide 814 and one or more polypeptides from Table 2.
In some embodiments, a composition herein comprises polypeptide 815 and one or more polypeptides from Table 2.
In some embodiments, a composition herein comprises polypeptide 816 and one or more polypeptides from Table 2.
In some embodiments, a composition herein comprises polypeptide 817 and one or more polypeptides from Table 2.
In some embodiments, a composition herein comprises polypeptide 818 and one or more polypeptides from Table 2.
In some embodiments, a composition herein comprises polypeptide 819 and one or more polypeptides from Table 2.
In some embodiments, a composition herein comprises polypeptide 821 and one or more polypeptides from Table 2.
In some embodiments, a composition herein comprises polypeptide 822 and one or more polypeptides from Table 2.
In some embodiments, a composition herein comprises polypeptide 823 and one or more polypeptides from Table 2.
In some embodiments, a composition herein comprises polypeptide 824 and one or more polypeptides from Table 2.
In some embodiments, a composition herein comprises polypeptide 825 and one or more polypeptides from Table 2.
In some embodiments, a composition herein comprises polypeptide 826 and one or more polypeptides from Table 2.
In some embodiments, a composition herein comprises polypeptide 827 and one or more polypeptides from Table 2.
In some embodiments, a composition herein comprises polypeptide 828 and one or more polypeptides from Table 2.
In some embodiments, a composition herein comprises polypeptide 829 and one or more polypeptides from Table 2.
In some embodiments, a composition herein comprises polypeptide 830 and one or more polypeptides from Table 2.
In some embodiments, a composition herein comprises polypeptide 831 and one or more polypeptides from Table 2.
In some embodiments, a composition herein comprises polypeptide 832 and one or more polypeptides from Table 2.
In some embodiments, a composition herein comprises polypeptide 833 and one or more polypeptides from Table 2.
In some embodiments, a composition herein comprises polypeptide 834 and one or more polypeptides from Table 2.
In some embodiments, a composition herein comprises polypeptide 835 and one or more polypeptides from Table 2.
In some embodiments, a composition herein comprises polypeptide 836 and one or more polypeptides from Table 2.
In some embodiments, a composition herein comprises polypeptide 837 and one or more polypeptides from Table 2.
In some embodiments, a composition herein comprises polypeptide 838 and one or more polypeptides from Table 2.
In some embodiments, a composition herein comprises polypeptide 839 and one or more polypeptides from Table 2.
In some embodiments, a composition herein comprises polypeptide 840 and one or more polypeptides from Table 2.
In some embodiments, a composition herein comprises polypeptide 841 and one or more polypeptides from Table 2.
In some embodiments, a composition herein comprises polypeptide 842 and one or more polypeptides from Table 2.
In some embodiments, a composition herein comprises polypeptide 843 and one or more polypeptides from Table 2.
In some embodiments, a composition herein comprises polypeptide 844 and one or more polypeptides from Table 2.
In some embodiments, a composition herein comprises polypeptide 845 and one or more polypeptides from Table 2.
In some embodiments, a composition herein comprises polypeptide 846 and one or more polypeptides from Table 2.
In some embodiments, a composition herein comprises polypeptide 847 and one or more polypeptides from Table 2.
In some embodiments, a composition herein comprises polypeptide 848 and one or more polypeptides from Table 2.
In some embodiments, a composition herein comprises polypeptide 849 and one or more polypeptides from Table 2.
In some embodiments, a composition herein comprises polypeptide 850 and one or more polypeptides from Table 2.
In some embodiments, a composition herein comprises polypeptide 851 and one or more polypeptides from Table 2.
In some embodiments, a composition herein comprises polypeptide 852 and one or more polypeptides from Table 2.
In some embodiments, a composition herein comprises polypeptide 853 and one or more polypeptides from Table 2.
In some embodiments, a composition herein comprises polypeptide 854 and one or more polypeptides from Table 2.
In some embodiments, a composition herein comprises polypeptide 855 and one or more polypeptides from Table 2.
In some embodiments, a composition herein comprises polypeptide 856 and one or more polypeptides from Table 2.
In some embodiments, a composition herein comprises polypeptide 857 and one or more polypeptides from Table 2.
In some embodiments, a composition herein comprises polypeptide 858 and one or more polypeptides from Table 2.
In some embodiments, a composition herein comprises polypeptide 859 and one or more polypeptides from Table 2.
In some embodiments, a composition herein comprises polypeptide 860 and one or more polypeptides from Table 2.
In some embodiments, a composition herein comprises polypeptide 861 and one or more polypeptides from Table 2.
In some embodiments, a composition herein comprises polypeptide 862 and one or more polypeptides from Table 2.
In some embodiments, a composition herein comprises polypeptide 863 and one or more polypeptides from Table 2.
In some embodiments, a composition herein comprises polypeptide 864 and one or more polypeptides from Table 2.
In some embodiments, a composition herein comprises polypeptide 865 and one or more polypeptides from Table 2.
In some embodiments, a composition herein comprises polypeptide 866 and one or more polypeptides from Table 2.
In some embodiments, a composition herein comprises polypeptide 867 and one or more polypeptides from Table 2.
In some embodiments, a composition herein comprises polypeptide 868 and one or more polypeptides from Table 2.
In some embodiments, a composition herein comprises polypeptide 869 and one or more polypeptides from Table 2.
In some embodiments, a composition herein comprises polypeptide 870 and one or more polypeptides from Table 2.
In some embodiments, a composition herein comprises polypeptide 871 and one or more polypeptides from Table 2.
In some embodiments, a composition herein comprises polypeptide 872 and one or more polypeptides from Table 2.
In some embodiments, a composition herein comprises polypeptide 873 and one or more polypeptides from Table 2.
In some embodiments, a composition herein comprises polypeptide 874 and one or more polypeptides from Table 2.

In some embodiments, a composition herein comprises polypeptide 875 and one or more polypeptides from Table 2. In some embodiments, a composition herein comprises polypeptide 876 and one or more polypeptides from Table 2.

In some cases, the one or more polypeptides from Table 2 comprises IL-15. In some cases, the one or more polypeptides from Table 2 comprises THBS4. In some cases, the one or more polypeptides from Table 2 comprises POSTN. In some cases, the one or more polypeptides from Table 2 comprises THBS1. In some cases, the one or more polypeptides from Table 2 comprises THBS2. In some cases, the one or more polypeptides from Table 2 comprises VTN. In some cases, the one or more polypeptides from Table 2 comprises FGF17. In some cases, the one or more polypeptides from Table 2 comprises IGF2. In some cases, the one or more polypeptides from Table 2 comprises polypeptide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, or 876. In some cases, one or a plurality of the polypeptides of the composition are heparin-associated polypolypeptides. In some cases, one or a plurality of the polypeptides of the composition are mitogenic and/or fusion promoting polypolypeptides. In certain embodiments, one or more of the polypeptides of the composition comprise one or more additional modifications to increase stability. In certain embodiments, one or more of the polypeptides is covalently conjugated to polyethylene glycol, polypropylene glycol, polyoxyalkylenes, or copolymers of polyethylene glycol, polysialic acid, glycolic acid, or polypropylene glycol. In certain embodiments, one or more of the polypeptides is fused or conjugated to another protein to increase stability and or bioavailability. In certain embodiments, one or more of the polypeptides is fused with an Fc region of an immunoglobulin or with serum albumin. In certain embodiments, one or more of the polypeptides is present in a concatemer with one, two, three, four or more distinct polypeptides selected from Table 2 and/or Table 1. In certain embodiments, one or more of the polypeptides is present in a concatemer with one, two, three, four, or more distinct polypeptides. In certain embodiments, one or more of the polypeptides is included in the composition with a biodegradable or bioabsorbable carrier that promotes polypeptide stability. In certain embodiments, the biodegradable or bioabsorable carrier comprises polylactic acid (PLA), polyglycolic acid (PGA), or Poly(D,L-lactic-coglycolic-acid) (PLGA). In certain embodiments, the biodegradable or bioabsorable carrier comprises polylactic acid (PLA). In certain embodiments, the biodegradable or bioabsorable carrier comprises polyglycolic acid (PGA). In certain embodiments, the biodegradable or bioabsorable carrier comprises Poly(D,L-lactic-coglycolic-acid) (PLGA).

In certain embodiments, the heparin-associated polypeptides increase the mitogenic (e.g., proliferative capacity) of a somatic cell that is a tissue cell or a tissue precursor, such as: a muscle cell, a muscle precursor cell, a tenocyte, a tenocyte precursor cell, a chondrocyte, a chondrocyte precursor, a mesenchymal stem cell, or a fibroblast. The cell can be a precursor cell derived from any mammal, such as, monkeys, apes, dogs, cats, horses, rats, mice, or humans. In certain embodiments, the precursor cell is a human precursor cell. In certain embodiments, the heparin-associated polypeptides increase the proliferative capacity of a mouse myoblast by at least about 1.5-fold, about 2-fold, about 3-fold, or about 4-fold as measured by BrdU or EdU incorporation.

Therapeutic Indications

In certain aspects, heparin-associated polypeptides and compositions comprising heparin-associated polypeptides, described herein, are useful for treating diseases and disorders that involve soft-tissue injury, degradation, or destruction. Aging disorders that result in the deterioration and loss of muscle tissue are such soft-tissue disorders. Sarcopenia, for example, is the degenerative loss of skeletal muscle mass quality, and strength associated with aging. Injuries that result in acute muscle damage are other such disorders. The disorders include muscle ruptures, strains, and contusions. A rupture is a separating of the muscle tissues. Muscle strains are contraction-induced injuries in which muscle fibers tear due to extensive mechanical stress, and can be classified as a grade I, II, or III. Muscle contusions are muscle hematomas. Muscle injury can also be caused by non-mechanical stresses such as cachexia. Cachexia may be caused by malnutrition, cancer, AIDS, coeliac disease, chronic obstructive pulmonary disease, multiple sclerosis, rheumatoid arthritis, congestive heart failure, tuberculosis, familial amyloid polyneuropathy, mercury poisoning (acrodynia), Crohn's disease, untreated/severe type 1 diabetes mellitus, anorexia nervosa, chemotherapy, muscular dystrophy or other genetic diseases which cause immobility, and hormonal deficiencies. Certain disorders that are weaknesses of specific muscles such as dysphagia or facioscapulohumeral muscular dystrophy may also be treated by the polypeptides described herein. Additional soft-tissues disorders that may be treated using the heparin-associated polypeptides described herein are those that inflict injury to the tendons, ligaments or cartilage. In certain embodiments, the muscle wasting disease is a muscular dystrophy. In certain embodiments, the muscular dystrophy comprises myotonic muscular dystrophy, Duchenne muscular dystrophy, Becker muscular dystrophy, Limb-girdle muscular dystrophy, facioscapulohumeral muscular dystrophy, congenital, muscular dystrophy, oculopharyngeal muscular dystrophy, or distal muscular dystrophy. In certain embodiments, the muscular dystrophy is Becker muscular dystrophy. In certain embodiments, the heparin-associated polypeptides useful for treating a soft-tissue disorder comprise any one, two, three, four, or five heparin-associated polypeptides selected from Vitronectin (VTN), Periostin (POSTN), Fribroblast growth factor (FGF17), Thrombospondin 2 (THBS2), Thrombospondin 4 (THBS4), Thrombospondin 1 (THBS1), Insulin-like growth factor 2 (IGF2), and Interleukin 15 (IL-15). In certain embodiments, the heparin-associated polypeptides useful for treating a soft-tissue disorder comprise any one, two, three, four, or five heparin-associated polypeptides selected from Vitronectin (VTN), Stanniocalcin-2 (STC2), Agrin (AGRN), Thrombospondin 2 (THBS2), follistatin (FST), Periostin (POSTN), Fribroblast growth factor (FGF17), Thrombospondin 4 (THBS4), Thrombospondin 1 (THBS1), Insulin-like growth factor 2 (IGF2), and Interleukin 15 (IL-15).

In certain embodiments, the heparin-associated polypeptides and compositions comprising heparin-associated polypeptides, described herein, are for use in treating an individual with an aging disorder, a muscle wasting disorder, a muscle injury, an injury to a connective tissue, or an injury to a non-muscle soft-tissue, or any combination thereof. In certain embodiments, the aging disorder is sarcopenia. In certain embodiments, the muscle wasting disorder is cachexia. In certain embodiments, the cachexia is a result of a cancer. In certain embodiments, the cachexia is a result of AIDS. In certain embodiments, the injury is a muscle injury. In certain embodiments, the muscle wasting is atrophy do to limb immobilization or disuse. In certain embodiments, the muscle injury is a strain or a tear. In certain embodiments, the muscle injury is a Grade III strain. In certain embodiments, sarcopenia contributes to the incidence of the muscle injury. In certain embodiments, the injury is ligament damage. In certain embodiments, the ligament damage is a rupture or a tear. In certain embodiments, the injury is tendon damage. In certain embodiments, the tendon damage is a rupture or a tear. In certain embodiments, the injury is cartilage damage. In certain embodiments, the heparin-associated polypeptides comprise any one, two, three, four, five or more heparin-associated polypeptides selected from Vitronectin (VTN), Periostin (POSTN), Fibroblast growth factor (FGF17), Thrombospondin 2 (THBS2), Thrombospondin 4 (THBS4), Thrombospondin 1 (THBS1), Insulin-like growth factor 2 (IGF2), and Interleukin 15 (IL-15). In certain embodiments, the heparin-associated polypeptides comprise any one, two, three, four, five or more heparin-associated polypeptides selected from Vitronectin (VTN), Stanniocalcin-2 (STC2), Agrin (AGRN), Thrombospondin 2 (THBS2), and follistatin (FST).

In certain embodiments, the heparin-associated polypeptides and compositions comprising heparin-associated polypeptides, described herein, are for use in a method of treating myositis. In certain embodiments, the myositis comprises dermatomyositis, polymyositis, necrotizing myopathy (also called necrotizing autoimmune myopathy or immune-mediated necrotizing myopathy), juvenile myositis, or sporadic inclusion-body myositis. In certain embodiments, the heparin-associated polypeptides comprise any one, two, three, four, five or more heparin-associated polypeptides selected from Vitronectin (VTN), Periostin (POSTN), Fribroblast growth factor (FGF17), Thrombospondin 2 (THBS2), Thrombospondin 4 (THBS4), Thrombospondin 1 (THBS1), Insulin-like growth factor 2 (IGF2), and Interleukin 15 (IL-15). In certain embodiments, the heparin-associated polypeptides comprise any one, two, three, four, or five heparin-associated polypeptides selected from Vitronectin (VTN), Stanniocalcin-2 (STC2), Agrin (AGRN), Thrombospondin 2 (THBS2), and follistatin (FST).

In certain embodiments, the heparin-associated polypeptides and compositions comprising heparin-associated polypeptides, described herein, are for use in a method of increasing proliferation or promoting survival of a cell associated with soft-tissue damage. In certain embodiments, the heparin-associated polypeptides described herein are useful in a method of increasing proliferation or promoting survival of any one or more of a muscle cell, a muscle precursor cell, a tenocyte, a tenocyte precursor cell, a chondrocyte, a chondrocyte precursor cell, a mesenchymal stem cell, or a fibroblast. In certain embodiments, the heparin-associated polypeptides comprise any one, two, three, four, five or more heparin-associated polypeptides selected from Vitronectin (VTN), Periostin (POSTN), Fribroblast growth factor (FGF17), Thrombospondin 2 (THBS2), Thrombospondin 4 (THBS4), Thrombospondin 1 (THBS1), Insulin-like growth factor 2 (IGF2), and Interleukin 15 (IL-15). In certain embodiments, the heparin-associated polypeptides comprise any one, two, three, four, or five heparin-associated polypeptides selected from Vitronectin (VTN), Stanniocalcin-2 (STC2), Agrin (AGRN), Thrombospondin 2 (THBS2), and follistatin (FST).

The heparin-associated polypeptides compositions described herein can be administered separately or as a mixture of 2, 3, 4, 5, 6, 7, 8, 9, 10 or more heparin-binding or heparin-associated polypeptides for the treatment of any disorder associated with muscle or soft-tissue.

In certain aspects, a method of treating a disease or condition, such as those described herein, in a subject in need thereof comprises administering to the subject a composition comprising a polypeptide of Table 2. In some embodiments, the polypeptide of Table 2 is a polypeptide of Table 1. In some embodiments, the composition comprises a pharmaceutically acceptable excipient, such as described herein. In some embodiments, the disease or condition comprises an aging disorder, muscle wasting disorder, muscle injury, or injury to connective tissue, or a combination thereof. In some embodiments, the aging disorder comprises sarcopenia. In some embodiments, the muscle wasting disorder comprises muscular dystrophy. In some embodiments, the muscle wasting is a result of obesity. In certain embodiments, the muscle wasting is the result of a metabolic disorder. In some cases the metabolic disorder is diabetes. In some cases the diabetes is Type 2 Diabetes. In some embodiments, muscle wasting is a result of disease progression. In some embodiments, muscle wasting is a result of therapeutic treatment. In some embodiments, the muscle wasting is cachexia. In some embodiments, the therapeutic polypeptide promotes fusion of myocytes.

In some embodiments, the polypeptide is a heparin-associated binding polypeptide as described herein. In some embodiments, the polypeptide is a mitogenic and/or fusion promoting polypeptide as described herein. In some embodiments, a composition comprising a plurality of heparin-associated binding polypeptides as described herein is administered. In some embodiments, a composition comprising a plurality of mitogenic and/or fusion promoting polypeptides as described herein is administered.

In some embodiments, the polypeptide has been recombinantly produced. In some embodiments, the polypeptide has been produced in a mammalian cell culture. In certain embodiments, the polypeptide has been produced in a mammalian cell and the mammalian cell is a human cell. In some cases the human cell is a human embryonic kidney-derived epithelial cell (e.g., HEK293 cells). In some embodiments, the mammalian cell culture is a mouse myeloma cell culture. In some embodiments, the mammalian cell culture is a Chinese Hamster Ovary (CHO) cell culture. In some embodiments, the polypeptide has been produced in a non-mammalian cell culture, e.g., in bacteria, yeast, or insect cells. In certain embodiments, the polypeptide has been purified from a human biological sample. In some cases, the human biological sample is human plasma. In some embodiments, the composition is formulated for administration by injection to the subject. In some embodiments, the composition comprises one or more polypeptides having at least about 90% homology to a sequence selected from SEQ ID NOS: 1-44, 55, 56, and 58-70. In some embodiments, the composition comprises polypeptide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, or 876, or any combination thereof.

In some embodiments, the polypeptide comprises VTN. In some cases, the VTN comprises a polypeptide comprising at least about 90% homology or identity to SEQ ID NO: 1. In some cases, the VTN comprises a polypeptide comprising at least about 90% homology or identity to amino acids 20-478 of SEQ ID NO: 1. In some cases, the VTN is purified from human plasma.

In some embodiments, the polypeptide comprises POSTN. In some cases, the POSTN comprises a polypeptide comprising at least about 90% homology or identity to SEQ ID NO: 6. In some cases, the POSTN comprises a polypeptide comprising at least about 90% homology or identity to amino acids 22-836 of SEQ ID NO: 6. In some cases, the POSTN is expressed in a mouse myeloma cell line.

In some embodiments, the polypeptide comprises FGF17. In some cases, the FGF17 comprises a polypeptide comprising at least about 90% homology or identity to SEQ ID NO: 7. In some cases, the FGF17 comprises a polypeptide comprising at least about 90% homology or identity to amino acids 23-216 of SEQ ID NO: 7. In some cases, the FGF17 is expressed in a bacterial cell. In some embodiments, the bacterial cell is *E. coli.*

In some embodiments, the polypeptide comprises THBS2. In some cases, the THBS2 comprises a polypeptide comprising at least about 90% homology or identity to SEQ ID NO: 4. In some cases, the THBS2 comprises a polypeptide comprising at least about 90% homology or identity to amino acids 19-1172 of SEQ ID NO: 4. In some cases, the THBS2 is expressed in a mouse myeloma cell line.

In some embodiments, the polypeptide comprises THBS4. In some cases, the THBS4 comprises a polypeptide comprising at least about 90% homology or identity to SEQ ID NO: 8. In some cases, the THBS4 comprises a polypeptide comprising at least about 90% homology or identity to amino acids 27-961 of SEQ ID NO: 8. In some cases, the THBS4 is expressed in Chinese hamster ovary cell.

In some embodiments, the polypeptide comprises IGF2. In some cases, the IGF2 comprises a polypeptide comprising at least about 90% homology or identity to SEQ ID NO: 11. In some cases, the IGF2 comprises a polypeptide comprising at least about 90% homology or identity to amino acids 25-91 of SEQ ID NO: 11. In some cases, the IGF2 is expressed in a bacterial cell. In some embodiments, the bacterial cell is *E. coli.*

In some embodiments, the polypeptide comprises IL-15. In some cases, the IL-15 comprises a polypeptide comprising at least about 90% homology or identity to SEQ ID NO: 10. In some cases, the IL-15 comprises a polypeptide comprising at least about 90% homology or identity to amino acids 49-162 of SEQ ID NO: 10. In some cases, the IL-15 is expressed in a bacterial cell. In some embodiments, the bacterial cell is *E. coli.*

In some embodiments, the polypeptide comprises THBS1. In some cases, the THBS1 comprises a polypeptide comprising at least about 90% homology or identity to SEQ ID NO: 9. In some cases, the THBS1 comprises a polypeptide comprising at least about 90% homology or identity to amino acids 19-1170 of SEQ ID NO: 9. In some cases, the THBS1 is expressed in a mouse myeloma cell line.

In some embodiments, the polypeptide comprises IL-15, and the composition further comprises THBS2. In some embodiments, the polypeptide comprises IL-15, and the composition further comprises THBS4. In some embodiments, the polypeptide comprises THBS4, and the composition further comprises THBS2. In some embodiments, the polypeptide comprises IL-15, and the composition further comprises THBS2 and THBS4.

In some embodiments, the polypeptide comprises IGF2, and the composition further comprises THBS2. In some embodiments, the polypeptide comprises IGF2, and the composition further comprises THBS4. In some embodiments, the polypeptide comprises THBS4, and the composition further comprises THBS2. In some embodiments, the polypeptide comprises IGF2, and the composition further comprises THBS2 and THBS4.

Schedules Routes of Administration and Amounts

In certain embodiments, the heparin-associated polypeptides can be administered by any suitable route such as, for example, subcutaneous, intravenous, or intramuscular. In certain embodiments, the heparin-associated polypeptides are administered on a suitable dosage schedule, for example, weekly, twice weekly, monthly, twice monthly, once every three weeks, or once every four weeks. The heparin-associated polypeptides can be administered in any therapeutically effective amount. In certain embodiments, the therapeutically acceptable amount is about 0.001 mg/kg to about 1 mg/kg. In certain embodiments, the therapeutically acceptable amount is about 0.001 mg/kg to about 0.002 mg/kg, about 0.001 mg/kg to about 0.005 mg/kg, about 0.001 mg/kg to about 0.01 mg/kg, about 0.001 mg/kg to about 0.02 mg/kg, about 0.001 mg/kg to about 0.05 mg/kg, about 0.001 mg/kg to about 0.1 mg/kg, about 0.001 mg/kg to about 0.2 mg/kg, about 0.001 mg/kg to about 0.5 mg/kg, about 0.001 mg/kg to about 1 mg/kg, about 0.002 mg/kg to about 0.005 mg/kg, about 0.002 mg/kg to about 0.01 mg/kg, about 0.002 mg/kg to about 0.02 mg/kg, about 0.002 mg/kg to about 0.05 mg/kg, about 0.002 mg/kg to about 0.1 mg/kg, about 0.002 mg/kg to about 0.2 mg/kg, about 0.002 mg/kg to about 0.5 mg/kg, about 0.002 mg/kg to about 1 mg/kg, about 0.005 mg/kg to about 0.01 mg/kg, about 0.005 mg/kg to about 0.02 mg/kg, about 0.005 mg/kg to about 0.05 mg/kg, about 0.005 mg/kg to about 0.1 mg/kg, about 0.005 mg/kg to about 0.2 mg/kg, about 0.005 mg/kg to about 0.5 mg/kg, about 0.005 mg/kg to about 1 mg/kg, about 0.01 mg/kg to about 0.02 mg/kg, about 0.01 mg/kg to about 0.05 mg/kg, about 0.01 mg/kg to about 0.1 mg/kg, about 0.01 mg/kg to about 0.2 mg/kg, about 0.01 mg/kg to about 0.5 mg/kg, about 0.01 mg/kg to about 1 mg/kg, about 0.02 mg/kg to about 0.05 mg/kg, about 0.02 mg/kg to about 0.1 mg/kg, about 0.02 mg/kg to about 0.2 mg/kg, about 0.02 mg/kg to about 0.5 mg/kg, about 0.02 mg/kg to about 1 mg/kg, about 0.05 mg/kg to about 0.1 mg/kg, about 0.05 mg/kg to about 0.2 mg/kg, about 0.05 mg/kg to about 0.5 mg/kg, about 0.05 mg/kg to about 1 mg/kg, about 0.1 mg/kg to about 0.2 mg/kg, about 0.1 mg/kg to about 0.5 mg/kg, about 0.1 mg/kg to about 1 mg/kg, about 0.2 mg/kg to about 0.5 mg/kg, about 0.2 mg/kg to about 1 mg/kg, or about 0.5 mg/kg to about 1 mg/kg. In certain embodiments, the therapeutically acceptable amount is about 0.001 mg/kg, about 0.002 mg/kg, about 0.005 mg/kg, about 0.01 mg/kg, about 0.02 mg/kg, about 0.05 mg/kg, about 0.1 mg/kg, about 0.2 mg/kg, about 0.5 mg/kg, or about 1 mg/kg. In certain embodiments, the therapeutically acceptable amount is at least about 0.001 mg/kg, about 0.002 mg/kg, about 0.005 mg/kg, about 0.01 mg/kg, about 0.02 mg/kg, about 0.05 mg/kg, about 0.1 mg/kg, about 0.2 mg/kg, or about 0.5 mg/kg. In certain embodiments, the therapeutically acceptable amount is at most about 0.002 mg/kg, about 0.005 mg/kg, about 0.01 mg/kg, about 0.02 mg/kg, about 0.05 mg/kg, about 0.1 mg/kg, about 0.2 mg/kg, about 0.5 mg/kg, or about 1 mg/kg. In certain embodiments, the therapeutically acceptable amount is about 0.1 mg/kg to about 50 mg/kg. In certain embodiments, the therapeutically acceptable amount is about 0.1 mg/kg to about 0.2 mg/kg, about 0.1 mg/kg to about 0.5 mg/kg, about 0.1 mg/kg to about 1 mg/kg, about 0.1 mg/kg to about 2 mg/kg, about 0.1 mg/kg to about 5 mg/kg, about 0.1 mg/kg to about 10 mg/kg, about 0.1 mg/kg to about 20 mg/kg, about 0.1 mg/kg to about 50 mg/kg, about 0.2 mg/kg to about 0.5 mg/kg, about 0.2 mg/kg to about 1 mg/kg, about 0.2 mg/kg to about 2 mg/kg, about 0.2 mg/kg to about 5 mg/kg, about 0.2 mg/kg to about 10 mg/kg, about 0.2 mg/kg to about 20 mg/kg, about 0.2 mg/kg to about 50 mg/kg, about 0.5 mg/kg to about 1 mg/kg, about 0.5 mg/kg to about 2 mg/kg, about 0.5 mg/kg to about 5 mg/kg, about 0.5 mg/kg to about 10 mg/kg, about 0.5 mg/kg to about 20 mg/kg, about 0.5 mg/kg to about 50 mg/kg, about 1 mg/kg to about 2 mg/kg, about 1 mg/kg to about 5 mg/kg, about 1 mg/kg to about 10 mg/kg, about 1 mg/kg to about 20 mg/kg, about 1 mg/kg to about 50 mg/kg, about 2 mg/kg to about 5 mg/kg, about 2 mg/kg to about 10 mg/kg, about 2 mg/kg to about 20 mg/kg, about 2 mg/kg to about 50 mg/kg, about 5 mg/kg to about 10 mg/kg, about 5 mg/kg to about 20 mg/kg, about 5 mg/kg to about 50 mg/kg, about 10 mg/kg to about 20 mg/kg, about 10 mg/kg to about 50 mg/kg, or about 20 mg/kg to about 50 mg/kg. In certain embodiments, the therapeutically acceptable amount is about 0.1 mg/kg, about 0.2 mg/kg, about 0.5 mg/kg, about 1 mg/kg, about 2 mg/kg, about 5 mg/kg, about 10 mg/kg, about 20 mg/kg, or about 50 mg/kg. In certain embodiments, the therapeutically acceptable amount is at least about 0.1 mg/kg, about 0.2 mg/kg, about 0.5 mg/kg, about 1 mg/kg, about 2 mg/kg, about 5 mg/kg, about 10 mg/kg, or about 20 mg/kg. In certain embodiments, the therapeutically acceptable amount is at most about 0.2 mg/kg, about 0.5 mg/kg, about 1 mg/kg, about 2 mg/kg, about 5 mg/kg, about 10 mg/kg, about 20 mg/kg, or about 50 mg/kg.

Nucleic Acids

Production of Heparin-Associated or Heparin-Binding Polypeptides

Once a polypeptide is determined as a heparin-associated or heparin-binding polypeptide it can be purified or synthesized in any suitable manner. A nucleic acid encoding the polypeptide can be cloned into a suitable vector and expressed in a suitable cellular system. In certain embodiments, the cellular system is a prokaryotic cell system. In certain embodiments, the cellular system is a eukaryotic cell system. In certain embodiments, the cellular system is a mammalian cell system. The supernatants from such an expression system can be subjected to one or more purification steps involving centrifugation, ultracentrifugation, filtration, diafiltration, tangential-flow filtration, dialysis, chromatography (e.g., cation exchange, ion exchange, hydrophobic interaction, reverse phase, affinity, or size exclusion). The polypeptides can be purified to an extent suitable for human administration. Additionally, polypeptides can be synthesized for inclusion in a formulation to be administered to a human subject. In certain embodiments, the polypeptides can be produced by a suitable peptide synthesis method, such as solid-phase synthesis.

TABLE 3

Nucleic acid sequences.

| Protein Name | Size (AA) | UniProtKB | Protein accession # | mRNA accession # | Gene ID | SEQ ID |
|---|---|---|---|---|---|---|
| FGF17 | 216 | O60258.1 | NP_003858.1 | NM_003867.4 | 8822 | 45 |
| THBS1 | 1170 | P07996.2 | NP_003237.2 | NM_003246.4 | 7057 | 46 |
| THBS2 | 1172 | P35442.2 | NP_003238.2 | NM_003247.3 | 7058 | 47 |
| THBS4 | 961 | P35443.2 | NP_003239.2 | NM_003248.6 | 7060 | 48 |
| IGF2 | 180 | P01344.1 | NP_000603.1 | NM_000612.6 | 3481 | 49 |
| IL15 | 162 | P40933.1 | NP_000576.1 | NM_000585.5 | 3600 | 50 |
| IGFBP7 | 282 | Q16270.1 | NP_001544.1 | NM_001553.3 | 3490 | 51 |
| VTN | 478 | P04004 | NP_000629.3 | NM_000638.4 | 7448 | 52 |
| POSTN | 836 | Q15063.2 | NP_006466.2 | NM_006475.3 | 10631 | 53 |
| PDGFRL | 375 | Q15198.1 | NP_006198.1 | NM_006207.2 | 5157 | 54 |
| ANOS1 | 3730 | P23352 | NP_000207.2 | NM_000216.4 | 3730 | 57 |

In certain embodiments, described herein, are nucleic acids that encode the heparin-associated polypeptides described herein. In certain embodiments, the nucleic acids are exogenous. In certain embodiments, the nucleic acid is a plasmid. In certain embodiments, the nucleic acid is a viral vector. In certain embodiments, the viral vector is an adenovirus, lentivirus, retrovirus, adeno-associated virus, or vaccinia virus. In certain embodiments, the nucleic acid comprises RNA. In certain embodiments, the nucleic acid encodes any of the polypeptides listed in Table 1 or Table 2, or VTN, STC2, AGRN, POSTN, FGF17, THBS2, FST, THBS1, IL-15, IGF2, or THBS4. In certain embodiments, the nucleic acid encodes any one or more polypeptide embodiments described herein. Nucleic acids according to this description can comprise additional nucleic acid sequences sufficient to propagate the vector or express a polypeptide encoded by the vector. In certain embodiments, the nucleic acid comprises a universal promoter, such as the CMV promoter, or an inducible promoter system such as a $TET_{ON}$, $TET_{OFF}$ or GAL4. In certain embodiments, the nucleic acid is expressed via a tissue specific promoter or one compatible with a eukaryotic or prokaryotic cellular expression system. The nucleic acid can further comprise a sequence encoding a suitable purification tag (e.g., HIS-tag, V5, FLAG, MYC).

Master Cell Bank and Transgenic Cells

In a certain embodiment, described herein is a master cell bank comprising a cell that comprises a nucleic acid encoding one or more heparin-associated polypeptides integrated into its genome creating a transgenic cell-line. In some embodiments, the master cell bank comprises a plurality of cells that each comprise a nucleic acid encoding a heparin-associated polypeptide. In certain embodiments, the nucleic acid is maintained extrachromosomally on a plasmid or yeast artificial chromosome. In certain embodiments, the nucleic acid is integrated into a chromosomal location. In certain embodiments, the cell is a yeast cell. In certain embodiments, the yeast is Pichia pastoris or Saccharomyces cerevisiae. In certain embodiments, the cell is a mammalian cell. In certain embodiments, the mammalian cell is a 293T cell or derivative thereof (e.g., 293T-Rex). In certain embodiments, the cell is a bacterial cell.

In certain embodiments, the transgenic mammalian, yeast, or bacterial cell is a master cell bank that comprises a cryopreservative suitable for freezing to at least about −80° or below. In certain embodiments, the master cell bank comprises glycerol at between about 10 and about 30%, and is suitable for long-term storage at about −80° or below. In certain embodiments, the master cell bank can preserve a transgenic mammalian, yeast, or bacterial strain for at least 1, 2, 3, 4, 5, 6, 7, 8, 9, 10 or more years.

Pharmaceutically Acceptable Excipients, Carriers, and Diluents

The heparin-associated polypeptide(s) described herein can be administered in a pharmaceutical composition that comprises one or more pharmaceutically acceptable excipients, carriers, or diluents. The exact components can differ based upon the preferred route of administration. The excipients used in a pharmaceutical composition can provide additional function to the polypeptide by making the polypeptide suitable for a particular route of administration (e.g., intravenous, topical, subcutaneous, or intramuscular), increasing polypeptide stability, increasing penetration of a desired tissue (e.g., muscle or skin), increasing residence time at particular site, increasing solubility, enhancing the efficacy of the polypeptide, and/or reducing inflammatory reactions coincident with administration.

In certain embodiments, the heparin-associated polypeptide(s) described herein are included in a pharmaceutical composition with a solubilizing emulsifying, or dispersing agent. In certain embodiments, the solubilizing agent can allow high-concentration solutions of heparin-associated polypeptides that exceed at least about 2 mg/mL, 5 mg/mL, 10 mg/mL, 15 mg/mL, or 20 mg/mL. Carbomers in an aqueous pharmaceutical composition serve as emulsifying agents and viscosity modifying agents. In certain embodiments, the pharmaceutically acceptable excipient comprises or consists of a carbomer. In certain embodiments, the carbomer comprises or consists of carbomer 910, carbomer 934, carbomer 934P, carbomer 940, carbomer 941, carbomer 1342, or combinations thereof. Cyclodextrins in an aqueous pharmaceutical composition serve as solubilizing and stabilizing agents. In certain embodiments, the pharmaceutically acceptable excipient comprises or consists of a cyclodextrin. In certain embodiments, the cyclodextrin comprises or consists of alpha cyclodextrin, beta cyclodextrin, gamma cyclodextrin, or combinations thereof. Lecithin in a pharmaceutical composition may serve as a solubilizing agent. In certain embodiments, the solubilizing agent comprises or consists of lecithin. Poloxamers in a pharmaceutical composition serve as emulsifying agents, solubilizing agents, and dispersing agents. In certain embodiments, the pharmaceutically acceptable excipient comprises or consists of a poloxamer. In certain embodiments, the poloxamer comprises or consists of poloxamer 124, poloxamer 188, poloxamer 237, poloxamer 338, poloxamer 407, or combinations thereof. Polyoxyethylene sorbitan fatty acid esters in a pharmaceutical composition serve as emulsifying agents, solubilizing agents, surfactants, and dispersing agents. In certain embodiments, the pharmaceutically acceptable excipient comprises or consists of a polyoxyethylene sorbitan fatty acid ester. In certain embodiments, the polyoxyethylene sorbitan fatty acid ester comprises or consists of polysorbate 20, polysorbate 21, polysorbate 40, polysorbate 60, polysorbate 61, polysorbate 65, polysorbate 80, polysorbate 81, polysorbate 85, polysorbate 120, or combinations thereof. Polyoxyethylene stearates in a pharmaceutical composition serve as emulsifying agents, solubilizing agents, surfactants, and dispersing agents. In certain embodiments, the pharmaceutically acceptable excipient comprises or consists of a polyoxyethylene stearate. In certain embodiments, the polyoxyethylene stearate comprises or consists of polyoxyl 2 stearate, polyoxyl 4 stearate, polyoxyl 6 stearate, polyoxyl 8 stearate, polyoxyl 12 stearate, polyoxyl 20 stearate, polyoxyl 30 stearate, polyoxyl 40 stearate, polyoxyl 50 stearate, polyoxyl 100 stearate, polyoxyl 150 stearate, polyoxyl 4 distearate, polyoxyl 8 distearate, polyoxyl 12 distearate, polyoxyl 32 distearate, polyoxyl 150 distearate, or combinations thereof. Sorbitan esters in a pharmaceutical composition serve as emulsifying agents, solubilizing agents, and non-ionic surfactants, and dispersing agents. In certain embodiments, the pharmaceutically acceptable excipient comprises or consists of a sorbitan ester. In certain embodiments, the sorbitan ester comprises or consists of sorbitan laurate, sorbitan oleate, sorbitan palmitate, sorbitan stearate, sorbitan trioleate, sorbitan sesquioleate, or combinations thereof. In certain embodiments, solubility can be achieved with a protein carrier. In certain embodiments the protein carrier comprises recombinant human albumin.

In certain embodiments, the heparin-associated polypeptide(s) of the current disclosure are formulated to increase stability. Polypeptides in aqueous formulations may require stabilization to prevent degradation. In certain embodiments, the stabilizer comprises pH buffers, salts, amino acids, polyols/disaccharides/polysaccharides, liposomes, surfactants, antioxidants, reducing agents, or chelating agents. In certain embodiments, the stabilizer comprises or consists of a polyol/non-reducing sugar. In certain embodiments, the non-reducing sugar comprises or consists of sucrose, mannitol, trehalose, raffinose, stachyose, xylitol, starch, verbascose, or combinations thereof. Polypeptides can be encapsulated in liposomes to increase stability. In certain embodiments, the stabilizer comprises or consists of liposomes. In certain embodiments, the liposomes comprise or consists of ipalmitoylphosphatidylcholine (DPPC) liposomes, phosphatidylcholine:cholesterol (PC:Chol) (70:30) liposomes, or dipalmitoylphosphatidylcholine:dipalmitoylphosphatidylserine (DPPC:DPPS) liposomes (70:30). Non-ionic surfactants can increase the stability of a polypeptide. In certain embodiments, the stabilizer comprises or consists of a non-ionic surfactant. In certain embodiments, the non-ionic surfactant comprises or consists of polysorbates (e.g., poly sorbate 80, poly sorbate 20), alkylsaccharides alkyl ethers and alkyl glyceryl ethers, polyoxyethelene (4) lauryl ether; polyoxyethylene cetyl ethers, polyoxyethylene stearyl ethers, sorbitan fatty acid esters, polyoxyethylene fatty acid esters, or combinations thereof. In certain embodiments, the polypeptide is formulated with a protein surfactant, such as recombinant human serum albumin as a stabilizer. Antioxidants or reducing agents can increase the stability of a polypeptide. In certain embodiments, the stabilizer comprises or consists of an antioxidant or reducing agent. In certain embodiments, the reducing agent comprises or consists of dithiothreitol, ethylenediaminetetraacetic acid, 2-Mercaptoethanol, Tris(2-carboxyethyl)phosphine hydrochloride, Tris(hydroxypropyl)phosphine, or combinations thereof. In certain embodiments, the antioxidant comprises or consists of methionine, ascorbic acid, citric acid, alpha tocopherol, sodium bisulfite, ascorbyl palmitate, erythorbic acid, or combinations thereof. Chelating agents can stabilize polypeptides by reducing the activity of proteases. In certain embodiments, the stabilizer comprises or consists of a chelating agent. In certain embodiments, the chelating agent comprises or consists of ethylenediaminetetraacetic acid (EDTA), ethylene glycol-bis(β-aminoethyl ether)-N,N,N',N'-tetraacetic acid (EGTA), metal complexes (e.g. Zn-protein complexes), or combinations thereof. Buffer agents can stabilize polypeptides by reducing the acid hydrolysis of polypeptides. In certain embodiments, the stabilizer comprises or consists of a buffer agent. In certain embodiments, the buffer agent comprises or consists sucrose octa-sulfate, ammonium carbonate, ammonium phosphate, boric acid, sodium citrate, potassium citrate, lactic acid, 3-(N-morpholino)propanesulfonic acid (MOPS), 2-(N-morpholino)

ethanesulfonic acid (MES), hydroxymethylaminomethane (Tris), calcium carbonate, calcium phosphate or combinations thereof.

The heparin-associated polypeptide(s) also may be entrapped in or associated with microcapsules prepared, for example, by coacervation techniques or by interfacial polymerization (for example, hydroxymethylcellulose or gelatin-microcapsules and poly-(methylmethacylate) microcapsules, respectively), in colloidal delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The heparin-associated polypeptide(s) of the current disclosure may be formulated or delivered with an anti-inflammatory agent. In certain embodiments, the anti-inflammatory agent comprises or consists of a corticosteroid. In certain embodiments, the corticosteroid comprises or consists of hydrocortisone, cortisone, ethamethasoneb (Celestone), prednisone (Prednisone Intensol), prednisolone (Orapred, Prelone), triamcinolone (Aristospan Intra-Articular, Aristospan Intralesional, Kenalog), methylprednisolone (Medrol, Depo-Medrol, Solu-Medrol), or dexamethasone (Dexamethasone Intensol). In certain embodiments, the anti-inflammatory comprises or consists of a non-steroidal anti-inflammatory (NSAID). In certain embodiments, the NSAID comprises or consists of aspirin, celecoxib, diclofenac, diflunisal, etodolac, ibuprofen, indomethacin, ketoprofen, ketorolac, nabumetone, naproxen, oxaprozin, piroxicam, salsalate, sulindac, or tolmetin.

In certain embodiments, the heparin-associated polypeptide(s) of the current disclosure are included in a pharmaceutical composition suitable for intravenous administration comprising one or more pharmaceutically acceptable excipients, carriers, and diluents. In certain embodiments, the polypeptides of the current disclosure are administered suspended in a sterile solution. In certain embodiments, the solution is one commonly used for administration of biological formulations, and comprises, for example, about 0.9% NaCl or about 5% dextrose. In certain embodiments, the solution further comprises one or more of: buffers, for example, acetate, citrate, histidine, succinate, phosphate, potassium phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine, histidine, leucine, or arginine; antioxidants, for example, ascorbic acid, methionine; or chelating agents, for example, EDTA, or EGTA.

In certain embodiments, the heparin-associated polypeptide(s) of the current disclosure are included in a pharmaceutical composition suitable for intramuscular or subcutaneous administration comprising one or more pharmaceutically acceptable excipients, carriers, and diluents. Formulations suitable for intramuscular or subcutaneous injection can include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include ethanol, polyols (inositol, propyleneglycol, polyethylene-glycol, glycerol, cremophor and the like) and suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

In certain embodiments, the heparin-associated polypeptide(s) of the current disclosure are formulated for topical administration as a cream, gel, paste, ointment, or emulsion. Excipients in a cream, gel, paste, ointment, or emulsion can comprise gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars, and starches.

The excipient used with the heparin-associated polypeptide(s) described herein will allow for storage, formulation, or administration of highly concentrated formulations. In certain embodiments, a highly concentrated heparin-associated polypeptide(s) comprises at least about 1, 2, 3, 4, 5, 6, 7, 8, 9, 10, 15, 20, 25, 20, 25, 40, 45, 50 or more milligrams per milliliter.

In certain embodiments, the polypeptides of the current disclosure are shipped/stored lyophilized and reconstituted before administration. In certain embodiments, lyophilized heparin-associated polypeptide formulations comprise a bulking agent such as, mannitol, sorbitol, sucrose, trehalose, and dextran 40. The lyophilized formulation can be contained in a vial comprised of glass. The heparin-associated polypeptides when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0.

Further Embodiments

1. A composition comprising a mitogenic and/or fusion promoting polypeptide, wherein the polypeptide is a heparin-associated polypeptide secreted from a stem cell or a transformed cell line, wherein the heparin-associated polypeptide possesses mitogenic and/or fusion promoting activity. 2. The composition of embodiment 1, comprising a plurality of mitogenic and/or fusion promoting polypeptides. 3. The composition of embodiment 2, wherein the plurality comprises three, four, five, six, seven, eight, nine, ten or more mitogenic and/or fusion promoting polypeptides. 4. The composition of embodiment 1 to 3, wherein the mitogenic and/or fusion promoting polypeptide or plurality of mitogenic and/or fusion promoting polypeptides are isolated and purified. 5. The composition of embodiment 1 to 3, wherein the mitogenic and/or fusion promoting polypeptide or plurality of mitogenic and/or fusion promoting polypeptides are recombinantly produced. 6. The composition of embodiment 1 to 3, wherein the mitogenic and/or fusion promoting polypeptide or plurality of mitogenic and/or fusion promoting polypeptides are secreted from a stem cell. 7. The composition of embodiment 1 to 3, wherein the stem cell is a pluripotent stem cell. 8. The composition of embodiment 1 to 3, wherein the stem cell is an induced pluripotent stem cell. 9. The composition of embodiment 1 to 3, wherein the mitogenic activity comprises the ability to increase proliferation in a somatic cell or increase the ability of another heparin-associated polypeptide to increase proliferation in a somatic cell. 10. The composition of embodiment 1 to 3, wherein the fusion promoting activity comprises the ability to increase fusion of a plurality of somatic cells or increase the ability of another heparin-associated polypeptide to increase fusion in a plurality of somatic cells. 11. The composition of embodiment 10, wherein the somatic cell is a muscle, muscle progenitor cell, tenocyte, or tenocyte precursor. 12. The composition of embodiment 11, wherein the somatic cell is a mammalian cell. 13. The composition of embodiment 11, wherein the somatic cell is a human cell. 14. The composition of any one of embodiments 1 to 13, wherein any one of the mitogenic and/or fusion promoting polypeptides or plurality of mitogenic and/or fusion promoting polypeptides are produced in a heterologous cellular production system. 15. The composition of any one of embodiments 1 to 13, wherein any one of the mitogenic and/or fusion promoting polypeptides or plurality of mitogenic and/or fusion promoting polypeptides are synthetically produced. 16. The composition of any one of embodiments 1 to 15, wherein the mitogenic and/or fusion promoting polypeptide or plurality of mitogenic and/or fusion promoting polypeptides comprise one or more modifications to improve activity, stability, or increase polypeptide yield from a heterologous cellular production system. 17. The composition of embodiment 16, wherein the modification is an alteration of one or more amino acids in the polypeptide sequence of the mitogenic and/or fusion promoting polypeptide compared to the wildtype polypeptide sequence of the mitogenic polypeptide. 18. A nucleic acid encoding at least one mitogenic and/or fusion promoting polypeptide of any one of embodiments 1 to 17. 19. A cell line comprising the nucleic acid of embodiment 18. 20. The cell line of embodiment 19, wherein the cell line is a eukaryotic cell line. 21. The composition comprising the mitogenic and/or fusion promoting polypeptide or plurality of mitogenic and/or fusion promoting polypeptides of any one of embodiments 1 to 17, and a pharmaceutically acceptable excipient, carrier, or diluent. 22. The composition of any one of embodiments 1 to 17 or 21, formulated in injectable form. 23. Use of the composition of any one of embodiments 1 to 17, 21, or 22 in a method of treating an aging disorder, a muscle wasting disorder, a muscle injury, or an injury to a connective tissue. 24. The use of embodiment 23, wherein the aging disorder is sarcopenia. 25. The use of embodiment 23, wherein the muscle wasting disorder is a muscular dystrophy. 26. A method of treating an individual with aging disorder, a muscle wasting disorder, a muscle injury, or an injury to a connective tissue comprising administering to the individual the composition of any one of embodiments 1 to 17, 21, or 22. 27. The method of embodiment 26, wherein the muscle wasting disorder is sarcopenia. 28. The method of embodiment 26, wherein the aging disorder is a muscular dystrophy. 29. A method of producing a composition suitable for the treatment of an aging disorder comprising admixing a pharmaceutically acceptable excipient, carrier, or diluent with the mitogenic and/or fusion promoting polypeptide or plurality of mitogenic and/or fusion promoting polypeptides of any one of embodiments 1 to 17. 30. A method of producing a mitogenic and/or fusion promoting polypeptide comprising culturing the cell line of embodiment 19 under conditions sufficient to produce the mitogenic and/or fusion promoting polypeptide.

31. A composition comprising a mitogenic and/or fusion promoting polypeptide, wherein the mitogenic and/or fusion promoting polypeptide is identified by: a) identifying at least one polypeptide in a mixture of a plurality of polypeptides secreted from a stem cell or a transformed cell line that binds heparin; and b) determining the mitogenic and/or fusion promoting activity of the at least one polypeptide for a somatic cell, wherein the at least one polypeptide is identified as a mitogenic and/or fusion promoting polypeptide if the at least one polypeptide exhibits mitogenic and/or fusion promoting activity. 32. The composition of embodiment 31, wherein the composition comprises a mixture of a plurality of mitogenic and/or fusion promoting polypeptides. 33. The composition of embodiment 32, wherein the plurality of mitogenic and/or fusion promoting polypeptides comprises three, four, five, six, seven, eight, nine, ten or more polypeptides. 34. The composition of any one of embodiments 31 to 33, wherein the mitogenic and/or fusion promoting polypeptide or plurality of mitogenic and/or fusion promoting polypeptides are isolated and purified. 35. The composition of any one of embodiments 31 to 33, wherein the mitogenic and/or fusion promoting polypeptide or plurality of mitogenic and/or fusion promoting polypeptides are recombinantly produced. 36. The composition of any one of embodiments 31 to 33, wherein the mitogenic and/or fusion promoting polypeptide or plurality of mitogenic and/or fusion promoting polypeptides are secreted from a stem cell. 37. The composition of any one of embodiments 31 to 33, wherein the stem cell is a pluripotent stem cell. 38. The composition of any one of embodiments 31 to 33, wherein the stem cell is an induced pluripotent stem cell. 39. The composition of any one of embodiments 31 to 33, wherein the mitogenic activity comprises the ability to increase proliferation in a somatic cell or increase the ability of another heparin-associated polypeptide to increase proliferation in a somatic cell. 40. The composition of any one of embodiments 31 to 33, wherein the fusion promoting activity comprises the ability to increase fusion of a plurality of somatic cells or increase the ability of another heparin-associated polypeptide to increase fusion in a plurality of somatic cells. 41. The composition of embodiment 40, wherein the somatic cell is a muscle, muscle progenitor cell, tenocyte, or tenocyte precursor. 42. The composition of embodiment 41, wherein the somatic cell is a mammalian cell. 43. The composition of embodiment 41, wherein the somatic cell is a human cell. 44. The composition of any one of embodiments 31 to 43, wherein any one of the mitogenic and/or fusion promoting polypeptides or plurality of mitogenic and/or fusion promoting polypeptides are produced in a heterologous cellular production system. 45. The composition of any one of embodiments 31 to 43, wherein any one of the mitogenic and/or fusion promoting polypeptides or plurality of mitogenic and/or fusion promoting polypeptides are synthetically produced. 46. The composition of any one of embodiments 31 to 43, wherein the mitogenic and/or fusion promoting polypeptide or plurality of mitogenic and/or fusion promoting polypeptides comprise one or more modifications to improve activity, stability, or increase polypeptide yield from a heterologous cellular production system. 47. The composition of embodiment 46, wherein the modification is an alteration of one or more amino acids in the polypeptide sequence of the mitogenic and/or fusion promoting polypeptide compared to the wildtype polypeptide sequence of the mitogenic and/or fusion promoting polypeptide. 48. A nucleic acid encoding at least one mitogenic and/or fusion promoting polypeptide of any one of embodiments 31 to 47. 49. A cell line comprising the nucleic acid of embodiment 48. 50. The cell line of embodiment 49, wherein the cell line is a eukaryotic cell line. 51. The composition comprising the mitogenic and/or fusion promoting polypeptide or plurality of mitogenic and/or fusion promoting polypeptides of any one of embodiments 31 to 47, and a pharmaceutically acceptable excipient, carrier, or diluent. 52. The composition of any one of embodiments 31 to 47 or 51, formulated in injectable form. 53. Use of the composition of any one of embodiments 31 to 47, 51, or 52 in a method of treating an aging disorder, a muscle wasting disorder, a muscle injury, or an injury to a connective tissue. 54. The use of embodiment 53, wherein the aging disorder is sarcopenia. 55. The use of embodiment 53, wherein the muscle wasting disorder is muscular dystrophy. 56. A method of treating an individual with an aging disorder, a muscle wasting disorder, a muscle injury, or an injury to a connective tissue comprising administering to the individual the composition of any one of embodiments 31 to 47, 51, or 52. 57. The method of embodiment 56, wherein the aging disorder is sarcopenia. 58. The method of embodiment 56, wherein the muscle wasting disorder is a muscular dystrophy. 59. A method of producing a composition suitable for the treatment of an aging disorder, a muscle wasting disorder, a muscle injury, or an injury to a connective tissue comprising admixing a pharmaceutically acceptable excipient, carrier, or diluent with the mitogenic and/or fusion promoting polypeptide or plurality of mitogenic and/or fusion promoting polypeptides of any one of embodiments 31 to 47. 60. A method of producing a mitogenic and/or fusion promoting polypeptide comprising culturing the cell line of embodiment 59 under conditions sufficient to produce the mitogenic and/or fusion promoting polypeptide.

61. A composition comprising a mitogenic and/or fusion promoting polypeptide, wherein the mitogenic and/or fusion promoting polypeptide comprises a protein listed in Table 2, and combinations thereof. 62. The composition of embodiment 61, wherein the mitogenic and/or fusion promoting polypeptide comprises VTN, POSTN, FGF17, THBS2, or THBS4. 63. The composition of embodiment 61, wherein the mitogenic and/or fusion promoting polypeptide comprises VTN. 64. The composition of embodiment 61, wherein the mitogenic and/or fusion promoting polypeptide comprises POSTN. 65. The composition of embodiment 61, wherein the mitogenic and/or fusion promoting polypeptide comprises FGF17. 66. The composition of embodiment 61, wherein the mitogenic and/or fusion promoting polypeptide comprises THBS2. 67. The composition of embodiment 61, wherein the mitogenic and/or fusion promoting polypeptide comprises THBS4. 68. The composition of any one of embodiments 61 to 67, wherein the composition comprises a mixture of a plurality of mitogenic and/or fusion promoting polypeptides. 69. The composition of embodiment 68, wherein the plurality of mitogenic and/or fusion promoting polypeptides comprises three, four, five, six, seven, eight, nine, ten or more mitogenic and/or fusion promoting polypeptides. 70. The composition of any one of embodiments 61 to 69, wherein the mitogenic and/or fusion promoting polypeptide or plurality of mitogenic and/or fusion promoting polypeptides are isolated and purified. 71. The composition of any one of embodiments 61 to 69, wherein the mitogenic and/or fusion promoting polypeptide or plurality of mitogenic and/or fusion promoting polypeptides are recombinantly produced. 72. The composition of any one of embodiments 61 to 69, wherein the mitogenic and/or fusion promoting polypeptide or plurality of mitogenic and/or fusion promoting polypeptides are secreted from a stem cell. 73. The composition of any one of embodiments 61 to 69, wherein the stem cell is a pluripotent stem cell. 74. The composition of any one of embodiments 61 to 69, wherein the stem cell is an induced pluripotent stem cell. 75. The composition of any one of embodiments 61 to 69, wherein the mitogenic activity comprises the ability to increase proliferation in a somatic cell or increase the ability of another heparin-associated polypeptide to increase proliferation in a somatic cell. 76. The composition of any one of embodiments 61 to 69, wherein the fusion promoting activity comprises the ability to increase fusion of a plurality of somatic cells or increase the ability of another heparin-associated polypeptide to increase fusion in a plurality of somatic cells. 77. The composition of embodiment 76, wherein the somatic cell is a muscle, muscle progenitor cell, tenocyte, or tenocyte precursor. 78. The composition of embodiment 77, wherein the somatic cell is a mammalian cell. 79. The composition of embodiment 77, wherein the somatic cell is a human cell. 80. The composition of any one of embodiments 61 to 79, wherein any one of the mitogenic and/or fusion promoting polypeptide or plurality of mitogenic and/or fusion promoting polypeptides are produced in a heterologous cellular production system. 81. The composition of any one of embodiments 61 to 79, wherein any one of the mitogenic and/or fusion promoting polypeptide or plurality of mitogenic and/or fusion promoting polypeptides are synthetically produced. 82. The composition of any one of embodiments 61 to 79, wherein the mitogenic and/or fusion promoting polypeptide or plurality of mitogenic and/or fusion promoting polypeptides comprise one or more modifications to improve activity, stability, or increase polypeptide yield from a heterologous cellular production system. 83. The composition of embodiment 82, wherein the modification is an alteration of one or more amino acids in the polypeptide sequence of the mitogenic and/or fusion promoting polypeptide compared to the wildtype polypeptide sequence of the mitogenic and/or fusion promoting polypeptide. 84. A nucleic acid encoding at least one mitogenic and/or fusion promoting polypeptide of any one of embodiments 61 to 83. 85. A cell line comprising the nucleic acid of embodiment 84. 86. The cell line of embodiment 85, wherein the cell line is a eukaryotic cell line. 87. The composition comprising the mitogenic and/or fusion promoting polypeptide or plurality of mitogenic and/or fusion promoting polypeptides of any one of embodiments 61 to 83, and a pharmaceutically acceptable excipient, carrier, or diluent. 88. The composition of any one of embodiments 61 to 83, formulated in injectable form. 89. Use of the composition of any one of embodiments 61 to 83 in a method of treating an aging disorder, a muscle wasting disorder, a muscle injury, or an injury to a connective tissue. 90. The use of embodiment 89, wherein the aging disorder is sarcopenia. 91. The use of embodiment 89, wherein the muscle wasting disorder is muscular dystrophy. 92. A method of treating an individual with an aging disorder, a muscle wasting disorder, a muscle injury, or an injury to a connective tissue comprising administering to the individual the composition of any one of embodiments 61 to 83. 93. The method of embodiment 92, wherein the aging disorder is sarcopenia. 94. The method of embodiment 92, wherein the muscle wasting disorder is a muscular dystrophy. 95. A method of producing a composition suitable for the treatment of an aging disorder, a muscle wasting disorder, a muscle injury, or an injury to a connective tissue comprising admixing a pharmaceutically acceptable excipient, carrier, or diluent with the mitogenic and/or fusion promoting polypeptide or plurality of mitogenic and/or fusion promoting polypeptides of any one of embodiments 61 to 83. 96. A method of producing a mitogenic and/or fusion promoting polypeptide comprising culturing the cell line of embodiment 95 under conditions sufficient to produce the mitogenic and/or fusion promoting polypeptide. 97. A composition comprising a mitogenic and/or fusion promoting polypeptide, wherein the mitogenic and/or fusion promoting polypeptide comprises VTN, POSTN, FGF17, THBS2, or THBS4. 98. The composition of embodiment 97, wherein the mitogenic and/or fusion promoting polypeptide comprises VTN. 99. The composition of embodiment 97, wherein the mitogenic and/or fusion promoting polypeptide comprises POSTN. 100. The composition of embodiment 97, wherein the mitogenic and/or fusion promoting polypeptide comprises FGF17. 101. The composition of embodiment 97, wherein the mitogenic and/or fusion promoting polypeptide comprises THBS2. 102. The composition of embodiment 97, wherein the mitogenic and/or fusion promoting polypeptide comprises THBS4. 103. The composition of any one of embodiments 97 to 102, wherein the composition comprises a mixture of a plurality of different mitogenic and/or fusion promoting polypeptides. 104. The composition of embodiment 103, wherein the plurality of different mitogenic and/or fusion promoting polypeptides comprise three, four, or five different mitogenic and/or fusion promoting polypeptides. 105. The composition of any one of embodiments 97 to 104, wherein the mitogenic and/or fusion promoting polypeptide or plurality of mitogenic and/or fusion promoting polypeptides are isolated and purified. 106. The composition of any one of embodiments 97 to 105, wherein the mitogenic and/or fusion promoting polypeptide or plurality of mitogenic and/or fusion promoting polypeptides are recombinantly or synthetically produced. 107. The composition of any one of embodiments 97 to 105, wherein the mitogenic and/or fusion promoting polypeptide or plurality of mitogenic and/or fusion promoting polypeptides are secreted from a stem cell. 108. The composition embodiment 107, wherein the stem cell is a pluripotent stem cell. 109. The composition of embodiment 108, wherein the stem cell is an induced pluripotent stem cell. 110. The composition of any one of embodiments 97 to 109, wherein the mitogenic activity comprises the ability to increase proliferation in a somatic cell or increase the ability of another heparin-associated polypeptide to increase proliferation in a somatic cell. 111. The composition of any one of embodiments 97 to 109, wherein the fusion promoting activity comprises the ability to increase fusion of a plurality of somatic cells or increase the ability of another heparin-associated polypeptide to increase fusion in a plurality of somatic cells. 112. The composition of embodiment 111, wherein the muscle cell precursor is a myoblast. 113. The composition of embodiment 112, wherein the somatic cell is a mammalian cell. 114. The composition of embodiment 112, wherein the somatic cell is a human cell. 115. The composition of any one of embodiments 97 to 114, wherein the mitogenic and/or fusion promoting polypeptide or plurality of mitogenic and/or fusion promoting polypeptides comprise one or more modifications to improve activity, stability, or increase polypeptide yield from a heterologous cellular production system. 116. The composition of embodiment 115, wherein the modification is an alteration of one or more amino acids in the polypeptide sequence of the mitogenic and/or fusion promoting polypeptide compared to the wildtype polypeptide sequence of the mitogenic and/or fusion promoting polypeptide. 117. The composition of embodiment 115, wherein the modification is a fusion of a mitogenic and/or fusion promoting polypeptide to a non-mitogenic and/or fusion promoting polypeptide. 118. The composition of embodiment 117, wherein the non-mitogenic and/or fusion promoting polypeptide comprises an immunoglobulin Fc region or serum albumin. 119. The composition of embodiment 117 or 108, wherein the non-mitogenic or fusion promoting polypeptide is a human polypeptide. 120. The composition of any one of embodiments 97 to 114, wherein the mitogenic and/or fusion promoting polypeptide or plurality of mitogenic and/or fusion promoting polypeptides are concatemerized. 121. The composition of embodiment 120, wherein the concatemerized polypeptides are separated by a polypeptide linker. 122. The composition of embodiment 120 or 121, wherein the concatemerized polypeptides are the same polypeptide. 123. The composition of embodiment 120 or 121, wherein the concatemerized polypeptides are different polypeptides. 124. The composition of embodiment 120 or 123, wherein the concatemerized polypeptides are covalently concatemerized through a non-peptide linkage. 125. The composition of embodiment 120 or 123, wherein the concatemerized polypeptides are non-covalently concatemerized. 126. A nucleic acid encoding a mitogenic and/or fusion promoting polypeptide of any one of embodiments 97 to 125. 127. A cell line comprising the nucleic acid of embodiment 126. 128. The cell line of embodiment 127, wherein the cell line is a eukaryotic cell line. 129. The composition comprising the mitogenic and/or fusion promoting polypeptide or plurality of mitogenic and/or fusion promoting polypeptides of any one of embodiments 97 to 125, and a pharmaceutically acceptable excipient, carrier, or diluent. 130. The composition comprising the mitogenic and/or fusion promoting polypeptide or plurality of mitogenic and/or fusion promoting polypeptides of embodiment 129, wherein the pharmaceutically acceptable excipient, carrier, or diluent increases the function of the mitogenic and/or fusion promoting polypeptide or plurality of mitogenic and/or fusion promoting polypeptides. 131. The composition comprising the mitogenic and/or fusion promoting polypeptide or plurality of mitogenic and/or fusion promoting polypeptides of embodiment 130, wherein the function comprises increasing proliferation in a muscle cell precursor, increasing stability of the mitogenic and/or fusion promoting polypeptide or plurality of mitogenic and/or fusion promoting polypeptides, or increasing bioavailability of the mitogenic and/or fusion promoting polypeptide or plurality of mitogenic and/or fusion promoting polypeptides. 132. The composition of any one of embodiments 97 to 131, formulated for subcutaneous, intravenous, intramuscular, or topical administration. 133. Use of the composition of any one of embodiments 97 to 132, in a method of treating an aging disorder, a muscle wasting disorder, a muscle injury, or an injury to a connective tissue. 134. The use of embodiment 133, wherein the aging disorder is sarcopenia. 135. The use of embodiment 133, wherein the muscle wasting disorder is a muscular dystrophy. 136. A method of treating an individual with an aging disorder, a muscle wasting disorder, a muscle injury, or an injury to a connective tissue comprising administering to the individual the composition of any one of embodiments 97 to 132. 137. A method of increasing proliferation of a muscle cell precursor or connective tissue cell precursor in an individual comprising administering to the individual the composition of any one of embodiments 97 to 132. 138. The method of embodiment 137, wherein the individual is afflicted with or suspected of being afflicted with an aging disorder, a muscle wasting disorder, a muscle injury, or an injury to a connective tissue. 139. The method of embodiment 138, wherein the aging disorder is sarcopenia. 140. The method of embodiment 138, wherein the muscle wasting disorder is a muscular dystrophy. 141. A method of producing a composition suitable for the treatment of an aging disorder, a muscle wasting disorder, a muscle injury, or an injury to a connective tissue comprising admixing a pharmaceutically acceptable excipient, carrier, or diluent with the mitogenic and/or fusion promoting polypeptide or plurality of mitogenic and/or fusion promoting polypeptides of any one of embodiments 97 to 125. 142. A method of producing a mitogenic and/or fusion promoting polypeptide comprising culturing the cell line of embodiment 127, under conditions sufficient to produce the mitogenic and/or fusion promoting polypeptide.

EXAMPLES

The following illustrative examples are representative of embodiments of the compositions and methods described herein and are not meant to be limiting in any way.

Example 1—Isolation of Heparin-Associated Polypeptides hESC Secretome Collection (Differentiated Vs Undifferentiated):

Human embryonic or induced pluripotent stem cells (H1, H9, H7 lines, and 2 iPSC lines derived from 1 healthy young adult female (18-25 years) and 1 aged female (greater than 65 year) donor), were cultured in triplicate on 10 cm plates on diluted Matrigel (1:30), in mTeSR-1 (Stem Cell Technologies), for a total media volume of 10 mL per plate. Another triplicate set of hPSCs/iPSCs were cultured on 10 cm plates and differentiated after plating in mTeSR-1 by changing the medium to DMEM/F12 with 10% Bovine Growth Serum (Hyclone), and culturing for an additional 7 days. hPSCs/iPSCs and differentiated hPSCs/iPSCs (6 plates in total) were washed twice with Opti-MEM (Gibco) and then cultured in Opti-MEM for 16 hours. 10 ml media was then collected per plate as hPSCs/iPSCs-secretome or differentiated hPSCs/iPSCs-secretome containing media. Media was spun for 5 min at 1000 g and transferred to new tubes to remove cell debris, aliquoted and flash frozen at 2 mL per plate as 0.5 mL aliquots and stored at −80 C; remaining 8 mL/plate was used immediately for heparin-associated protein purification.

Heparin-Associated Protein Purification 10 mL of Heparin-Agarose Type I Beads (H 6508, Sigma Aldrich) was washed with molecular grade water and pre-conditioned in 1 mL OptiMEM as recommended by manufacturer. 8-9 ml secretome containing media was incubated with 1 ml Heparin-Agarose Beads for 2 hours shaking at 4° C. to allow binding. Remaining heparin-depleted hPSCs/iPSCs-conditioned medium or differentiated hPSCs/iPSCs-conditioned medium was aliquoted in 15 mL tubes, flash frozen and stored at −80 C to serve as negative controls for efficacy testing. Protein bound heparin beads were washed twice via a 10 minute incubation at 4° C. in 1 mL sterile PBS+0.05% Tween. Proteins were eluted twice for 15 minutes at 4° C. in 400 µl of elution buffer A (Eluted-A) (0.01M HEPES pH 7.5+1.5M NaCl+0.1% BSA) per 10 cm plate for the first two plates, or elution buffer B (Eluted-B) lacking BSA (0.01M HEPES pH 7.5+1.5M NaCl)** for the 3rd 10 cm plate, to collect proteins in a total of 800 µl of elute per original plate. The proteins were desalted by diffusion dialysis (3500 MWCO) (by a 2 hour dialysis shaking at 4 C in 500 ml McCoy's 5A Medium or similar tissue culture medium (Gibco) followed by overnight (not more than 16 hours) dialysis shaking at 4 C in 200 ml OptiMEM (Gibco). The collected eluate was aliquoted in appropriately capped tubes, flash frozen and stored at −80 C.

Secretome Heparin-Associated Fraction Validation Assays:

BCA assay (Pierce) was performed for total protein yield in the eluate using 2 ul per sample in triplicate according to manufacturer's instructions from each Elution A sample and Elution B.

SDS-PAGE Silver Stain/SDS-PAGE Coomassie was performed for protein integrity and rough MW analysis (loading <5-10 ug per lane for each sample).

Mouse Myoblast Proliferation Assay

Reduced regeneration from an individual's tissue progenitor cells is a hallmark of aging, therefore assays that measure mitogenic capacity in tissue progenitor cells serve as a read-out for potential success of any given heparin-associated polypeptide as a regenerative factor. Measuring the increased proliferation rate of treated mouse or human muscle progenitor cells will provide good basis for potentially therapeutic regenerative factors for treating individuals who have suffered illness, injury, or who possess genetic or developmental defects leading to premature tissue loss, wasting, or weakening. As a control, the assay will also be performed on proteins purified from differentiated cells, which result in no in myoblast proliferation, cultured in medium conditioned by differentiated cells, or purified heparin-associated fractions.

Mouse muscle progenitor cells (early passage myoblasts) were cultured and expanded in mouse growth medium: Ham's F-10 (Gibco), 20% Bovine Growth Serum (Hyclone), 5 ng/mL FGF2 and 1% penicillin-streptomycin on Matrigel coated plates (1:300 matrigel: PBS), at 37° C. and 5% CO2. For experimental conditions, cells were plated at 40,000 cells/well on Matrigel coated 8-well chamber slides in 250-500 uL medium per well (1:100 matrigel: PBS) in mouse fusion medium: DMEM (Gibco)+2% horse serum (Hyclone). One hour after plating, mouse myoblasts were treated with 50% respective medias:

TABLE 4

8-well Chamber Slide A: Eluted Heparin-associated Proteins from H9/H7 hPSCs and 2 iPSC lines-4 slides total, 1 for each cell line tested.

| Fusion Media (FM) (250 uL) | 50% FM/ 50% Eluted-A Heparin-associated proteins | 50% FM/50% Differentiated hPSC-conditioned OptiMem | 50% FM/50% Differentiated hPSC-conditioned OptiMem |
|---|---|---|---|
| 50% FM (125 ul)/ 50% Growth Media (125 uL) | 50% FM/50% hPSC-conditioned OptiMEM | 50% FM/50% Heparin-depleted hESC-conditioned OptiMEM | 50% FM/ 50% Eluted-B Heparin-associated proteins (no BSA) |

TABLE 5

Assay for Eluted heparin-associated proteins purified from Differentiated hPSSs/iPSCs (Control).

| 50% FM/ 50% OptiMEM | 50% FM/ 50% Eluted-A Heparin-associated proteins | 50% FM/50% Differentiated hPSC-conditioned OptiMem | 50% FM/ 50% Eluted-B Heparin-associated proteins (no BSA) |
|---|---|---|---|

TABLE 6

8-well Chamber Slide B: Eluted Heparin-associated Protein Serial Dilution.

| Fusion Media (FM) (250 uL) | 50% FM/ 50% Eluted-A Heparin-associated protein | 75% FM/ 25% Eluted-A Heparin-associated protein | 75% FM/ 12.5% Eluted-A Heparin-associated protein |
|---|---|---|---|
| 81.25% FM/6.25% Eluted-A Heparin-associated protein | 84.375% FM/3.125% Eluted-A Heparin-associated protein | 98.44% FM/1.56% Eluted-A Heparin-associated protein | 75% FM/25% hPSC-conditioned OptiMEM |

Mouse Myoblasts were cultured for 24 hours in the above conditions, at 37° C. in 10% $CO_2$ incubator. BrdU (300 μM) in DMSO was added for 2 hours prior to fixation with cold 70% ethanol and stored at 4° C. until staining.

Quantifying Regenerative Index

Following permeabilization in PBS+0.25% Triton X-100, antigen retrieval was performed via a 10 minute 4 N HCl treatment followed by PBS washes. Primary staining was performed overnight at 4° C. in PBS+2% FBS. Primary antibodies include: a species-specific monoclonal antibody for mouse anti-embryonic Myosin Heavy Chain (eMyHC, hybridoma clone 1.652, Developmental Studies Hybridoma Bank) and Rat-anti-BrdU (Abcam Inc. ab6326). Secondary staining with fluorophore-conjugated, species-specific antibodies (Donkey anti-Rat-488, #712-485-150; Donkey anti-Mouse-488, #715-485-150; all secondary antibodies from Jackson ImmunoResearch) was performed for 1 hour at room temperature at a 1:500 dilution in PBS +2% FBS. Nuclei are visualized by Hoechst staining. For cell quantification, 5 images per well were collected at 20× in each of the channels as well as DIC to achieve at least 2000 imaged cells per condition. Using the Hoechst stain to tally cell number, the percent of cells positive for BrdU and eMyHC were tabulated and reported.

Human muscle progenitor cells (myoblasts) were similarly activated to proliferate when conditioned with hPSC-secreted heparin-associated proteins. Proliferation assays were performed on human myoblasts to test protein candidate factors for enhanced precursor cell activity in an in vitro screening assay. Conditions for culturing human muscle cells were optimized to reflect the slower rate of growth and differentiation of human muscle cells, where early passage human myoblasts were cultured for 72 hours with daily medium changes rather 24 hours, and pulsed for 4 hours with BrdU instead of 2 hours.

Example 2—Characterization of the Protein Components of the Heparin Bead Binding hPSC Secretomes Protein Quantification The protein concentration in the eluted sample was determined using the bicinchoninic acid (BCA) protein assay (Thermo Fisher Scientific, Waltham, Mass.). The protocol was performed as follows: A volume containing 100 ug protein was extracted and disulfide bonds were reduced with 5 mM tris-(2-carboxyethyl)-phosphine (TCEP), at room temperature for 25 min, and alkylated with 10 mM iodoacetamide at room temperature for 30 min in the dark). Excess iodoacetamide was quenched with 15 mM dithiothreitol (room temperature, 15 min in the dark). At this point the sample were split, with 20 μg analyzed immediately via SDS-PAGE Silver Stain, 20 μg saved for SDS-PAGE Coomassie stained gel band analysis, and 60 ug proceeded to in-solution mass spectrometry sample preparation.

Quantify the Size Distribution of Proteins

Silver staining provides a sensitive, rapid, low cost way to survey the complexity and general molecular weight distribution of the proteins in a complex mixture. By running a matched sample treated to remove glycans, the presence of this PTM common secreted proteins can be determined by the resulting shift in apparent molecular weight. Additional rounds of selective glycosylation reactions can then be run to gain insight into the identity and structure of glycan modifications on proteins of interest. Five micrograms of sample can be removed and treated with Protein Deglycosylation Mix II (NEB) to remove all N-linked and simple O-linked glycans as well as some complex O-linked glycans, which can be visualized by molecular weight shifts relative to an untreated control on a silver stained SDS-PAGE gel.

A 4-12% acrylamide gel (BioRad) in 1×MOPS buffer was loaded gel with samples (>0.20 ug/lane) and ladder (as per manufacturer's instructions), run at 200V for 45 minutes or until sample front neared the bottom of the gel, and incubated in 50% methanol/50% LC grade water >1 hour. Stain solution was prepared adding a solution of 0.8 g AgNO3 in 4 mL LC grade $H_2O$ dropwise into a solution of 1 mL 0.36% NaOH+1.4 mL 14.8M ammonium hydroxide under constant stirring followed by the addition of LC grade water to a final volume of 100 mL. Gel staining proceeded by incubating gel in stain solution for 15 minutes, before washing twice with LC grade water, allowing 5-8 minutes of incubation per wash step. The silver stain was developed by incubation in a solution of 0.25 mL 1% citric acid+25 uL 37% formaldehyde in 50 mL LC grade water for 10-15 minutes in the dark (or until desired density was achieved). Developer solution was removed and the gel washed with LC grade water to slow development for an imaging series, or development was stopped by incubation in a solution of 45% methanol, 10% acetic acid.

In-Solution Mass Spectrometry Sample Preparation

Methanol-chloroform precipitation was performed prior to protease digestion (a standard trichloroacetic acid-based precipitation protocol would be substituted here if protein yield from the heparin bead eluates are below 25 ug total). In brief, four parts neat methanol was added to each sample and vortexed, one part chloroform was added to the sample and vortexed, and three parts water was added to the sample and vortexed. The sample was centrifuged at 4,000 RPM for 15 min at room temperature and subsequently washed twice with 100% methanol, prior to air-drying. Samples were resuspended in 50 mM HEPES pH 8.5 and digested at room temperature for 12 hrs with LysC protease at a 100:1 protein-to-protease ratio. Trypsin was then added at a 100:1 protein-to-protease ratio and the reaction was incubated 6 hours at 37° C. Peptide concentrations in the digests were measured using the Quantitative Colorometric Peptide assay kit (Pierce). From each sample bug of peptide digestion solution was taken and enzymatic activity quenched with formic acid to a final pH of <2 before de-salting via C-18 Stagetips, using a standard formic acid/acetonitrile buffer system. Stagetips were eluted directly into autosampler vials in a buffer of 70% acetonitrile and 1% formic acid, dried in a vacuum concentrator, and stored at −80 C until being resuspended to ~1 ug/µl of Buffer A (typically ~0.2% formic acid, 5% acetonitrile) for mass spectrometry analysis.

SDS-PAGE Coomassie and in-Gel Band Mass Spectrometry Sample Preparation

A gel based sample preparation pipeline may be employed if the abundance distribution of the sample is heavily skewed, or where only a few species of proteins account for a substantial majority of the molecules in the sample. This size based separation method has been shown to effectively improve depth of proteomic coverage in biochemically purified protein mixtures.

Briefly, the protocol begins by running >20 ug per lane of sample out on an SDS-PAGE as in the Silver Stain method above, staining and destaining by Coomassie as per manufacturer's instructions, excising sections of the gel containing potentially interesting proteins, and cutting excised gel sections into 1 mm×1 mm squares. Ensure gel pieces are at neutral pH by adding 50-100 µl 100 mM Ammonium bicarbonate, let sit for 10 minutes and discard. Wash gel pieces with 100-150 µl 50 mM Ammonium bicarbonate/50% acetonitrile for 10 minutes, vortexing every 5 minutes to dehydrate. Depending on intensity of stain, repeat step 9 until the gel pieces are clear. Discard solution phase and dry samples in speed vac for 5-10 minutes. To digest proteins add 5 pmol sequencing grade trypsin (Promega Corp.) in 50 mM Ammonium bicarbonate and 0.02% Protease Max to each sample and incubate overnight in 37° C. on a shaking heatblock. Spin down samples at 1000G for 2 minutes, pull off all liquid, and transfer to a glass autosampler vial. Add 40-50 µl 1% formic acid, 66% acetonitrile 33% 100 mM Ammonium bicarbonate and incubate for 10 minutes at 37° C. to increase peptide release from gel. Spin at 10,000G for 2 minutes to pellet insoluble protein or detergent degradation production. Extract all solution being sure to avoid pellet areas and combine into autosampler vial. Speed vac total combined extracts to dryness and store at −80 C until being resuspended to ~1 ug/µl of Buffer A (typically ~0.2% formic acid, 5% acetonitrile) for mass spectrometry analysis.

nHPLC-MS2 Instrumentation and Analysis

Two, 3-hr gradients were collected per sample using an Orbitrap Fusion instrument coupled to a Waters liquid chromatography (LC) pump (Thermo Fisher Scientific). Peptides are fractionated on a 100 µm inner diameter microcapillary column packed with ~25 cm of Accucore 150 resin (1.2 µm, 150 Å, ThermoFisher Scientific). For each analysis, 1 µg per sample was loaded onto the column. Peptides were separated using a 3 hr gradient of 6 to 46% acetonitrile in 0.2% formic acid at a flow rate of ~400 nL/min. Instrument settings for the Orbitrap fusion were as follows: FTMS1 resolution (120,000), ITMS2 isolation window (0.4 m/z), ITMS2 max ion time (120 ms), ITMS2 AGC (2E4), ITMS2 CID energy (35%), dynamic exclusion window (90 sec). A TOP10 method was used where each FTMS1 scan was used to select up to 10 FTMS2 precursors for interrogation by HCD-MS2 with readout in the orbitrap.

Data Analysis

Resulting mass spectra were searched using commercially available analysis software (e.g., Byonic) against a human database publicly available from Uniprot which was concatenated with common contaminants and reversed sequences of the human and contaminant proteins as decoys for FDR determination. Searches restricted the precursor ion tolerance to 20 ppm, and product ion tolerance window was set to 0.5 m/z. Searches allowed up to two missed cleavages, including static carbamidomethylation of cysteine residues (+57.021 Da) and variable oxidation of methionine residues (+15.995 Da). Additional variable modifications may be included, particularly glycosylations, based on the results of the gel shift assay following de-glycosylation treatment or the preview search PTM scan. Results were filtered to a 1% FDR at the protein level per sample.

Example 3—In Vitro Screening of Stem Cell Secreted Factors

A deeper understanding of a given protein factor's contribution to the regenerative effects of the pool of heparin-associated hPSC secretome will be gained by screening against an established panel of assays for cellular age. Assays include measurements of reactive oxygen species (ROS) production or tolerance, cytoplasmically and in the mitochondria, telomerase activity, measurements of proteostasis capacity via lysosomal, autophagy, and proteasomal routes, epigenetic re-patterning, and cellular energy balance (e.g., ATP/ADP and NAD/NADH ratios). Many of these assay leverage the high-throughput automated microscopy described above to make these measurements in a variety of cell types, including fibroblast, endothelial cells, mesenchymal stem cells, and chondrocytes. Collectively these metrics can inform both the pathway and the mechanisms by which the heparin-associated hPSC secretome or its individual components enact their regenerative effects.

To begin screening and validating potential regenerative protein factors protein coding sequences will be collected from a publicly available source, such as used for the proteomics analysis (e.g., UniProt). The sequence for each of the proteins will be used to construct a DNA sequence encoding the proteins. The sequences are then each cloned into a plasmid vector system tailored for inducible or constitutive high-copy expression (in mammalian or prokaryotic settings). Alternatively such a plasmid vector system may be designed in silico. Such a plasmid can be transformed into a pool of cells where the encoded protein was transiently expressed from the plasmid. Alternatively the gene of interest could be incorporated in the genomes of a pool of cells (e.g. lentiviral transduction for mammalian cells or homologous recombination for *S. cerevisiae*) to create stable cell lines for recombinant protein production.

To de-bulk the target factor list and validate recombinant expression for factor production, a viable route would be to express the construct in a human cell line (like 293T-REx), which exploits: 1) that proteins of interest naturally purify themselves during the secretion process; and 2) will be processed in a natural context, potentially preserving important post translational processing steps. T-REx cells will be grown on 10 cm plates to ~50% confluence in DMEM with 10% Bovine Growth Serum (Hyclone), 2 mM L-glutamine, and 1% Pen-Strep before initiating translation of a target protein of interest for 48 hr. The media would be collected, spun at 2,000 g to purify, and the supernatant used for heparin-associated enrichment of target factors in mouse myoblast regeneration assays.

Machine Learning Classifier

By combining and statistically comparing the information from the Regenerative index assay, the Panel of Cellular Age Makers, the Proteomics we can create deep feature vectors for each protein factor, the pool of all factors (from each repeat of the assays), and the negative control pool (from each repeat of the assays). Treating the pool of all factors (or known factors such as FGF-2) as True Positives, and the negative control pool (or known non-functional proteins such as BSA) as True Negatives a supervised clustering algorithm can be trained to classify protein factors. Using a standard 10-fold cross validation scheme to assess the relative accuracy, recall, and confusion matrix graphs of the output of various algorithms' outputs (eg, Naive Bayes, Support Vector Machine, Linear Regression, or Random Forest) trained classifier most likely to successfully distinguish proteins with regenerative potential from the set of target factors can be selected. Target factors (or tested combinations) can then be rank ordered by the probability they derive from the regenerative set compared to the null set. A number of the top scoring target factors (or tested combinations) will then be selected for GMP-grade production for in vivo and in vitro validation.

Based on the complexity of the original heparin-associated fraction of the hPSC secretome and the limits to which individual proteins can recapitulate the activity of the whole pool, we will test combinations of factors as well. In the simplest approach, we would combine the 293T-REx secretome containing media from two or more cell lines each producing a given factor, and test their combined regenerative efficacy across a range of concentrations in an isobologram analysis using the regenerative index from the Myoblast Regeneration assay.

Example 4—In Vivo Testing of Stem Cell Secreted Factors

There are two main aspects of muscle degeneration with aging, acute loss following trauma and chronic wasting (sarcopenia), and both of them will be tested. As the therapeutic approach to each case is expected to be different two arms for the in vivo validation is envisioned to specifically test each use-case for the factors as therapeutics in humans. The following Acute Injury Model and Sarcopenia/Chronic Administration Model for the most promising proteins emerging from the machine learning classifier can be carried out.

Acute Injury Model

Animals were kept under standard animal husbandry condition. Animals were fed standard chow, and have ad libitum access to food and water. Temperature were kept at 22° C. and 12 h light/12 h dark cycles. Animals were acclimated prior to study initiation. The experimental design was: C57BL/6J male mice, N=18; Young: 12-13 week old (3-month-old) mice, n=6; Aged: 77-78 week old (18-month-old) mice, n=12. This design was used to test any single factor identified and validated in in vitro assays or complex mixtures of 2 or more factors.

TABLE 7

Experimental design of acute injury model.

| No | Group | n | Test | Dose (mg/kg) | Administration | Blood collection | Tissue collection |
|---|---|---|---|---|---|---|---|
| 1 | Young, Vehicle | 6 | vehicle | n/a | i.m, q.d; into injured muscle site on day 0, and 2 | terminal | TA/GA muscles into 25% sucrose; Brain, liver, heart, and lung into 4% PFA |
| 2 | Aged, Vehicle | 6 | vehicle | n/a | | | |
| 3 | Aged, Test factor | 6 | Test factor | 0.1 | | | |

On Day 0, mice were weighed and underwent muscle injury with focal injection of barium chloride (BaCl, 10 µL, 1.2% w/v in saline, Sigma-Aldrich) in the Tibialis anterior (TA; Day 0) of both the right and left hindlegs. Injections of vehicle or factor A (0.1 mg/kg) were co-administered intramuscularly (i.m) following the BaCl into the TA injured hindleg sites, and again 48 hours later on day 2 (i.m.) into the TA injured hindleg sites. Also on day 2, BaCl (Ctx; 10 µL, 1.2% w/v in saline, Sigma-Aldrich) was injected into the Gastrocnemius (GA, Day 2, i.m.) muscles of both right and left hind legs. Injections of vehicle or a factor were sequentially administered (i.m.) following the BaCl into the TA hindleg sites post-injury, and again 48 hours later on day 4 (i.m.) into the GA injured hind leg sites. Bromodeoxyuridine (BrdU) was be administered (100 mg/kg, i.p.) once daily for 3 days, day 2-4, before sacrifice to label proliferating cells.

On day 5, animals were sacrificed and animal weight recorded followed by collecting 0.5 ml of terminal blood via cardiac puncture which was processed to plasma and stored at 80° C. We then perfused the animal with 1×PBS, carefully dissected the skin from the GA/TA muscles of each hind leg and took photos (prior to excision). After excision of exclusively the GA or TA muscle, excised tissue was photographed, weighed, then placed into 25% sucrose in PBS at 4° C. for 4 hr rinsed in 1×PBS, immersed in Tissue-TEK OCT and rapidly frozen efore storing the muscles tissues frozen at 80° C. Cryosectioning and H&E were performed to ensure muscle injury site was appropriately visualized. A diagram of the time points for these experiments can be seen in FIG. 2A. Muscle tissue composition from new skeletal muscle fibers, fibrotic tissue, and adipose (fat), were measured. Muscle regeneration, as defined as the number of number of new myofibers with centrally located nuclei per millimeter, fibrosis as defined as the area of fibrotic scarring, size of the fibers, as defined as the width and area, adipose tissue, as defined by the amount of fat surrounding the muscle, were measured to assess level of regeneration.

Figure 2C:
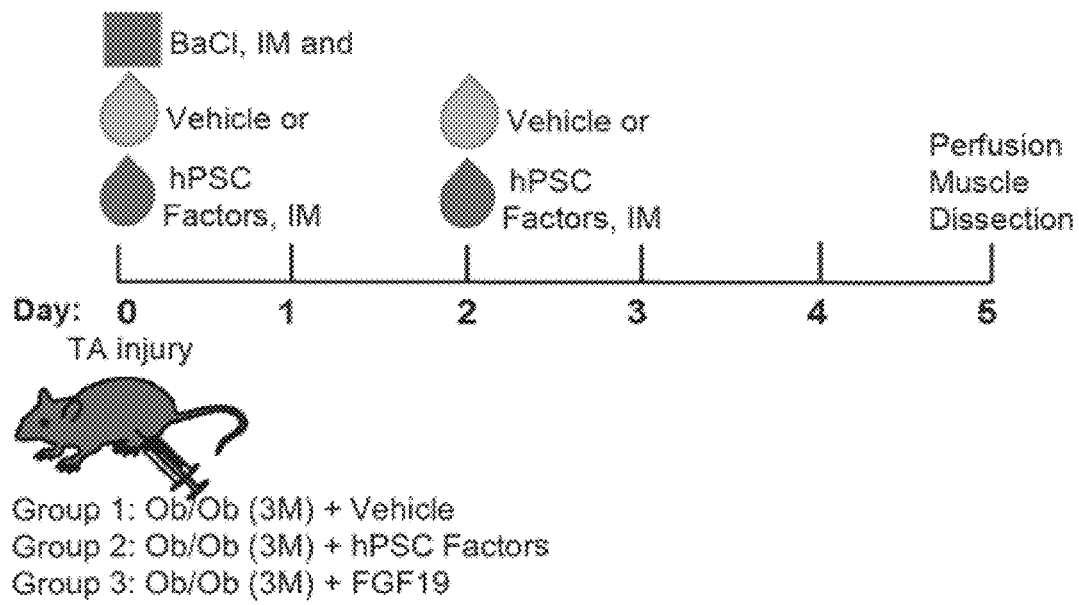
FIG. 2C shows time-points for dosing and analysis of the effects of the entire pool of heparin-associated polypeptides in an acute injury model in transgenic mice prone to obesity. Squares denote injury inducing intramuscular injection (IM) with Barium Chloride; circles denote administration of treatment or vehicle.
Figure 2D:
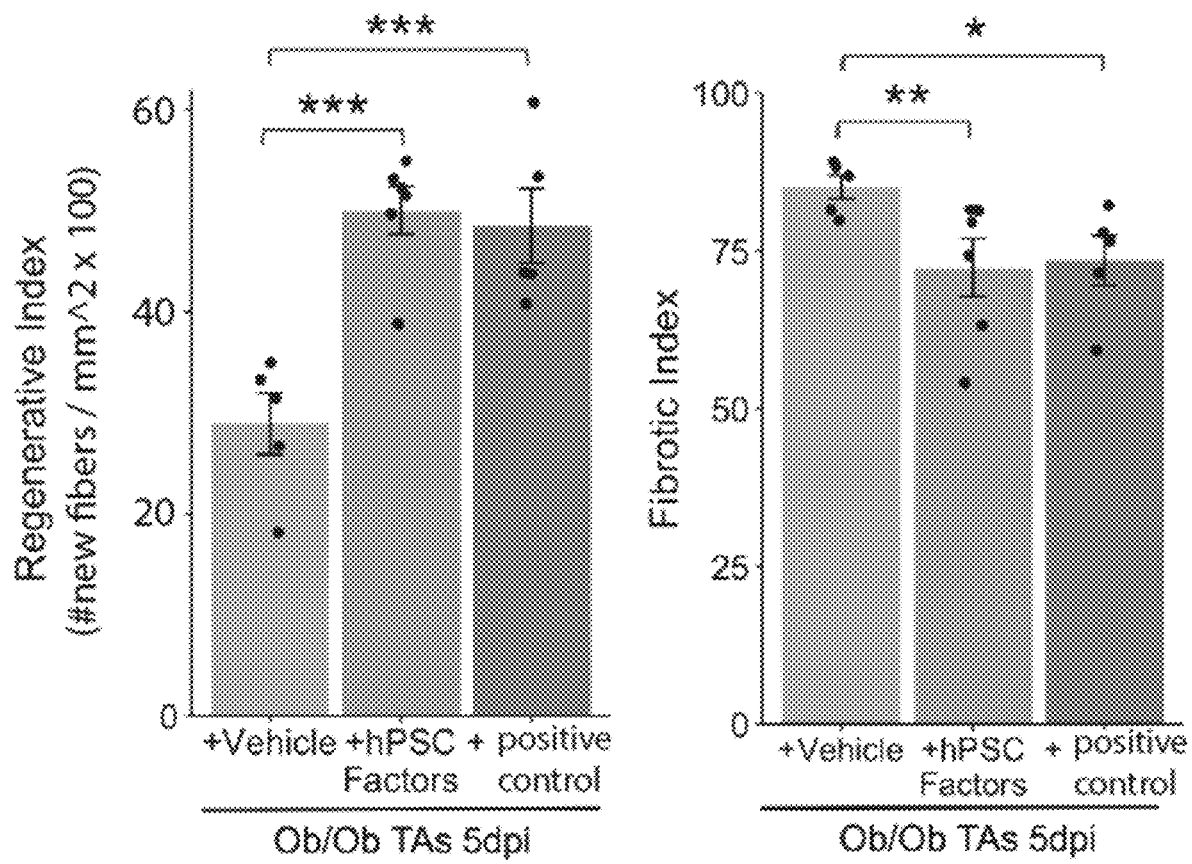
FIG. 2D shows the results of the experiment outlined in FIG. 2C. Administration of hPSC derived factors resulted in improved new fiber formation (regenerative index, left, $p<3.5E-6$) and reduced scaring (fibrotic index, right, $p<8.44E-3$) in transgenic obese mice to levels similar to those in positive control (8 ng FGF19) treated mice ($p<2.3E-5$ and $p<2.32E-2$, respectively), both of which were markedly better than vehicle-treated transgenic obese mice. Stars indicate degree of significance from one-way ANOVA tests.

Young muscle regeneration after acute focal injury had the highest regenerative index (measured as the number of new myofibers with centrally located nuclei per millimeter squared). Aged muscle regeneration following acute injuries performed on average 30-50% less than young muscle regeneration, in part due to the reduction of mitogenic muscle precursor/progenitor cell activity (FIG. 2B). It was predicted that systemic treatment of aged animals, injured animals, animals with genetic diseases causing muscle wasting, or animals injured by radiation or other tissue damaging treatment, the heparin-associated polypeptides, individually or in various combinations, will improve skeletal muscle regeneration by 20-50%, approaching comparable levels to young healthy animals. It was also predicted that the composition of fibrous scar tissue and fat tissue will be reduced to levels comparable to younger animals by treatment with the heparin-associated polypeptides. And indeed, treatment with the heparin-associated polypeptides did improve the skeletal muscle regeneration of sarcopenic mice to level indistinguishable from the young by both the number of new myoblasts and the reduction in fibrous scar tissue (FIG. 2B).

Sarcopenia/Chronic Administration Model

After arrival, animals will be kept under standard animal husbandry condition. Animals will be fed standard chow, and have ad libitum access to food and water. Temperature will be kept at 22° C. and 12 h light/12 h dark cycles. Animals will be acclimated prior to study initiation, including any in vivo assay acclimation, if necessary. The experimental design was C57BL/6J male mice, N=18; Young: 12-13 week old (3-month-old) mice, n=6; Aged: 77-78 week old (18-month-old) mice, n=12. This design can be used to test any single factor identified and validated in in vitro assays or complex mixtures of 2 or more factors.

ensuring muscle injury site is appropriately visualized. Carefully excise the inguinal white adipose tissue (WAT) and weigh tissue. Discard WAT post-weighing.

Collected brain, liver, heart and lung can be post-fixed in 4% PFA for 72 hours, after 72 hours, transferred into 30% sucrose in 1×PBS and stored at −4° C. (brain, liver, heart, lung).

Muscle tissue composition, from new skeletal muscle fibers, fibrotic tissue, and adipose (fat), will be measured. Muscle regeneration, as defined as the number of number of new myofibers with centrally located nuclei per millimeter, fibrosis, as defined as the area of fibrotic scarring, size of the fibers, as defined as the width and area, adipose tissue, as defined by the amount of fat surrounding the muscle, will be measured to assess level of regeneration. Weights of the animals during the duration of treatment with heparin-associated polypeptide(s), as well as healthspan assays including performance on a running wheel (speed, distance, duration), grip strength, and performance on a horizontal bar will take into account the phenotypic outcomes of treatment of the aged animals systemically with the heparin-associated polypeptides for sarcopenia.

TABLE 8

Design of sarcopenia/chronic administration model.

| No | Group | n | Test | Dose (mg/kg) | Administration | In vivo assay | Blood collection | Tissue collection |
|---|---|---|---|---|---|---|---|---|
| 1 | Young, Vehicle | 6 | vehicle | n/a | i.p, q.d; on day −8 to +5 | 2 sets of: Animal weight, grip strength, running wheel performance; horizontal bar 1 set of: In capacitance | terminal | TA/GA muscles into 25% sucrose; Brain, liver, heart, and lung into 4% PFA |
| 2 | Aged, Vehicle | 6 | vehicle | n/a | | | | |
| 3 | Aged, Test factor | 6 | Test factor | 0.1 | | | | |

On Day −10, mice will have the following in vivo healthspan measurements will be performed over 1 day as a baseline for age-based parameters: Weight, running wheel performance, grip strength, and horizontal bar. Each assay should be run for 4 trials per assay per animal. These healthspan assays will be repeated on day −1. After one day of rest on day −9, mice will begin 1× daily injections (0.1 mg/kg) of vehicle or factor A for the remainder of the experiment until sacrifice (days −8 to +5, 13 days of dosing). On day −4, 6 days after dosing begins, mice will undergo a repeat of the healthspan assays. On day 0, 5 days prior to sacrifice, mice will undergo muscle injury with focal injection of cardiotoxin (Ctx; 10 Sigma-Aldrich) in the Tibialis anterior (TA; Day 0) of the right hindleg only. On day 2, the Gastrocnemius (GA; Day 2) muscle of the right hind leg will then receive cardiotoxin (Ctx; 10 Sigma-Aldrich). BrdU will be administered (100 mg/kg, i.p.) once daily for 3 days, day 2-4, before sacrifice. On day +5, prior to take-down, the animals will have an in vivo incapacitance assay run. On day +5, animals will be sacrificed and animal weight recorded. Collect 0.5 ml of blood via cardiac puncture, process to plasma and store plasma samples at 80° C. The animals will then be perfused with 1×PBS. Carefully dissect the skin from the GA/TA muscles of each hind leg and take photos (prior to excision). After excision of exclusively the GA or TA muscle, weigh the muscles, then place muscles into 25% sucrose in PBS at 4° C. for 4 hr. Then rinse the muscles in 1×PBS, adding Tissue-TEK OCT and storing the muscles tissues frozen at 80° C. Perform cryosectioning and H&E, The horizontal bar test is performed as described previously (Malinowska et al. 2010) at 8 months (n=6 WT, n=7 MPS IIIB) and 10 months (n=3 WT, n=4 MPS IIIB) of age. In brief, a 300-mm metal wire, 2 mm in diameter, was secured between two posts 320 mm above a padded surface. The mouse was allowed to grip the center of the wire and the time to fall or reach the side was recorded, and after 2 min the test was stopped. Crossing the bar in x seconds was scored as 240−x, remaining on the bar was scored as 120, and falling off the bar after y seconds was recorded as the value of y. The test was repeated three times as a practice run followed by a 10-min rest prior to three tests where the score was recorded.

Young muscle regeneration after acute focal injury has the highest regenerative index (measured as the number of new myofibers with centrally located nuclei per millimeter squared). Aged muscle regeneration following acute injuries performs on average 30-50% less than young muscle regeneration, in part due to the reduction of mitogenic muscle precursor/progenitor cell activity. We predict systemic treatment of aged animals, injured animals, animals with genetic diseases causing muscle wasting, or animals injured by radiation or other tissue damaging treatment, the heparin-associated polypeptides, individually or in various combinations, will improve skeletal muscle regeneration by 20-50%, approaching comparable levels to young healthy animals. We also predict the composition of fibrous scar tissue and fat tissue will be reduced to levels comparable to younger animals by treatment with the heparin-associated polypeptides.

Animals will also have better healthspan outcomes: reduced weight, fat composition, scar tissue around muscles, increased running speed, duration, and distance, increased grip strength, and enhanced performance on the horizontal bar test.

Example 5—Additional Tests for Pro-Regenerative Factors

Mechanistic insight into a given heparin-associated polypeptide factor's pathway of action will be gained by establishing and screening against a panel of assays for cellular age. Assays include measurements of reactive oxygen species (ROS) production or tolerance cytoplasmically and in the mitochondria, telomerase activity, measurements of proteostasis capacity via lysosomal, autophagy, and proteasomal routes, epigenetic re-patterning, and cellular energy balance (e.g., ATP/ADP and NAD/NADH ratios). Many of these assay leverage high-throughput automated microscopy to make these measurements in a variety of cell types, including fibroblast, endothelial cells, mesenchymal stem cells, and chondrocytes. Collectively these metrics can inform both the pathway and the mechanisms by which the heparin-associated hPSC secretome or its individual components enact their regenerative effects. These deep profile vectors can be crucial for approaching combinations of factors rationally, and for machine learning predictions.

To test the cellular effects of secretomes toward reversing the hallmarks of aging, high-throughput automated imaging and quantification of single cells to achieve deep population level statistical power can be employed. Cellular component state profiles of Young, Aged, and Aged+Treatment in human fibroblasts and epithelial cells, myoblasts, mesenchymal stem cells, chondrocytes, and neural progenitor cells will be compared. Some examples of tests and methods include:

1) Epigenetic reprogramming: repressive mark H3K9me3, the heterochromatin-associated protein HP1γ, nuclear lamina support protein LAP2α
2) Nuclear membrane Folding/Blebbing: immunofluorescence of the nuclear membrane protein Lamin A/C
3) Proteolytic Activity: Cleavage of fluorescent-tagged chymotrypsin like substrate corresponds to proteasome 20S core particle activity. Wells are first stained with PrestoBlue Cell Viability dye (Life Technologies) for 10 minutes. Well signals are read using a TECAN fluorescence plate reader as a measure of cell count. Then cells are washed with HBSS/Ca/Mg before switching to original media containing the chymotrypsin like fluorogenic substrate LLVY-R110 (Sigma) which is cleaved by the proteasome 20S core particle. Cells are then incubated at 37° C. in 5% CO2 for 2 hours before signals are again read on the TECAN fluorescence plate reader. Readings are then normalized by PrestoBlue cell count.
4) Formation of autophagosomes: Autophagosome number and volume are measured by staining with CellTracker Deep Red (Sigma). The cells are then incubated at 37° C. in 5% CO2 for 20 minutes, washed 2 times using HBSS/Ca/Mg, and stained for 15 minutes using CellTracker Deep Red cell labeling dye. Cells are then switched to HBSS/Ca/Mg for single cell imaging using the Operetta High Content Imaging System (Perkin Elmer).
5) Energy Metabolism: ATP in the cells is measured using colorimetric assay using an ATP assay kit (ab83355; Abcam, Cambridge, Mass.) following manufacturer's instructions. Cells are washed in cold phosphate buffered saline and homogenized and centrifuged to collect the supernatant. The samples are loaded with assay buffer in triplicate. ATP reaction mix and background control (50 μL) is added to the wells and incubated for 30 min in dark. The plate is read at OD 570 nm using SpectraMax M2e (Molecular Devices, Sunnyvale, Calif.). The mean optical density is used to estimate of the intracellular ATP concentration relative to the standard curve.
6) Mitochondrial Activity: To measure Mitochondria Membrane Potential, cells are washed twice with Ham's F10 (no serum or pen/strep). Subsequently, MuSCs are stained with MitoTracker Green FM (ThermoFisher, M7514) and DAPI for 30 minutes at 37° C., washed three times with Ham's F10, and analyzed using a BD FACSAria III flow cytometer. To measure
7) Mitochondrial ROS Measurement. Cells are washed with HBSS/Ca/Mg and then switched to HBSS/Ca/Mg containing MitoSOX (Thermo), a live cell permeant flurogenic dye that is selectively targeted to mitochondria and fluoresces when oxidized by superoxide. Cells are incubated for 10 minutes at 37° C. in 5% CO2. Cells are then washed twice with HBSS/Ca/Mg, and stained for 15 minutes using CellTracker Deep Red. Finally, cells are imaged in fresh HBSS/Ca/Mg using the Operetta High Content Imaging System (Perkin Elmer).
8) Deregulated Nutrient Sensing: levels of SIRT1 are measured.
9) Senescence: Senescence-associated beta-galactosidase staining is measured in cells washed twice with PBS then fixed with 15% Paraformaldehyde in PBS for 6 minutes. Cells are rinsed 3 times with PBS before staining with X-gal chromogenic substrate, which is cleaved by endogenous Beta galactosidase. Plates are kept in the staining solution, Parafilmed, to prevent from drying out, and incubated overnight at 37° C. with ambient CO2. The next day, cells are washed again with PBS before switching to a 70% glycerol solution for imaging under a Leica brightfield microscope.
10) Secretome of the cells: Mass-Spec or O-Link for inflammatory cytokines profiles Soft Tissue Deposition: Immunofluorescence for SOX9, MMP3, MMP13, and COL2A1 expression, the decrease of which is characterized by cartilage loss, pain, cleft-lip, and joint destruction.

Example 6—Identification of Pro-Regenerative Factors by Mass Spectroscopy

Figure 3A:
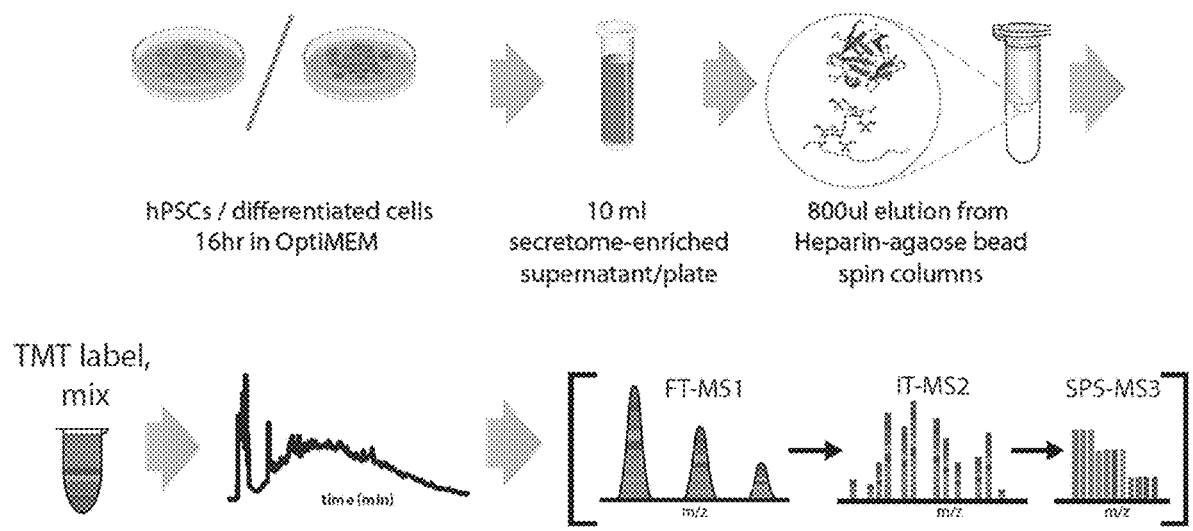
FIGS. 3A to 3D. Heparin-column enrichment of secreted factors from hESC and differentiated cells can be deeply profiled in an unbiased way using isobaric labeling, online reverse phase fractionation, and an SPS-MS3 instrument method.

Factors enriched in the secretome of undifferentiated hPSCs can be determined by Mass spectroscopy. A schematic of a type of mass spectroscopy experiment employed herein is shown in FIG. 3A.

Five confluent, 15 cm plates of cells per biological replicate were washed with OptiMEM—a basal, synthetic medium—, and then incubated in OptiMEM for 16 hours, yielding roughly 100 ml of media. The media, now containing secreted factors, was collected, cells and cell debris removed by centrifugation, and flash frozen for storage at −80 C until processing. The target factors were enriched via affinity purification for heparin binding using heparin-agarose bead columns. Heparin-agarose beads (Sigma) were washed with water twice, and once with OptiMEM (minus phenol red), before incubating with factor containing culture media for 2 h at 4° C. shaking at 100 rpm. The ratio of bead slurry (~50% beads) to media can be effective at 1:10, 1:20, 1:30, 1:40, and 1:50. Heparin-agarose beads were then collected into a column by centrifugation in an Amicon Pro Purification System column set in a 50 ml conical tube at 1000 g for 5 min, washed with 10× column volumes of PBS+0.05% tween at 4° C. twice. Factors were eluted via two repeats of the following: addition of a high salt solution (1.5M NaCl, 0.01M HEPES, pH 7.2, at ratio of 0.4 ml elution buffer per milliliter of bead slurry), incubated at 4° C. for 10 minutes at 100 rpm, and centrifugation at 1000 g for 5 min into a fresh collection tube.

Figure 3B:
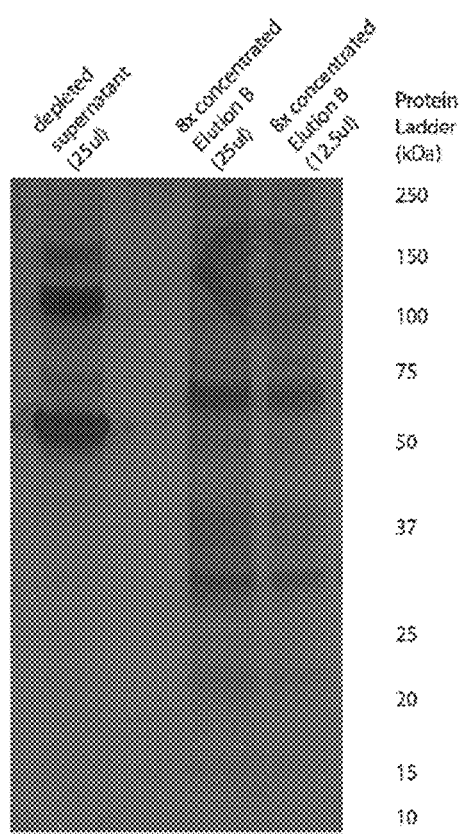

Protein concentration in the eluted fraction was assayed by silver stain densitometry as shown in FIG. 3B, and a BCA assay against standard curves for bovine serum albumin. Protein disulfide bonds were reduced by incubation in 5 mM tris-(2-carboxyethyl)-phosphine (TCEP) for 25 min, and the free cysteines alkylated with 10 mM iodoacetamide at room temperature for 30 min in the dark. Excess iodoacetamide was quenched with 15 mM dithiothreitol during a 15 min incubation. The eluates from all samples were then further purified by protein precipitation using trichloroacetic acid, prior to resuspending in digest buffer and 16 hr of digestion using a mixture of modified Trypsin and Lys-C to yield peptides predominantly with terminal arginine or lysine residues. The resulting peptide concentration were measured using a quantitative colorimetric peptide assay (Promega), and equimolar amounts of peptides from each biological replicate labeled at their free amines with tandem mass tags (TMT) using manufacturer recommended conditions before mixing the peptides. The mixed sample was desalted via reverse phase separation on a C18 StageTip prior to analysis via nHPLC-SPSMS3 on a Fusion Lumos (Thermo Fisher). A TOP10 method was used to select up to 10 MS2 precursors for identification by CID-MS2 analyzed in the ion trap. For synchronous precursor selection of up to 10 ion windows, the FTMS3 isolation window was 0.4 m/z, max ion time 150 ms, automatic gain control 1.5E5, and FTMS3 resolution was 50,000. Resulting spectra were searched using commercial MS analysis software against the Uniprot human database (2018) protein sequences (Swiss-Prot and TrEMBL) concatenated with their reversed sequences as decoys for FDR determination, appended to common contaminant sequences. Searches restricted the precursor ion tolerance to 50 ppm and the product ion tolerance window to 0.9 m/z (or 50 ppm), allowed no more than two missed cleavages, included static modification of lysine residues, arginine residues and peptide N-termini with TMT tags (+229.163 Da), static carbamidomethylation of cysteine residues (+57.021 Da), and variable oxidation of methionine residues (+15.995 Da).

Results were filtered to a 1% FDR at the peptide and then protein level using the target-decoy strategy. Peptides were assigned to protein groups, and individual proteins by the parsimony principle. Proteins were quantified by summing reporter ion intensities across all PSMs with greater than 70% of their spectral intensity deriving from matched ions and a summed signal to noise intensity greater than 200, normalizing channel level intensities, and computing the percent contribution of a given channel to the total signal. These values were then used for additional statistical modelling of differential abundance.

Figure 3C:
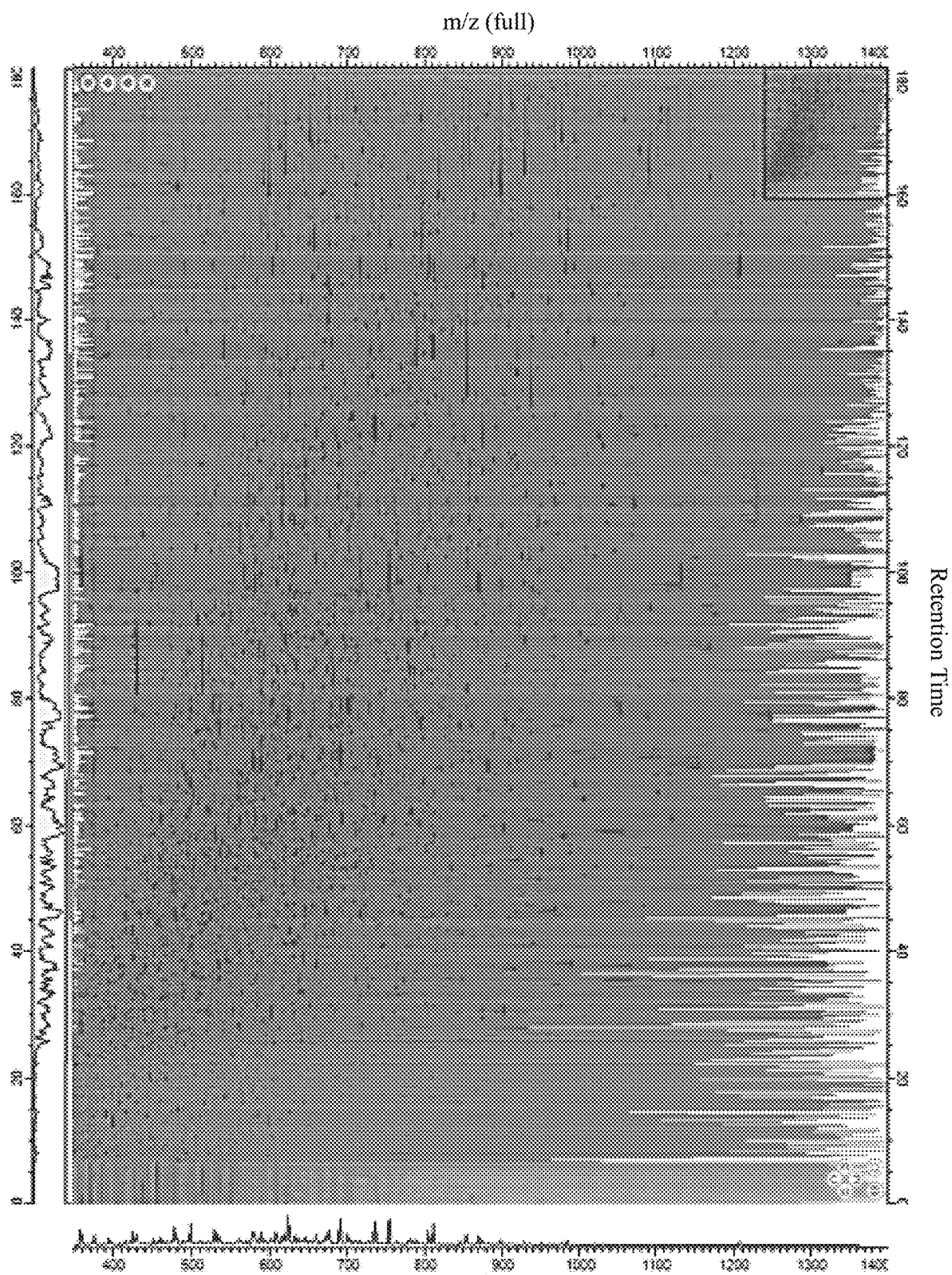
Figure 3D:
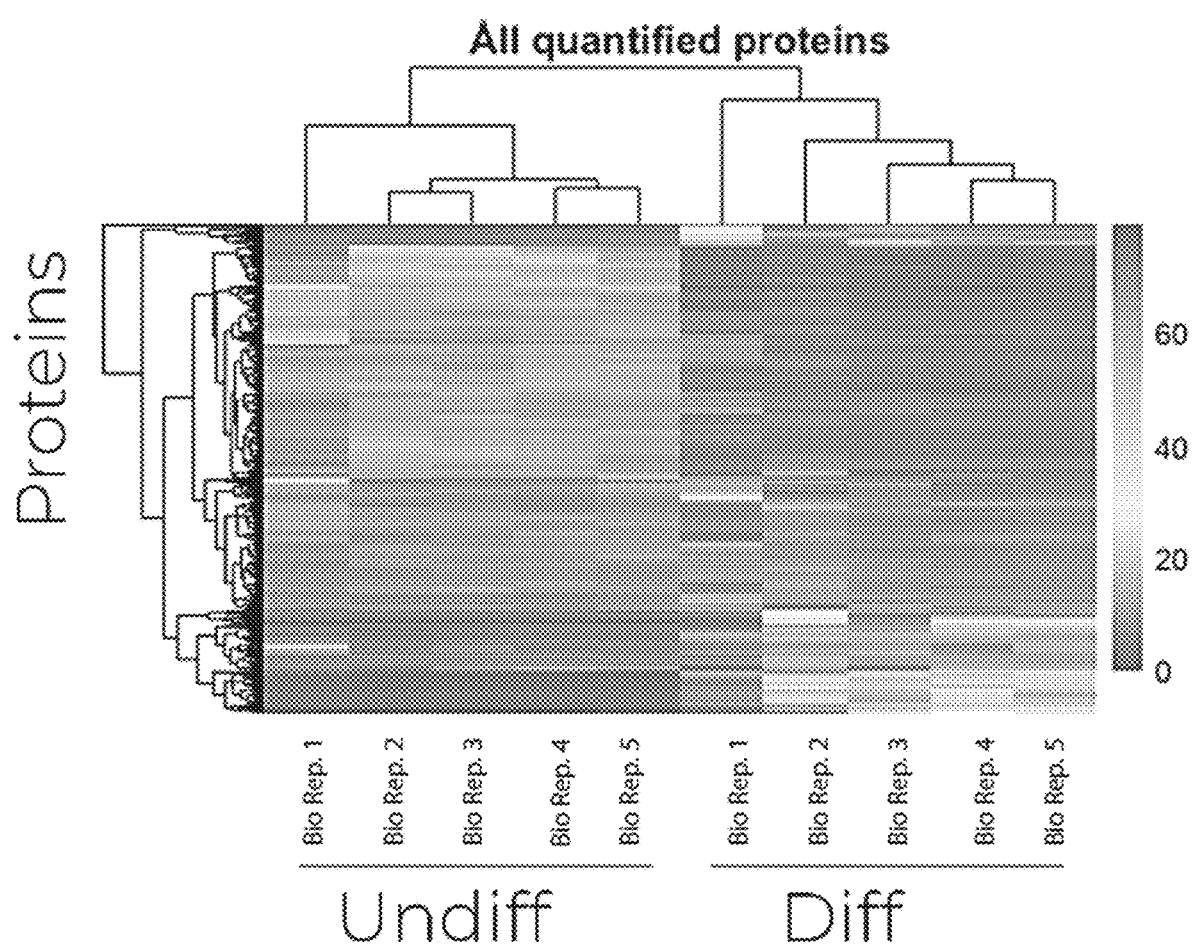
Figure 3E:
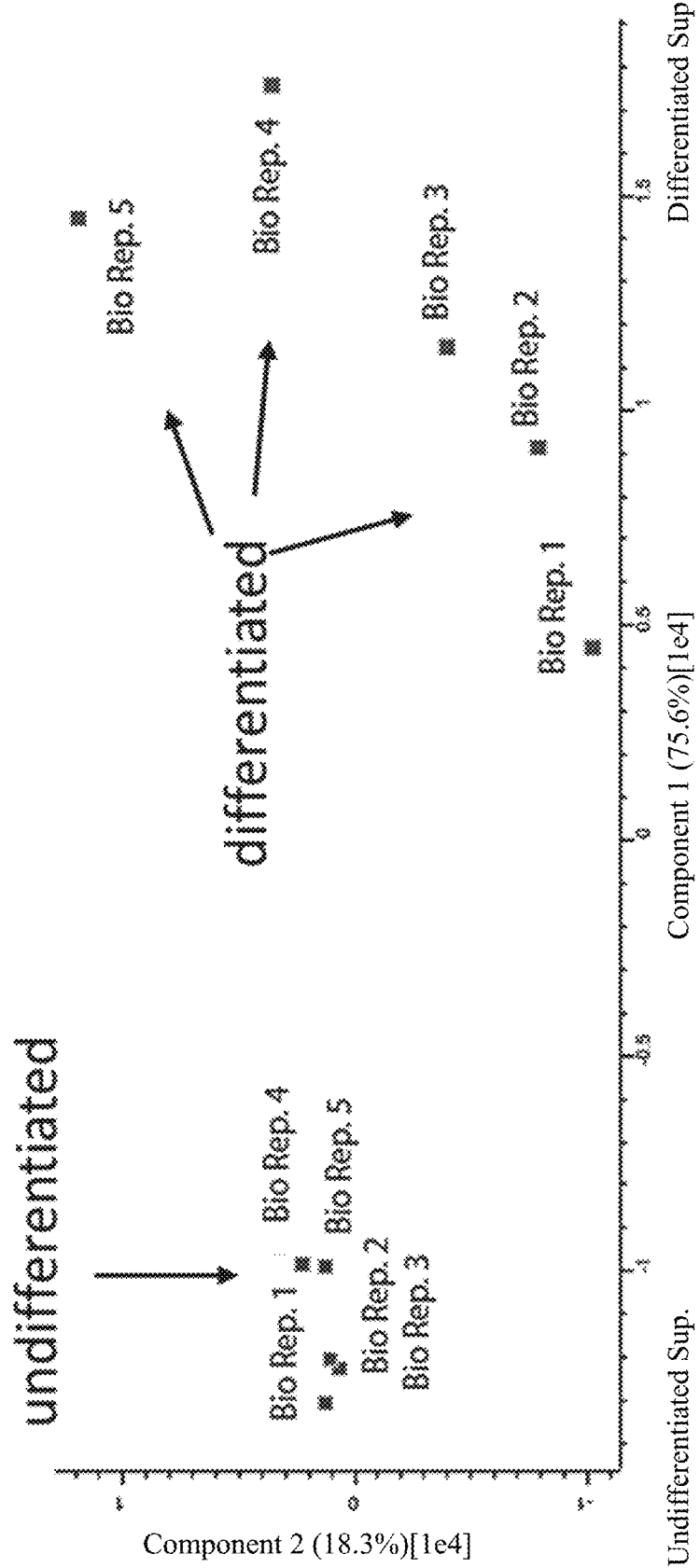
FIG. 3E depicts Principle Component Analysis of proteins from the same run demonstrating again the differential expressionless (PC1) as well as a high relative degree of reproducibility from undifferentiated hPSCs compared to differentiated cells.

Heparin-associated proteins from undifferentiated and differentiated supernatants generated distinct sets of secreted factors as indicated by FIGS. 3C, 3D and 3E. Combined results from such experiments are summarized in Table 2 shown previously herein, by the gene name, UniProt ID, Entrez Gene ID, and Ensembl ID.

Figure 4A:
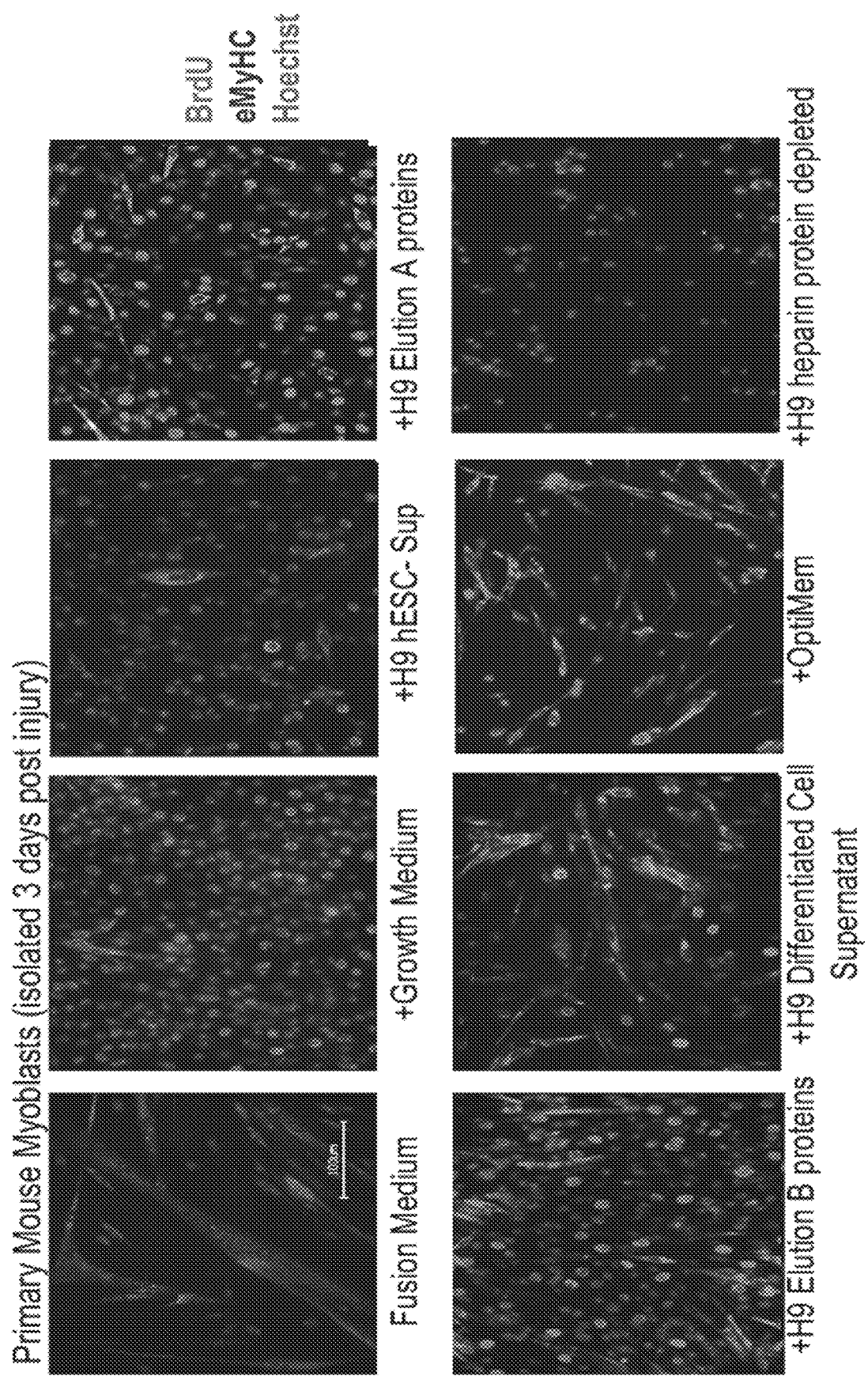
FIGS. 4A and 4B illustrate representative results from an in vitro assay useful to validate the regenerative capacity of factors identified by mass spectroscopy.
Figure 4B:
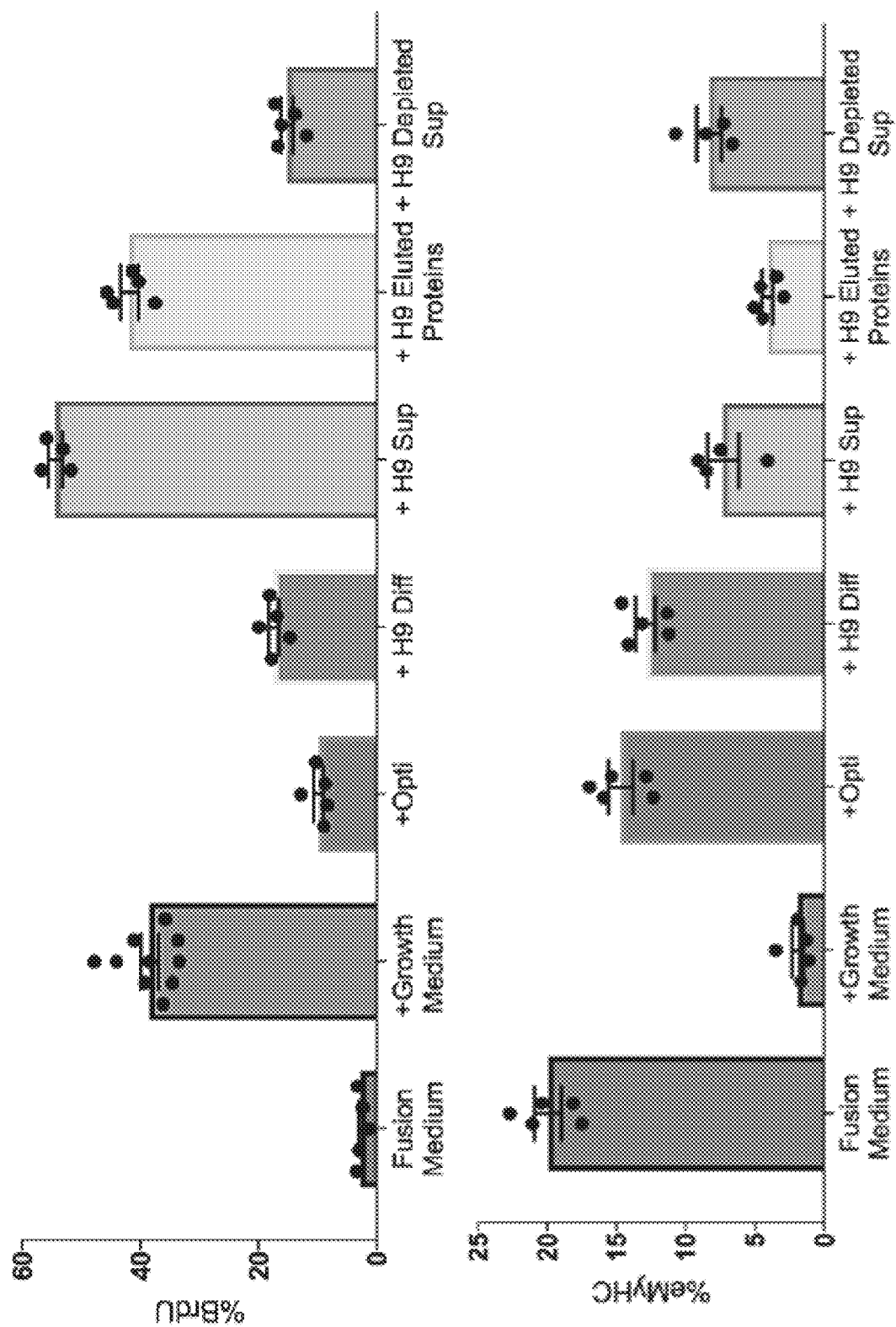
Figure 5A:
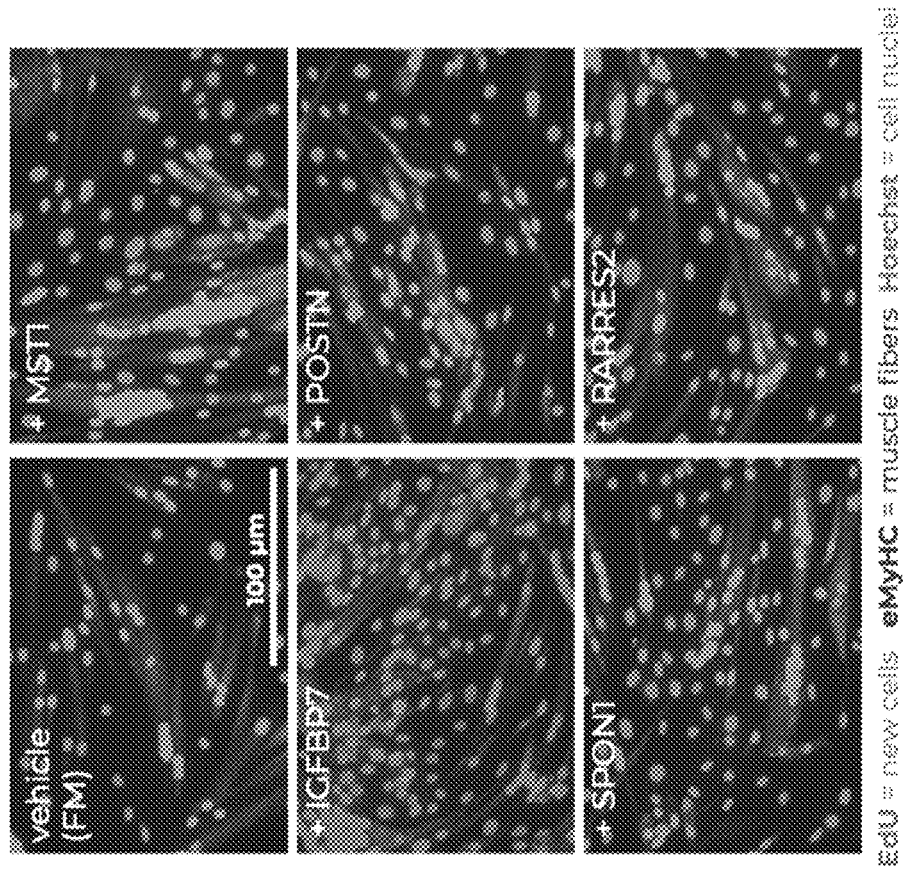
FIGS. 5A-5B show quantitation and representative images demonstrating the proliferation effect of IGFBP7 (330 ng/mL), POSTN (330 ng/mL), SPON1 (330 ng/mL), MST1 (330 ng/mL), and RARRES2 (330 ng/mL) (FIG. 5A); and VTN (10 ug/mL), FGF17 (500 ng/mL), IGF2 (2 ug/mL), FGF4 (500 ng/mL), FGF1 (500 ng/mL), and FGF6 (1 ug/mL) (FIG. 5B) in injury activated primary mouse myoblasts grown in vitro.
Figure 5A:
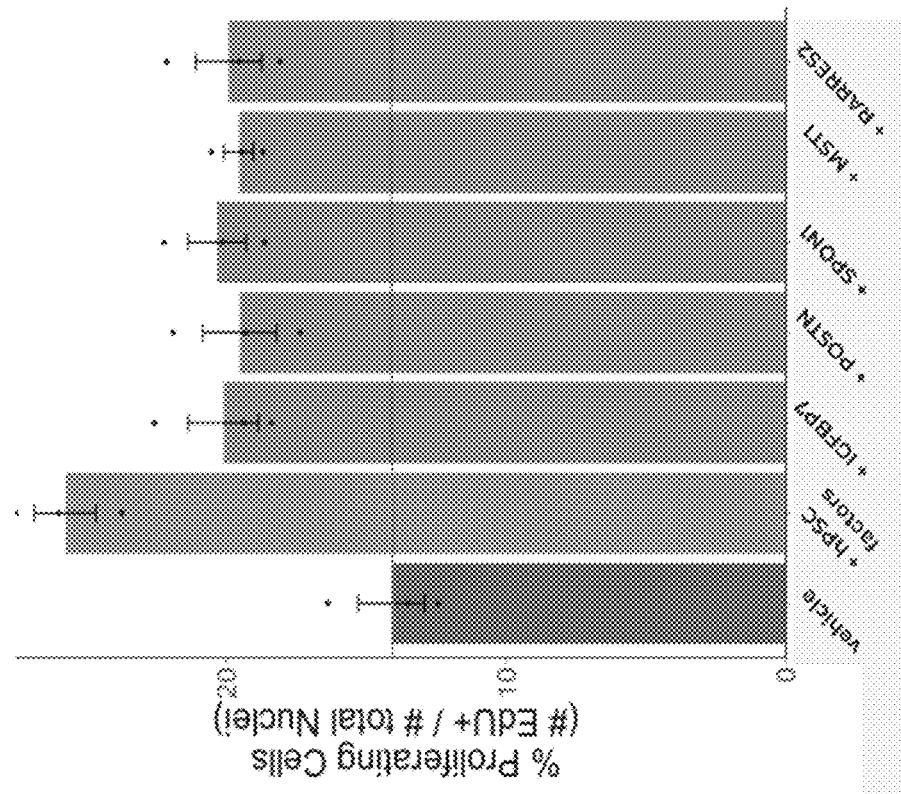
Figure 5B:
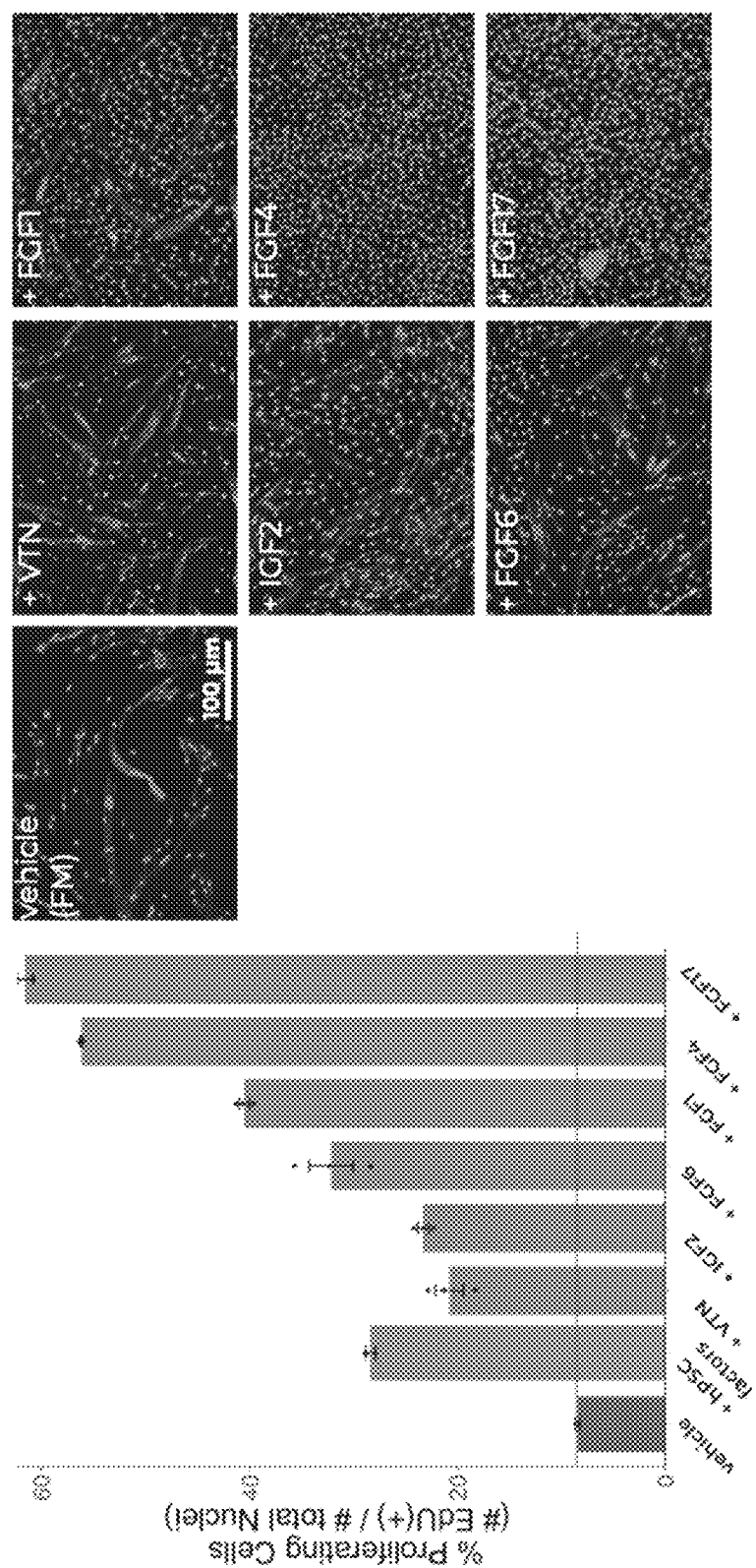
Figure 5C:
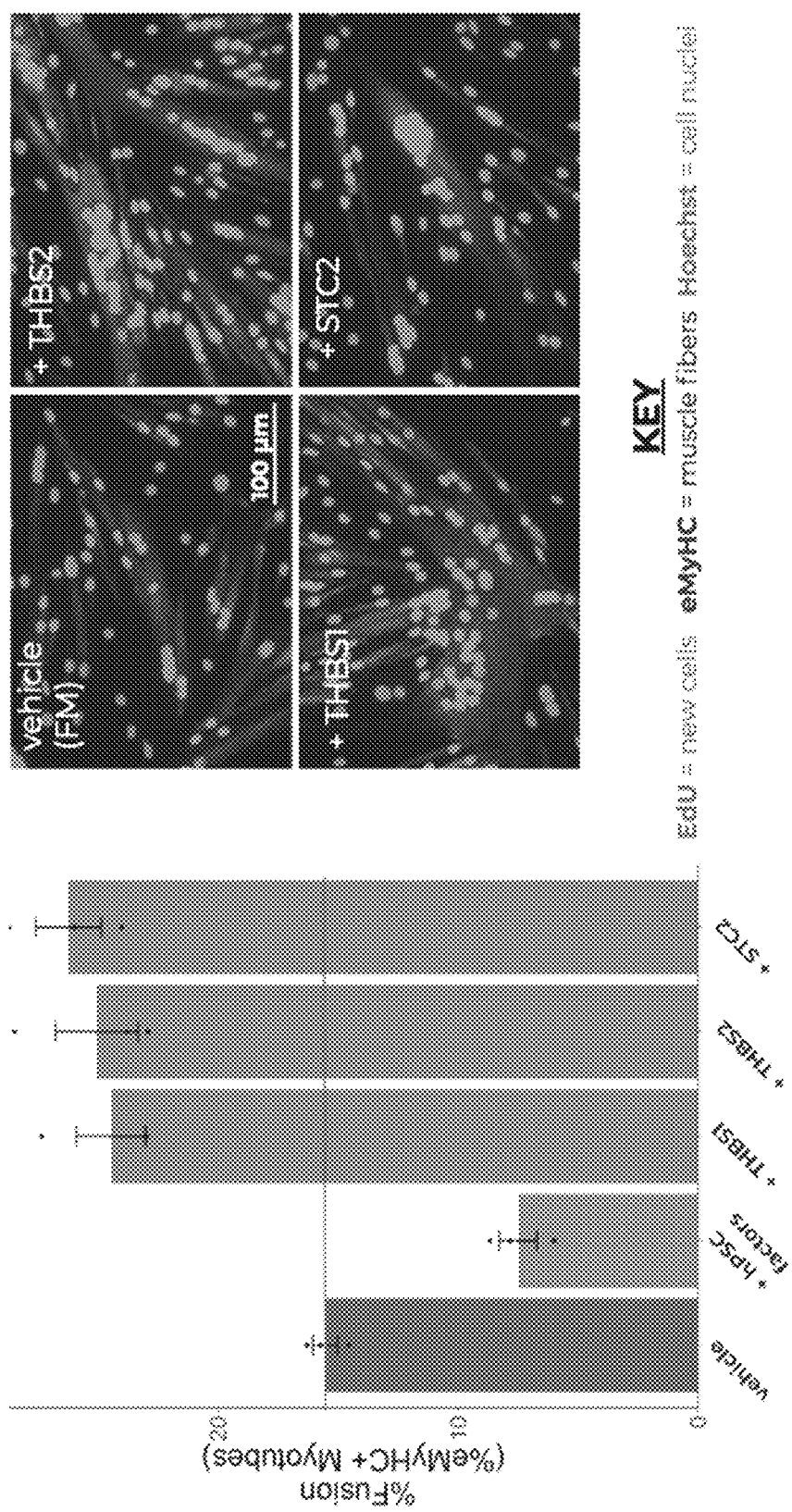
FIG. 5C shows quantitation and representative images demonstrating the increased cellular fusion effect of THBS1 (330 ng/mL), THBS2 (330 ng/mL), and STC2 (875 ng/mL) in injury activated primary mouse myoblasts grown in vitro.
Figure 6A:
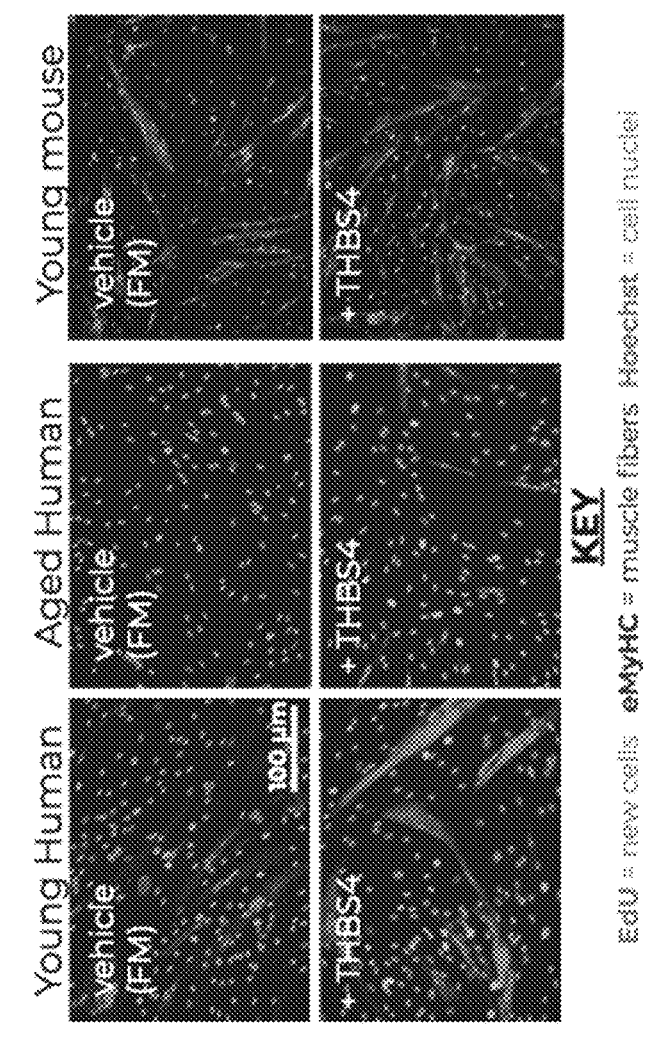
FIGS. 6A-6E show quantitation and representative immunofluorescent stained cell images demonstrating the proliferation effect specific heparin-associated polypeptides.
Figure 6A:
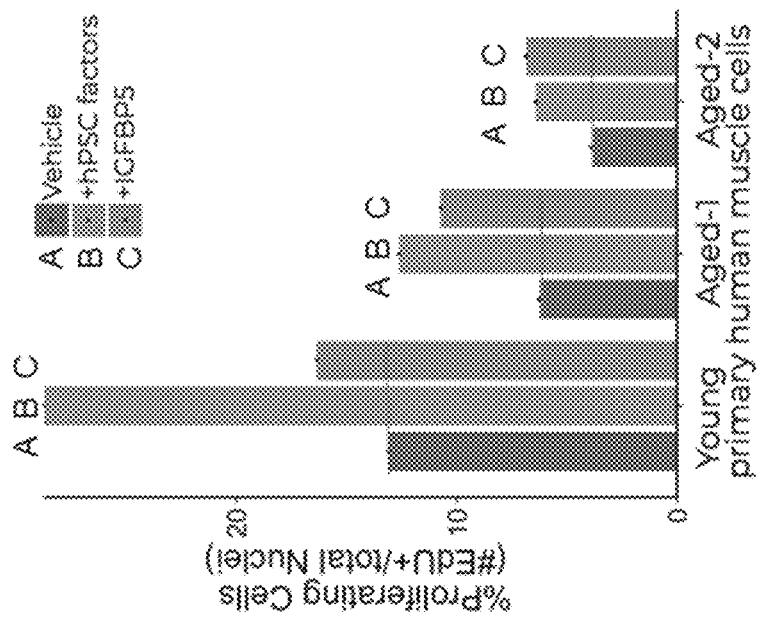
Figure 6B:
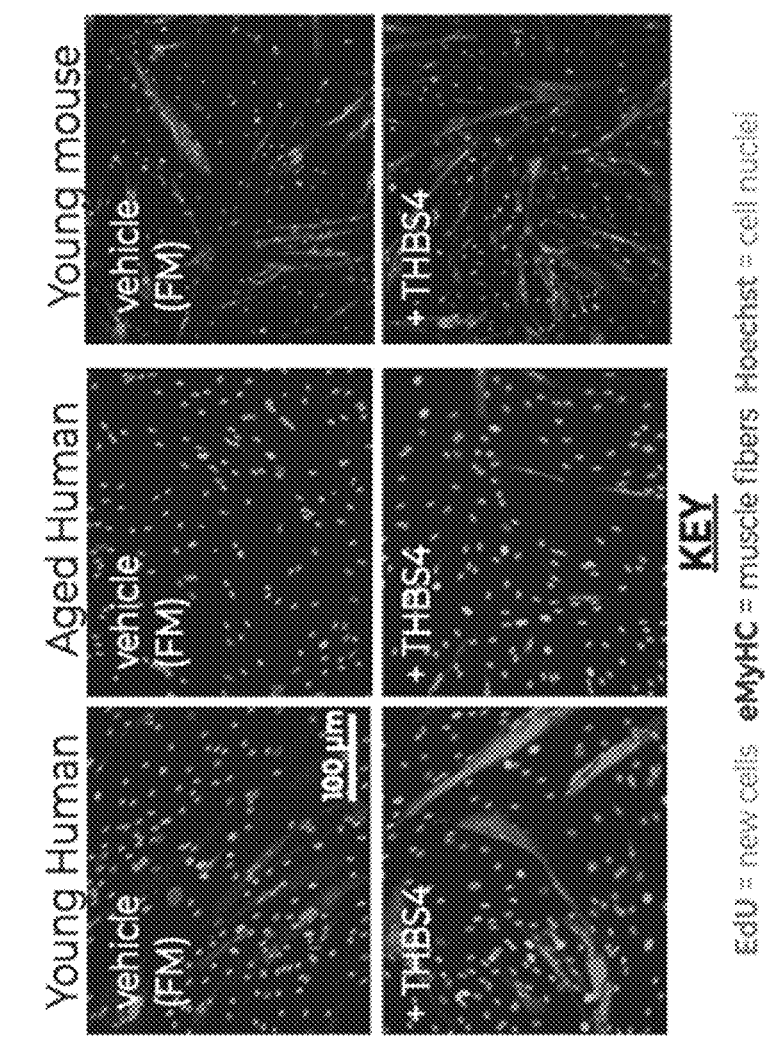
Figure 6B:
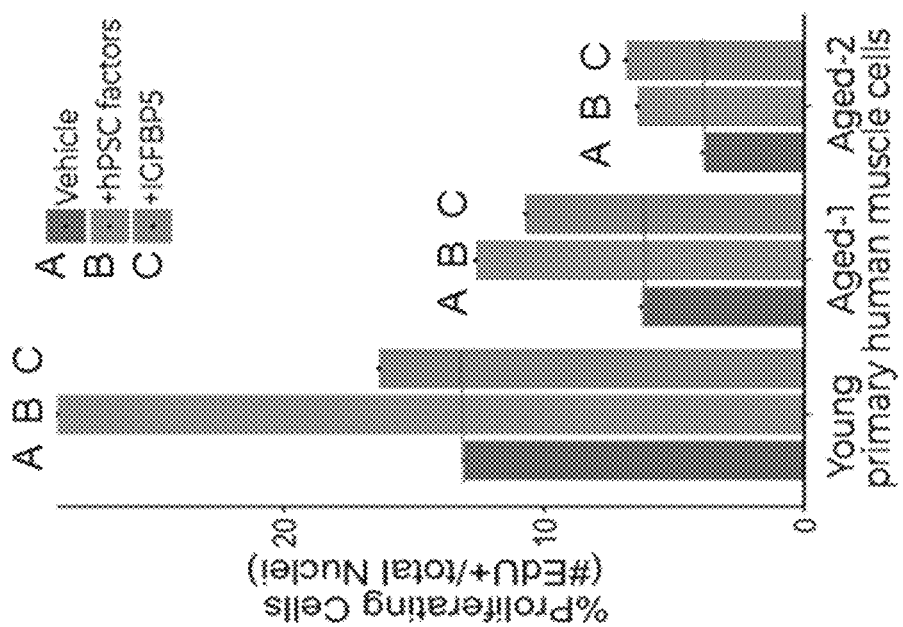
Figure 6C:
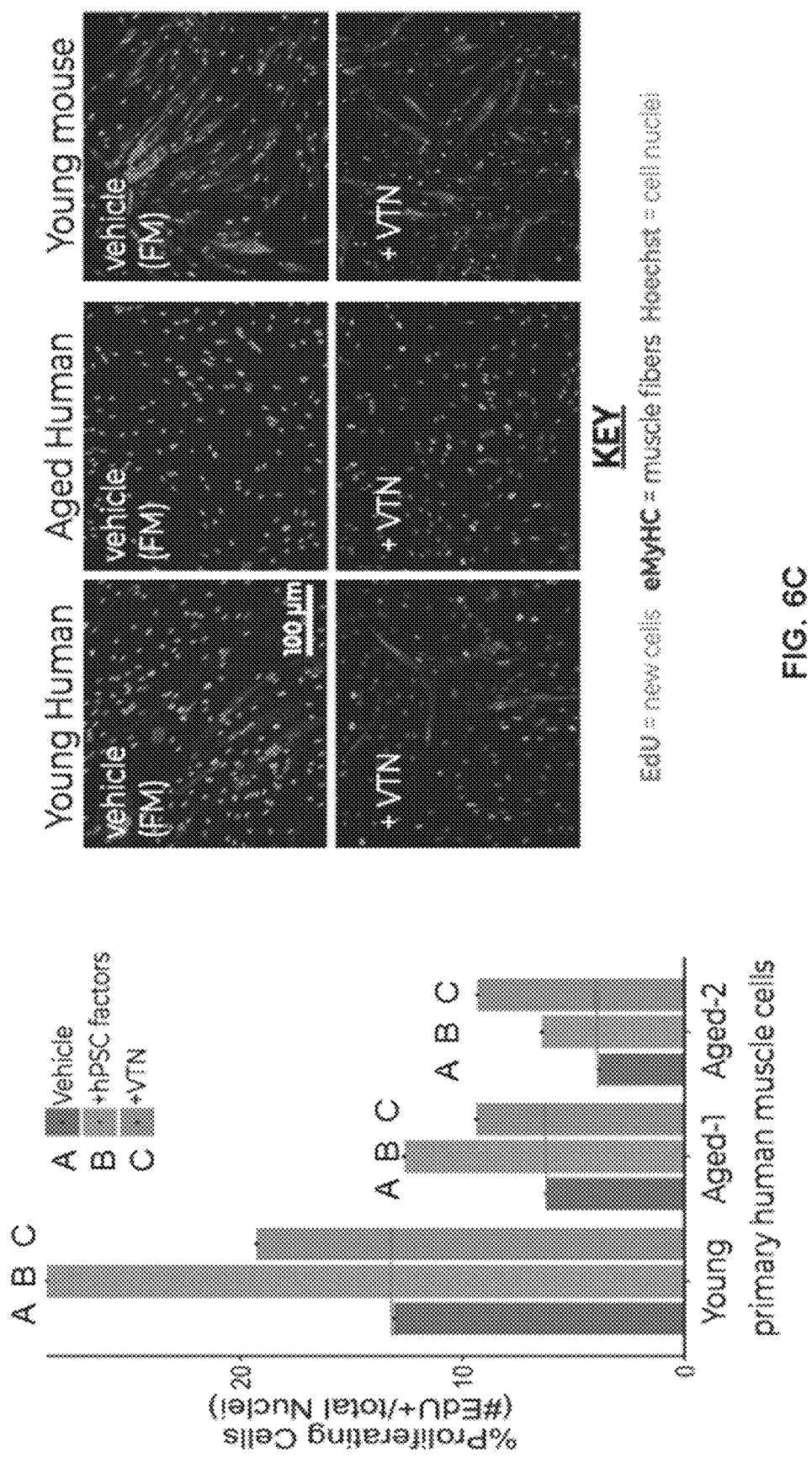
Figure 6D:
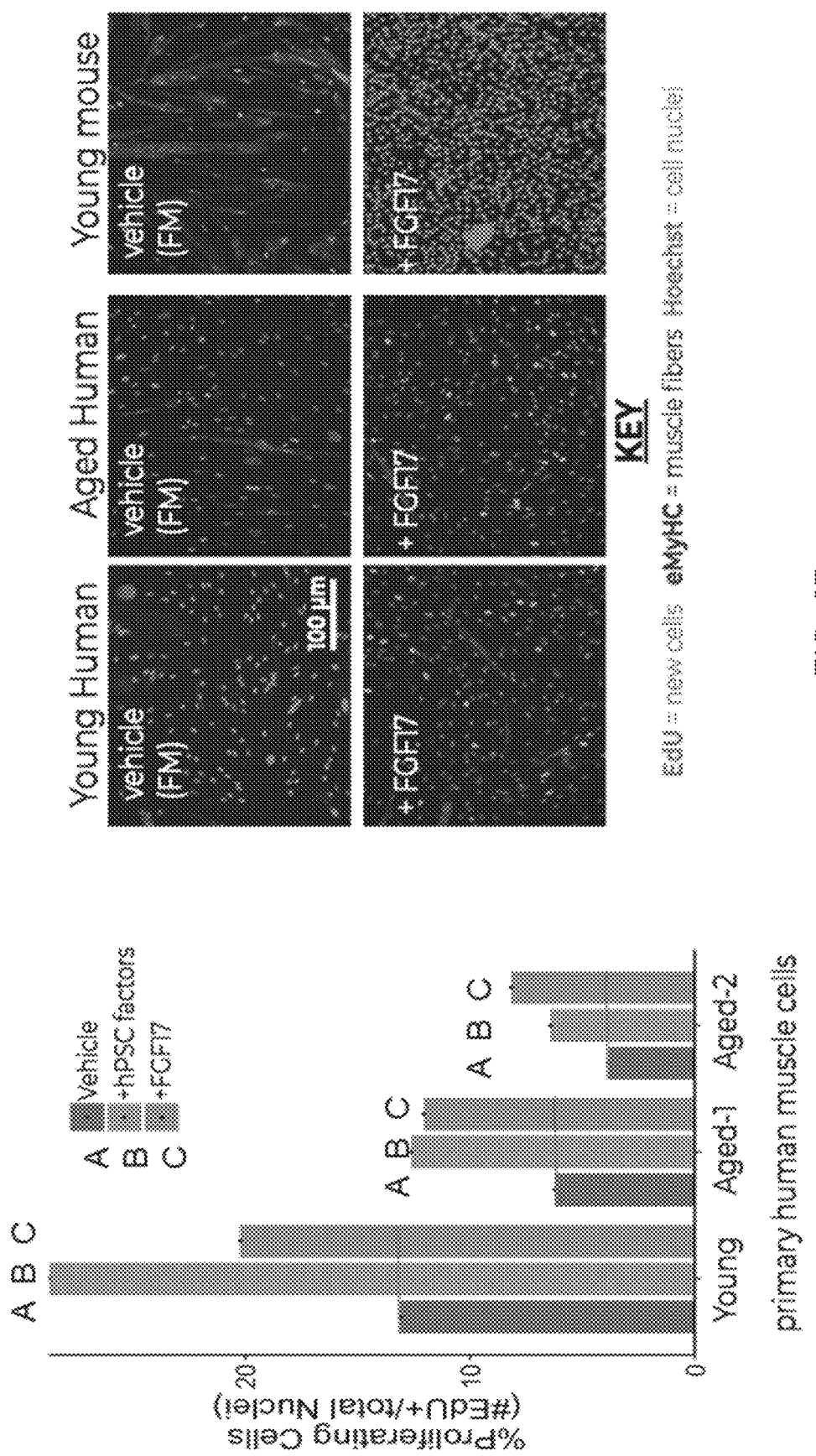
Figure 6E:
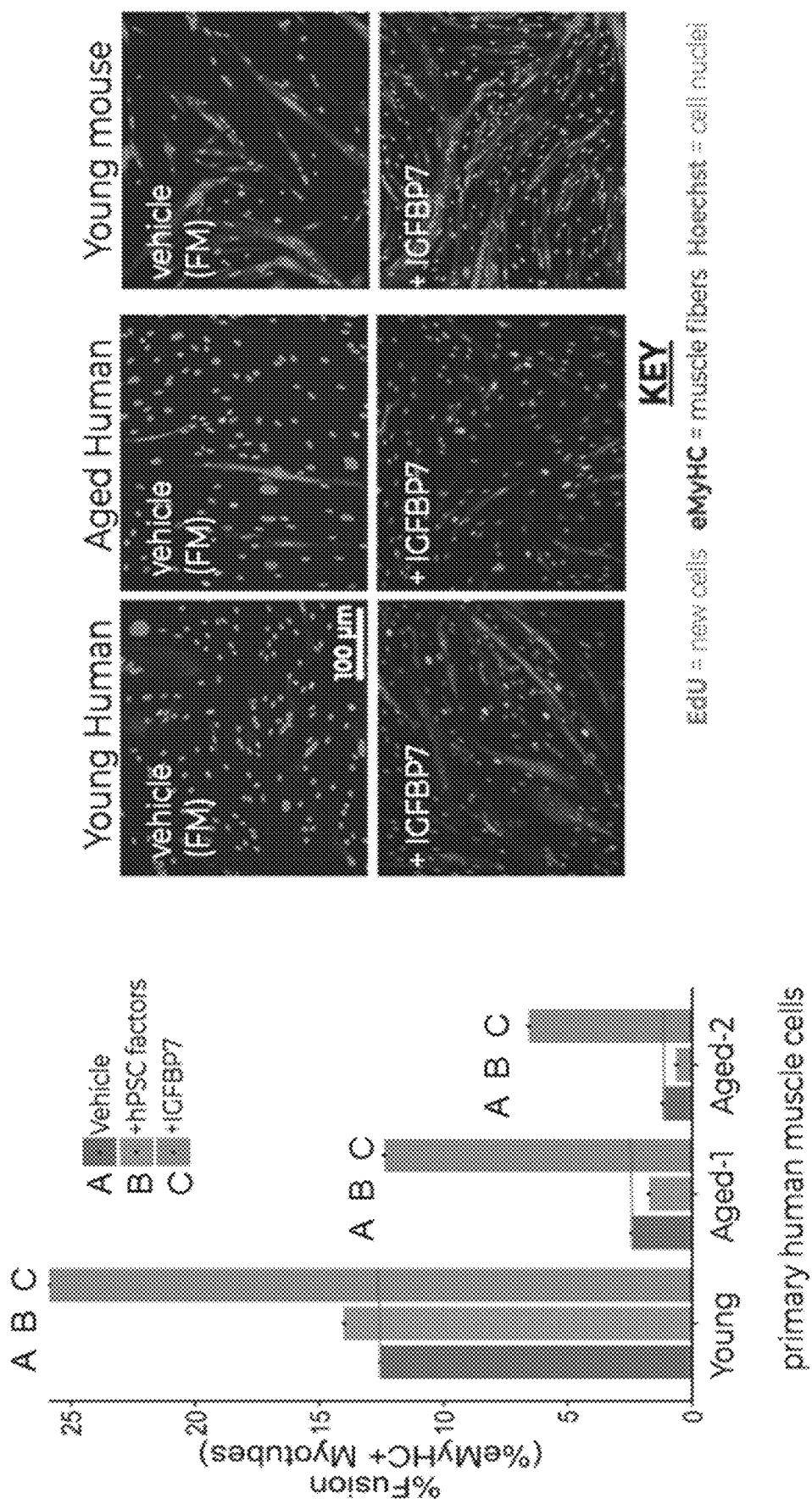
Figure 6F:
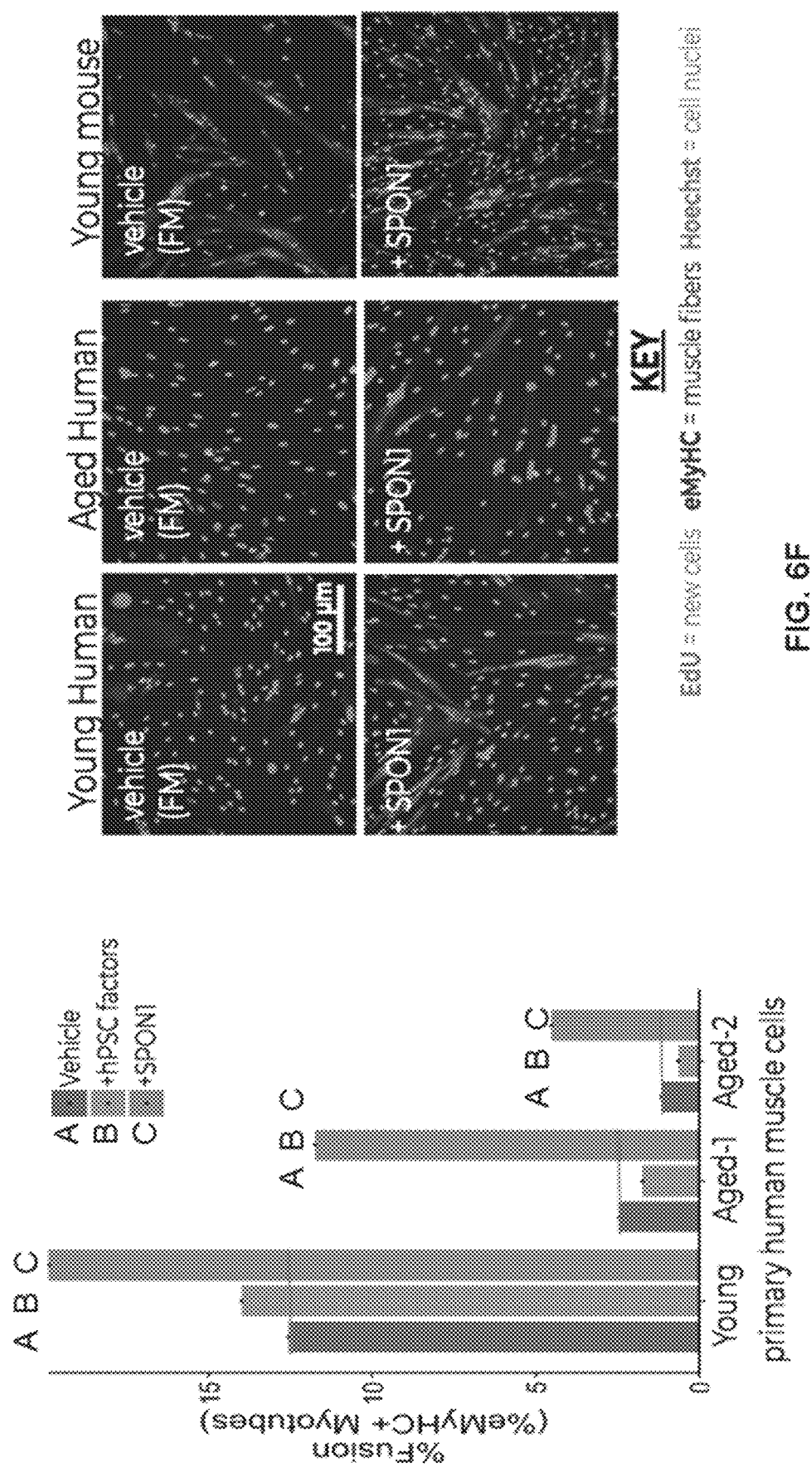
FIGS. 6F-6H, show quantitation and representative images demonstrating the increased cellular fusion effect of SPON1 (1 ug/mL) (FIG. 6F), POSTN (1 ug/mL) (FIG. 6G), PDGFRL (5 ug/mL) (FIG. 6H) in injury activated primary human myoblasts, young (18 years) and old (both 69 years old), grown in vitro.
Figure 6G:
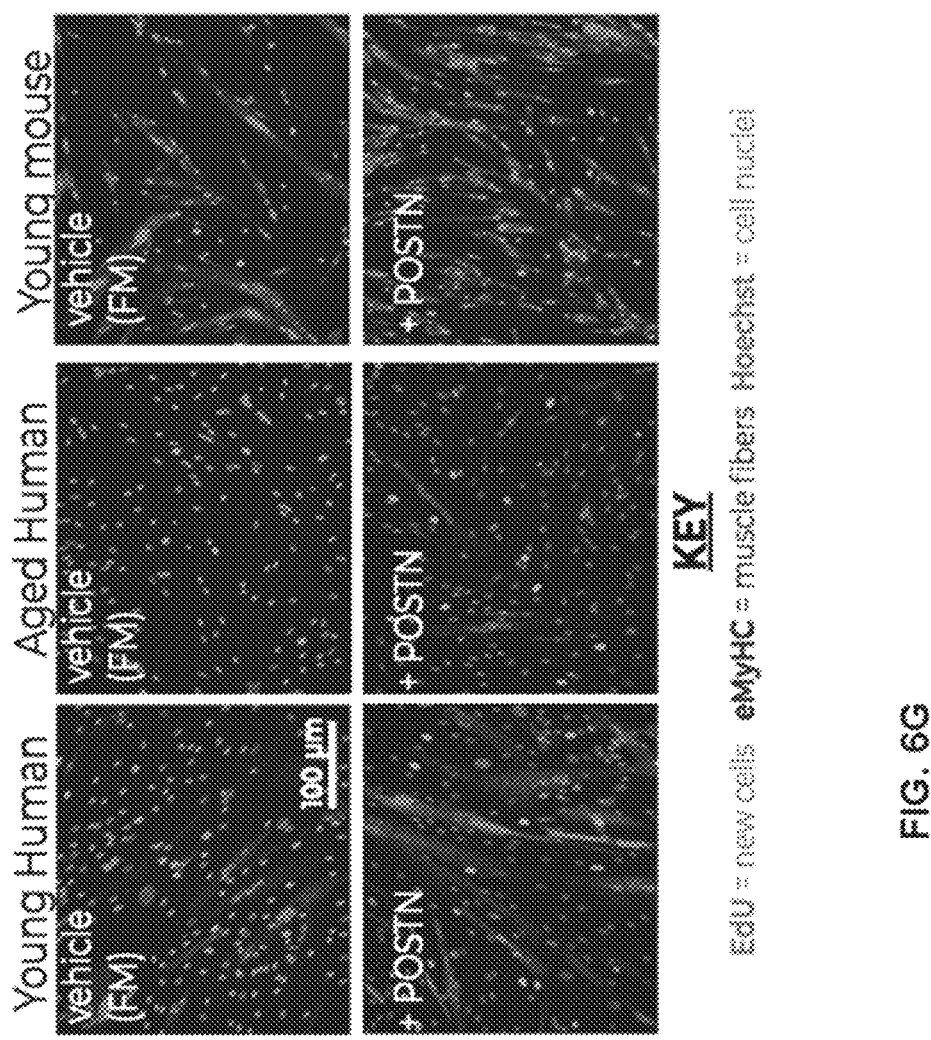
Figure 6G:
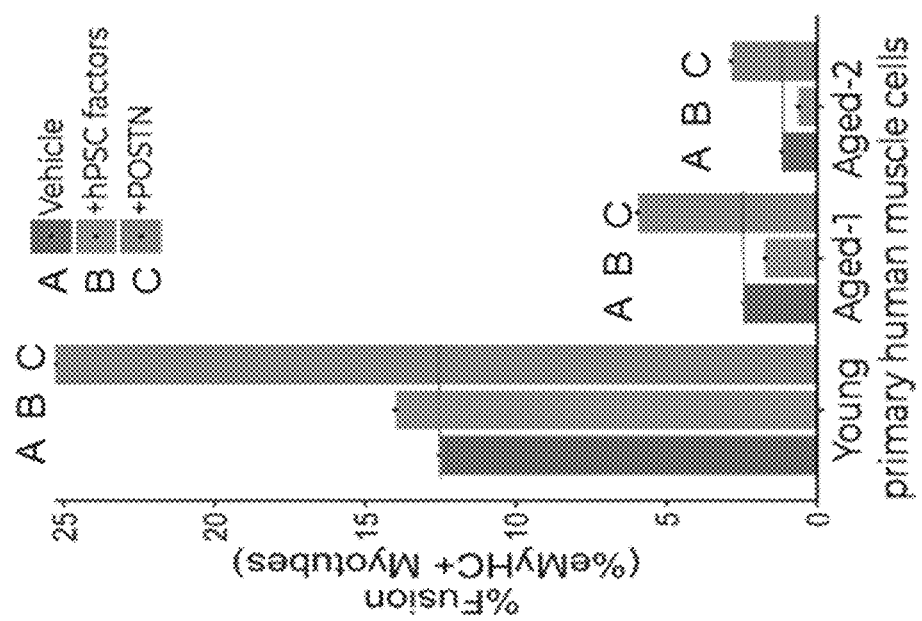
Figure 6H:
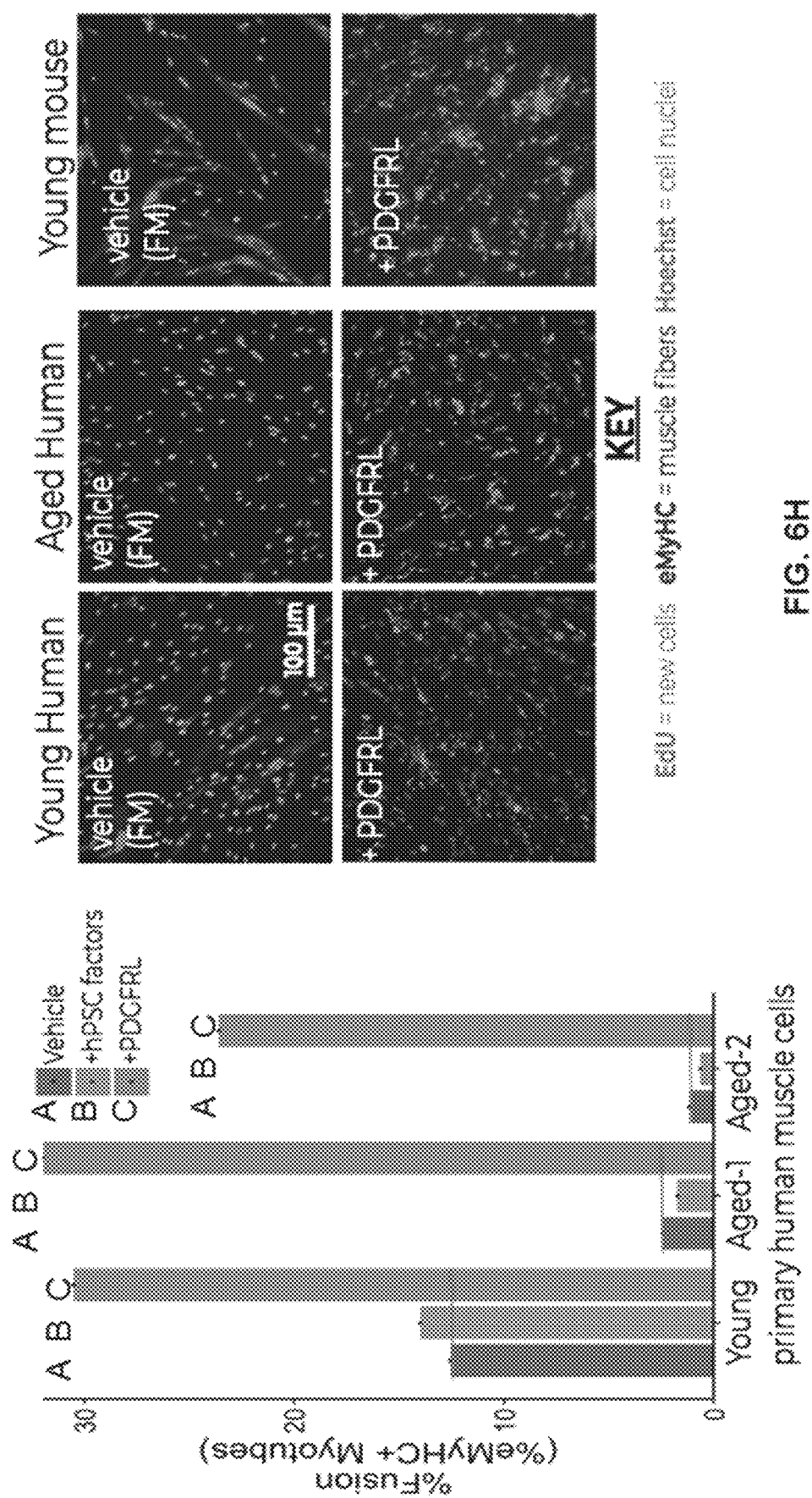

Example 7—Validation of Pro-Regenerative Factors In Vitro Using High-Throughput Imaging Mass spectroscopy can define candidate pro-regenerative factors, however, as shown in example 6, these experiments can generate large amounts of data that need to be further validated in relevant in vitro and in vivo models. The use of high-throughput imaging can help define individual factors and mixtures of factors that possess regenerative potential. Mouse muscle progenitor cells can be cultured with BrdU or Edu, in the presence or absence of specific potential pro-regenerative factors, and the degree of proliferation determined using high-throughput microscopy. BrdU or Edu staining indicates proliferation, while embryonic Myosin Heavy-Chain (eMyHC) staining indicates terminal differentiation of the progenitor cells. FIGS. 4A and 4B shows an example of data generated using high-throughput imaging.

Many of the factors detailed in Table 2 were tested individually for their ability to promote proliferation and/or fusion of mouse muscle progenitor cells in vitro FIG. 5 and FIG. 6.

Figure 7A:
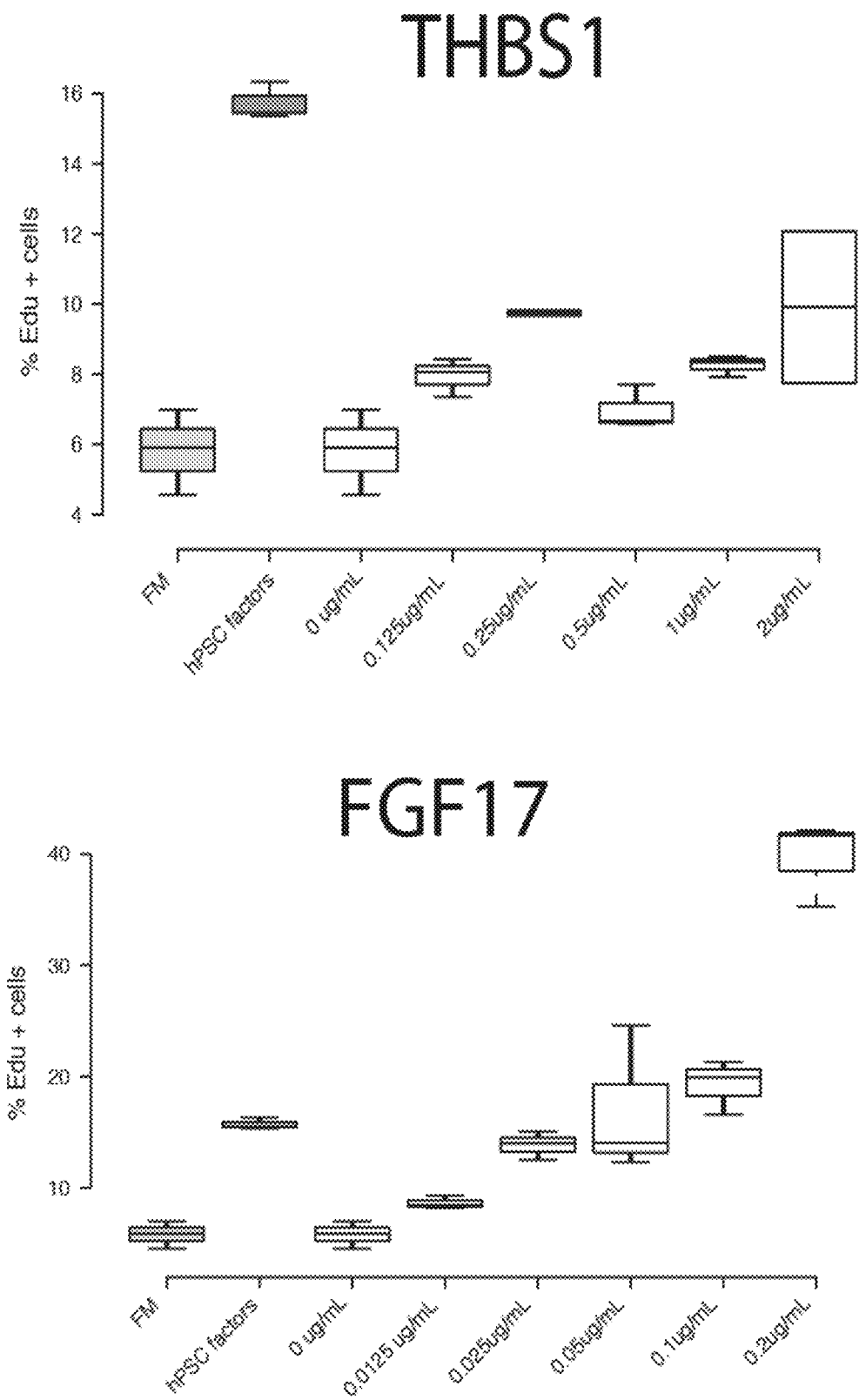
FIG. 7A provides an exemplary proliferative dose response of mouse myoblasts cultured with hPSC-derived factors Thrombospondin 1 (THBS1) applied at 125 ng/mL, 250 ng/mL, and 500 ng/mL, 1000 ng/ml and 2000 ng/ml, and Fibroblast growth factor 17 (FGF17) applied at 12.5 ng/ml, 25 ng/ml, 50 ng/ml, 100 ng/ml, and 200 ng/ml.
Figure 7B:
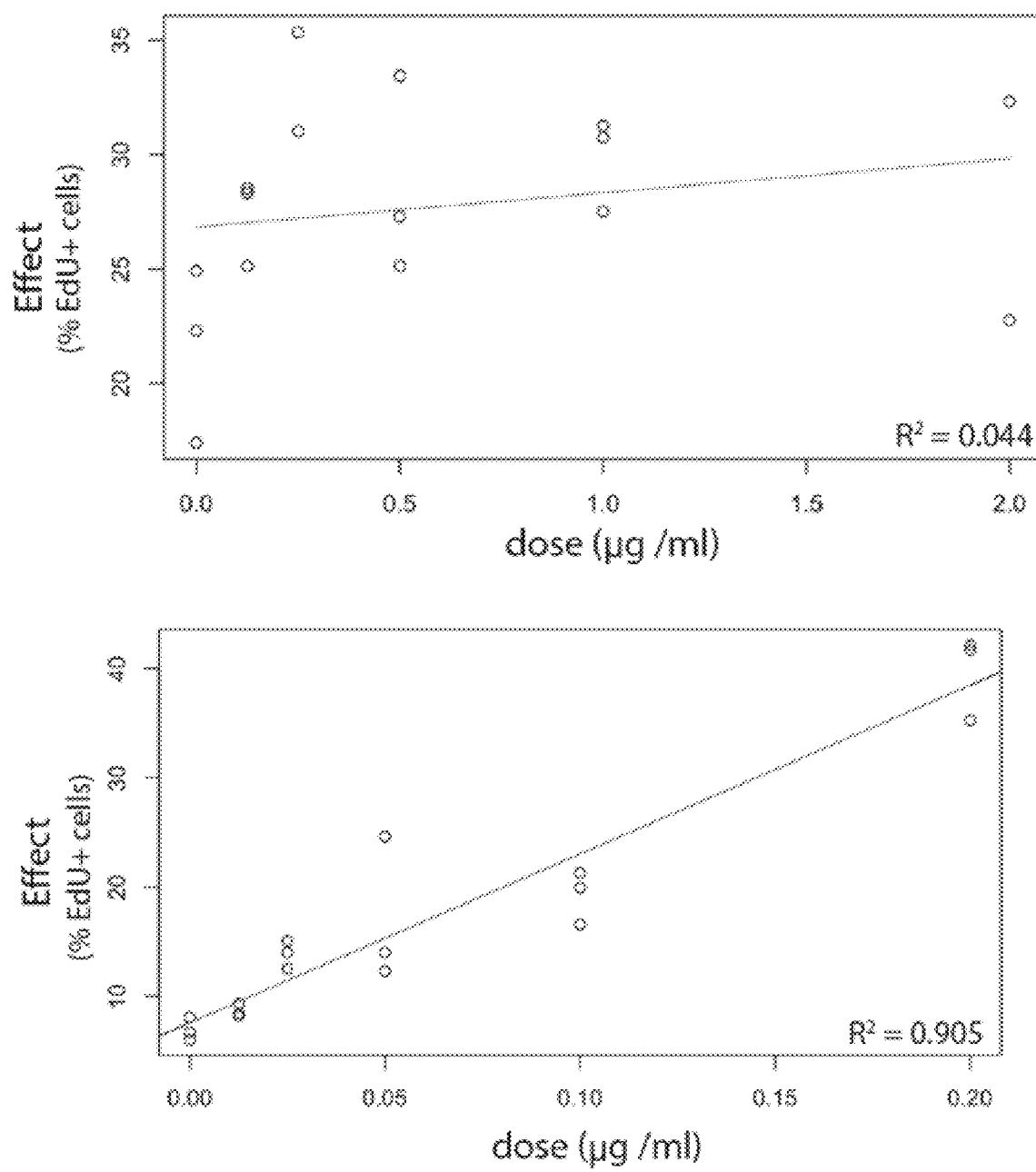
FIG. 7B shows that while THBS1 showed non-significant effects on proliferation of myoblasts (top), FGF17 produced a linear dose-dependent increase in proliferation of myoblasts (bottom).
Figure 7C:
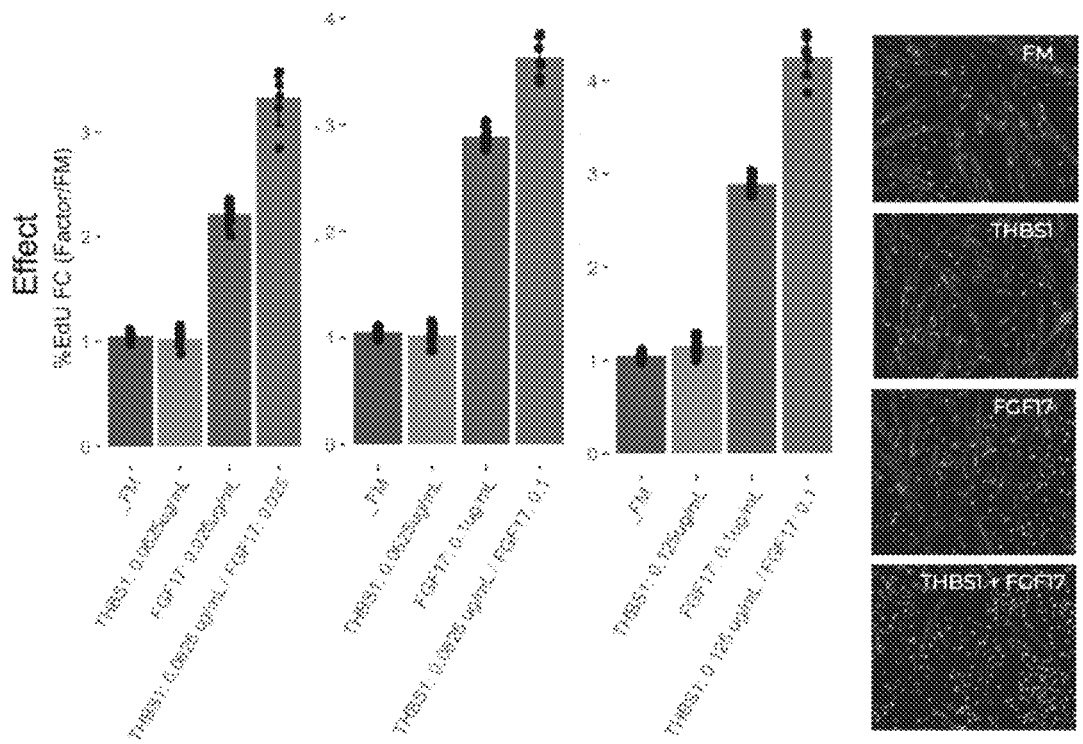
FIG. 7C shows that the combination of the two produced potentiation type synergy (CI<0.68, p<7.92E-7).
Figure 7D:
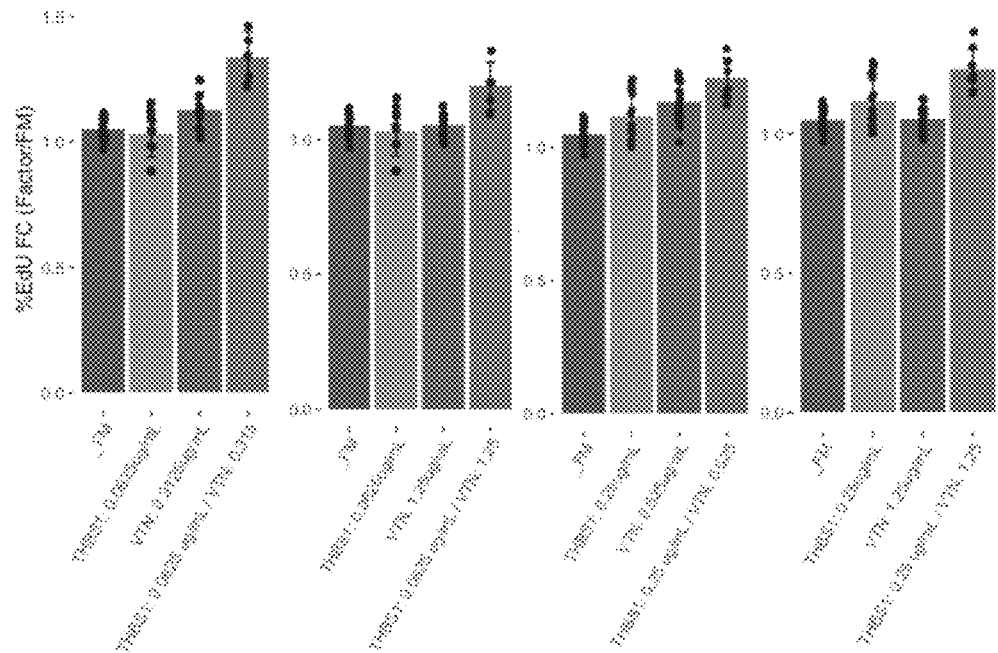
FIGS. 7D-7M provide examples of synergistic combinations of heparin-associated polypeptides relative to the vehicle only control (_FM) or to treatment with either of the individual heparin-associated polypeptides. Combination Index (CI) values and probability values (p-values) from statistical tests for the synergy models are reported in Table 10.
Figure 7E:
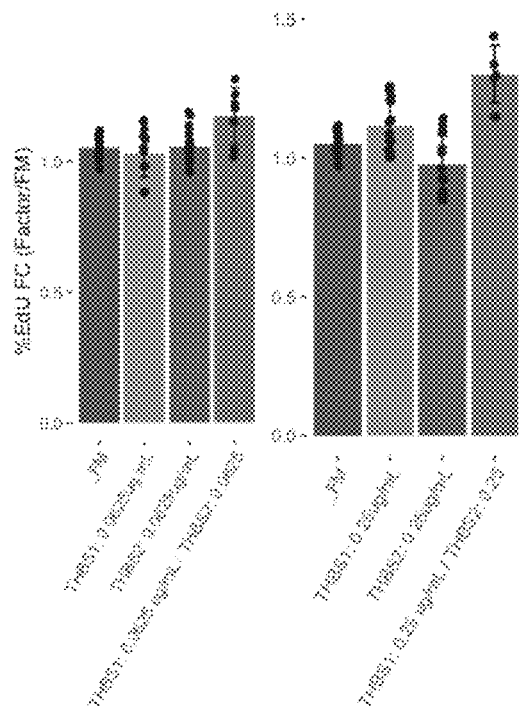
Figure 7F:
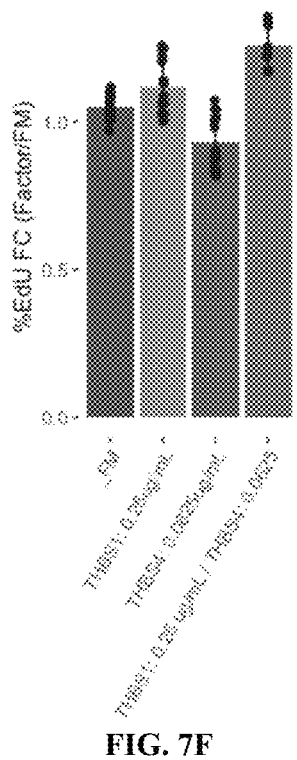
Figure 7G:
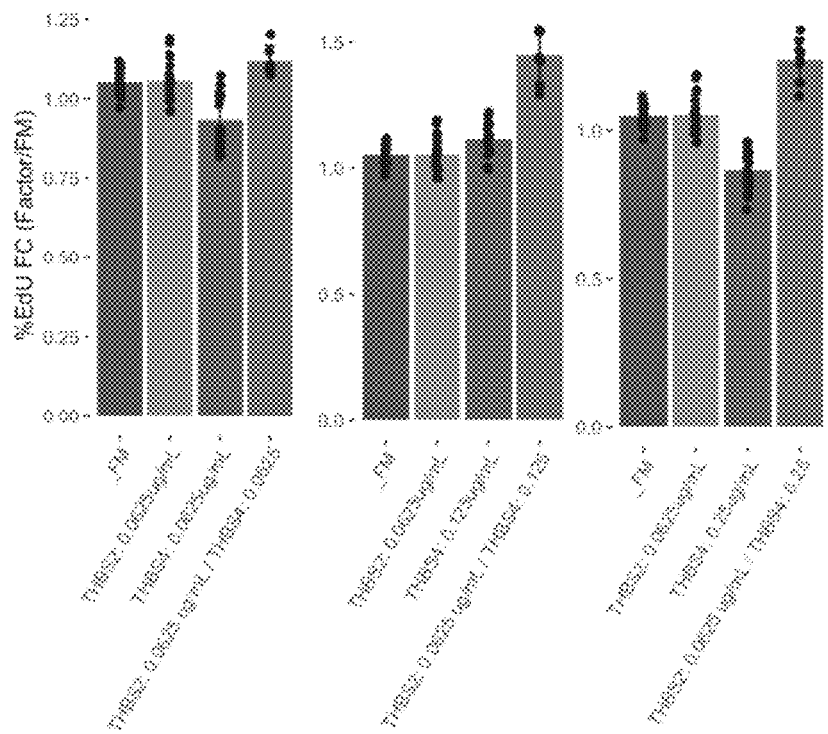
Figure 7H:
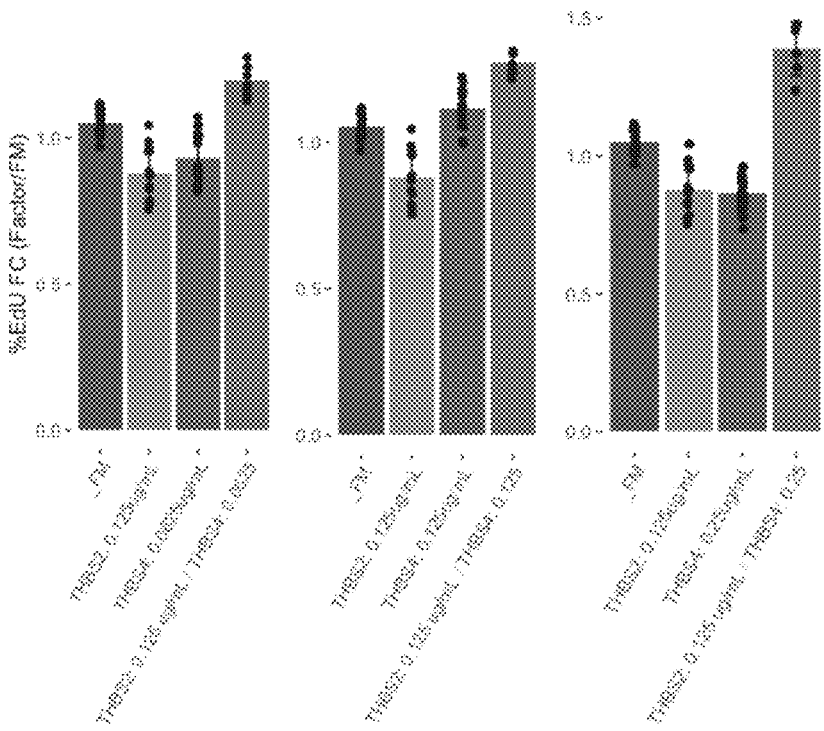
Figure 7I:
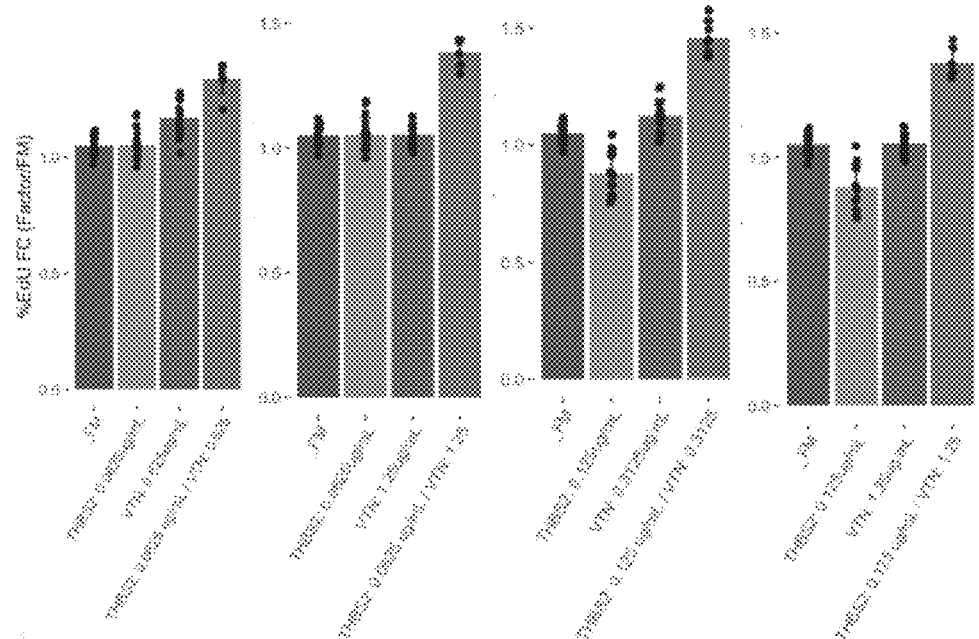
Figure 7J:
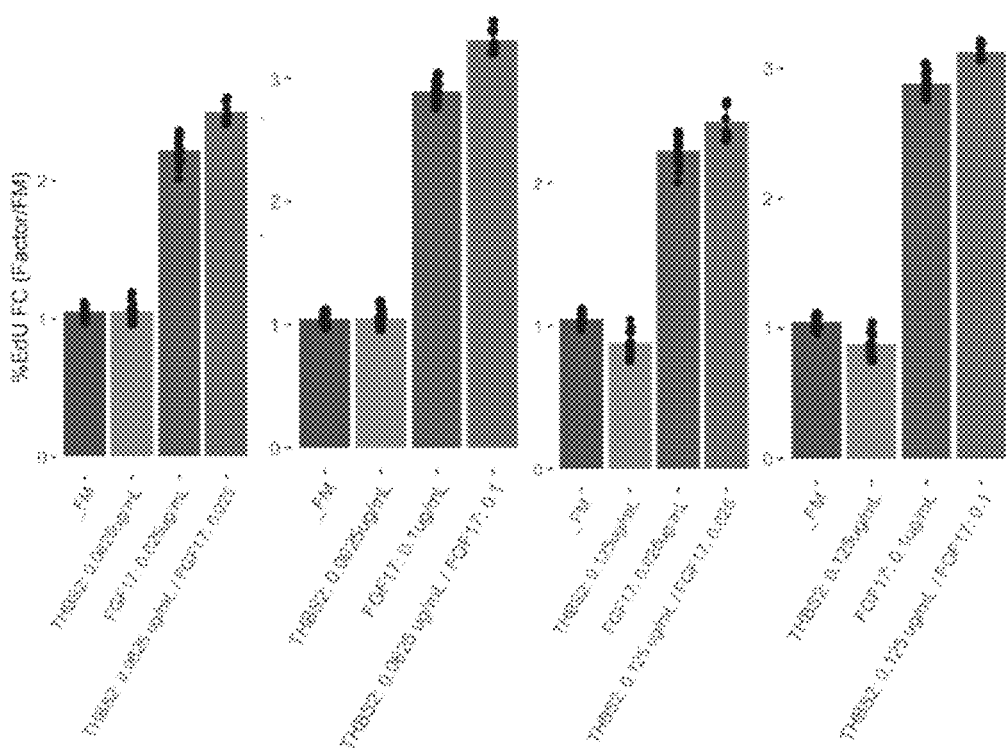
Figure 7K:
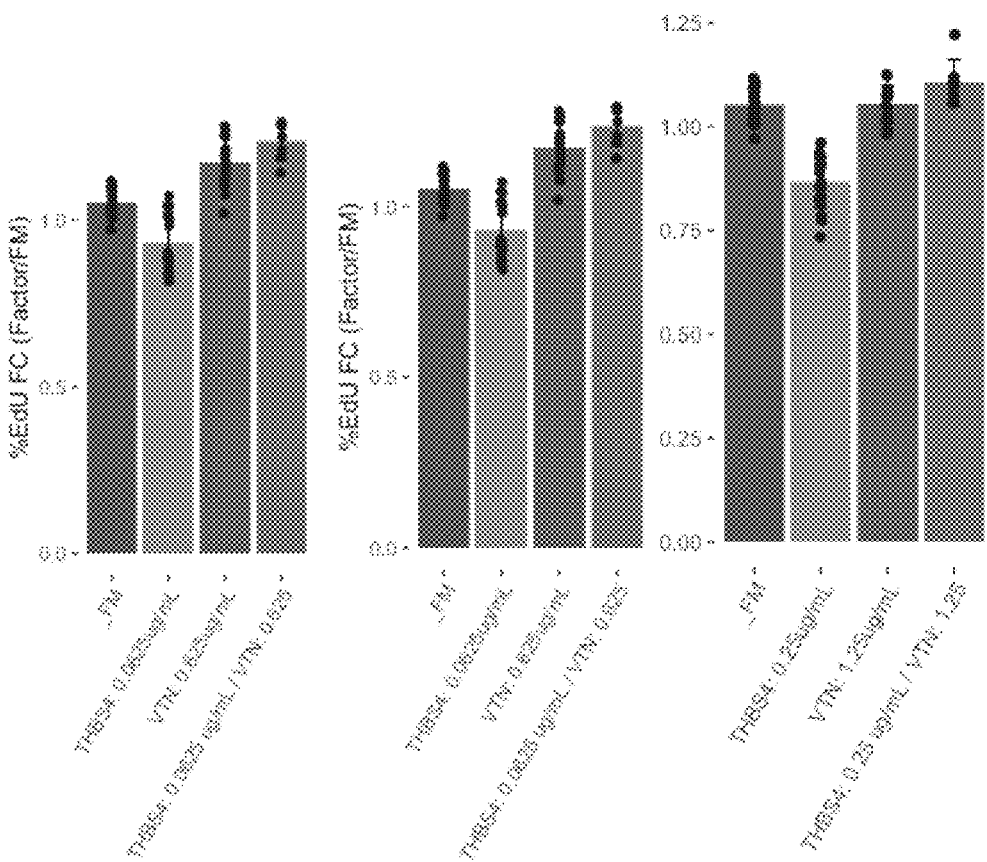
Figure 7L:
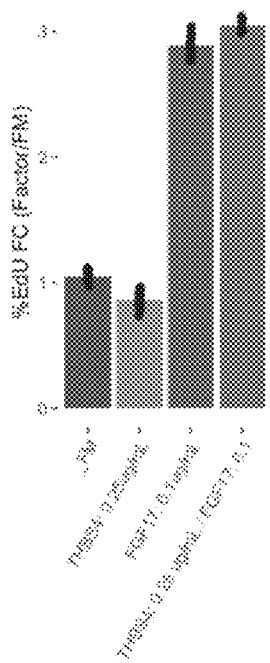
Figure 7M:
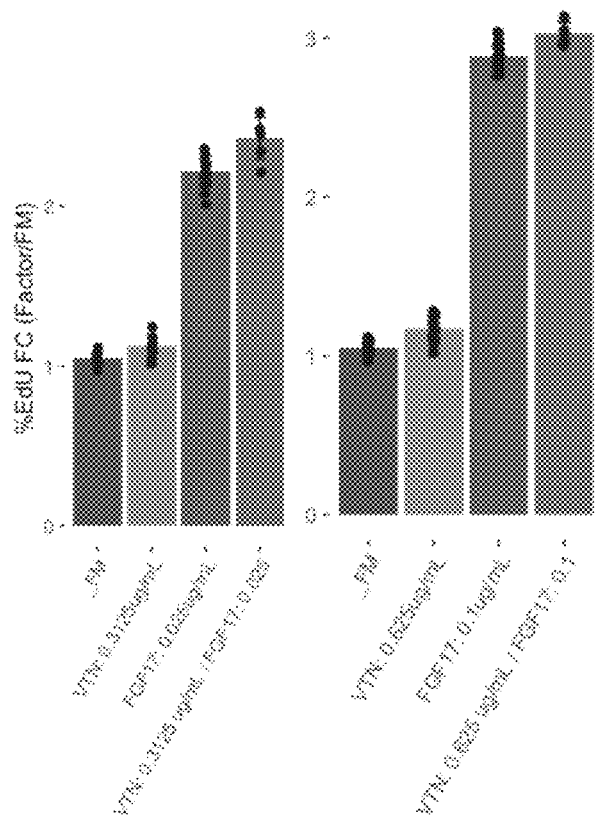
Figure 8:
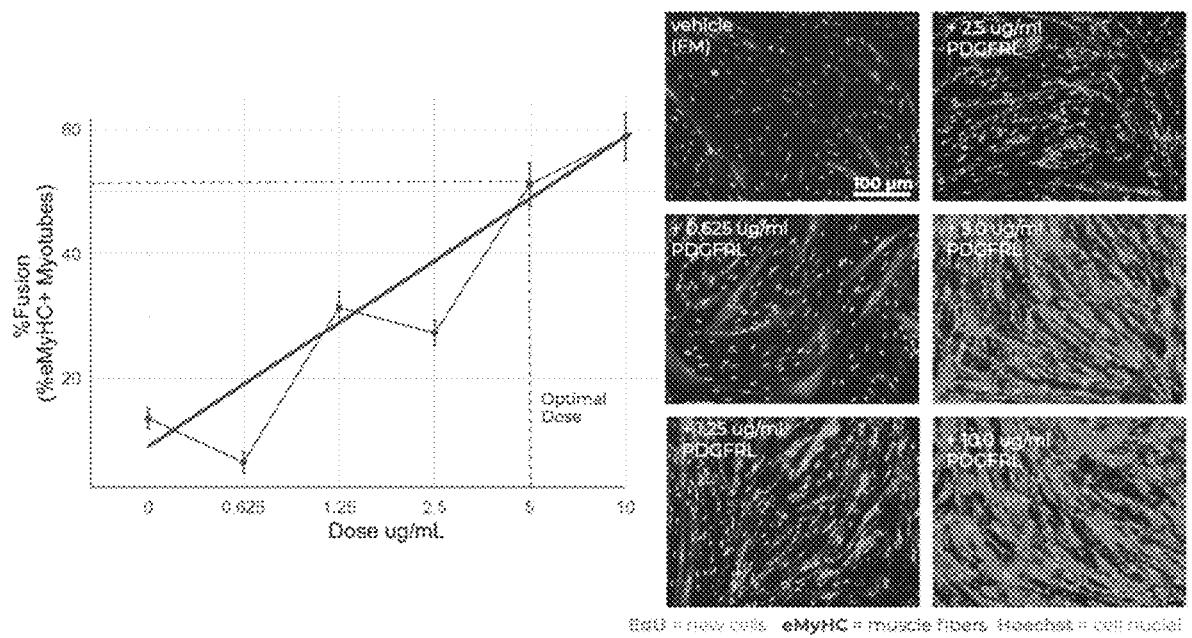
FIG. 8 shows an example of the dose dependent increasing cellular fusion of mouse myoblasts cultured with a heparin-associated polypeptide. In this case Platelet derived growth factor-like (PDGFRL) proteins were applied at 625 ng/mL, 1250 ng/mL, 2500 ng/mL, 5000 ng/mL, and 10000 ng/mL.

The effect of the candidate factors on myogenic activity was assayed in biological triplicate across a range of concentrations centered around expected physiological levels by adding each factor to mouse myoblasts for 48 hours or human myoblasts for 72 hours with daily media changes (DMEM+2% horse serum) and a second pulse of factors. After 24 hours, cells were pulsed for 2-5 hours with EdU (30 uM), ethanol fixed, stained with Hoescht 3342, immunostained for proliferation—as measured by the percent of cells staining positive for EdU (% EdU)—, and immunostained for differentiation—as measured by the increase in cellular area staining positive for embryonic myosin heavy chain (% eMyHC) relative to the negative controls, which received media and vehicle only. Wells were imaged on a Keyence BZ-100 at 4×, the images quantified in Cell Profiler, and the statistics were computed in R. FIGS. 7A-7B show an example of the proliferation dose response for two of the factors tested. Results for additional factors are summarized below in Table 9.

TABLE 9

Effect of individual factors on mouse myoblast growth and fusion

| Factor Name | Concentration (ug/mL) | Proliferation (% EdU) | | Fusion (% eMyHC) | |
| --- | --- | --- | --- | --- | --- |
| | | Effect Size (% relative to-control) | Statistical Significance (p-value) | Effect Size (% relative to-control) | Statistical Significance (p-value) |
| FST | 0.33 | 72% | 0.001 | 202% | 0.005 |
| CTGF | 5 | | | 154% | 0.00005 |
| THBS1 | 5 | | | 157% | 0.004 |
| THBS2 | 0.33 | | | 161% | 0.006 |

TABLE 9-continued

Effect of individual factors on mouse myoblast growth and fusion

| Factor Name | Concentration (ug/mL) | Proliferation (% EdU) | | Fusion (% eMyHC) | |
|---|---|---|---|---|---|
| | | Effect Size (% relative to-control) | Statistical Significance (p-value) | Effect Size (% relative to-control) | Statistical Significance (p-value) |
| IGFBP3 | 0.33 | 131% | 0.03 | | |
| IGFBP5 | 2 | 69% | 0.04 | | |
| IGFBP7 | 0.33 | 78% | 0.03 | | |
| STC2 | 2.5 | 133% | 0.02 | −31% | 0.003 |
| SPON1 | 0.33 | 139% | 0.04 | | |
| MST1 | 0.33 | 144% | 0.02 | | |
| POSTN | 0.33 | 139% | 0.01 | | |
| RARRES2 | 0.33 | 141% | 0.03 | | |
| AGRN | 2.5 | 148% | 0.008 | | |
| CHRDL1 | 1.25 | 150% | 0.00009 | | |
| VTN | 5 | 125% | 0.004 | | |
| FGF17 | 0.5 | 244% | 0.0004 | | |
| ANOS1 | 1 | 165% | 0.03 | | |
| FGF4 | 0.3 | 239% | 4.6E−13 | | |
| HGF | 0.56 | 114% | 1.6E−10 | | |
| IGF2 | 1 | 97% | 1.3E−5 | | |
| FGF1 | 1 | 96% | 2.3E−7 | | |
| FGF6 | 0.002 | 115% | 1.8E−5 | | |
| MST1 | 0.33 | 79% | 0.002 | | |
| PDGFD | 0.1 | 89% | 4E−5 | | |

The effect of the combination of candidate factors on myogenic activity was assayed in biological triplicate across a range of concentrations centered around expected physiological levels by adding each factor to mouse myoblasts for 48 hours or human myoblasts for 72 hours with daily media changes (DMEM+2% horse serum) and a second pulse of factors. After 24 hours, cells were pulsed for 2-5 hours with EdU (30 uM), ethanol fixed, stained with Hoescht 3342, immunostained for proliferation—as measured by the percent of cells staining positive for EdU (% EdU)—, and immunostained for differentiation—as measured by the increase in cellular area staining positive for embryonic myosin heavy chain (% eMyHC) relative to the negative controls, which received media, individual factors, or vehicle only. Wells were imaged on a Keyence BZ-100 at 4×, the images quantified in Cell Profiler, and the statistics were computed in R. FIGS. 7C-7M show examples of the proliferation dose response for two or more of the factors tested individually and as a combination to test for synergy. Statistical metrics for increased myogenetic activity from the pair of factors relative to the controls are summarized below in Tables 10-14. Each polypeptide was produced using the method listed in Table 1. Each polypeptide was produced using the method listed in Table 1. The magnitude of the combinations' effects relative to control (FM—negative control, hESC factors—positive control) is shown. The Combination Index (CI) for synergy was calculated using the Highest Single Agent (HAS) model due to the linear dose responses for the individual factor, e.g. FIG. 7B.

TABLE 10

Synergistic combinations of heparin-associated polypeptides.

| Factor 1 | | Factor 2 | | Factor 3 | | p-value | CI (HSA) |
|---|---|---|---|---|---|---|---|
| Name | ug/mL | Name | ug/mL | Name | ug/mL | | |
| THBS2 | 0.125 | THBS4 | 0.25 | VTN | 1 | <0.05 | 0.886 |
| THBS2 | 0.125 | THBS4 | 0.25 | ANOS1 | 1 | <0.005 | 0.532 |
| THBS2 | 0.125 | THBS4 | 0.25 | | | <0.005 | 0.633 |
| THBS1 | 0.0625 | FGF17 | 0.025 | | | <0.005 | 0.667 |
| THBS1 | 0.125 | FGF17 | 0.1 | | | <0.005 | 0.679 |
| THBS2 | 0.125 | THBS4 | 0.25 | IL-15 | 1 | <0.005 | 0.680 |
| THBS2 | 0.125 | THBS4 | 0.25 | IGF2 | 0.05 | <0.05 | 0.733 |
| THBS2 | 0.0625 | VTN | 1.25 | | | <0.005 | 0.763 |
| THBS2 | 0.125 | VTN | 1.25 | | | <0.005 | 0.763 |
| THBS2 | 0.125 | VTN | 0.3125 | | | <0.005 | 0.771 |
| THBS2 | 0.0625 | THBS4 | 0.125 | | | <0.005 | 0.772 |
| THBS2 | 0.125 | THBS4 | 0.0625 | | | <0.005 | 0.779 |
| THBS1 | 0.0625 | FGF17 | 0.1 | | | <0.005 | 0.796 |
| THBS1 | 0.0625 | VTN | 0.315 | | | <0.005 | 0.840 |
| THBS2 | 0.0625 | THBS4 | 0.25 | | | <0.005 | 0.850 |
| THBS1 | 0.25 | THBS2 | 0.25 | | | <0.05 | 0.859 |
| THBS2 | 0.0625 | FGF17 | 0.1 | | | <0.005 | 0.871 |
| THBS2 | 0.0625 | VTN | 0.625 | | | <0.005 | 0.876 |
| THBS2 | 0.125 | THBS4 | 0.125 | | | <0.005 | 0.878 |
| THBS1 | 0.0625 | VTN | 1.25 | | | <0.05 | 0.880 |
| THBS1 | 0.25 | THBS4 | 0.0625 | | | <0.005 | 0.888 |

TABLE 10-continued

Synergistic combinations of heparin-associated polypeptides.

| Factor 1 | | Factor 2 | | Factor 3 | | | |
|---|---|---|---|---|---|---|---|
| Name | ug/mL | Name | ug/mL | Name | ug/mL | p-value | CI (HSA) |
| THBS2 | 0.0625 | FGF17 | 0.025 | | | <0.005 | 0.890 |
| THBS1 | 0.0625 | THBS2 | 0.0625 | | | <0.05 | 0.900 |
| THBS1 | 0.25 | VTN | 1.25 | | | <0.005 | 0.907 |
| THBS2 | 0.125 | FGF17 | 0.025 | | | <0.005 | 0.913 |
| VTN | 0.3125 | FGF17 | 0.025 | | | <0.05 | 0.915 |
| THBS4 | 0.25 | VTN | 0.3125 | | | <0.05 | 0.922 |
| THBS2 | 0.125 | FGF17 | 0.1 | | | <0.005 | 0.923 |
| THBS1 | 0.25 | VTN | 0.625 | | | <0.005 | 0.930 |
| THBS2 | 0.0625 | THBS4 | 0.0625 | | | <0.05 | 0.942 |
| THBS4 | 0.25 | FGF17 | 0.1 | | | <0.005 | 0.945 |
| THBS4 | 0.0625 | VTN | 0.625 | | | <0.05 | 0.950 |
| VTN | 0.625 | FGF17 | 0.1 | | | <0.005 | 0.952 |
| THBS4 | 0.25 | VTN | 1.25 | | | <0.05 | 0.954 |

TABLE 11

Additional data regarding synergistic combinations of heparin-associated polypeptides (mouse myoblasts)

| Factor Name | Single Dose @ saturation (ug/mL) | Single Dose % of EB | Single Dose % EdU Fold Change to FM | Single Dose % EdU | Combo Dose (ug/mL) | Combo Dose % of EB | Combo Dose % EdU Fold Change to FM | Combo Dose % EdU | HSA CI |
|---|---|---|---|---|---|---|---|---|---|
| THBS1 | 2 | 50% | 1.7 | 15% | 0.125 | 64% | 1.16 | 14% | |
| FGF17 | 0.5 | 239% | 4.5 | 69% | 0.1 | 148% | 2.89 | 33% | |
| Combo | | | | | | 163% | 3.63 | 29% | 0.679091 |
| THBS2 | 2 | 50% | 1.25 | 13% | 0.125 | 46% | 0.88 | 10% | |
| THBS4 | 2 | 40% | 1.87 | 10% | 0.25 | 53% | 1.11 | 12% | |
| Combo | | | | | | 71% | 1.39 | 17% | 0.632548 |
| THBS1 | 2 | 50% | 1.7 | 15% | 0.0625 | 44.08% | 0.75 | 10.63% | |
| VTN | 10 | 50% | 1.5 | 16% | 10 | 59.18% | 1.01 | 14.27% | |
| Combo | | | | | | 69.47% | 1.19 | 16.75% | 0.851842 |
| THBS2 | 2 | 50% | 1.25 | 13% | 0.125 | 31.08% | 0.85 | 7.86% | |
| THBS4 | 2 | 40% | 1.87 | 10% | 0.25 | 29.33% | 0.8 | 7.41% | |
| IL15 | 0.5 | 52% | 1.4 | 12.50% | 1 | 47.25% | 1.28 | 11.90% | |
| Combo | | | | | | 57.91% | 1.66 | 16.21% | 0.679578 |
| THBS2 | 2 | 50% | 1.25 | 13% | 0.125 | 45.08% | 0.79 | 9.64% | |
| THBS4 | 2 | 40% | 1.87 | 10% | 0.25 | 61.15% | 1.08 | 13.08% | |
| VTN | 10 | 50% | 1.5 | 16% | 10 | 54.46% | 0.94 | 12.67% | |

TABLE 12

Additional data regarding synergistic combinations of heparin-associated polypeptides (mouse myoblasts)

| Factor | Single Dose (ug/mL) | Single Dose % of Eb | Single Dose % EdU | Combo Dose (ug/mL) | Combo Dose % of EB | Combo Dose % EdU Fold Change to FM | Combo Dose % EdU |
|---|---|---|---|---|---|---|---|
| THBS1 | 2 | 50% | 15% | 0.125 | 64% | 1.16 | 14% |
| FGF17 | 0.5 | 239% | 69% | 0.1 | 148% | 2.89 | 33% |
| Combo | | | | | 163% | 3.63 | 29% |
| THBS2 | 2 | 50% | 13% | 0.125 | 46% | 0.88 | 10% |
| THBS4 | 2 | 40% | 10% | 0.25 | 53% | 1.11 | 12% |
| Combo | | | | | 71% | 1.39 | 17% |
| THBS1 | 2 | 50% | 15% | 0.0625 | 44.08% | 0.75 | 10.63% |
| VTN | 10 | 50% | 16% | 10 | 59.18% | 1.01 | 14.27% |
| Combo | | | | | 69.47% | 1.19 | 16.75% |
| THBS2 | 2 | 50% | 13% | 0.125 | 31.08% | 0.85 | 7.86% |
| THBS4 | 2 | 40% | 10% | 0.25 | 29.33% | 0.8 | 7.41% |
| IL15 | 0.5 | 52% | 12.50% | 1 | 47.25% | 1.28 | 11.90% |
| Combo | | | | | 57.91% | 1.66 | 16.21% |
| THBS2 | 2 | 50% | 13% | 0.125 | 45.08% | 0.79 | 9.64% |
| THBS4 | 2 | 40% | 10% | 0.25 | 61.15% | 1.08 | 13.08% |
| VTN | 10 | 50% | 16% | 1 | 54.46% | 0.94 | 12.67% |
| Combo | | | | | 69.02% | 1.22 | 14.76% |
| THBS2 | 2 | 50% | 13% | 0.125 | 58.62% | 0.86 | 15.23% |

TABLE 12-continued

Additional data regarding synergistic combinations of heparin-associated polypeptides (mouse myoblasts)

| Factor | Single Dose (ug/mL) | Single Dose % of Eb | Single Dose % EdU | Combo Dose (ug/mL) | Combo Dose % of EB | Combo Dose % EdU Fold Change to FM | Combo Dose % EdU |
|---|---|---|---|---|---|---|---|
| THBS4 | 2 | 40% | 10% | 0.25 | 62.99% | 0.93 | 16.37% |
| IGF2 | 2 | 89% | 23% | 0.5 | 85.78% | 1.27 | 22.29% |
| Combo | | | | | 116.95% | 1.72 | 30.39% |

TABLE 13

Additional data regarding synergistic combinations of heparin-associated polypeptides (human myoblasts)

| Factor Name | Single Dose @ saturation (ug/mL) | Single Dose % of EB | Single Dose % EdU Fold Change to FM | Single Dose % EdU | Combo Dose (ug/mL) | Combo Dose % of EB | Combo Dose % EdU Fold Change to FM | Combo Dose % EdU | HSA CI |
|---|---|---|---|---|---|---|---|---|---|
| THBS1 | 7.5 | 98.93 | 1.61 | 10.99 | 0.5 | 78.22 | 0.85 | 8.95 | |
| FGF17 | 0.25 | 222.09 | 3.62 | 24.67 | 0.05 | 121.74 | 1.33 | 13.93 | |
| Combo | | | | | | 157.29 | 1.72 | 18 | 0.77 |
| THBS2 | 7.5 | 112.8469 | 1.2 | 12.53448 | 0.125 | 57.09 | 0.95 | 7.82 | |
| THBS4 | 0.5 | 126.7002 | 2.07 | 14.07323 | 0.25 | 62.67 | 1.04 | 8.59 | |
| IL15 | 0.1 | 67.81 | 1.13 | 9.29 | 0.1 | 67.81 | 1.13 | 9.29 | |
| Combo | | | | | | 69 | 1.15 | 9.46 | 0.98 |

TABLE 14

Additional data regarding synergistic combinations of heparin-associated polypeptides (human myoblasts)

| Factor Name | Single Dose @ saturation (ug/mL) | Single Dose % of EB | Single Dose % EdU Fold Change to FM | Single Dose % EdU | Combo Dose (ug/mL) | Combo Dose % of EB | Combo Dose % EdU Fold Change to FM | Combo Dose % EdU |
|---|---|---|---|---|---|---|---|---|
| THBS1 | 7.5 | 98.93 | 1.61 | 10.99 | 0.5 | 78.22 | 0.85 | 8.95 |
| FGF17 | 0.25 | 222.09 | 3.62 | 24.67 | 0.05 | 121.74 | 1.33 | 13.93 |
| Combo | | | | | | 157.29 | 1.72 | 18 |

Figure 9A:
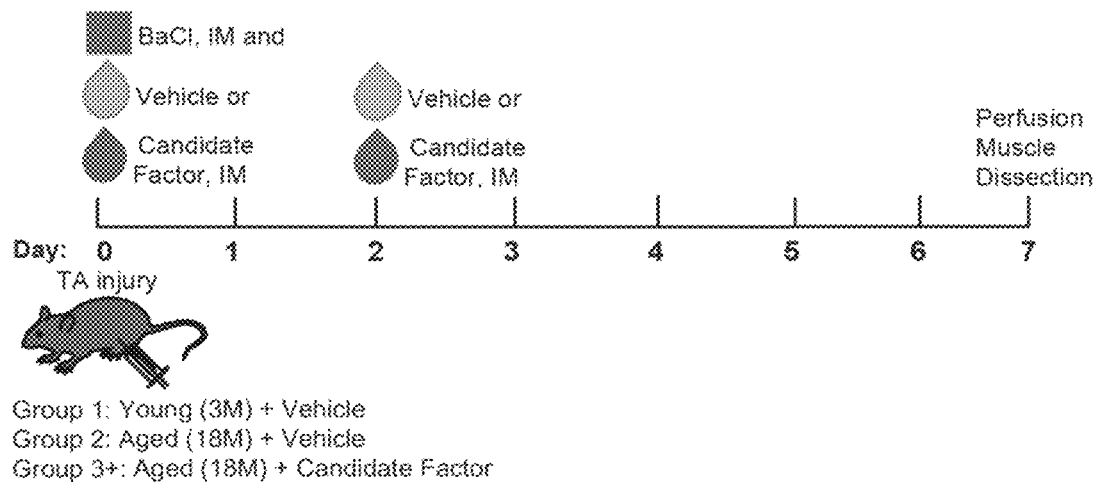
FIG. 9A shows the experimental schematic of time-points for dosing and analysis using an acute injury model in aged mice of the effects of individual heparin-associated polypeptides with proliferative effects in vitro. Squares denote injury inducing intramuscular injection (IM) with Barium Chloride; circles denote administration of treatment or vehicle.
Figure 9B:
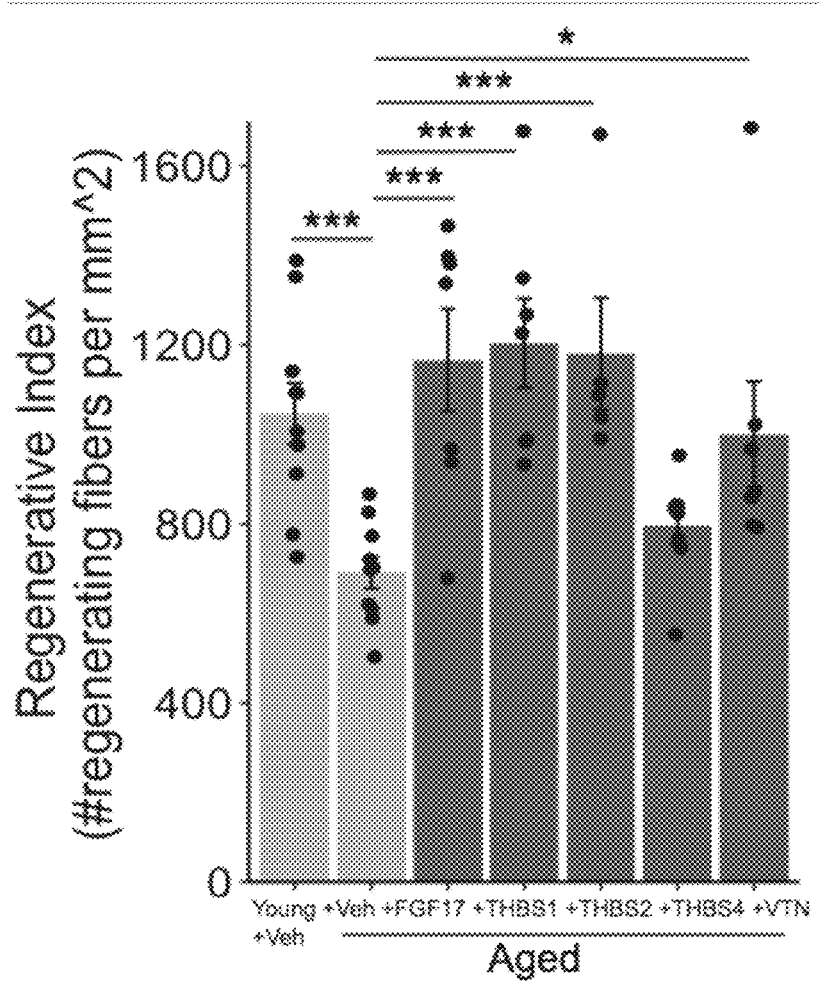
FIG. 9B shows the results of the experiment outlined in FIG. 9A. Administration of 20 ul of heparin-associated polypeptides FGF17 (500 ng/mL, p<2.23E-4), THBS1 (2 ug/mL, p<5.83E-5), THBS2 (2 ug/mL, p<2.67E-4), and VTN (10 ug/mL, p<1.13E-2) resulted in improved new fiber formation (regenerative index) in aged mice compared to vehicle-treated aged mice to levels similar or better than young mice. Stars indicate degree of significance from one-way ANOVA tests.
Figure 9C:
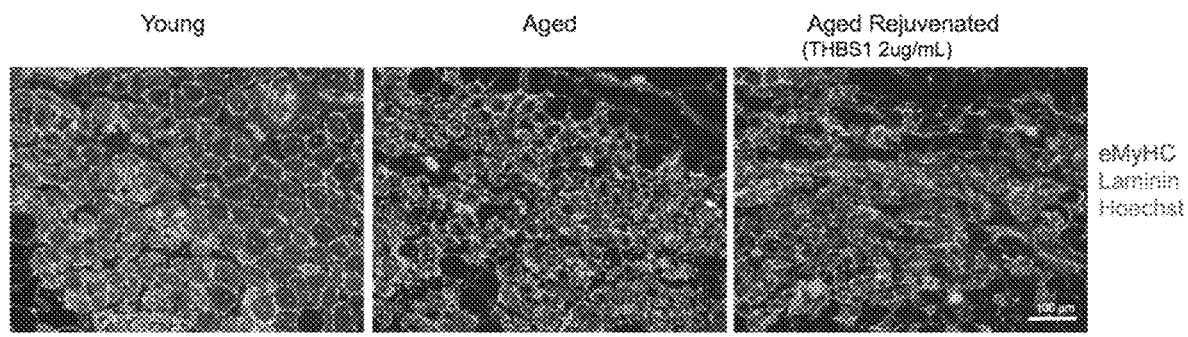
FIG. 9C Representative images of immunofluorescence staining of sectioned mouse muscle (tibialis anterior) demonstrated increased muscle regeneration for injured, aged mouse muscle treated with THBS1 (2 ug/mL) compared to young and vehicle-treated, aged mouse muscle.

Example 8—In Vivo Testing of hPSC Factors Increases Regenerative Index and Reduces Fibrotic Index in an Acute Injury Model in Aged Mice FIGS. 9A-9F show that aged mice (18 months) administered isolated, heparin-agarose bead purified hPSC show improved regenerative index and reduced fibrotic index. FIG. 9A shows a schematic of the experiment in this example. This experiment shows that hPSC derived factors can improve histological metrics of muscle health and function. As shown in FIG. 9B heparin-associated polypeptides isolated from human pluripotent stem cells increase regenerative potential and reduce muscle fibrosis in aged mice subjected to a model of acute muscle injury. As shown in FIG. 9C, there was increased muscle regeneration for injured, aged mouse muscle treated with THBS1 (2 ug/mL) compared to young and vehicle-treated, aged mouse muscle.

Figure 9D:
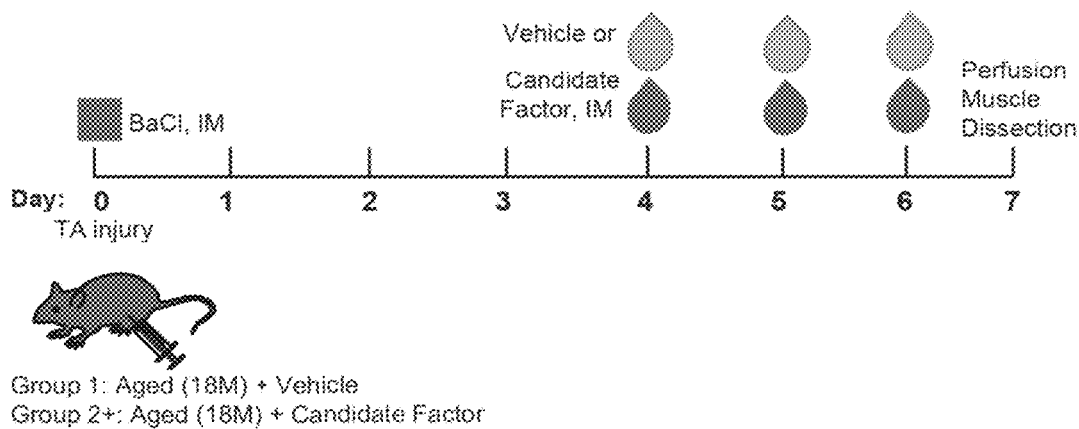
FIG. 9D shows the experimental schematic of time-points for dosing and analysis using an acute injury model in aged mice of the effects of individual heparin-associated polypeptides with fusion enhancing effects in vitro. Squares denote injury inducing intramuscular injection (IM) with Barium Chloride; circles denote administration of treatment or vehicle.
Figure 9E:
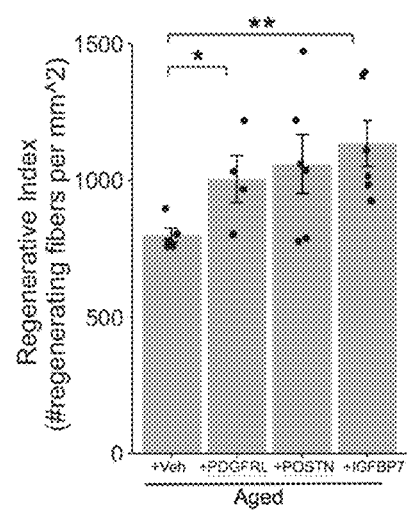
FIG. 9E shows the results of the experiment outlined in FIG. 9D. Administration of 20 ul of heparin-associated polypeptides PPDGFRL (5 ug/mL, p<3.85E-2) and IGFBP7 (1 ug/mL, p<6.63E-3) resulted in improved new fiber formation (regenerative index compared to vehicle-treated aged mice. Stars indicate degree of significance from one-way ANOVA tests.
Figure 9F:
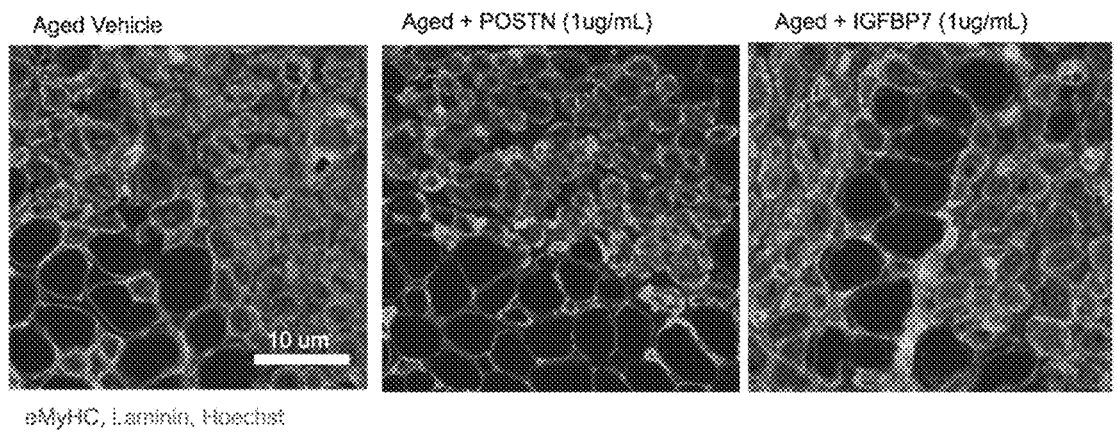
FIG. 9F provides representative images of immunofluorescence staining of sectioned mouse muscle (tibialis anterior) demonstrating increased muscle regeneration for injured, aged mouse muscle treated with POSTN (1 ug/mL) or IGFBP7 (1 ug/mL) compared to vehicle-treated, aged mouse muscle.
Figure 10A:
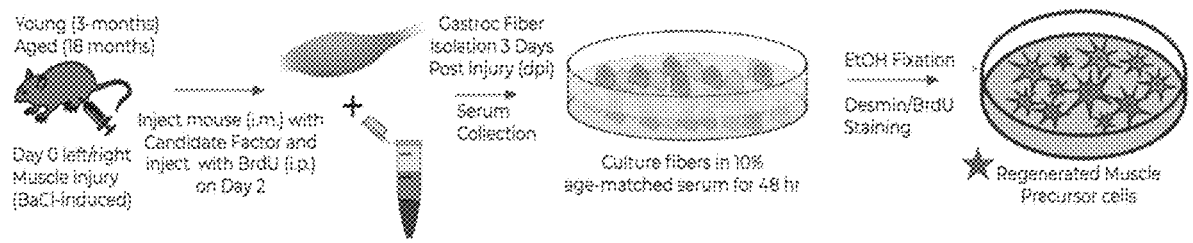
FIG. 10A shows the experimental schematic of time-points for in vivo injury and individual heparin-associated polypeptide administration followed by muscle excision, dissociation, ex vivo culturing of activated myoblasts and quantitation by chemical and immunofluorescent labelling.
Figure 10B:
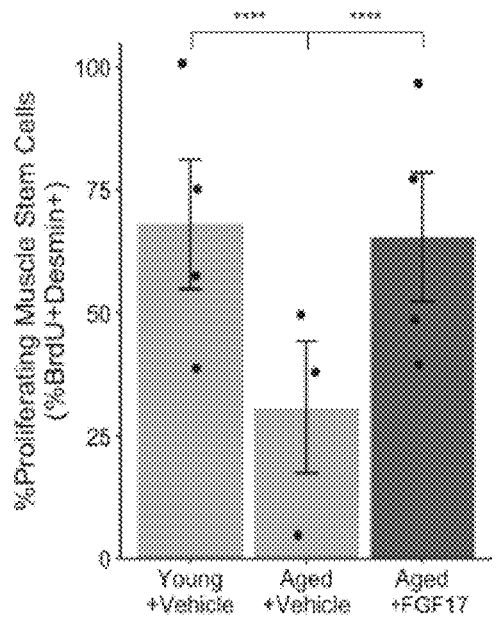
FIG. 10B provides resulting quantitation that demonstrates the regenerative effect of heparin-associated polypeptide administration (FGF17) of 20 ul at 500 ng/ml improved the regeneration of new myoblasts in aged mice above the vehicle-treated aged mice (p<7.57E-8) to a level similar to those seen in young mice.
Figure 10C:
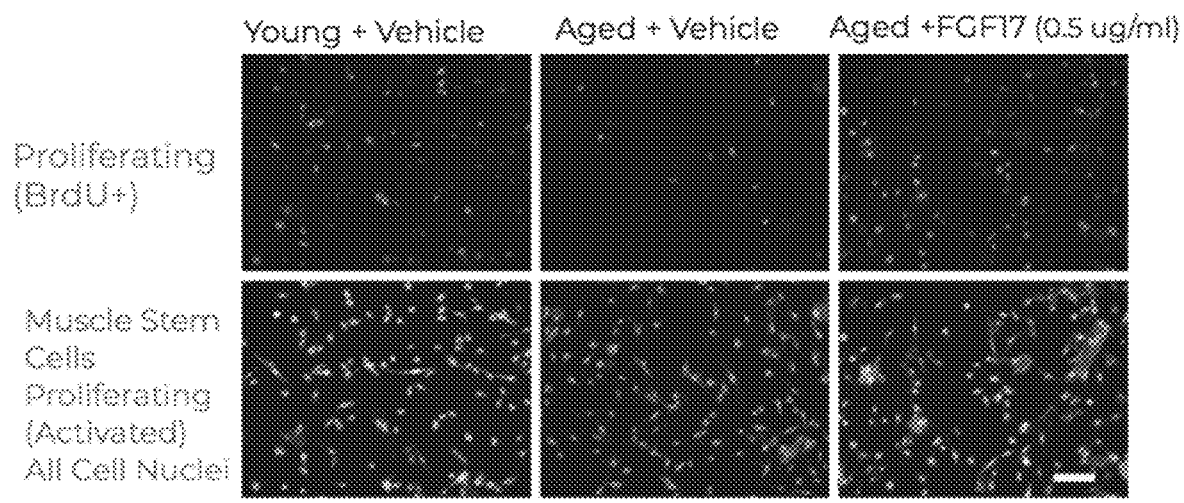
FIG. 10C provides representative immunofluorescence images for ex vivo cultured, injury activated myoblasts used for quantitative evaluation of factor efficacy.
Figure 11A:
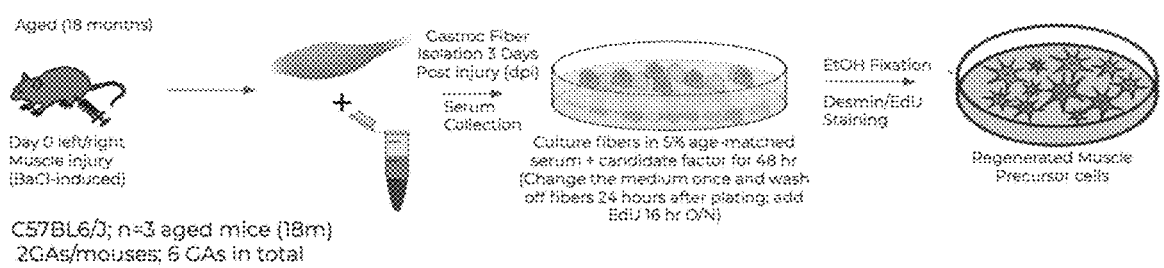
FIG. 11A shows the experimental schematic of time-points for in vivo injury followed by muscle excision, dissociation, ex vivo culturing of activated myoblasts, then individual heparin-associated polypeptide administration and quantitation by chemical and immunofluorescent labelling.
Figure 11B:
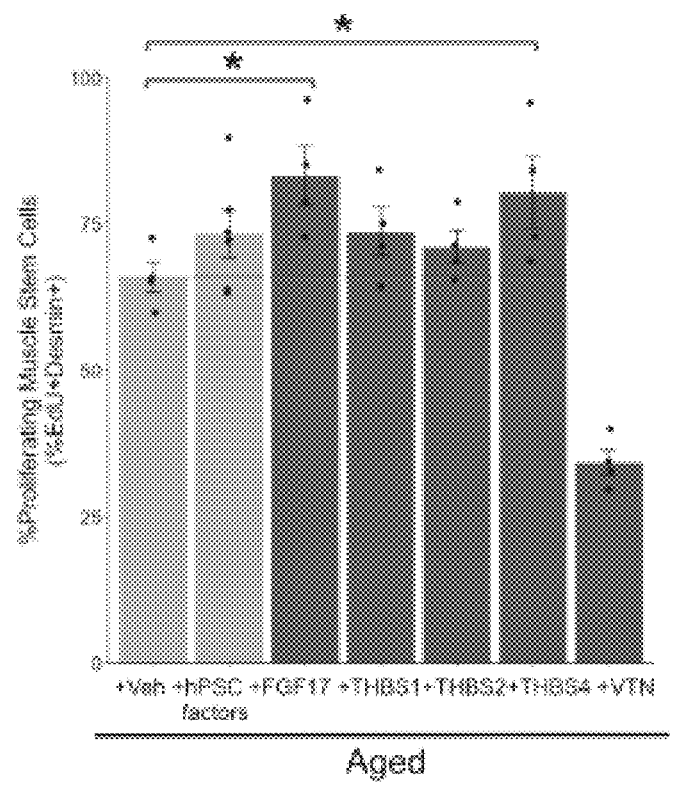
FIG. 11B provides resulting quantitation that demonstrates the regenerative effect of administration of heparin-associated polypeptides FGF17 (500 ng/ml) and THBS4 (2 ug/mL)—each improved the regeneration of new myoblasts in aged mice above the vehicle-treated aged mice (p<1.57E-2, 4.64E-2 respectively, one-sided test) compared to vehicle treated control.
Figure 11C:
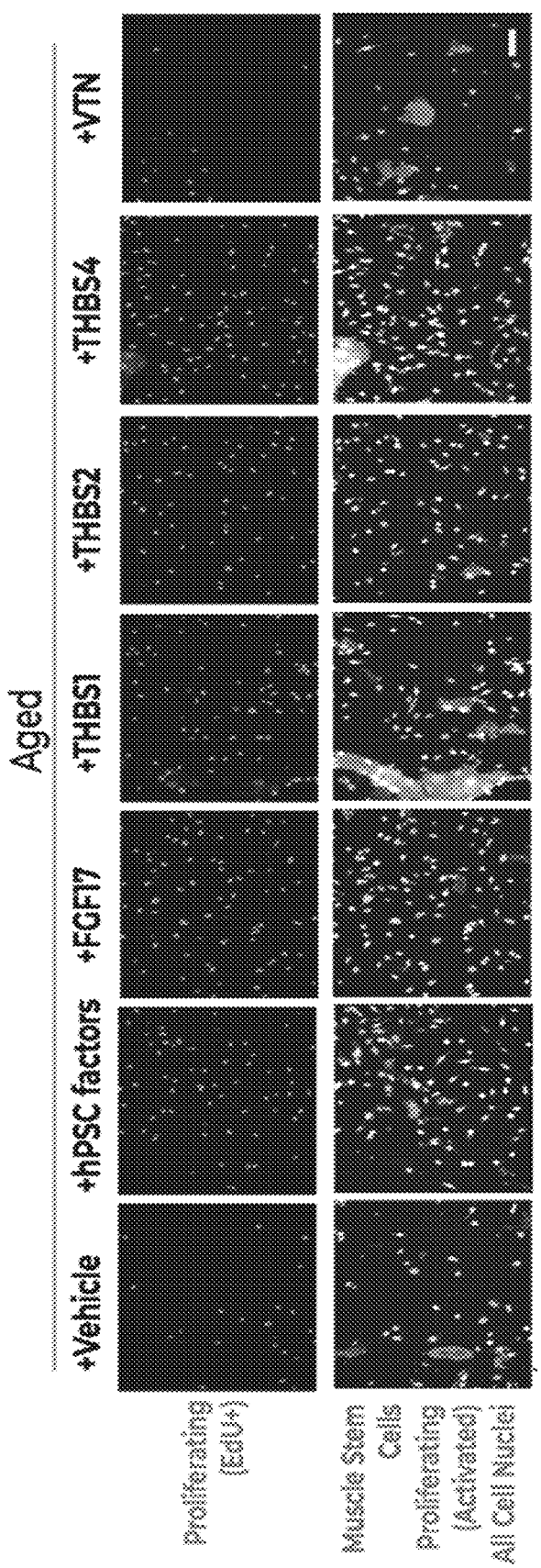
FIG. 11C provides representative immunofluorescence images for ex vivo cultured, injury activated myoblasts used for quantitative evaluation of factor efficacy.

FIG. 9D shows the experimental schematic of time-points for dosing and analysis using an acute injury model in aged mice of the effects of individual heparin-associated polypeptides with fusion enhancing effects in vitro. Square denote injury inducing intramuscular injection (IM) with Barium Chloride while circles denote administration of treatment or vehicle. FIG. 9E shows the results of the experiment outlined in FIG. 9D shows that administration of 20 ul of heparin-associated polypeptides PPDGFRL (5 ug/mL, p<3.85E-2) and IGFBP7 (1 ug/mL, p<6.63E-3) resulted in improved new fiber formation (regenerative index compared to vehicle treated aged mice. Stars indicate degree of significance from one-way ANOVA tests. FIG. 9F provides representative images of immunofluorescence staining of sectioned mouse muscle (tibialis anterior) demonstrating increased muscle regeneration for injured, aged mouse muscle treated with POSTN (1 ug/mL) or IGFBP7 (1 ug/mL) compared to vehicle-treated, aged mouse muscle.

Other models for in vivo testing of hSPC factors include: Disuse-Reload Injury Model This mouse model is a way to observe muscle atrophy in a non-invasive way by contracting the hind limbs of a mouse and preventing extension and flexion, thus reducing the size and strength. The model will serve as an important measurement of muscle regeneration with biologic candidates.

The hind limb will be immobilized with Cast Tape extended position using sports tape to prevent flexion of the limb. Once the sports tape is in place, a strip of casting tape will be wrapped over the sports tape from the ankle upward, and air dried. The extension of the hind limb should stay rigid in its position of the duration of the study parameters.

The study begins after mice are acclimated and on Day −3, in which mice from all groups will be weighed. Assigned animals will be given daily i.p. injections of Vehicle control or Candidate Biologic for 3 days before undergoing hind limb immobilization on Day 0 for 7 days with continuous daily i.p. injections. Hind limbs will be observed for any adverse effects due to immobilization. On Day 7 of the study, all animals will be sacrificed and muscle tissue weighed and harvested for further analysis.

Force Measurement

This study will be used to measure the force of pull in the hind limbs that the animal exerts upon skeletal muscle injury of the tibialis anterior (TA) and gastrocnemius (GA) muscles after injury induction with Barium chloride ($BaCl_2$). This model will serve to determine which of our biological candidates are efficacious in muscle regeneration.

Skeletal Muscle Injury Induction: Under anesthesia, $BaCl_2$ will be administered in two sites on the TA and four sites on the GA (as previously described). Hair will be shaved on the left and right hind limbs prior to injection with small animal hair clippers. On Day 0 of the study, the TA muscle will undergo $BaCl_2$ induced injury on two sites (previously described). On Day 4 of the study, the GA muscle will follow with $BaCl_2$ induced injury on four sites. Candidate biologic will be administered on Days 0 and 2 in the injury sites of the TA and GA muscles. BrdU will be injected via IP (QD) on days 4-7 to label proliferating muscle precursor and fibrotic cells in order to measure their regenerative potential.

On terminal day 7, animals will be deeply anesthetized and a force transducer will be used to measure twitch reactions in the hind limbs of each mouse being tested in the study, via a small incision in the TA to a small metal hook. This will be a terminal procedure. Grip strength measurements: the mice will rest on an angled mesh, facing away from the force meter and with its hind limbs at least one-half of the way down the length of the mesh. The mouse's tail is pulled directly toward the meter and parallel to the mesh. During this procedure, the mouse resists by grasping the mesh with all four limbs. Pulling is continued toward the meter until the hind limbs release.

Ex Vivo Regenerative Measurement

To confirm these data with age matched, primary muscle stem cells, injury-activated satellite cells associated with myofibers will be isolated from young and old muscle by dissecting the muscle groups of interest and dissociating the tissue to single cell suspensions by incubating in digestion medium (250 U/mL Collagenase type II in DMEM medium, buffered with 30 mM HEPES, pH 7.4) at 37 C for 1 hr., triturating the cell suspension, the myofibers were collected by centrifugation and myofibers further digested with 1 U/mL Dispase and 40 U/mL Collagenase type II in 30 mM HEPES at 37 C for 1 hr to free muscle stem cells. Muscle stem cells can then be plated and cultured growth media containing serum (2-5%) from the same mouse. The regenerative and fusion potential of the cells will then be assayed as described above in Example 7 and as demonstrated in FIGS. 10B, 10C, 11B, and 11C. This has the advantage of testing the effect of treatment while maintaining the exogenous, often inhibitory extracellular environmental ques contributed by the age appropriate serum.

Example 9—Modelling Treatment of a Muscular Dystrophy with Pro-Regenerative Factors In Vitro Using High-Throughput Imaging Muscular dystrophies (MD) encompass a variety of muscular degeneration diseases typically due to genetic mutations in genes encoding proteins responsible for forming and stabilizing skeletal muscle. The phenotypic consequence of these genetic mutations is the progressive loss of muscle mass and strength over time, similar to sarcopenia but with different underlying causes. As heparin-associated polypeptides provided phenotypic improvements on sarcopenic muscle, we tested for similar improvements in a model for MD.

Many of the factors detailed in Table 2 were tested individually for their ability to promote proliferation and/or fusion of human muscle progenitor cells from a patient with myotonic dystrophy type 1 (hMD)—a muscular dystrophy caused by mutations in the DMPK1 gene.

Figure 12A:
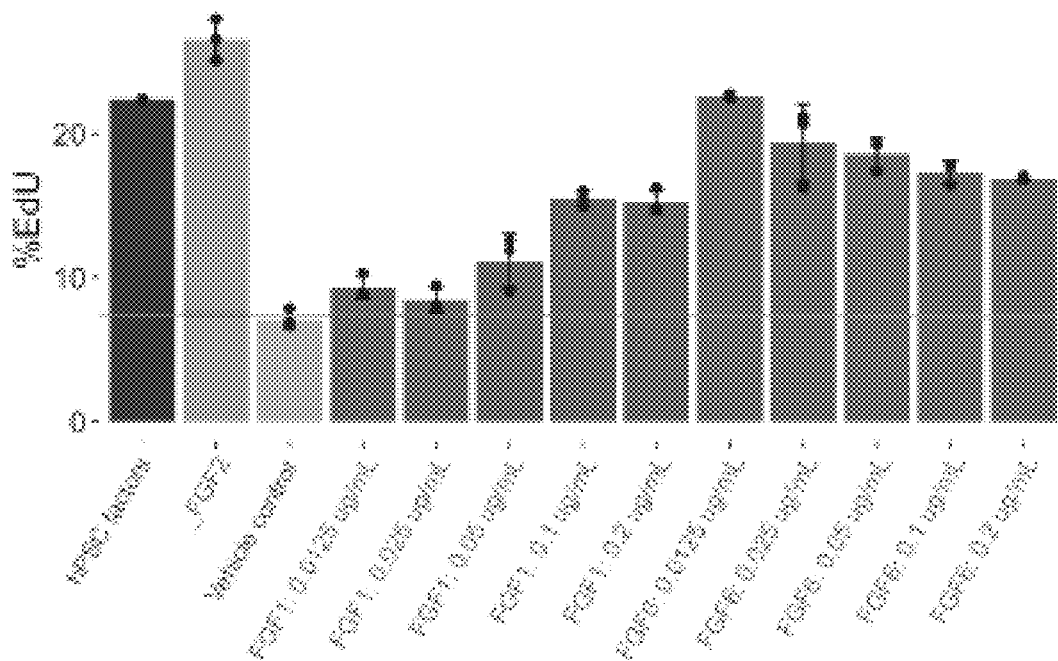
FIG. 12A provides representative quantitation of immunofluorescence images demonstrating the proliferation enhancing effects of heparin-associated polypeptides administration at various does on primary human myoblasts derived from a patient with type 1 myotonic dystrophy.
Figure 12B:
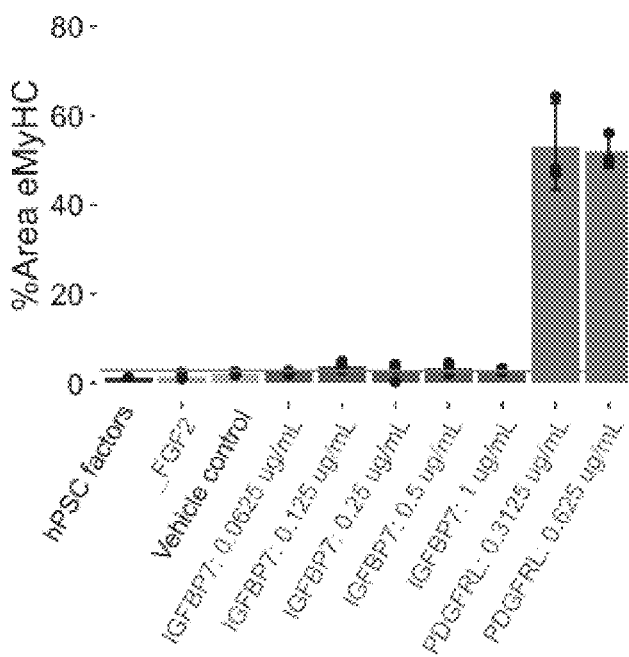
FIG. 12B provides representative quantitation of immunofluorescence images demonstrating the hypertrophy enhancing effects of heparin-associated polypeptides administration at various does on primary human myoblasts derived from a patient with type 1 myotonic dystrophy.

The effect of the candidate factors on myogenic activity was assayed in biological triplicate across a range of concentrations centered around expected physiological levels by adding each factor to hMD myoblasts for 72 hours with daily media changes (DMEM+2% horse serum) and a second pulse of factors at the first media change. After 72 hours, cells were pulsed for 2-5 hours with EdU (30 uM), ethanol fixed, stained with Hoescht 3342, immunostained for proliferation—as measured by the percent of cells staining positive for EdU (% EdU)—, and immunostained for differentiation—as measured by the increase in cellular area staining positive for embryonic myosin heavy chain (% eMyHC) relative to the negative controls, which received media and vehicle only. Wells were imaged on a Keyence BZ-100 at 4×, the images quantified in Cell Profiler, and the statistics were computed in R. FIGS. 12A and 12B show examples of the quantitation of the proliferation response and fusion response for several of the factors tested, respectively. Results those and additional factors are summarized below in Table 15.

TABLE 15

Effect of individual factors on distrophic human myoblast growth and fusion

| | | Proliferation (% EdU) | | Fusion (% eMyHC) | |
|---|---|---|---|---|---|
| Factor Name | Concentration (ug/mL) | Effect Size (% relative to-control) | Statistical Significance (p-value) | Effect Size (% relative to-control) | Statistical Significance (p-value) |
| FGF17 | 0.2 | 208% | <9E−14 | | |
| FGF4 | 0.0125 | 269% | 9.52E−13 | | |
| FGF4 | 0.025 | 244% | 6.83E−12 | | |
| FGF4 | 0.05 | 235% | 7.22E−10 | | |
| FGF4 | 0.1 | 213% | 8.11E−07 | | |
| FGF4 | 0.2 | 184% | 1.46E−02 | | |
| IGF2 | 0.2 | 53% | 2.57E−02 | | |
| FGF1 | 0.05 | 157% | 1.65E−06 | | |
| FGF1 | 0.1 | 217% | 2.87E−06 | | |
| FGF1 | 0.2 | 213% | 1.10E−10 | | |

TABLE 15-continued

Effect of individual factors on distrophic human myoblast growth and fusion

| Factor Name | Concentration (ug/mL) | Proliferation (% EdU) | | Fusion (% eMyHC) | |
|---|---|---|---|---|---|
| | | Effect Size (% relative to-control) | Statistical Significance (p-value) | Effect Size (% relative to-control) | Statistical Significance (p-value) |
| FGF6 | 0.0125 | 277% | 1.34E−09 | | |
| FGF6 | 0.025 | 272% | 4.54E−09 | | |
| FGF6 | 0.05 | 261% | 4.75E−08 | | |
| FGF6 | 0.1 | 243% | 1.03E−07 | | |
| FGF6 | 0.2 | 237% | 8.49E−06 | | |
| PDGFRL | 0.03125 | | | 2580% | 1.47E−06 |
| PDGFRL | 0.0625 | | | 2240% | 6.34E−07 |
| PDGFRL | 0.125 | | | 1410% | 4.53E−03 |
| PDGFRL | 0.25 | | | 2570% | 1.86E−08 |
| PDGFRL | 0.5 | | | 3440% | 5.75E−11 |

Example 10 Assess hPSC Factors In Vivo Using Rodent Models of Becker Muscular Dystrophy for their Ability to Improve Muscle Regeneration and Muscle Mass Mdx−/− mice will receive intramuscular injections of the top 3 select hPSC secreted factors selected from the in vitro screen. Indications of enhanced functional regeneration will be assessed through quantification of twitch force measurements and walking track analysis. The Mdx−/− mouse model for BMD is chosen as it has a spontaneous point mutation in the dystrophin gene leading to near complete absence of dystrophin protein. Despite having phenotypic markers of myopathy there are only mild skeletal muscle defects, suggesting that the model best reflects Becker muscular dystrophy. This animal model also mimics the complex paracrine signaling environment, where immune cells and other systemic factors would be involved. Thus, a screen in injured dystrophic muscle for regeneration will efficiently narrow the candidate list for those proteins needed for the ultimate goal of restoring muscle mass and strength to the BMD patients. Myogenesis in a muscle regeneration model will be compared between controls (vehicle-treated) and with the top 3-5 efficacious, dose-optimized factors. Hind limb muscles, the Tibialis anterior (TA) and gastrocnemius (GA) muscle will receive i.m. injection of vehicle control or candidate factor every day for 7 days (t=5 days). BrdU will be also be injected 3 days prior to tissue collection for ex vivo analysis. Muscle regeneration will be assessed in 10 micrometer muscle cryosections. The histological analysis of hematoxylin and eosin staining and immunodetection of eMyHC and BrdU will be used to quantify the numbers of de-novo eMyHC+ myofibers with centrally-located BrdU+ nuclei throughout the injury site. Additionally, myofiber size and muscle weights will also be assessed. For twitch for measurements, mice hindlimbs will be immobilize to a frame. A small incision will be made in the skin directly above the tibialis anterior (TA) muscle to hook to a thin metal hook and then attached to a 300C-LR force transducer (Aurora Scientific). A bipolar electrical stimulation cuff will wrap around the TA and stimulate with a single 0.1-ms pulse for 3 seconds.

It is expected that administration of select pro-myogenic factors will increase Delta/Notch and MapK signaling, dependent on BMP signaling in Mdx−/− myogenic cells, resulting in increased proliferation, allowing the injury site to heal similar to wildtype muscle—with new muscle fibers—instead of filling with fibrotic scar tissue or adipose tissue as is common in dystrophic muscle. Administration of candidate factors to Mdx−/− injured TA muscle is expected to improve regeneration indicated by quantification of muscle fiber repair and twitch force measurement.

Example 11—Clinical Testing of Pro-Regenerative Factors

The purpose of this study is to determine the efficacy of repeat dosing with multiple dose levels of heparin-associated proteins on patient physical function, skeletal muscle mass and strength in older adults with sarcopenia. In addition, this study will generate data on the safety, tolerability, and pharmacokinetics of heparin-associated proteins in older adults with sarcopenia. Individuals will administered placebo or heparin-associated binding proteins and monitored for 25 weeks of study. The following primary and secondary outcome measures will be assessed:

Primary Outcome Measures:
  Short Physical Performance Battery (SPPB) [Time Frame: Baseline, week 25]. Change from baseline to week 25.

Secondary Outcome Measures:
  Safety and tolerability as assessed by various measures such as adverse events. Assessed by various measures such as adverse events over 24 weeks.
  Change in 6-minute walk test [Time Frame: baseline, week 25]. Change from baseline to week 25.
  Gait speed [Time Frame: baseline, week 25]. Change from baseline to week 25.
  Change in total lean body mass and appendicular skeletal muscle index measured by DXA from baseline to week 25.

Inclusion Criteria:
  Otherwise healthy adults aged at least 70 years; Low muscle mass as confirmed by DXA; Low gait speed; SPPB score less than or equal to 9; Weigh at least 35 kg; with adequate dietary intake as determined by patient interview.

Protocol
  Patients will be i.v.-administered placebo (5% dextrose solution) or heparin-associated binding proteins (in 5% dextrose). Starting on day 1, week 1 and repeated every other week (day one of weeks 3, 5, 7, 9, 11, 13, 15, 17, 19, 21, and 23. At the end of week 12 and 24 patients will be assessed by the above methods for improvement. Doses will be selected from a traditional 3+3 design, and selected as the top two-doses that lack dose-limiting toxicity.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A composition comprising: (a) a first recombinant or synthetic polypeptide comprising an amino acid sequence with at least about 90% identity to amino acids 19 to 1170 of THBS1 (SEQ ID NO: 9); (b) a second recombinant or synthetic polypeptide comprising an amino acid sequence with at least about 90% identity to amino acids 23 to 216 of FGF17 (SEQ ID NO: 7); and (c) a solubilizing, emulsifying, or dispersing agent, wherein the first polypeptide is present in an amount about 1 mg/mL or greater and the second polypeptide is present in an amount about 1 mg/mL or greater.

2. The composition of claim 1, provided that the first recombinant or synthetic polypeptide has been recombinantly produced, the second recombinant or synthetic polypeptide has been recombinantly produced, or both the first and second recombinant or synthetic polypeptides have been recombinantly produced.

3. The composition of claim 1, provided that the first recombinant or synthetic polypeptide has been produced in a mammalian, yeast, insect or bacteria cell, the second recombinant or synthetic polypeptide has been produced in a mammalian, yeast, insect or bacteria cell, or both the first and second recombinant or synthetic polypeptides have been produced in a mammalian, yeast, insect or bacteria cell.

4. The composition of claim 3, provided that the first recombinant or synthetic polypeptide, the second recombinant or synthetic polypeptide, or both the first and the second recombinant or synthetic polypeptides have been produced in a mammalian cell and the mammalian cell is a human cell, Chinese Hamster Ovary (CHO) cell or mouse myeloma cell.

5. The composition of claim 1, further comprising an IL-15 polypeptide or a polypeptide comprising an amino acid sequence at least about 90% identical to amino acids 49-162 of SEQ ID NO: 10.

6. The composition of claim 1, further comprising an IGF2 polypeptide or a polypeptide comprising an amino acid sequence at least about 90% identical to amino acids 25-91 of SEQ ID NO: 11.

7. The composition of claim 1, formulated for administration by injection.

8. The composition of claim 7, provided that the injection is intramuscular injection.

9. The composition of claim 7, provided that the injection is systematic, subcutaneous, or intravenous injection.

10. The composition of claim 1, further comprising a VTN polypeptide or a polypeptide comprising an amino acid sequence comprising at least about 90% identical to amino acids 20-478 of SEQ ID NO: 1.

11. The composition of claim 1, wherein the first polypeptide comprises an amino acid sequence with at least about 95% identity to amino acids 19 to 1170 of THBS1 (SEQ ID NO: 9).

12. The composition of claim 1, wherein the second polypeptide comprises an amino acid sequence with at least about 95% identity to amino acids 23 to 216 of FGF17 (SEQ ID NO: 7).

13. The composition of claim 1, wherein the first polypeptide comprises an amino acid sequence with at least about 97% identity to amino acids 19 to 1170 of THBS1 (SEQ ID NO: 9).

14. The composition of claim 1, wherein the second polypeptide comprises an amino acid sequence with at least about 97% identity to amino acids 23 to 216 of FGF17 (SEQ ID NO: 7).

* * * * *